US009289398B2

(12) United States Patent
Almstead et al.

(10) Patent No.: US 9,289,398 B2
(45) Date of Patent: *Mar. 22, 2016

(54) METHODS FOR THE PRODUCTION OF FUNCTIONAL PROTEIN FROM DNA HAVING A NONSENSE MUTATION AND THE TREATMENT OF DISORDERS ASSOCIATED THEREWITH

(75) Inventors: Neil Almstead, Princeton, NJ (US); Guangming Chen, Bridgewater, NJ (US); Samit Hirawat, Chatham, NJ (US); Peter Seongwoo Hwang, Edison, NJ (US); Gary M. Karp, Princeton Junction, NJ (US); Langdon Miller, Lebanon, NJ (US); Young-Choon Moon, Belle Meade, NJ (US); Hongyu Ren, Dayton, NJ (US); James J. Takasugi, Lawrenceville, NJ (US); Ellen M. Welch, Califon, NJ (US); Richard G. Wilde, Somerville, NJ (US); Paul Kennedy, Brighton, MI (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 1608 days.

This patent is subject to a terminal disclaimer.

(21) Appl. No.: 12/294,952

(22) PCT Filed: Mar. 29, 2007

(86) PCT No.: PCT/US2007/008268
§ 371 (c)(1),
(2), (4) Date: Nov. 11, 2010

(87) PCT Pub. No.: WO2007/117438
PCT Pub. Date: Oct. 18, 2007

(65) Prior Publication Data
US 2011/0046136 A1 Feb. 24, 2011

Related U.S. Application Data

(60) Provisional application No. 60/787,333, filed on Mar. 30, 2006, provisional application No. 60/813,085, filed on Jun. 12, 2006.

(51) Int. Cl.
| | | |
|---|---|---|
| A61K 31/4245 | (2006.01) |
| A61P 21/00 | (2006.01) |
| A61K 31/00 | (2006.01) |
| A61K 31/40 | (2006.01) |
| A61K 31/41 | (2006.01) |
| A61K 31/4162 | (2006.01) |
| A61K 31/44 | (2006.01) |
| A61K 31/46 | (2006.01) |
| A61K 31/5377 | (2006.01) |
| A61K 31/496 | (2006.01) |
| A61K 31/454 | (2006.01) |
| A61K 31/4709 | (2006.01) |
| A61K 31/4439 | (2006.01) |
| A61K 31/519 | (2006.01) |
| A61K 31/498 | (2006.01) |
| A61K 31/53 | (2006.01) |
| A61K 31/506 | (2006.01) |
| A61K 31/497 | (2006.01) |
| A61K 31/501 | (2006.01) |
| A61K 31/433 | (2006.01) |
| A61K 31/421 | (2006.01) |
| A61K 31/415 | (2006.01) |
| A61K 31/426 | (2006.01) |

(Continued)

(52) U.S. Cl.
CPC .............. *A61K 31/00* (2013.01); *A61K 31/40* (2013.01); *A61K 31/41* (2013.01); *A61K 31/4162* (2013.01); *A61K 31/44* (2013.01); *A61K 31/46* (2013.01)

(58) Field of Classification Search
CPC ....... A61K 31/00; A61K 31/40; A61K 31/41; A61K 31/4162; A61K 31/44; A61K 31/46
USPC ........................................ 514/236.2
See application file for complete search history.

(56) References Cited

U.S. PATENT DOCUMENTS 3,192,103 A 6/1965 Sousa et al.
3,325,446 A 6/1967 Chang et al.

(Continued)

FOREIGN PATENT DOCUMENTS

DE 4320801 1/1995
EP 675122 A2 10/1995

(Continued)

OTHER PUBLICATIONS

Da-Zhi Wang, M. Renee Valdez, John McAnally, James Richardson, and Eric N. Olson, The Mef2c gene is a direct transcriptional target of myogenic bHLH and MEF2 proteins during skeletal muscle development, Development 128, 4623-4633 (2001).*
Suminaga et al. (C-Terminal Truncated Dystrophin Identified in Skeletal Muscle of an Asymptomatic Boy with a Novel Nonsense Mutation of the Dystrophin Gene, Ryo Suminaga, Yasuhiro Takeshima, Hiroko Wada, Mariko Yagi, and Masafumi Matsuo, Pediatric Research vol. 56, No. 5, 2004, 739-743).*

(Continued)

*Primary Examiner* — Sarah Pihonak
*Assistant Examiner* — Jason A Deck
(74) *Attorney, Agent, or Firm* — Jones Day

(57) ABSTRACT

The present invention relates to functional proteins encoded by nucleic acid sequences comprising a nonsense mutation. The present invention also relates to methods for the production of functional proteins encoded by nucleic acid sequences comprising a nonsense mutation and the use of such proteins for prevention, management and/or treatment of diseases associated with a nonsense mutation(s) in a gene.

6 Claims, 3 Drawing Sheets

Figure 1:
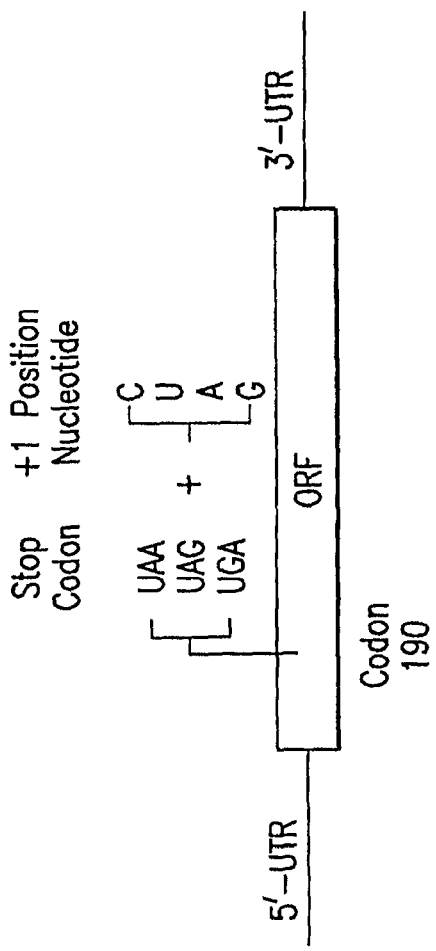

(51) Int. Cl.

| | | |
|---|---|---|
| A61K 31/427 | (2006.01) | |
| A61K 31/428 | (2006.01) | |
| A61K 31/42 | (2006.01) | |
| A61K 31/4164 | (2006.01) | |
| A61K 31/34 | (2006.01) | |
| A61K 31/381 | (2006.01) | |
| A61K 31/4196 | (2006.01) | |
| A61P 11/00 | (2006.01) | |
| A61P 7/00 | (2006.01) | |
| A61P 25/00 | (2006.01) | |
| A61P 13/12 | (2006.01) | |
| A61P 27/02 | (2006.01) | |

(56) References Cited

U.S. PATENT DOCUMENTS

| | | |
|---|---|---|
| 4,016,170 A | 4/1977 | Nadelson |
| 4,022,901 A | 5/1977 | Narayanan et al. |
| 4,135,910 A | 1/1979 | Howe |
| 4,166,732 A | 9/1979 | Howe |
| 4,210,762 A | 7/1980 | Howe |
| 4,268,299 A | 5/1981 | Howe |
| 4,414,221 A | 11/1983 | Parsons et al. |
| 5,484,944 A | 1/1996 | Albaugh et al. |
| 5,972,050 A | 10/1999 | Wiesenfeldt et al. |
| 6,034,106 A | 3/2000 | Biftu et al. |
| 6,180,648 B1 | 1/2001 | Kozikowski et al. |
| 6,472,422 B2 | 10/2002 | Kozikowski et al. |
| 6,498,151 B2 | 12/2002 | Li et al. |
| 6,620,828 B2 | 9/2003 | Chu et al. |
| 6,660,753 B2 | 12/2003 | Van Wagenen et al. |
| 6,759,538 B2 | 7/2004 | Singh et al. |
| 6,878,734 B2 | 4/2005 | Kalindijian et al. |
| 6,992,096 B2 | 1/2006 | Karp et al. |
| 7,041,685 B2 | 5/2006 | Cai et al. |
| 7,112,595 B2 | 9/2006 | Van Wagenen et al. |
| 7,153,880 B2 | 12/2006 | Singh et al. |
| 7,202,262 B2 | 4/2007 | Karp et al. |
| 7,304,080 B2 | 12/2007 | Karp et al. |
| 7,419,991 B2 | 9/2008 | Karp et al. |
| 2002/0025976 A1 | 2/2002 | Chu et al. |
| 2002/0055521 A1 | 5/2002 | Kozikowski et al. |
| 2002/0147188 A1 | 10/2002 | Marquis |
| 2004/0204461 A1* | 10/2004 | Karp et al. ............ 514/364 |
| 2005/0154012 A1 | 7/2005 | Cai et al. |
| 2005/0164973 A1 | 7/2005 | Karp et al. |
| 2005/0233327 A1 | 10/2005 | Welch et al. |
| 2007/0161687 A1 | 7/2007 | Karp et al. |
| 2008/0114039 A1 | 5/2008 | Hirawat et al. |
| 2008/0139632 A1 | 6/2008 | Almstead et al. |
| 2008/0139818 A1 | 6/2008 | Almstead et al. |
| 2008/0171377 A1 | 7/2008 | Almstead et al. |
| 2011/0086833 A1 | 4/2011 | Paushkin et al. |

FOREIGN PATENT DOCUMENTS

| | | |
|---|---|---|
| JP | 51-143669 | 12/1976 |
| JP | 2001-247569 | 9/2001 |
| JP | 2002-105073 | 4/2002 |
| WO | WO 95/11885 | 5/1995 |
| WO | WO 97/09335 | 3/1997 |
| WO | WO 97/44333 | 11/1997 |
| WO | WO 97/46556 | 12/1997 |
| WO | WO 98/00465 | 1/1998 |
| WO | WO 98/33927 | 8/1998 |
| WO | WO 98/45263 | 10/1998 |
| WO | WO 98/49190 | 11/1998 |
| WO | WO 99/54317 | 10/1999 |
| WO | WO 00/21959 | 4/2000 |
| WO | WO 00/25768 | 5/2000 |
| WO | WO 00/38687 | 7/2000 |
| WO | WO 00/58278 | 10/2000 |
| WO | WO 00/58280 | 10/2000 |
| WO | WO 00/58304 | 10/2000 |
| WO | WO 00/69810 | 11/2000 |
| WO | WO 00/75120 | 12/2000 |
| WO | WO 01/66534 | 9/2001 |
| WO | WO 01/85723 | 11/2001 |
| WO | WO 01/90101 | 11/2001 |
| WO | WO 02/072621 | 9/2002 |
| WO | WO 02/085869 | 10/2002 |
| WO | WO 02/100826 | 12/2002 |
| WO | WO 03/002559 | 1/2003 |
| WO | WO 04/001010 | 12/2003 |
| WO | WO 2004/014370 | 2/2004 |
| WO | WO 2004/014902 | 2/2004 |
| WO | WO 2004/072050 | 8/2004 |
| WO | WO 2004/091502 | 10/2004 |
| WO | WO 2004091502 A2 * | 10/2004 |
| WO | WO 2004/110351 | 12/2004 |
| WO | WO 2005/060961 | 7/2005 |
| WO | WO 2005/077373 | 8/2005 |
| WO | WO 2005/086768 | 9/2005 |
| WO | WO 2006/044456 | 4/2006 |
| WO | WO 2006/110483 | 10/2006 |
| WO | WO 2008/030570 | 3/2008 |
| WO | WO 2008/039431 | 4/2008 |
| WO | WO 2008/045566 | 4/2008 |

OTHER PUBLICATIONS

Weisenthal et al. (Current Status of Cell Culture Drug Resistance Testing, Larry M Weisenthal MD PhD and Peter Nygren MD PhD, 2002).*
Roest et al. (Application of In Vitro Myo-Differentiation of Non-Muscle Cells to Enhance Gene Expression and Facilitate Analysis of Muscle Proteins P. A. M. Roest, A. C. Van Der Tuijn, H. B. Ginjaar, R. C. Hoebeni, F. B. L. Hogervorst, E. Bakker, J. T. Den Dunnen and G. J. B. Van Ommen, Neuromusc. Disord., vol. 6. No. 3, pp. 195-202, 1996).*
Patel et al., 2005, Investigative Ophthalmology & Visual Science, vol. 46(7):2282-2290.
Suminaga et al., 2004, Pediatric Research, vol. 56(5): 739-743.
Hill et al., 2005, Haemophilia, vol. 11(2):133-141.
Hamosh et al., 1991, J. Clin. Invest., vol. 88(6):1880-1885.
De Boulle et al., 1993, Nature Genetics, vol. 3(1):31-35.
Grace et al., 1999, The Journal of Clinical Investigation, vol. 103(6):817-823.
U.S. Appl. No. 11/918,114, filed Oct. 4, 2007, Hirawat et al.
U.S. Appl. No. 60/149,464, filed Aug. 19, 1999, Van Wagenen et al.
U.S. Appl. No. 60/269,847, filed Feb. 21, 2001, McLeod.
U.S. Appl. No. 60/350,107, filed Nov. 2, 2001, Singh et al.
U.S. Appl. No. 60/405,472, filed Aug. 23, 2002, Singh et al.
Ainsworth, 2005, "Running the red light," Nature, vol. 438(7069):726-728.
Benchair et al., 1997, "Anodic behavior of aromatic oximes: an electrochemical deoximation reaction," Electrohimica Acta., vol. 42(23-24):3509-3512.
Bernhard et al., 2001, "Metabolism of surfactant phosphatidylcholine molecular species in cftr(tm1 HGU/tm1 HGU) mice compared to MF-1 mice," Exp. Lung Res., vol. 27(4):349-66).
Bhattacharyya et al., 2001, "A novel missense mutation in lysosomal sulfamidase is the basis of MPS III A in a spontaneous mouse mutant," Glycobiology, Vo. 11(1):99-110.
Bhaumik et al., 1999, "A mouse model for mucopolysaccharidosis type III A (Sanfilippo syndrome)," Glycobiology, vol. 9(12):1389-96.
Bi et al., 1995, "Targeted disruption of the mouse factor VIII gene produces a model of haemophilia A," Nat Genet., vol. 10(1):119-21.
Burke et al., 1985,"Suppression of a nonsense mutation in mammalian cells in vivo by the aminoglycoside antibiotics G-418 and paromomycin," Nucleic Acids Research, Oxford University Press., vol. 13(17):6265-6272.
Carvalho et al., 1997, "Excited-state acidity of bifunctional compounds," J. Chem. Soc., Farady Trans., vol. 93(18):3325-3329.
Connelly et al., 1998, "Sustained phenotypic correction of murine hemophilia A by in vivo gene therapy," Blood, vol. 91(9):3273-81.
Connolly et al., 2002, "Complement 3 deficiency and oral prednisolone improve strength and prolong survival of laminin apha2-deficient mice," J Neuroimmunol., vol. 127(1-2):80-7.

(56) References Cited

OTHER PUBLICATIONS

Connolly, 2005,"Neurodegeneration caused by the translation of nonsense: Does macromolecular misfolding impair the synchrony of gene expression?" Medical Hypotheses, Eden Press, Penrith, US, vol. 64(5):968-972.
D'Hooge et al., 1999, "Decline in brainstem auditory-evoked potentials coincides with loss of spiral ganglion cells in arylsulfatase A-deficient mice," Brain Res., vol. 847(2):352-6.
D'Hooge et al., 1999, "Neuromotor alterations and cerebellar deficits in aged arylsulfatase A-deficient transgenic mice," Neurosci Lett., vol. 273(2):93-6.
Deegan et al., 1999, "Paralet Synthesis of 1,2,4-Oxadiazoles Using CDI Activation," Bioorg. & Med. Chem. Lett., vol. 9:2029-212.
Dubowitz et al., 2000, "High resolution magnetic resonance imaging of the brain in the dy/dy mouse with merosin-deficient congenital muscular dystrophy," Neuromuscul Disor., vol. 10(4-5):292-8.
Fang et al., 1996, "Lack of persistence of E1-recombinant adenoviral vectors containing a temperature-sensitive E2A mutation in immunocompetent mice and hemophilia B dogs," Gene Ther, vol. 3(3):217-22.
Fetizon et al., 1974, "Oxidation par le carbonate D'Argent—XII," Tetrahedron, vol. 31:165-170 (w/English summary).
Freedman et al., 2001, "Pancreatic acinar cell dysfunction in CFTR(-/-) mice is associated with impairments in luminal pH and endocytosis," Gastroenterology, vol. 121(4):950-7.
Gallo-Penn et al., 1999, "In vivo evaluation of an adenoviral vector encoding canine factor VIII: high-level, sustained expression in hemophiliac mice," Hum Gene Ther., vol. 10(11):1791-802.
Garvey et al., 2002, "The muscular dystrophy with myositis (mdm) mouse mutation disrupts a skeletal muscle-specific domain of titin," Genomics, vol. 79(2):146-9.
Hamed et al., 2006,"Drug evaluation: PCT-124—a potential treatment for cystic fibrosis and Duchenne muscular dystrophy," ID Drugs, Current Drugs, Ltd., vol. 9(11):783-789.
Haugwitz et al., 1985, "Antiparasitic agents. 6. Synthesis and anthelmintic activities of novel isothiocyanatophenyl-1,2,4-oxadiazoles," J. Med. Chem. 28:1234-1241.
Hino et al., 1999, "TSC2 gene mutant (Eker) rat model of a Mendelian dominantly inherited cancer," Prog Exp Tumor Res., vol. 35:95-108.
Hino, 2000, "Cancer genetics of TSC2 gene mutant(Eker) rat model," Nippon Rinsho, vol. 58(6):1255-61 (w/English summary).
Jarvis et al., 1996, "Induction of human factor VIII inhibitors in rats by immunization with human recombinant factor VIII: a small animal model for humans with high responder inhibitor phenotype," Thromb Haemost., vol. 75(2):318-25.
Kay et al., 1994, "In vivo hepatic gene therapy: complete albeit transient correction of factor IX deficiency in hemophilia B dogs," Proc Natl. Acad Sci USA, vol. 91(6):2353-7.
Kellermayer et al., 2006,"Translational read through induction of pathogenic nonsense mutations," Eur. J. of Medical Genetics, vol. 49(6):445-450.
Kobayashi et al., 2001, "A germ-line Tsc1 mutation causes tumor development and embryonic lethality that are similar, but not identical to, those caused by Tsc2 mutation in mice," Proc Natl Acad Sci USA., vol. 98(15):8762-7.
Kramer et al., 1998, "Myotonic ADR-MDX mutant mice show less severe muscular dystrophy than MDX mice," Neuromuscul Disord., vol. 8(8):542-50.
Kulyte et al., 2005, "Gene selective suppression of nonsense termination using antisense agents," Biochemica et Biophysica Acta, Gene Structure and Expression, vol. 1730(3)165-172.
Kuzmiak et al., 2006, "Applying nonsense-mediated mRNA Decay research to the clinic: progress and challenges," Trends in Molecular Medicine., vol. 12(7):306-316.
Kwiatkowski et al., 2002, "A mouse model of TSC1 reveals sex-dependent lethality from liver hemangiomas, and up-regulation of p70S6 kinase activity in Tsc1 null cells," Hum Mol Genet., vol. 11(5):525-34.

Lozier et al., 1999, "The rhesus macaque as an animal model for hemophilia B gene therapy," Blood, vol. 93(6):1875-81.
Mizuguchi et al., 2000, "Novel cerebral lesions in the Eker rat model of tuberous sclerosis: cortical tuber and anaplastic gangliogli," J Neuropathol Exp Neurol., vol. 59(3):188-9.
Mount et al., 2002, "Sustained phenotypic correction of hemophilia B dogs with a factor IX null mutation by liver-directed gene therapy," Blood, vol. 99(8):2670-6.
Nakamura et al., 2001, "Activation of calcineurin and stress activated protein kinase/p38-mitogen activated protein kinase in hearts of utrophin-dystrophin knockout mice," Neuromuscul Disord., vol. 11(3):251-9.
Nudelman et al., 2006, "Redesign of aminoglycosides for treatment of human genetic diseases caused by premature stop mutations," Bioorganic & Medicinal Chemistry Letters, vol. 16(24):6310-6315.
Onda et al., 1999, "Tsc2(+/-) mice develop tumors in multiple sites that express gelsolin and are influenced by genetic background," J Clin Invest., vol. 104(6):687-95).
Pillers et al., 1999, "Normal cochlear function in mdx and mdx(Cv3) Duchenne muscular dystrophy mouse models," Laryngoscope, vol. 109(8):1310-2.
Reipert et al., 2000, "Characterization of antibodies induced by human factor VIII in a murine knockout model of hemophilia A," Thromb Haemost., vol. 84(5):826-32).
Snyder et al., 1999, "Correction of hemophilia B in canine and murine models using recombinant adeno-associated viral vectors," Nat Med., vol. (51):64-70.
Sokolenko et al., 1972, Vaprosy Khimii I Khimichesko Teklnolugii, No. 27:107-112 (with English language abstract).
Stotland et al., 2000, "Mouse models of chronic lung infection with *Pseudomonas aeruginosa*: models for the study of cystic fibrosis," Pediatr., Pulmonol., vol. 30(5):413-24.
Wang et al., 1997, "A factor IX-deficient mouse model for hemophilia B gene therapy," Proc Natl. Acad Sci USA, vol. 94(21):11563-6.
Yurigi et al., 1973, "Studies of the synthesis of N-heterocyclic compounds. IV. Hypocholesterolemic 1,2,4-oxadiazole derivatives," Chem Pharm. Bull., vol. 21(9):1885-1893.
Welch et al., 2007, "PTC124 Targets Genetic Disorders Caused by Nonsense Mutations," *Nature* 447:87-91.
Supplementary Information from Welch et al., 2007, "PTC124 Targets Genetic Disorders Caused by Nonsense Mutations," *Nature* 447:87-91 (pp. 1-23).
Hirawat et al., 2007, "Safety, Tolerability, and Pharmacokinetics of PTC124, a Nonaminoglycoside Nonsense Mutation Suppressor, Following Single- and Multiple-Dose Administration to Healthy Male and Female Adult Volunteers," *Journal of Clinical Pharmacology* 47(4):430-444.
Du et al., 2008, "PTC124 is an orally bioavailable compound that promotes suppression of the human CFTR-G542X nonsense allele in a CF mouse model." *PNAS* 105(6):2064-2069.
Kerem et al., 2008, "Effectiveness of PTC124 treatment of cystic fibrosis caused by nonsense mutations: a prospective phase II trial," *The Lancet* 372:719-27.
Auld et al., 2009, "Mechanism of PTC124 activity in cell based luciferase assays of nonsense codon suppression," *PNAS Early Edition*:1-6 (document sent via fax Jan. 28, 2009).
Auld et al., 2009, "Mechanism of PTC124 activity in cell based luciferase assays of nonsense codon suppression," *PNAS Early Edition*: 1-6 (document previously available from www.genome.gov website in Feb. 2008).
Auld et al., 2009, "Mechanism of PTC124 activity in cell based luciferase assays of nonsense codon suppression," *PNAS Early Edition*: 1-6.
Supplemental Information Methods from Auld et al., 2009, "Mechanism of PTC124 activity in cell based luciferase assays of nonsense codon suppression," *PNAS Early Edition*:1-6 (pp. 1-17).
Announcement by PTC Therapeutics, Inc. and Genzyme Corporation dated Mar. 3, 2010.
Auld et al., 2010, "Molecular basis for the high-affinity binding and stabilization of firefly luciferase by PTC124," *PNAS Early Edition*:1-6.

* cited by examiner

METHODS FOR THE PRODUCTION OF FUNCTIONAL PROTEIN FROM DNA HAVING A NONSENSE MUTATION AND THE TREATMENT OF DISORDERS ASSOCIATED THEREWITH

This application claims the benefit of U.S. provisional application Ser. No. 60/787,333, filed Mar. 30, 2006 and U.S. provisional application Ser. No. 60/813,085, filed Jun. 12, 2006, the disclosures of which are incorporated by reference herein in their entireties.

1. FIELD OF INVENTION

The present invention relates to functional proteins encoded by nucleic acid sequences comprising a nonsense mutation. The present invention also relates to methods for the production of functional proteins encoded by nucleic acid sequences comprising a nonsense mutation and the use of such proteins for prevention, management and/or treatment of diseases associated with a nonsense mutation(s) in a gene.

2. BACKGROUND OF THE INVENTION

Gene expression in cells depends upon the sequential processes of transcription and translation. Together, these processes produce a protein from the nucleotide sequence of its corresponding gene.

Transcription involves the synthesis of RNA from DNA by RNA polymerase. Transcription begins at a promoter region of the gene and continues until termination is induced, such as by the formation of a stem-loop structure in the nascent RNA or the binding of the rho gene product.

Protein is then produced from mRNA by the process of translation, occurring on the ribosome with the aid of tRNA, tRNA synthetases and various other protein and RNA species. Translation comprises the three phases of initiation, elongation and termination. Translation is initiated by the formation of an initiation complex consisting of protein factors, mRNA, tRNA, cofactors and the ribosomal subunits that recognize signals on the mRNA that direct the translation machinery to begin translation on the mRNA.

Once the initiation complex is formed, growth of the polypeptide chain occurs by the repetitive addition of amino acids by the peptidyl transferase activity of the ribosome as well as tRNA and tRNA synthetases. The presence of one of the three termination codons (UAA, UAG, UGA) in the A site of the ribosome signals the polypeptide chain release factors (RFs) to bind and recognize the termination signal. Subsequently, the ester bond between the 3' nucleotide of the tRNA located in the ribosome's P site and the nascent polypeptide chain is hydrolyzed. The completed polypeptide chain is released, and the ribosome subunits are recycled for another round of translation.

Mutations of the DNA sequence in which the number of bases is altered are categorized as insertion or deletion mutations (frameshift mutations) and can result in major disruptions of the genome. Mutations of the DNA that change one base into another are labeled missense mutations and are subdivided into the classes of transitions (one purine to another purine, or one pyrimidine to another pyrimidine) and transversions (a purine to a pyrimidine, or a pyrimidine to a purine).

Insertions, deletions, transition and transversion mutations can all result in a nonsense mutation, or chain termination mutation, in which the base mutation frameshift mutation or in-frame mutation changes an amino acid codon into one of the three stop codons. These premature stop codons can produce aberrant proteins in cells as a result of premature translation termination. A nonsense mutation in a gene can result in a number of diseases, such as, cancers, lysosomal storage disorders, muscular dystrophies, cystic fibrosis and hemophilia, to name a few.

In bacterial and eukaryotic strains with nonsense mutations, suppression of the nonsense mutation can arise as a result of a mutation in one of the tRNA molecules so that the mutant tRNA can recognize the nonsense codon, as a result of mutations in proteins that are involved in the translation process, as a result of mutations in the ribosome (either the ribosomal RNA or ribosomal proteins), or by the addition of compounds that alter the translation process. The result is that an amino acid is incorporated into the polypeptide chain at the site of the nonsense mutation, and translation does not prematurely terminate at the nonsense codon. The inserted amino acid will not necessarily be identical to the original amino acid of the wild-type protein; however, many amino acid substitutions do not have a gross effect on protein structure or function. Thus, a protein produced by the suppression of a nonsense mutation would be likely to possess activity similar to that of the wild-type protein. This scenario provides an opportunity to treat diseases associated with nonsense mutations by avoiding premature termination of translation through suppression of the nonsense mutation.

There remains a need in the art for methods for treating, managing and/or preventing a disease associated with a nonsense mutation(s) in a gene(s) in a human subject by administering a compound that suppresses premature translation termination in a human(s) by mediating the misreading of a nonsense codon and producing a non-wild-type protein(s) in vivo in an amount sufficient to treat, manage and/or prevent the disease.

3. SUMMARY OF THE INVENTION

The present invention is based, in part, upon the discovery of nonsense codon suppressor agents that can be systemically administered to a subject (including a human) to suppress a nonsense codon in RNA transcribed from a gene(s) comprising a nonsense mutation(s), allowing for readthrough of the nonsense codon and the insertion of an amino acid at the location of the nonsense codon. In certain embodiments, the amino acid inserted is an amino acid other than the amino acid which occurs at the corresponding location in the wild-type protein to produce a functional readthrough protein. The functional readthrough protein produced by the suppression of the nonsense codon in RNA transcribed from a gene(s) comprising a nonsense mutation is useful for treating, preventing and/or managing a disease associated with the nonsense mutation(s) in the gene(s).

The production of a functional readthrough protein in a subject (including a human) by the suppression of a nonsense codon in RNA transcribed from a gene(s) comprising a nonsense mutation using a nonsense codon suppressor agent has several advantages over other types of therapies contemplated for the prevention, treatment and/or management of a disease associated with a nonsense mutation in a gene(s). For example, the production of a functional readthrough protein using a nonsense codon suppressor agent does not involve the introduction of foreign genetic material into a subject as it does with gene therapy. Thus, the risk of inserting foreign genetic material into the wrong location in chromosomal DNA, the risk of overexpressing the protein encoded by the foreign genetic material introduced into the subject, and the risk of transmitting a vector, such as a virus, used to introduce the foreign genetic material into the subject to other subjects are eliminated.

The present invention provides methods of producing in a subject (preferably, a human) in need thereof an effective amount of a functional readthrough protein(s) encoded by a nucleic acid sequence comprising a nonsense mutation, the methods comprising administering to the subject an effective amount of a nonsense codon suppressor agent(s). In particular, the present invention provides methods for the treatment, management and/or prevention of a disease associated with a nonsense mutation in a gene(s), the methods comprising administering to a subject (preferably, a human) in need thereof an effective amount of a nonsense codon suppressor agent(s), wherein the effective amount of the agent(s) is the amount that is sufficient to produce an effective amount of a functional readthrough protein(s) encoded by the gene comprising the nonsense mutation. Non-limiting examples of diseases associated with a nonsense mutation in a gene(s) that can be treated, managed and/or prevented in accordance with the methods of the invention include: amyloidosis, LINCL, hemophilia, Alzheimer's disease, atherosclerosis, giantism, dwarfism, hypothyroidism, hyperthyroidism, cystic fibrosis, aging, obesity, Parkinson's disease, Niemann Pick's disease, familial hypercholesterolemia, retinitis pigmentosa, muscular dystrophy (e.g. Duchenne muscular dystrophy), spinal muscular atrophy and Marfan syndrome.

In one aspect, the present invention provides nonsense codon suppressor agents that can be orally administered to a subject (preferably, a human) to prevent, treat and/or manage a disease associated with a nonsense mutation in a gene. The nonsense codon suppressor agents administered orally have none or few (if any) adverse side effects at the dosage(s) that produces an effective amount of functional readthrough protein. In a specific embodiment, the nonsense codon suppressor agents do not result in renal failure and/or hearing loss when orally administered to a subject (preferably, a human) at the dosage(s) that produces an effective amount of functional readthrough protein. Thus, the nonsense codon suppressor agents can be systemically (e.g., orally) administered long-term without toxicities, such as renal failure and hearing loss.

The oral administration of a nonsense codon suppressor agent enables a subject to take his/her prescribed dosage of a nonsense codon suppressor agent without the need for a medical professional to administer the agent. This reduces the medical costs associated with preventing, treating and/or managing a disease associated with a nonsense mutation in a gene(s) because the cost of having a medical professional administer the agent has been eliminated. The oral administration of a nonsense codon suppressor agent also improves a subject's quality of life since the subject is not restricted and/or inconvenienced by appointments to see medical professionals to receive his/her dosage of nonsense codon suppressor agent. Further, the oral administration of a nonsense codon suppressor agent permits delivery of systemic therapy to all disease-affected organ sites.

In another aspect, the present invention provides nonsense codon suppressor agents that do not exhibit significant antibacterial activity against a gram-negative microorganism and/or a gram-positive microorganism. In contrast to nonsense codon suppressor agents with antibacterial activity, the use of nonsense codon suppressor agents that do not exhibit significant antibacterial activity against a gram-negative microorganism and/or a gram-positive microorganism do not contribute to the development of bacterial resistance to drugs with antibiotic activity. Further, the use of nonsense codon suppressor agents that do not exhibit significant antibacterial activity against a gram-negative microorganism and/or a gram-positive organism will be unlikely to induce complications related to pathological overgrowth of normal microbial flora as can happen with many chronically administered antibiotics.

Thus, the present invention provides functional readthrough proteins encoded by nucleic acid sequences comprising a nonsense mutation that are produced by methods that include administering a nonsense codon suppressor agent(s) that is well-tolerated in subjects and does not have significant antibacterial activity against a gram-negative microorganism and/or a gram-positive microorganism.

4. DESCRIPTION OF THE FIGURES

FIG. 1. Schematic of mRNA derived from luciferase reporter constructs.

FIGS. 2A-2E. mRNA derived from Luciferase-CD40 reporter in mRNA constructs.

Figure 3:
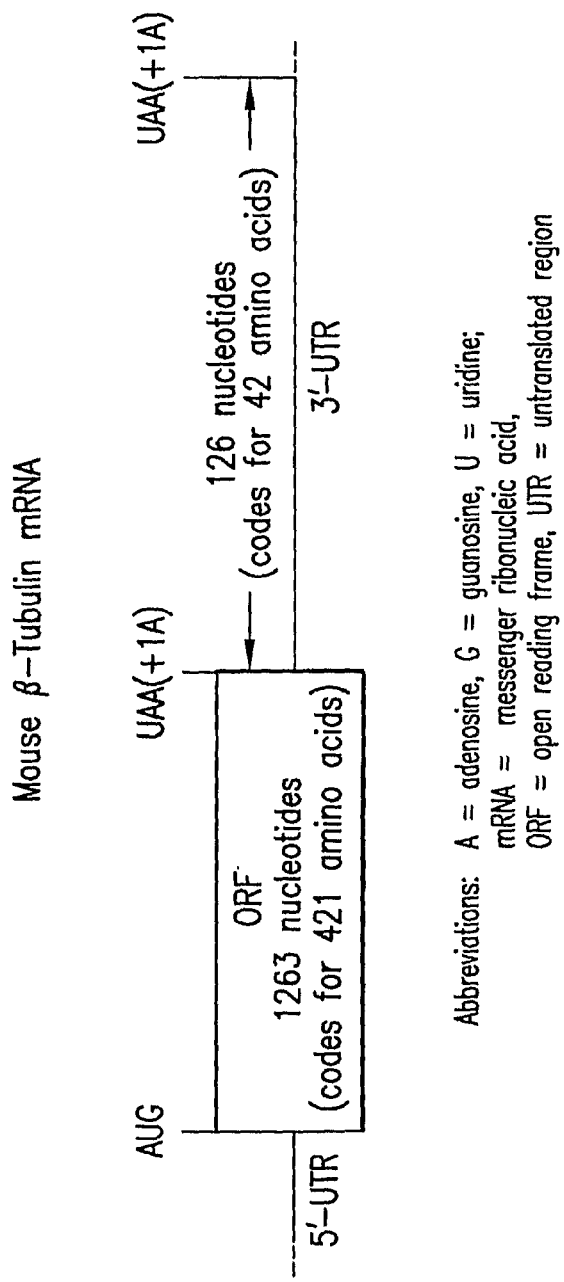

FIG. 3. Schematic of mouse β-tubulin mRNA.

5. DETAILED DESCRIPTION OF THE INVENTION

The present invention is based, in part, upon the discovery of nonsense codon suppressor agents that can be systemically administered to a subject (including humans) to suppress a nonsense mutation in RNA transcribed from a gene(s) comprising a nonsense mutation(s), allowing for readthrough of the nonsense mutation and the insertion of an amino acid at the location of the nonsense codon. In certain embodiments, the amino acid inserted is an amino acid other than the amino acid residue which occurs at the corresponding location in the wild-type protein to produce a functional non-wild-type protein. The functional readthrough protein produced by the suppression of the nonsense codon in RNA transcribed from the gene(s) comprising a nonsense mutation is useful for treating, preventing and/or managing a disease associated with the nonsense mutation(s) in the gene(s).

The present invention provides methods of producing in a subject (preferably, a human) in need thereof an effective amount of a functional readthrough protein(s) encoded by nucleic acid sequence comprising a nonsense mutation, the methods comprising administering to the subject an effective amount of a nonsense codon suppressor agent(s). In accordance with the invention, the functional readthrough protein(s) has one or more functions of the full-length wild-type protein(s). In specific embodiments, the functional readthrough protein(s) produced by the methods of the invention is a functional non-wild-type protein(s). In another embodiment, the functional non-wild-type protein is full-length. In other embodiments, the functional non-wild-type protein(s) is not full-length. The production of a functional readthrough protein(s) may be assessed by an in vitro assay and/or in an animal model. For example, a reporter assay may be used to determine whether a functional readthrough protein(s) is produced. Alternatively, an animal model, such as an mdx mouse, may be used to determine whether a functional readthrough protein(s) is produced.

In certain embodiments, the effective amount of a nonsense codon suppressor agent administered to the subject in accordance with the invention is equivalent to the amount that suppresses a nonsense codon in a reporter gene assay comprising the steps of: (a) contacting the agent with a cell having a nucleic acid sequence comprising a reporter gene, wherein the reporter gene comprises a premature stop codon; and (b) detecting the expression and/or activity of a functional readthrough protein encoded by the reporter gene. In other embodiments, the effective amount of a nonsense codon suppressor agent is equivalent to the amount that suppresses a nonsense codon in a reporter gene assay comprising the steps of: (a) contacting the agent with a cell lysate and a nucleic acid sequence comprising a reporter gene, wherein the reporter gene comprises a premature stop codon; and (b) detecting the expression and/or activity of a functional readthrough protein encoded by the reporter gene. See Section 5.4 for more details regarding these assays.

In one aspect, the present invention provides methods for producing in a subject (preferably, a human) in need thereof an effective amount of a functional readthrough protein(s) encoded by a nucleic acid sequence(s) comprising a nonsense mutation, the methods comprising orally administering to the subject an effective amount of a nonsense codon suppressor agent(s). In certain embodiments, the effective amount of the nonsense codon suppressor agent(s) orally administered is between 0.1 mg/kg and 500 mg/kg per day. In some embodiments, the effective amount of the nonsense codon suppressor agent(s) orally administered is between 0.1 mg/kg and 500 mg/kg administered as a single dose, two doses, three doses, four doses or more. In a specific embodiment, the effective amount of the nonsense codon suppressor agent(s) orally administered is between 0.1 mg/kg and 500 mg/kg per day, divided into three doses with the first and second doses each being 25% of the total amount administered and the third dose being 50% of the total amount administered. In other embodiments, the effective amount of a nonsense codon suppressor agent(s) orally administered to the human is less than 35 mg/kg per day. In specific embodiments, the effective amount of the nonsense codon suppressor agent(s) orally administered to the human is between 0.1/mg/kg and 30 mg/kg per day.

In another aspect, the present invention provides methods for producing in a subject (preferably, a human) in need thereof an effective amount of a functional readthrough protein(s) encoded by a nucleic acid sequence(s) comprising a nonsense mutation, the methods comprising administering to the subject an effective amount of a nonsense codon suppressor agent(s), wherein the effective amount of the agent(s) is sufficient to produce a plasma concentration of 0.5 µg/ml to 500 µg/ml of the agent(s) for 2 hours, 2.5 hours, 3 hours or more. In certain embodiments, the effective amount of the agent(s) is between 0.1 mg/kg and 500 mg/kg per day. In a specific embodiment, the effective amount of the agent(s) is between 0.1 mg/kg and 500 mg/kg per day, divided into three doses with the first and second doses each being of 25% of the total amount administered and the third dose being 50% of the total amount administered. In certain embodiments, the nonsense codon suppressor agent(s) is orally administered to the subject.

In another aspect, the present invention provides methods for producing in a subject (preferably, a human) in need thereof an effective amount of a functional readthrough protein(s) encoded by a nucleic acid sequence(s) comprising a nonsense mutation, the methods comprising administering to the subject an effective amount of a nonsense codon suppressor agent(s), wherein the nonsense codon suppressor agent(s) does not exhibit significant antibacterial activity against a gram-negative microorganism and/or a gram-positive microorganism. In some embodiments, the nonsense codon suppressor agent(s) is administered orally. In certain embodiments, the effective amount of the nonsense codon suppressor agent(s) is between 0.1 mg/kg and 500 mg/kg per day. In specific embodiments, the effective amount of the nonsense codon suppressor agent(s) is between 0.1 mg/kg and 500 mg/kg per day, divided into three doses with the first and second doses each being 25% of the total amount administered and the third dose being 50% of the total amount administered. In certain other embodiments, the effective amount of the agent(s) is sufficient to produce a plasma concentration of 0.1 µg/ml to 500 µg/ml of the agent(s) for 2 hours, 2.5 hours, 3 hours or more.

The production of a functional readthrough protein(s) encoded by a nucleic acid sequence comprising a nonsense mutation by the administration of a nonsense codon suppressor agent(s) to a subject is useful for treatment, management and/or prevention of a disease associated with a nonsense mutation in a gene(s). Non-limiting examples of diseases that can be treated, managed and/or prevented by the production of a functional readthrough protein(s) encoded by a gene(s) comprising a nonsense mutation(s) include: amyloidosis, LINCL, hemophilia, Alzheimer's disease, atherosclerosis, giantism, dwarfism, hypothyroidism, hyperthyroidism, cystic fibrosis, aging, obesity, Parkinson's disease, Niemann Pick's disease, familial hypercholesterolemia, retinitis pigmentosa, muscular dystrophy (e.g., Duchenne muscular dystrophy), spinal muscular atrophy and Marfan syndrome.

In certain embodiments, the disease treated, managed and/or prevented by the production of functional readthrough protein encoded by a gene(s) comprising a nonsense mutation(s) is not a gastrointestinal disorder. In other embodiments, the disease treated, managed and/or prevented by the production of functional readthrough protein encoded by a gene(s) comprising a nonsense mutation(s) is not a cutaneous disorder. In some embodiments, the disease treated, managed and/or prevented by the production of functional readthrough protein encoded by a gene(s) comprising a nonsense mutation(s) is not one or more, or all of the following diseases: basal cell nevus syndrome (e.g., PTCH gene), sporadic basal cell carcinoma (e.g., PTCH gene), melanoma (e.g., CDKN2a gene), junctional epidermolysis bullosa (e.g., LAMB3, LAMC2, LAMA3 genes), generalized atrophic benign epidermolysis bullosa (e.g., COL17A1 gene), dystrophic epidermolysis bullosa (e.g., COL7A1 gene), Hailey-Hailey disease (e.g., ATP2C1 gene), Darier's disease (e.g., ATP2A2 gene), lamellar icthyosis (e.g., TGM1 gene), X-linked icthyosis (e.g., STS gene), xeroderma pigmentosa (e.g., XPA, XPC, XPG genes), Bloom syndrome (e.g., BLM gene), striate palmo-plantar keratoderma (e.g., DSP, DSG1 genes), Cockayne syndrome (e.g., ERCC6 gene), oculocutaneous albinism (e.g., TYR, TYRP1 genes), Hermansky-Pudlack syndrome (e.g., HPS1, HPS4 genes), ataxia-telangiectasia (e.g., ATM gene), Griscelli syndrome (e.g., RAB27A, MYO5A genes), and ectodermal dysplasia/skin fragility (e.g., PKP1 gene). In some embodiments, the disease treated, managed and/or prevented by the production of functional readthrough protein encoded by a gene(s) comprising a nonsense mutation(s) is not one or more, or all of the following diseases: sporadic cancers of the esophagus (p53 gene) and colon (APC, p53 genes), Barrett's esophagus (p53 gene), hereditary cancer syndromes such as adenomatous polyposis coli (APC gene), hereditary nonpolyposis colon cancer (MLH1, MSH2 genes), Peutz-Jeghers syndrome (STK 11 gene), and Cowden's syndrome (PTEN gene).

The present invention provides methods for the treatment, management and/or prevention of a disease associated with a nonsense mutation in a gene(s), the methods comprising administering to a subject (preferably, a human) in need thereof an effective amount of a nonsense codon suppressor agent(s), wherein the effective amount of the agent(s) is the amount that is sufficient to produce an effective amount of a functional readthrough protein(s) encoded by the gene comprising the nonsense mutation. In certain embodiments, the effective amount of the functional readthrough protein(s) is the amount of protein(s) necessary to prevent the onset, development and/or progression of the disease or a symptom thereof. In other embodiments, the effective amount of the functional readthrough protein(s) is the amount of protein(s) necessary to reduce the duration and/or severity of the disease or a symptom thereof. In certain embodiments, the effective amount of the functional readthrough protein is equivalent to the amount produced in an animal model for the disease of interest. In other embodiments, the effective amount of the functional readthrough protein(s) is the amount that is produced in an animal model for the disease that has a therapeutic and/or prophylactic benefit.

In certain embodiments, the effective amount of the functional readthrough protein is equivalent to the amount produced in a reporter gene assay comprising the steps of: (a) contacting the nonsense codon suppressor agent with a cell having a nucleic acid sequence comprising a reporter gene, wherein the reporter gene comprises a premature stop codon; and (b) determining the amount of functional readthrough protein encoded by the reporter gene that is produced. In other embodiments, the effective amount of the functional readthrough protein is equivalent to the amount produced in a reporter gene assay comprising the steps of: (a) contacting the nonsense codon suppressor agent with a cell lysate and a nucleic acid sequence comprising the reporter gene, wherein the reporter gene comprises a premature stop codon, and (b) determining the amount of functional readthrough protein encoded by the reporter gene that is produced. The amount of functional readthrough protein can be determined by measuring the expression level of the functional readthrough protein using, e.g., an immunoassay, or by measuring the activity of the functional readthrough protein.

In certain embodiments, the effective amount of the functional readthrough protein is the amount produced by a cell comprising the gene(s) associated with the disease (i.e., the gene(s) comprises the nonsense mutation(s) associated with the disease). In some embodiments, the amount produced by the cell is about 0.1%, about 1%, about 2%, about 5%, about 7% or about 10% (in other embodiments, about 15%, about 20%, about 25%, about 30%, about 35%, about 40%, about 45%, about 50%, about 75%, or about 90%, and in other embodiments, 0.1-25%, 0.1-50%, 10-50%, 10-90%, 0.1-98%, 5-98%, or 10-98%) of the amount produced by a cell of the same species and type that comprises the normal gene(s) (i.e., the gene that does not comprise the nonsense mutation) encoding the corresponding wild-type protein(s). The amount of the functional readthrough protein(s) and the amount of wild-type protein(s) can be measured using any assay known to one of skill in the art so long as the methodology that is used to measure both proteins is consistent. In certain embodiments, the amount of the functional readthrough protein(s) and the amount of wild-type protein(s) are measured by an immunoassay (e.g., an ELISA). In a specific embodiment, the cell is engineered to comprise the gene(s). In an alternative embodiment, the cell naturally comprises the gene(s).

In certain embodiments, the effective amount of the functional readthrough protein(s) is the amount produced by a cell from a patient with the disease associated with the gene(s) comprising the nonsense mutation(s). In some embodiments, the amount produced by the patient cell is about 1%, about 2%, about 5%, about 7% or about 10% (in other embodiments, about 15%, about 20%, about 25%, about 30%, about 35%, about 40%, about 45%, about 50%, about 75%, about 90%, and in other embodiments, 0.1-25%, 0.1-50%, 0.1-90%, 10-90%, 5-25%, 5-90%, 10-98%, 0.1-98% or 5-98%) of the amount produced by a cell of the same species and type from a subject that does not have the disease, which cell comprises the gene(s) encoding the corresponding wild-type protein(s). The amount of the functional readthrough protein(s) and the amount of wild-type protein(s) can be measured using any assay known to one of skill in the art so long as the methodology that is used to measure both proteins is consistent. In certain embodiments, the amount of functional readthrough protein(s) and the amount of wild-type protein(s) are measured by an immunoassay (e.g., an ELISA). In a specific embodiment, the patient cell is from the patient that is or will be receiving doses of a nonsense codon suppressor agent(s).

The invention provides methods for the treatment, management and/or prevention of a disease associated with a nonsense mutation(s) in a gene(s), the methods comprising orally administering to a subject (preferably, a human) in need thereof an effective amount of a nonsense codon suppressor agent(s), wherein the effective amount of the agent(s) is sufficient to produce an effective amount of a functional readthrough protein(s) encoded by the gene(s) comprising the nonsense mutation(s). In certain embodiments, the effective amount of the agent(s) is between 0.1 mg/kg and 500 mg/kg per day. In a specific embodiment, the effective amount of a nonsense codon suppressor agent(s) is between 0.1 mg/kg and 500 mg/kg per day, divided into three doses with the first and second doses each being 25% of the total amount administered and the third dose being 50% of the total amount administered. In other embodiments, the effective amount of the agent(s) is the amount of the agent(s) that results in a plasma concentration of 0.1 µg/ml, 2 µg/ml or more (in some embodiments, 5 µg/ml, 10 µg/ml, 15 µg/ml, 20 µg/ml, 25 µg/ml, 30 µg/ml, 35 µg/ml, 40 µg/ml, 45 µg/ml, 50 µg/ml, 75 µg/ml, 100 µg/ml, 125 µg/ml, 150 µg/ml, 175 µg/ml, 200 µg/ml, 225 µg/ml, 250 µg/ml, 275 µg/ml, 300 µg/ml, 325 µg/ml, 375 µg/ml, 400 µg/ml, 425 µg/ml, 450 µg/ml, 475 µg/ml or 500 µg/ml) of the agent for at least 2 hours, at least 2.5 hours, at least 3 hours or more. In certain embodiments, the nonsense codon suppressor agent(s) does not exhibit significant antibacterial activity against a gram-negative microorganism and/or a gram-positive microorganism.

The invention provides methods for the treatment, management and/or prevention of a disease associated with a nonsense mutation in a gene(s), the methods comprising administering to a subject (preferably, a human) in need thereof an effective amount of a nonsense codon suppressor agent(s), wherein the effective amount of the agent(s) is sufficient to produce a plasma concentration of 0.1 µg/ml to 500 µg/ml of the agent(s) for 2 hours, 2.5 hours, 3 hours or more. In certain embodiments, the effective amount of the agent(s) is between 0.1 mg/kg to 500 mg/kg per day. In a specific embodiment, the effective amount of the agent(s) is between 0.1 mg/kg and 500 mg/kg per day, divided into three doses with the first and second doses each being 25% of the total amount administered and the third does being 50% of the total amount administered. In certain other embodiments, the agent(s) does not have significant antibacterial against a gram-negative microorganism and/or a gram-positive microorganism.

The invention provides methods for the treatment, management and/or prevention of a disease associated with a nonsense codon in a gene(s), the methods comprising administering to a subject (preferably, a human) in need thereof an effective amount of a nonsense codon suppressor agent that does not exhibit significant antibacterial activity against a gram-negative microorganism and/or a gram-positive microorganism. In certain embodiments, the effective amount of the agent(s) is between 0.1 mg/kg to 500 mg/kg per day. In a specific embodiment, the effective amount of the agent(s) is between 0.1 mg/kg and 500 mg/kg per day, divided into three doses with the first and second doses each being 25% of the total amount administered and the third dose being 50% of the total amount administered.

The production of a functional readthrough protein(s) encoded by a nucleic acid sequence comprising a nonsense mutation is useful: (i) in subjects that do not express a sufficient amount of the corresponding wild-type protein(s), and/or (ii) in subjects that could benefit from the expression of a particular functional readthrough protein(s). In one aspect, the invention provides methods for producing in a subject (preferably, a human) in need thereof a functional readthrough protein(s) encoded a nucleic acid sequence comprising a nonsense mutation(s), the methods comprising administering to the subject an effective amount of a nonsense codon suppressor agent(s), wherein the subject has been engineered to comprise the nucleic acid sequence. In a specific embodiment, the functional readthrough protein(s) corresponds to a wild-type protein that has a beneficial effect in a subject. In certain embodiments, the subject administered the agent(s) does not produce a sufficient amount of the wild-type protein(s) that corresponds to the functional readthrough protein(s). In a specific embodiment, the subject administered the agent(s) has a disease associated with insufficient production of the wild-type protein(s) that corresponds to the functional readthrough protein. In certain embodiments of the invention, the subject that is going to receive a nonsense codon suppressor agent(s) is screened before receiving the agent(s). In a specific embodiment, the subject is screened to determine if the agent(s) will produce a functional readthrough protein(s). In another embodiment, the subject is screened to determine the effective amount of the agent(s) to administer to the subject. Section 5.6 below provides methods for screening subjects.

The invention encompasses the use of a nonsense codon suppressor agent to produce a functional readthrough protein from a nucleic acid sequence comprising a mutation that results in a different stop codon in the RNA transcribed from the nucleic acid sequence relative to the stop codon found in the RNA coding for the corresponding wild-type protein. In particular, the invention provides a method of preventing, managing and/or treating a disease associated with a gene comprising a mutation that results in a different stop codon in the RNA transcribed from the gene relative to the stop codon found in the RNA coding for the corresponding wild-type protein, the method comprising administering to a subject (preferably, a human) in need thereof an effective amount of a nonsense codon suppressor agent. In certain embodiments, the effective amount of the nonsense codon suppressor agent is the amount that is sufficient to produce an effective amount of a functional readthrough protein encoded by the gene. In some embodiments, the effective amount of the nonsense codon suppressor agent is between 0.1 mg/kg to 500 mg/kg per day. In some other embodiments, the effective amount of the nonsense codon suppressor agent is the amount of agent that results in a plasma concentration of between 0.1 µg/ml to 500 µg/ml.

In certain embodiments, the nonsense codon suppressor agent used in accordance with the invention is not an aminoglycoside. Non-limiting examples of aminoglycosides include gentamicin, streptomycin, amikacin, kanamycin, tobramycin, netilmicin, neomycin, framycetin, negamycen, paromycen, sisomicin, G-418 and derivatives and analogs thereof. In specific embodiments, the nonsense codon suppressor agent used in accordance with the invention is not one, two, three or more of the following: gentamicin, streptomycin, amikacin, kanamycin, tobramycin, netilmicin, neomycin framycetin, negamycen, paromycen, sisomicin, G418 and/or a derivative or analog thereof. In other embodiments, the nonsense codon suppressor agent is used in accordance with the invention is not chloramphenicol and derivatives or analogs thereof that retain activity in promoting readthrough of a premature termination codon. In other embodiments, the nonsense codon suppressor agent used in accordance with the invention is not an oxazolidinone. Non-limiting examples of oxazolidinones are linezolid, eperzolid and analogs or derivatives thereof. In certain embodiments, a nonsense codon suppressor agent used in accordance with the invention produces a greater amount (in some embodiments, 5%, 10%, 15%, 20%, 25%, 30%, 35%, 40%, 45%, 50%, 55%, 60%, 65%, 70%, 75%, 80% or more and in other embodiments, 5-95%, 10%-95%, 25%-95%, or 10%-65% more) of functional readthrough protein than an equivalent dose of an aminoglycoside, an oxazolidinone, and/or chloramphenicol in a cell based assay, animal model assay or other assay described herein or known in the art for nonsense codon suppression.

In certain embodiments, the nonsense codon suppressor agent used in accordance with the invention is not a compound of formula I, formula II, formula III or formula IV. In specific embodiments, the nonsense codon suppressor used in accordance with the invention is not a compound of Table 1, Table 2, Table 3 or Table 4. In other embodiments, the nonsense codon suppressor is not a compound of formula V, formula VI, formula VII, formula VIII or formula IX. In specific embodiments, the nonsense codon suppressor used in accordance with the invention is not a compound of Table 5, Table 6, Table 7, Table 8 of Table 9.

In certain embodiments, the nonsense codon suppressor agent used in accordance with the invention does not exhibit significant antibacterial activity against a gram-negative microorganism and/or a gram-positive microorganism. In a specific embodiment, the nonsense codon suppressor agent used in accordance with the invention is a compound described in Section 5.2. In certain embodiments, the nonsense codon suppressor agent used in accordance with the invention is a compound of formula I, formula II, formula III or formula IV. In specific embodiments, the nonsense codon suppressor agent used in accordance with the invention is a compound of Table 1, Table 2, Table 3 or Table 4. In other embodiments, the nonsense codon suppressor agent used in accordance with the invention is a compound of formula V, formula VI, formula VII, formula VIII or formula XI. In specific embodiments, the nonsense codon suppressor agent used in accordance with the invention is a compound of Table 5, Table 6, Table 7, Table 8 or Table 9.

In certain embodiments, the nonsense codon suppressor agent used in accordance with the invention interacts with 28S rRNA. In a specific embodiment, the nonsense codon suppressor agent used in accordance with the invention binds to specific regions of 28S rRNA. In other embodiments, the nonsense codon suppressor agent used in accordance with the invention does not interact with 18S rRNA.

The present invention provides a functional readthrough protein(s) encoded by a nucleic acid sequence comprising nonsense mutation, which protein(s) is produced by the methods described herein. In certain embodiments, the functional readthrough protein is found localized in the cell at the same location as the corresponding wild-type protein. In some embodiments, the functional readthrough protein is a functional non-wild-type protein. In specific embodiments, the functional non-wild-type protein(s) only differs from the corresponding wild-type protein(s) at the amino acid residue in the non-wild-type protein(s) that was inserted at the position encoded by the premature termination codon. In other embodiments, the functional non-wild-type protein(s) differs from the corresponding wild-type protein(s): (i) at the amino acid residue in the non-wild-type protein(s) that was inserted at the position encoded by the premature termination codon; and (ii) at an amino acid residue(s) in the non-wild-type protein(s) other than those encoded by a premature termination codon. In other embodiments, the non-wild-type protein is full-length (i.e., the same length as the corresponding wild-type protein). The amino acid sequence of the functional readthrough protein(s) produced by the methods of the invention may be determined by sequencing the protein(s) produced by a cell comprising a nucleic acid sequence of interest (i.e., the nucleic acid sequence comprising the nonsense mutation(s) of interest). In certain embodiments, the cell naturally comprises the nucleic acid sequence. In a specific embodiment, the cell is a cell from a patient that is receiving or will be receiving a nonsense codon suppressor agent(s). In other embodiments, the cell has been engineered to comprise the nucleic acid sequence.

Accordingly, disclosed herein are: illustrative, structurally diverse nonsense codon suppressor agents; references setting forth methods for making the agents; methods for assaying the agents for nonsense codon suppressing activity; routes of administration and dosage formulations for administering nonsense codon suppressor agents, including preferred dosing regimens and pharmacokinetic profiles; diseases associated with nonsense mutations, including disclosure regarding the nexus between nonsense mutations and the diseases recited herein; patient populations suitable for the disclosed methods of treatment, management and prevention, including methods of patient screening; and therapeutic endpoints useful for determining efficacy of nonsense codon suppressor agents.

5.1 Definitions

As used herein, the term "premature translation termination" refers to the result of a mutation that changes a codon corresponding to an amino acid to a stop codon.

As used herein, the term "nonsense-mediated mRNA decay" refers to any mechanism that mediates the decay of mRNAs containing a premature translation termination codon.

As used herein, the terms "premature termination codon," "premature stop codon" and "nonsense codon" refer to the occurrence of a stop codon where a codon corresponding to an amino acid should be.

As used herein, the term "nonsense mutation" refers to a mutation that changes a codon that codes for an amino acid to a stop codon.

As used herein, the terms "nonsense codon suppression" and "nonsense codon suppressing" refer to the inhibition or suppression of premature translation and/or nonsense-mediated mRNA decay. In one embodiment, the inhibition or suppression of premature translation and/or nonsense-mediated mRNA decay is in vivo. In another embodiment, the inhibition or suppression of premature translation and/or nonsense-mediated mRNA decay is in vitro.

As used herein, the phrase "modulation of premature translation termination and/or nonsense-mediated mRNA decay" refers to the regulation of gene expression by altering the level of nonsense codon suppression. For example, if it is desirable to increase production of a functional readthrough protein encoded by a gene with a premature stop codon, i.e., to permit readthrough of the premature stop codon of the disease gene so translation of the RNA can occur, then modulation of premature translation termination and/or nonsense-mediated mRNA decay entails up-regulation of nonsense codon suppression. Conversely, if it is desirable to promote the degradation of an mRNA with a premature stop codon, then modulation of premature translation termination and/or nonsense-mediated mRNA decay entails down-regulation of nonsense codon suppression.

As used herein, the terms "subject" and "patient" are used herein interchangeably to refer to an animal (e.g., cow, horse, sheep, pig, chicken, turkey, quail, cat, dog, mouse, rat, rabbit, guinea pig, etc.), preferably a mammal such as a non-primate and a primate (e.g., monkey and human), most preferably a human. In certain embodiments, the patient is an embryo, fetus, infant, child, adolescent or adult. In one embodiment, it has been determined through pre-screening that the patient possesses a nonsense mutation. In another embodiment, it has been determined through pre-screening which nonsense mutation the patient has (i.e., UAA, UGA, or UAG). In another embodiment, the patient is infected with bacterial cells (e.g., *Pseudomonas aeruginosa*). In another embodiment, the cells of the patient are virally infected.

As used herein, the phrase "does not exhibit significant antibacterial activity against a gram-negative microorganism and/or a gram-positive microorganism" refers to a nonsense codon suppressor agent(s) that has a minimum inhibitory concentration (MIC) of 250 µg/ml or more (in certain embodiments, 300 µg/ml, 350 µg/ml, 400 µg/ml, 450 µg/ml or 500 µg/ml, and in other embodiments, about 250 µg/ml to about 1000 µg/ml or 250 µg/ml to about 500 µg/ml) when added to a culture medium of a gram-negative microorganism and/or a culture medium of a gram-positive microorganism. In a specific embodiment, the phrase refers to a nonsense codon suppressor agent(s) that has a MIC of 250 µg/ml or more (in certain embodiments, 300 µg/ml, 350 µg/ml, 400 µg/ml, 450 µg/ml or 500 µg/ml, and in other embodiments, about 250 µg/ml to about 1000 µg/ml or 250 µg/ml to about 500 µg/ml) when added to a culture medium of *E. coli* BAS 849 (permeable), a culture medium of *P. aeruginosa* 27853, a culture medium of *S. aureus* 29213, a culture medium of *S. epidermidis* 12228 (CNSA), a culture medium of *Enterococcus faecium* 49624, and/or a culture medium of *Enterococcus faecalis* 29212.

As used herein, unless otherwise specified, the term "milk" includes standardized, whole, reduced fat (2%), low fat (1%), skimmed, non-fat and lactose-free milk. The term "milk" also includes that from a human or a domesticated animal (e.g., cow, buffalo, goat, sheep or camel) as well as soy milk and any milk-based or containing product.

As used herein, unless otherwise specified, the term "substituted" means a group substituted by one to four or more substituents, such as, halo, trifluoromethyl, trifluoromethoxy, hydroxy, alkoxy, cycloalkyoxy, heterocylooxy, oxo, alkanoyl, alkylcarbonyl, cycloalkyl, aryl, aryloxy, aralkyl, alkanoyloxy, cyano, azido, amino, alkylamino, arylamino, aralkylamino, cycloalkylamino, heterocycloamino, mono and disubstituted amino in which the two substituents on the amino group are selected from alkyl, aryl, aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g., $SO_2NH_2$), substituted sulfonamido, nitro, carboxy, carbamyl (e.g. $CONH_2$), substituted carbamyl (e.g., CONH alkyl, CONH aryl, CONH aralkyl or instances where there are two substituents on the nitrogen selected from alkyl, aryl or aralkyl), alkoxycarbonyl, aryl, substituted aryl, guanidino and heterocyclo, such as, indolyl, imidazolyl, furyl, thienyl, thiazolyl, pyrrolidyl, pyridyl, pyrimidyl and the like. Wherein, as noted above, the substituents themselves are further substituted, such further substituents are selected from the group consisting of halogen, alkyl, alkoxy, aryl and aralkyl. In a particular embodiment, the term substituted does not mean cyano.

As used herein, unless otherwise specified, the term "alkyl" means a saturated straight chain or branched non-cyclic hydrocarbon having from 1 to 20 carbon atoms, preferably 1-10 carbon atoms and most preferably 1-4 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl group can be unsubstituted or substituted. Unsaturated alkyl groups include alkenyl groups and alkynyl groups, which are discussed below.

As used herein, unless otherwise specified the term "alkenyl group" means a straight chain or branched non-cyclic hydrocarbon having from 2 to 20 carbon atoms, more preferably 2-10 carbon atoms, most preferably 2-6 carbon atoms, and including at least one carbon-carbon double bond. Representative straight chain and branched ($C_2$-$C_{10}$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like. The double bond of an alkenyl group can be unconjugated or conjugated to another unsaturated group. An alkenyl group can be unsubstituted or substituted.

As used herein, unless otherwise specified the term "alkynyl group" means a straight chain or branched non-cyclic hydrocarbon having from 2 to 20 carbon atoms, more preferably 2-10 carbon atoms, most preferably 2-6 carbon atoms, and including at lease one carbon-carbon triple bond. Representative straight chain and branched —($C_2$-$C_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. The triple bond of an alkynyl group can be unconjugated or conjugated to another unsaturated group. An alkynyl group can be unsubstituted or substituted.

As used herein, unless otherwise specified the term "halogen" or "halo" means fluorine, chlorine, bromine, or iodine.

As used herein, unless otherwise specified the term "haloalkyl" means an alkyl group as described herein substituted with one or more halogen atoms.

As used herein, unless otherwise specified the term "haloalkoxy" means an alkoxy group as described herein substituted with one or more halogen atoms.

As used herein, unless otherwise specified the term "alkyl sulfonyl" means -Alkyl-$SO_3H$ or —$SO_3$-alkyl, wherein alkyl is defined as above, including —$SO_2$—$CH_3$, —$SO_2$—$CH_2CH_3$, —$SO_2$—$(CH_2)_2CH_3$, —$SO_2$—$(CH_2)_3CH_3$, —$SO_2$—$(CH_2)_4CH_3$, —$SO_2$—$(CH_2)_5CH_3$, and the like.

As used herein, unless otherwise specified the term "carboxyl" and "carboxy" mean —COOH.

As used herein, unless otherwise specified the term "alkoxy" means —O-(alkyl), wherein alkyl is defined above, including —$OCH_3$, —$OCH_2CH_3$, —$O(CH_2)_2CH_3$, —$O(CH_2)_3CH_3$, —$O(CH_2)_4CH_3$, —$O(CH_2)_5CH_3$, and the like.

As used herein, unless otherwise specified the term "alkoxycarbonyl" means —C(=O)O-(alkyl), wherein alkyl is defined above, including —C(=O)O—$CH_3$, —C(=O)O—$CH_2CH_3$, —C(=O)O—$(CH_2)_2CH_3$, —C(=OC)O—$(CH_2)_3CH_3$, —C(=O)O—$(CH_2)_4CH_3$, —C(=O)O—$(CH_2)_5CH_3$, and the like. In a preferred embodiment, the esters are biohydrolyzable (i.e., the ester is hydrolyzed to a carboxylic acid in vitro or in vivo).

As used herein, unless otherwise specified the term "alkoxyalkyl" means -(alkylene)-O-(alkyl), wherein each "alkyl" is independently an alkyl group as defined above, including —$CH_2OCH_3$, —$CH_2OCH_2CH_3$, —$(CH_2)_2OCH_2CH_3$, —$(CH_2)_2$—O—$(CH_2)_2CH_3$, and the like.

As used herein, unless otherwise specified the term "aryl" means a carbocyclic aromatic ring containing from 5 to 14 ring atoms. The ring atoms of a carbocyclic aryl group are all carbon atoms. Aryl ring structures include compounds having one or more ring structures such as mono-, bi-, or tricyclic compounds as well as benzo-fused carbocyclic moieties such as 5,6,7,8-tetrahydronaphthyl and the like. Preferably, the aryl group is a monocyclic ring or bicyclic ring. Representative aryl groups include phenyl, tolyl, anthracenyl, fluorenyl, indenyl, azulenyl, phenanthrenyl and naphthyl. A carbocyclic aryl group can be unsubstituted or substituted.

As used herein, unless otherwise specified the term "heteroaryl" means a carbocyclic aromatic ring containing from 5 to 14 ring atoms and the ring atoms contain at least one heteroatom, preferably 1 to 3 heteroatoms, independently selected from nitrogen, oxygen, or sulfur. Heteroaryl ring structures include compounds having one or more ring structures such as mono-, bi-, or tricyclic compounds as well as fused heterocycle moieties. Representative heteroaryls are triazolyl, tetrazolyl, oxadiazolyl, pyridyl, furyl, benzofuranyl, thiophenyl, benzothiophenyl, benzoisoxazolyl, benzoisothiazolyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, benzoquinazolinyl, acridinyl, pyrimidyl and oxazolyl. A group can be unsubstituted or substituted.

As used herein, unless otherwise specified the term "aryloxy" means —O-aryl group, wherein aryl is as defined above. An aryloxy group can be unsubstituted or substituted.

As used herein, unless otherwise specified the term "aralkyl" means -(alkyl)-(aryl), wherein alkyl and aryl are defined above, including, but not limited to —($CH_2$)phenyl, —$(CH_2)_2$phenyl, —$(CH_2)_3$phenyl, —CH(phenyl)$_2$, —CH(phenyl)$_3$, —($CH_2$)tolyl, —($CH_2$)anthracenyl, —($CH_2$)fluorenyl, —($CH_2$)indenyl, —($CH_2$)azulenyl, —($CH_2$)naphthyl, and the like.

As used herein, unless otherwise specified the term "heteroarylalkyl" means -(alkyl)-(heteroaryl), wherein alkyl and heteroaryl are defined above, including, but not limited to —(CH$_2$)pyridyl, —(CH$_2$)$_2$pyridyl, —(CH$_2$)$_3$pyridyl, —CH(pyridyl)$_2$, —C(pyridyl)$_3$, —(CH$_2$)triazolyl, —(CH$_2$)tetrazolyl, —(CH$_2$)oxadiazolyl, —(CH$_2$)furyl, —(CH$_2$)benzofuranyl, —(CH$_2$)thiophenyl, —(CH$_2$)benzothiophenyl, and the like.

As used herein, unless otherwise specified the term "arylalkyloxy" means —O-(alkyl)-(aryl), wherein alkyl and aryl are defined above, including, but not limited to —O—(CH$_2$)$_2$phenyl, —O—(CH$_2$)$_3$phenyl, —O—CH(phenyl)$_2$, —O—CH(phenyl)$_3$, —O—(CH$_2$)tolyl, —O—(CH$_2$)anthracenyl, —O—(CH$_2$)fluorenyl, —O—(CH$_2$)indenyl, —O—(CH$_2$)azulenyl, —O—(CH$_2$)naphthyl, and the like.

As used herein, unless otherwise specified the term "cycloalkyl" means a monocyclic or polycyclic saturated ring comprising carbon and hydrogen atoms and having no carbon-carbon multiple bonds. A cycloalkyl group can be unsubstituted or substituted. Examples of cycloalkyl groups include, but are not limited to, (C$_3$-C$_7$)cycloalkyl groups, including cyclopropyl, cyclobutyl, cyclopentyl, cyclohexyl, and cycloheptyl, and saturated cyclic and bicyclic terpenes. A cycloalkyl group can be unsubstituted or substituted. Preferably, the cycloalkyl group is a monocyclic ring or bicyclic ring.

As used herein, unless otherwise specified the term "heterocyclyl" means a monocyclic or polycyclic ring comprising carbon and hydrogen atoms, optionally having 1 to 4 multiple bonds, and the ring atoms contain at least one heteroatom, preferably 1 to 3 heteroatoms, independently selected from nitrogen, oxygen, and sulfur. Heterocyclyl ring structures include compounds having one or more ring structures such as mono-, bi-, or tricyclic compounds. Preferably, the heterocyclyl group is a monocyclic ring or bicyclic ring. Representative heterocycles include, but are not limited to morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, and the like. A heterocyclyl ring can be unsubstituted or substituted.

As used herein, unless otherwise specified the term "cycloalkyloxy" means —O-(cycloalkyl), wherein cycloalkyl is defined above.

As used herein, unless otherwise specified the term "cycloallylalkyloxy" means —O-(alkyl)-(cycloalkyl), wherein cycloalkyl and alkyl are defined above, including, but not limited to —O-cyclopropyl, —O-cyclobutyl, —O-cyclopentyl, —O-cyclohexyl, —O-cycloheptyl and the like.

As used herein, unless otherwise specified the term "aminoalkoxy" means —O-(alkyl)-NH$_2$, wherein alkyl is defined above, including, but not limited to —O—CH$_2$—NH$_2$, —O—(CH$_2$)$_2$—NH$_2$, —O—(CH$_2$)$_3$—NH$_2$, —O—(CH$_2$)$_4$—NH$_2$, —O—(CH$_2$)$_5$—NH$_2$, and the like.

As used herein, unless otherwise specified the term "alkylamino" means —NH(alkyl) or —N(alkyl)(alkyl), wherein alkyl is defined above, including, but not limited to NHCH$_3$, —NHCH$_2$CH$_3$, —NH(CH$_2$)$_2$CH$_3$, —NH(CH$_2$)$_3$CH$_3$, —NH(CH$_2$)$_4$CH$_3$, —NH(CH$_2$)$_5$CH$_3$, —N(CH$_3$)$_2$, —N(CH$_2$CH$_3$)$_2$, —N((CH$_2$)$_2$CH$_3$)$_2$, —N(CH$_3$)(CH$_2$CH$_3$), and the like.

As used herein, unless otherwise specified the term "arylamino" means —NH(aryl), wherein aryl is defined above, including, but not limited to —NH(phenyl), —NH(tolyl), —NH(anthracenyl), —NH(fluorenyl), —NH(indenyl), —NH(azulenyl), —NH(pyridinyl), —NH(naphthyl), and the like.

As used herein, unless otherwise specified the term "arylalkylamino" means —NH-(alkyl)-(aryl), wherein alkyl and aryl are defined above, including —NH—CH$_2$— (phenyl), —NH—CH$_2$-(tolyl), —NH—CH$_2$— (anthracenyl), —NH—CH$_2$— (fluorenyl), —NH—CH$_2$— (indenyl), —NH—CH$_2$— (azulenyl), —NH—CH$_2$— (pyridinyl), —NH—CH$_2$— (naphthyl), —NH—(CH$_2$)$_2$-(phenyl) and the like.

As used herein, unless otherwise specified the term "cycloalkylamino" means —NH-(cycloalkyl), wherein cycloalkyl is defined above, including —NH-cyclopropyl, —NH-cyclobutyl, —NH-cyclopentyl, —NH-cyclohexyl, —NH-cycloheptyl, and the like.

As used herein, unless otherwise specified the term "aminoalkyl" means -(alkyl)-NH$_2$, wherein alkyl is defined above, including —CH$_2$—NH$_2$, —(CH$_2$)$_2$—NH$_2$, —(CH$_2$)$_3$—NH$_2$, —(CH$_2$)$_4$—NH$_2$, —(CH$_2$)$_5$—NH$_2$ and the like.

As used herein, unless otherwise specified the term "alkylaminoalkyl" means -(alkyl)-NH(alkyl) or -(alkyl)-N(alkyl)(alkyl), wherein each "alkyl" is independently an alkyl group defined above, including —CH$_2$—NH—CH$_3$, —CH$_2$—NHCH$_2$CH$_3$, —CH$_2$—NH(CH$_2$)$_2$CH$_3$, —CH$_2$—NH(CH$_2$)$_3$CH$_3$, —CH$_2$—NH(CH$_2$)$_4$CH$_3$, —CH$_2$—NH(CH$_2$)$_5$CH$_3$, —(CH$_2$)$_2$—NH—CH$_3$, —CH$_2$—N(CH$_3$)$_2$, —CH$_2$—N(CH$_2$CH$_3$)$_2$, —CH$_2$—N((CH$_2$)$_2$CH$_3$)$_2$, —CH$_2$—N(CH$_3$)(CH$_2$CH$_3$), —(CH$_2$)$_2$—N(CH$_3$)$_2$, and the like.

As used herein, the terms "compound having nonsense codon suppressing activity," a "nonsense codon suppressor agent," and "nonsense codon suppressor" refer to any compound, or pharmaceutically acceptable salt, prodrug, solvate, hydrate, polymorph or enantiomer thereof, which can cause the readthrough of a nonsense codon in vitro or in vivo.

As used herein, a "therapeutic protocol" refers to a regimen of timing and dosing of one or more therapies.

As used herein, a "prophylactic protocol" refers to a regimen of timing and dosing of one or more therapies.

A used herein, a "protocol" includes dosing schedules and dosing regimens.

As used herein, "in combination" refers to the use of more than one therapy. The use of the term "in combination" does not restrict the order in which therapies are administered to a subject with a disease. A first therapy can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject which had, has, or is susceptible to a disease. The therapies are administered to a subject in a sequence and within a time interval such that an agent of the invention can act together with another therapy to provide an increased benefit than if they were administered otherwise. Non-limiting examples of therapies that can be administered in combination with the other codon suppressor agent include analgesics, anesthetics, anti-convulsants, supportive therapies and any other therapies listed in the *U.S. Pharmacopoeia* and/or *Physician's Desk Reference*.

As used herein, the terms "manage", "managing" and "management" in the context of the administration of a therapy to a subject refer to the beneficial effects that a subject derives from a therapy, which does not result in a cure of the disease. In certain embodiments, a subject is administered one or more therapies to "manage" a disease so as to prevent the progression or worsening of the disease or a symptom thereof.

As used herein, the term "therapy" refers to any protocol, method and/or agent that can be used in the prevention, management and/or treatment of a disorder or a symptom thereof. In certain embodiments, the term "therapy" refers to a biological therapy, surgery and/or supportive therapy useful in the prevention, management and/or treatment of a disorder or a symptom thereof. In a specific embodiment, a nonsense codon suppressor agent is a therapy.

As used herein, the terms "prevent", "preventing" and "prevention" in the context of the administration of a therapy to a subject refer to the prevention of the onset, development, recurrence, spread and/or worsening of a disease or a symptom thereof in a subject resulting from the administration of a therapy.

As used herein, the terms "treat", "treating" and "treatment" in the context of the administration of a therapy to a subject refer to the eradication or amelioration of a disease or a symptom associated with the disease. In certain embodiments, such terms refer to minimizing the spread or worsening of the disease resulting from the administration of one or more therapies to a subject with such a disease. In other embodiments, such terms refer to a reduction in the severity and/or duration of a disease or a symptom(s) associated with the disease.

As used herein, the term "full-length" in the context of a functional readthrough protein refers to a functional readthrough protein that is composed of the same number of amino acid residues as the corresponding wild-type protein.

As used herein, the term "non-wild-type protein" refers to a protein having an amino acid sequence that is different from the corresponding wild-type protein. In certain embodiments, the non-wild-type protein only differs from the corresponding wild-type protein at the amino acid residue(s) in the non-wild-type protein that was inserted at the position(s) encoded by a premature termination codon. In other embodiments, the non-wild-type protein differs from the corresponding wild-type protein: (i) at an amino acid residue(s) in the non-wild-type protein(s) that was inserted at the position encoded by a premature termination codon; and (ii) at an amino acid residue(s) in the non-wild-type protein other than those encoded by a premature termination codon.

As used herein, the term "wild-type" in the context of a protein refers to a protein that is found in nature (often (but not necessarily) it is the predominant protein) and is designated as a standard or reference protein.

As used herein, the phase "functional readthrough protein" refers to a functional protein produced as a result of readthrough of a nonsense codon in a RNA (e.g., mRNA) transcribed from a gene. In a specific embodiment, the phrase "functional readthrough protein" refers to a functional protein produced as a result of readthrough of a nonsense codon in a RNA transcribed from a gene comprising a nonsense mutation. In certain embodiments, the functional readthrough protein is composed of the same amino acid sequence as the corresponding wild-type protein encoded by a gene without a nonsense mutation. In other embodiments, the functional readthrough protein is a functional non-wild-type protein.

As used herein, the term "cutaneous disorder" refers to a disorder of the skin, particularly disorders of the epidermis or dermis, more particularly the epidermis, components of the skin. "Epidermis" includes: the stratum corneum, stratum lucidum, stratum granulosum, stratum spinosum and stratum germinativum (stratum basale, basal cell layer). In a specific embodiment, the disorder treated, prevented and/or managed in accordance with the invention is not a cutaneous disorder.

As used herein, the term "gastrointestinal disorder" refers to a disorder of the gastrointestinal (GI) tract, including the mouth, pharynx, esophagus, stomach and duodenum (e.g., small intestine, large intestine (e.g., colon)). In a specific embodiment, the disorder treated, prevented and/or managed in accordance with the invention is not a gastrointestinal disorder.

As used herein, the terms "disease" and "disorder" are used interchangeably.

As used herein, the phrases "disease associated with a nonsense mutation in a gene(s)" and "disorder associated with a nonsense mutation in a gene(s)" are used interchangeably to refer to a disease that results from, directly or indirectly, a nonsense mutation(s) in a gene(s), where the nonsense mutation(s) prevents production of a wild-type protein in an affected cell. Diseases associated with a nonsense mutation encompass diseases in which a single gene contains one, two, three or more nonsense mutations as well as diseases in which two, three or more (multiple) genes contain one, two, three or more nonsense mutations.

As used herein, the term "functional" in the context of a functional readthrough protein refers to a protein that has enough of the functions of the corresponding wild-type protein to have a beneficial effect in a cell or subject which does not produce or produces insufficient amounts of the wild-type protein as a result of a mutation (e.g., a nonsense mutation) in the nucleic acid sequence (e.g., gene) encoding the protein.

As used herein, the term "pharmaceutically acceptable salts" refer to salts prepared from pharmaceutically acceptable non-toxic acids or bases including inorganic acids and bases and organic acids and bases. Suitable pharmaceutically acceptable base addition salts for the compound of the present invention include, but are not limited to, metallic salts made from aluminum, Calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Other examples of salts are well known in the art, see, e.g., *Remington's Pharmaceutical Sciences,* 18th ed., Mack Publishing, Easton Pa. (1990).

As used herein and unless otherwise indicated, the term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6th ed.

(Donald J. Abraham ed., 2001, Wiley) and *Design and Application of Prodrugs* (H. Bundgaard ed., 1985, Harwood Academic Publishers Gmfh).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocycle and heteroaromatic amines, and polyether amines.

As used herein and unless otherwise indicated, the term "optically pure" or "stereomerically pure" means a the stereoisomer of a compound is substantially free of the other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "enantiomerically pure" means a stereomerically pure composition of a compound having one chiral center.

As used herein, the term "unit dosage form(s)" includes tablets; chewable tablets; caplets; capsules, such as soft elastic gelatin capsules; sachets; cachets; troches; lozenges; dispersions; powders; solutions; gels; liquid dosage forms suitable for oral or mucosal administration to a patient, including suspensions (e.g., aqueous or non-aqueous liquid suspensions), emulsions (e.g., oil-in-water emulsions, or a water-in-oil liquid emulsion), solutions, and elixirs; and sterile solids (e.g., crystalline or amorphous solids) that can be reconstituted to provide liquid dosage forms suitable for oral or parenteral administration to a patient. The unit dosage form does not necessarily have to be administered as a single dose.

As used herein, the term "library" in the context of compounds refers to a plurality of compounds. A library can be a combinatorial library, e.g., a collection of compounds synthesized using combinatorial chemistry techniques, or a collection of unique chemicals of low molecular weight (less than 1000 daltons) that each occupy a unique three-dimensional space.

As used herein, a "reporter gene" refers to a gene by which modulation of premature translation termination and/or nonsense-mediated mRNA decay is ascertained. In a specific embodiment, the expression of a reporter gene is easily assayed and has an activity which is not normally found in the organism of which the cells or translation extract is obtained or derived.

As used herein, "nonsense-mediated mRNA decay" refers to any mechanism that mediates the decay of mRNAs containing a premature translation termination codon.

As used herein, the term "previously determined reference range" refers to a reference range for the readout of a particular assay. In a specific embodiment, the term refers to a reference range for the expression of a reporter gene and/or the activity of a reporter gene product by a particular cell or in a particular cell-free extract. In some embodiments, each laboratory establishes its own reference range for each particular assay, each cell type and each cell-free extract. In a preferred embodiment, at least one positive control and at least one negative control are included in each batch of compounds analyzed.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.2 Illustrative Compounds with Nonsense Mutation Suppressing Activity

In one embodiment, the nonsense codon suppressor is a compound of formula I:

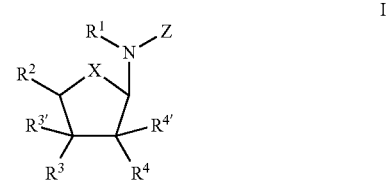

or a pharmaceutically acceptable salt, hydrate, solvate, clathrate, racemate or stereoisomer thereof, wherein:

Z is substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, substituted or unsubstituted arylcarbonyl;

X is $CH_2$, O, S or NH;

$R^1$ is hydrogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl;

$R^2$ is substituted or unsubstituted alkyl, carboxy, amido, acyl, alkylcarbonyl, halogen, a biohydrolyzable group, $OP(O)_3^{2-}$, $O[P(O)_3]_2^{3-}$, $O[P(O)_3]_3^{4-}$, $N_3$, $CH_2$—$NR_6R_7$ or $CH_2$—$OR^6$;

$R^3$, $R^{3'}$, $R^4$ and $R^{4'}$ are at each occurrence independently $OR^7$, $OR^8$, hydrogen, halogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, substituted or unsubstituted arylcarbonyl, substituted or unsubstituted alkylcarbonyl, a biohydrolyzable group, or $R^3$ and $R^4$ taken together form a bond, or $R^3$ and $R^4$ taken together with the atoms to which they are attached form a substituted or unsubstituted heterocyclo, or $R^3$ and $R^{3'}$ and/or $R^4$ and $R^{4'}$ taken together with the carbon to which they are attached form C(=O); and $R^6$, $R^7$ and $R^8$ are at each occurrence independently hydrogen, substituted or unsubstituted alkyl, substituted or unsubstituted aryl, substituted or unsubstituted heteroaryl, substituted or unsubstituted cycloalkyl, substituted or unsubstituted heterocyclo, substituted or unsubstituted arylalkyl, substituted or unsubstituted heteroarylalkyl, substituted or unsubstituted cycloalkylalkyl, substituted or unsubstituted heterocycloalkyl, substituted or unsubstituted arylcarbonyl, substituted or unsubstituted alkylcarbonyl, a biohydrolyzable group, or $R^3$ and $R^4$ taken together with the atoms to which they are attached form a substituted or unsubstituted heterocyclo.

Preferred compounds of formula I are set forth in Table 1, below.

TABLE 1

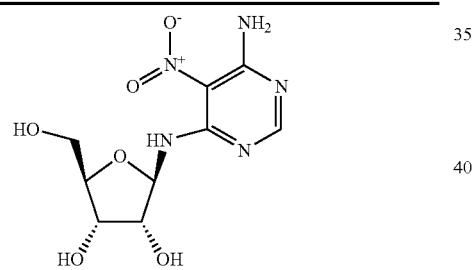

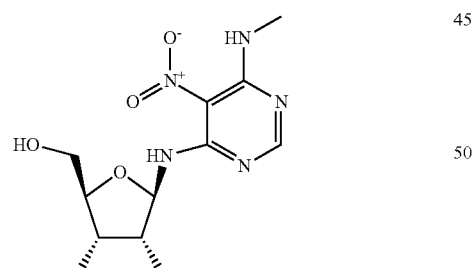

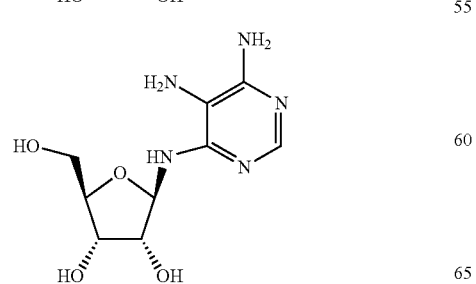

TABLE 1-continued

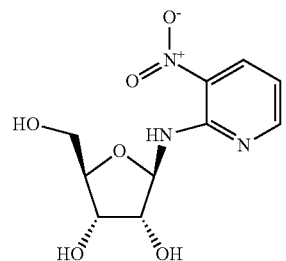 [SMILES: O=[N+]([O-])c1cccnc1N[C@@H]1O[C@H](CO)[C@@H](O)[C@H]1O]

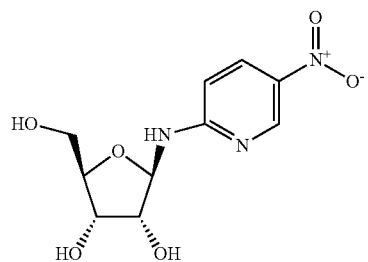 [SMILES: O=[N+]([O-])c1ccc(N[C@@H]2O[C@H](CO)[C@@H](O)[C@H]2O)nc1]

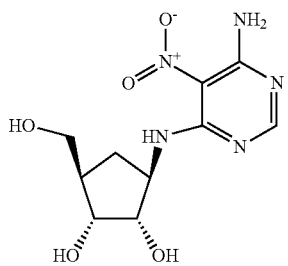 [SMILES: Nc1ncnc(N[C@@H]2C[C@H](CO)[C@@H](O)[C@H]2O)c1[N+](=O)[O-]]

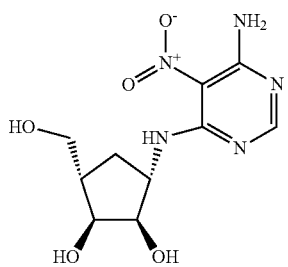 [SMILES: Nc1ncnc(N[C@H]2C[C@@H](CO)[C@H](O)[C@@H]2O)c1[N+](=O)[O-]]

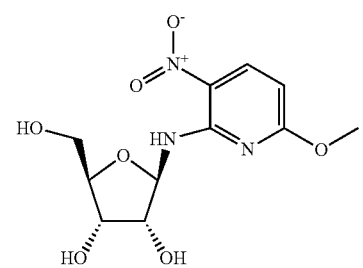 [SMILES: COc1ccc([N+](=O)[O-])c(N[C@@H]2O[C@H](CO)[C@@H](O)[C@H]2O)n1]

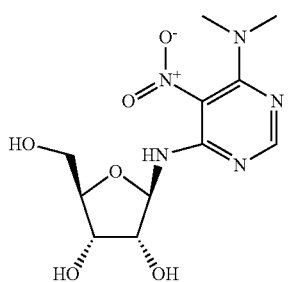 [SMILES: CN(C)c1ncnc(N[C@@H]2O[C@H](CO)[C@@H](O)[C@H]2O)c1[N+](=O)[O-]]

TABLE 1-continued
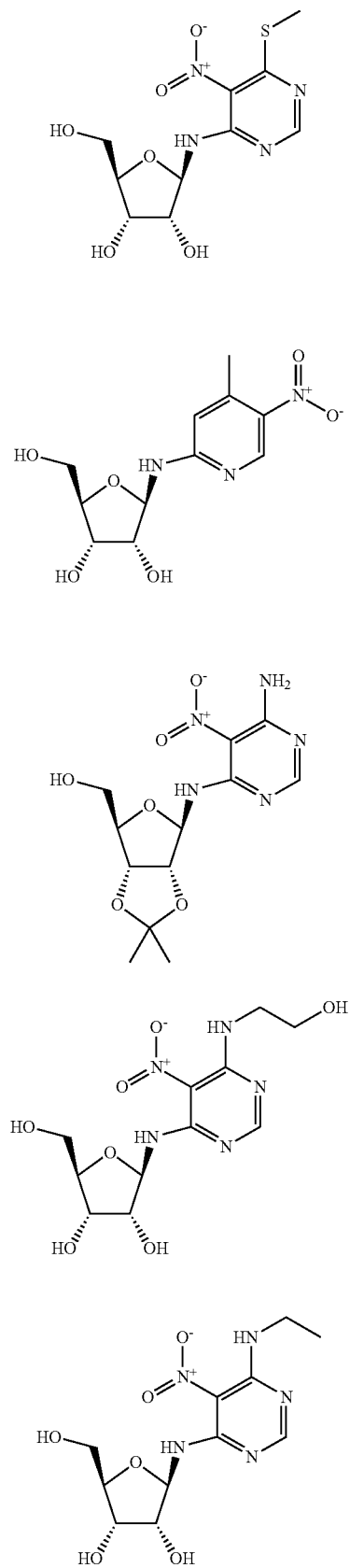
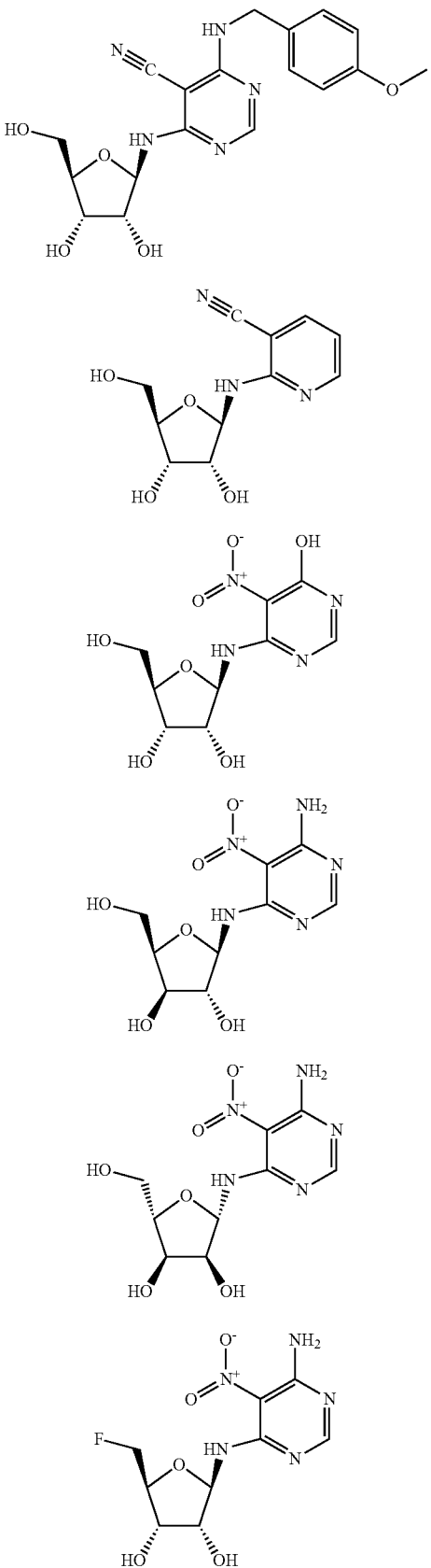

TABLE 1-continued
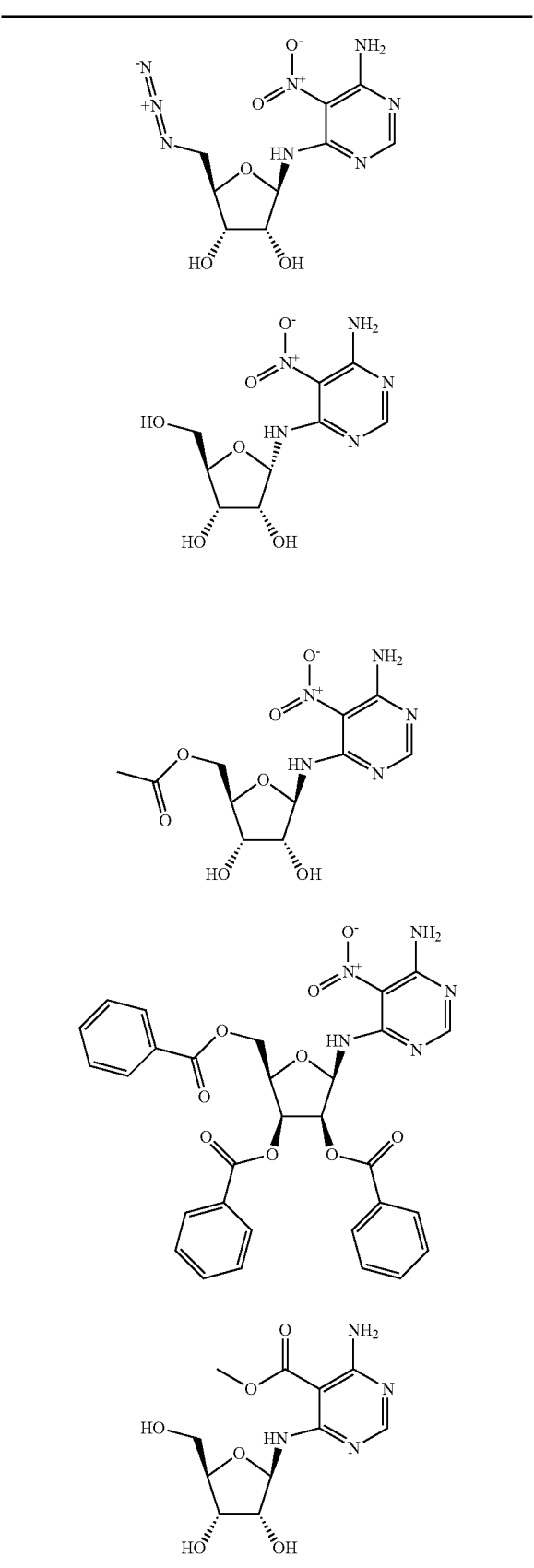
TABLE 1-continued
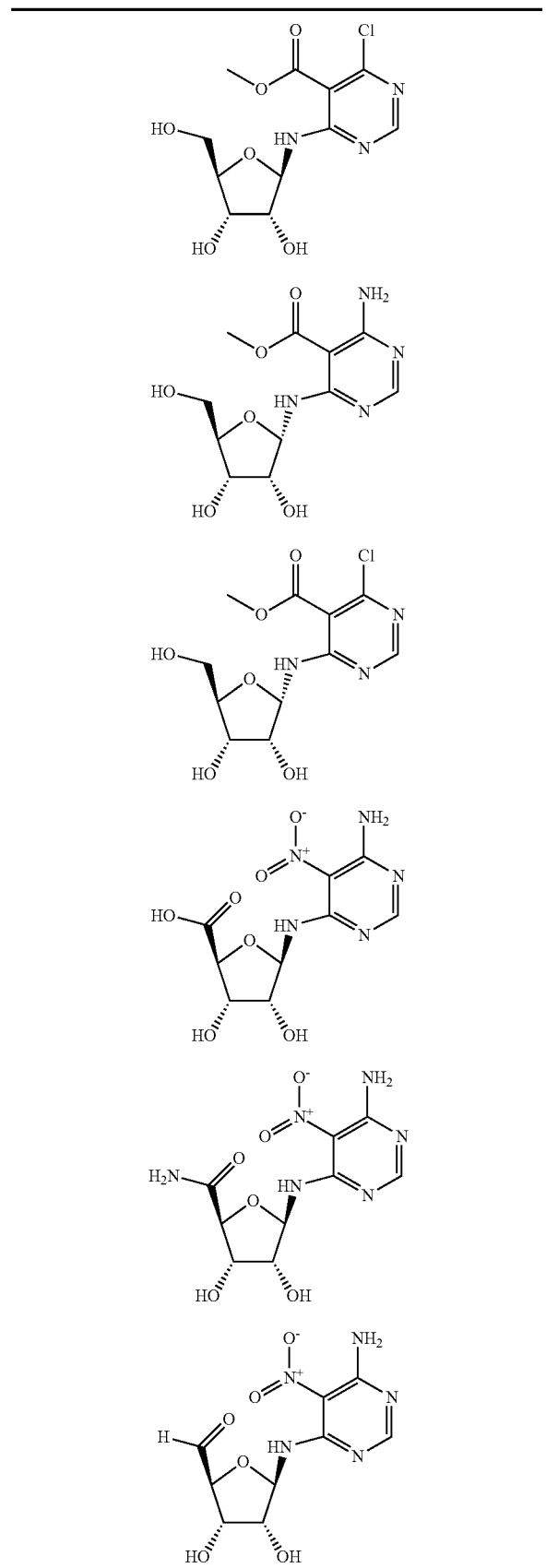

TABLE 1-continued
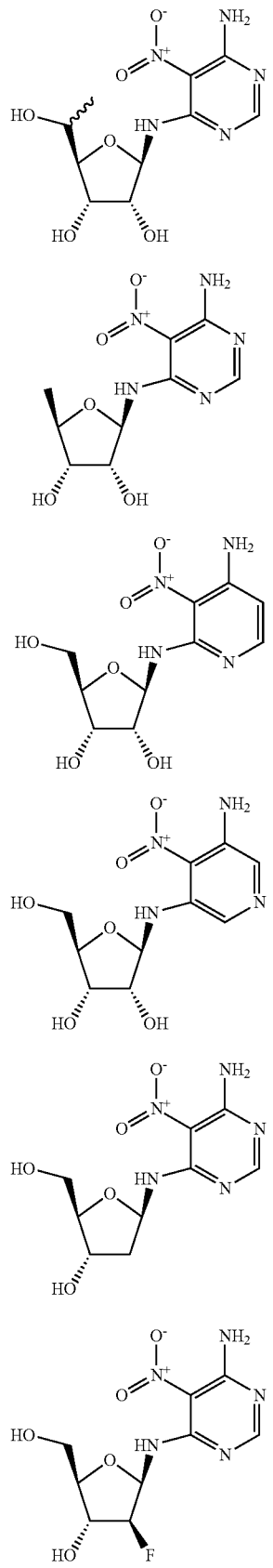
TABLE 1-continued
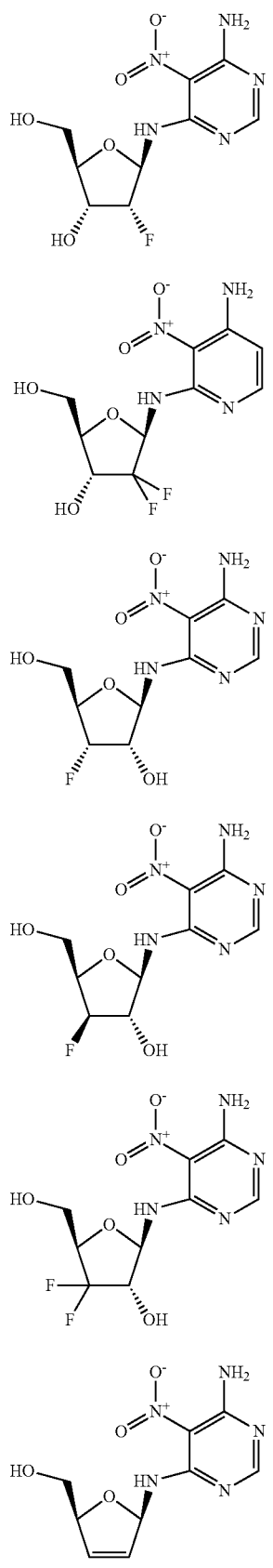

TABLE 1-continued
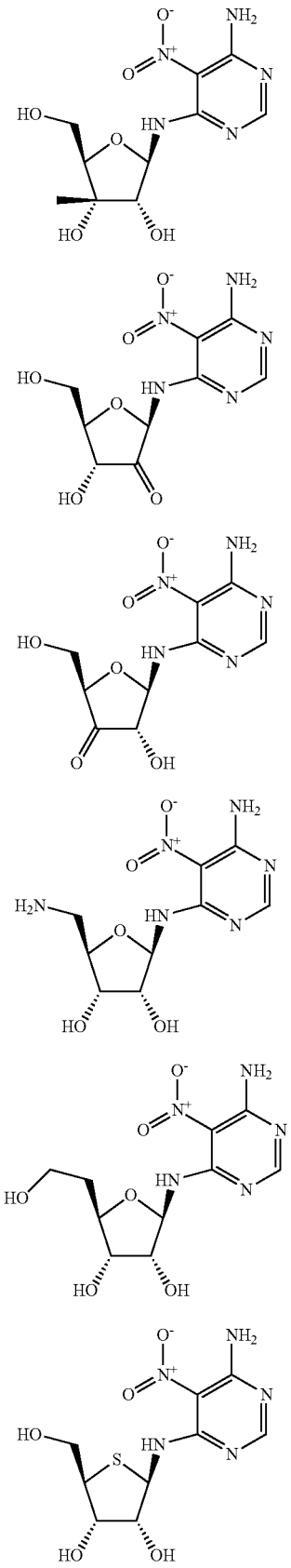
TABLE 1-continued
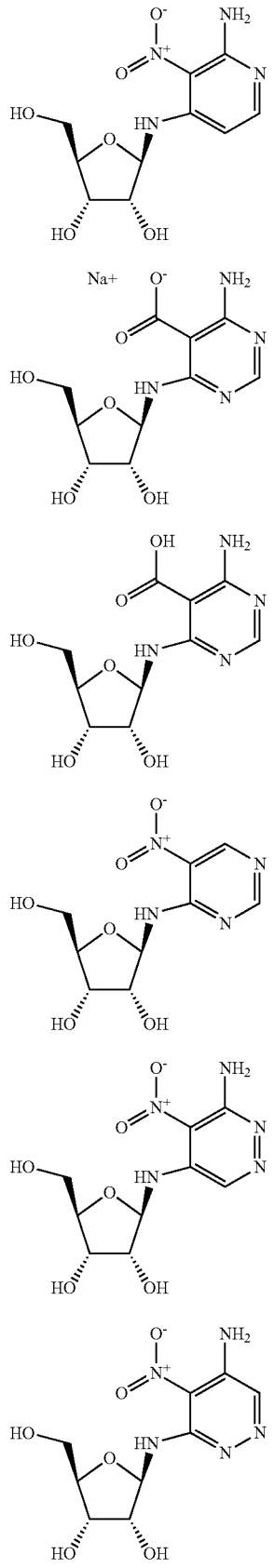

TABLE 1-continued

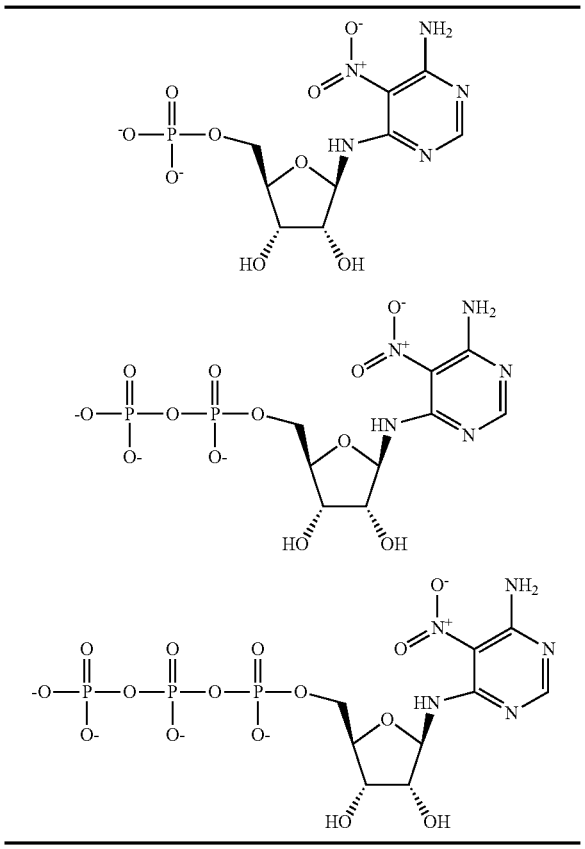

Compounds of formula I can be obtained via standard, well-known synthetic methodology, see e.g., March, J. Advanced Organic Chemistry; Reactions Mechanisms, and Structure, 4th ed., 1992. Starting materials useful for preparing compounds of formula I and intermediates therefore, are commercially available or can be prepared from commercially available materials using known synthetic methods and reagents.

Particular methods for preparing compounds of formula I are disclosed in US 2004-0067900, published Apr. 8, 2004, incorporated by reference herein in its entirety.

In another embodiment, the nonsense codon suppressor is a compound of formula II:

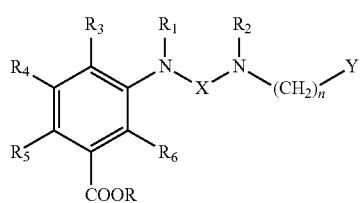

or a pharmaceutically acceptable salt, hydrate, clathrate, polymorph, prodrug or stereoisomer thereof wherein:

X is C(=O), C(=S), S, S(=O) or S(O)$_2$;

Y is substituted or unsubstituted alkyl, substituted or unsubstituted aryl, substituted or unsubstituted heteroaryl, substituted or unsubstituted cycloalkyl, substituted or unsubstituted heterocyclo;

R is hydrogen, substituted or unsubstituted alkyl, substituted or unsubstituted cycloalkyl, substituted or unsubstituted heterocyclo, substituted or unsubstituted aryl, substituted or unsubstituted heteroaryl, substituted or unsubstituted arylalkyl, substituted or unsubstituted heteroarylalkyl, substituted or unsubstituted cycloalkylalkyl, substituted or unsubstituted heterocycloalkyl;

n is an integer ranging from 0-4;

$R_1$ and $R_2$ are each independently hydrogen, substituted or unsubstituted alkyl, substituted or unsubstituted alkenyl, substituted or unsubstituted alkynyl, —(CH$_2$)$_m$—W, carboxyalkyl, alkylcarbonyl, alkyloxyalkyl, alkyloxycarbonyl, arylalkyl, sulfonyl, amide or $R_1$ and $R_2$ together with the atoms to which they are attached form an optionally substituted 5-7 membered heterocyclic, an optionally substituted 5-7 membered heteroaryl ring or $R_1$ and $R_2$ together form:

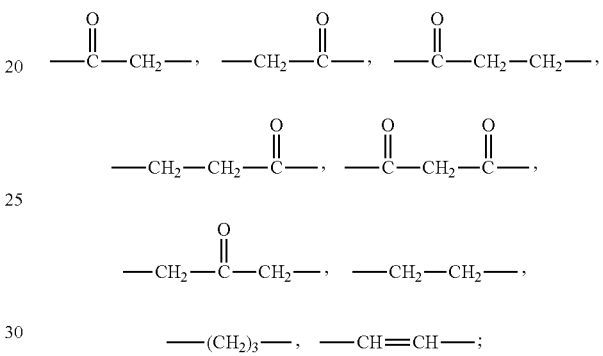

W is at each occurrence independently hydrogen, halogen, hydroxy, alkoxy, carboxy, aldehyde, NH$_2$, NR$^{14}$R$^{14'}$, nitro, cycloalkyl, heteroaryl, heteroarylalkyl;

where (i) each occurrence of R$^{14}$ and R$^{14'}$ is independently selected from hydrogen, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl or CF$_3$; or (ii) R$^{14}$ and R$^{14'}$, together with the nitrogen atom to which they are bonded, join to form an optionally substituted heterocyclic ring containing from 5 to 8 ring atoms of which from 1 to 3 are heteroatoms;

m is an integer ranging from 1-4;

$R_3$-$R_6$ are each independently hydrogen, halogen, substituted or unsubstituted alkyl, substituted or unsubstituted alkenyl, substituted or unsubstituted alkynyl, substituted or unsubstituted cycloalkyl, substituted or unsubstituted heterocyclo, substituted or unsubstituted aryl, substituted or unsubstituted heteroaryl, substituted or unsubstituted arylalkyl, substituted or unsubstituted heteroarylalkyl, substituted or unsubstituted cycloalkylalkyl, substituted or unsubstituted heterocycloalkyl, alkylamino, aminoalkyl, alkoxy, aryloxy, heteroaryloxy, cycloalkoxy, heterocycloalkyloxy, amide, haloalkyl (e.g., CF$_3$), haloalkoxy (e.g., OCF$_3$ or OCHF$_2$), OH, CN, COOH, COOR$^{15}$, SO$_2$R$^{15}$, NO$_2$, NH$_2$, or NR$^{14}$R$^{14'}$ and R$^{15}$ is selected from hydrogen, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl or CF$_3$.

Preferred compounds of formula II are set forth in Table 2, below.
TABLE 2
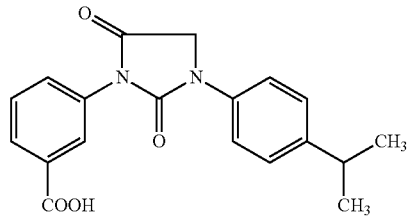 [SMILES: CC(C)c1ccc(N2CC(=O)N(c3cccc(C(=O)O)c3)C2=O)cc1]
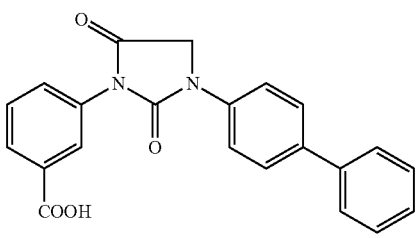 [SMILES: O=C(O)c1cccc(N2C(=O)CN(c3ccc(-c4ccccc4)cc3)C2=O)c1]
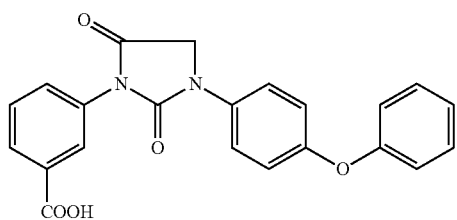 [SMILES: O=C(O)c1cccc(N2C(=O)CN(c3ccc(Oc4ccccc4)cc3)C2=O)c1]
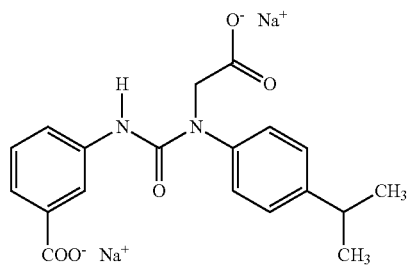
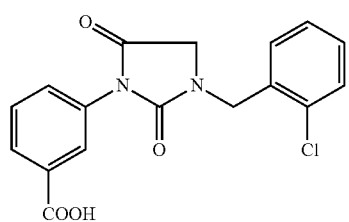 [SMILES: O=C(O)c1cccc(N2C(=O)CN(Cc3ccccc3Cl)C2=O)c1]
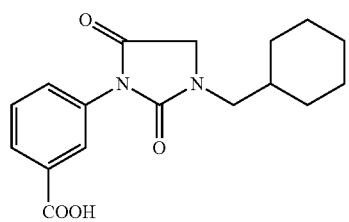 [SMILES: O=C(O)c1cccc(N2C(=O)CN(CC3CCCCC3)C2=O)c1]

TABLE 2-continued
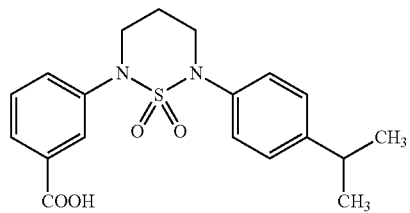 [SMILES: CC(C)c1ccc(N2CCCN(c3cccc(C(=O)O)c3)S2(=O)=O)cc1]
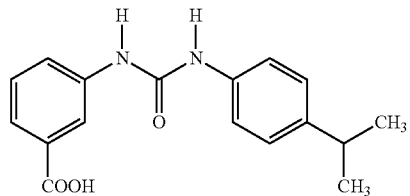 [SMILES: CC(C)c1ccc(NC(=O)Nc2cccc(C(=O)O)c2)cc1]
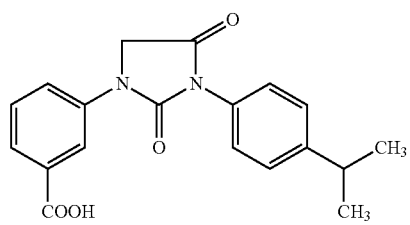 [SMILES: CC(C)c1ccc(N2C(=O)CN(c3cccc(C(=O)O)c3)C2=O)cc1]
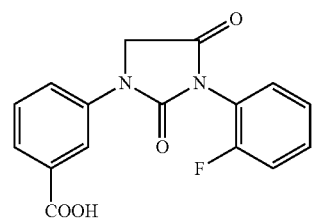 [SMILES: O=C(O)c1cccc(N2CC(=O)N(c3ccccc3F)C2=O)c1]
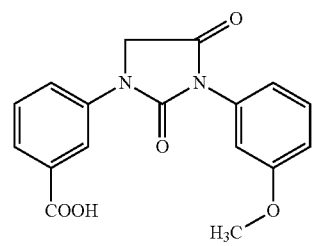 [SMILES: COc1cccc(N2C(=O)CN(c3cccc(C(=O)O)c3)C2=O)c1]
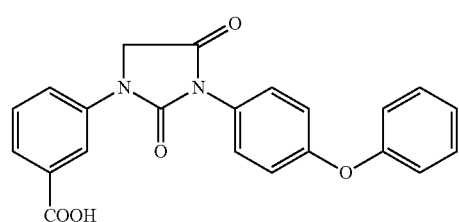 [SMILES: O=C(O)c1cccc(N2CC(=O)N(c3ccc(Oc4ccccc4)cc3)C2=O)c1]
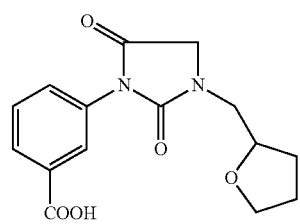 [SMILES: O=C(O)c1cccc(N2C(=O)CN(CC3CCCO3)C2=O)c1]

TABLE 2-continued
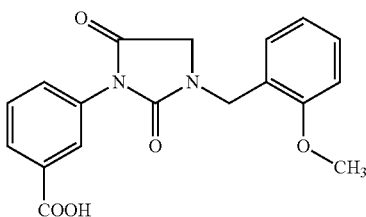 [SMILES: COc1ccccc1CN1CC(=O)N(c2cccc(C(=O)O)c2)C1=O]
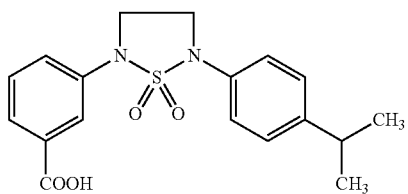 [SMILES: CC(C)c1ccc(N2CCN(c3cccc(C(=O)O)c3)S2(=O)=O)cc1]
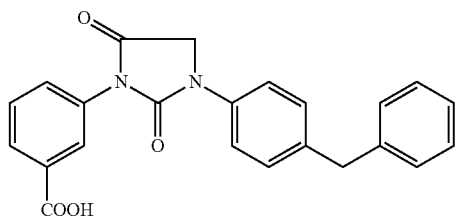 [SMILES: O=C(O)c1cccc(N2C(=O)CN(c3ccc(Cc4ccccc4)cc3)C2=O)c1]
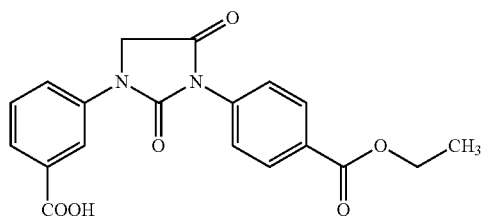 [SMILES: CCOC(=O)c1ccc(N2C(=O)CN(c3cccc(C(=O)O)c3)C2=O)cc1]
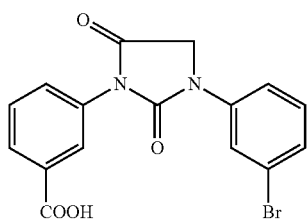 [SMILES: O=C(O)c1cccc(N2C(=O)CN(c3cccc(Br)c3)C2=O)c1]
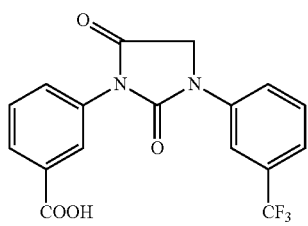 [SMILES: O=C(O)c1cccc(N2C(=O)CN(c3cccc(C(F)(F)F)c3)C2=O)c1]
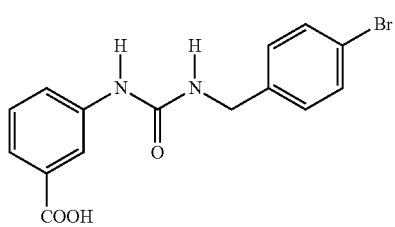 [SMILES: O=C(NCc1ccc(Br)cc1)Nc1cccc(C(=O)O)c1]

TABLE 2-continued
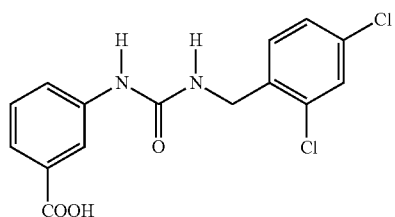 [SMILES: O=C(NCc1ccc(Cl)cc1Cl)Nc1cccc(C(=O)O)c1]
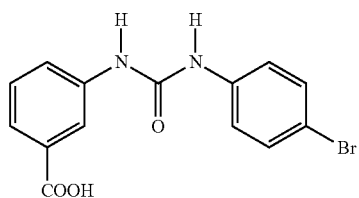 [SMILES: O=C(Nc1ccc(Br)cc1)Nc1cccc(C(=O)O)c1]
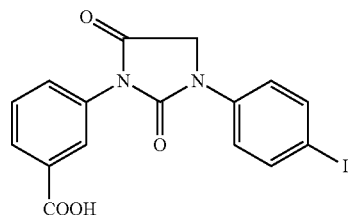 [SMILES: O=C(O)c1cccc(N2C(=O)CN(c3ccc(I)cc3)C2=O)c1]
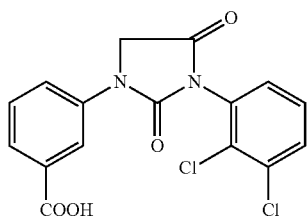 [SMILES: O=C(O)c1cccc(N2CC(=O)N(c3cccc(Cl)c3Cl)C2=O)c1]
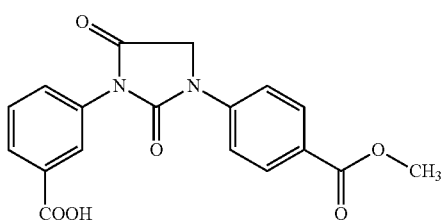 [SMILES: COC(=O)c1ccc(N2CC(=O)N(c3cccc(C(=O)O)c3)C2=O)cc1]
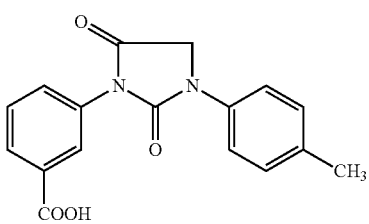 [SMILES: Cc1ccc(N2CC(=O)N(c3cccc(C(=O)O)c3)C2=O)cc1]
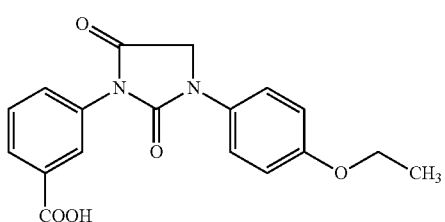 [SMILES: CCOc1ccc(N2CC(=O)N(c3cccc(C(=O)O)c3)C2=O)cc1]

TABLE 2-continued
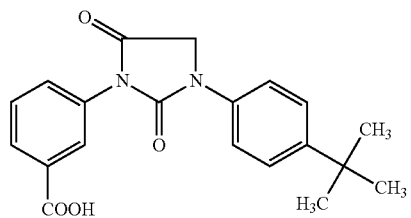 [SMILES: CC(C)(C)c1ccc(N2CC(=O)N(c3cccc(C(=O)O)c3)C2=O)cc1]
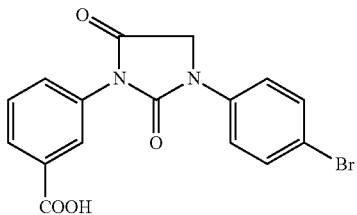 [SMILES: O=C(O)c1cccc(N2C(=O)CN(c3ccc(Br)cc3)C2=O)c1]
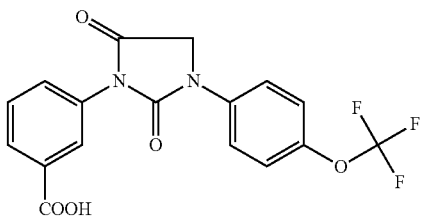 [SMILES: O=C(O)c1cccc(N2C(=O)CN(c3ccc(OC(F)(F)F)cc3)C2=O)c1]
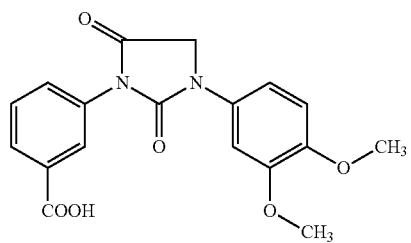 [SMILES: COc1ccc(N2CC(=O)N(c3cccc(C(=O)O)c3)C2=O)cc1OC]
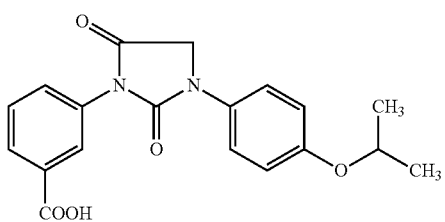 [SMILES: CC(C)Oc1ccc(N2CC(=O)N(c3cccc(C(=O)O)c3)C2=O)cc1]
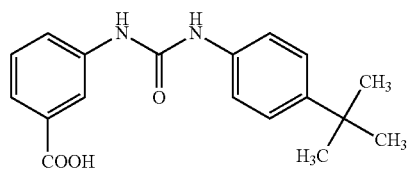 [SMILES: CC(C)(C)c1ccc(NC(=O)Nc2cccc(C(=O)O)c2)cc1]
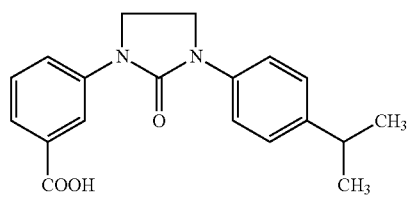 [SMILES: CC(C)c1ccc(N2CCN(c3cccc(C(=O)O)c3)C2=O)cc1]

TABLE 2-continued
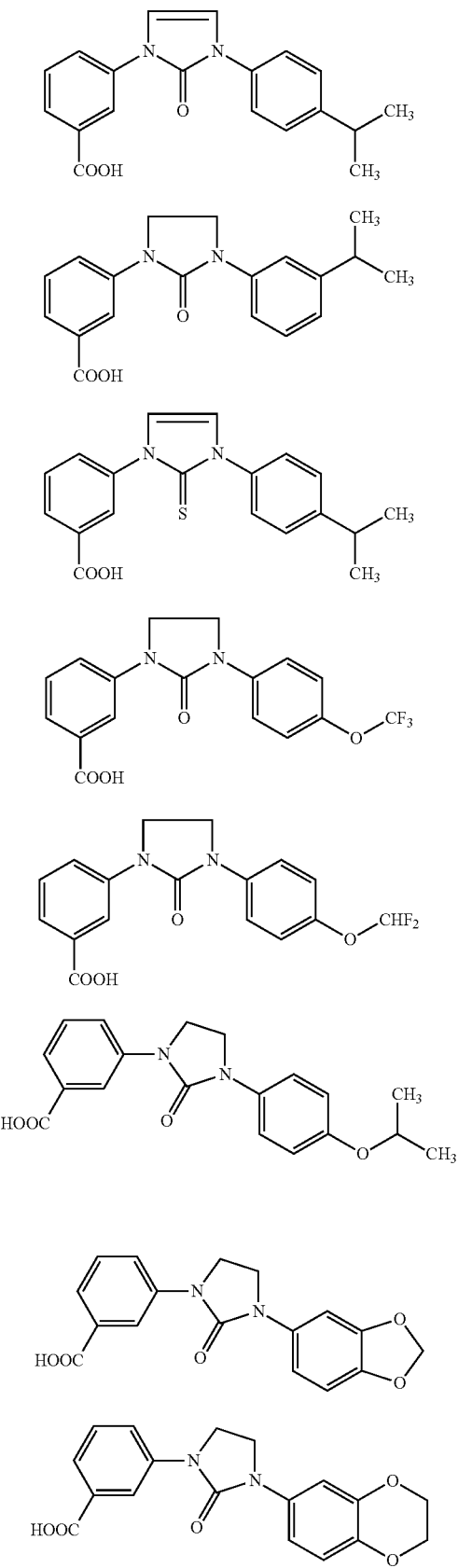

TABLE 2-continued
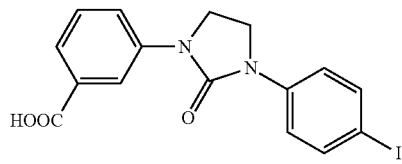 [SMILES: O=C(O)c1cccc(N2CCN(c3ccc(I)cc3)C2=O)c1]
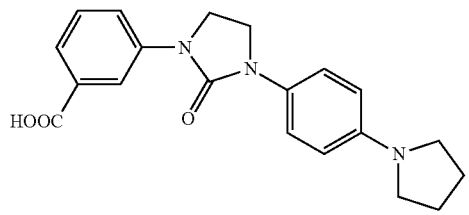 [SMILES: O=C(O)c1cccc(N2CCN(c3ccc(N4CCCC4)cc3)C2=O)c1]
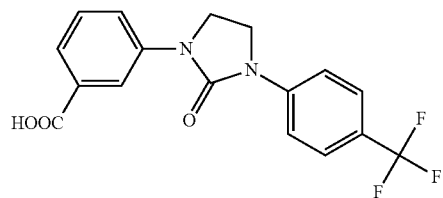 [SMILES: O=C(O)c1cccc(N2CCN(c3ccc(C(F)(F)F)cc3)C2=O)c1]
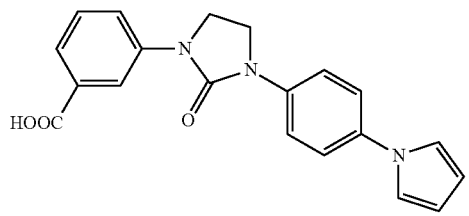 [SMILES: O=C(O)c1cccc(N2CCN(c3ccc(-n4cccc4)cc3)C2=O)c1]
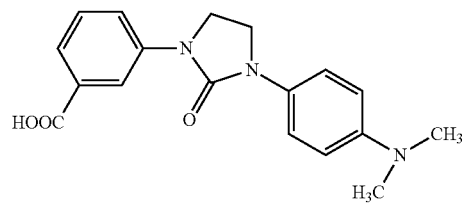 [SMILES: CN(C)c1ccc(N2CCN(c3cccc(C(=O)O)c3)C2=O)cc1]
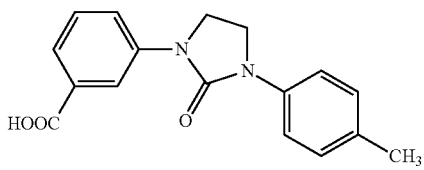 [SMILES: Cc1ccc(N2CCN(c3cccc(C(=O)O)c3)C2=O)cc1]
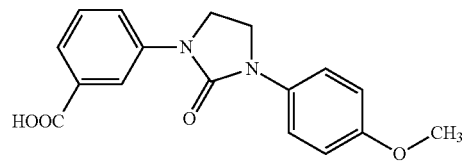 [SMILES: COc1ccc(N2CCN(c3cccc(C(=O)O)c3)C2=O)cc1]
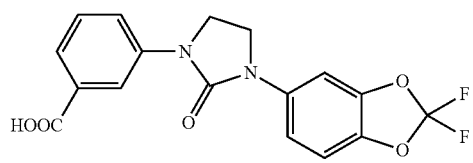 [SMILES: O=C(O)c1cccc(N2CCN(c3ccc4c(c3)OC(F)(F)O4)C2=O)c1]

TABLE 2-continued
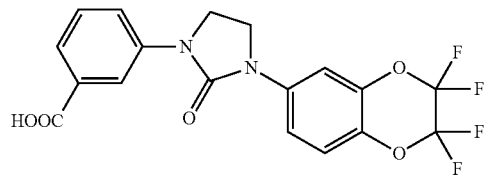 [SMILES: O=C(O)c1cccc(N2CCN(c3ccc4c(c3)OC(F)(F)C(F)(F)O4)C2=O)c1]
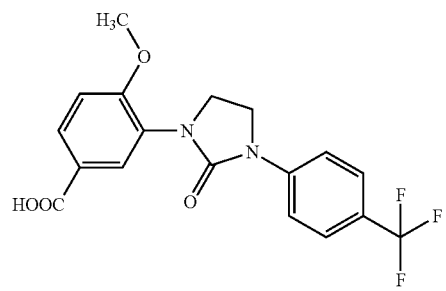 [SMILES: COc1ccc(C(=O)O)cc1N1CCN(c2ccc(C(F)(F)F)cc2)C1=O]
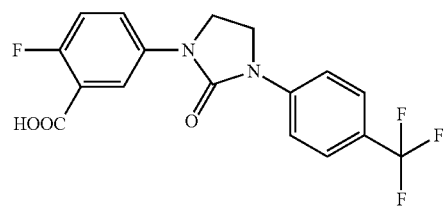 [SMILES: O=C(O)c1cc(N2CCN(c3ccc(C(F)(F)F)cc3)C2=O)ccc1F]
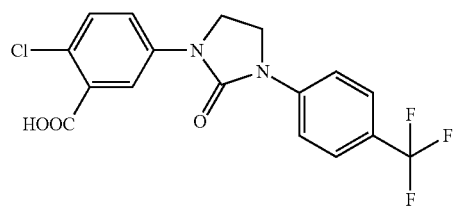 [SMILES: O=C(O)c1cc(N2CCN(c3ccc(C(F)(F)F)cc3)C2=O)ccc1Cl]
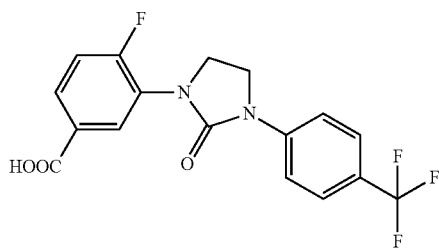 [SMILES: O=C(O)c1ccc(F)c(N2CCN(c3ccc(C(F)(F)F)cc3)C2=O)c1]
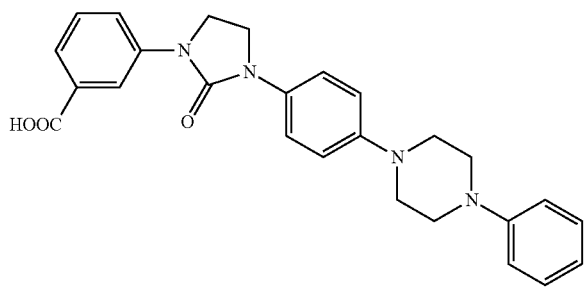 [SMILES: O=C(O)c1cccc(N2CCN(c3ccc(N4CCN(c5ccccc5)CC4)cc3)C2=O)c1]

TABLE 2-continued
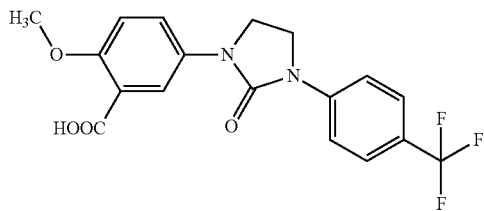 [SMILES: COc1ccc(N2CCN(c3ccc(C(F)(F)F)cc3)C2=O)cc1C(=O)O]
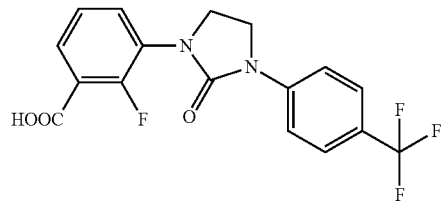 [SMILES: O=C(O)c1cccc(N2CCN(c3ccc(C(F)(F)F)cc3)C2=O)c1F]
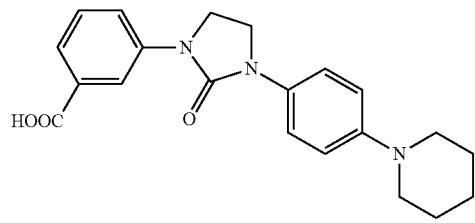 [SMILES: O=C(O)c1cccc(N2CCN(c3ccc(N4CCCCC4)cc3)C2=O)c1]
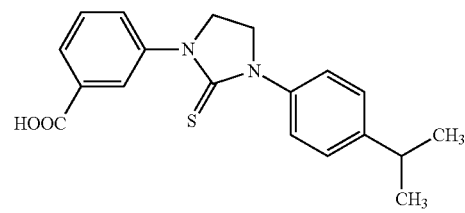 [SMILES: CC(C)c1ccc(N2CCN(c3cccc(C(=O)O)c3)C2=S)cc1]
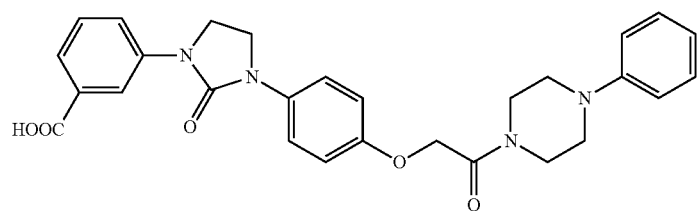 [SMILES: O=C(O)c1cccc(N2CCN(c3ccc(OCC(=O)N4CCN(c5ccccc5)CC4)cc3)C2=O)c1]
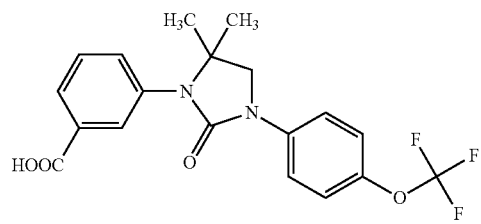 [SMILES: CC1(C)CN(c2ccc(OC(F)(F)F)cc2)C(=O)N1c1cccc(C(=O)O)c1]
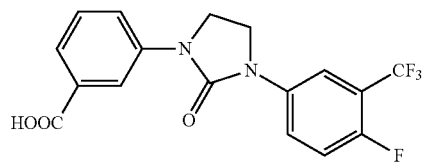 [SMILES: O=C(O)c1cccc(N2CCN(c3ccc(F)c(C(F)(F)F)c3)C2=O)c1]

TABLE 2-continued
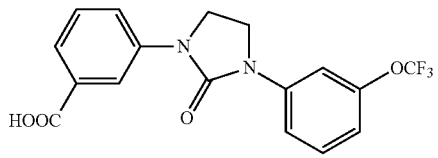 [SMILES: O=C(O)c1cccc(N2CCN(c3cccc(OC(F)(F)F)c3)C2=O)c1]
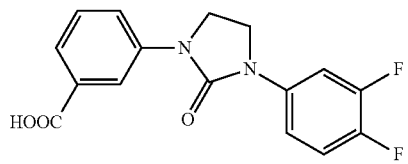 [SMILES: O=C(O)c1cccc(N2CCN(c3ccc(F)c(F)c3)C2=O)c1]
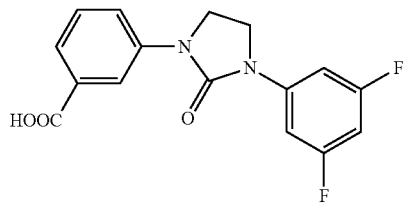 [SMILES: O=C(O)c1cccc(N2CCN(c3cc(F)cc(F)c3)C2=O)c1]
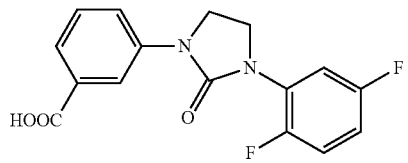 [SMILES: O=C(O)c1cccc(N2CCN(c3cc(F)ccc3F)C2=O)c1]
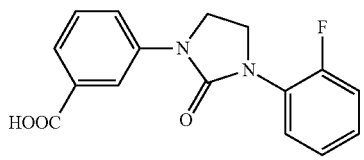 [SMILES: O=C(O)c1cccc(N2CCN(c3ccccc3F)C2=O)c1]
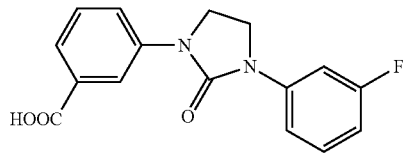 [SMILES: O=C(O)c1cccc(N2CCN(c3cccc(F)c3)C2=O)c1]
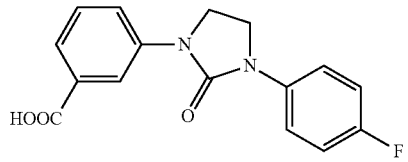
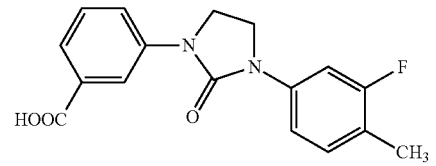 [SMILES: Cc1ccc(N2CCN(c3cccc(C(=O)O)c3)C2=O)cc1F]
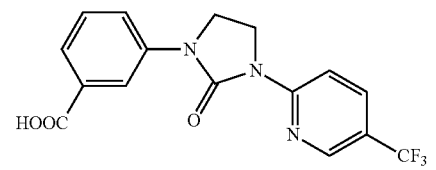 [SMILES: O=C(O)c1cccc(N2CCN(c3ccc(C(F)(F)F)cn3)C2=O)c1]

TABLE 2-continued
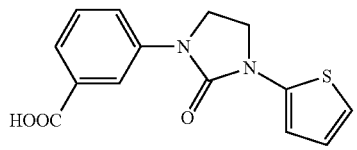 [SMILES: O=C(O)c1cccc(N2CCN(c3cccs3)C2=O)c1]
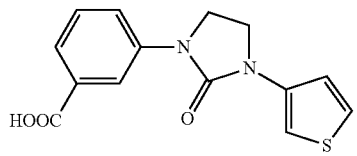 [SMILES: O=C(O)c1cccc(N2CCN(c3ccsc3)C2=O)c1]
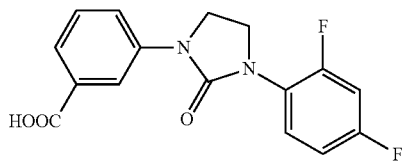 [SMILES: O=C(O)c1cccc(N2CCN(c3ccc(F)cc3F)C2=O)c1]
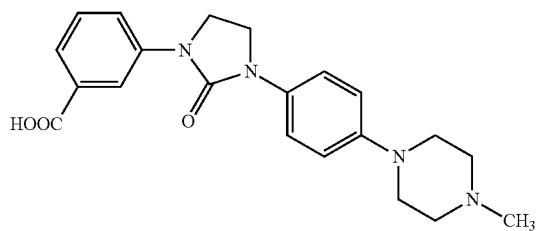 [SMILES: CN1CCN(c2ccc(N3CCN(c4cccc(C(=O)O)c4)C3=O)cc2)CC1]
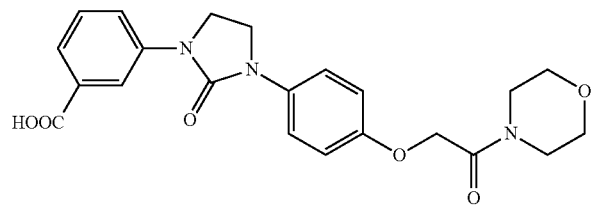 [SMILES: O=C(O)c1cccc(N2CCN(c3ccc(OCC(=O)N4CCOCC4)cc3)C2=O)c1]
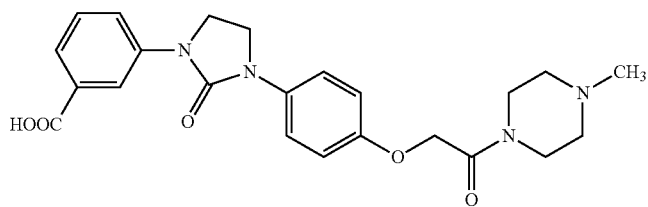 [SMILES: CN1CCN(C(=O)COc2ccc(N3CCN(c4cccc(C(=O)O)c4)C3=O)cc2)CC1]

TABLE 2-continued

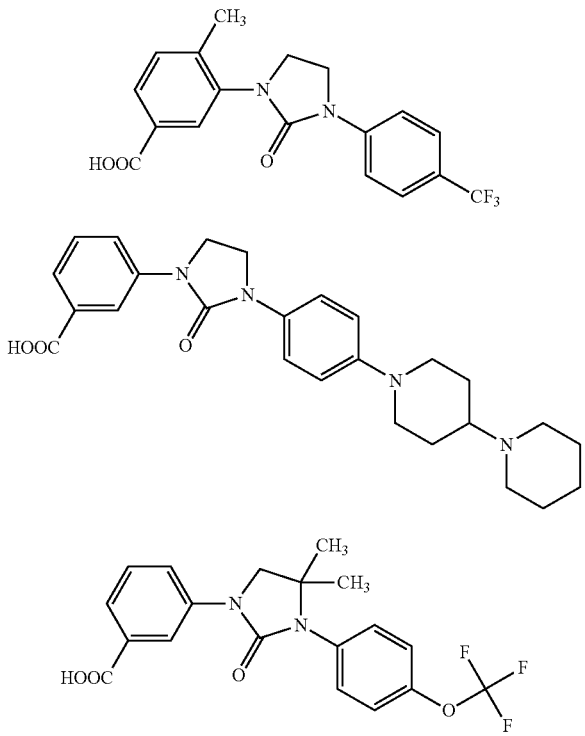

Compounds of formula II can be obtained via standard, well-known synthetic methodology, see e.g., March, J. Advanced Organic Chemistry; Reactions Mechanisms, and Structure, 4th ed., 1992. Starting materials useful for preparing compounds of formula I and intermediates therefore, are commercially available or can be prepared from commercially available materials using known synthetic methods and reagents.

Particular methods for preparing compounds of formula II are disclosed in WO 2004/009558 A2, published Jan. 29, 2004, incorporated by reference herein in its entirety.

In another embodiment, the nonsense codon suppressor is a compound of formula III:

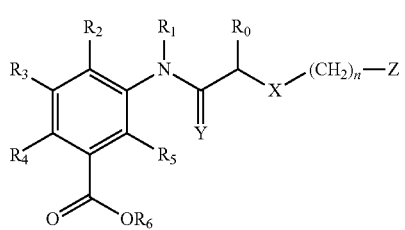

III or pharmaceutically acceptable salts, hydrates, clathrates, prodrugs, polymorphs, stereoisomers, including enantiomers, diastereomers, racemates or mixtures of stereoisomers, thereof wherein:

X is oxygen, sulfur, CO, SO or $S(O)_2$;

Y is oxygen or sulfur;

Z is substituted or unsubstituted aryl, substituted or unsubstituted heteroaryl, substituted or unsubstituted cycloalkyl;

n is an integer from 0 to 4;

$R^1$ is hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, $SO_2R^7$, $CF_3$, CN, COOH, $COR^7$, or $COOR^7$;

$R^0$ is hydrogen, or taken together with $R^1$ and the atoms to which they are attached form an optionally substituted 5-7 membered heterocyclic, or heteroaryl ring;

$R^2$, $R^3$, $R^4$ and $R^5$ are independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen, $CF_3$, $OCF_3$, $OCHF_2$, CN, COOH, $COOR^7$, $SO_2R^7$, $NO_2$, $NH_2$, or $N(R^7)_2$;

$R^6$ is hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, or any biohydrolyzable group; and each occurrence of $R^7$ is independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen or $CF_3$;

with the proviso that when X is O, Y is O, n is O and $R^1$ is hydrogen, then Z is not 4-chlorophenyl, 4-methylphenyl, 3-chlorophenyl, or 2,4-dichlorophenyl; and with the proviso that when X is O, Y is O, n is O, $R^1$ is hydrogen, and Z is unsubstituted phenyl at least one of $R^2$-$R^5$ is not hydrogen; and with the proviso that when $R^3$ is COOH, $R^2$, $R^4$, and $R^5$ are not all halogen.

Preferred compounds of formula III are set forth in Table 3, below.
TABLE 3
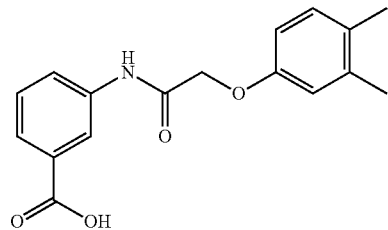 [SMILES: Cc1ccc(OCC(=O)Nc2cccc(C(=O)O)c2)cc1C]
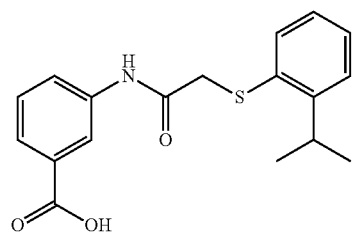 [SMILES: CC(C)c1ccccc1SCC(=O)Nc1cccc(C(=O)O)c1]
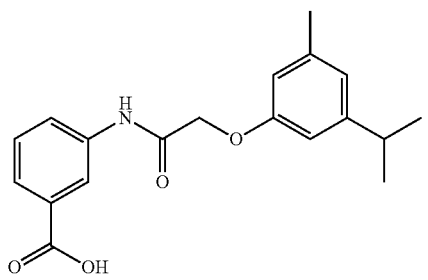 [SMILES: Cc1cc(OCC(=O)Nc2cccc(C(=O)O)c2)cc(C(C)C)c1]
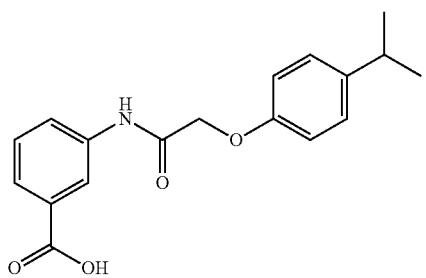 [SMILES: CC(C)c1ccc(OCC(=O)Nc2cccc(C(=O)O)c2)cc1]
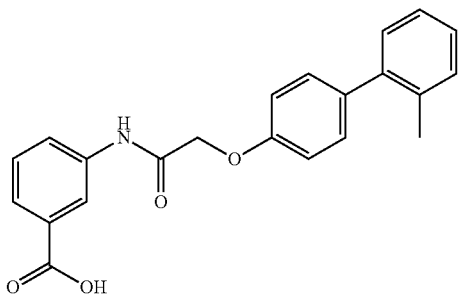 [SMILES: Cc1ccccc1-c1ccc(OCC(=O)Nc2cccc(C(=O)O)c2)cc1]

TABLE 3-continued
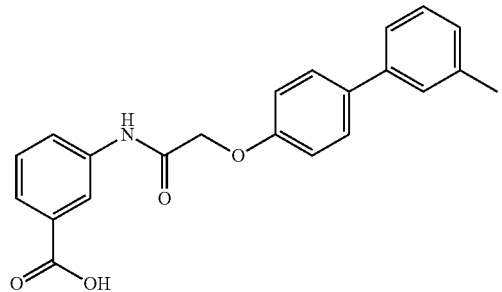 [SMILES: Cc1cccc(-c2ccc(OCC(=O)Nc3cccc(C(=O)O)c3)cc2)c1]
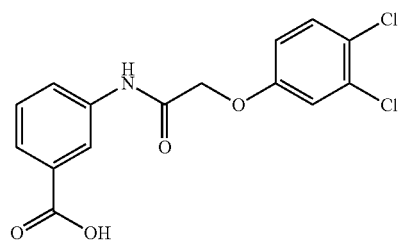 [SMILES: O=C(COc1ccc(Cl)c(Cl)c1)Nc1cccc(C(=O)O)c1]
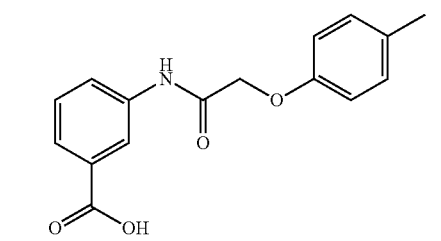 [SMILES: Cc1ccc(OCC(=O)Nc2cccc(C(=O)O)c2)cc1]
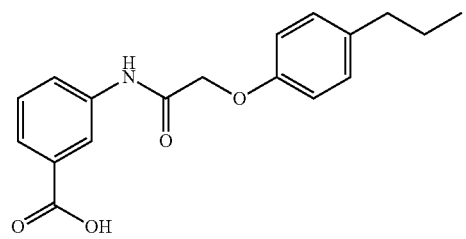 [SMILES: CCCc1ccc(OCC(=O)Nc2cccc(C(=O)O)c2)cc1]
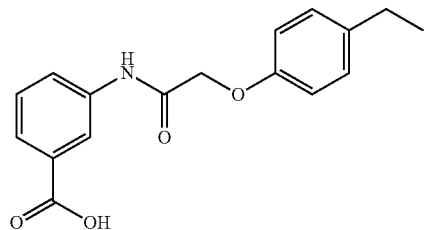 [SMILES: CCc1ccc(OCC(=O)Nc2cccc(C(=O)O)c2)cc1]
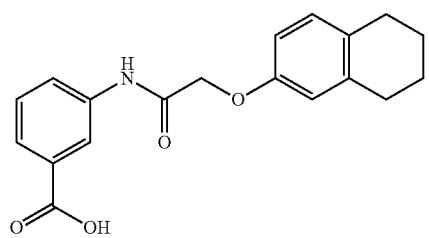 [SMILES: O=C(COc1ccc2c(c1)CCCC2)Nc1cccc(C(=O)O)c1]

TABLE 3-continued
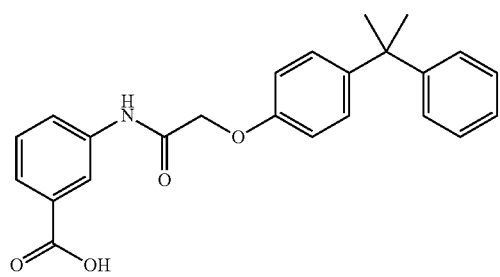 [SMILES: CC(C)(c1ccccc1)c1ccc(OCC(=O)Nc2cccc(C(=O)O)c2)cc1]
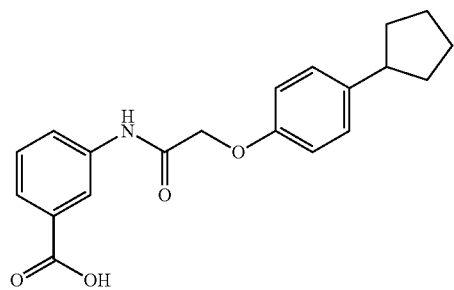 [SMILES: O=C(COc1ccc(C2CCCC2)cc1)Nc1cccc(C(=O)O)c1]
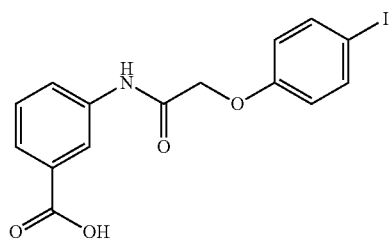 [SMILES: O=C(COc1ccc(I)cc1)Nc1cccc(C(=O)O)c1]
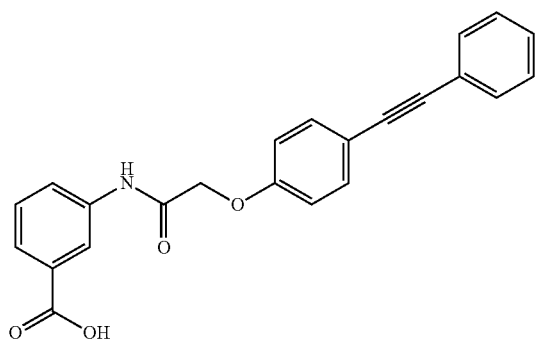 [SMILES: O=C(COc1ccc(C#Cc2ccccc2)cc1)Nc1cccc(C(=O)O)c1]
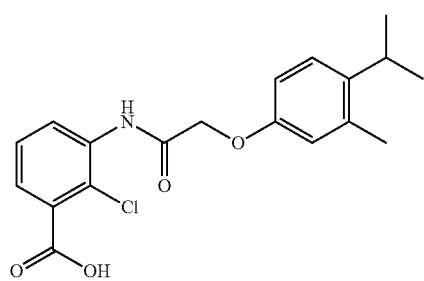 [SMILES: Cc1cc(OCC(=O)Nc2cccc(C(=O)O)c2Cl)ccc1C(C)C]

TABLE 3-continued
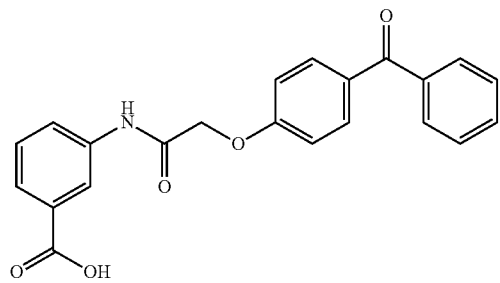 [SMILES: O=C(COc1ccc(C(=O)c2ccccc2)cc1)Nc1cccc(C(=O)O)c1]
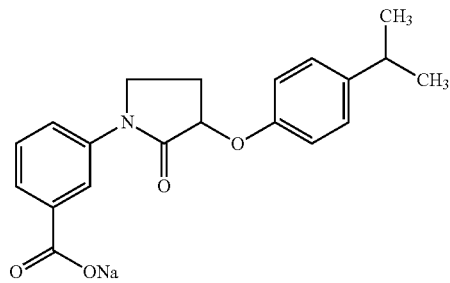
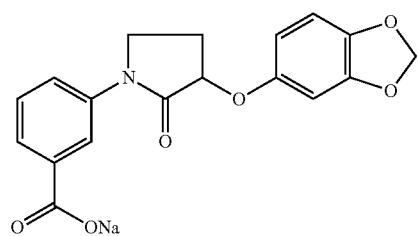
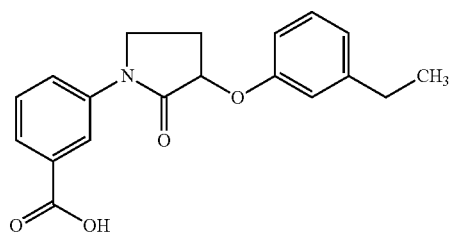 [SMILES: CCc1cccc(OC2CCN(c3cccc(C(=O)O)c3)C2=O)c1]
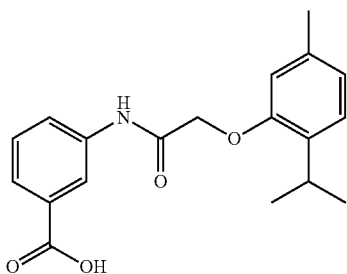 [SMILES: Cc1ccc(C(C)C)c(OCC(=O)Nc2cccc(C(=O)O)c2)c1]
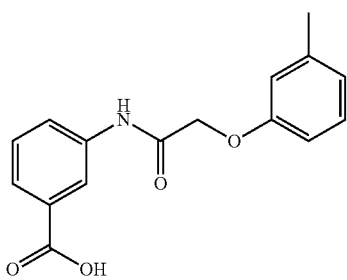 [SMILES: Cc1cccc(OCC(=O)Nc2cccc(C(=O)O)c2)c1]

TABLE 3-continued
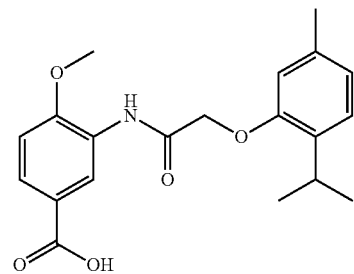 [SMILES: COc1ccc(C(=O)O)cc1NC(=O)COc1cc(C)ccc1C(C)C]
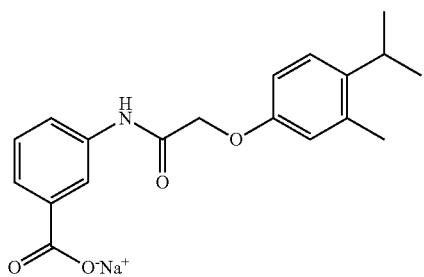
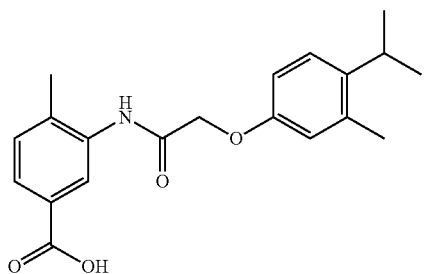 [SMILES: Cc1ccc(C(=O)O)cc1NC(=O)COc1ccc(C(C)C)c(C)c1]
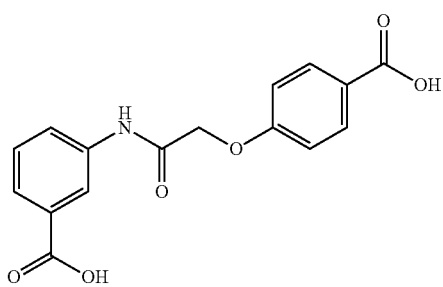 [SMILES: O=C(COc1ccc(C(=O)O)cc1)Nc1cccc(C(=O)O)c1]
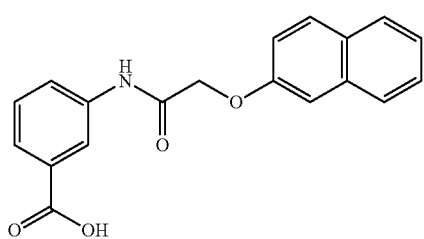 [SMILES: O=C(COc1ccc2ccccc2c1)Nc1cccc(C(=O)O)c1]
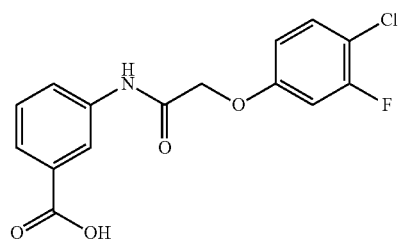 [SMILES: O=C(COc1ccc(Cl)c(F)c1)Nc1cccc(C(=O)O)c1]

TABLE 3-continued
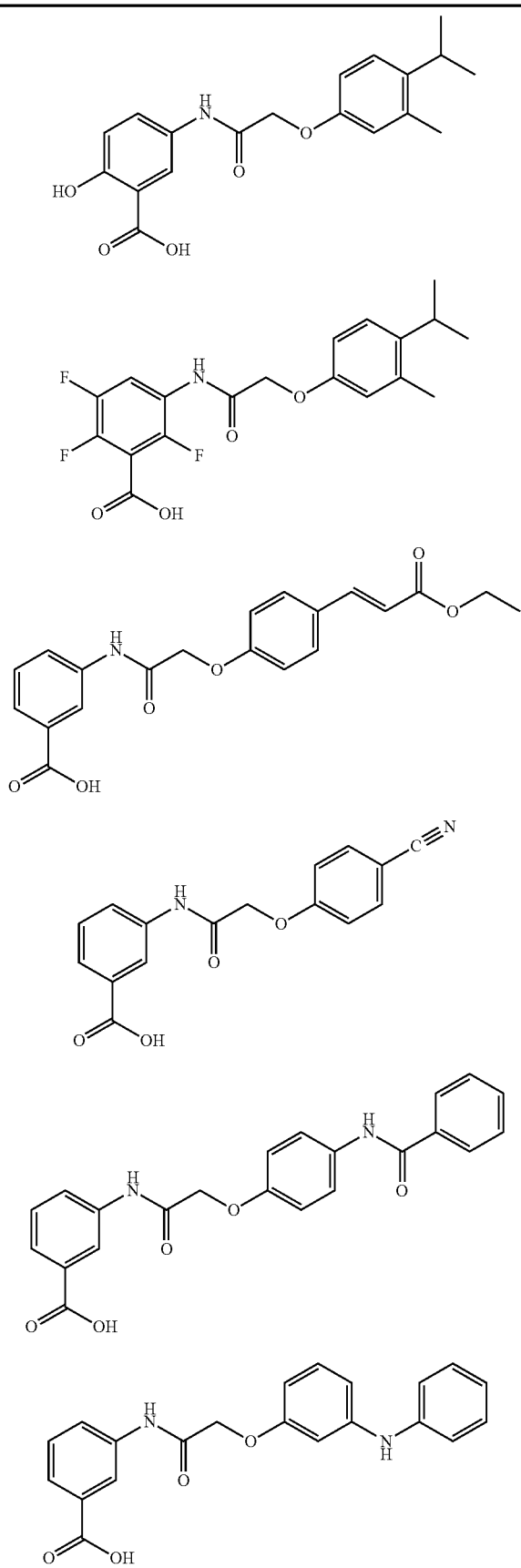

TABLE 3-continued
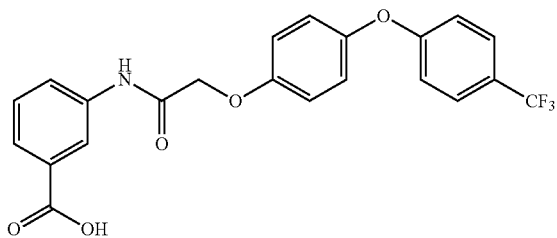 [SMILES: O=C(COc1ccc(Oc2ccc(C(F)(F)F)cc2)cc1)Nc1cccc(C(=O)O)c1]
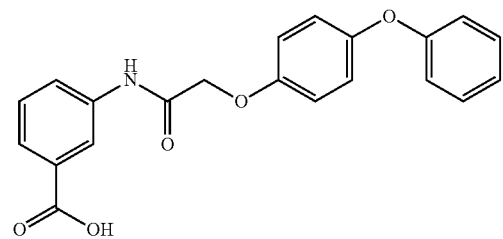 [SMILES: O=C(COc1ccc(Oc2ccccc2)cc1)Nc1cccc(C(=O)O)c1]
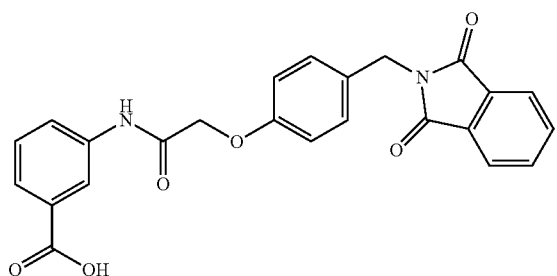 [SMILES: O=C(COc1ccc(CN2C(=O)c3ccccc3C2=O)cc1)Nc1cccc(C(=O)O)c1]
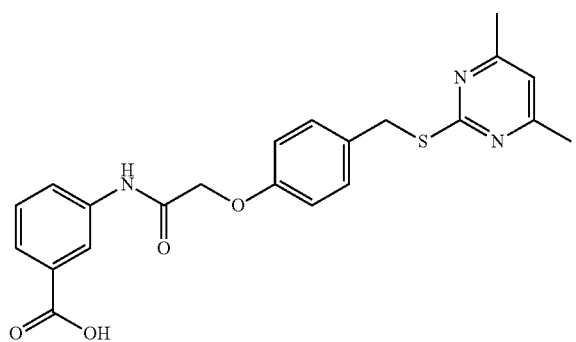 [SMILES: Cc1cc(C)nc(SCc2ccc(OCC(=O)Nc3cccc(C(=O)O)c3)cc2)n1]
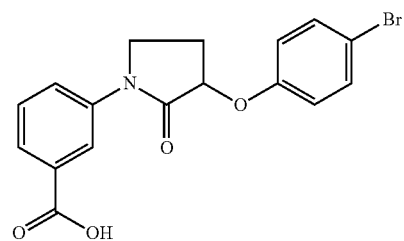 [SMILES: O=C(O)c1cccc(N2CCC(Oc3ccc(Br)cc3)C2=O)c1]
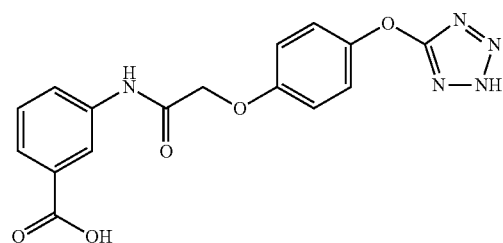 [SMILES: O=C(COc1ccc(Oc2nn[nH]n2)cc1)Nc1cccc(C(=O)O)c1]

TABLE 3-continued
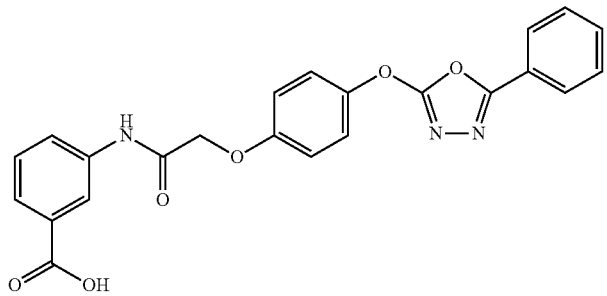 [SMILES: O=C(COc1ccc(Oc2nnc(-c3ccccc3)o2)cc1)Nc1cccc(C(=O)O)c1]
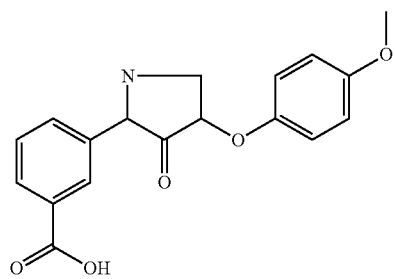 [SMILES: COc1ccc(OC2CNC(c3cccc(C(=O)O)c3)C2=O)cc1]
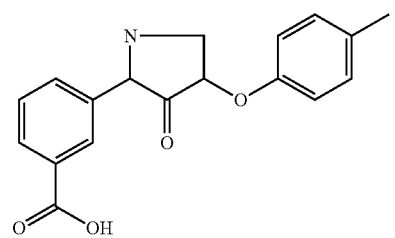 [SMILES: Cc1ccc(OC2CNC(c3cccc(C(=O)O)c3)C2=O)cc1]
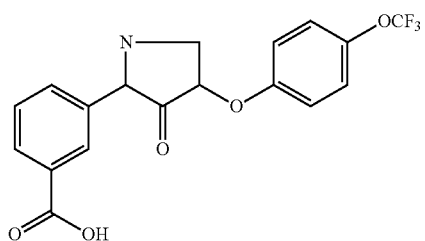 [SMILES: O=C(O)c1cccc(C2NCC(Oc3ccc(OC(F)(F)F)cc3)C2=O)c1]
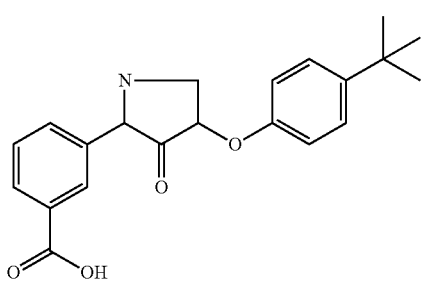 [SMILES: CC(C)(C)c1ccc(OC2CNC(c3cccc(C(=O)O)c3)C2=O)cc1]
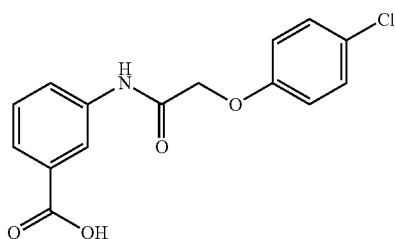 [SMILES: O=C(COc1ccc(Cl)cc1)Nc1cccc(C(=O)O)c1]

TABLE 3-continued
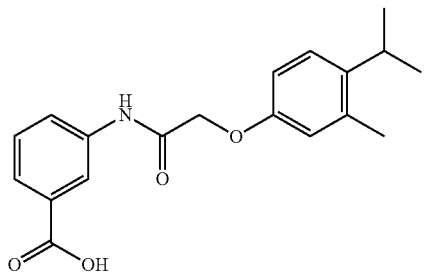 [SMILES: Cc1cc(OCC(=O)Nc2cccc(C(=O)O)c2)ccc1C(C)C]
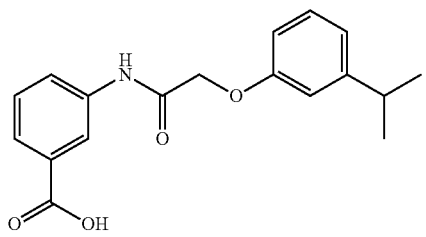 [SMILES: CC(C)c1cccc(OCC(=O)Nc2cccc(C(=O)O)c2)c1]
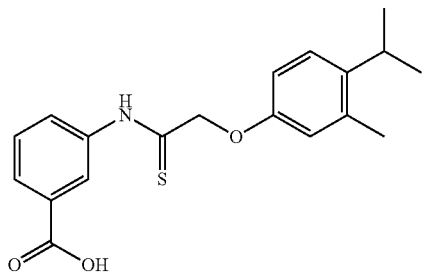
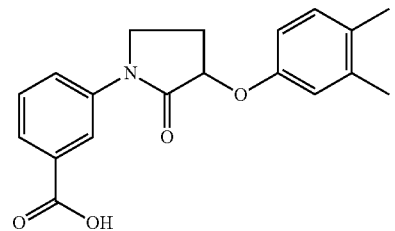 [SMILES: Cc1ccc(OC2CCN(c3cccc(C(=O)O)c3)C2=O)cc1C]
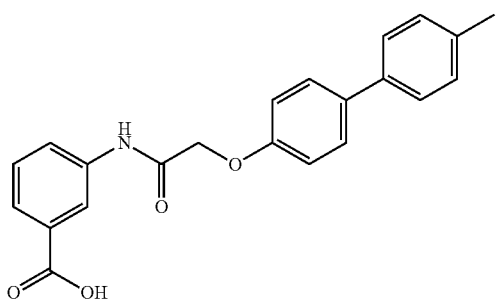 [SMILES: Cc1ccc(-c2ccc(OCC(=O)Nc3cccc(C(=O)O)c3)cc2)cc1]
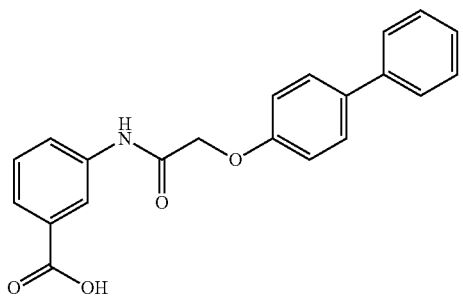 [SMILES: O=C(COc1ccc(-c2ccccc2)cc1)Nc1cccc(C(=O)O)c1]

TABLE 3-continued
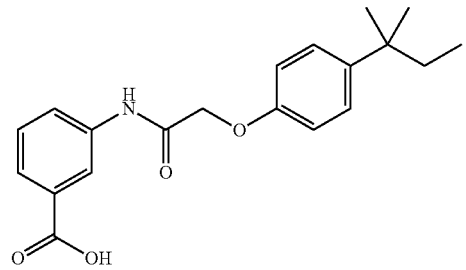 [SMILES: CCC(C)(C)c1ccc(OCC(=O)Nc2cccc(C(=O)O)c2)cc1]
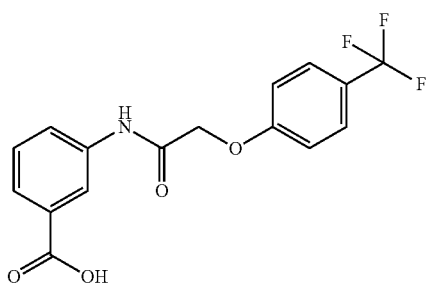 [SMILES: O=C(COc1ccc(C(F)(F)F)cc1)Nc1cccc(C(=O)O)c1]
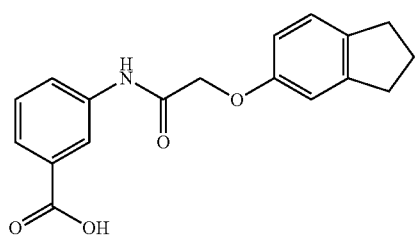 [SMILES: O=C(COc1ccc2c(c1)CCC2)Nc1cccc(C(=O)O)c1]
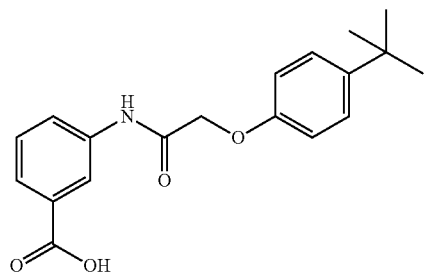 [SMILES: CC(C)(C)c1ccc(OCC(=O)Nc2cccc(C(=O)O)c2)cc1]
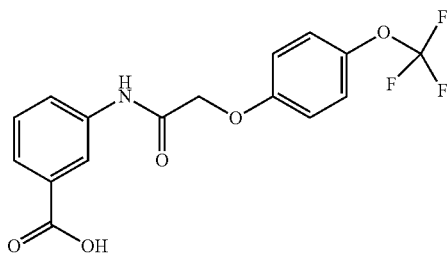 [SMILES: O=C(COc1ccc(OC(F)(F)F)cc1)Nc1cccc(C(=O)O)c1]
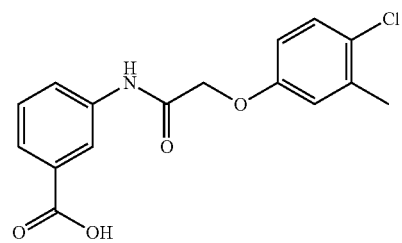 [SMILES: Cc1cc(OCC(=O)Nc2cccc(C(=O)O)c2)ccc1Cl]

TABLE 3-continued
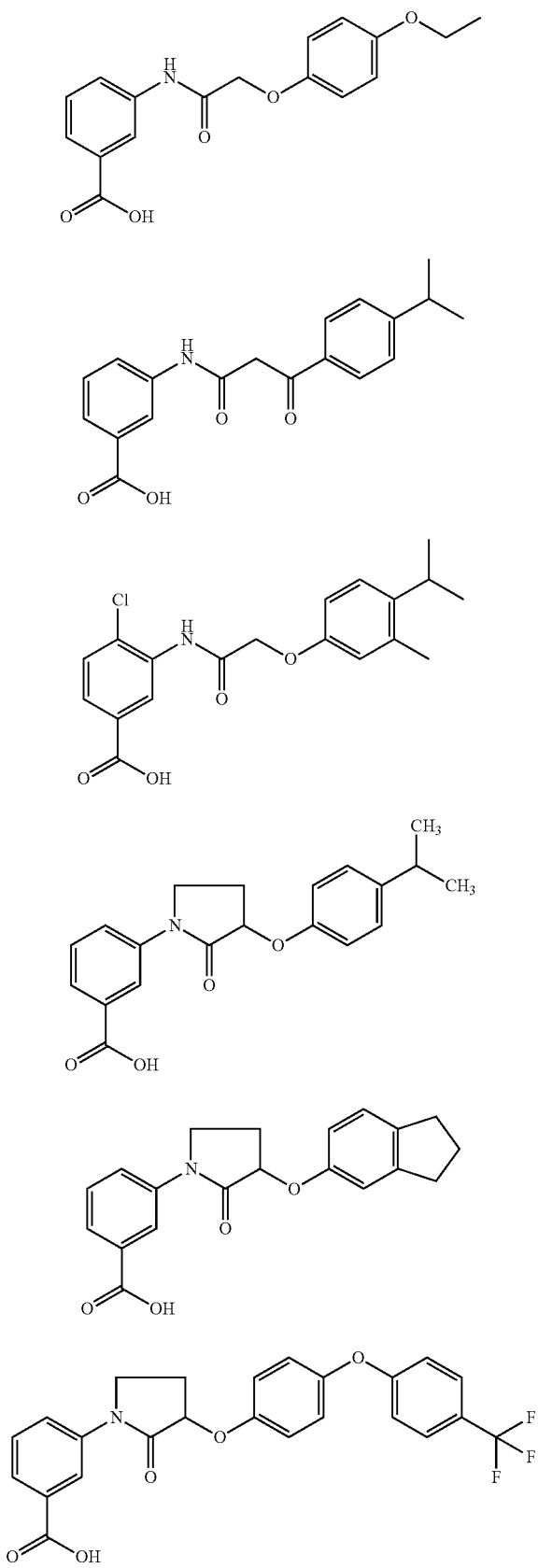

TABLE 3-continued
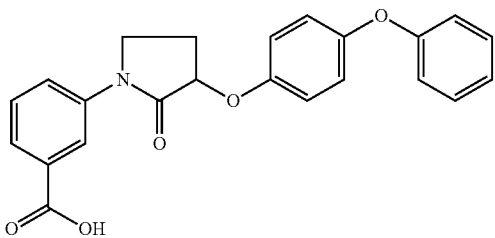 [SMILES: O=C(O)c1cccc(N2CCC(Oc3ccc(Oc4ccccc4)cc3)C2=O)c1]
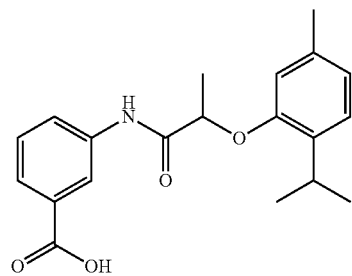 [SMILES: Cc1ccc(C(C)C)c(OC(C)C(=O)Nc2cccc(C(=O)O)c2)c1]
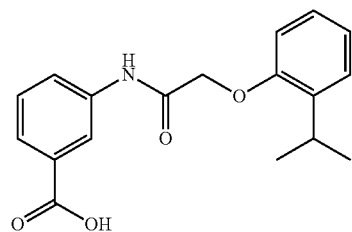 [SMILES: CC(C)c1ccccc1OCC(=O)Nc1cccc(C(=O)O)c1]
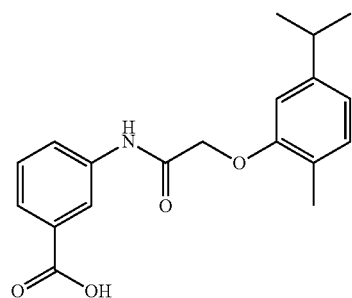 [SMILES: Cc1ccc(C(C)C)cc1OCC(=O)Nc1cccc(C(=O)O)c1]
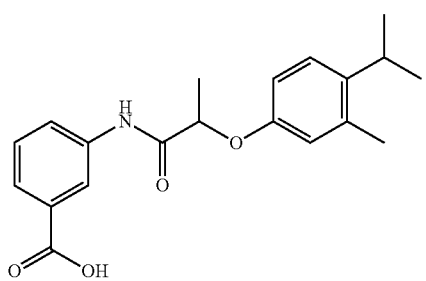 [SMILES: Cc1cc(OC(C)C(=O)Nc2cccc(C(=O)O)c2)ccc1C(C)C]
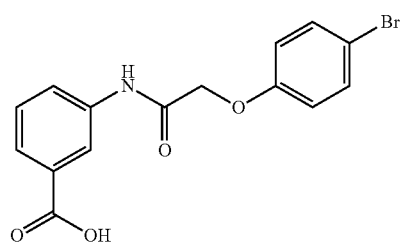 [SMILES: O=C(COc1ccc(Br)cc1)Nc1cccc(C(=O)O)c1]

TABLE 3-continued
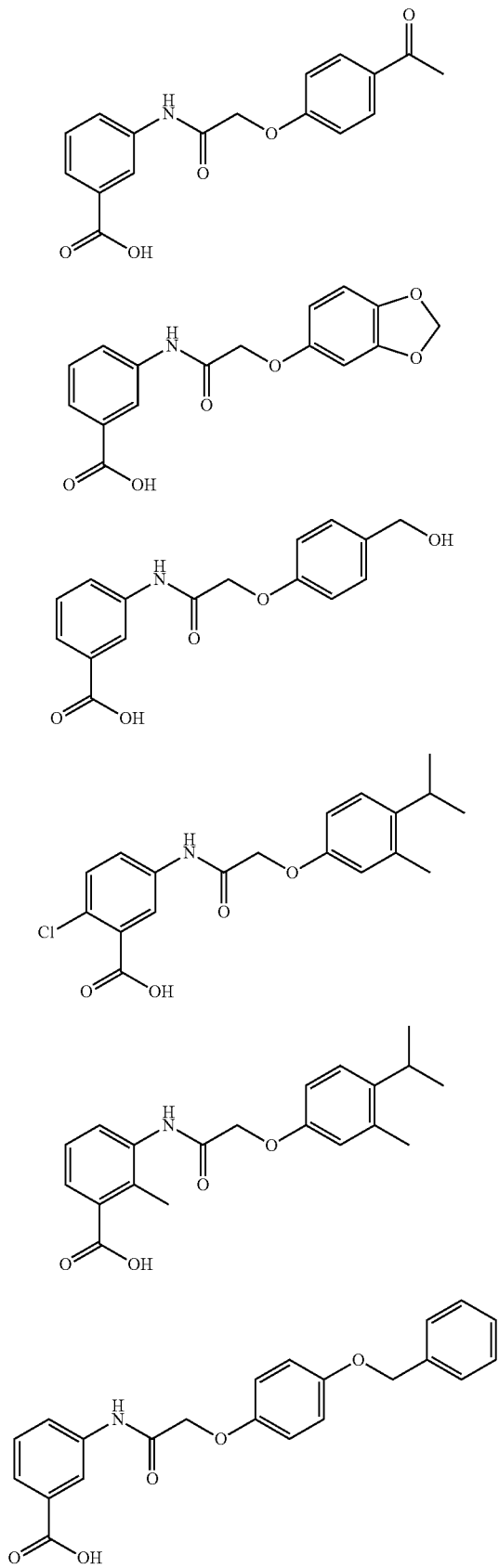

TABLE 3-continued
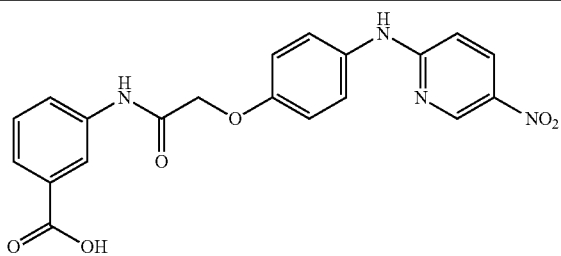
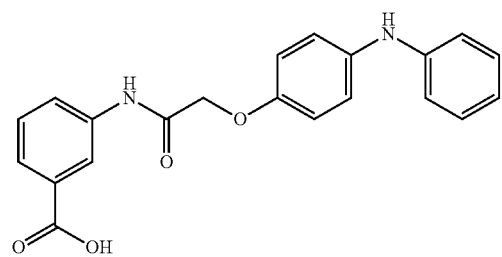 [SMILES: O=C(COc1ccc(Nc2ccccc2)cc1)Nc1cccc(C(=O)O)c1]
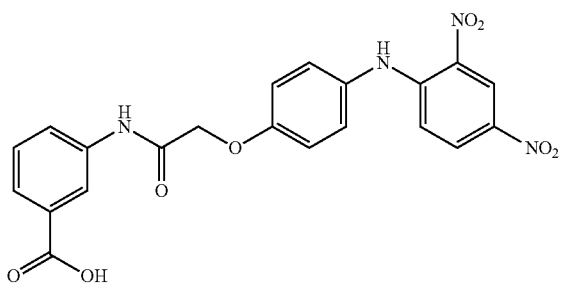 [SMILES: O=C(COc1ccc(Nc2ccc([N+](=O)[O-])cc2[N+](=O)[O-])cc1)Nc1cccc(C(=O)O)c1]
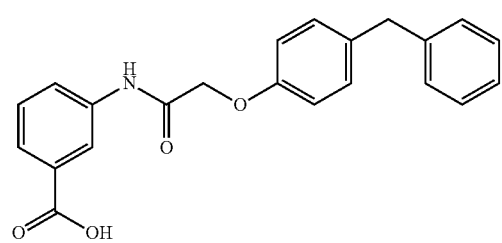 [SMILES: O=C(COc1ccc(Cc2ccccc2)cc1)Nc1cccc(C(=O)O)c1]
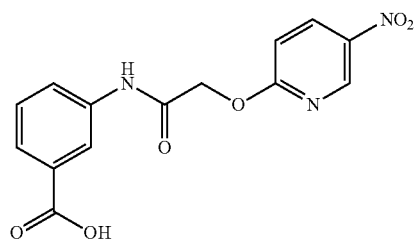 [SMILES: O=C(COc1ccc([N+](=O)[O-])cn1)Nc1cccc(C(=O)O)c1]
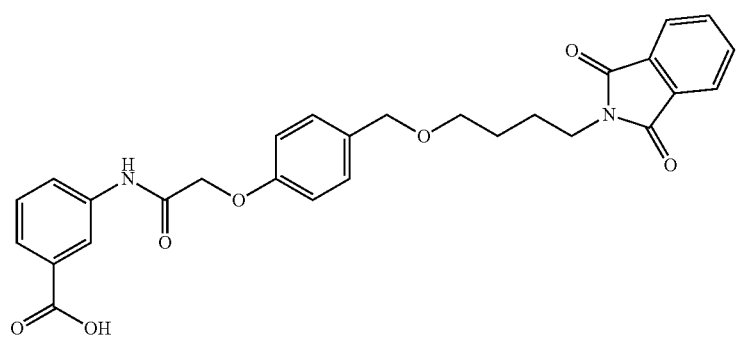 [SMILES: O=C(COc1ccc(COCCCCN2C(=O)c3ccccc3C2=O)cc1)Nc1cccc(C(=O)O)c1]

TABLE 3-continued
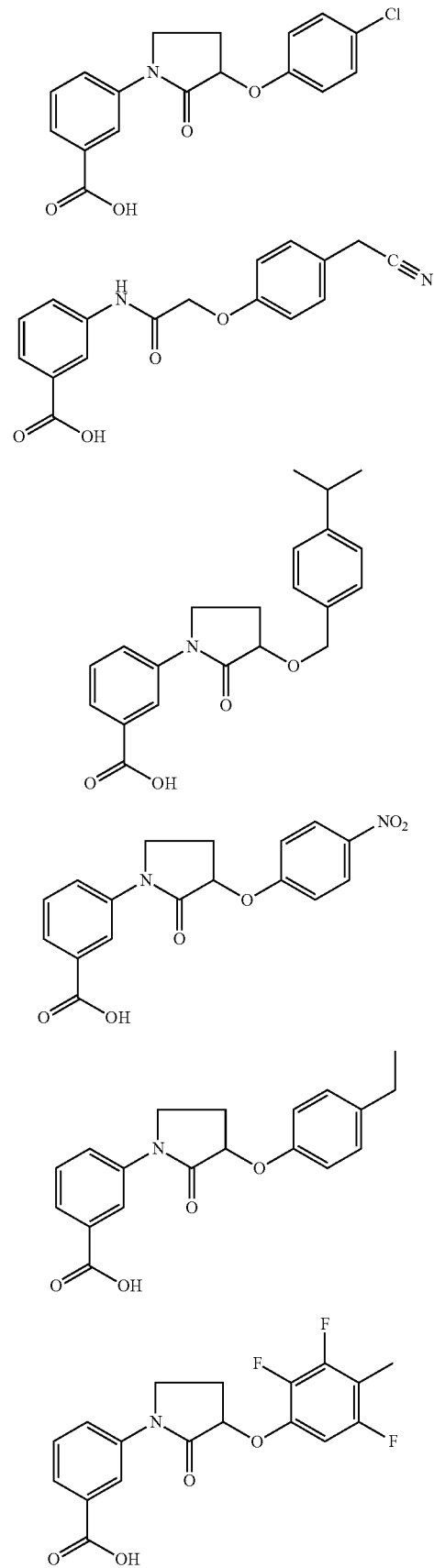

TABLE 3-continued

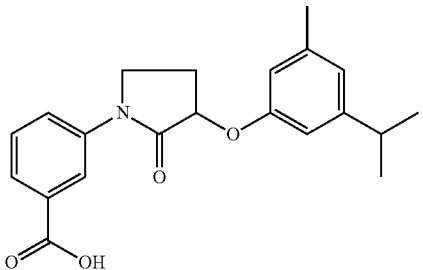 [SMILES: Cc1cc(OC2CCN(c3cccc(C(=O)O)c3)C2=O)cc(C(C)C)c1]

Compounds of formula III can be obtained via standard, well-known synthetic methodology, see e.g., March, J. Advanced Organic Chemistry; Reactions Mechanisms, and Structure, 4th ed., 1992. Starting materials useful for preparing compounds of formula I and intermediates therefore, are commercially available or can be prepared from commercially available materials using known synthetic methods and reagents.

Particular methods for preparing compounds of formula III are disclosed in WO 2004/009533 A1, published Jan. 29, 2004, incorporated by reference herein in its entirety.

In another embodiment, the nonsense codon suppressor is a compound of formula IV:

IV or pharmaceutically acceptable salts, hydrates, clathrates, prodrugs, polymorphs, stereoisomers, including enantiomers, diastereomers, racemates or mixtures of stereoisomers, thereof wherein:

Z is substituted or unsubstituted aryl, substituted or unsubstituted heteroaryl, substituted or unsubstituted cycloalkyl, substituted or unsubstituted alkyl, substituted or unsubstituted alkenyl, substituted or unsubstituted heterocycle, substituted or unsubstituted arylalkyl;

$R^1$ is hydrogen, substituted or unsubstituted alkyl, substituted or unsubstituted cycloalkyl, substituted or unsubstituted heterocycloalkyl, substituted or unsubstituted aryl, substituted or unsubstituted heteroaryl, —$(CH_2CH_2O)_nR^6$ or any biohydrolyzable group;

$R^2$, $R^3$, $R^4$, $R^5$ and $R^6$ are independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy, halogen, $CF_3$, $OCF_3$, $OCHF_2$, CN, COOH, $COOR^7$, $SO_2R^7$, $NO_2$, $NH_2$, or $NR^7)_2$;

each occurrence of $R^7$ is independently hydrogen, substituted or unsubstituted alkyl, substituted or unsubstituted alkenyl, substituted or unsubstituted alkynyl; substituted or unsubstituted cycloalkyl, substituted or unsubstituted heterocycloalkyl, substituted or unsubstituted aryl, substituted or unsubstituted heteroaryl, alkoxy, aryloxy, heteroaryloxy; halogen or $CF_3$; and n is an integer from 1 to 7.

Preferred compounds of formula IV are set forth in Table 4, below.

TABLE 4

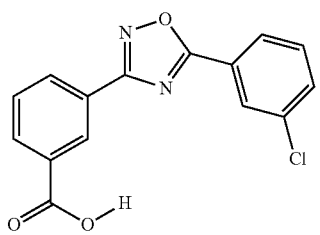 [SMILES: O=C(O)c1cccc(-c2noc(-c3cccc(Cl)c3)n2)c1]

TABLE 4-continued
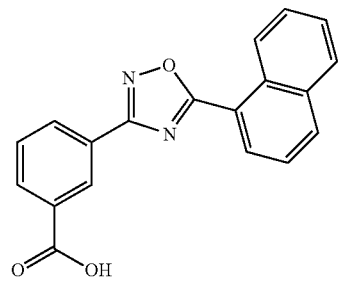 [SMILES: O=C(O)c1cccc(-c2noc(-c3cccc4ccccc34)n2)c1]
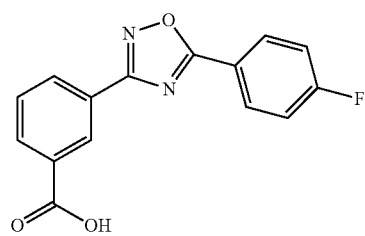 [SMILES: O=C(O)c1cccc(-c2noc(-c3ccc(F)cc3)n2)c1]
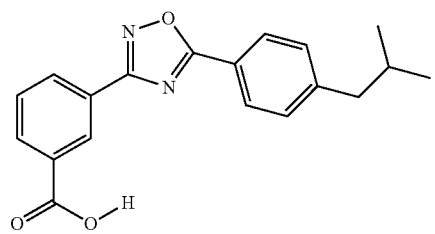 [SMILES: CC(C)Cc1ccc(-c2nc(-c3cccc(C(=O)O)c3)no2)cc1]
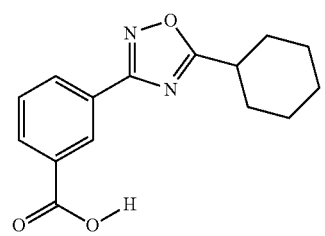 [SMILES: O=C(O)c1cccc(-c2noc(C3CCCCC3)n2)c1]
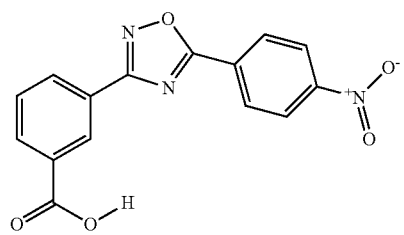 [SMILES: O=C(O)c1cccc(-c2noc(-c3ccc([N+](=O)[O-])cc3)n2)c1]
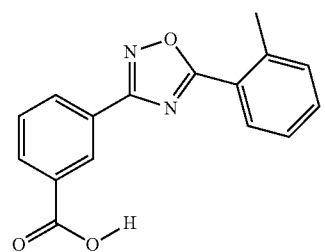 [SMILES: Cc1ccccc1-c1nc(-c2cccc(C(=O)O)c2)no1]

TABLE 4-continued
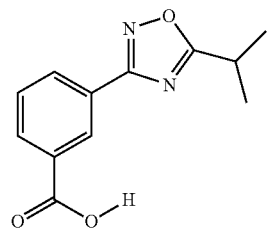
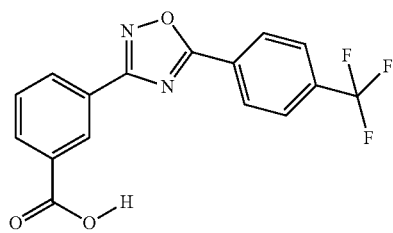 [SMILES: O=C(O)c1cccc(-c2noc(-c3ccc(C(F)(F)F)cc3)n2)c1]
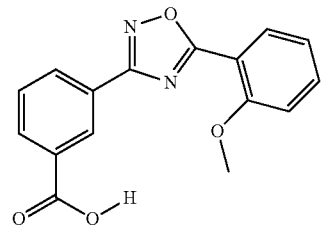 [SMILES: COc1ccccc1-c1nc(-c2cccc(C(=O)O)c2)no1]
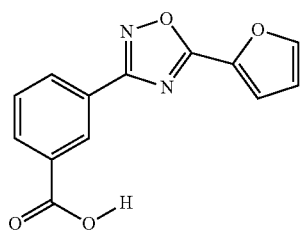 [SMILES: O=C(O)c1cccc(-c2noc(-c3ccco3)n2)c1]
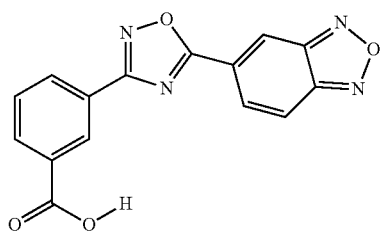 [SMILES: O=C(O)c1cccc(-c2noc(-c3ccc4nonc4c3)n2)c1]
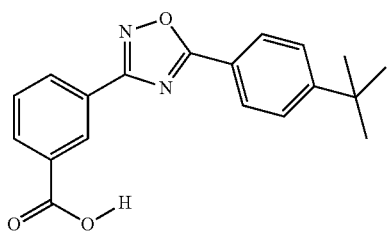 [SMILES: CC(C)(C)c1ccc(-c2nc(-c3cccc(C(=O)O)c3)no2)cc1]

TABLE 4-continued
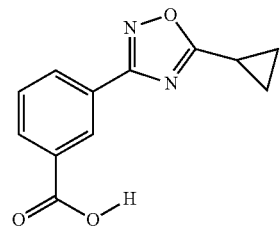 [SMILES: O=C(O)c1cccc(-c2noc(C3CC3)n2)c1]
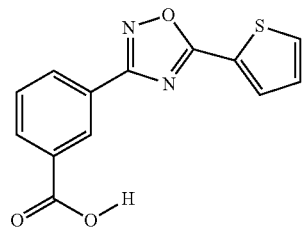 [SMILES: O=C(O)c1cccc(-c2noc(-c3cccs3)n2)c1]
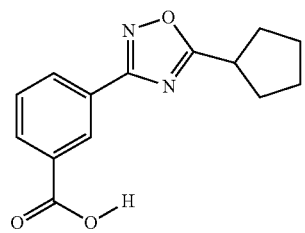 [SMILES: O=C(O)c1cccc(-c2noc(C3CCCC3)n2)c1]
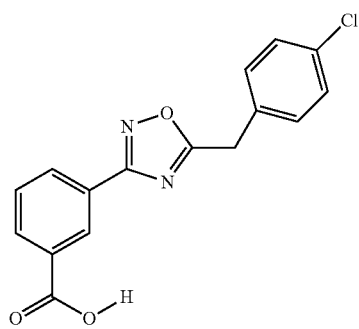 [SMILES: O=C(O)c1cccc(-c2noc(Cc3ccc(Cl)cc3)n2)c1]
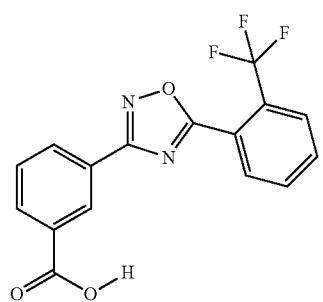 [SMILES: O=C(O)c1cccc(-c2noc(-c3ccccc3C(F)(F)F)n2)c1]
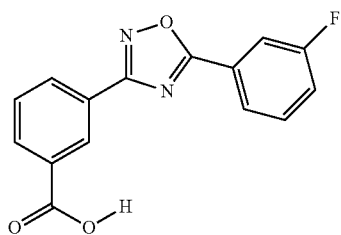 [SMILES: O=C(O)c1cccc(-c2noc(-c3cccc(F)c3)n2)c1]

TABLE 4-continued
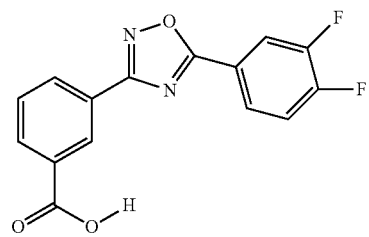 [SMILES: O=C(O)c1cccc(-c2noc(-c3ccc(F)c(F)c3)n2)c1]
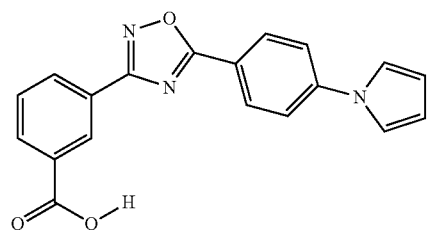 [SMILES: O=C(O)c1cccc(-c2noc(-c3ccc(-n4cccc4)cc3)n2)c1]
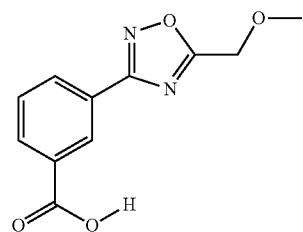 [SMILES: COCc1nc(-c2cccc(C(=O)O)c2)no1]
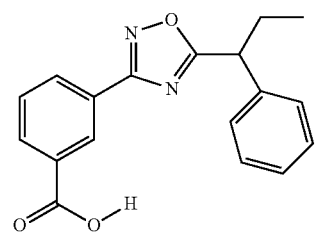 [SMILES: CCC(c1ccccc1)c1nc(-c2cccc(C(=O)O)c2)no1]
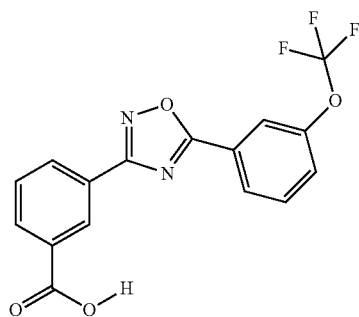 [SMILES: O=C(O)c1cccc(-c2noc(-c3cccc(OC(F)(F)F)c3)n2)c1]
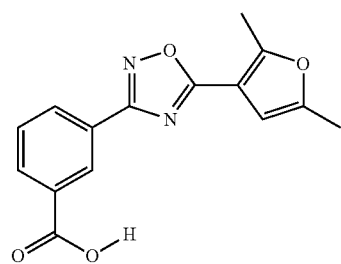 [SMILES: Cc1cc(-c2nc(-c3cccc(C(=O)O)c3)no2)c(C)o1]

TABLE 4-continued
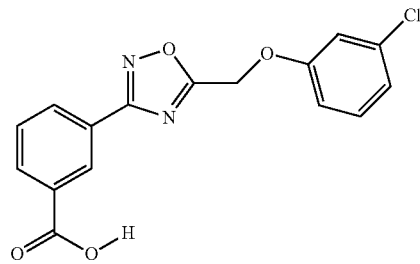 [SMILES: O=C(O)c1cccc(-c2noc(COc3cccc(Cl)c3)n2)c1]
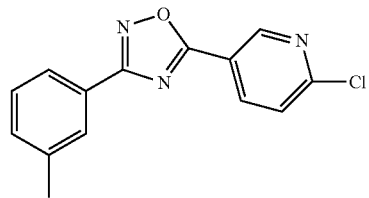 [SMILES: Cc1cccc(-c2noc(-c3ccc(Cl)nc3)n2)c1]
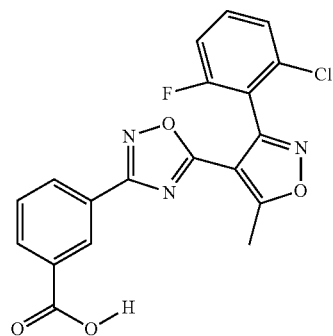 [SMILES: Cc1onc(-c2c(F)cccc2Cl)c1-c1nc(-c2cccc(C(=O)O)c2)no1]
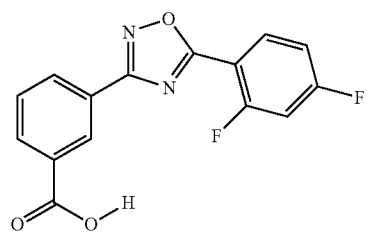 [SMILES: O=C(O)c1cccc(-c2noc(-c3ccc(F)cc3F)n2)c1]
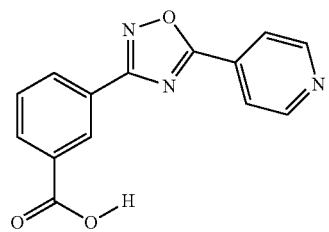 [SMILES: O=C(O)c1cccc(-c2noc(-c3ccncc3)n2)c1]
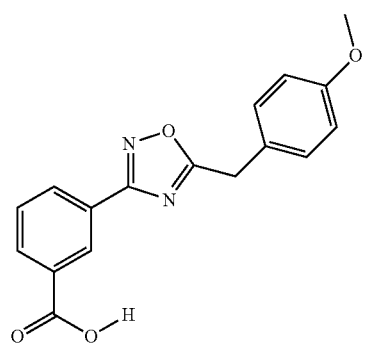 [SMILES: COc1ccc(Cc2nc(-c3cccc(C(=O)O)c3)no2)cc1]

TABLE 4-continued
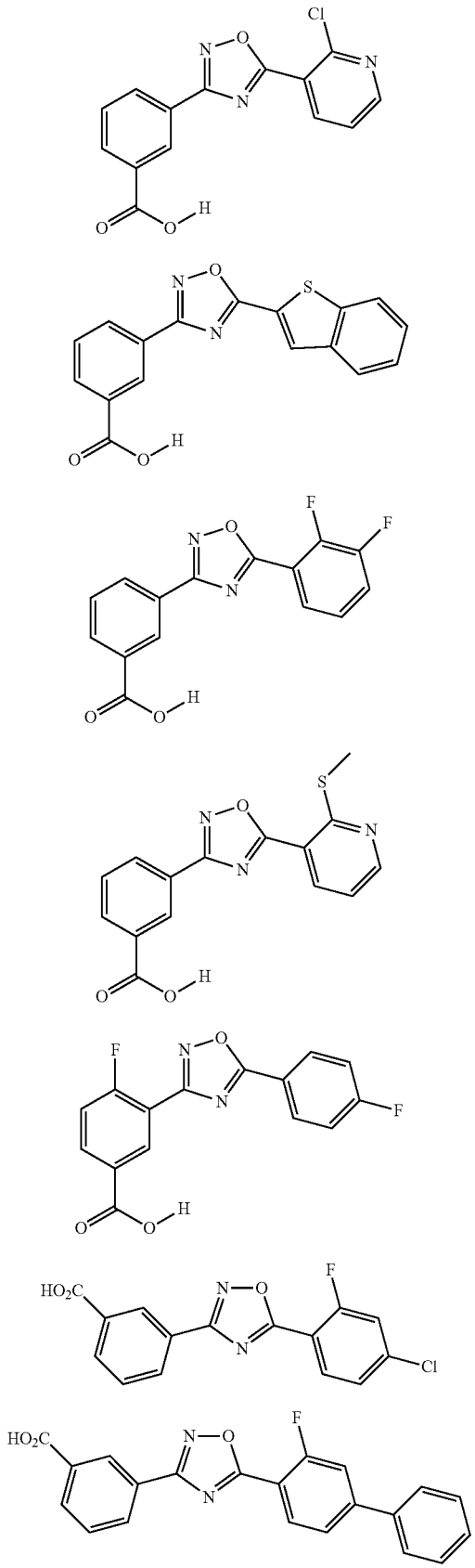

TABLE 4-continued
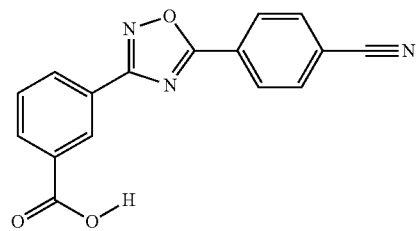 [SMILES: N#Cc1ccc(-c2nc(-c3cccc(C(=O)O)c3)no2)cc1]
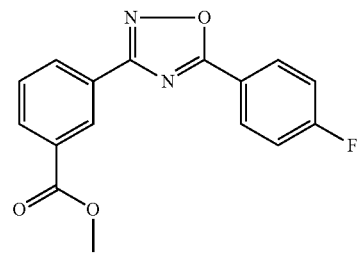 [SMILES: COC(=O)c1cccc(-c2noc(-c3ccc(F)cc3)n2)c1]
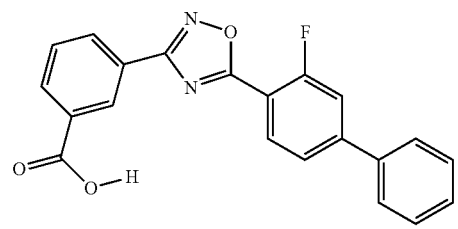 [SMILES: O=C(O)c1cccc(-c2noc(-c3ccc(-c4ccccc4)cc3F)n2)c1]
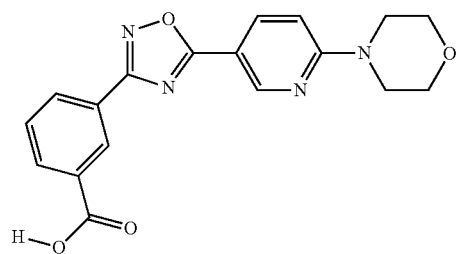 [SMILES: O=C(O)c1cccc(-c2noc(-c3ccc(N4CCOCC4)nc3)n2)c1]
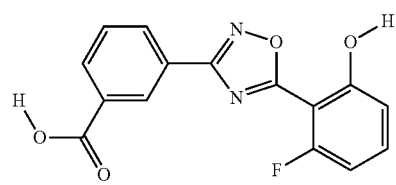 [SMILES: O=C(O)c1cccc(-c2noc(-c3c(O)cccc3F)n2)c1]
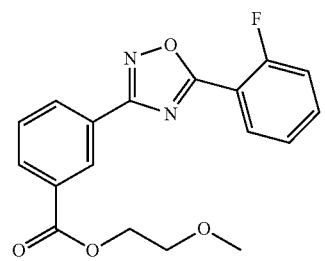 [SMILES: COCCOC(=O)c1cccc(-c2noc(-c3ccccc3F)n2)c1]

TABLE 4-continued
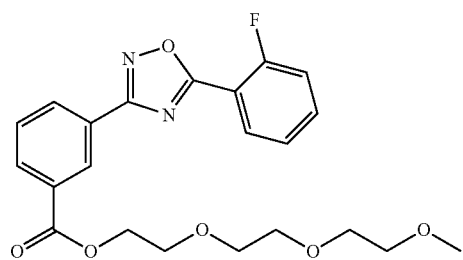 [SMILES: COCCOCCOCCOC(=O)c1cccc(-c2noc(-c3ccccc3F)n2)c1]
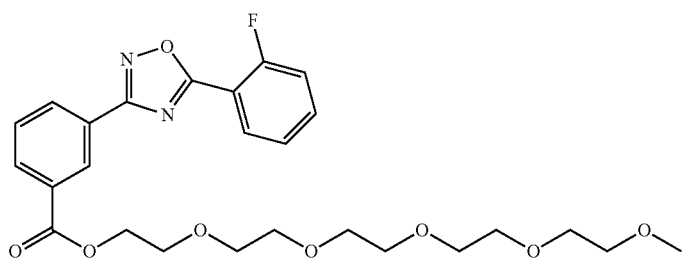 [SMILES: COCCOCCOCCOCCOCCOC(=O)c1cccc(-c2noc(-c3ccccc3F)n2)c1]
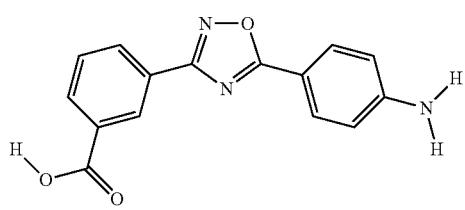 [SMILES: Nc1ccc(-c2nc(-c3cccc(C(=O)O)c3)no2)cc1]
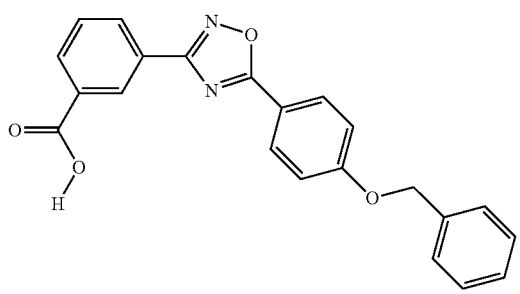 [SMILES: O=C(O)c1cccc(-c2noc(-c3ccc(OCc4ccccc4)cc3)n2)c1]
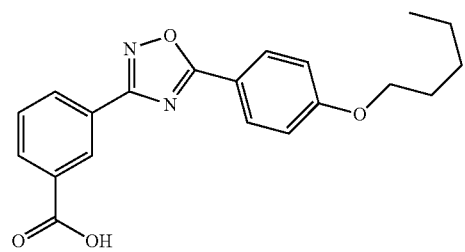 [SMILES: CCCCCOc1ccc(-c2nc(-c3cccc(C(=O)O)c3)no2)cc1]
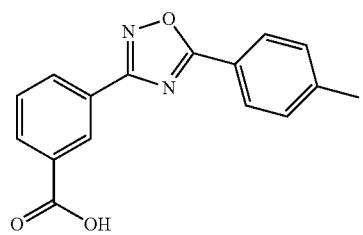 [SMILES: Cc1ccc(-c2nc(-c3cccc(C(=O)O)c3)no2)cc1]

TABLE 4-continued
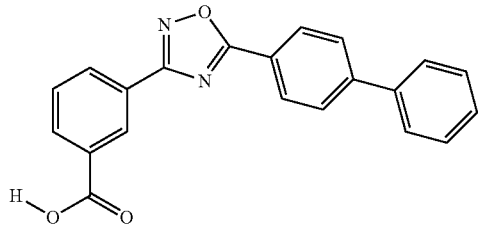 [SMILES: O=C(O)c1cccc(-c2noc(-c3ccc(-c4ccccc4)cc3)n2)c1]
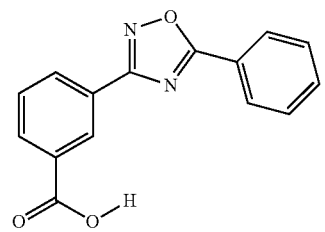 [SMILES: O=C(O)c1cccc(-c2noc(-c3ccccc3)n2)c1]
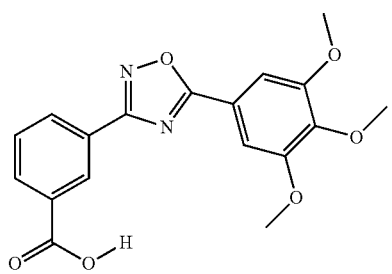 [SMILES: COc1cc(-c2nc(-c3cccc(C(=O)O)c3)no2)cc(OC)c1OC]
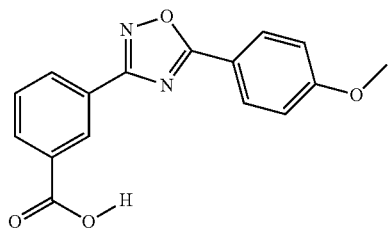 [SMILES: COc1ccc(-c2nc(-c3cccc(C(=O)O)c3)no2)cc1]
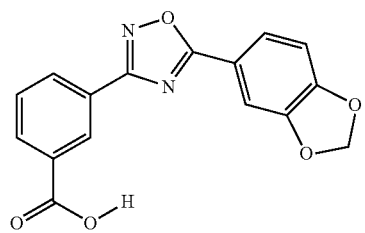 [SMILES: O=C(O)c1cccc(-c2noc(-c3ccc4c(c3)OCO4)n2)c1]
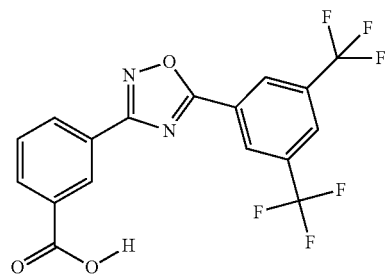 [SMILES: O=C(O)c1cccc(-c2noc(-c3cc(C(F)(F)F)cc(C(F)(F)F)c3)n2)c1]

TABLE 4-continued
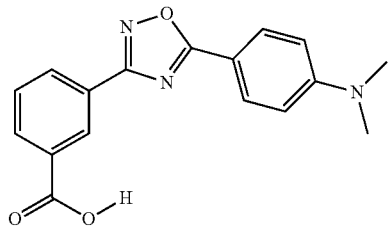 [SMILES: CN(C)c1ccc(-c2nc(-c3cccc(C(=O)O)c3)no2)cc1]
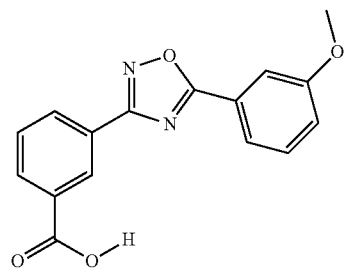 [SMILES: COc1cccc(-c2nc(-c3cccc(C(=O)O)c3)no2)c1]
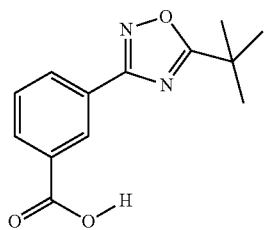 [SMILES: CC(C)(C)c1nc(-c2cccc(C(=O)O)c2)no1]
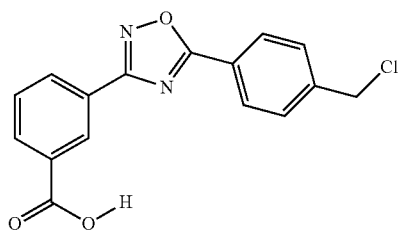 [SMILES: O=C(O)c1cccc(-c2noc(-c3ccc(CCl)cc3)n2)c1]
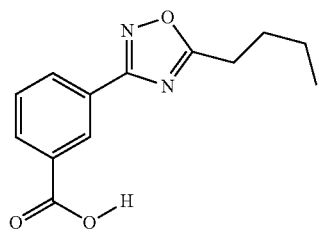 [SMILES: CCCCc1nc(-c2cccc(C(=O)O)c2)no1]
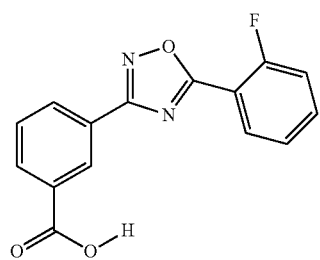 [SMILES: O=C(O)c1cccc(-c2noc(-c3ccccc3F)n2)c1]

TABLE 4-continued
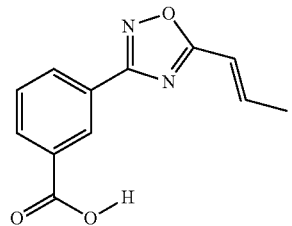 [SMILES: C/C=C/c1nc(-c2cccc(C(=O)O)c2)no1]
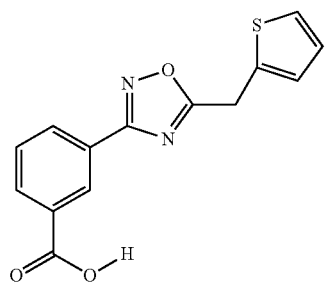 [SMILES: O=C(O)c1cccc(-c2noc(Cc3cccs3)n2)c1]
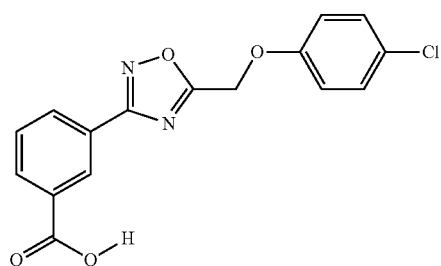 [SMILES: O=C(O)c1cccc(-c2noc(COc3ccc(Cl)cc3)n2)c1]
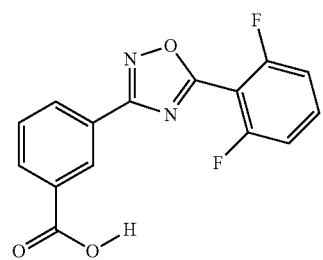 [SMILES: O=C(O)c1cccc(-c2noc(-c3c(F)cccc3F)n2)c1]
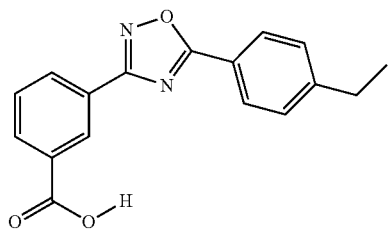 [SMILES: CCc1ccc(-c2nc(-c3cccc(C(=O)O)c3)no2)cc1]
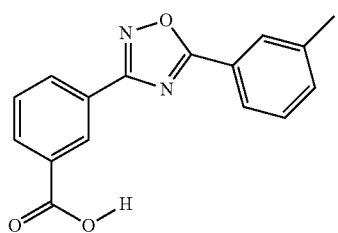 [SMILES: Cc1cccc(-c2nc(-c3cccc(C(=O)O)c3)no2)c1]

TABLE 4-continued
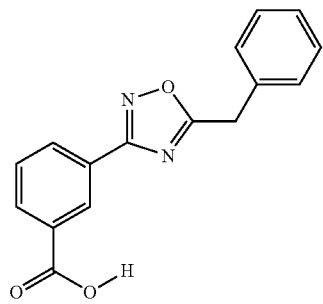 [SMILES: O=C(O)c1cccc(-c2noc(Cc3ccccc3)n2)c1]
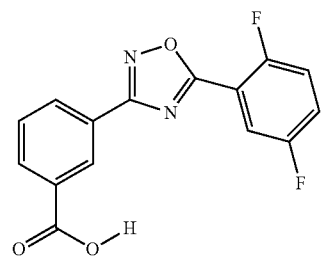 [SMILES: O=C(O)c1cccc(-c2noc(-c3cc(F)ccc3F)n2)c1]
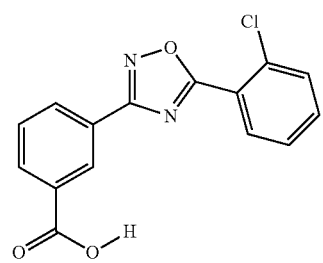
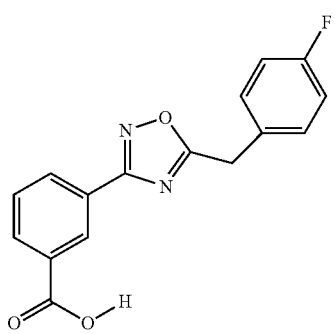 [SMILES: O=C(O)c1cccc(-c2noc(Cc3ccc(F)cc3)n2)c1]
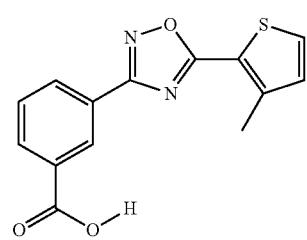 [SMILES: Cc1ccsc1-c1nc(-c2cccc(C(=O)O)c2)no1]
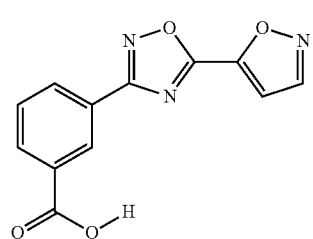 [SMILES: O=C(O)c1cccc(-c2noc(-c3ccno3)n2)c1]

TABLE 4-continued
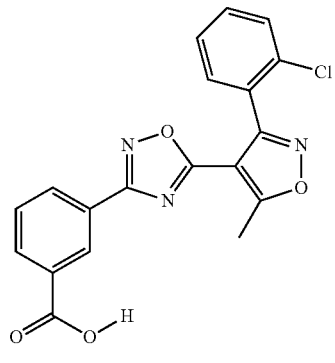 [SMILES: Cc1onc(-c2ccccc2Cl)c1-c1nc(-c2cccc(C(=O)O)c2)no1]
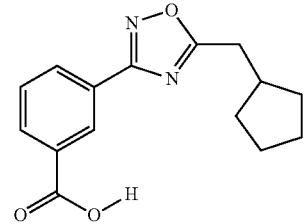 [SMILES: O=C(O)c1cccc(-c2noc(CC3CCCC3)n2)c1]
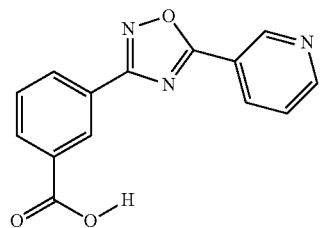 [SMILES: O=C(O)c1cccc(-c2noc(-c3cccnc3)n2)c1]
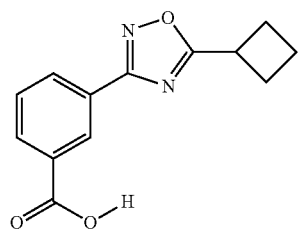 [SMILES: O=C(O)c1cccc(-c2noc(C3CCC3)n2)c1]
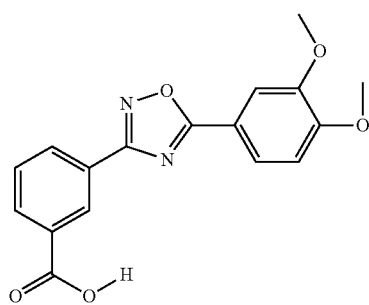 [SMILES: COc1ccc(-c2nc(-c3cccc(C(=O)O)c3)no2)cc1OC]
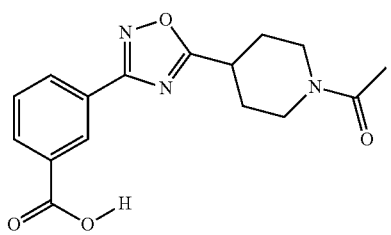 [SMILES: CC(=O)N1CCC(c2nc(-c3cccc(C(=O)O)c3)no2)CC1]

TABLE 4-continued
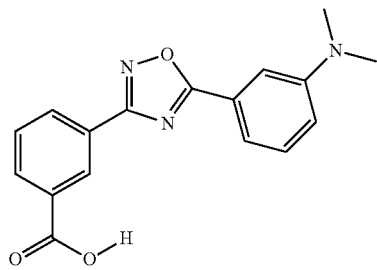 [SMILES: CN(C)c1cccc(-c2nc(-c3cccc(C(=O)O)c3)no2)c1]
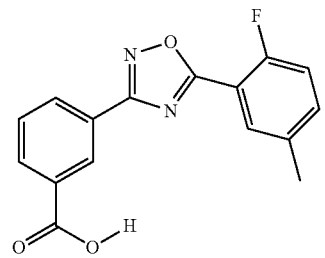 [SMILES: Cc1ccc(F)c(-c2nc(-c3cccc(C(=O)O)c3)no2)c1]
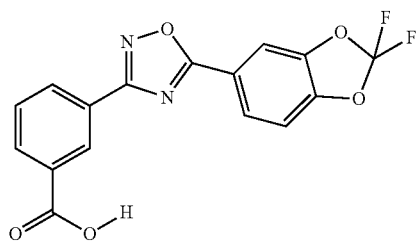 [SMILES: O=C(O)c1cccc(-c2noc(-c3ccc4c(c3)OC(F)(F)O4)n2)c1]
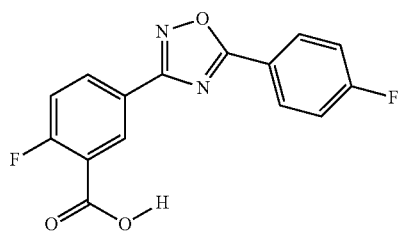 [SMILES: O=C(O)c1cc(-c2noc(-c3ccc(F)cc3)n2)ccc1F]
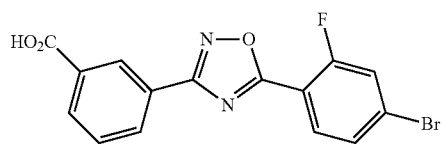 [SMILES: O=C(O)c1cccc(-c2noc(-c3ccc(Br)cc3F)n2)c1]
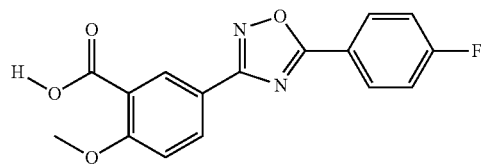 [SMILES: COc1ccc(-c2noc(-c3ccc(F)cc3)n2)cc1C(=O)O]
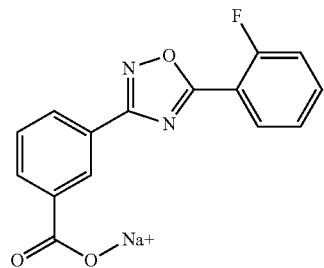

TABLE 4-continued
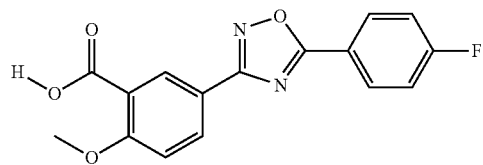 [SMILES: COc1ccc(-c2noc(-c3ccc(F)cc3)n2)cc1C(=O)O]
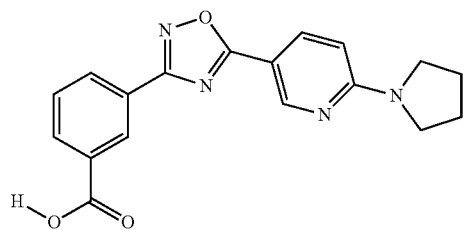 [SMILES: O=C(O)c1cccc(-c2noc(-c3ccc(N4CCCC4)nc3)n2)c1]
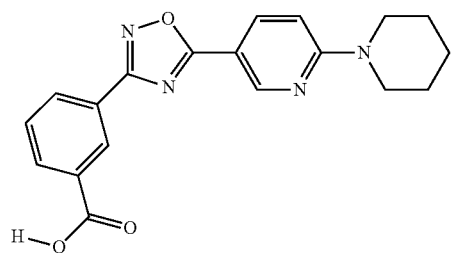 [SMILES: O=C(O)c1cccc(-c2noc(-c3ccc(N4CCCCC4)nc3)n2)c1]
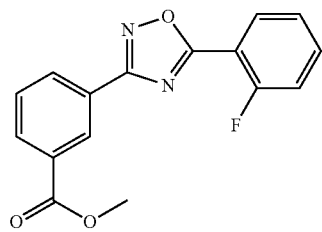 [SMILES: COC(=O)c1cccc(-c2noc(-c3ccccc3F)n2)c1]
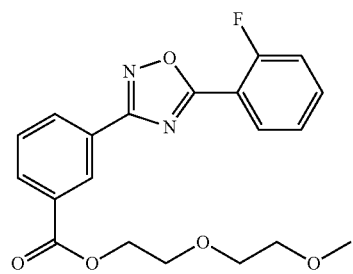 [SMILES: COCCOCCOC(=O)c1cccc(-c2noc(-c3ccccc3F)n2)c1]
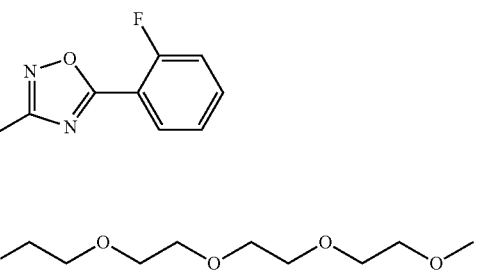

TABLE 4-continued

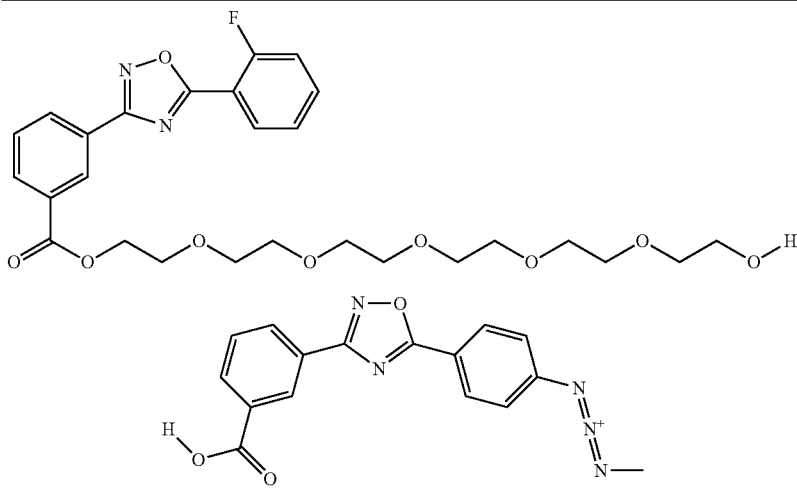

Compounds of formula IV can be obtained via standard, well-known synthetic methodology, see e.g., March, J. Advanced Organic Chemistry; Reactions Mechanisms, and Structure, 4th ed., 1992. Starting materials useful for preparing compounds of formula I and intermediates therefore, are commercially available or can be prepared from commercially available materials using known synthetic methods and reagents.

Particular methods for preparing compounds of formula IV are disclosed in US 2004-0204461 A1, published Oct. 14, 2004, incorporated by reference herein in its entirety.

In another embodiment, the nonsense codon suppressor is a compound of formula V:

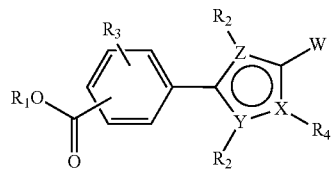

or pharmaceutically acceptable salts, hydrates, clathrates, prodrugs, polymorphs, stereoisomers, including enantiomers, diastereomers, racemates or mixtures of stereoisomers, thereof wherein:

X, Y, and Z are independently selected from N, S, O, and C wherein at least one of X, Y or Z is a heteroatom;

$R_1$ is hydrogen, a $C_1$-$C_6$ alkyl, or Na$^+$, or Mg$^{2+}$;

$R_2$ is independently absent; a hydrogen; a —CH═N—OH group; a cyano group; a $C_1$-$C_6$ alkyl which is optionally substituted with a hydroxy group; or a carbonyl group which is optionally substituted with a hydrogen, a hydroxyl, or a $C_1$-$C_4$ alkoxy group;

$R_3$ is independently absent, a halogen, a hydroxy, a $C_1$-$C_6$ alkyl, $C_1$-$C_4$ alkoxy, or a nitro group;

$R_4$ is independently absent, a hydrogen, a $C_1$-$C_6$ alkyl, or when taken together with W, $R_4$ may be a bond, and W and the heterocycle to which $R_4$ and W are attached form an eleven to thirteen membered hetero-tricycle ring structure;

W is selected from:

(a) a $C_2$-$C_6$ alkynyl, optionally substituted with a phenyl;

(b) a $C_1$-$C_8$ straight chain or branched chain alkyl which is optionally substituted with one or more of the following independently selected groups: a $C_1$-$C_6$ alkyl; a halogen; a —C(═O)—NH-phenyl which phenyl is optionally substituted with one or more independently selected halogens or $C_1$-$C_4$ alkyl groups; a five to six-membered heterocycle; a $C_6$-$C_8$ aryl which is optionally substituted with one or more groups independently selected from a hydroxy, a halogen, a $C_1$-$C_4$ alkyl group, a $C_1$-$C_4$ haloalkyl group, a $C_1$-$C_4$ alkoxy group or an amino group which is optionally substituted with one or more $C_1$-$C_4$ alkyl groups; an aryloxy which is optionally substituted with one or more of the following independently selected groups: a hydroxy, a halogen, a $C_1$-$C_4$ alkyl group, a $C_1$-$C_4$ haloalkyl group, a $C_1$-$C_4$ alkoxy group or an amino group which is optionally substituted with one or more $C_1$-$C_4$ alkyl groups;

(c) $C_2$ to $C_8$ alkenyl;

(d) a $C_3$-$C_8$ cycloalkyl optionally substituted with a $C_1$-$C_6$ alkyl;

(e) a $C_6$-$C_8$ aryl which is optionally substituted with one or more of the following independently selected groups: a hydroxy; a halogen; a $C_1$-$C_4$ straight chain or branched chain alkyl which is optionally substituted with one or more independently selected halogen or hydroxy groups; a $C_1$-$C_4$ alkoxy which is optionally substituted with one or more independently selected halogen or phenyl groups; a $C_3$-$C_8$ cycloalkyl which is optionally substituted with one or more independently selected $C_1$-$C_4$ alkyl groups; a $C_6$-$C_8$ aryl which is optionally substituted with one or more independently selected $C_1$-$C_4$ alkyl groups; an aryloxy which is optionally substituted with one or more of the following independently selected groups: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more independently selected $C_1$-$C_4$ alkyl groups; a five to six-membered heterocycle which is optionally substituted with one or more independently selected $C_1$-$C_4$ alkyl, oxo, or $C_6$-$C_8$ aryl which is optionally substituted with one or more of the following independently selected groups: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more independently selected $C_1$-$C_4$ alkyl groups; a naphthyl group which is optionally substituted with an amino or aminoalkyl or alkoxy group; a —C(O)—NR$_x$R$_y$ group; a —C(O)—R$_x$ group; a isoindole-1,3-dione group; a nitro group; a cyano group; a —SO$_3$H group; alkylthio group; alkyl sulfonyl group; a —NR$_x$—C(O)—R$_z$ group; a —NR$_x$R$_y$ group; a —NR$_x$—SO$_2$—R$_z$ group; a —NR$_x$—C(O)—NR$_x$R$_y$ group; a —NR$_x$—C(O)O—R$_z$ group;

(f) a C$_{10}$-C$_{14}$ aryl group optionally substituted with one or more independently selected halogens, amino groups or aminoalkyl groups, or alkoxy groups;

(g) a —C(O)—NR$_x$R$_y$ group;

(h) a five or six membered heterocycle which is optionally substituted with one or more independently selected oxo groups; halogens; C$_1$-C$_4$ alkyl groups; C$_1$-C$_4$ alkoxy groups; C$_1$-C$_4$ haloalkyl groups; C$_1$-C$_4$ haloalkoxy groups; aryloxy groups; —NR$_x$R$_y$ groups; alkylthio groups; —C(O)—R$_x$ groups; or C$_6$ to C$_8$ aryl groups which are optionally substituted with one or more independently selected halogens, C$_1$-C$_4$ alkyl groups, C$_1$-C$_4$ alkoxy groups;

(i) a heterocycle group having two to three ring structures that is optionally substituted with one or more independently selected halogens, oxo groups, C$_1$-C$_4$ alkyl groups, C$_1$-C$_4$ haloalkyl groups, or C$_1$-C$_4$ alkoxy groups;

(j) or W together with R$_4$, including where R$_4$ is a bond, and the heterocycle to which R$_4$ and W are attached form an eleven to thirteen membered hetero-tricycle ring structure;

wherein R$_x$ is hydrogen, a C$_1$-C$_6$ alkyl group, or R$_x$ and R$_y$ together with the atoms to which they are attached form a four to seven membered carbocycle or heterocycle;

R$_y$ is hydrogen, a C$_1$-C$_6$ alkyl group; an aryl group optionally substituted with one or more independently selected C$_1$-C$_4$ alkyl groups, or R$_x$ and R$_y$ together with the atoms to which they are attached form a four to seven membered carbocycle or heterocycle; and R$_z$ is an C$_1$-C$_6$ alkyl optionally substituted with an aryl or a halogen; or an aryl optionally substituted with a halogen, a C$_1$-C$_6$ alkyl, or a C$_1$-C$_6$ alkoxy.

Preferred compounds of formula V are set forth in Table 5, below.

TABLE 5

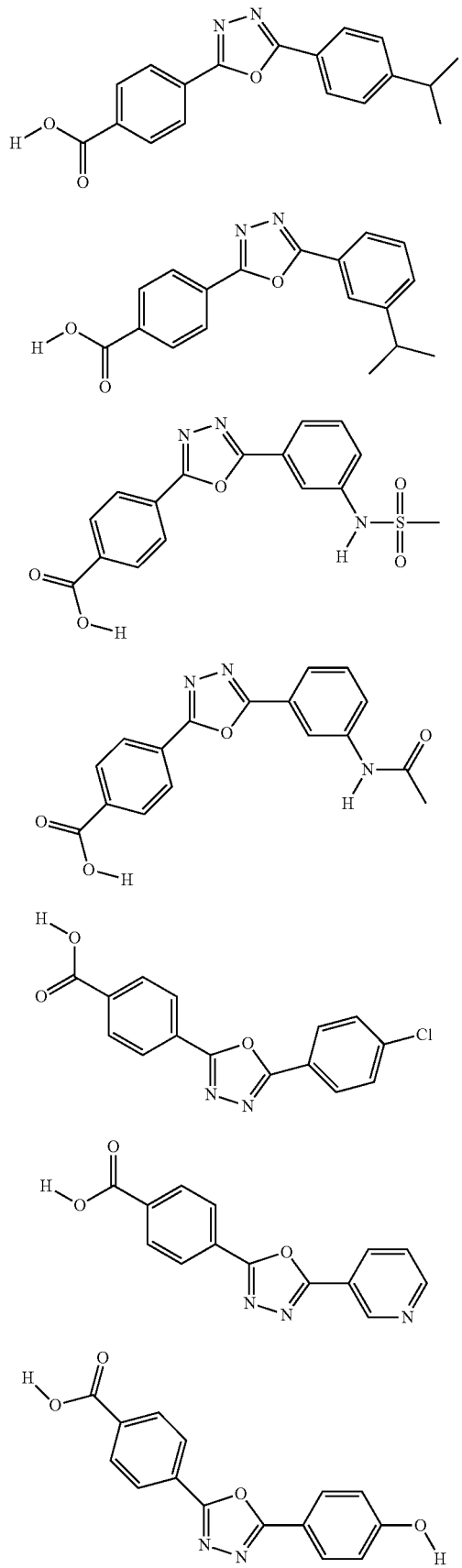

TABLE 5-continued
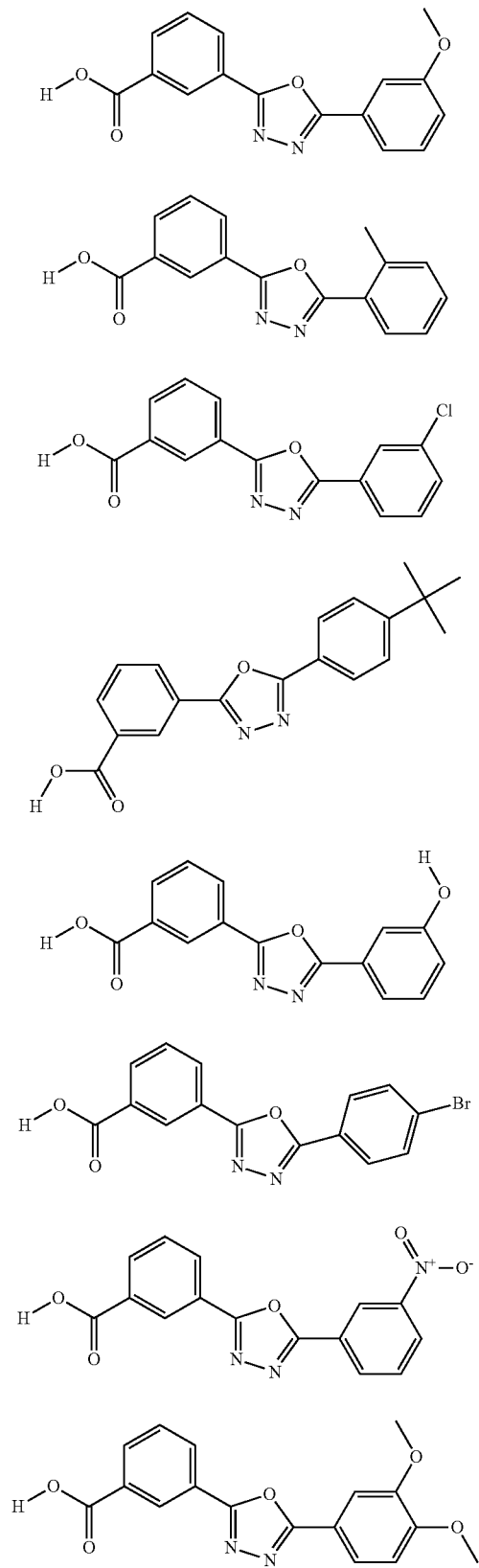
TABLE 5-continued
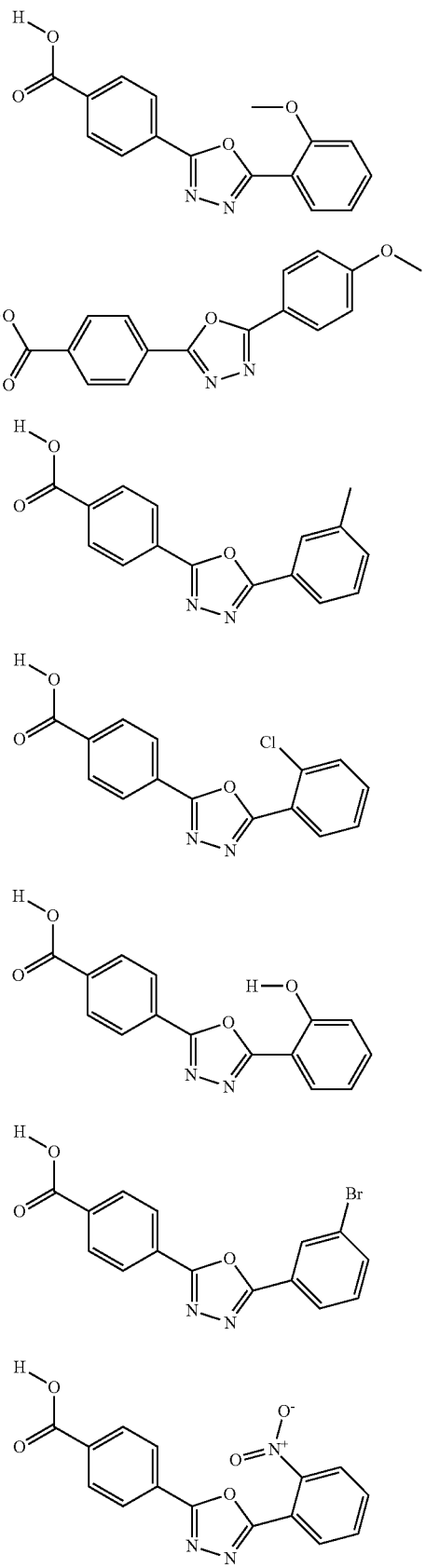

TABLE 5-continued
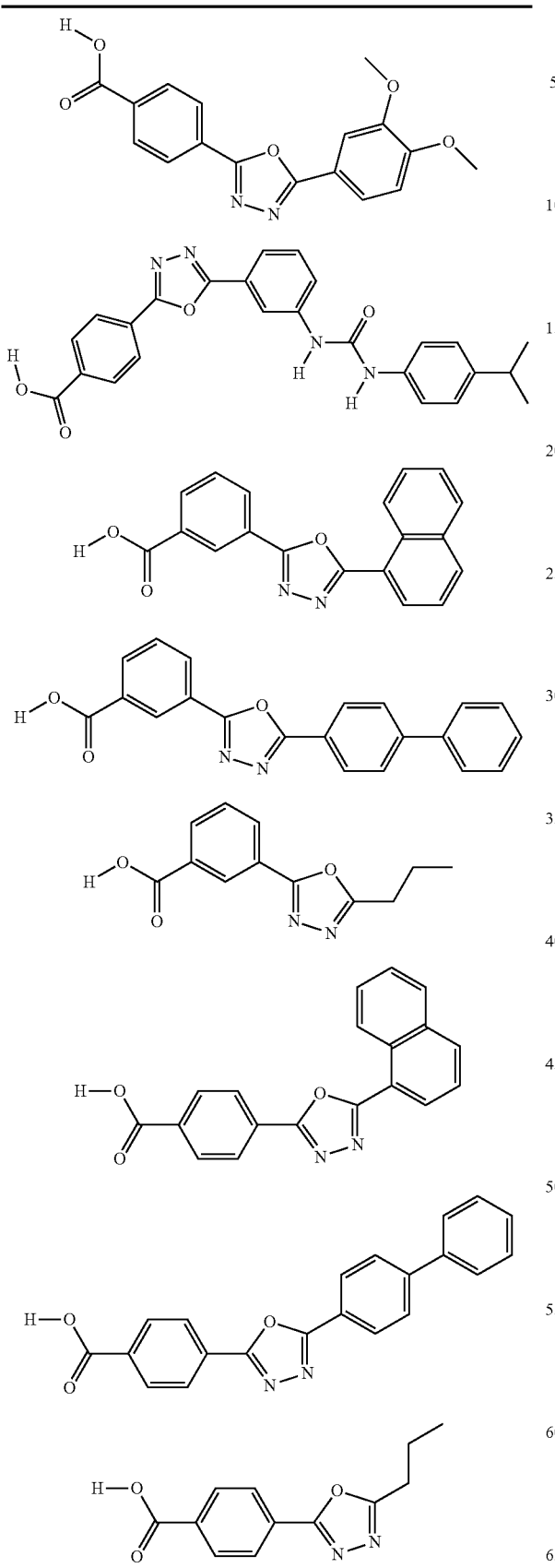
TABLE 5-continued
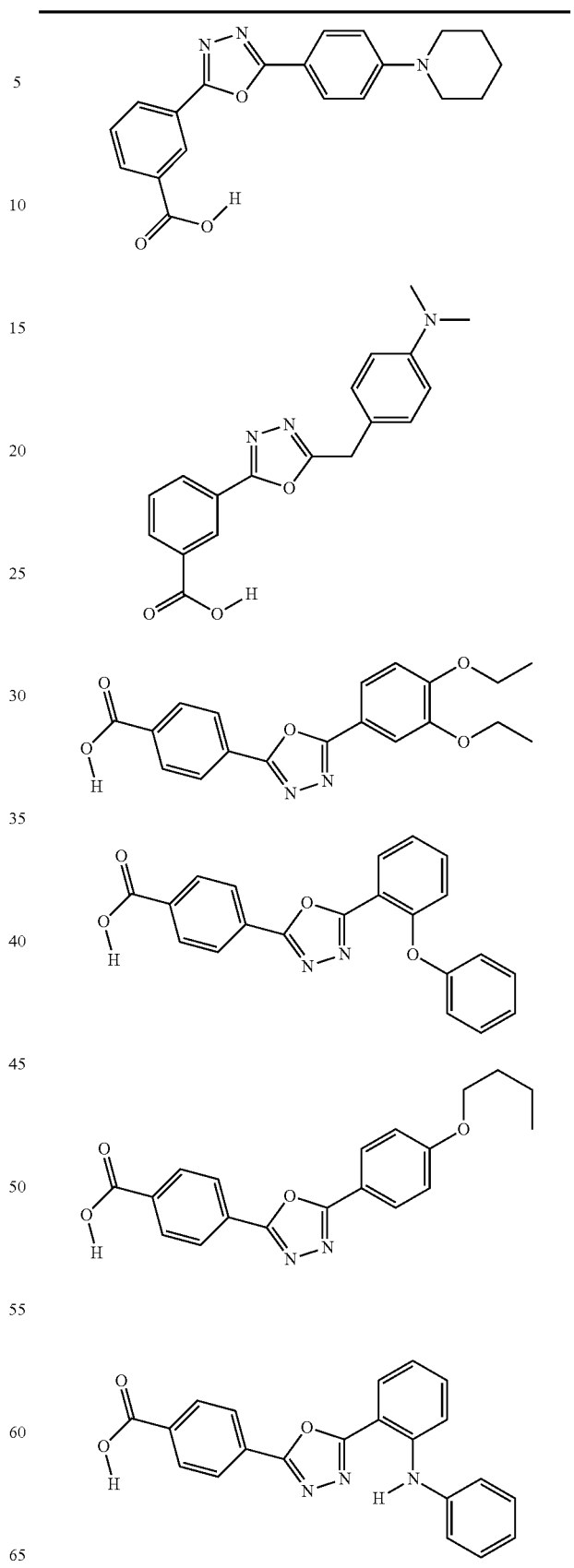

TABLE 5-continued
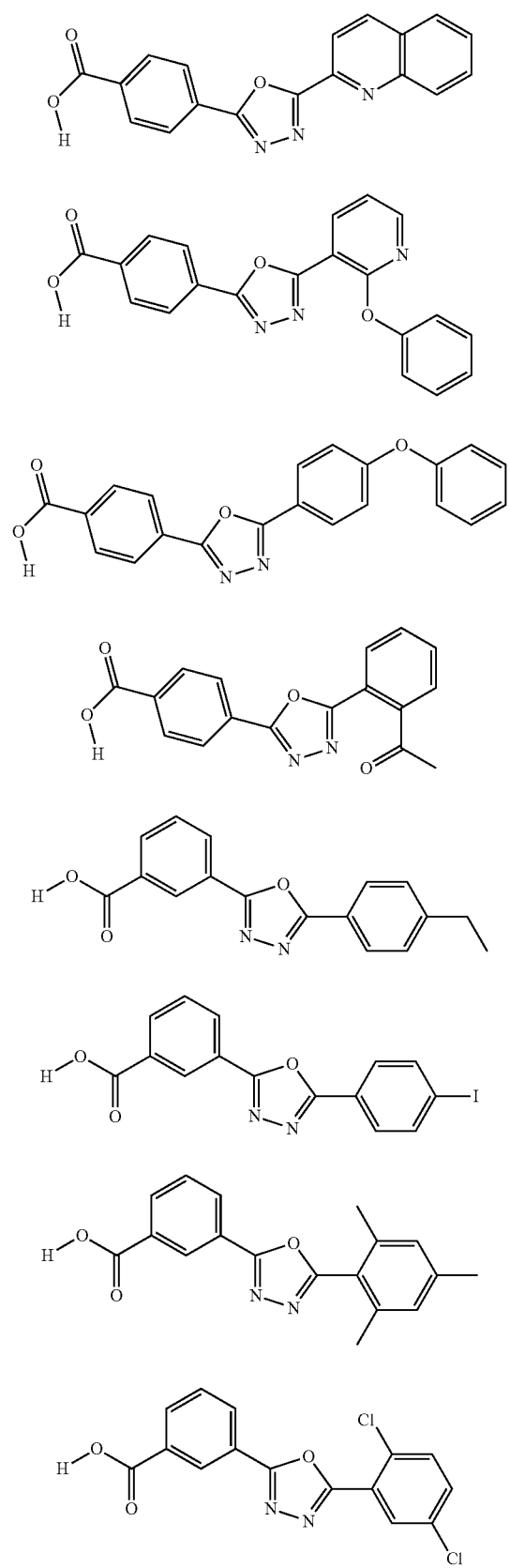

TABLE 5-continued
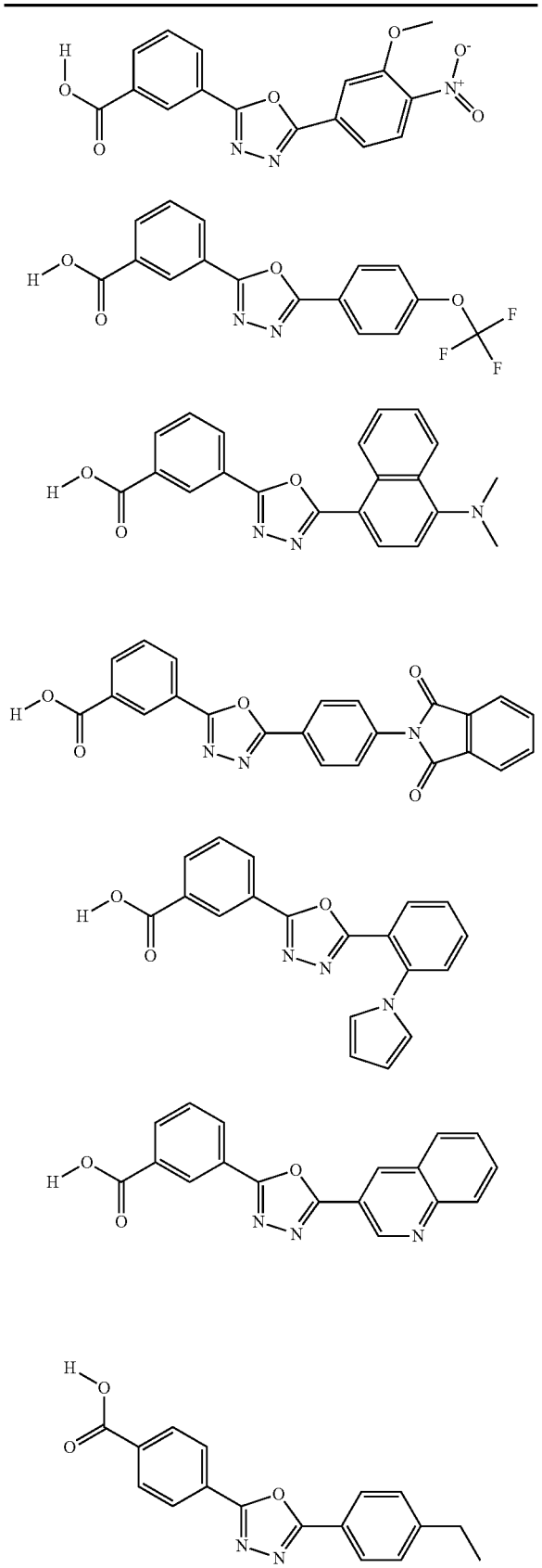
TABLE 5-continued
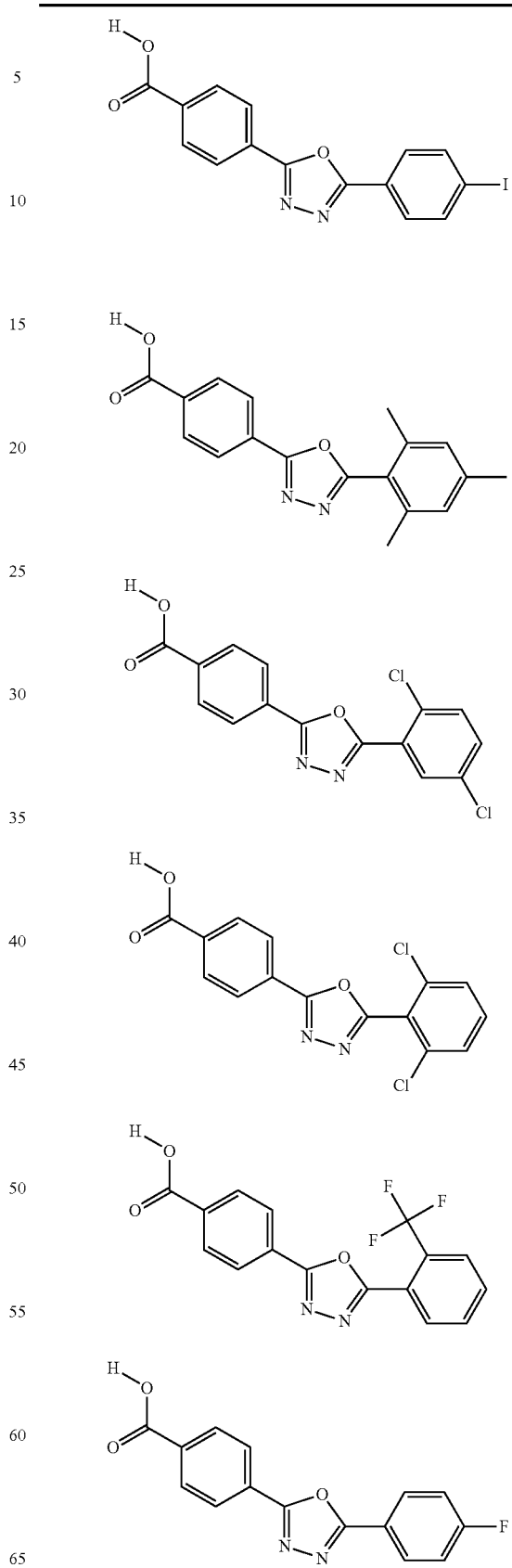

TABLE 5-continued
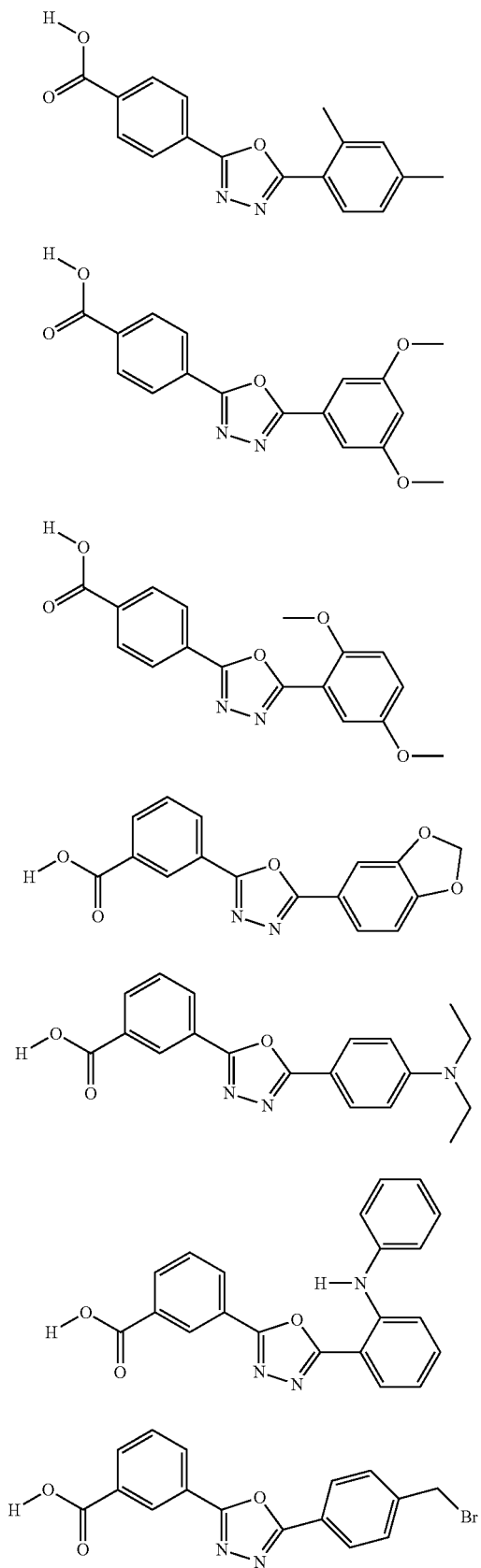
TABLE 5-continued
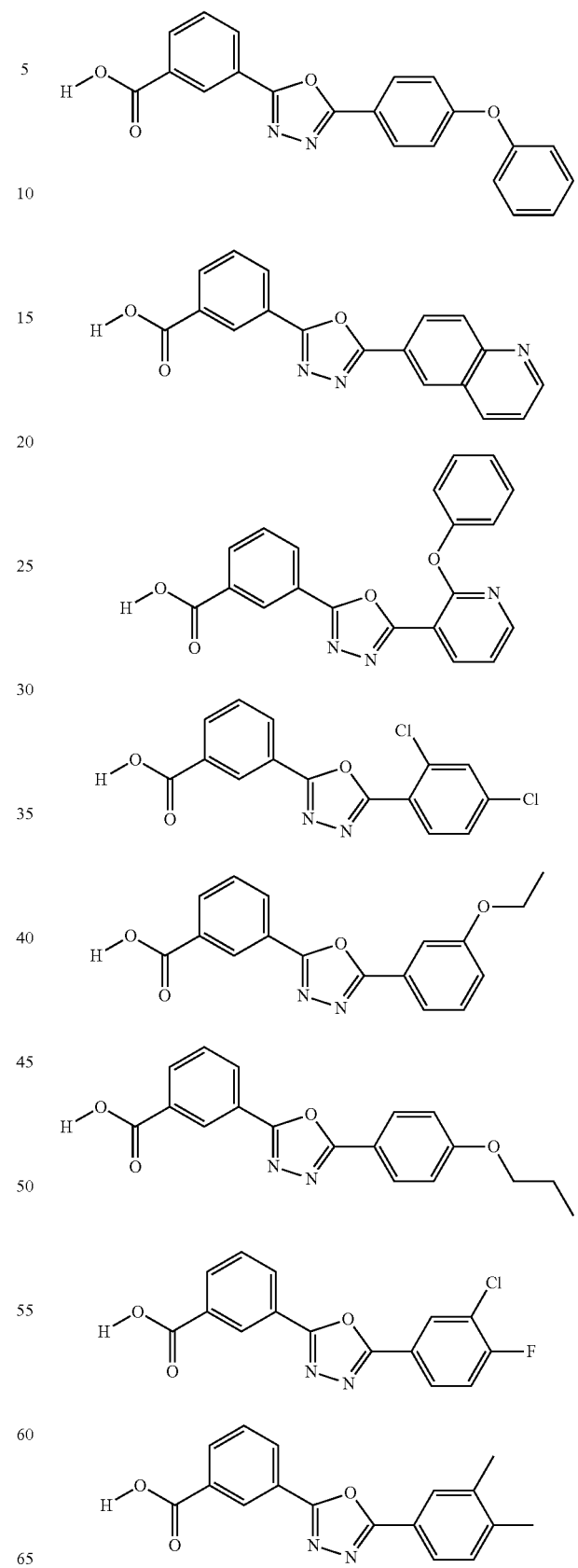

TABLE 5-continued
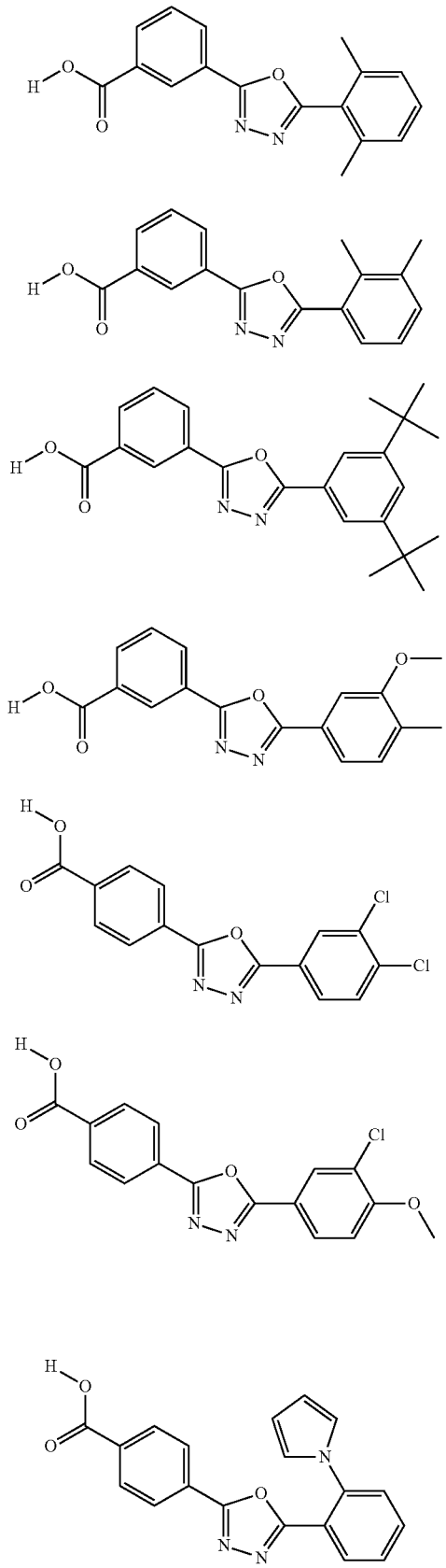
TABLE 5-continued
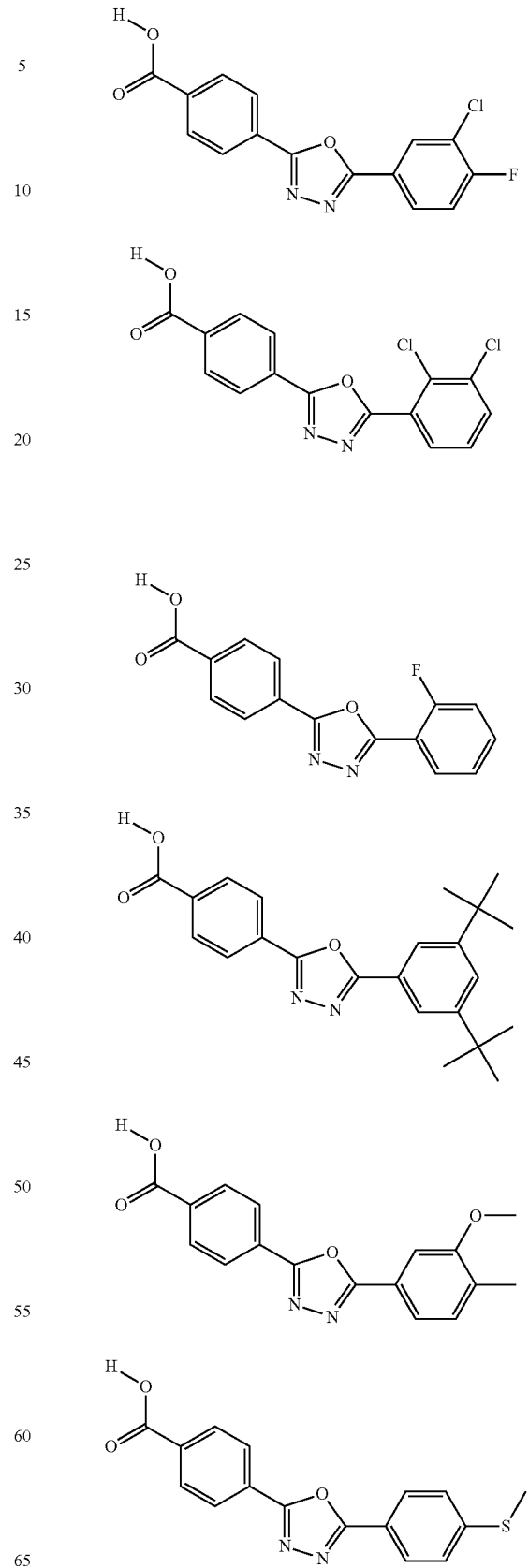

TABLE 5-continued
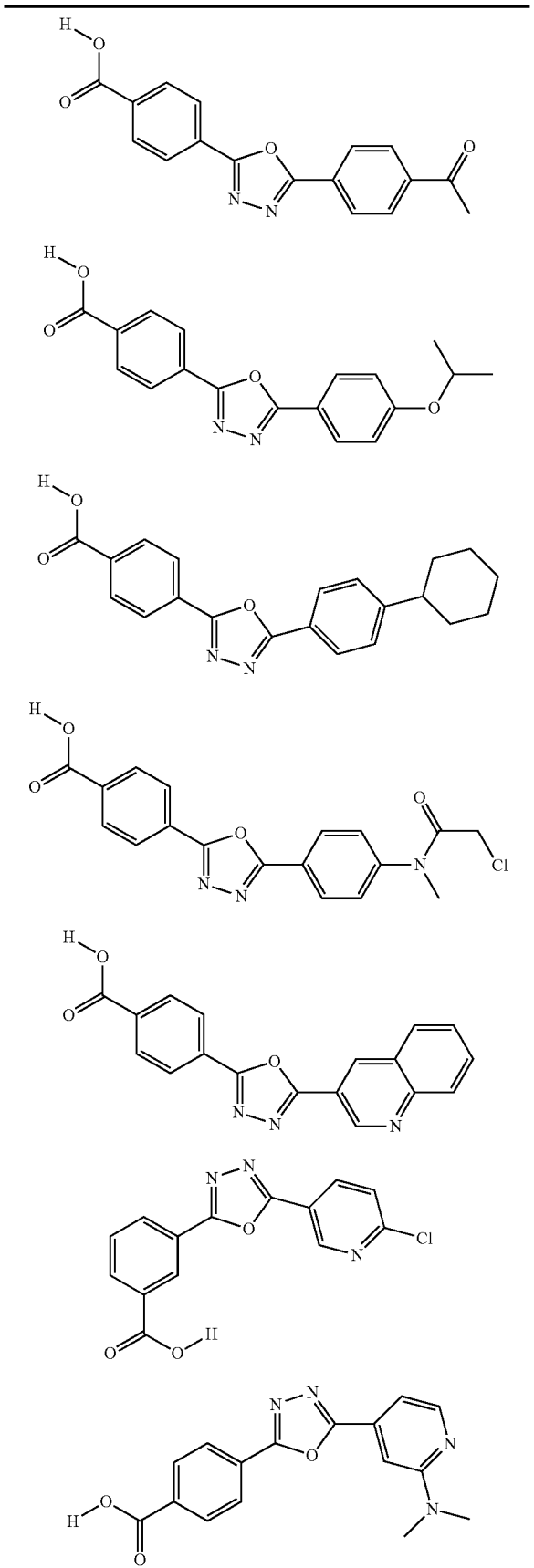
TABLE 5-continued
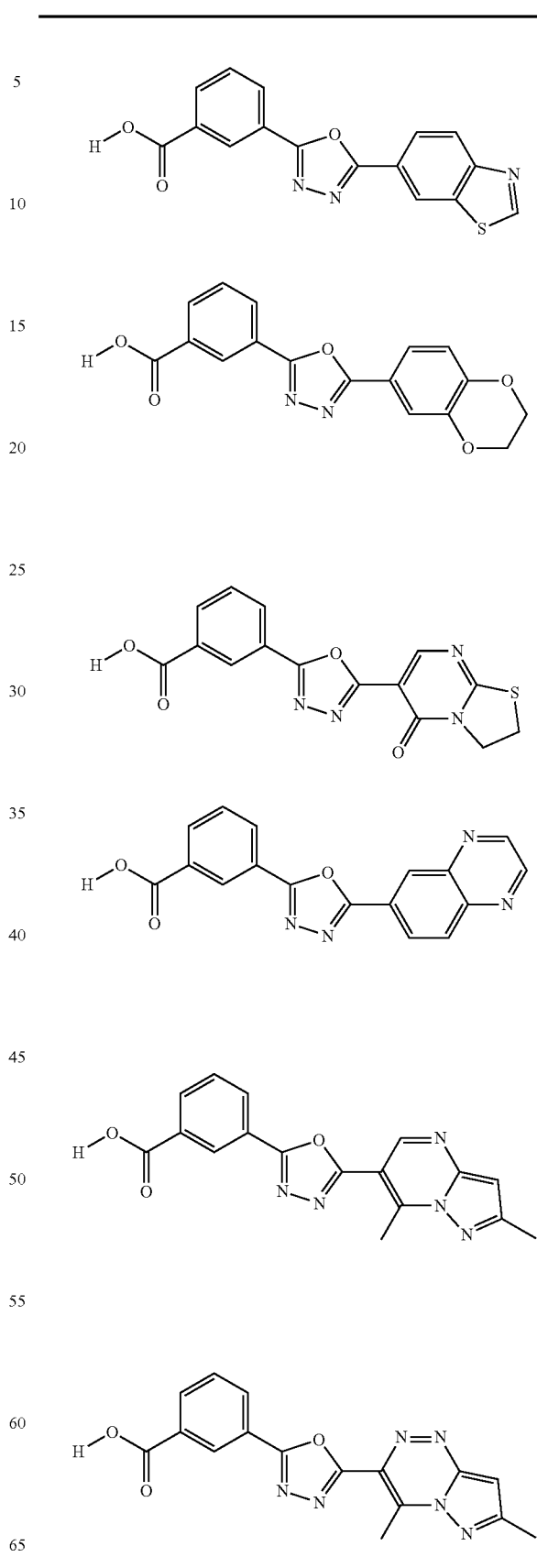

TABLE 5-continued
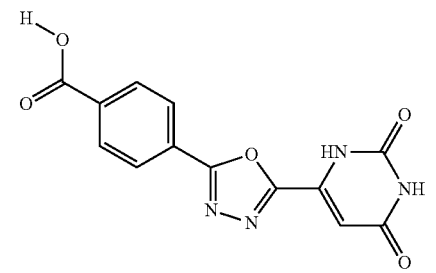 [SMILES: O=C(O)c1ccc(-c2nnc(-c3cc(=O)[nH]c(=O)[nH]3)o2)cc1]
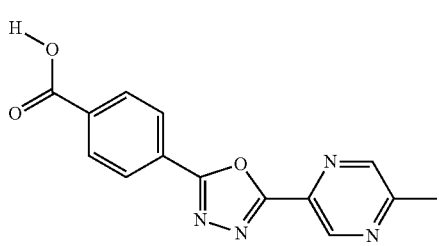 [SMILES: Cc1cnc(-c2nnc(-c3ccc(C(=O)O)cc3)o2)cn1]
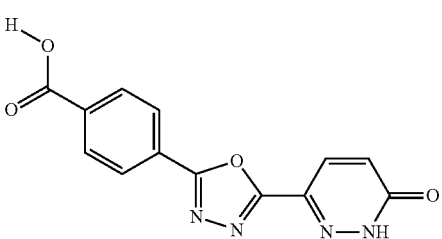 [SMILES: O=C(O)c1ccc(-c2nnc(-c3ccc(=O)[nH]n3)o2)cc1]
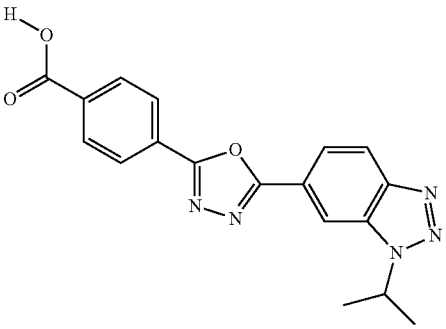 [SMILES: CC(C)n1nnc2ccc(-c3nnc(-c4ccc(C(=O)O)cc4)o3)cc21]
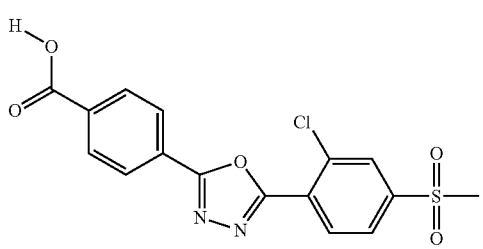 [SMILES: CS(=O)(=O)c1ccc(-c2nnc(-c3ccc(C(=O)O)cc3)o2)c(Cl)c1]
TABLE 5-continued
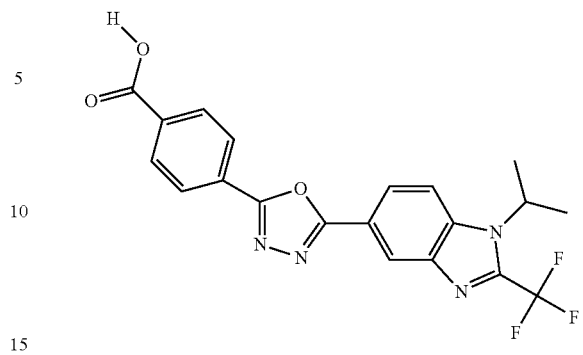
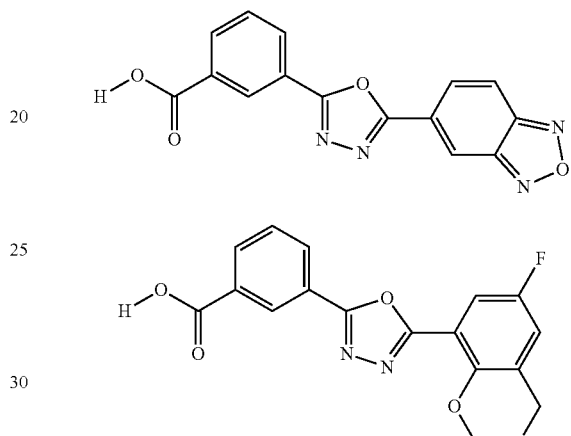
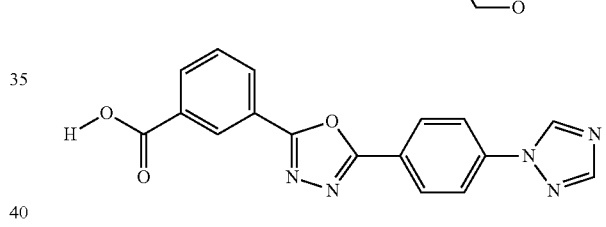
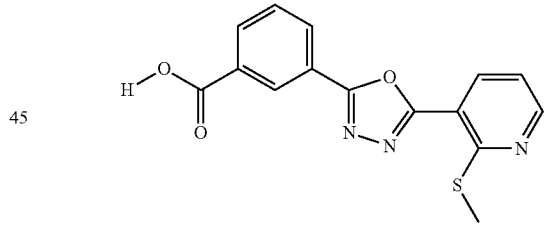
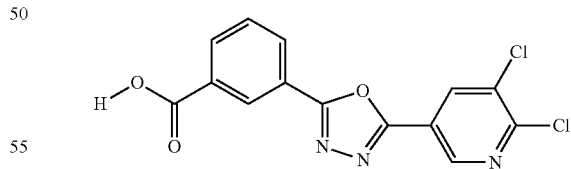
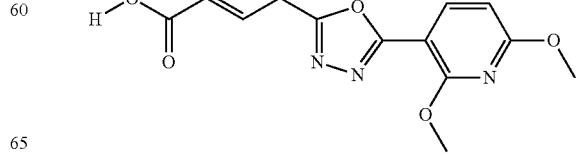

TABLE 5-continued
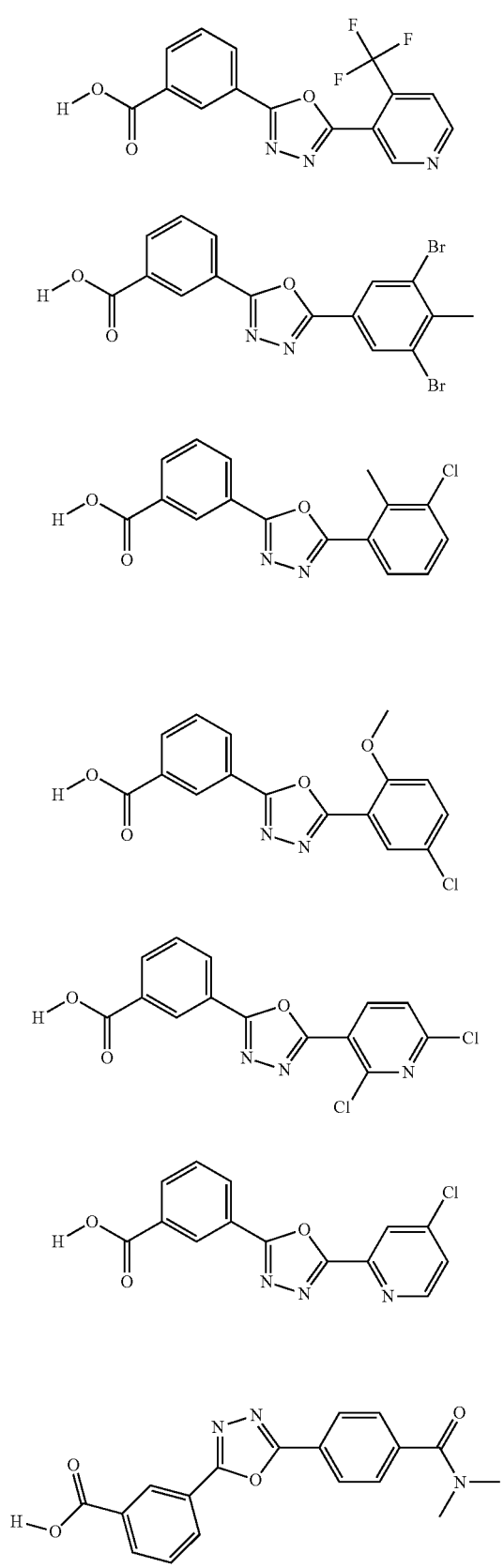
TABLE 5-continued
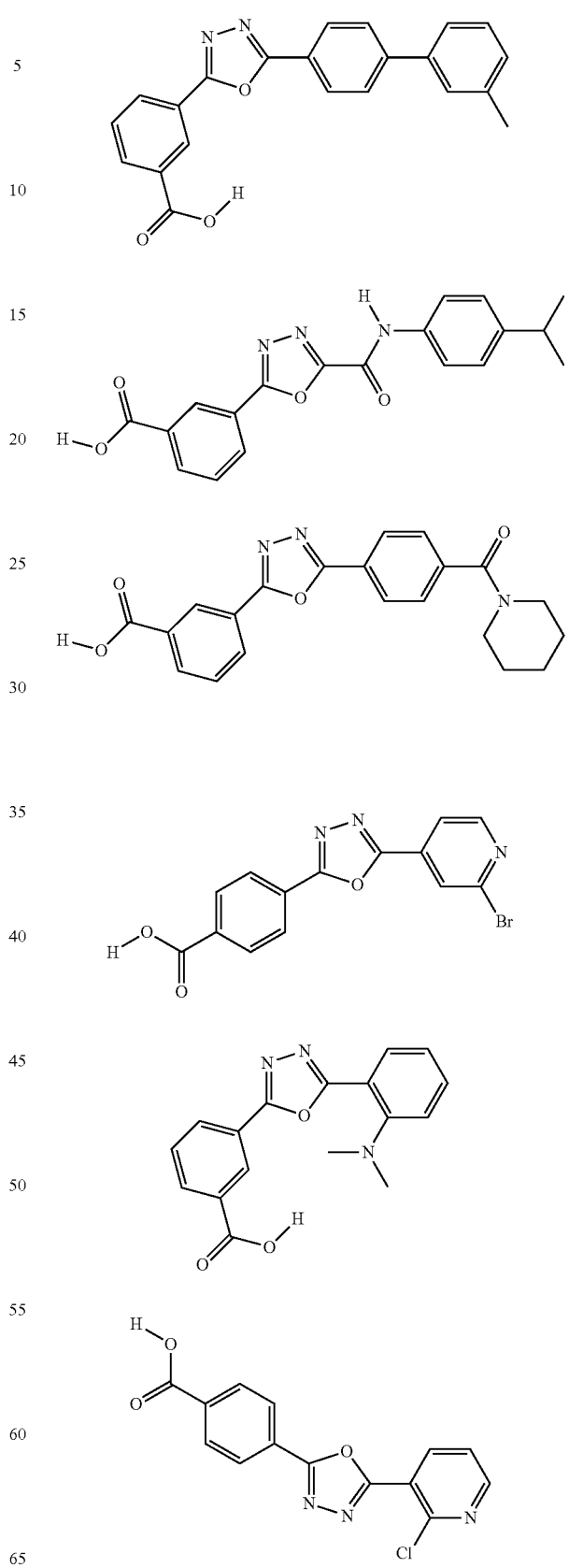

TABLE 5-continued
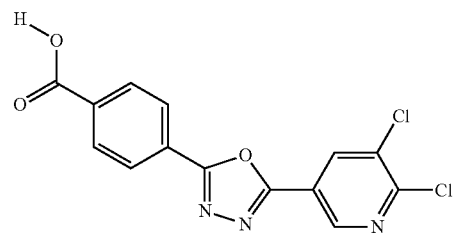 [SMILES: O=C(O)c1ccc(-c2nnc(-c3cnc(Cl)c(Cl)c3)o2)cc1]
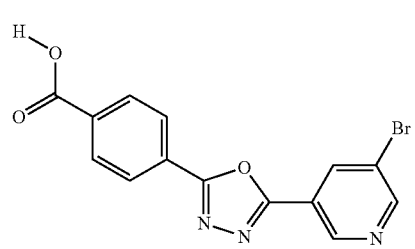 [SMILES: O=C(O)c1ccc(-c2nnc(-c3cncc(Br)c3)o2)cc1]
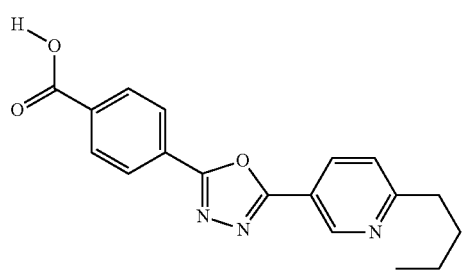 [SMILES: CCCCc1ccc(-c2nnc(-c3ccc(C(=O)O)cc3)o2)cn1]
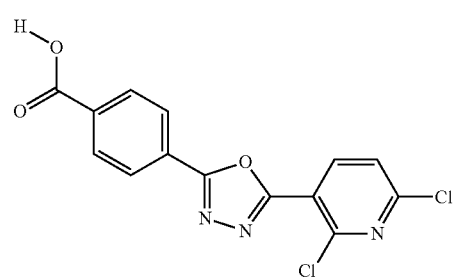 [SMILES: O=C(O)c1ccc(-c2nnc(-c3ccc(Cl)nc3Cl)o2)cc1]
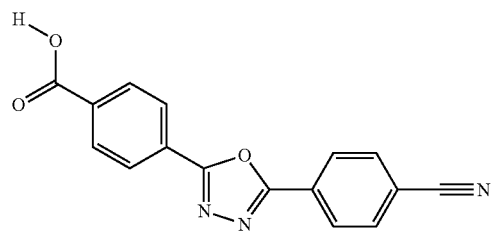 [SMILES: N#Cc1ccc(-c2nnc(-c3ccc(C(=O)O)cc3)o2)cc1]
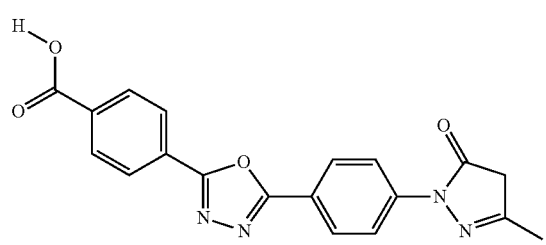 [SMILES: CC1=NN(c2ccc(-c3nnc(-c4ccc(C(=O)O)cc4)o3)cc2)C(=O)C1]
TABLE 5-continued
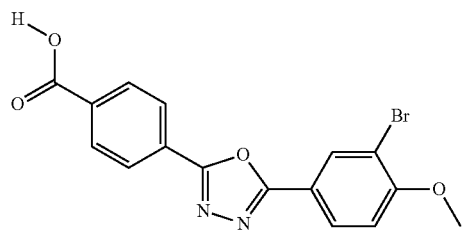
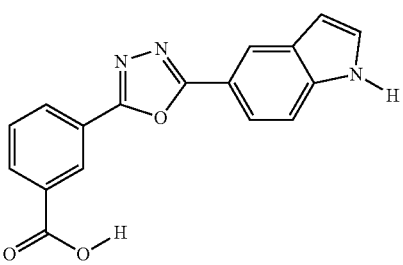 [SMILES: O=C(O)c1cccc(-c2nnc(-c3ccc4[nH]ccc4c3)o2)c1]
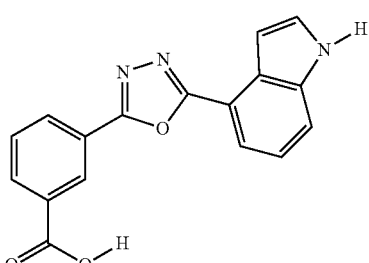
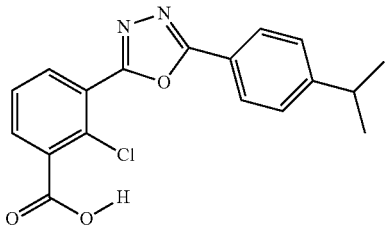 [SMILES: CC(C)c1ccc(-c2nnc(-c3cccc(C(=O)O)c3Cl)o2)cc1]
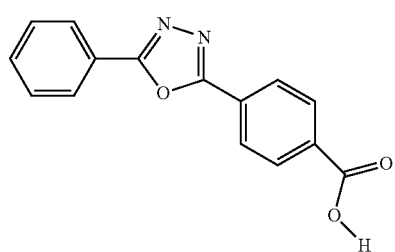 [SMILES: O=C(O)c1ccc(-c2nnc(-c3ccccc3)o2)cc1]
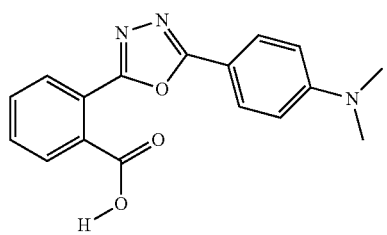 [SMILES: CN(C)c1ccc(-c2nnc(-c3ccccc3C(=O)O)o2)cc1]

143
TABLE 5-continued
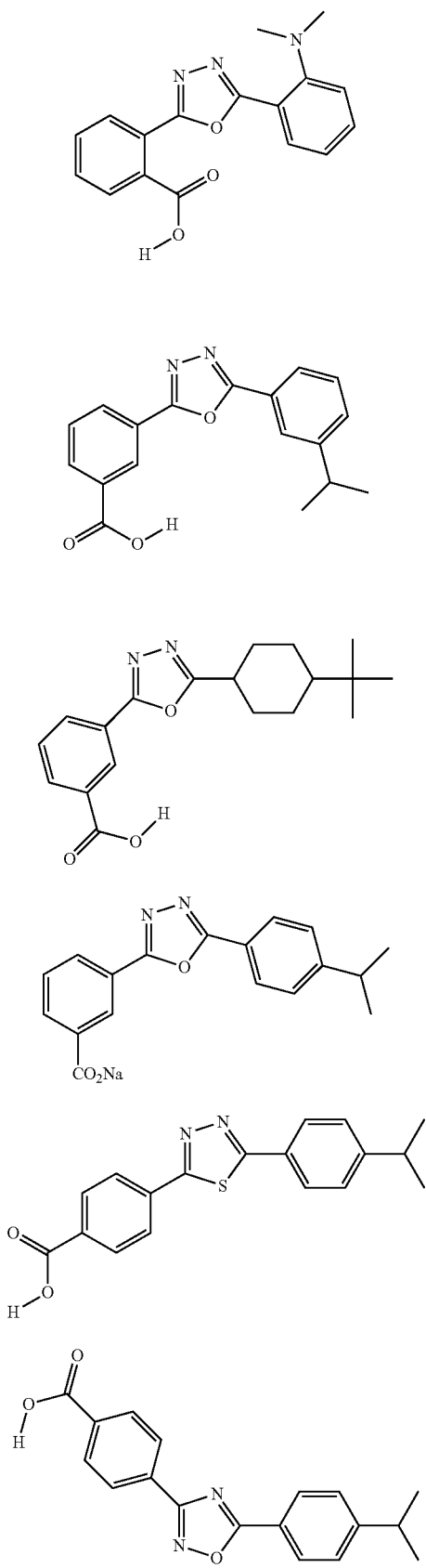
144
TABLE 5-continued
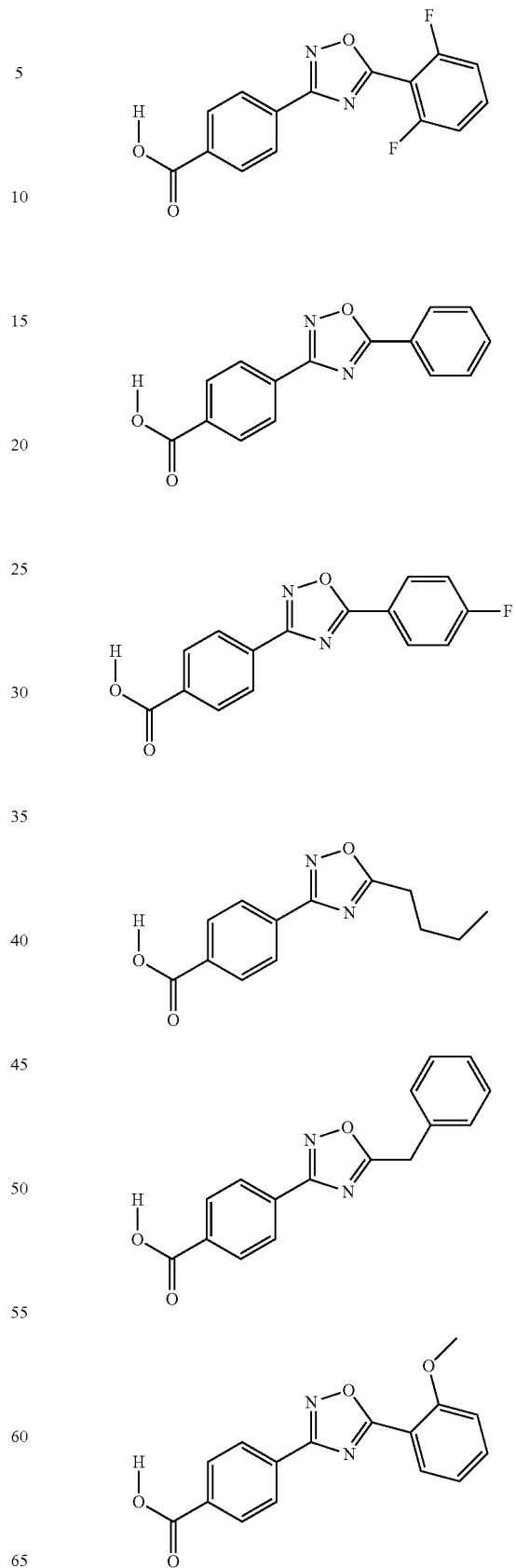

TABLE 5-continued
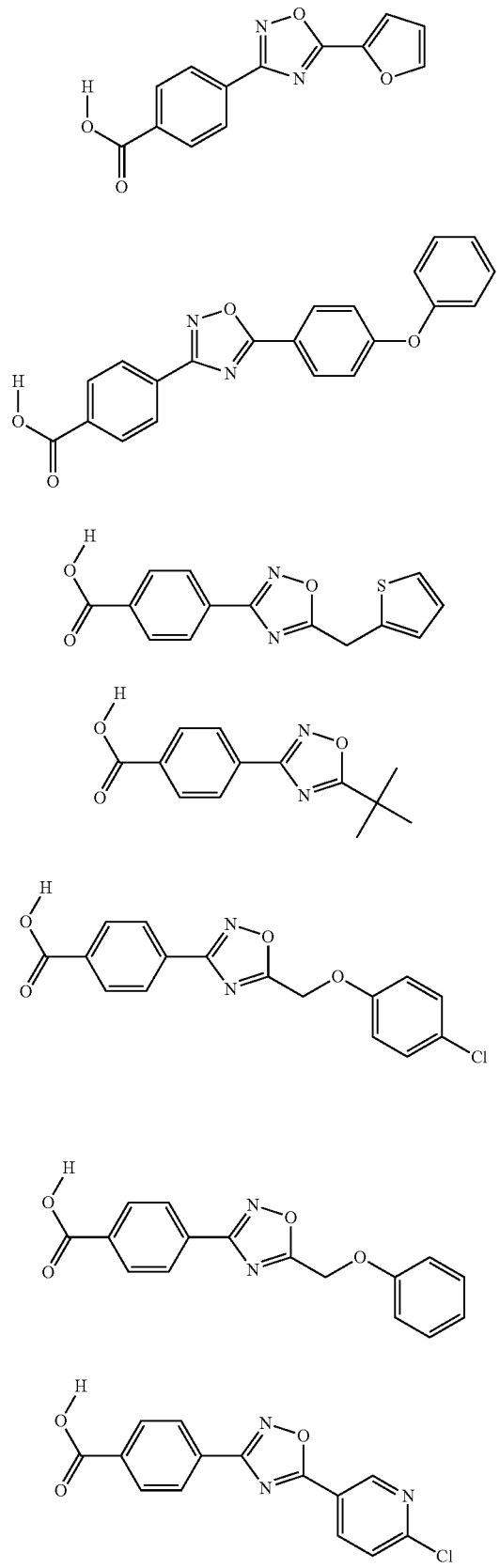
TABLE 5-continued
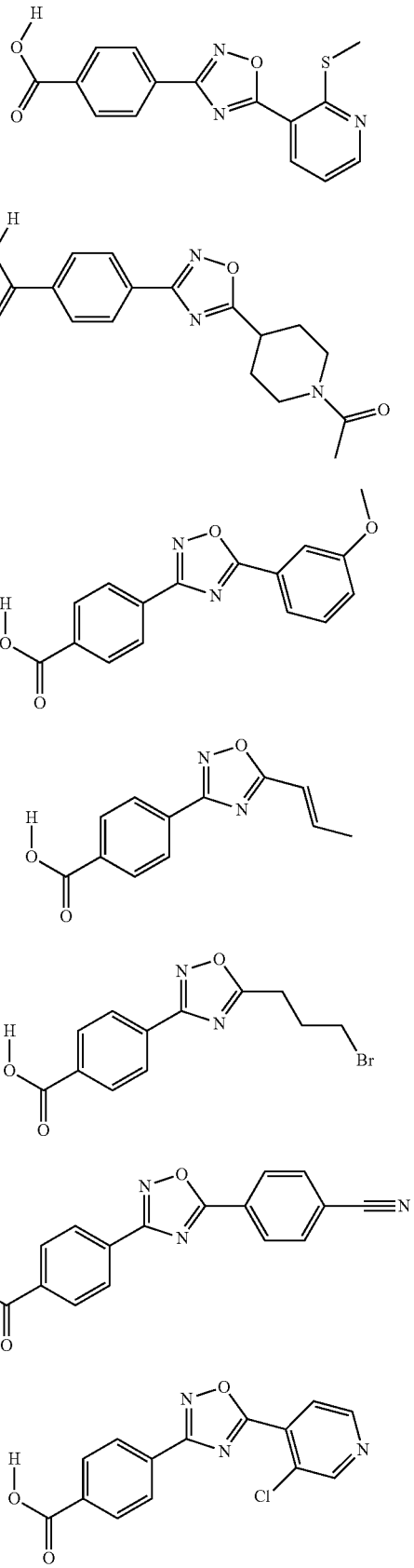

TABLE 5-continued
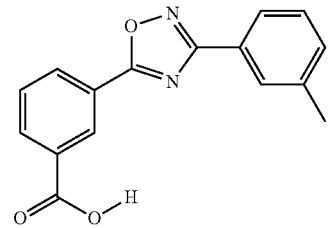 [SMILES: Cc1cccc(-c2noc(-c3cccc(C(=O)O)c3)n2)c1]
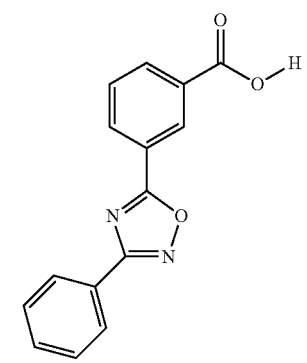 [SMILES: O=C(O)c1cccc(-c2nc(-c3ccccc3)no2)c1]
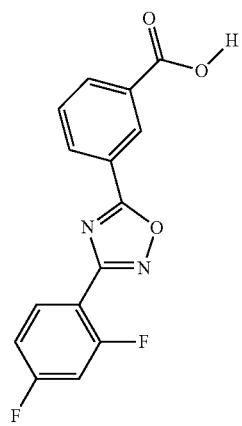 [SMILES: O=C(O)c1cccc(-c2nc(-c3ccc(F)cc3F)no2)c1]
TABLE 5-continued
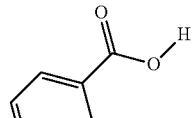
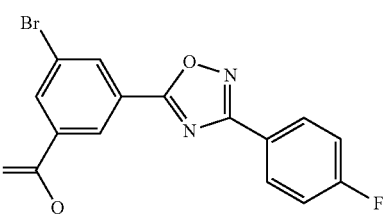
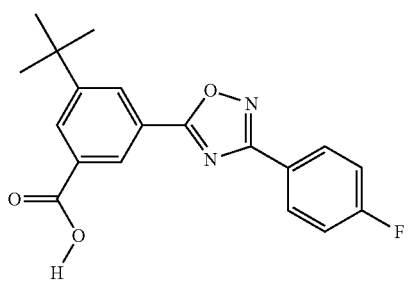 [SMILES: CC(C)(C)c1cc(C(=O)O)cc(-c2nc(-c3ccc(F)cc3)no2)c1]
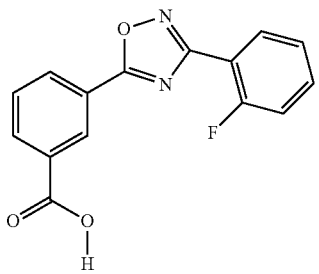 [SMILES: O=C(O)c1cccc(-c2nc(-c3ccccc3F)no2)c1]
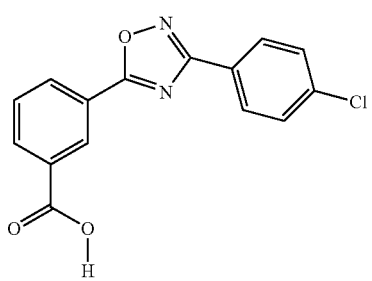 [SMILES: O=C(O)c1cccc(-c2nc(-c3ccc(Cl)cc3)no2)c1]

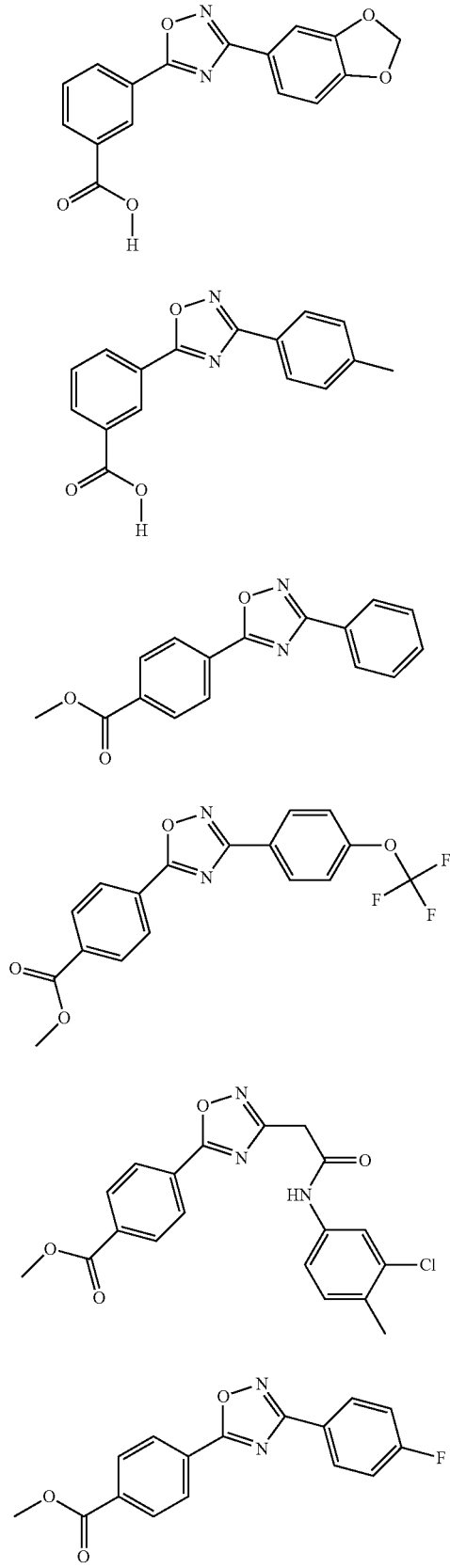

TABLE 5-continued
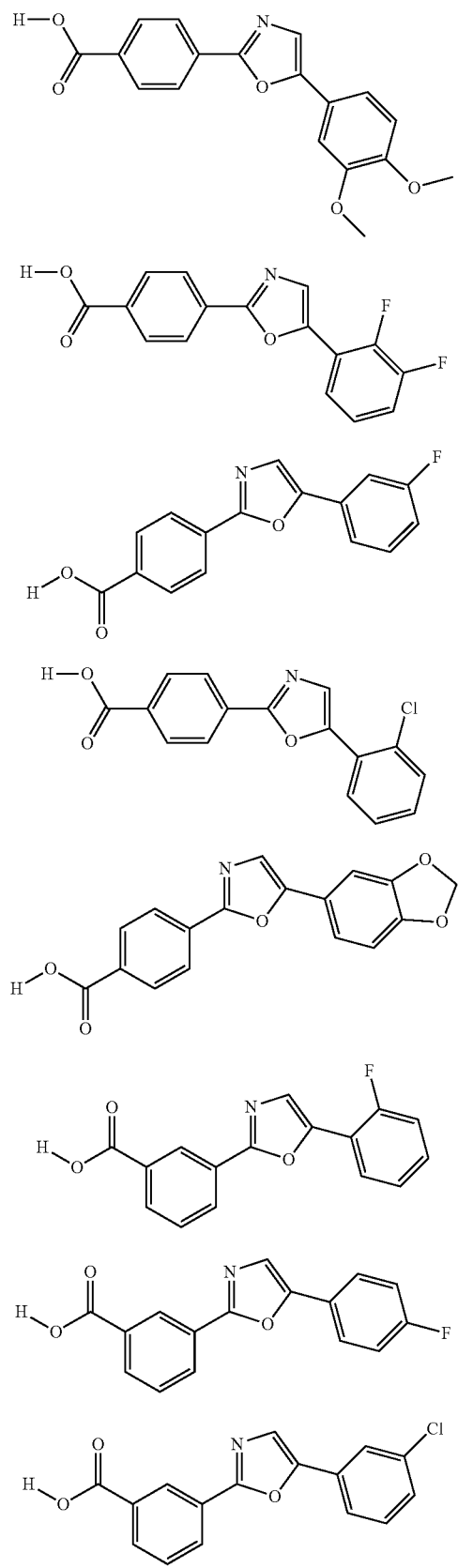
TABLE 5-continued
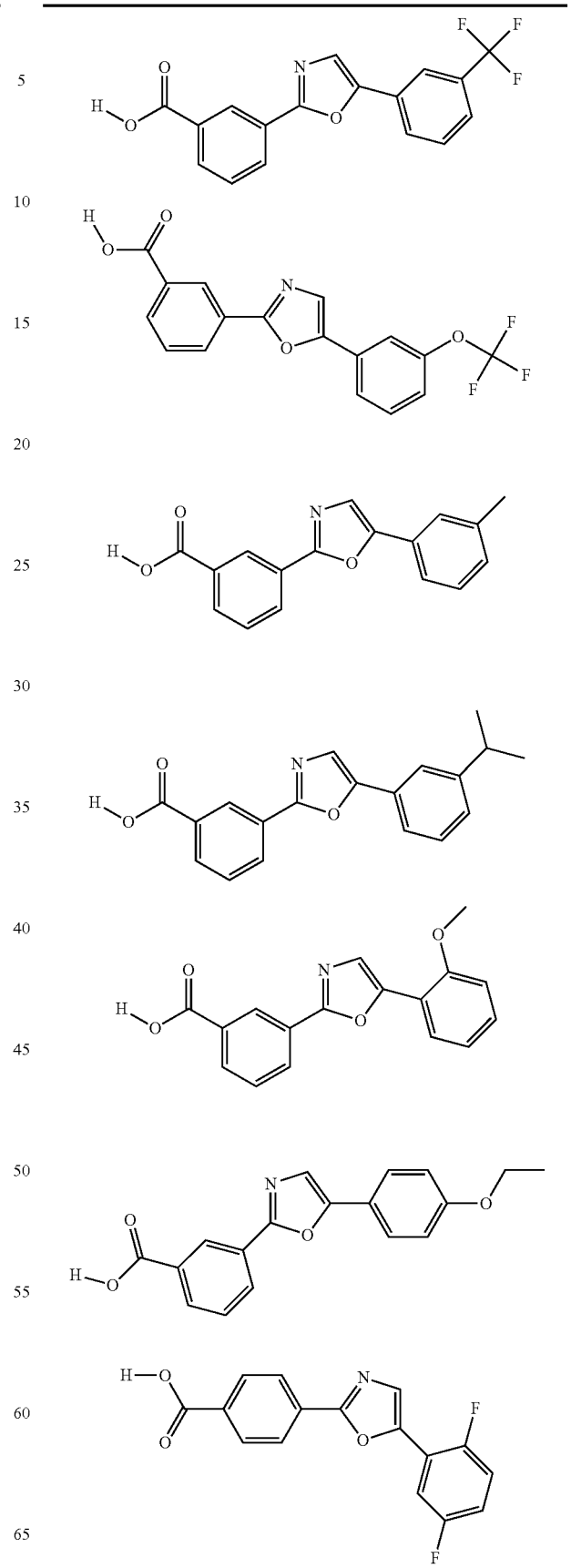

TABLE 5-continued
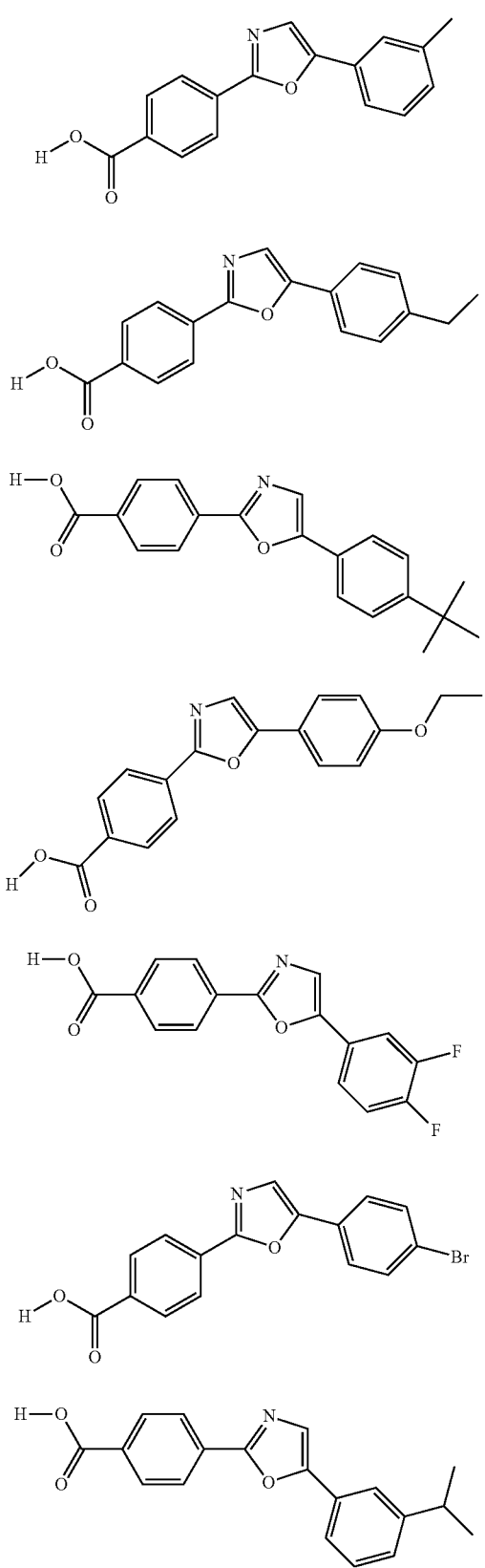
TABLE 5-continued
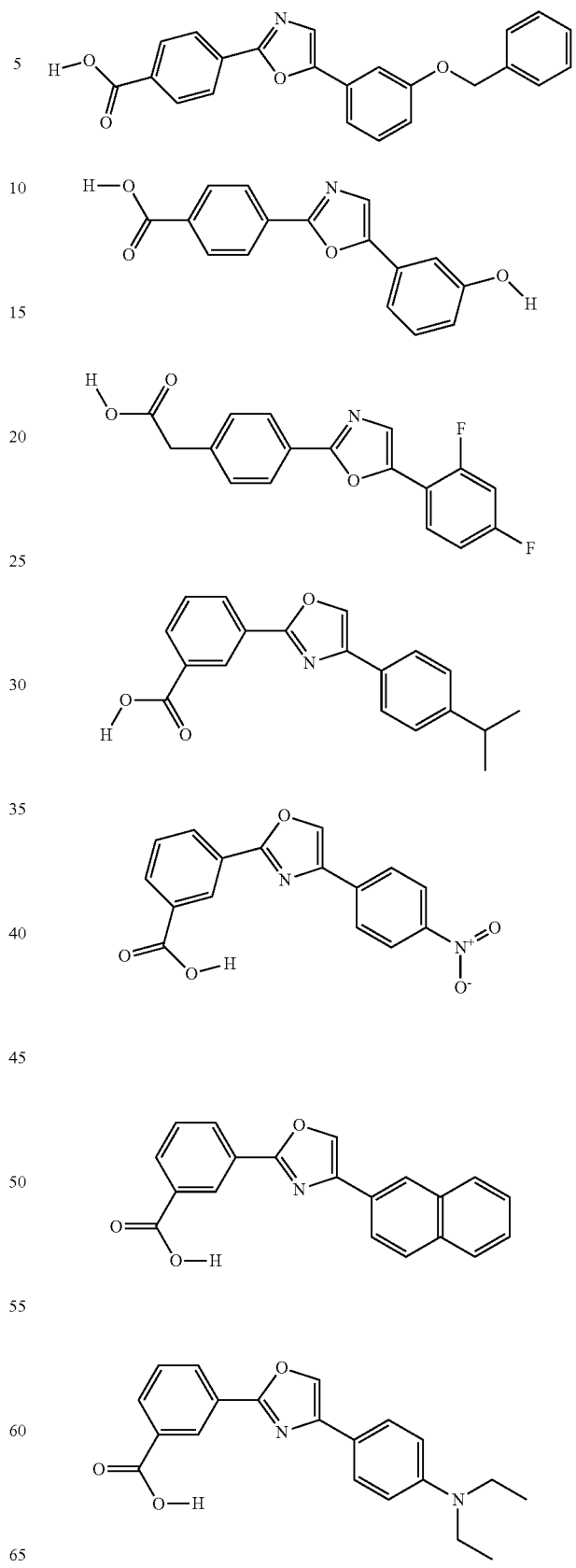

TABLE 5-continued
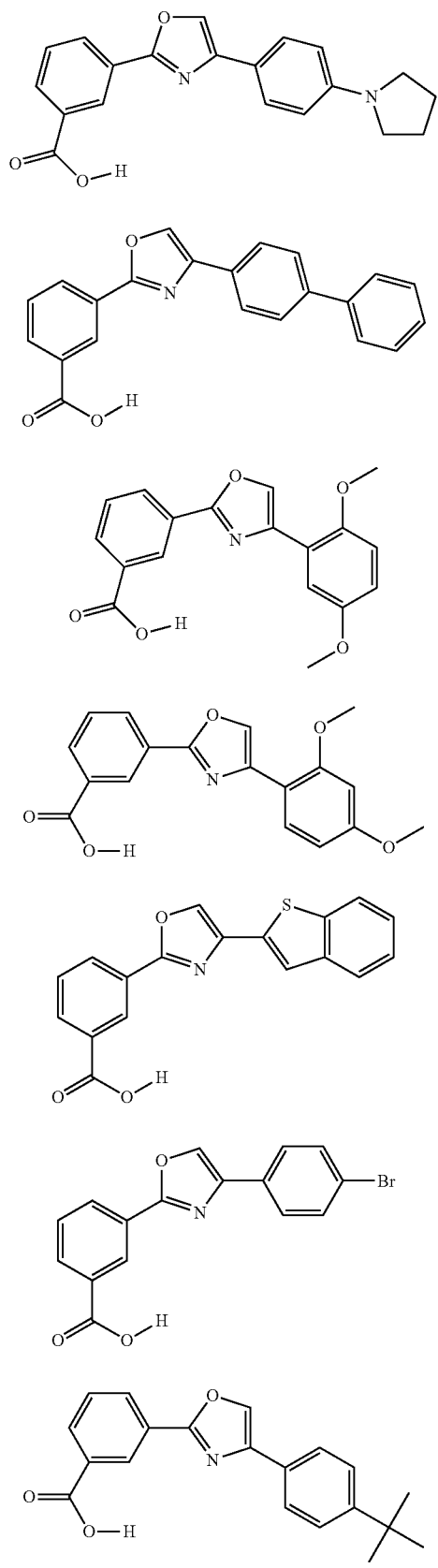
TABLE 5-continued
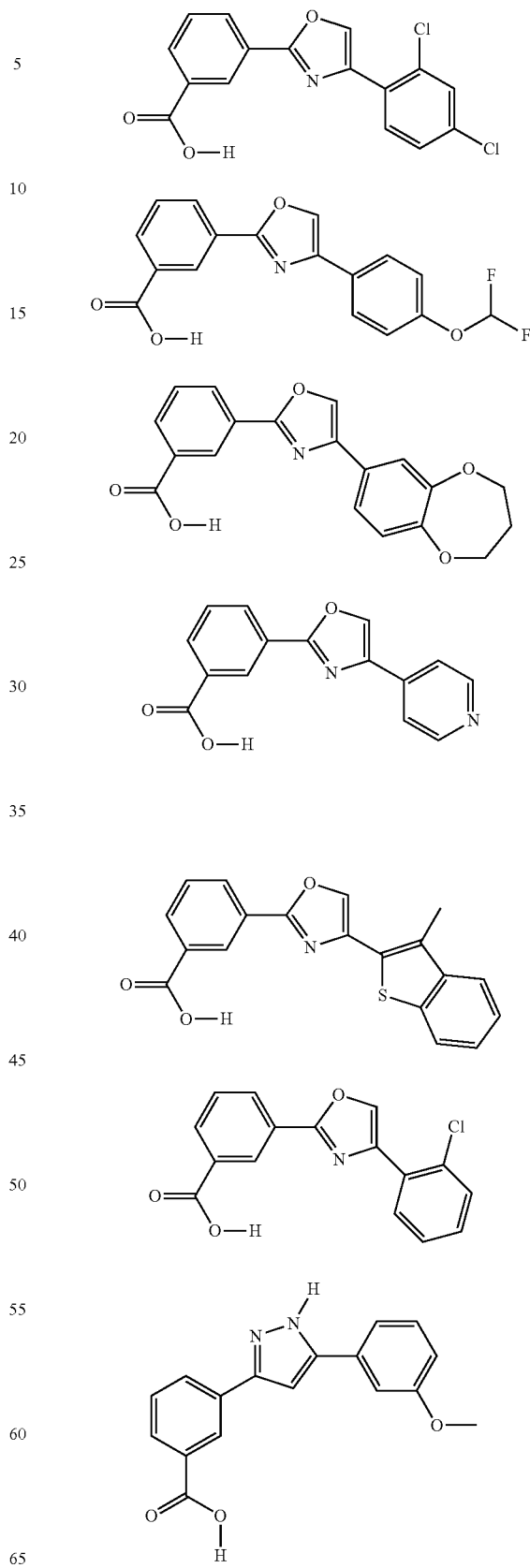

TABLE 5-continued
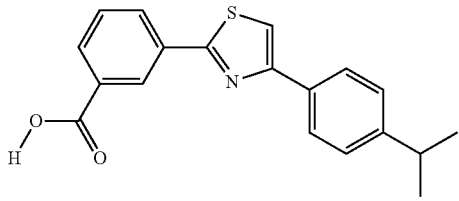 [SMILES: CC(C)c1ccc(-c2csc(-c3cccc(C(=O)O)c3)n2)cc1]
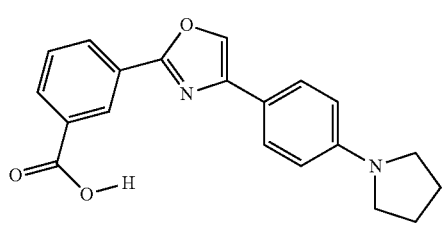 [SMILES: O=C(O)c1cccc(-c2nc(-c3ccc(N4CCCC4)cc3)co2)c1]
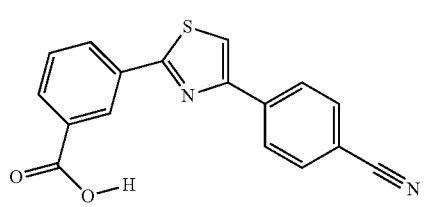 [SMILES: N#Cc1ccc(-c2csc(-c3cccc(C(=O)O)c3)n2)cc1]
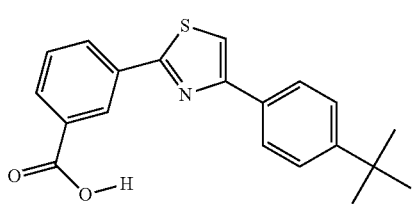 [SMILES: CC(C)(C)c1ccc(-c2csc(-c3cccc(C(=O)O)c3)n2)cc1]
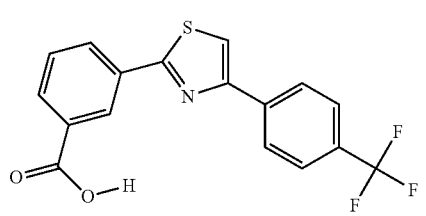 [SMILES: O=C(O)c1cccc(-c2nc(-c3ccc(C(F)(F)F)cc3)cs2)c1]
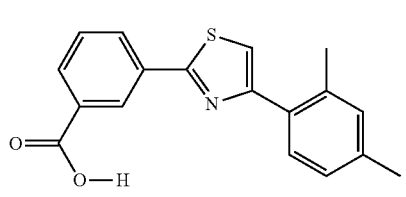 [SMILES: Cc1ccc(-c2csc(-c3cccc(C(=O)O)c3)n2)c(C)c1]
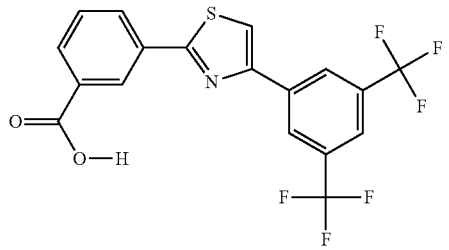 [SMILES: O=C(O)c1cccc(-c2nc(-c3cc(C(F)(F)F)cc(C(F)(F)F)c3)cs2)c1]
TABLE 5-continued
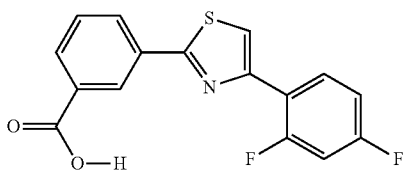 [SMILES: O=C(O)c1cccc(-c2nc(-c3ccc(F)cc3F)cs2)c1]
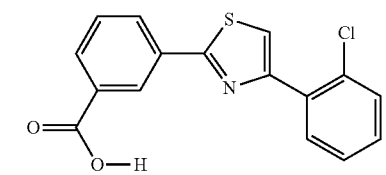 [SMILES: O=C(O)c1cccc(-c2nc(-c3ccccc3Cl)cs2)c1]
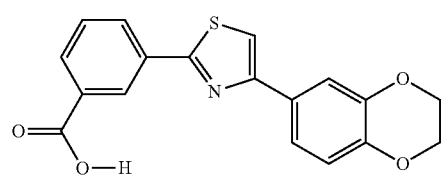 [SMILES: O=C(O)c1cccc(-c2nc(-c3ccc4c(c3)OCCO4)cs2)c1]
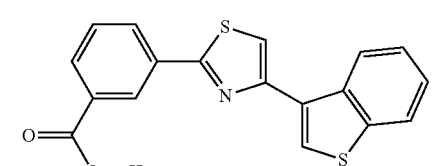
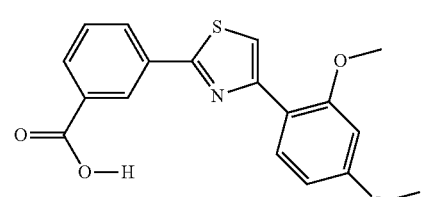
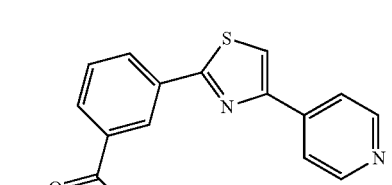
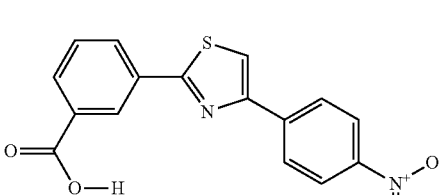
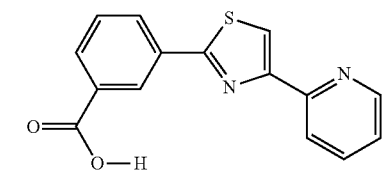

TABLE 5-continued
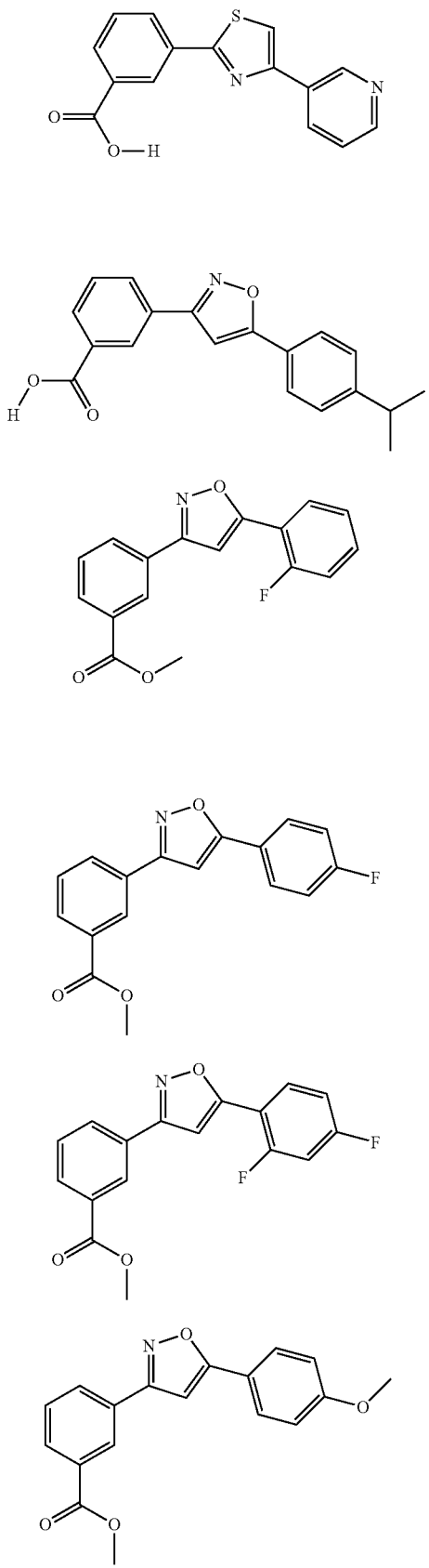
TABLE 5-continued
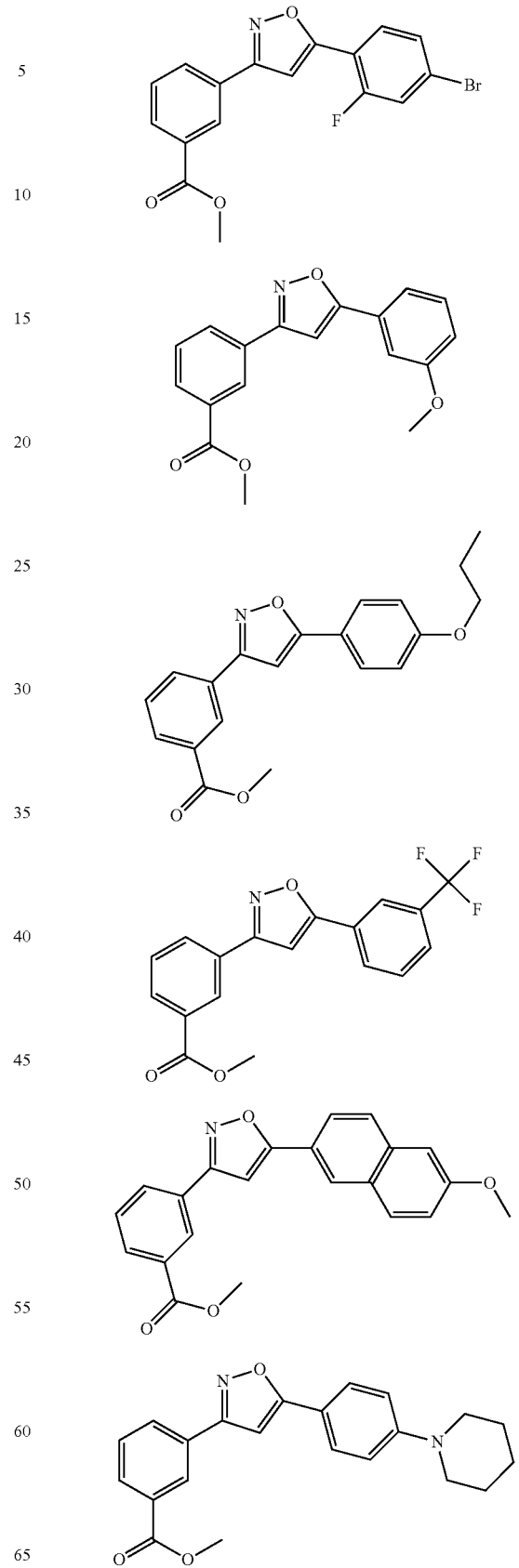

TABLE 5-continued
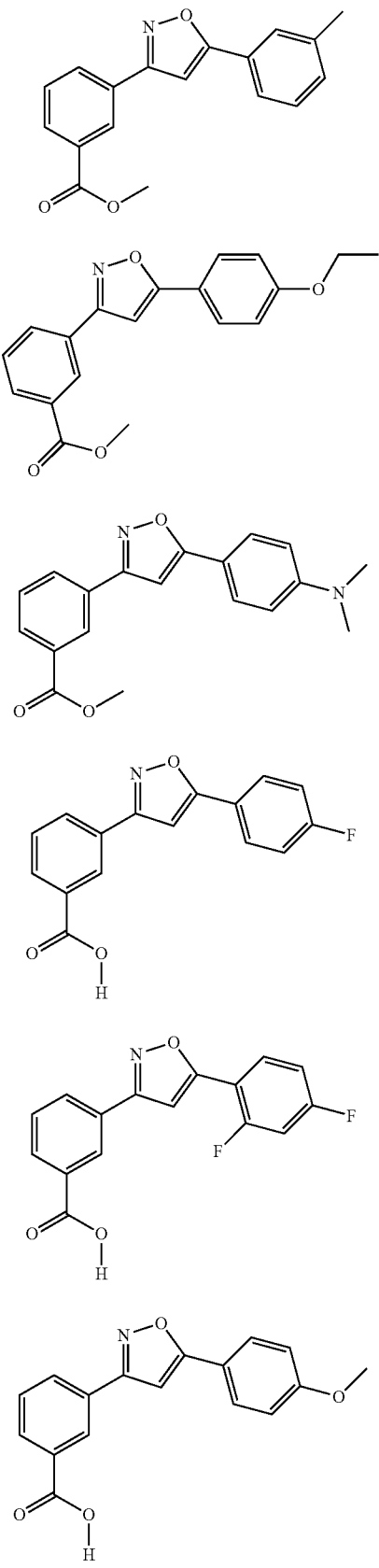
TABLE 5-continued
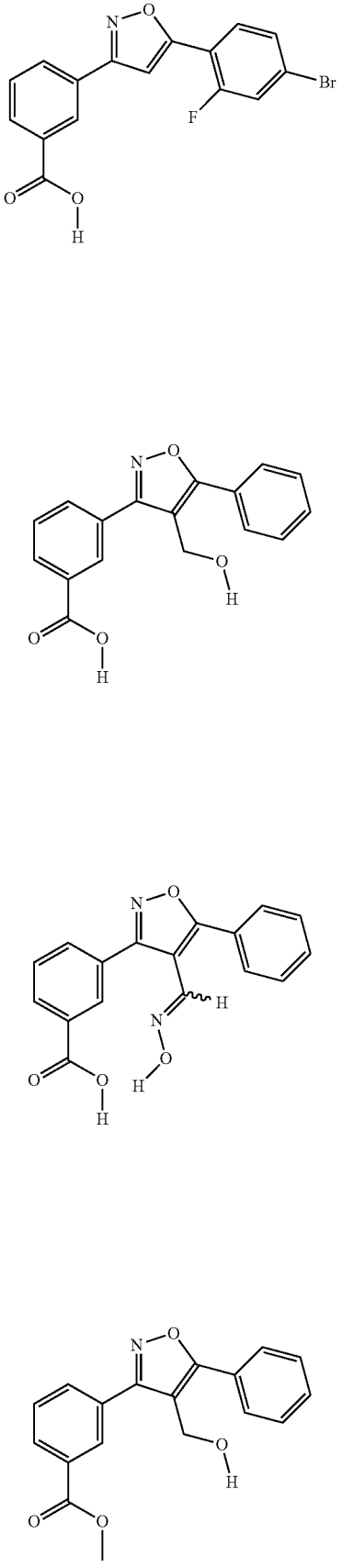

TABLE 5-continued
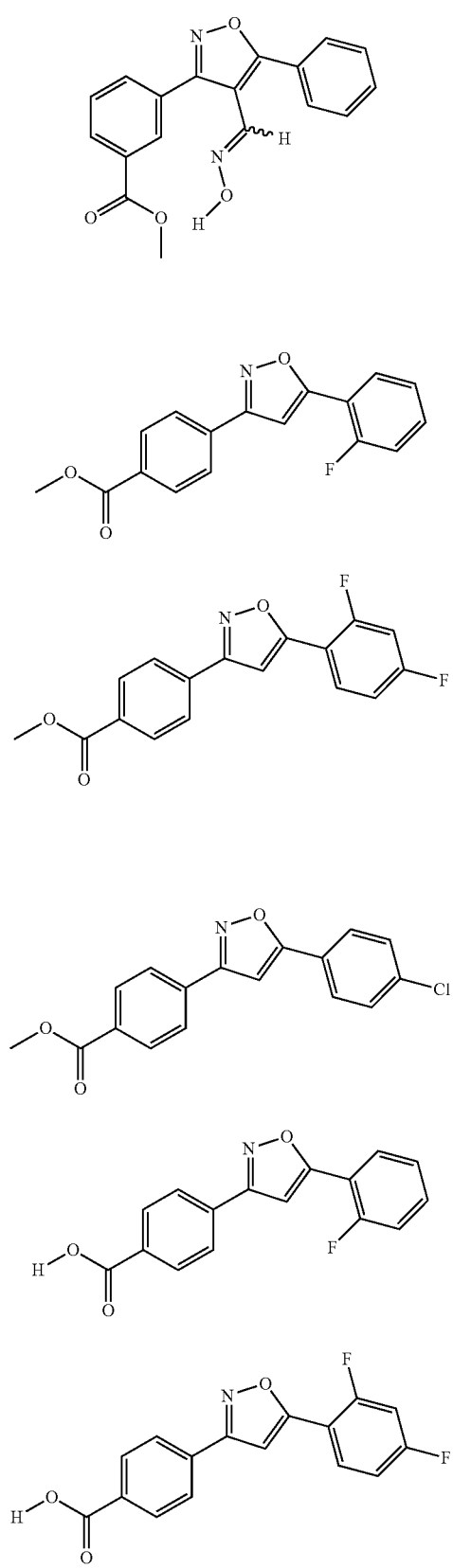
TABLE 5-continued
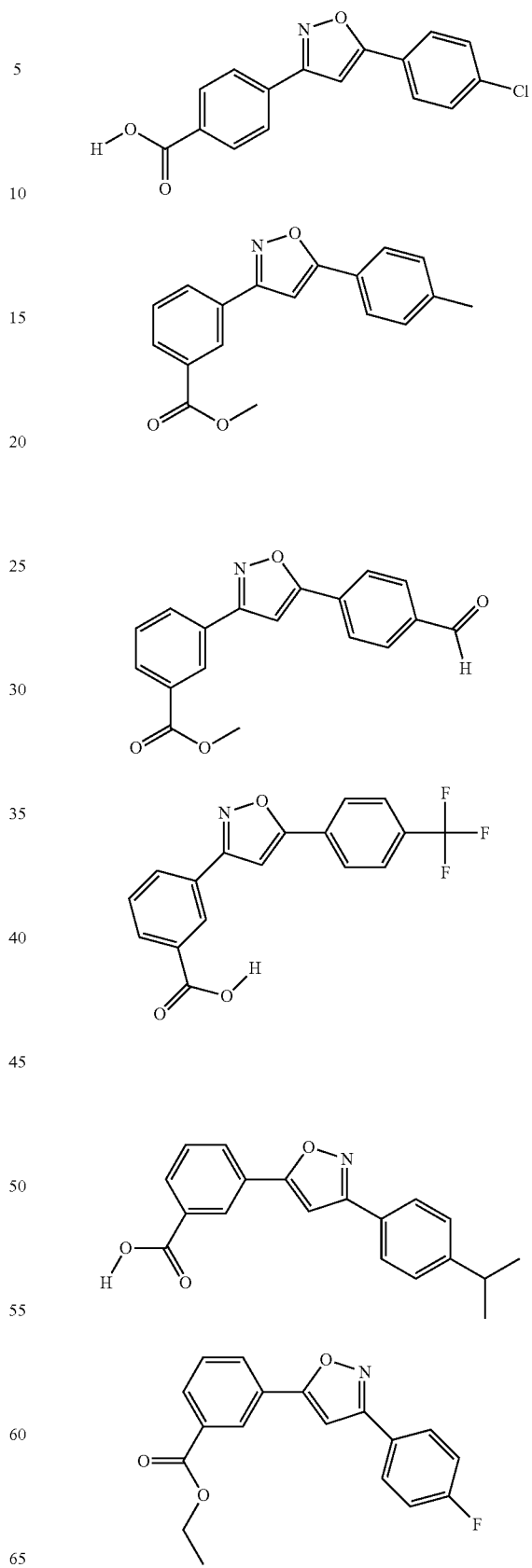

TABLE 5-continued
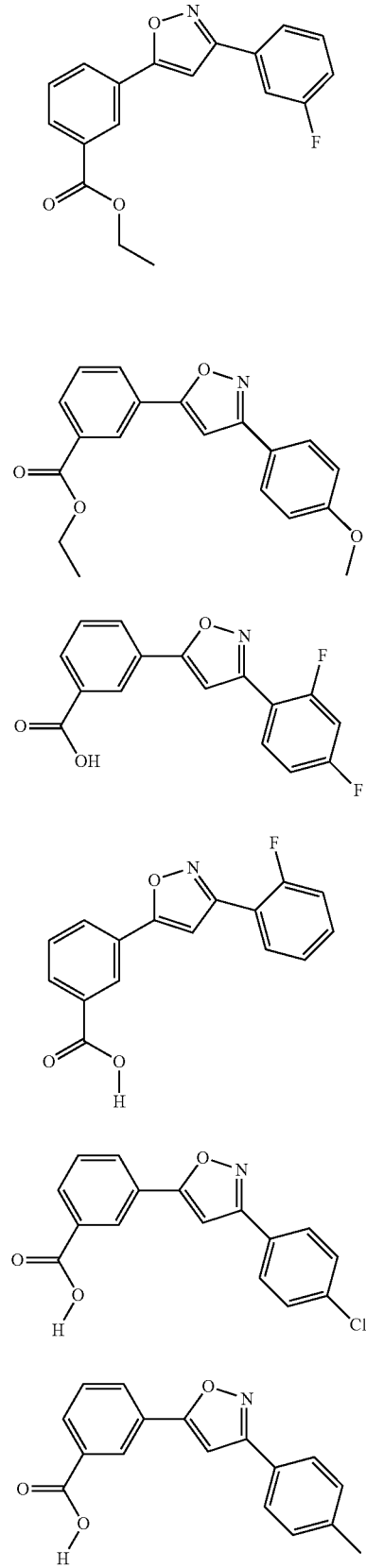
TABLE 5-continued
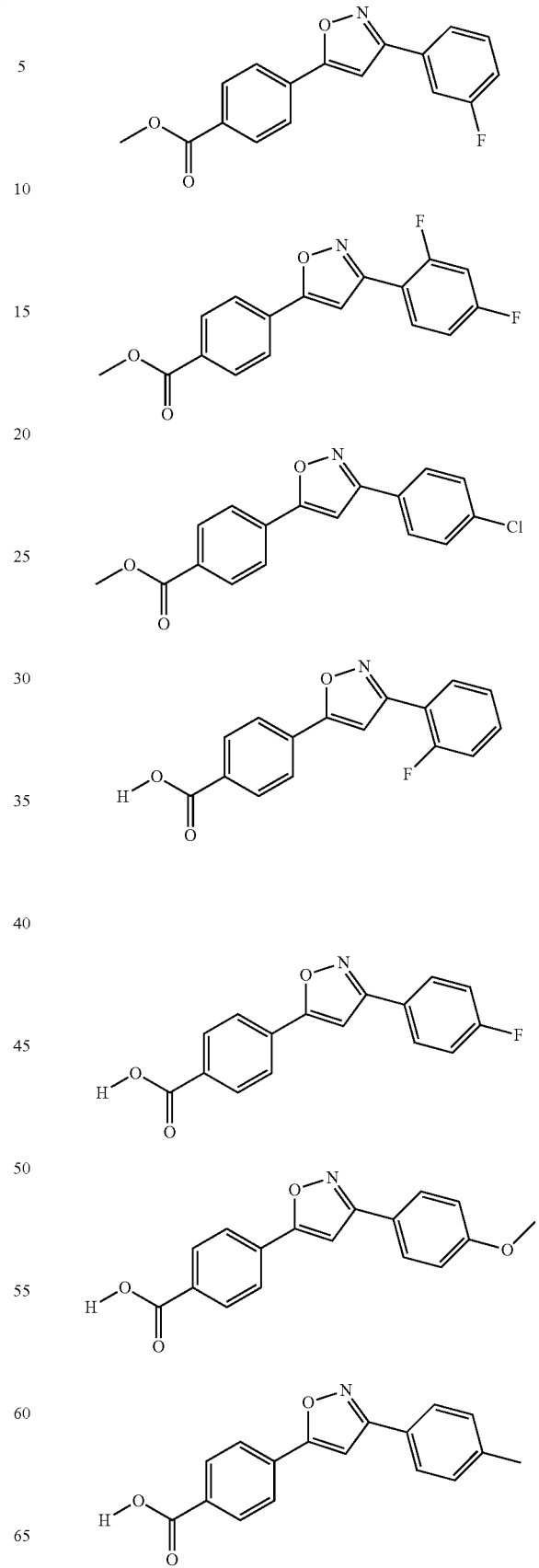

TABLE 5-continued
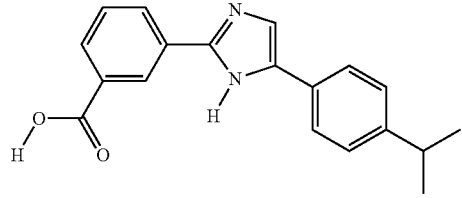 [SMILES: CC(C)c1ccc(-c2cnc(-c3cccc(C(=O)O)c3)[nH]2)cc1]
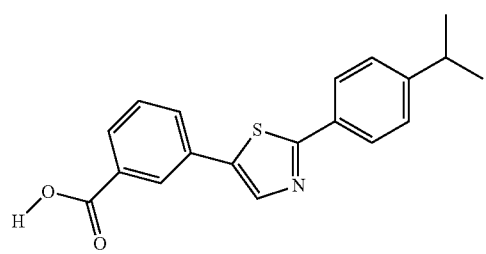
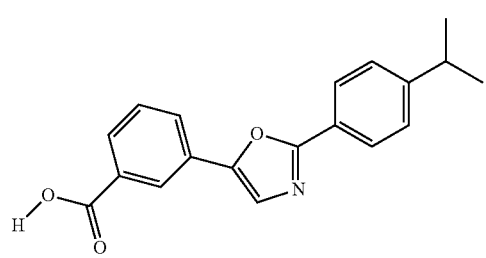 [SMILES: CC(C)c1ccc(-c2ncc(-c3cccc(C(=O)O)c3)o2)cc1]
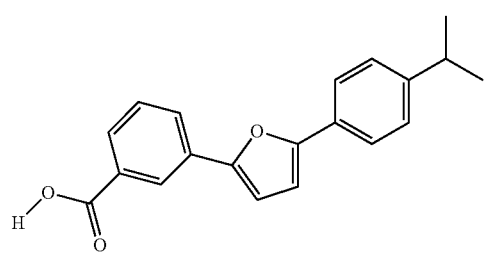 [SMILES: CC(C)c1ccc(-c2ccc(-c3cccc(C(=O)O)c3)o2)cc1]
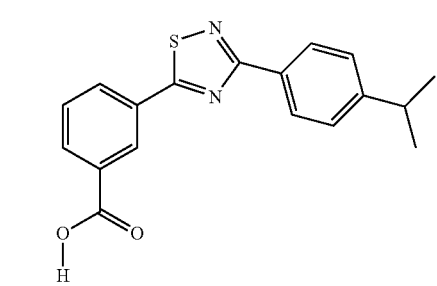 [SMILES: CC(C)c1ccc(-c2nsc(-c3cccc(C(=O)O)c3)n2)cc1]
TABLE 5-continued
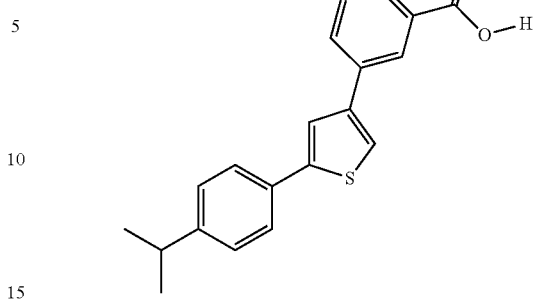
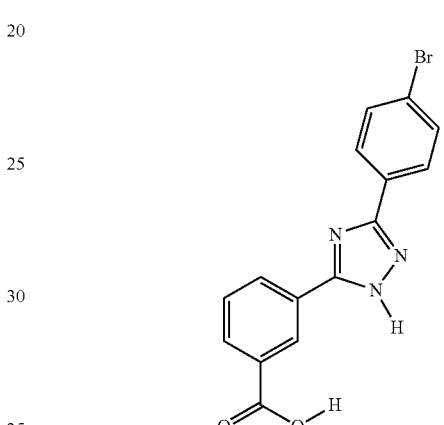
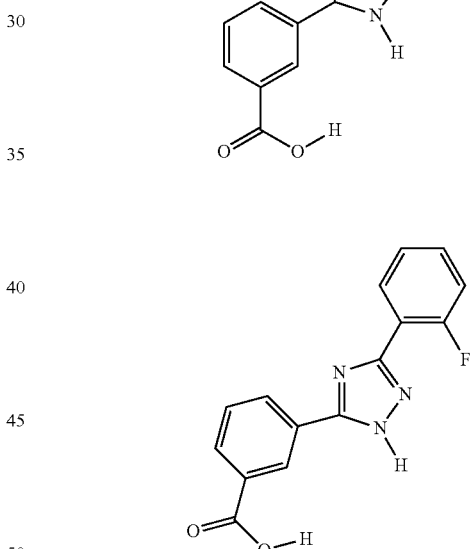
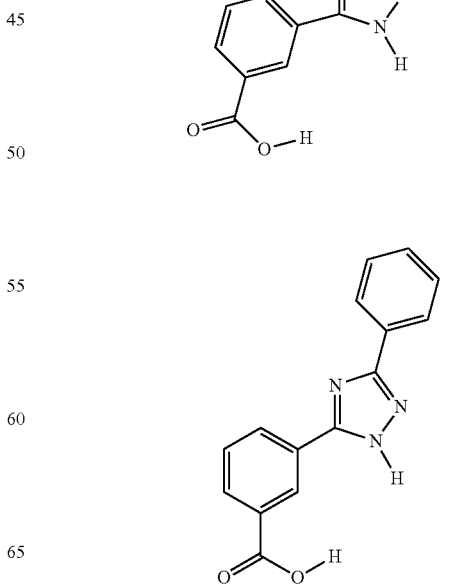

TABLE 5-continued
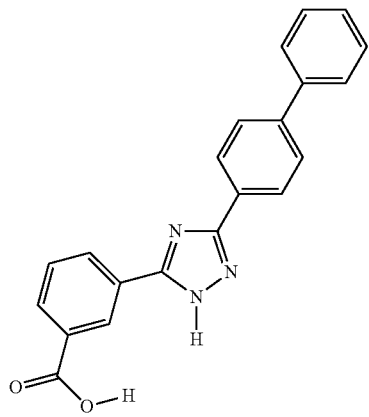 [SMILES: O=C(O)c1cccc(-c2nc(-c3ccc(-c4ccccc4)cc3)n[nH]2)c1]
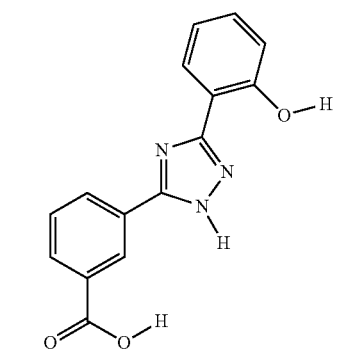 [SMILES: O=C(O)c1cccc(-c2nc(-c3ccccc3O)n[nH]2)c1]
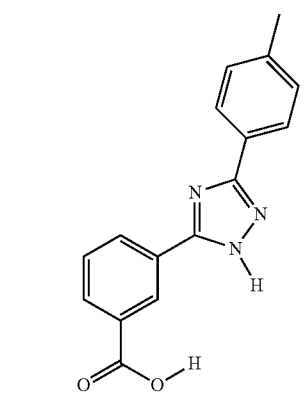 [SMILES: Cc1ccc(-c2n[nH]c(-c3cccc(C(=O)O)c3)n2)cc1]
TABLE 5-continued
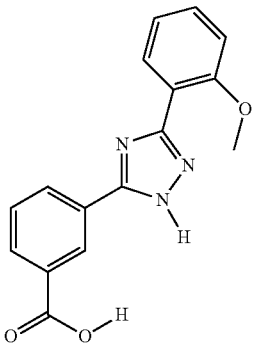 [SMILES: COc1ccccc1-c1n[nH]c(-c2cccc(C(=O)O)c2)n1]
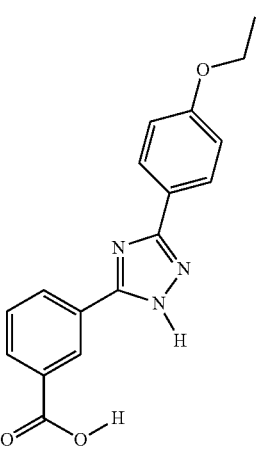 [SMILES: CCOc1ccc(-c2n[nH]c(-c3cccc(C(=O)O)c3)n2)cc1]
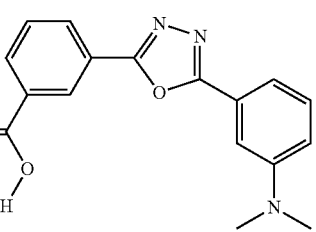
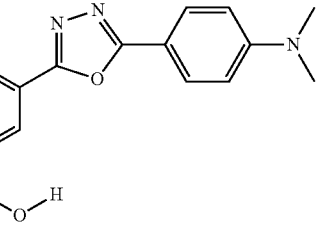
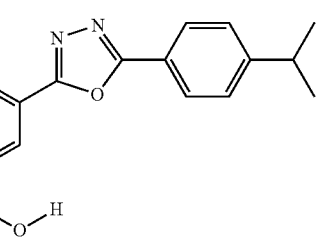

TABLE 5-continued
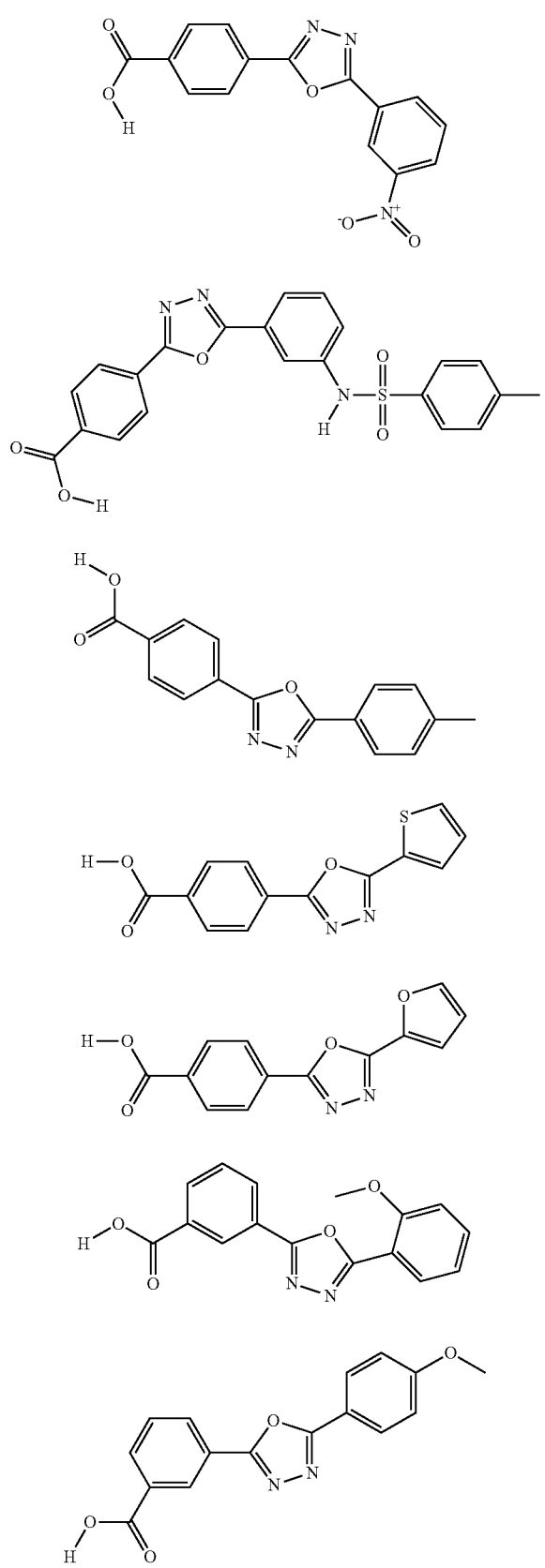
TABLE 5-continued
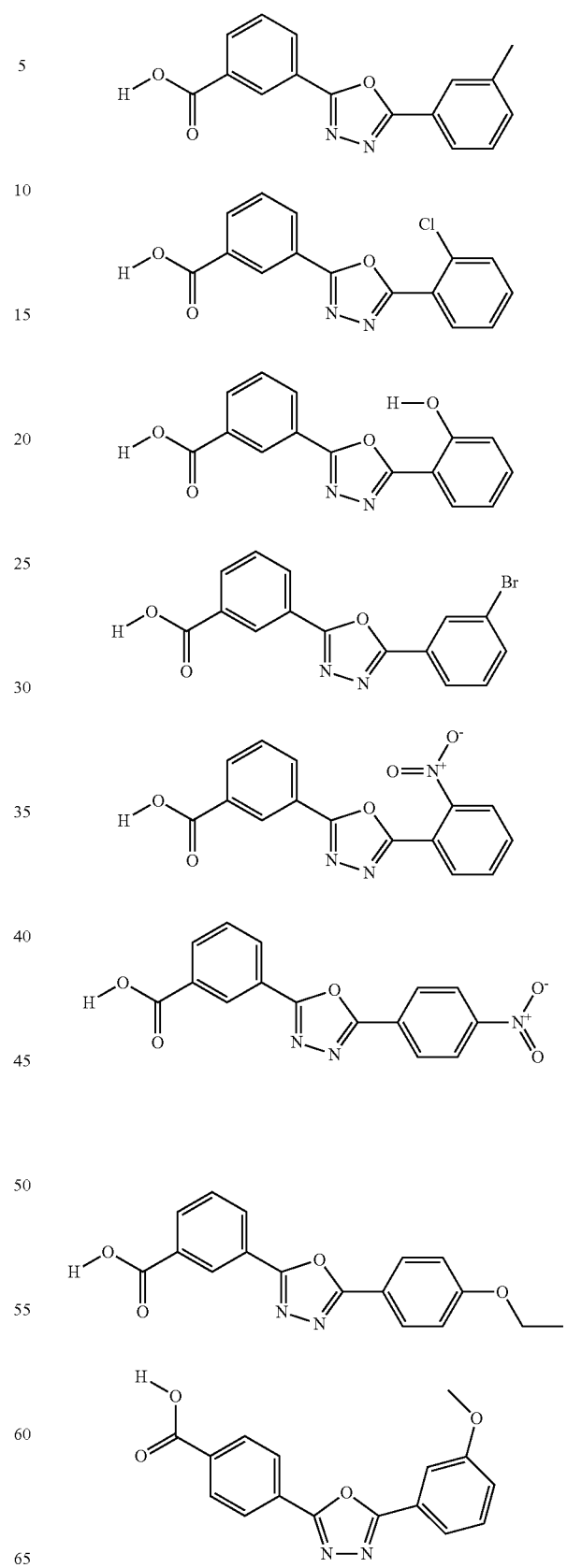

TABLE 5-continued
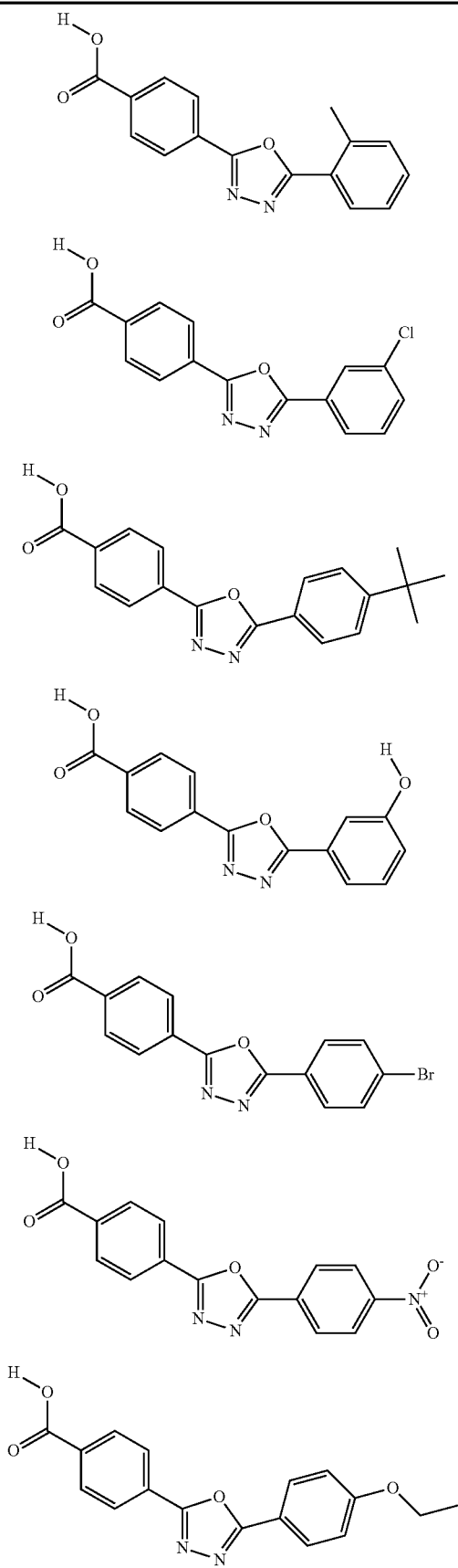
TABLE 5-continued
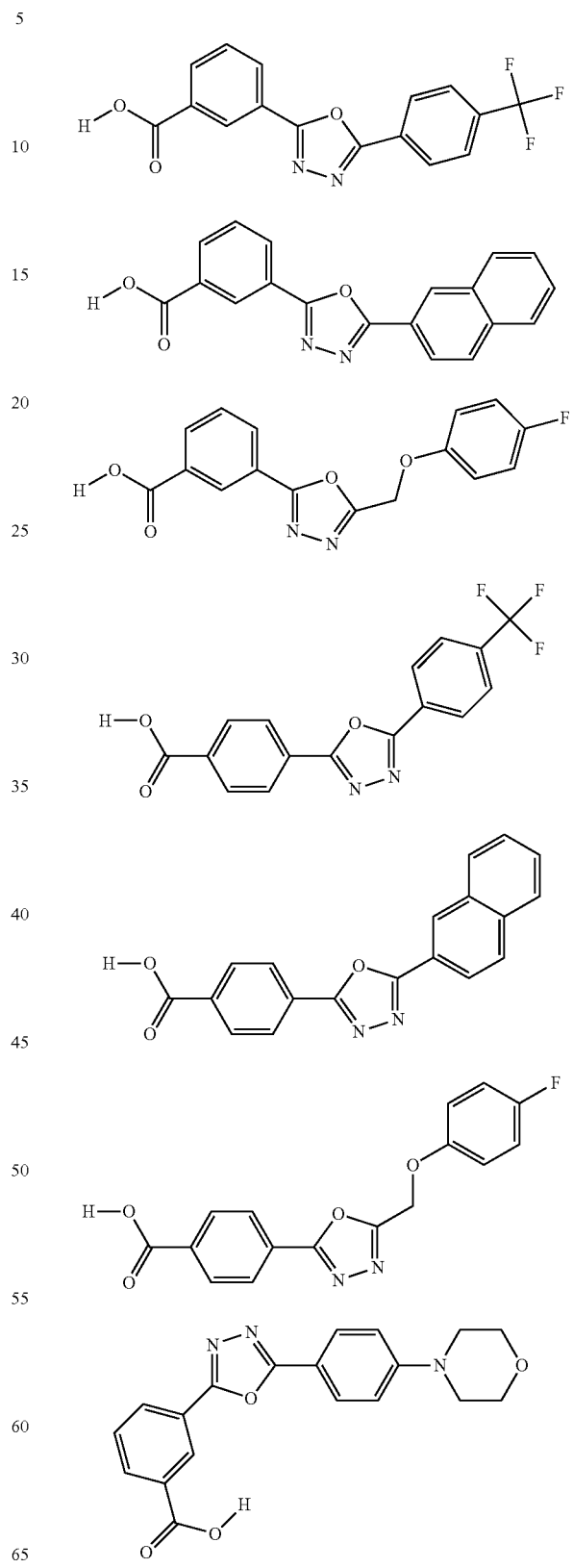

TABLE 5-continued
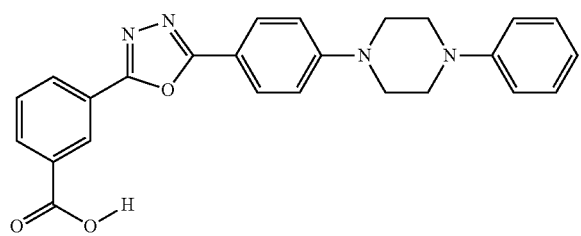 [SMILES: O=C(O)c1cccc(-c2nnc(-c3ccc(N4CCN(c5ccccc5)CC4)cc3)o2)c1]
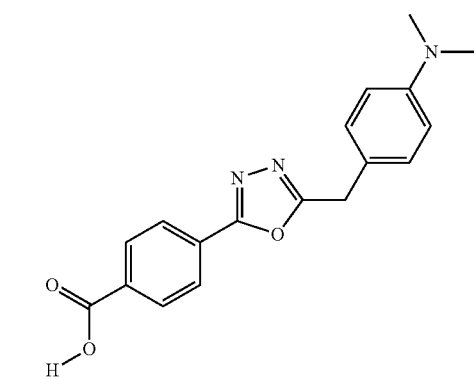 [SMILES: CN(C)c1ccc(Cc2nnc(-c3ccc(C(=O)O)cc3)o2)cc1]
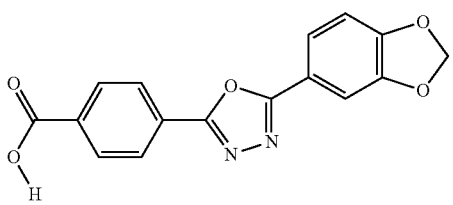 [SMILES: O=C(O)c1ccc(-c2nnc(-c3ccc4c(c3)OCO4)o2)cc1]
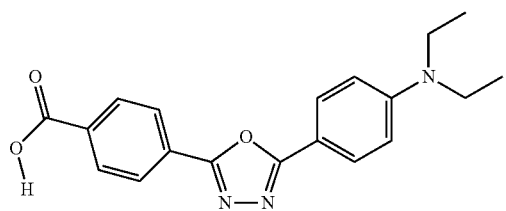 [SMILES: CCN(CC)c1ccc(-c2nnc(-c3ccc(C(=O)O)cc3)o2)cc1]
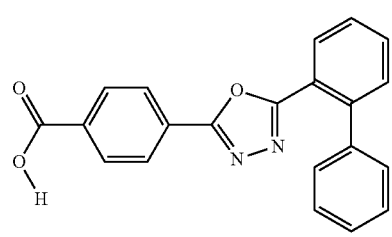 [SMILES: O=C(O)c1ccc(-c2nnc(-c3ccccc3-c3ccccc3)o2)cc1]
TABLE 5-continued
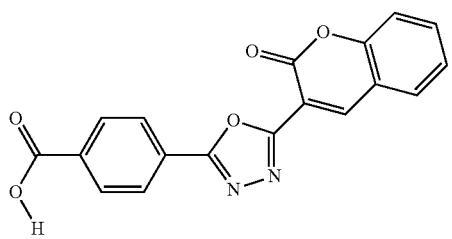 [SMILES: O=C(O)c1ccc(-c2nnc(-c3cc4ccccc4oc3=O)o2)cc1]
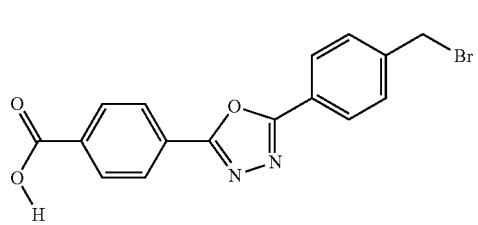 [SMILES: O=C(O)c1ccc(-c2nnc(-c3ccc(CBr)cc3)o2)cc1]
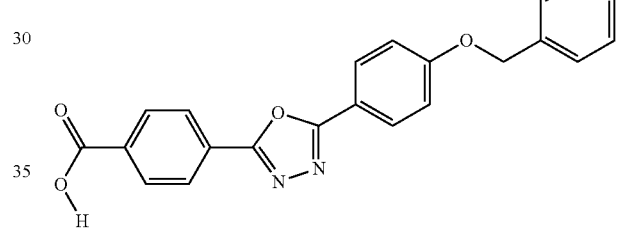
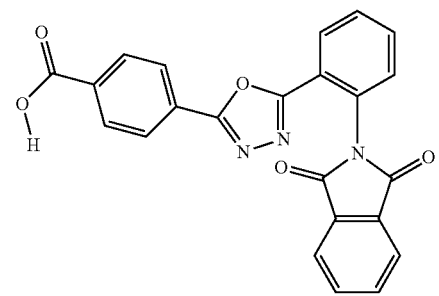 [SMILES: O=C(O)c1ccc(-c2nnc(-c3ccccc3N3C(=O)c4ccccc4C3=O)o2)cc1]
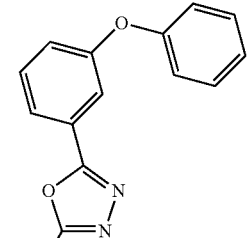
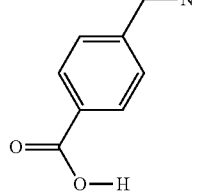
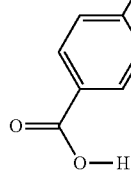

TABLE 5-continued
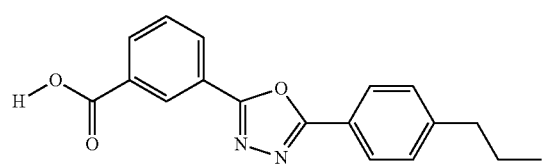 [SMILES: CCCc1ccc(-c2nnc(-c3cccc(C(=O)O)c3)o2)cc1]
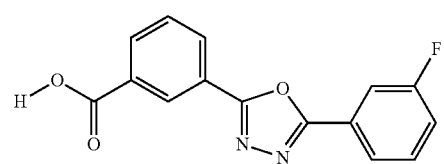 [SMILES: O=C(O)c1cccc(-c2nnc(-c3cccc(F)c3)o2)c1]
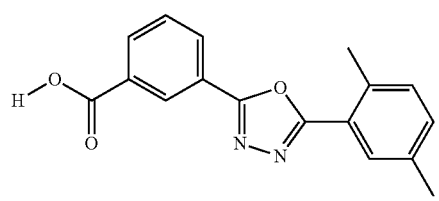 [SMILES: Cc1ccc(C)c(-c2nnc(-c3cccc(C(=O)O)c3)o2)c1]
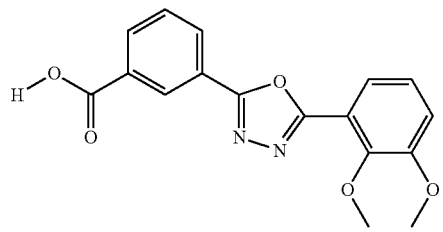 [SMILES: COc1cccc(-c2nnc(-c3cccc(C(=O)O)c3)o2)c1OC]
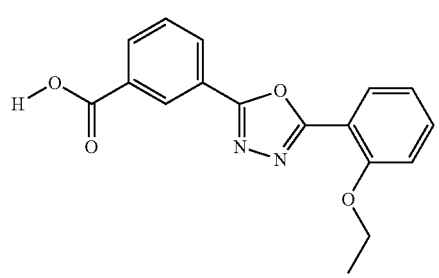 [SMILES: CCOc1ccccc1-c1nnc(-c2cccc(C(=O)O)c2)o1]
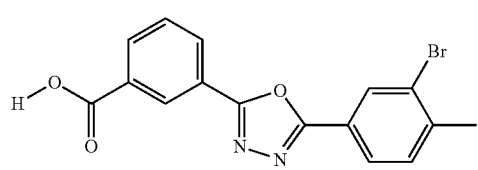
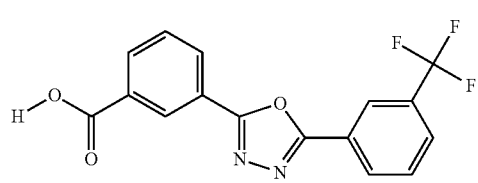 [SMILES: O=C(O)c1cccc(-c2nnc(-c3cccc(C(F)(F)F)c3)o2)c1]
TABLE 5-continued
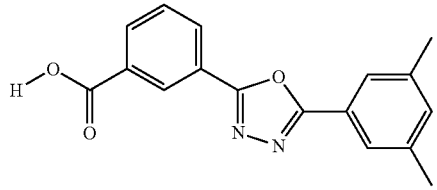 [SMILES: Cc1cc(C)cc(-c2nnc(-c3cccc(C(=O)O)c3)o2)c1]
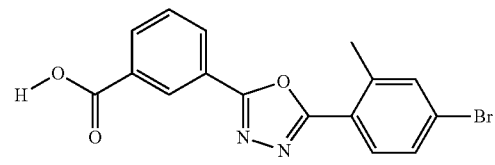 [SMILES: Cc1cc(Br)ccc1-c1nnc(-c2cccc(C(=O)O)c2)o1]
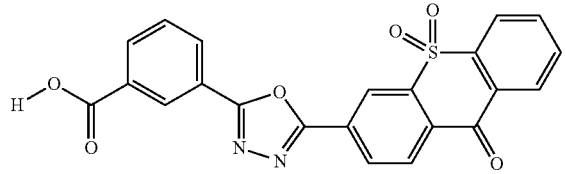 [SMILES: O=C(O)c1cccc(-c2nnc(-c3ccc4c(c3)S(=O)(=O)c3ccccc3C4=O)o2)c1]
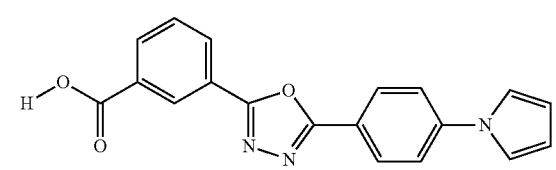 [SMILES: O=C(O)c1cccc(-c2nnc(-c3ccc(-n4cccc4)cc3)o2)c1]
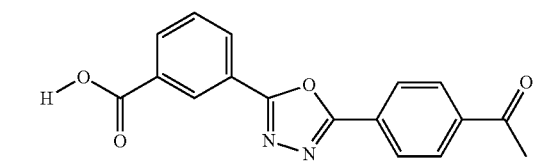 [SMILES: CC(=O)c1ccc(-c2nnc(-c3cccc(C(=O)O)c3)o2)cc1]
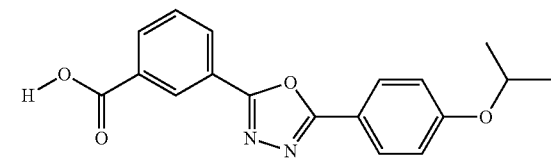 [SMILES: CC(C)Oc1ccc(-c2nnc(-c3cccc(C(=O)O)c3)o2)cc1]
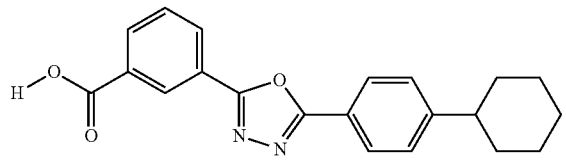 [SMILES: O=C(O)c1cccc(-c2nnc(-c3ccc(C4CCCCC4)cc3)o2)c1]
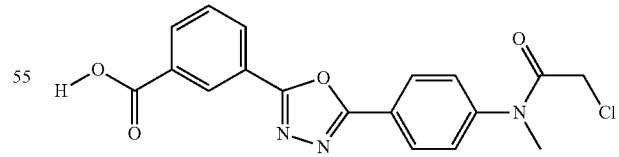
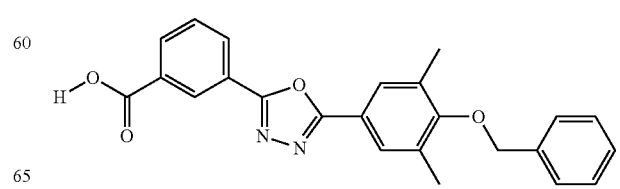

TABLE 5-continued
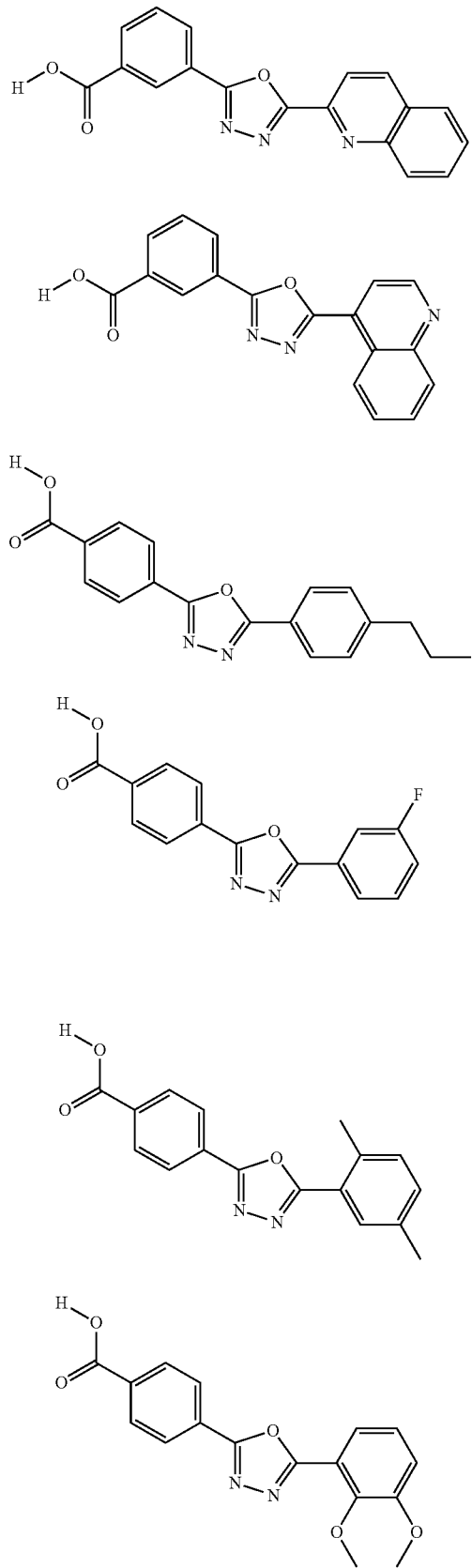
TABLE 5-continued
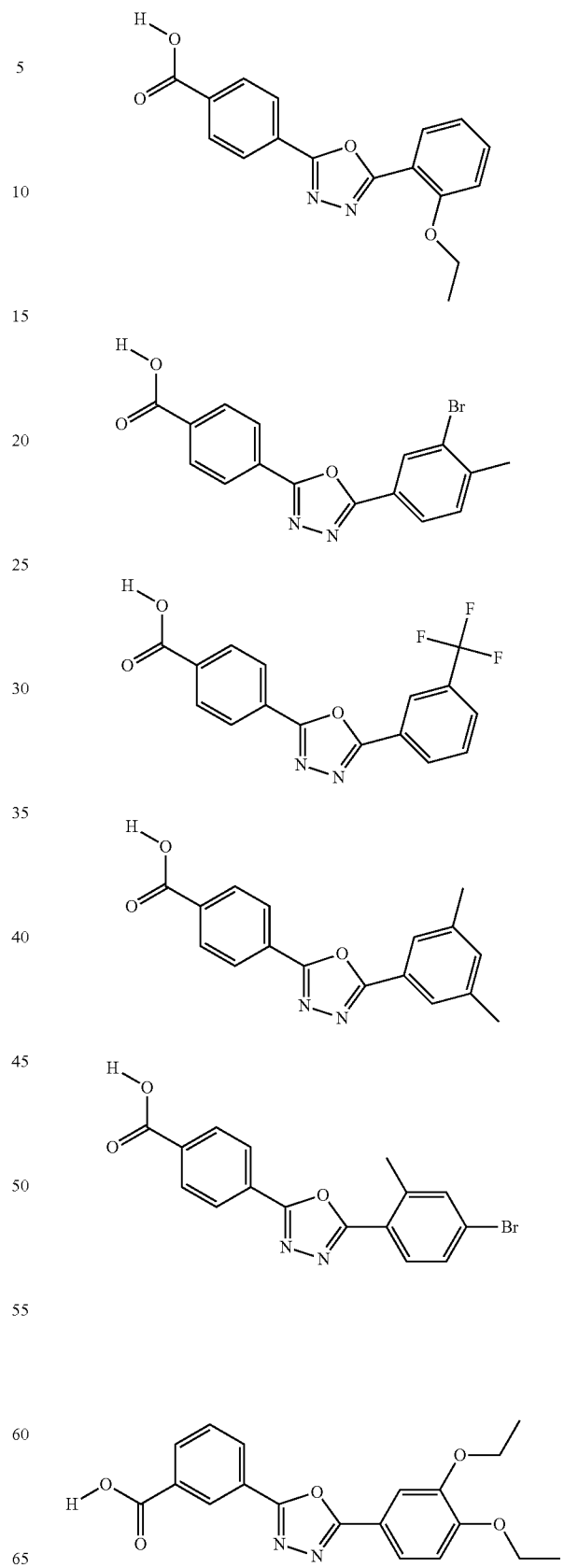

TABLE 5-continued
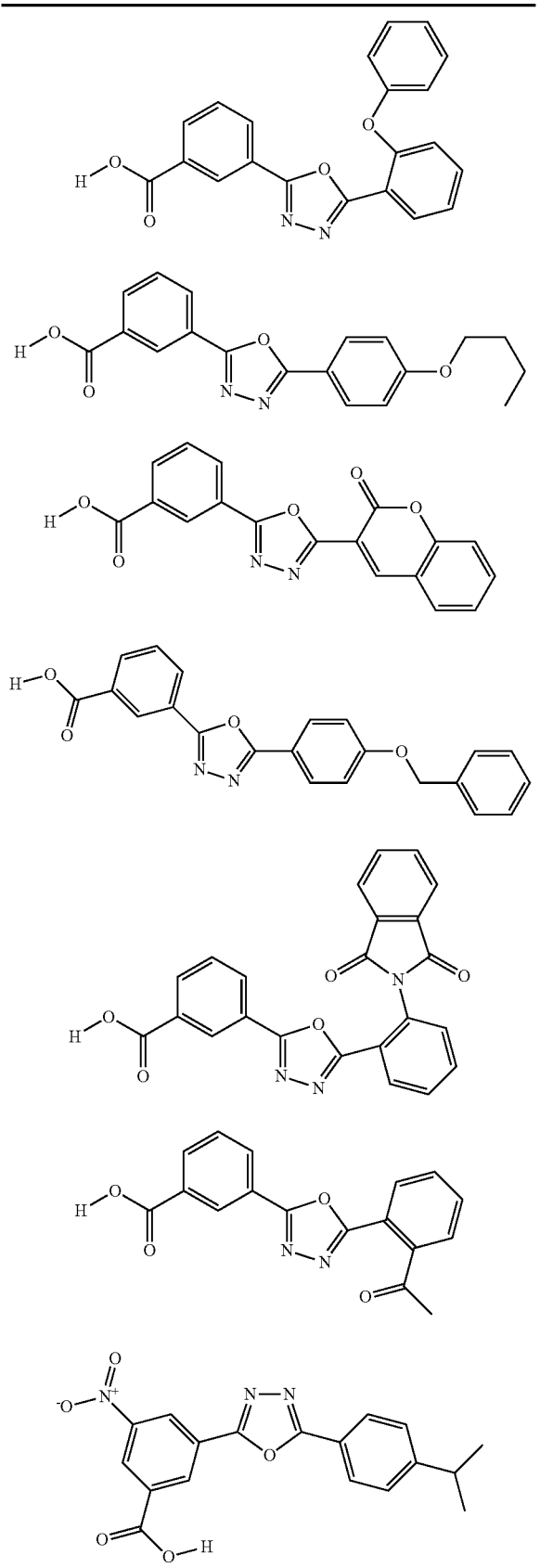
TABLE 5-continued
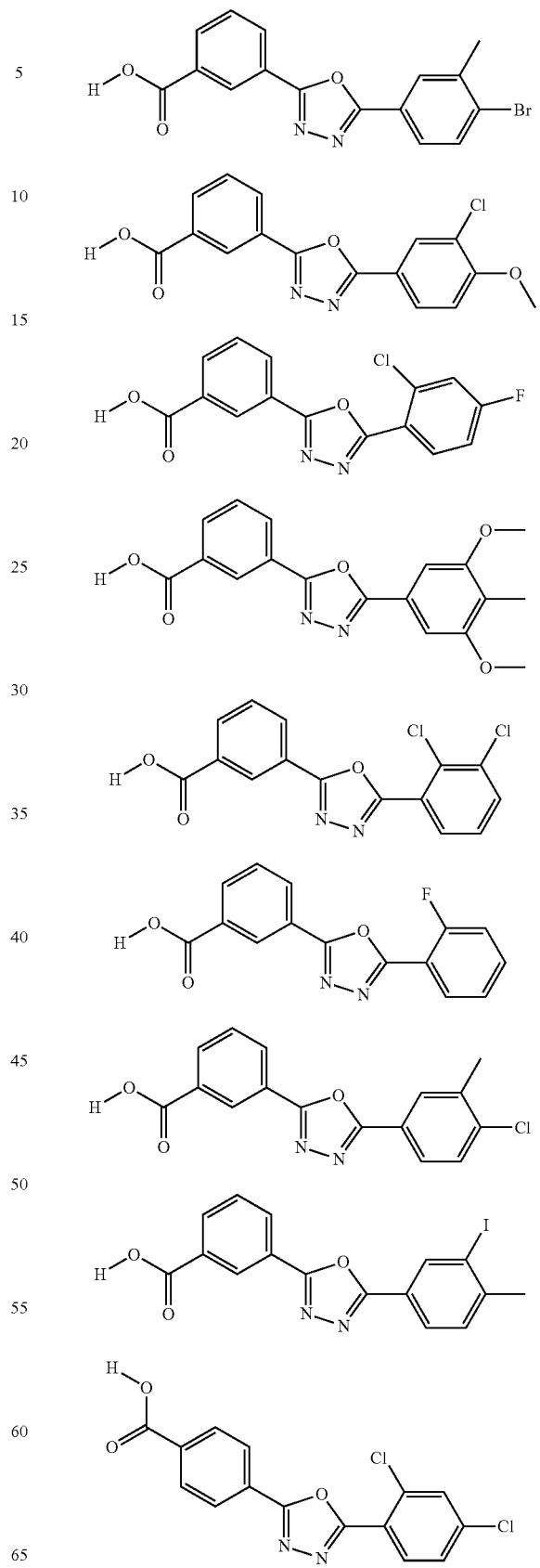

TABLE 5-continued
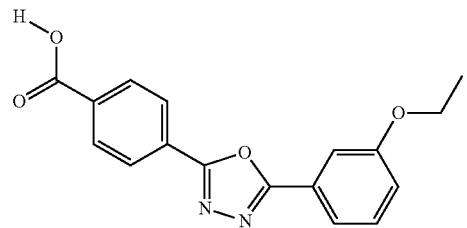 [SMILES: CCOc1cccc(-c2nnc(-c3ccc(C(=O)O)cc3)o2)c1]
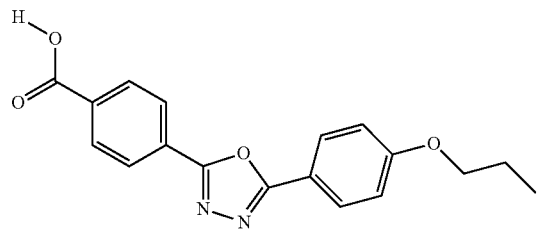 [SMILES: CCCOc1ccc(-c2nnc(-c3ccc(C(=O)O)cc3)o2)cc1]
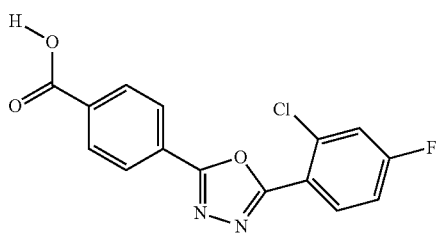 [SMILES: O=C(O)c1ccc(-c2nnc(-c3ccc(F)cc3Cl)o2)cc1]
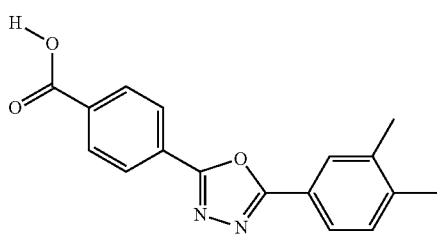
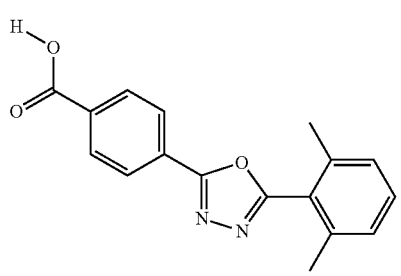 [SMILES: Cc1cccc(C)c1-c1nnc(-c2ccc(C(=O)O)cc2)o1]
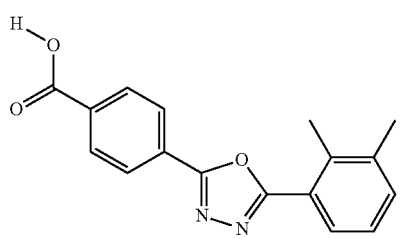 [SMILES: Cc1cccc(-c2nnc(-c3ccc(C(=O)O)cc3)o2)c1C]
TABLE 5-continued
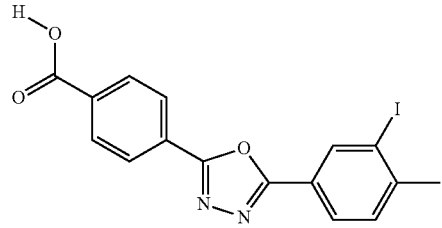
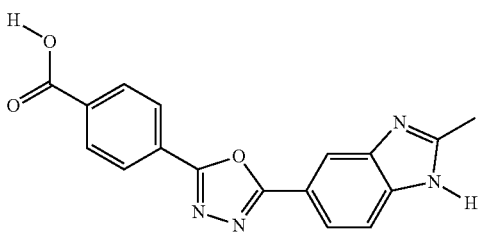 [SMILES: Cc1nc2cc(-c3nnc(-c4ccc(C(=O)O)cc4)o3)ccc2[nH]1]
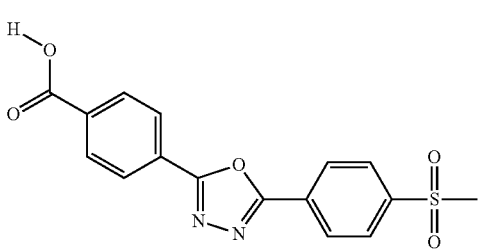 [SMILES: CS(=O)(=O)c1ccc(-c2nnc(-c3ccc(C(=O)O)cc3)o2)cc1]
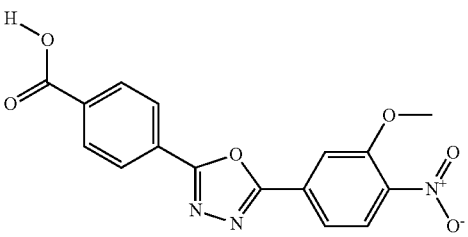 [SMILES: COc1cc(-c2nnc(-c3ccc(C(=O)O)cc3)o2)ccc1[N+](=O)[O-]]
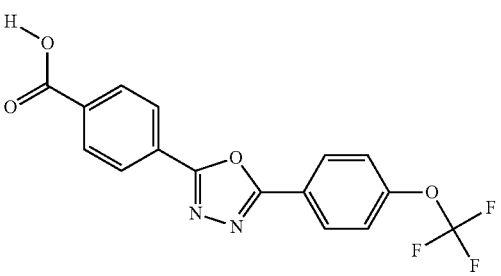 [SMILES: O=C(O)c1ccc(-c2nnc(-c3ccc(OC(F)(F)F)cc3)o2)cc1]
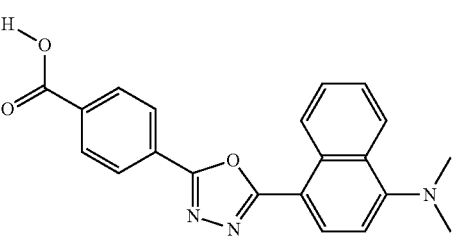 [SMILES: CN(C)c1ccc(-c2nnc(-c3ccc(C(=O)O)cc3)o2)c2ccccc12]

TABLE 5-continued
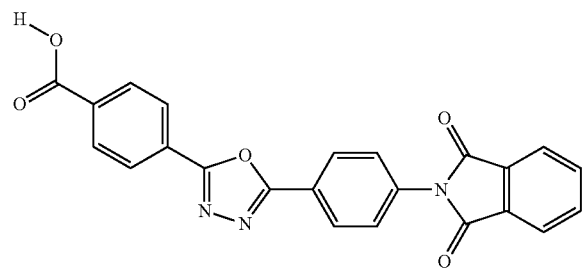 [SMILES: O=C(O)c1ccc(-c2nnc(-c3ccc(N4C(=O)c5ccccc5C4=O)cc3)o2)cc1]
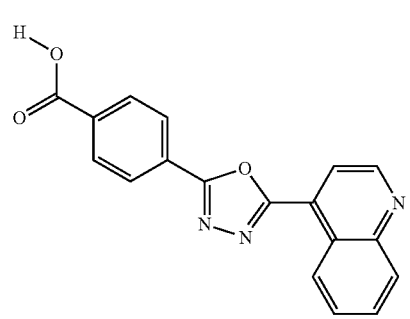 [SMILES: O=C(O)c1ccc(-c2nnc(-c3ccnc4ccccc34)o2)cc1]
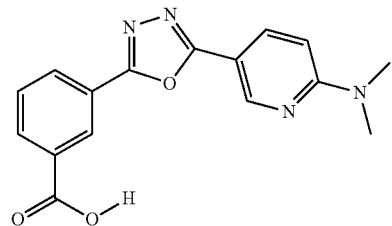 [SMILES: CN(C)c1ccc(-c2nnc(-c3cccc(C(=O)O)c3)o2)cn1]
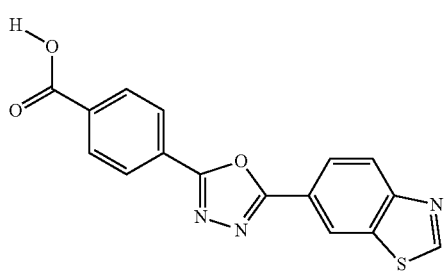 [SMILES: O=C(O)c1ccc(-c2nnc(-c3ccc4ncsc4c3)o2)cc1]
TABLE 5-continued
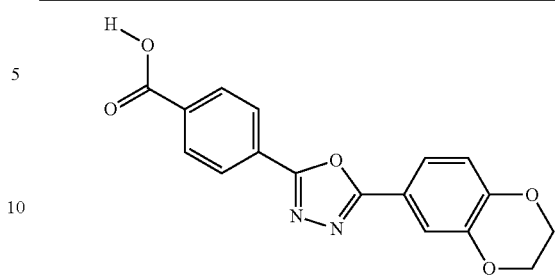
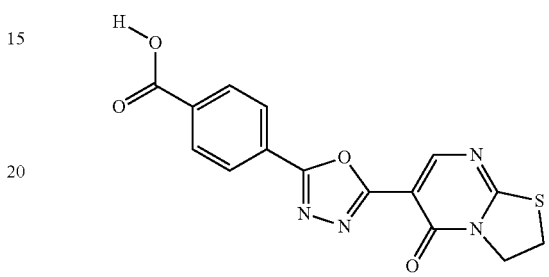
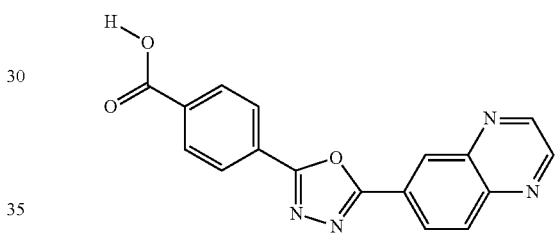
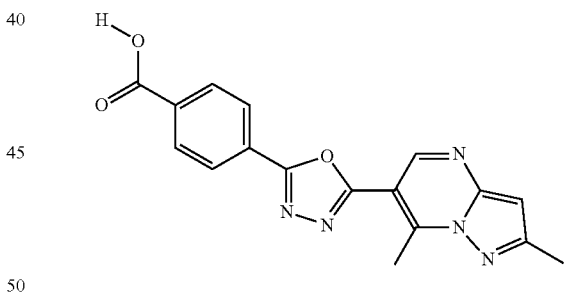
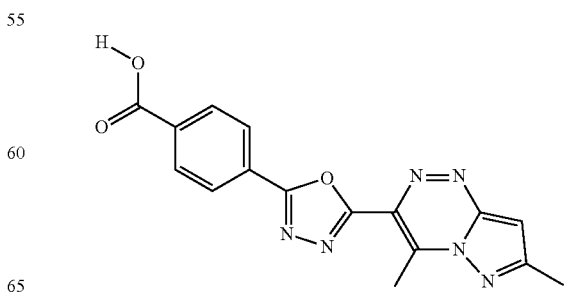

TABLE 5-continued
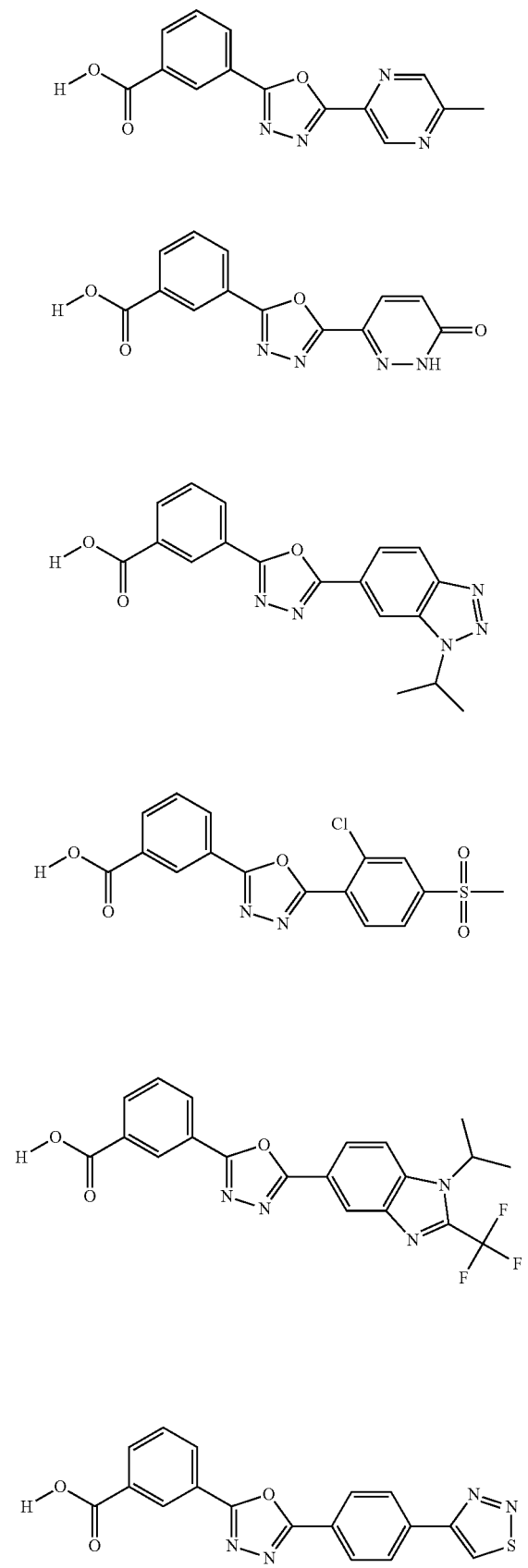
TABLE 5-continued
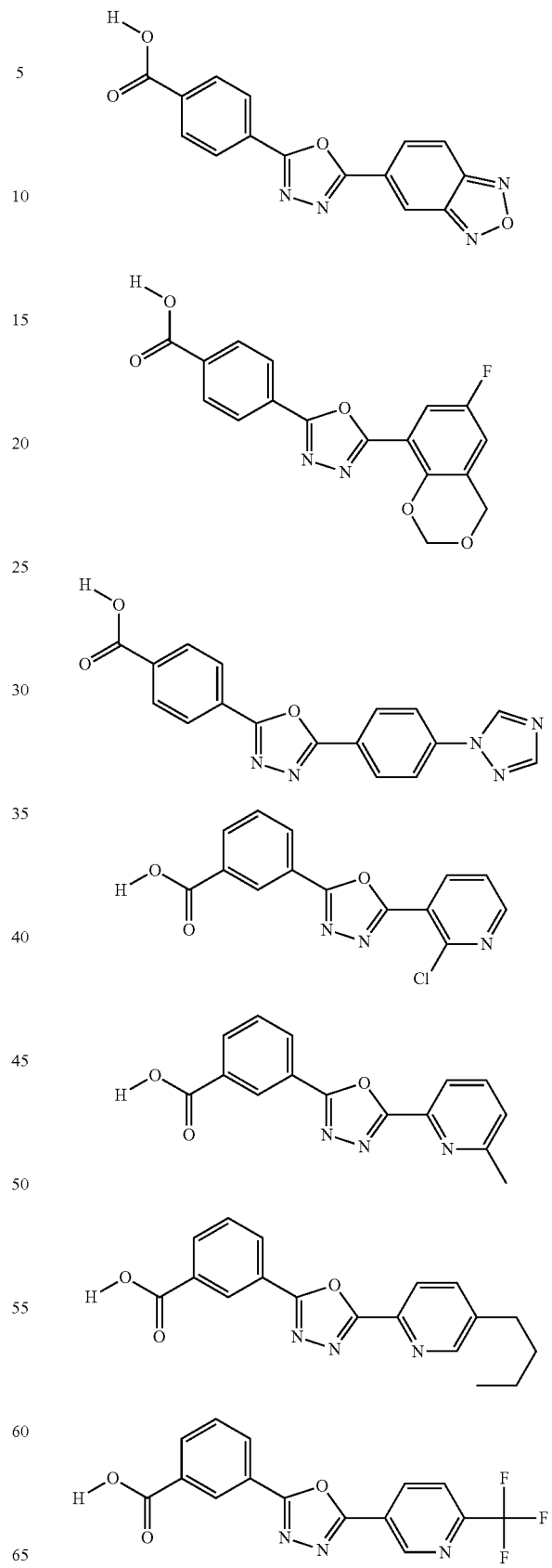

TABLE 5-continued
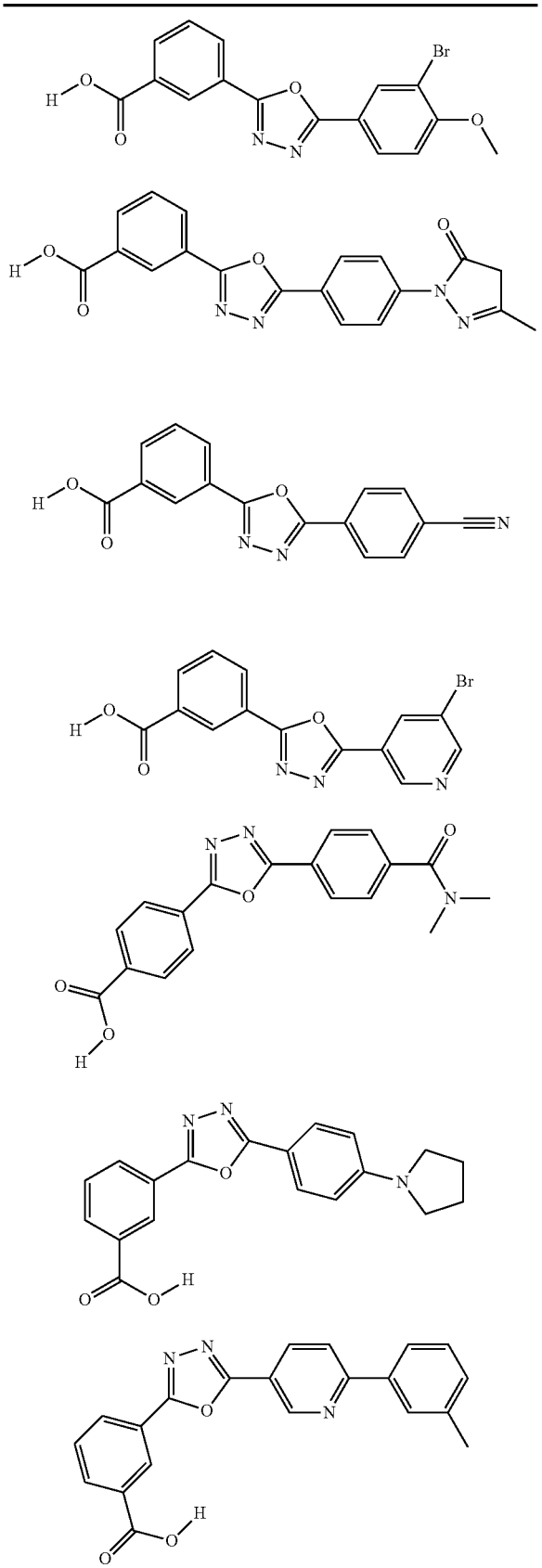
TABLE 5-continued
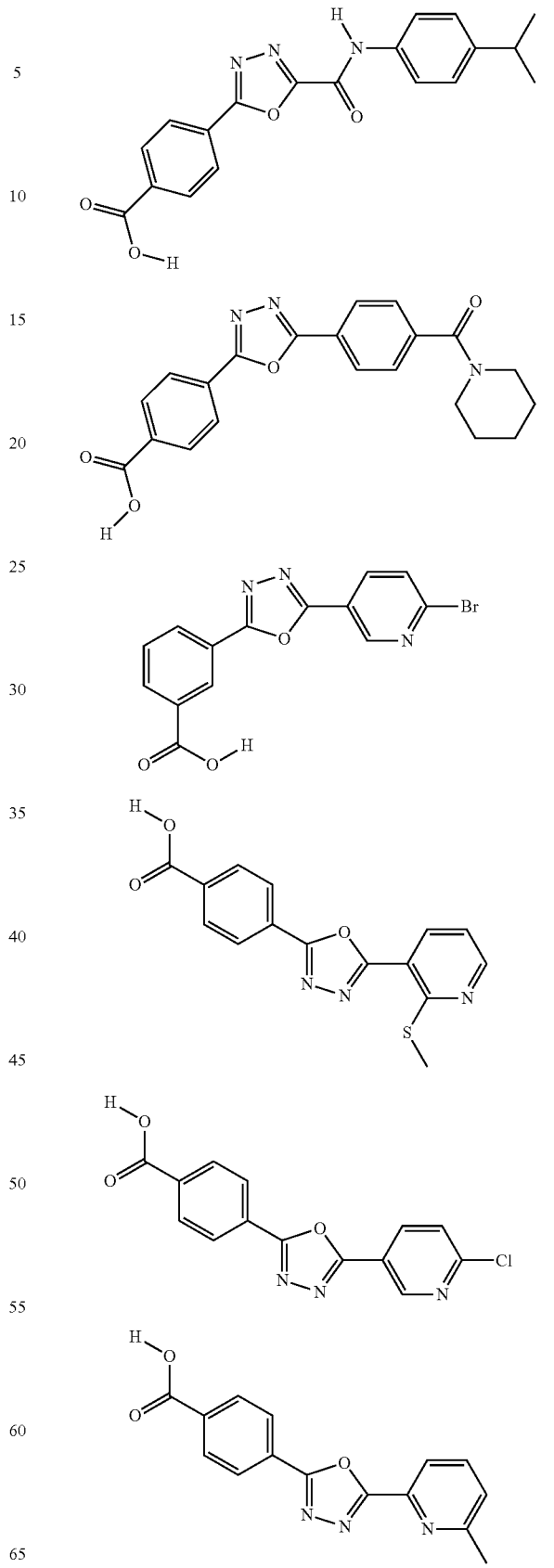

TABLE 5-continued
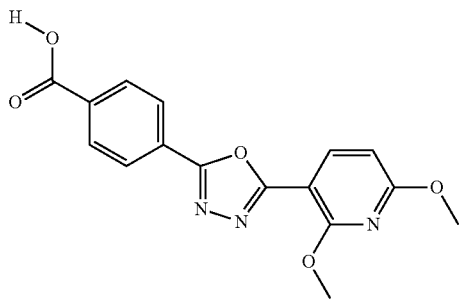 [SMILES: COc1ccc(-c2nnc(-c3ccc(C(=O)O)cc3)o2)c(OC)n1]
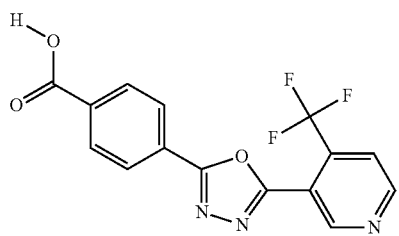 [SMILES: O=C(O)c1ccc(-c2nnc(-c3cnccc3C(F)(F)F)o2)cc1]
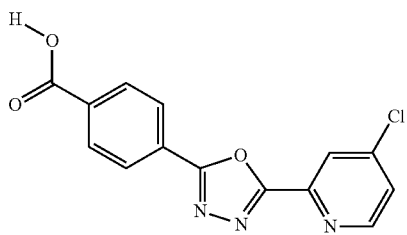 [SMILES: O=C(O)c1ccc(-c2nnc(-c3cc(Cl)ccn3)o2)cc1]
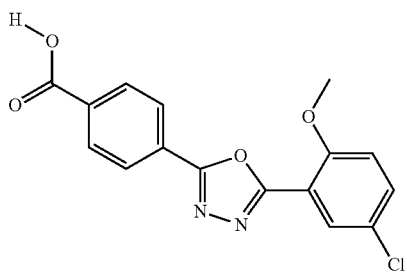 [SMILES: COc1ccc(Cl)cc1-c1nnc(-c2ccc(C(=O)O)cc2)o1]
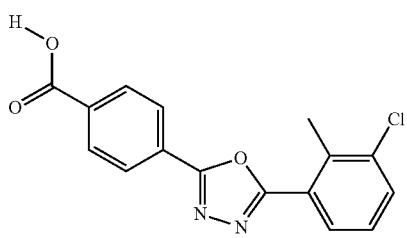 [SMILES: Cc1c(Cl)cccc1-c1nnc(-c2ccc(C(=O)O)cc2)o1]
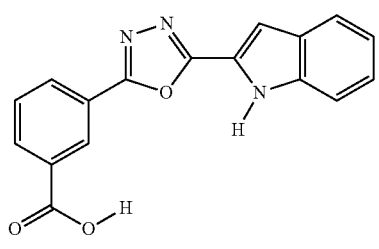 [SMILES: O=C(O)c1cccc(-c2nnc(-c3cc4ccccc4[nH]3)o2)c1]
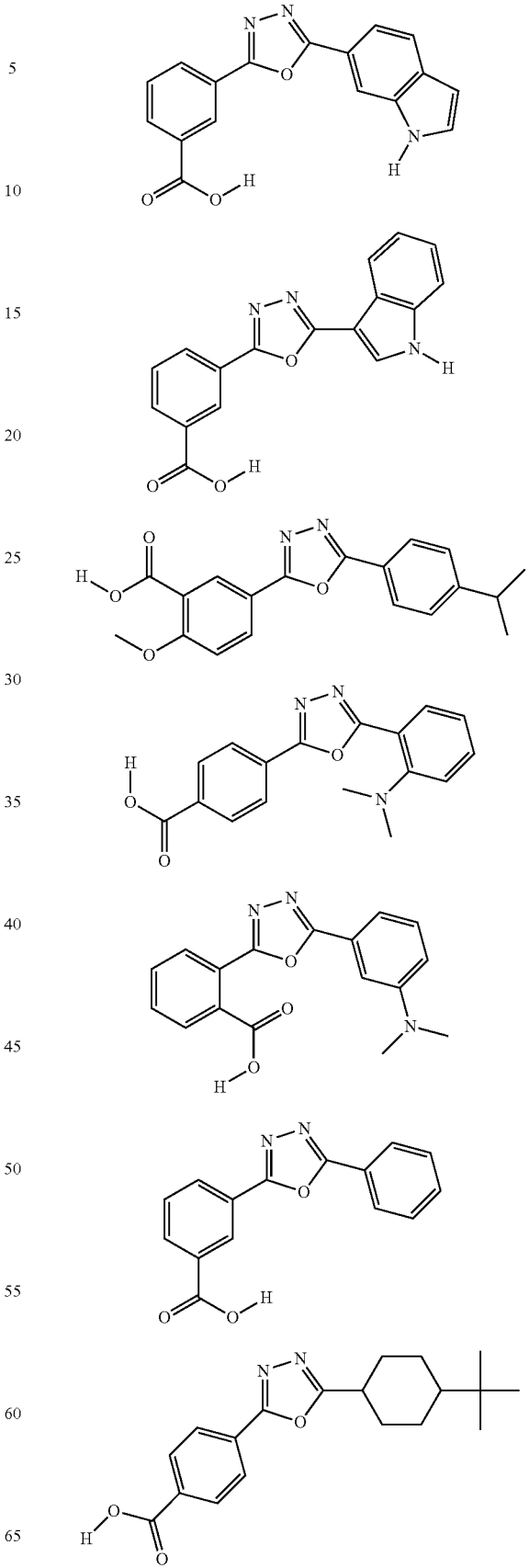

TABLE 5-continued
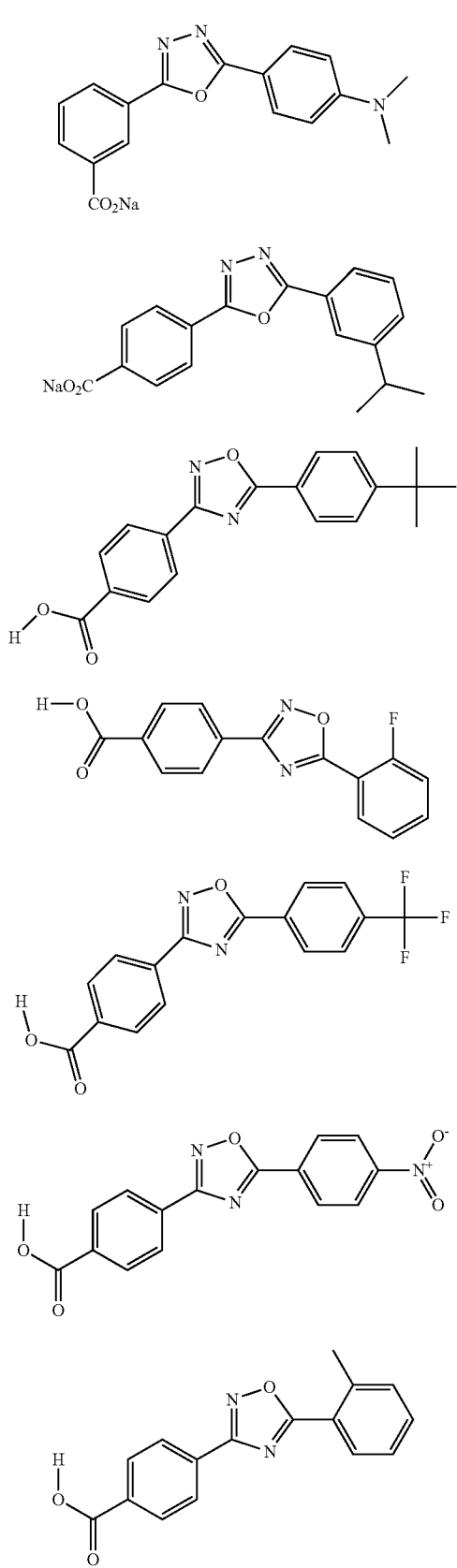
TABLE 5-continued
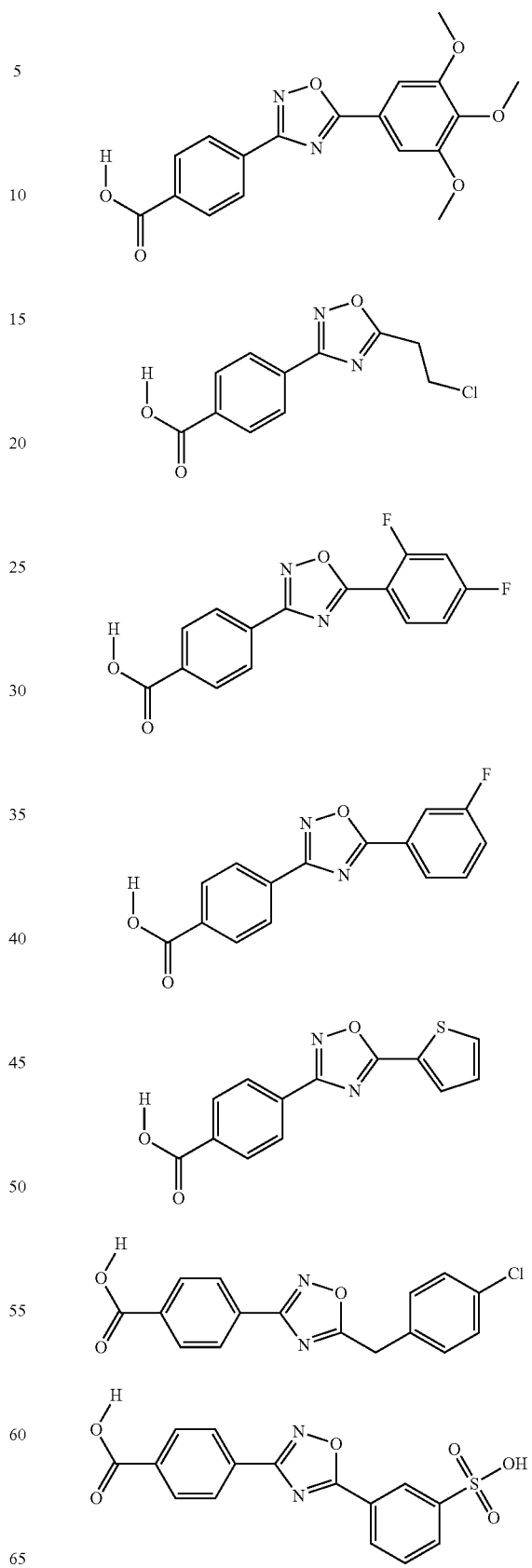

TABLE 5-continued
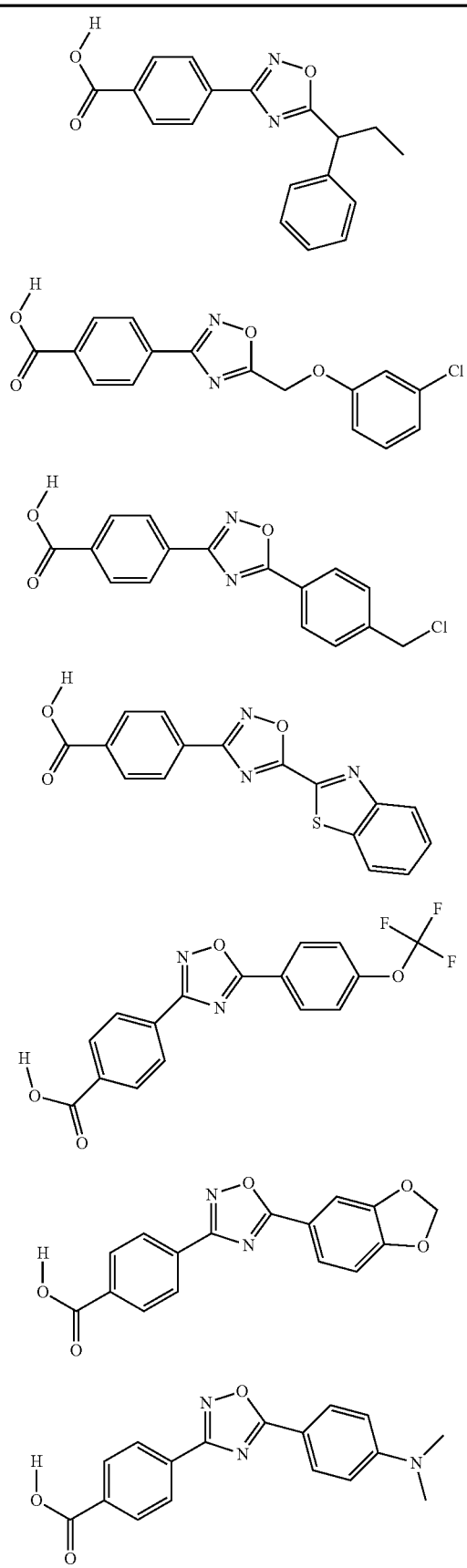
TABLE 5-continued
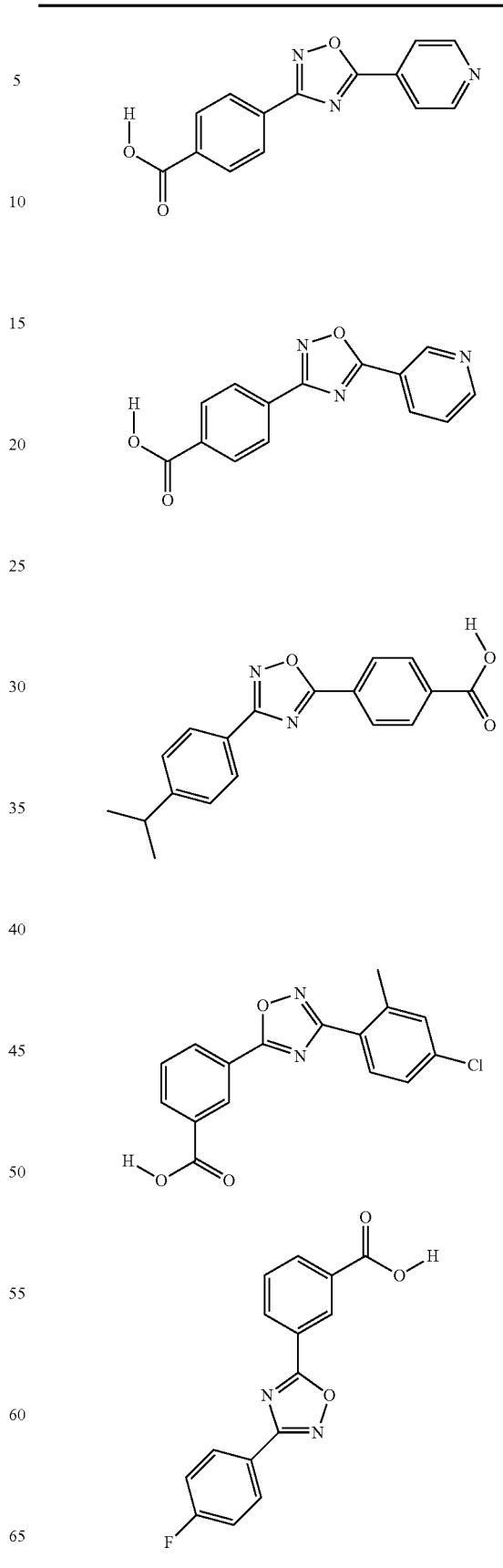

TABLE 5-continued
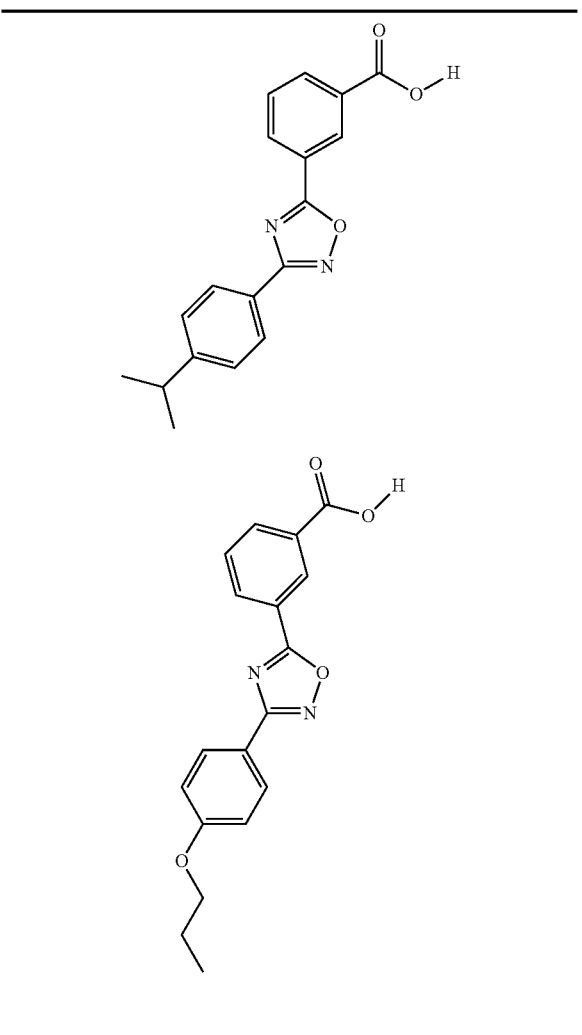
TABLE 5-continued
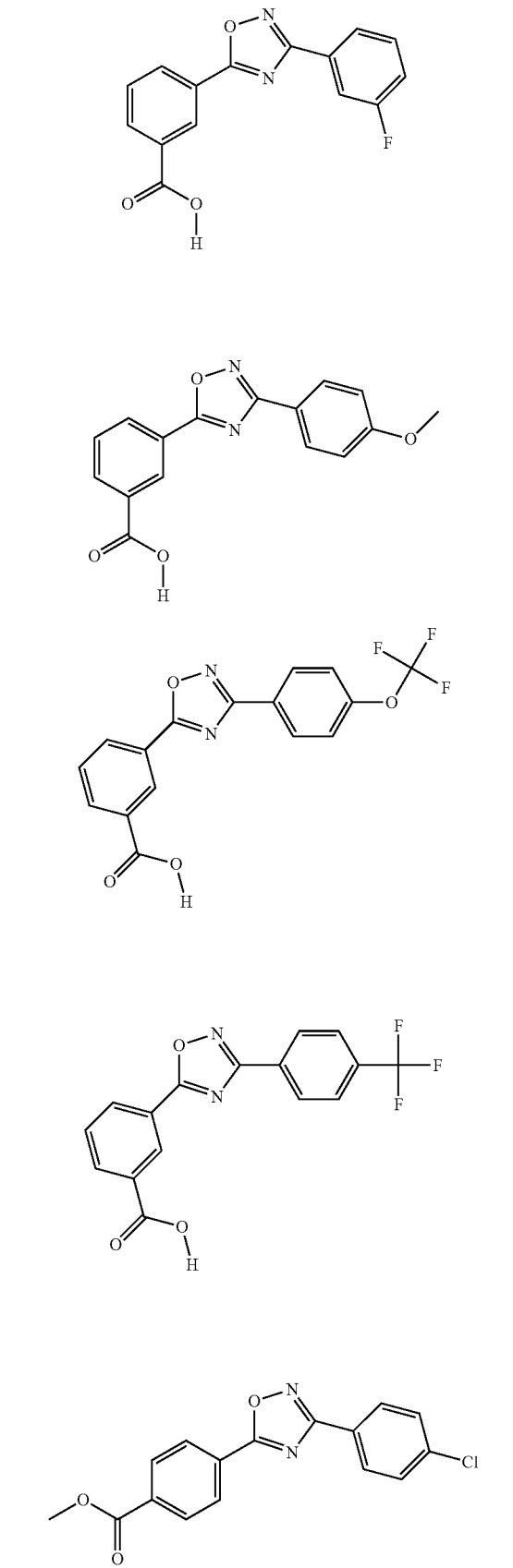

TABLE 5-continued
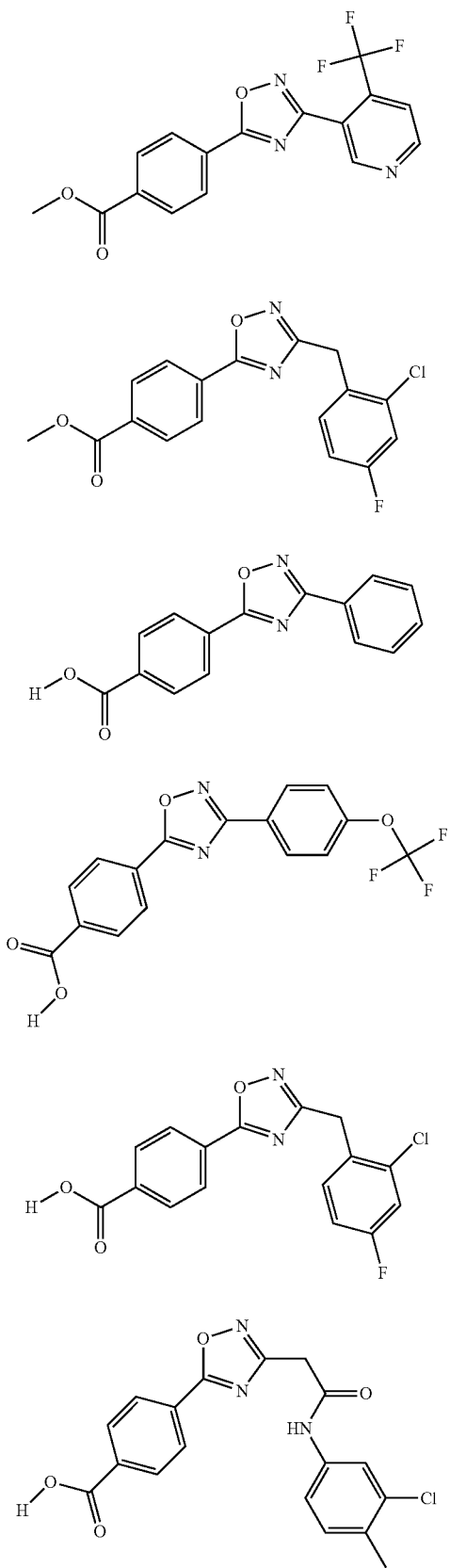
TABLE 5-continued
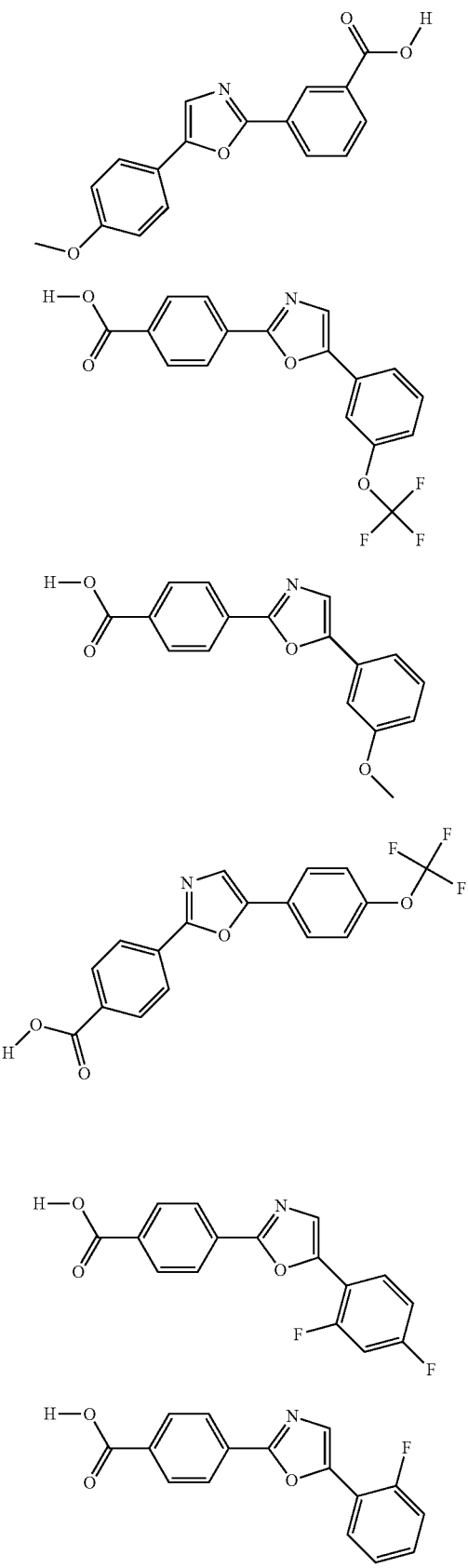

201
TABLE 5-continued
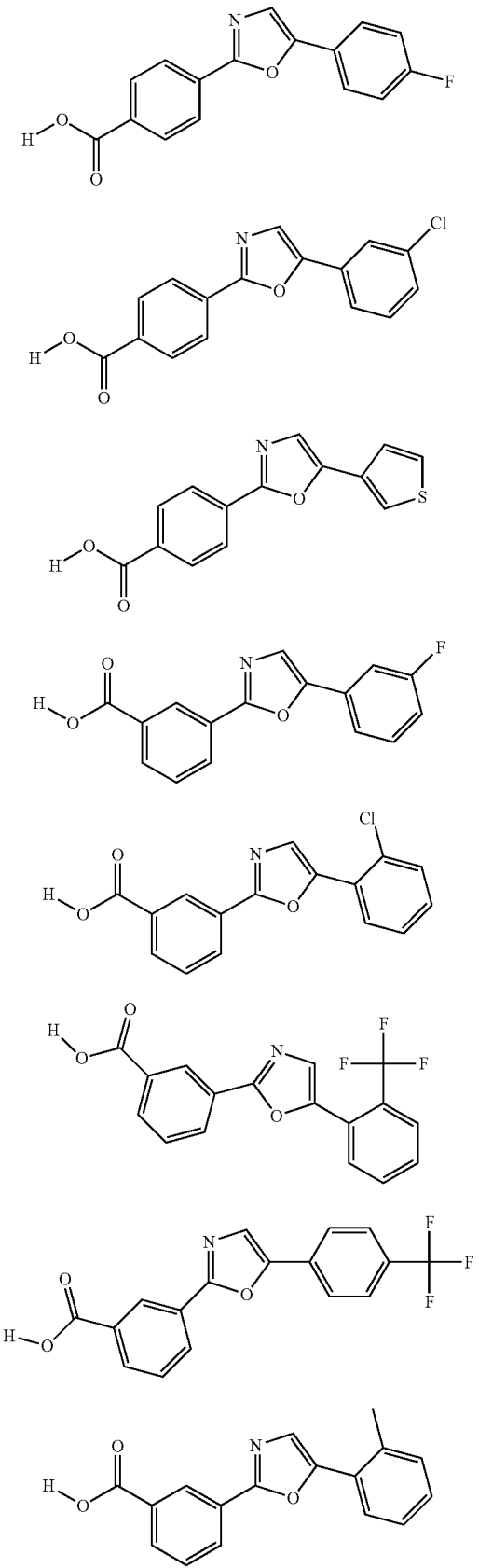
202
TABLE 5-continued
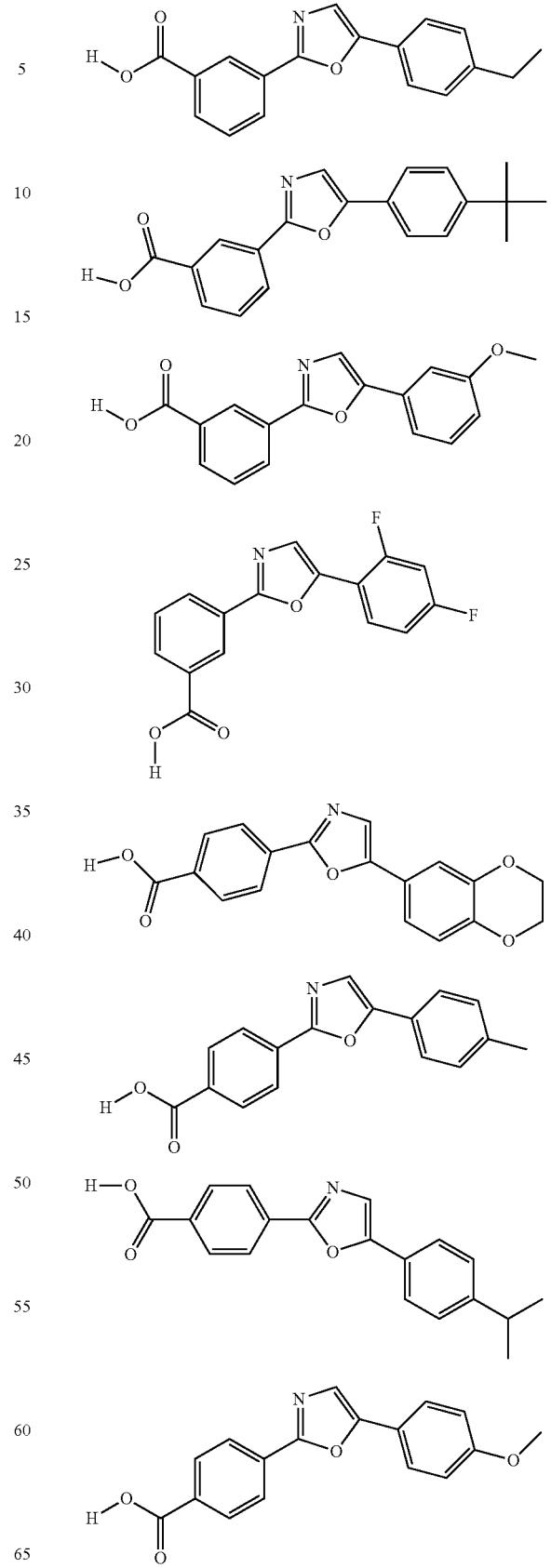

TABLE 5-continued
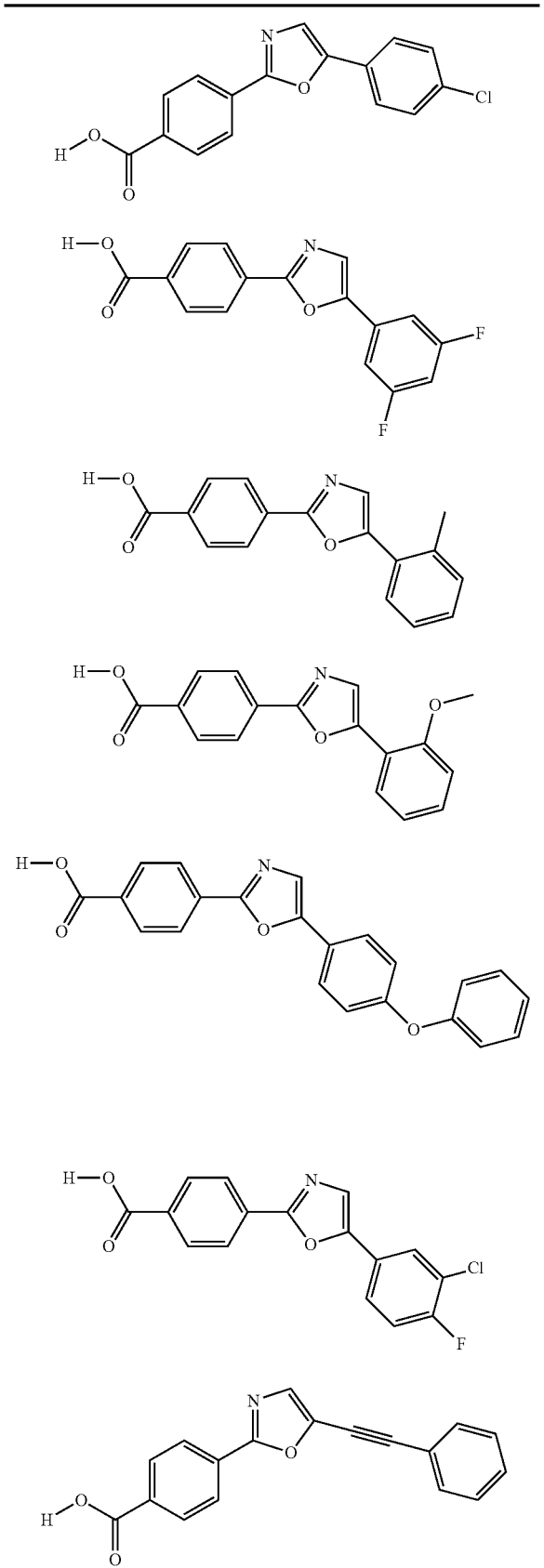
TABLE 5-continued
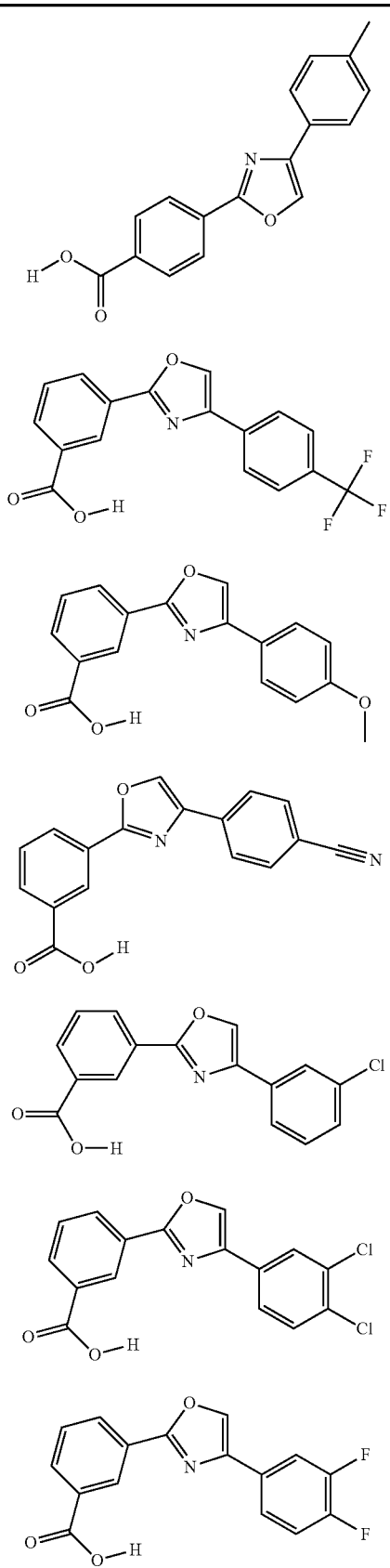

TABLE 5-continued
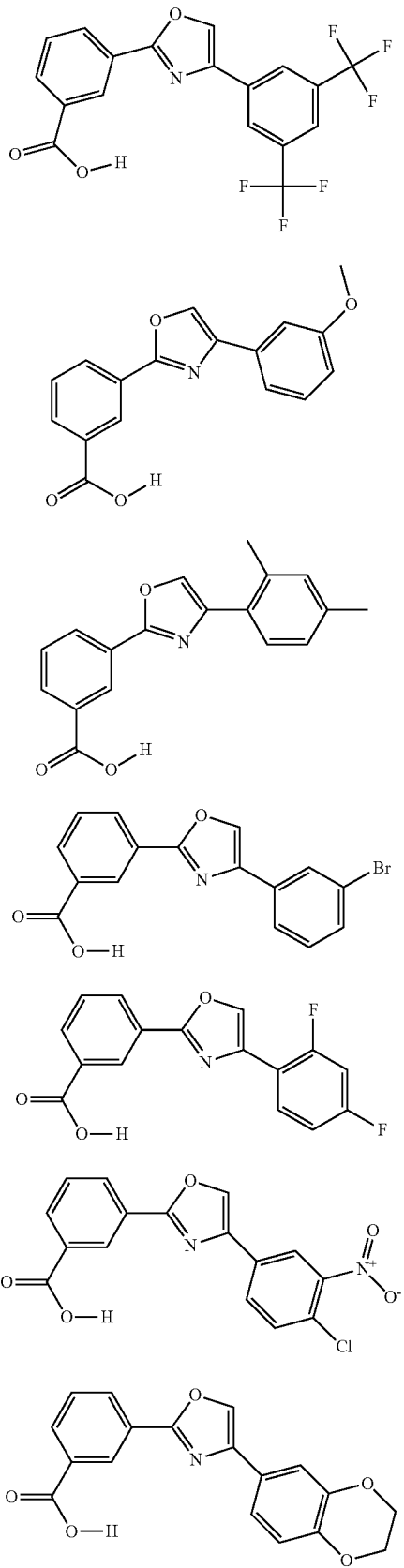
TABLE 5-continued
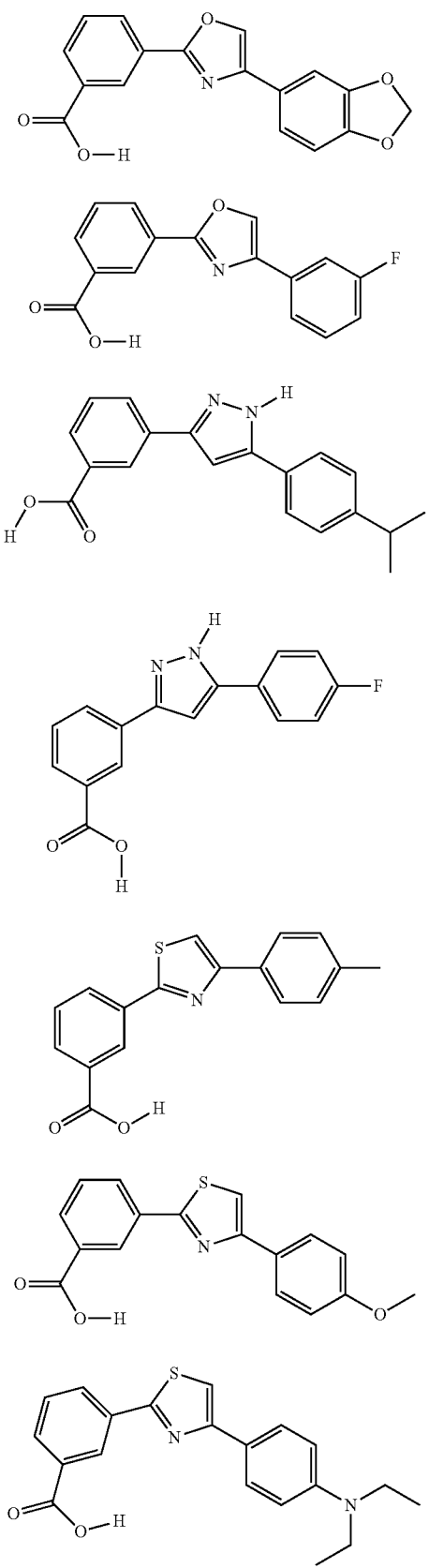

TABLE 5-continued
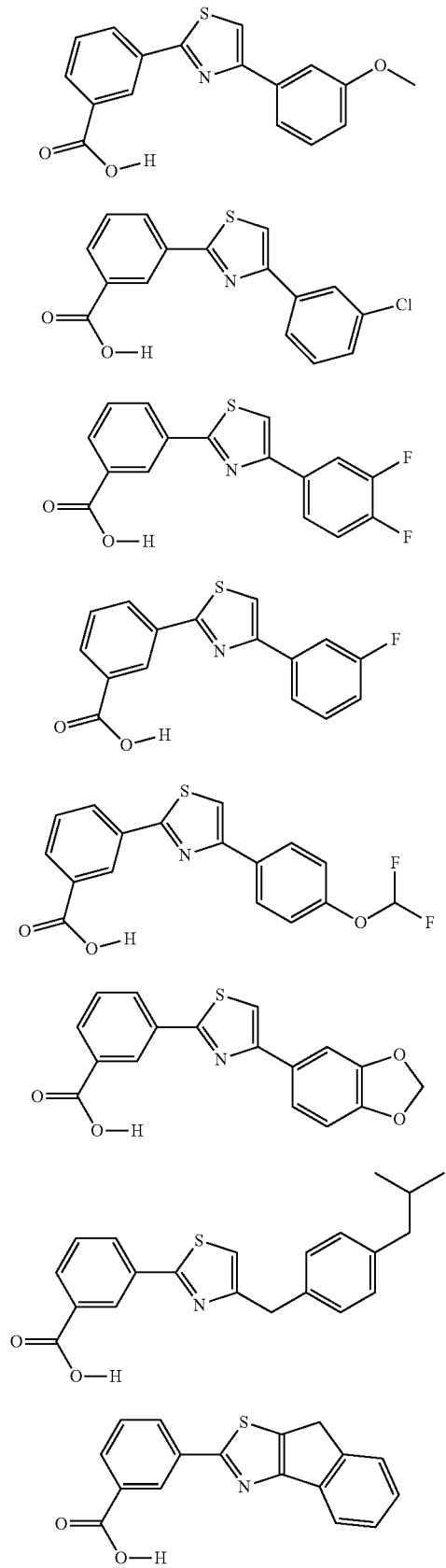
TABLE 5-continued
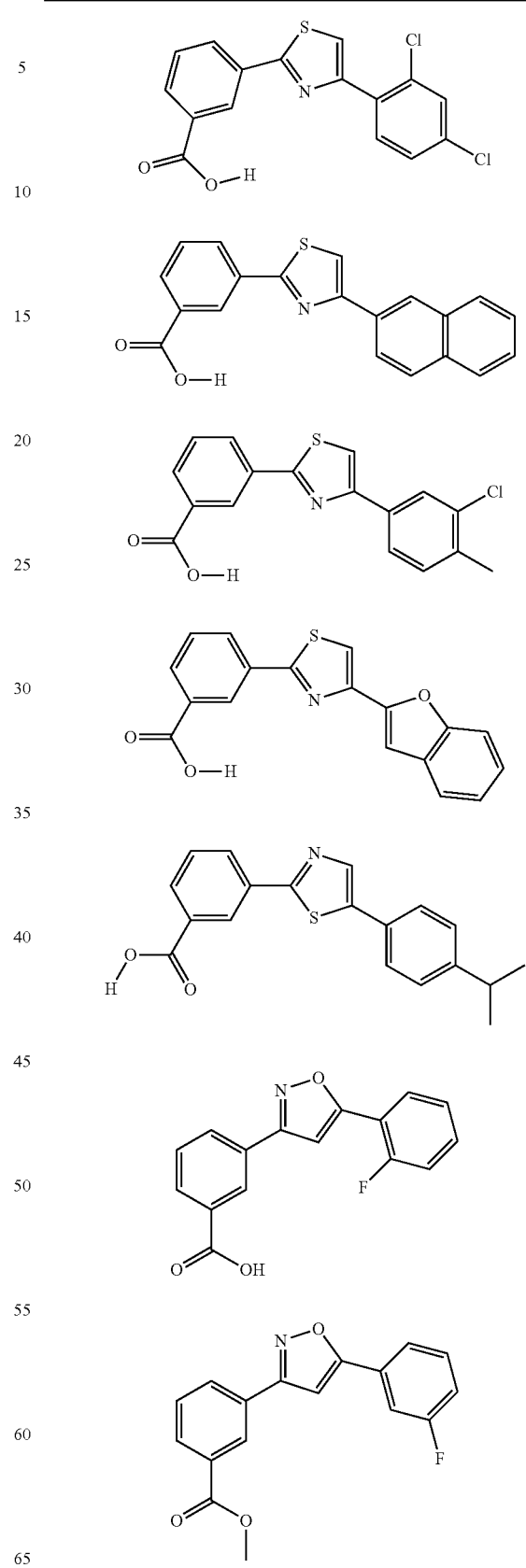

TABLE 5-continued
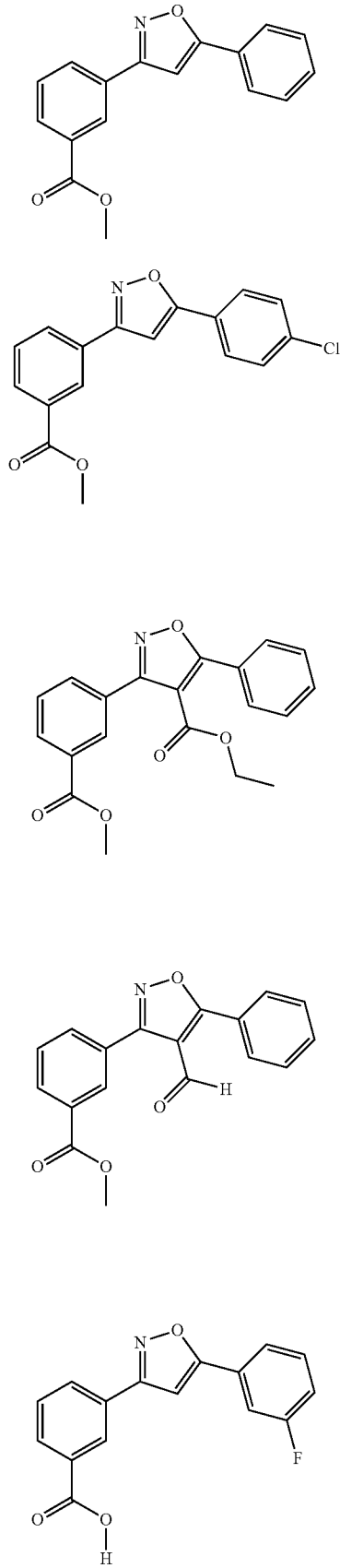
TABLE 5-continued
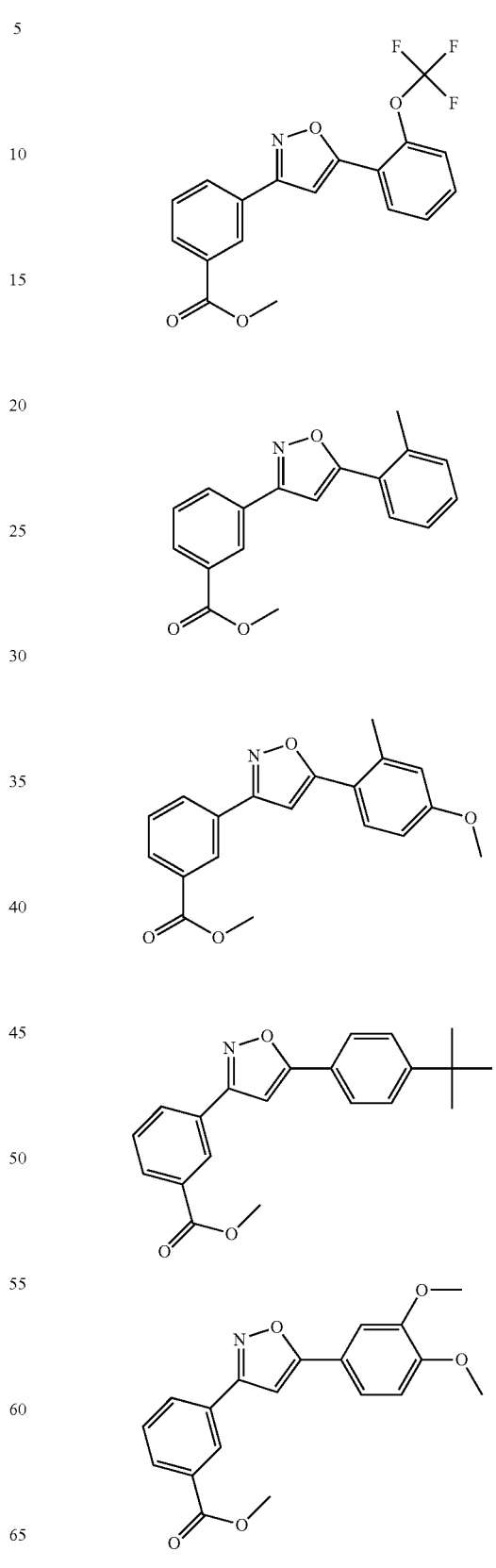

TABLE 5-continued
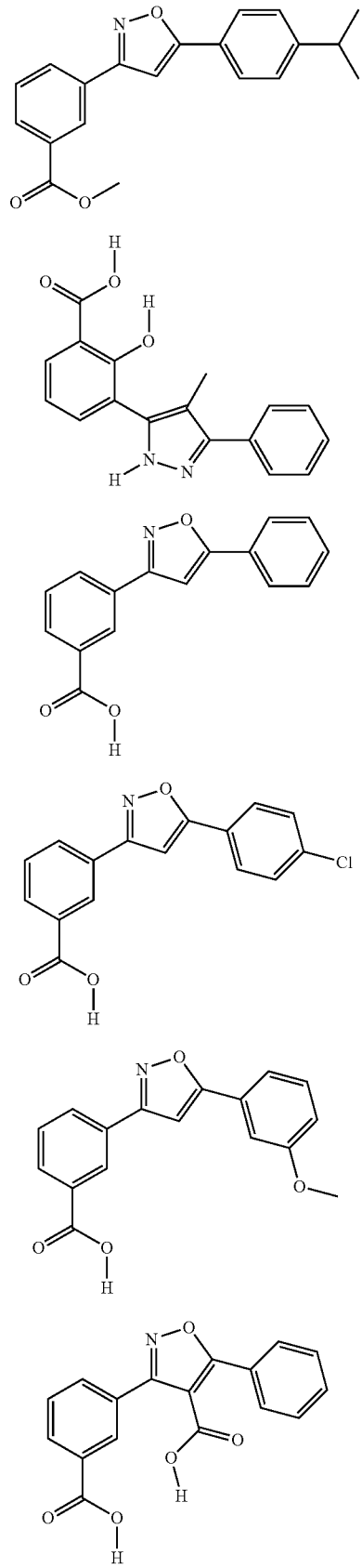
TABLE 5-continued
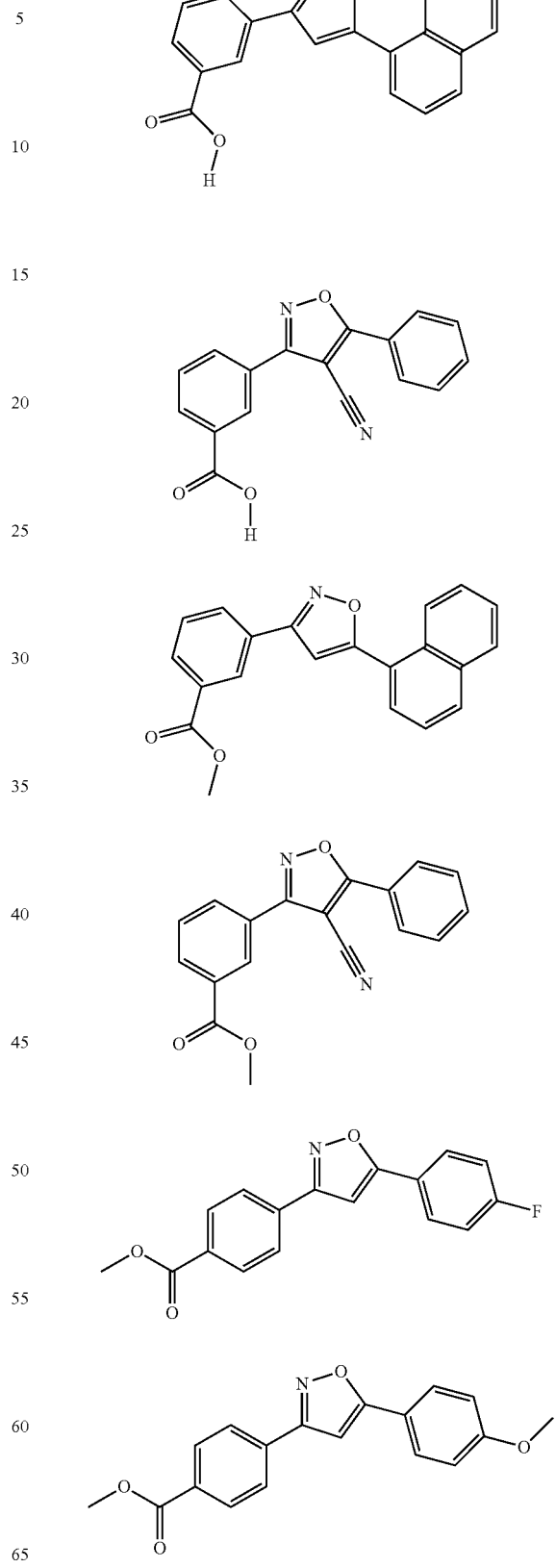

TABLE 5-continued
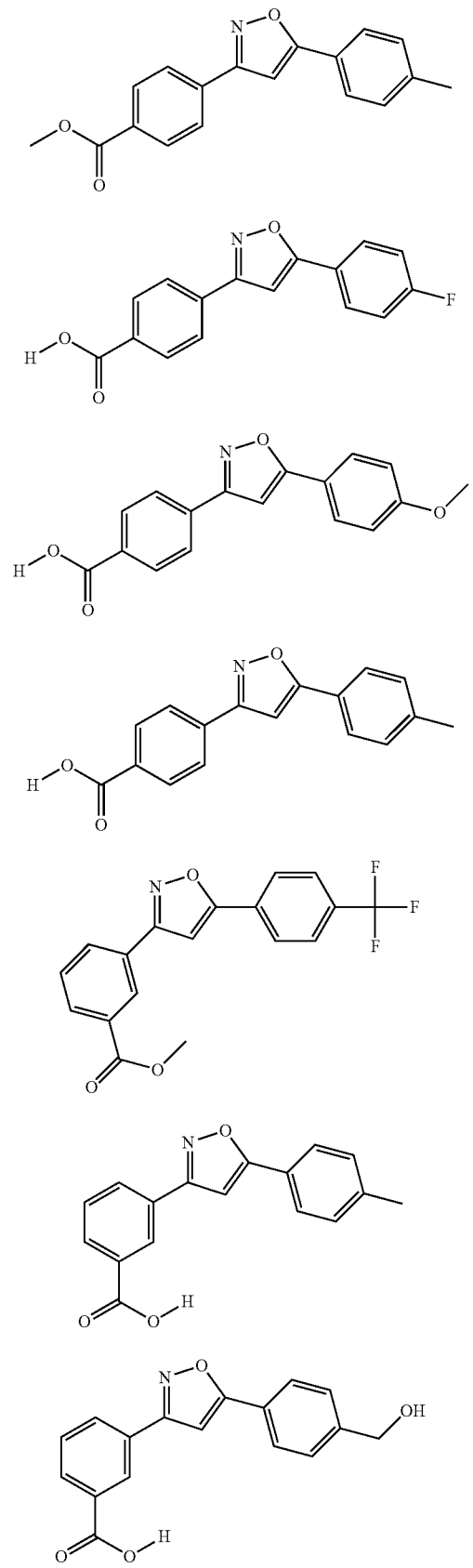
TABLE 5-continued
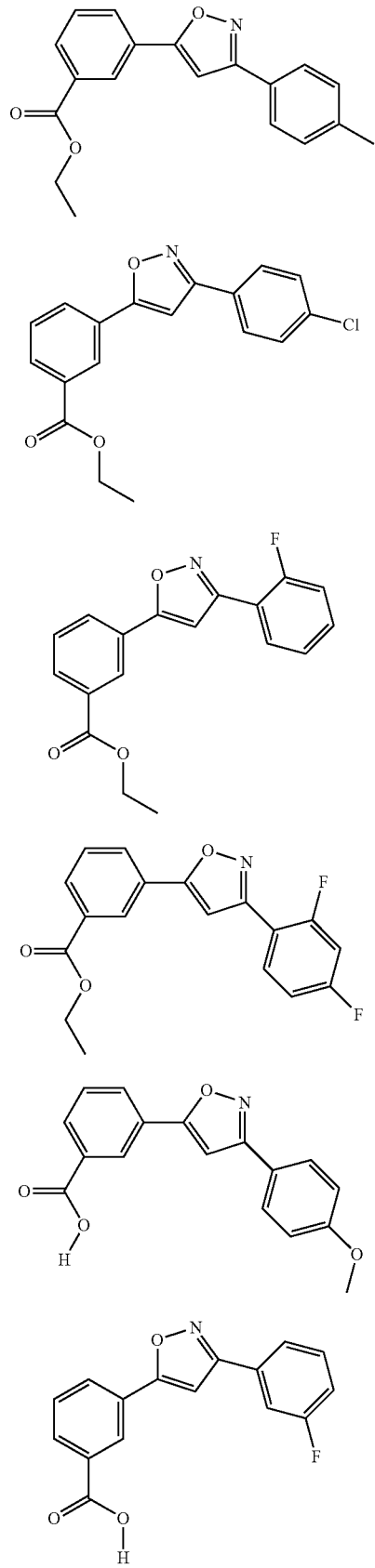

TABLE 5-continued
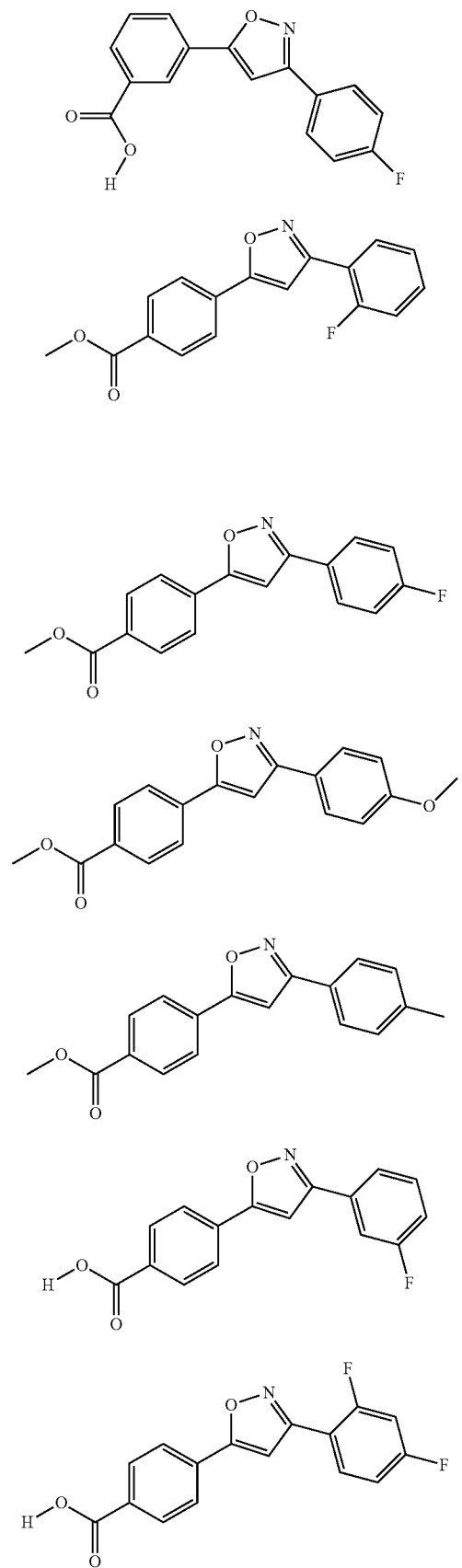
TABLE 5-continued
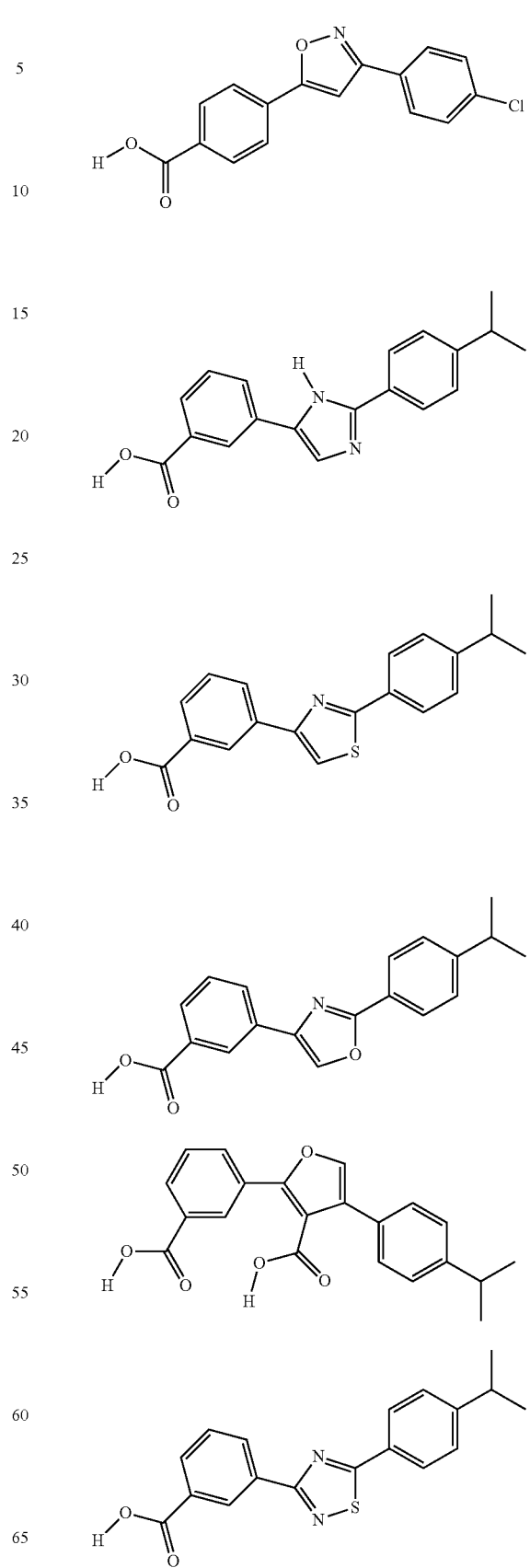

TABLE 5-continued
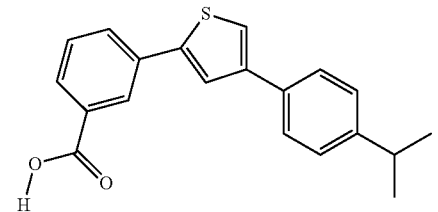 [SMILES: CC(C)c1ccc(-c2csc(-c3cccc(C(=O)O)c3)c2)cc1]
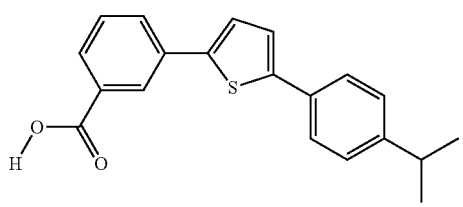 [SMILES: CC(C)c1ccc(-c2ccc(-c3cccc(C(=O)O)c3)s2)cc1]
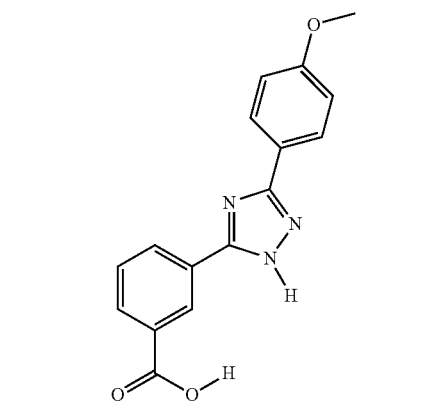 [SMILES: COc1ccc(-c2n[nH]c(-c3cccc(C(=O)O)c3)n2)cc1]
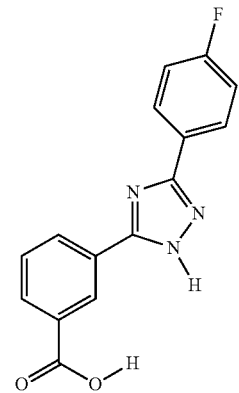 [SMILES: O=C(O)c1cccc(-c2nc(-c3ccc(F)cc3)n[nH]2)c1]
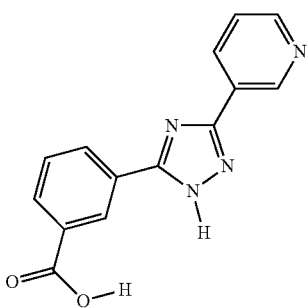 [SMILES: O=C(O)c1cccc(-c2nc(-c3cccnc3)n[nH]2)c1]
TABLE 5-continued
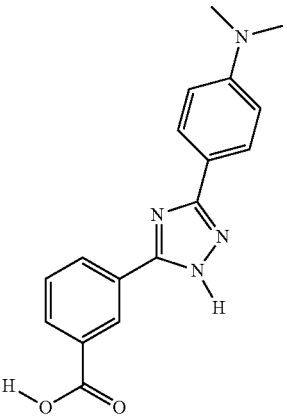 [SMILES: CN(C)c1ccc(-c2n[nH]c(-c3cccc(C(=O)O)c3)n2)cc1]
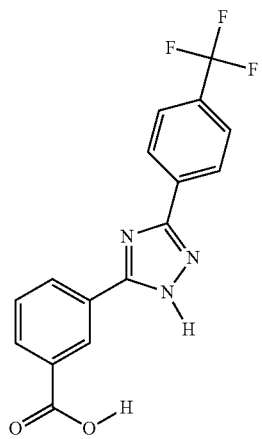 [SMILES: O=C(O)c1cccc(-c2nc(-c3ccc(C(F)(F)F)cc3)n[nH]2)c1]
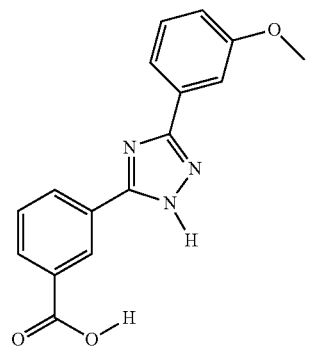 [SMILES: COc1cccc(-c2n[nH]c(-c3cccc(C(=O)O)c3)n2)c1]

TABLE 5-continued

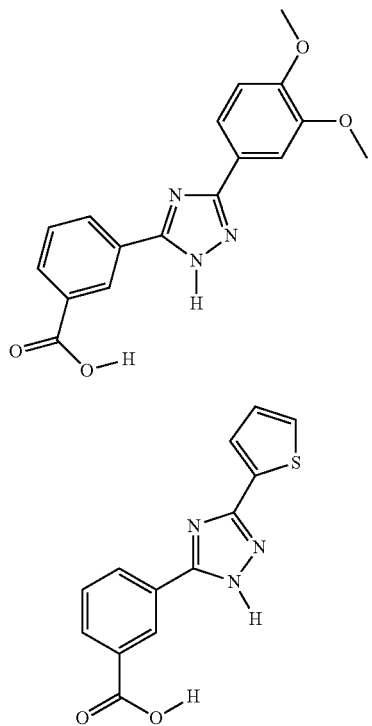

Compounds of formula V can be obtained via standard, well-known synthetic methodology, see e.g., March, J. Advanced Organic Chemistry; Reactions Mechanisms, and Structure, 4th ed., 1992. Starting materials useful for preparing compounds of formula I and intermediates therefore, are commercially available or can be prepared from commercially available materials using known synthetic methods and reagents.

Particular methods for preparing compounds of formula V are disclosed in International Application No. PCT/US05/036673, filed Oct. 13, 2005, incorporated by reference herein in its entirety.

In another embodiment, the nonsense codon suppressor is a compound of formula VI:

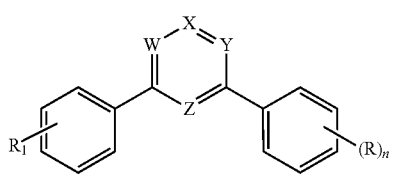

VI or pharmaceutically acceptable salts, hydrates, clathrates, prodrugs, polymorphs, stereoisomers, including enantiomers, diastereomers, racemates or mixtures of stereoisomers, thereof wherein:

W, X, Y and Z are independently selected from N or C—$R_a$, where $R_a$ is hydrogen or a $C_1$-$C_4$ alkyl group, wherein at least one of W, X, Y, or Z is N;

n is 0, 1, 2, or 3;

$R_1$ is a cyano group; a carbamoyl which is optionally substituted with one or two $C_1$-$C_4$ alkyl groups; or a carbonyl group which is substituted with a hydroxy, a $C_1$-$C_4$ alkyl, or a $C_1$-$C_4$ alkoxy group;

R is a hydroxy group; a halogen; a $C_1$-$C_4$ alkyl which is optionally substituted with one or more independently selected halogen or hydroxy groups; a $C_1$-$C_4$ alkoxy which is optionally substituted with one or more independently selected halogen or phenyl groups; a $C_4$-$C_8$ cycloalkyl which is optionally substituted with one or more independently selected $C_1$-$C_4$ alkyl groups; an —$R_b$ group; an —O—$R_b$ group; a five to six-membered heterocycle which is optionally substituted with one or more independently selected $C_1$-$C_4$ alkyl, oxo, or —$R_b$ groups; a nine to ten membered heterocycle having two ring structures; a carbonyl which is substituted with a hydroxy, a $C_1$-$C_4$ alkyl, or a $C_1$-$C_4$ alkoxy group; a carbamoyl which is optionally substituted with one or two $C_1$-$C_4$ alkyl groups; a nitro group; a cyano group; a thio which is optionally substituted with a hydroxy, a $C_1$-$C_4$ alkyl, or —$R_b$ group; a sulfonyl which is optionally substituted with a hydroxy, a $C_1$-$C_4$ alkyl, or —$R_b$ group; an amino which is optionally substituted with one or two independently selected $C_1$-$C_4$ alkyl, sulfonyl, or carbonyl groups, wherein the aminosulfonyl group is optionally substituted with a hydroxy, a $C_1$-$C_4$ alkyl, or —$R_b$ group and wherein the aminocarbonyl group is optionally substituted with a $C_1$-$C_4$ alkyl, a $C_1$-$C_4$ haloalkyl, a benzoxy, or an amino group which is optionally substituted with an —$R_b$ group; or two R groups together with the phenyl ring to which they are attached form a benzo[1,3]dioxole or a 2,3-dihydro-benzo[1,4]dioxinyl group, wherein —$R_b$ is a $C_6$-$C_8$ aryl which is optionally substituted with one or more of the following: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more $C_1$-$C_4$ alkyl groups.

Preferred compounds of formula VI are set forth in Table 6, below:

TABLE 6

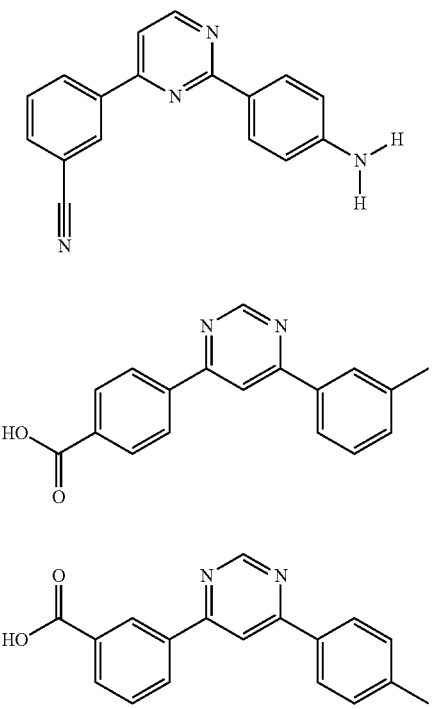

TABLE 6-continued
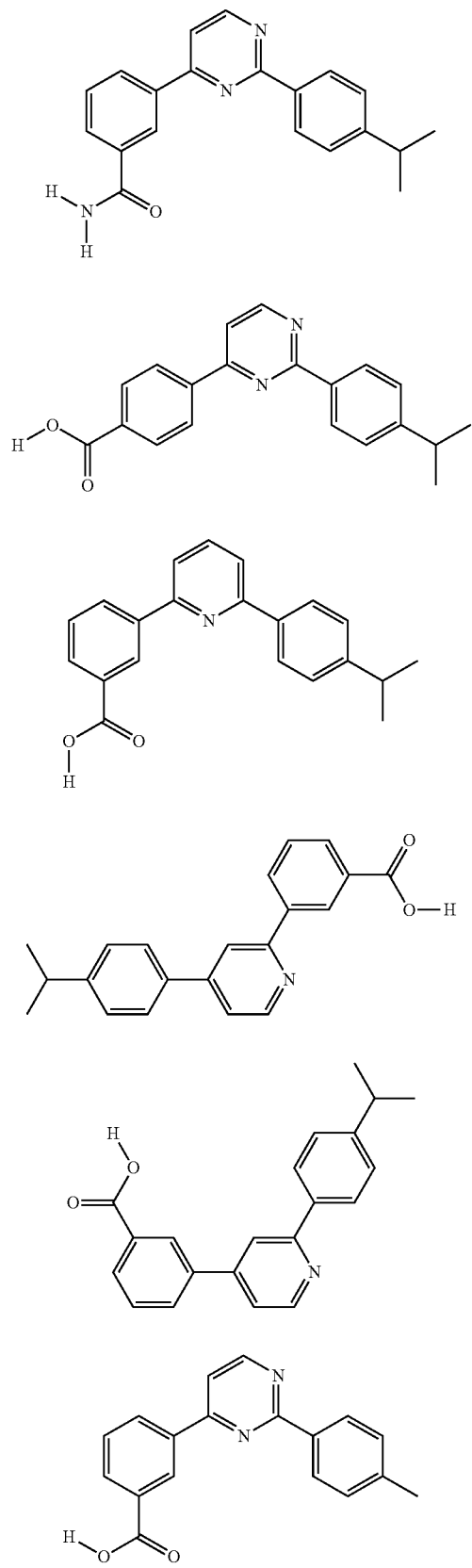
TABLE 6-continued
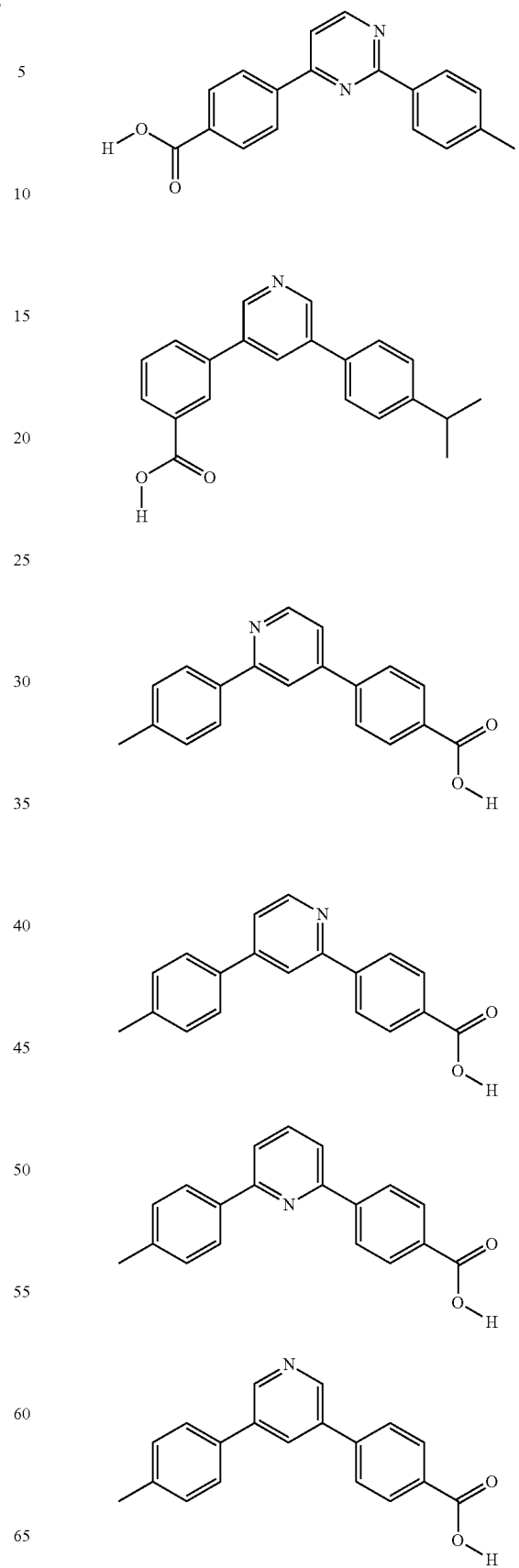

TABLE 6-continued
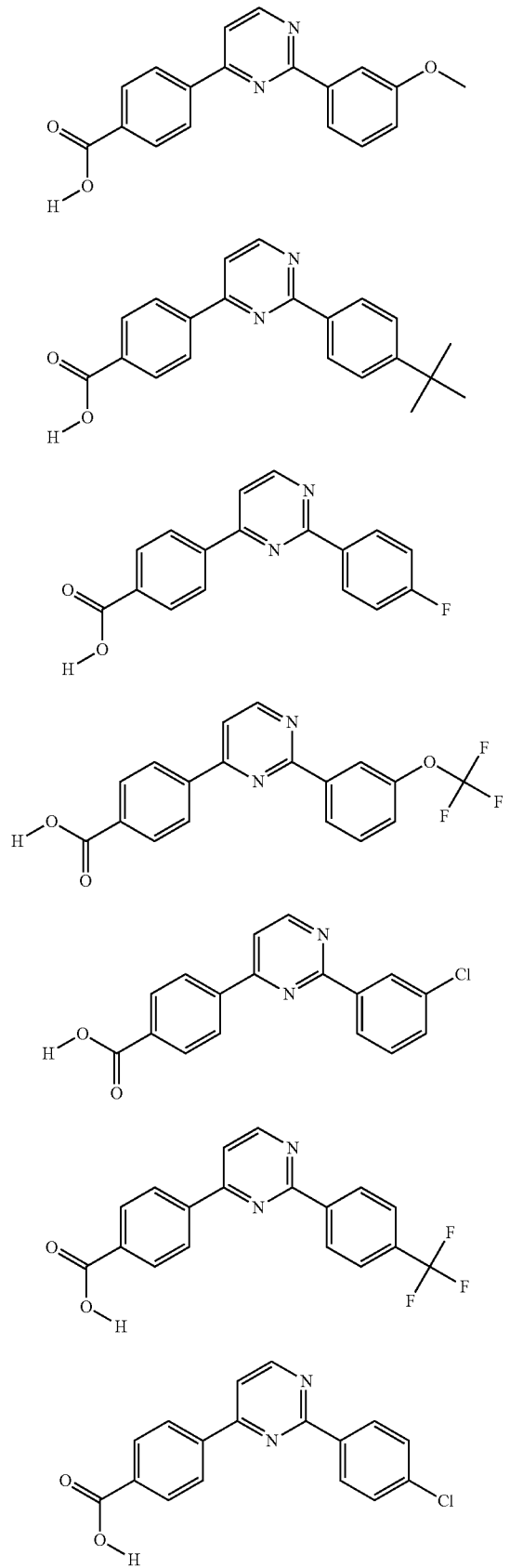
TABLE 6-continued
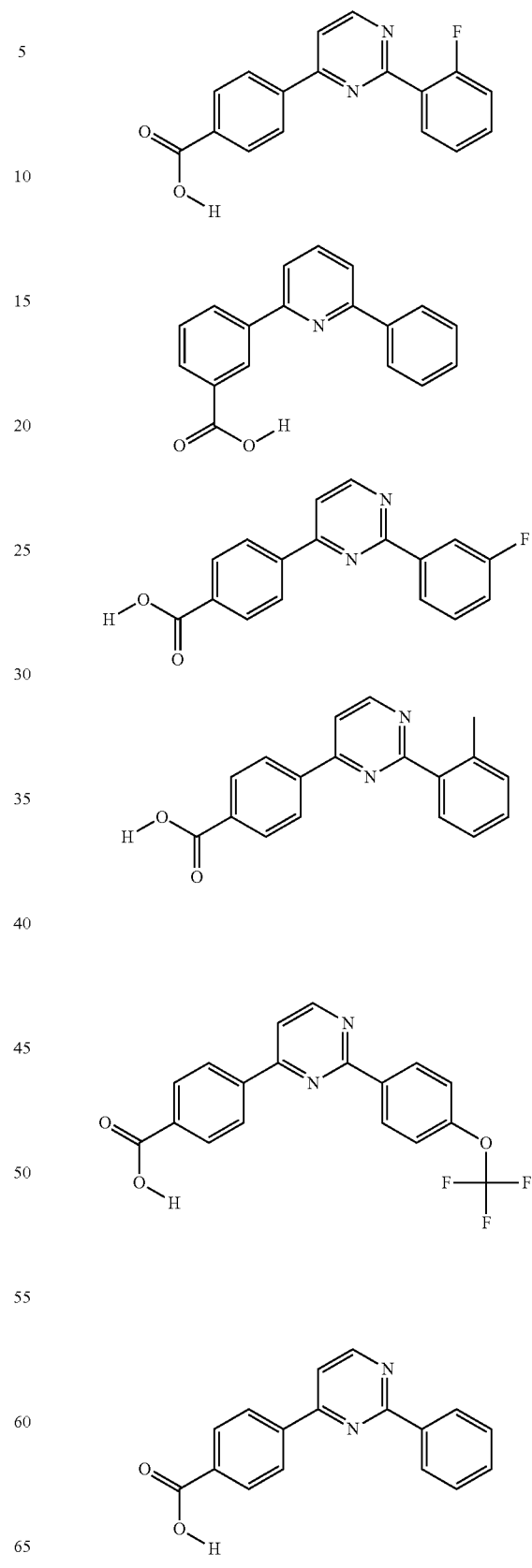

TABLE 6-continued
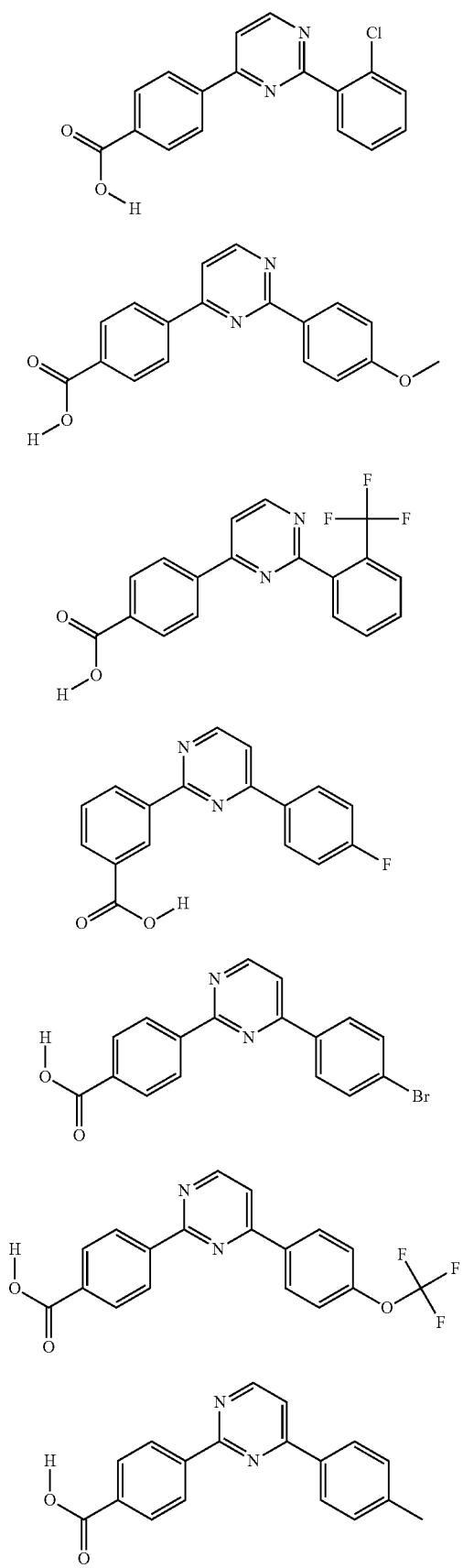
TABLE 6-continued
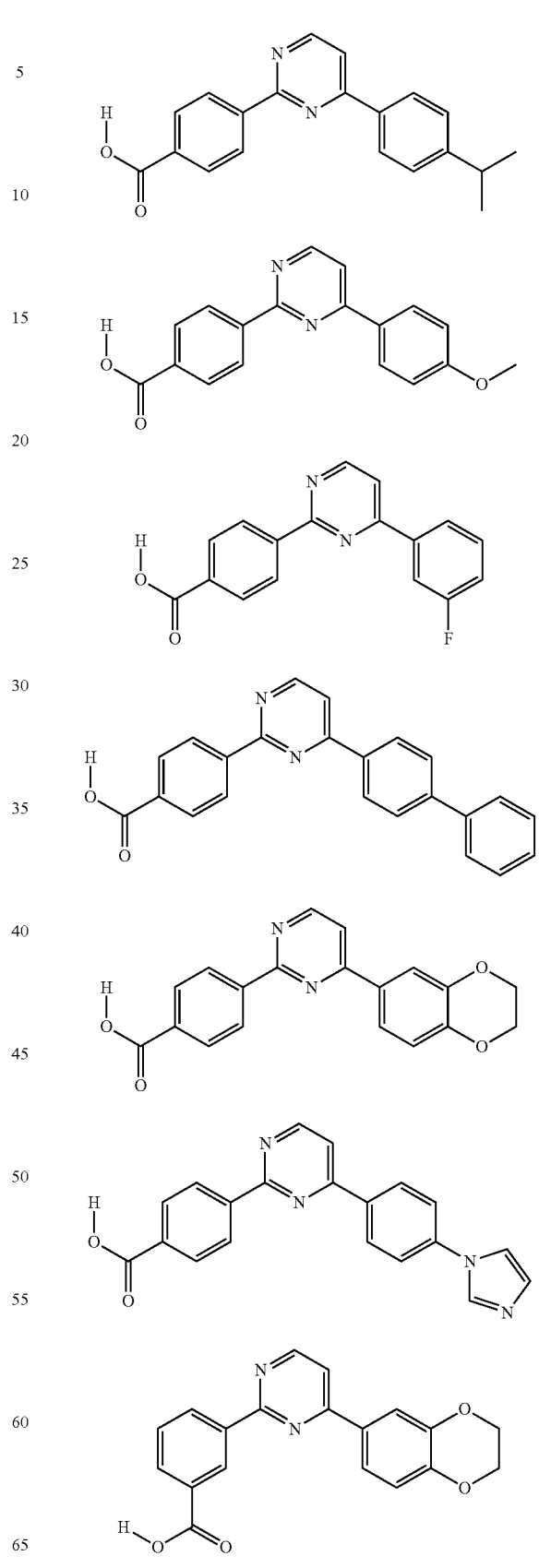

TABLE 6-continued
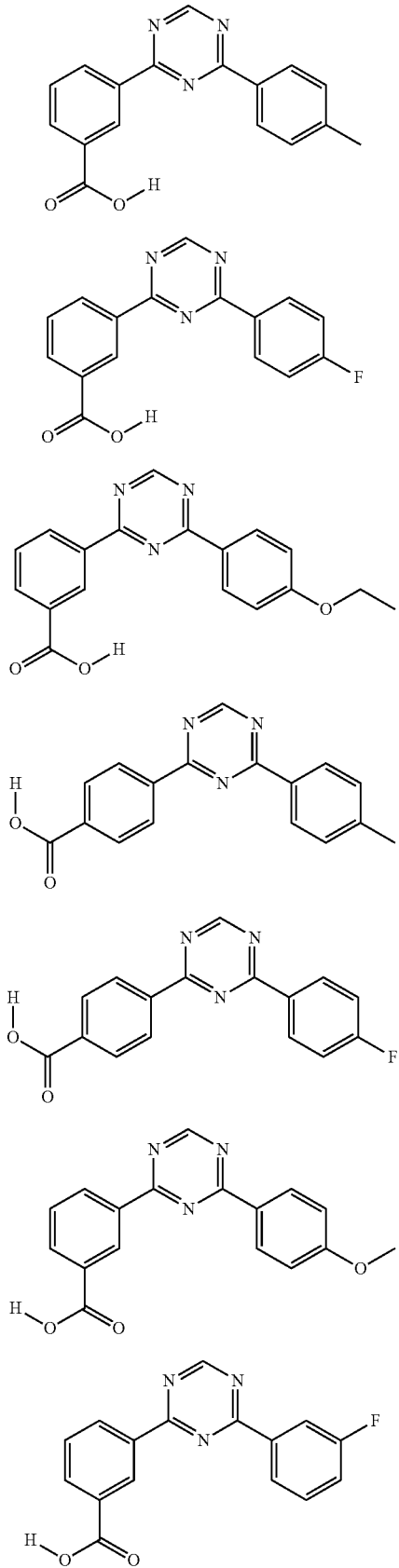
TABLE 6-continued
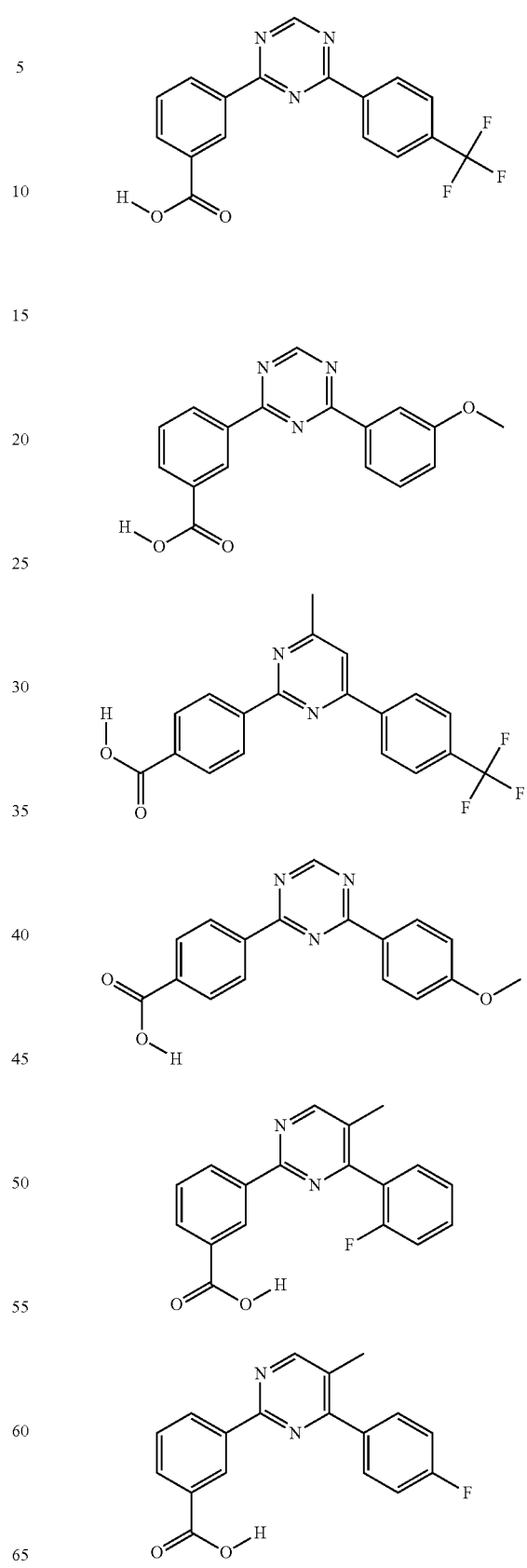

TABLE 6-continued
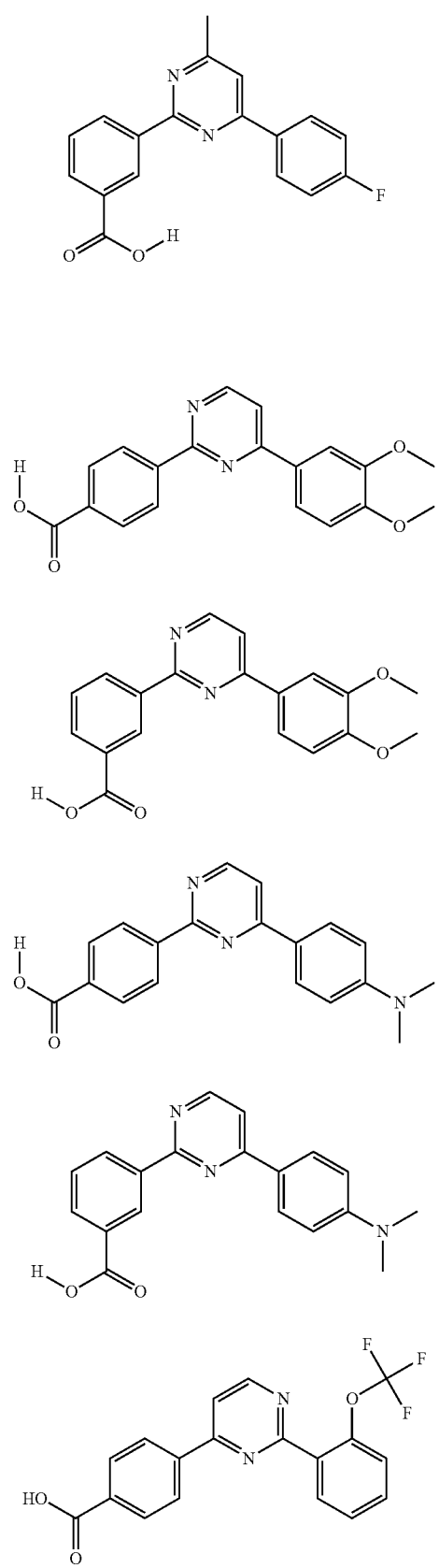
TABLE 6-continued
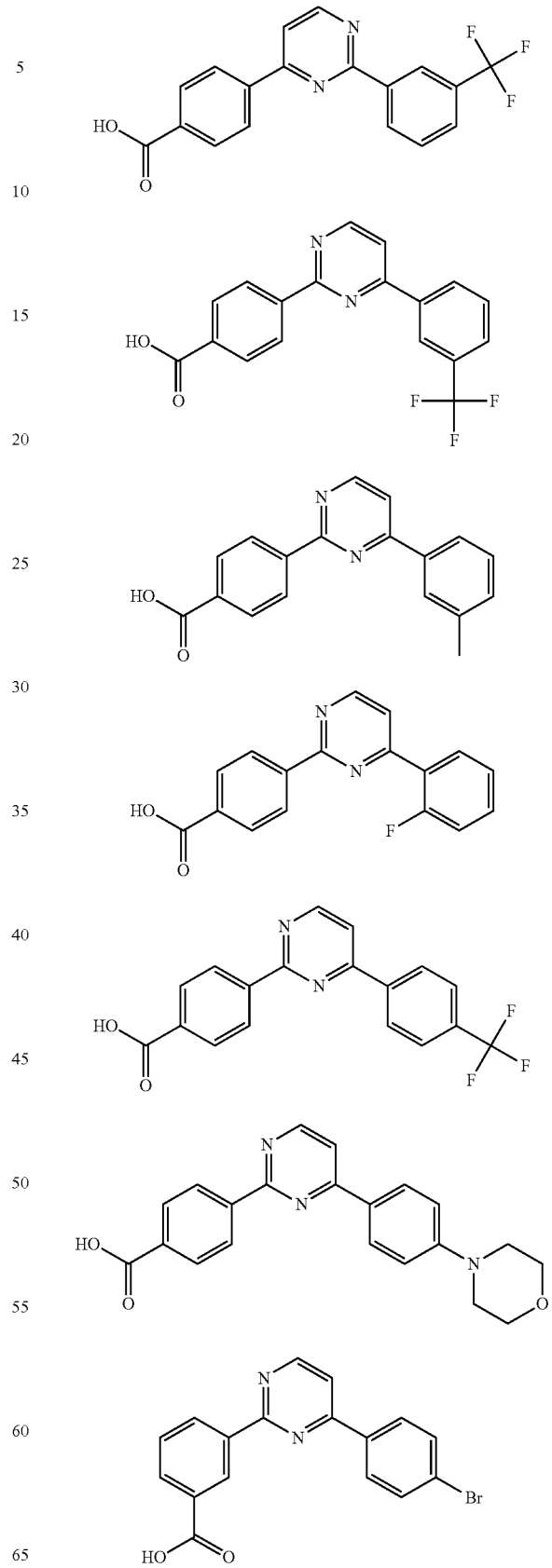

TABLE 6-continued
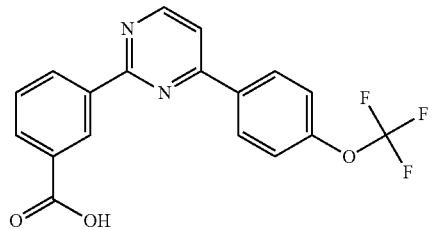 [SMILES: O=C(O)c1cccc(-c2nccc(-c3ccc(OC(F)(F)F)cc3)n2)c1]
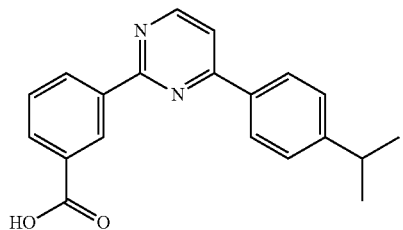 [SMILES: CC(C)c1ccc(-c2ccnc(-c3cccc(C(=O)O)c3)n2)cc1]
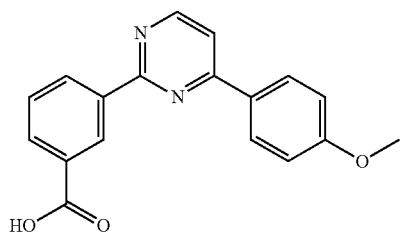 [SMILES: COc1ccc(-c2ccnc(-c3cccc(C(=O)O)c3)n2)cc1]
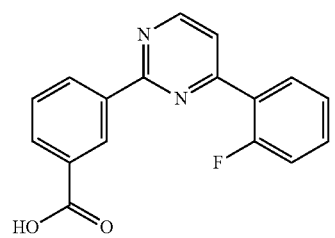 [SMILES: O=C(O)c1cccc(-c2nccc(-c3ccccc3F)n2)c1]
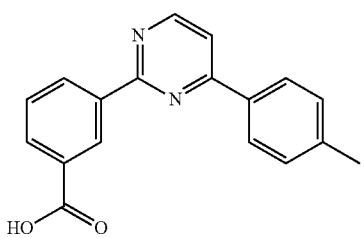 [SMILES: Cc1ccc(-c2ccnc(-c3cccc(C(=O)O)c3)n2)cc1]
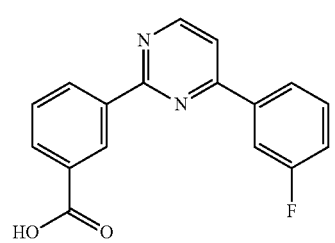
TABLE 6-continued
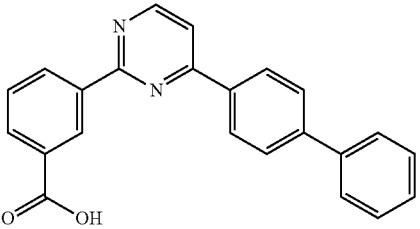 [SMILES: O=C(O)c1cccc(-c2nccc(-c3ccc(-c4ccccc4)cc3)n2)c1]
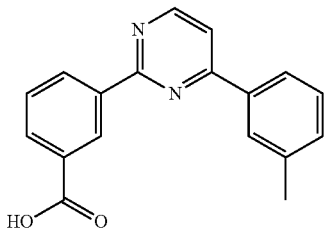 [SMILES: Cc1cccc(-c2ccnc(-c3cccc(C(=O)O)c3)n2)c1]
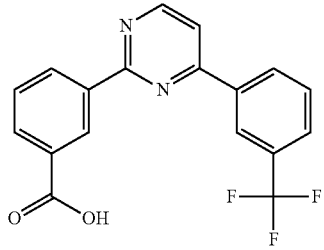 [SMILES: O=C(O)c1cccc(-c2nccc(-c3cccc(C(F)(F)F)c3)n2)c1]
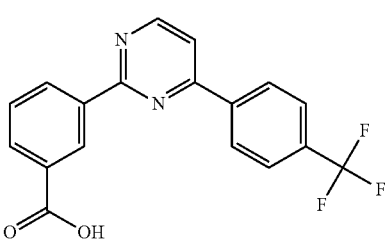 [SMILES: O=C(O)c1cccc(-c2nccc(-c3ccc(C(F)(F)F)cc3)n2)c1]
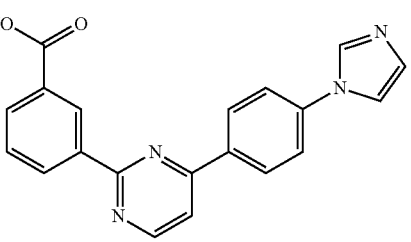
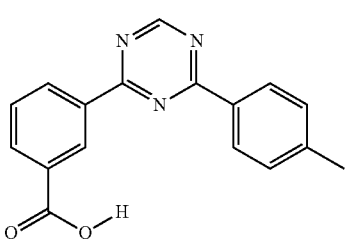 [SMILES: Cc1ccc(-c2ncnc(-c3cccc(C(=O)O)c3)n2)cc1]

TABLE 6-continued

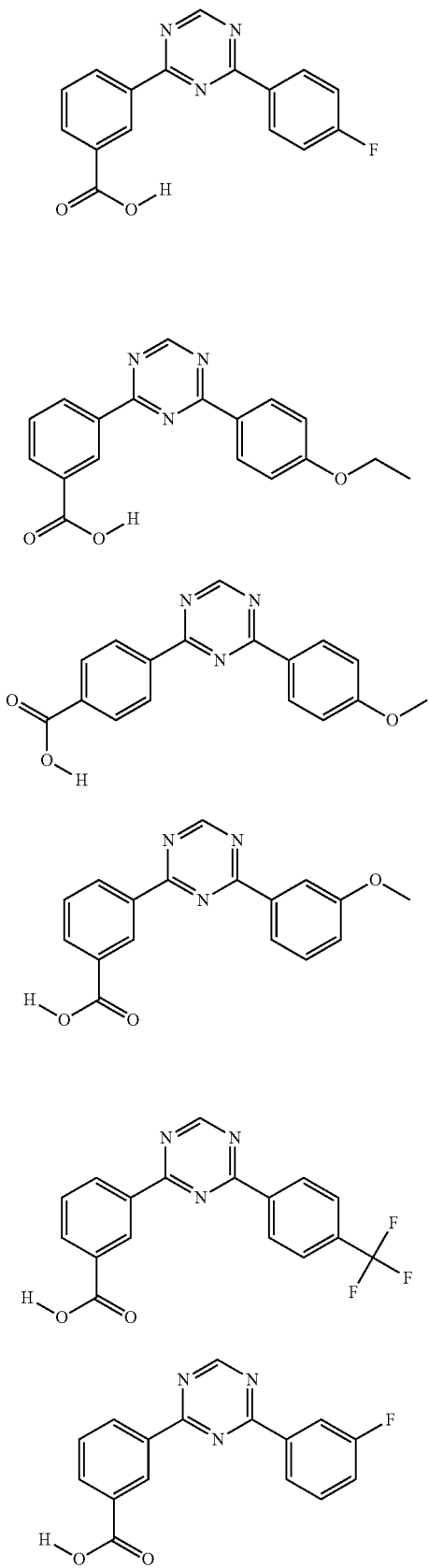

TABLE 6-continued

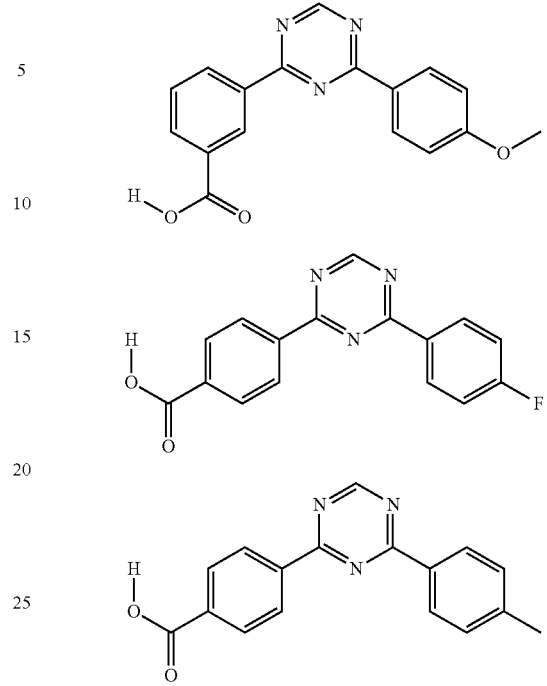

Compounds of formula VI can be obtained via standard, well-known synthetic methodology, see e.g., March, J. Advanced Organic Chemistry; Reactions Mechanisms, and Structure, 4th ed., 1992. Starting materials useful for preparing compounds of formula I and intermediates therefore, are commercially available or can be prepared from commercially available materials using known synthetic methods and reagents.

Particular methods for preparing compounds of formula VI are disclosed in International Application No. PCT/US05/036764, filed Oct. 13, 2005, incorporated by reference herein in its entirety.

In another embodiment, the nonsense codon suppressor is a compound of formula VII:

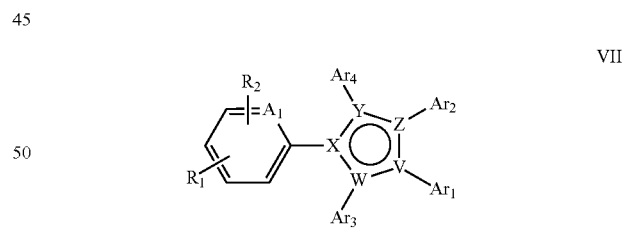

VII or pharmaceutically acceptable salts, hydrates, clathrates, prodrugs, polymorphs, stereoisomers, including enantiomers, diastereomers, racemates or mixtures of stereoisomers, thereof wherein:

$A_1$ is C, CH or N;

V and X are independently selected from N or C;

W is selected from N, C or CH;

wherein at least one of V, W, or X is N, and wherein if W is N, at least one of V or X is also N;

Y and Z are independently selected from N, C, C—$R_c$, C=O, C=S, wherein $R_c$ is H, $CH_3$, or $NH_2$; with the proviso that when one of Y or Z is C=O or C=S, the other may also be selected from NH, S, or O;

$R_1$ is carboxy, cyano, or a carbonyl group which is optionally substituted with a $C_1$-$C_4$ alkoxy group, $R_2$ is absent or a nitro;

$Ar_1$ is a $C_1$ to $C_4$ alkyl which is optionally substituted with an R group; a $C_6$ to $C_{10}$ aryl which is optionally substituted with one, two or three independently selected R groups; a five to ten membered heterocycle which is optionally substituted with one, two or three independently selected R groups; together with $Ar_2$ and the heterocycle to which $Ar_1$ and $Ar_2$ are attached form a ring structure selected from $Ar_{1-2}$; or together with $Ar_3$ and the heterocycle to which $Ar_1$ and $Ar_3$ are attached form a ring structure selected from $Ar_{1-3}$;

$Ar_2$ is absent or together with $Ar_1$ and the heterocycle to which $Ar_1$ and $Ar_2$ are attached form a ring structure selected from $Ar_{1-2}$;

$Ar_3$ is absent or together with $Ar_1$ and the heterocycle to which $Ar_1$ and $Ar_3$ are attached form a ring structure selected from $Ar_{1-3}$;

$Ar_4$ is absent; or is a $C_1$-$C_4$ alkyl, a $C_1$-$C_4$ alkoxy, or a $C_1$-$C_4$ thioalkyl, any of which together with $A_1$ forms a four to seven membered carbocycle or heterocycle;

R is hydrogen; a —$R_a$ group; or two R groups, where R may also include an oxy group, together with the phenyl or heterocycle to which they are attached form a ring structure selected from RR;

wherein:

$Ar_{1-2}$ and $Ar_{1-3}$ are selected from an eleven to fourteen membered hetero-tricycle ring structure optionally substituted with one or more halogens, $C_1$-$C_4$ alkyl groups, $C_1$-$C_4$ haloalkyl groups, $C_1$-$C_4$ alkoxy groups optionally substituted with a halogen or a $C_1$-$C_4$ alkoxy group, $C_1$-$C_4$ haloalkoxy groups, or amino groups optionally substituted with a carbonyl group which is substituted with a $C_1$-$C_4$ alkyl group;

RR is a nine to ten membered bicyclic ring structure optionally substituted with one or more halogens, $C_1$-$C_4$ alkyl groups, $C_1$-$C_4$ haloalkyl groups, $C_1$-$C_4$ alkoxy groups, oxo groups, or $C_1$-$C_4$ haloalkoxy groups;

$R_a$ is selected from the group consisting of: a hydroxy group; a halogen; a $C_1$-$C_4$ alkyl which is optionally substituted with one or more independently selected halogen or hydroxy groups; a $C_1$-$C_4$ alkoxy which is optionally substituted with one or more independently selected halogen or phenyl groups; a $C_4$-$C_8$ cycloalkyl which is optionally substituted with one or more independently selected $C_1$-$C_4$ alkyl groups; an —$R_b$ group; a —O—$R_b$ group; a four to six-membered heterocycle which is optionally substituted with one or more independently selected $C_1$-$C_4$ alkyl, oxo, or —$R_b$ groups; a nine to ten membered heterocycle having two ring structures; a carbonyl which is optionally substituted with a hydroxy, a $C_1$-$C_4$ alkyl, or a $C_1$-$C_4$ alkoxy group; a carbamoyl which is optionally substituted with one or two $C_1$-$C_4$ alkyl groups; a nitro group; a cyano group; a thio which is optionally substituted with a hydroxy, a $C_1$-$C_4$ alkyl, or —$R_b$ group; a sulfonyl which is optionally substituted with a hydroxy, a $C_1$-$C_4$ alkyl, or —$R_b$ group; or an amino which is optionally substituted with one or two independently selected $C_1$-$C_4$ alkyl, sulfonyl, or carbonyl groups, wherein the aminosulfonyl group is optionally substituted with a hydroxy, a $C_1$-$C_4$ alkyl, or —$R_b$ group and wherein the aminocarbonyl group is optionally substituted with a $C_1$-$C_4$ alkyl, a $C_1$-$C_4$ haloalkyl, a benzoxy, or an amino group which is optionally substituted with an —$R_b$ group; and wherein —$R_b$ is a $C_6$-$C_8$ aryl which is optionally substituted with one or more of the following: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more $C_1$-$C_4$ alkyl groups.

Preferred compounds of formula VII are set forth in Table 7, below:

TABLE 7

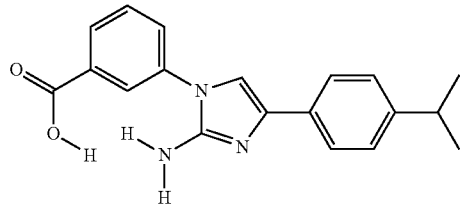 [SMILES: CC(C)c1ccc(-c2cn(-c3cccc(C(=O)O)c3)c(N)n2)cc1]

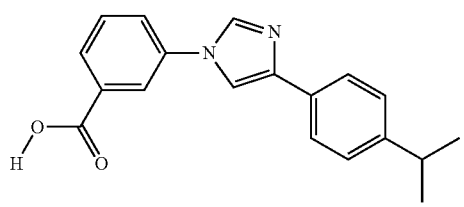 [SMILES: CC(C)c1ccc(-c2cn(-c3cccc(C(=O)O)c3)cn2)cc1]

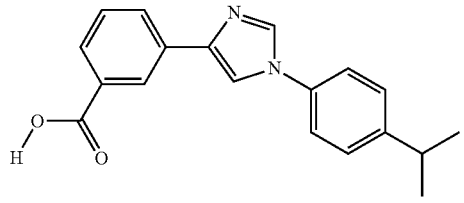 [SMILES: CC(C)c1ccc(-n2cnc(-c3cccc(C(=O)O)c3)c2)cc1]

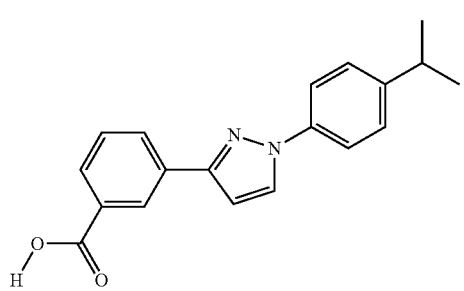 [SMILES: CC(C)c1ccc(-n2ccc(-c3cccc(C(=O)O)c3)n2)cc1]

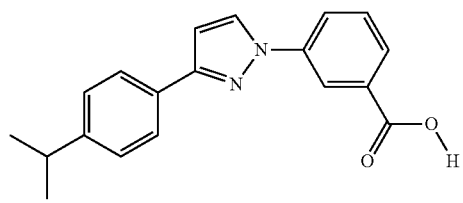 [SMILES: CC(C)c1ccc(-c2ccn(-c3cccc(C(=O)O)c3)n2)cc1]

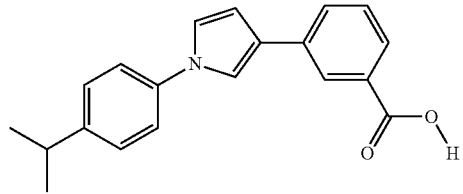 [SMILES: CC(C)c1ccc(-n2ccc(-c3cccc(C(=O)O)c3)c2)cc1]

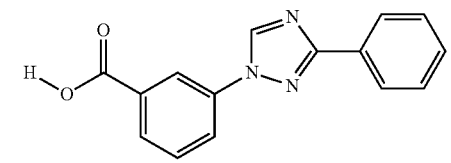 [SMILES: O=C(O)c1cccc(-n2cnc(-c3ccccc3)n2)c1]

TABLE 7-continued
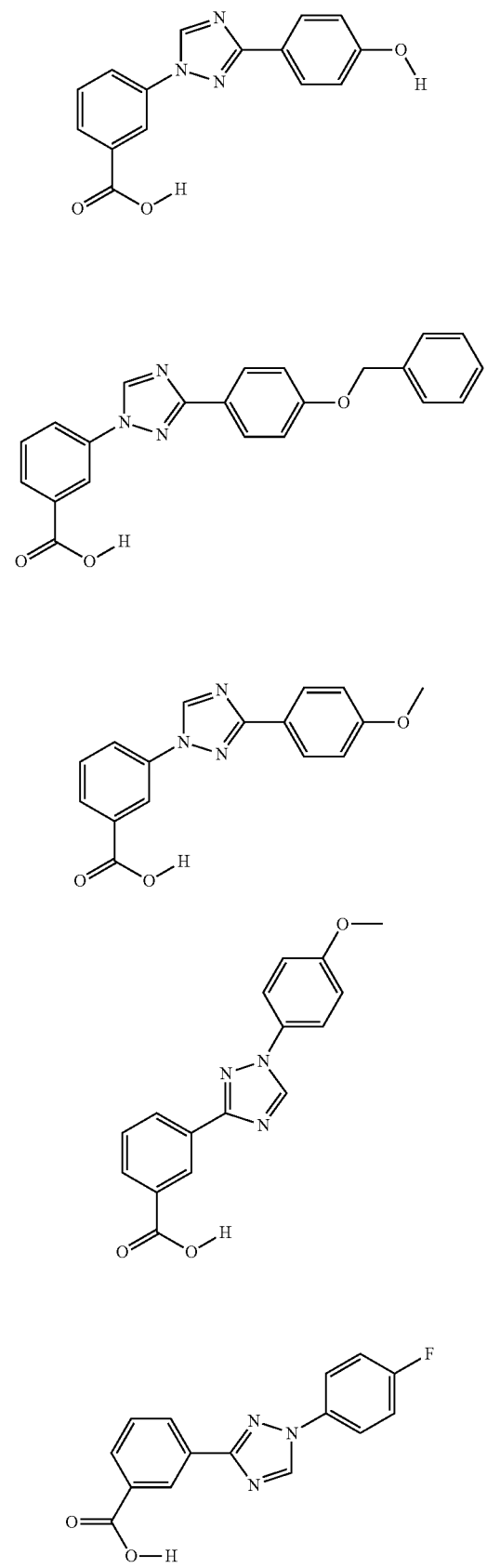
TABLE 7-continued
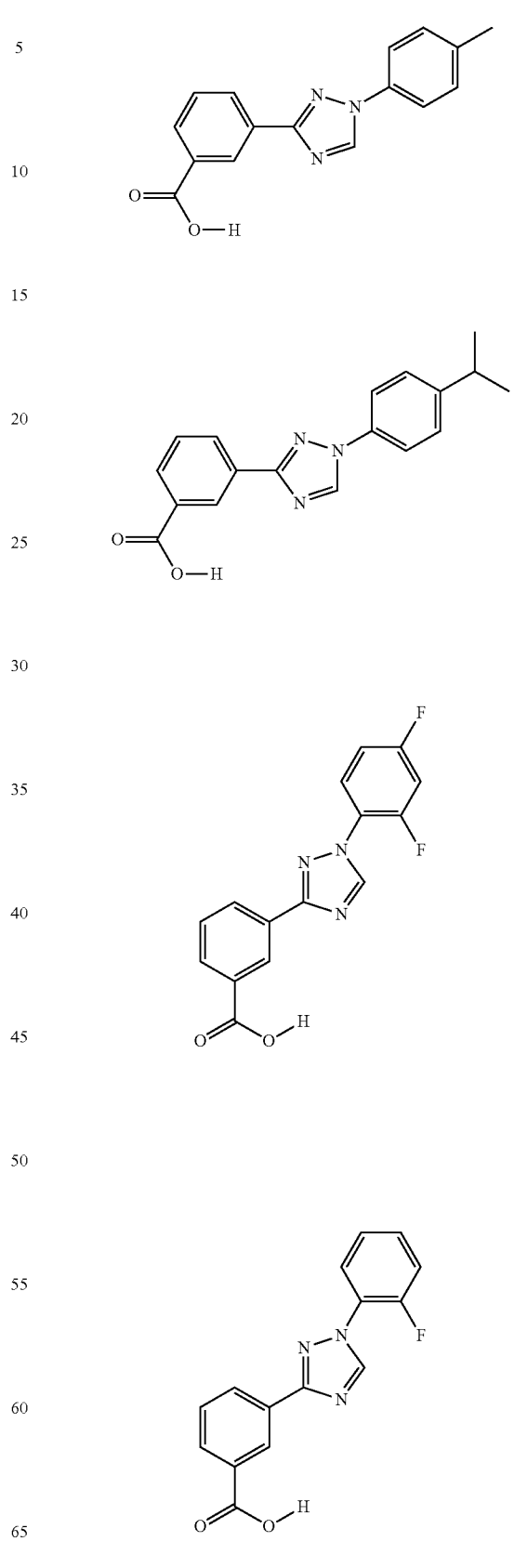

TABLE 7-continued
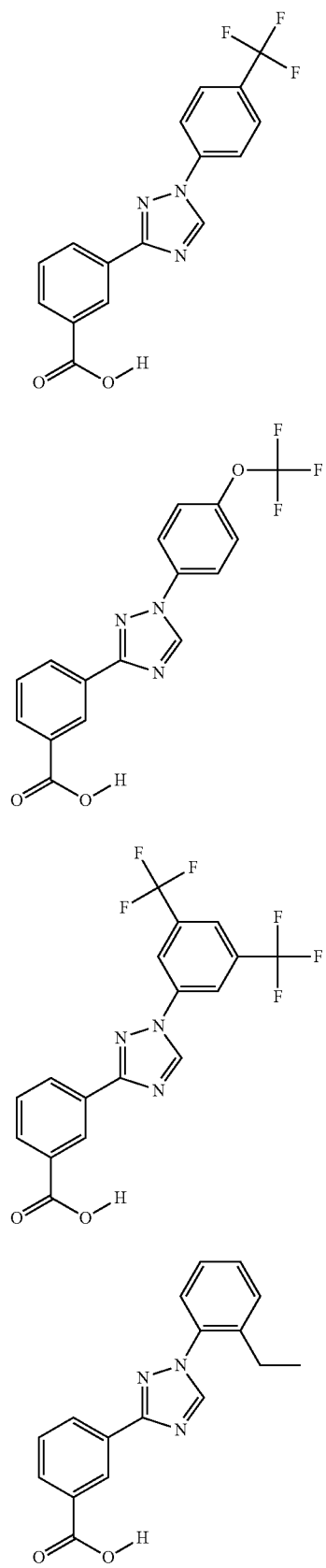
TABLE 7-continued
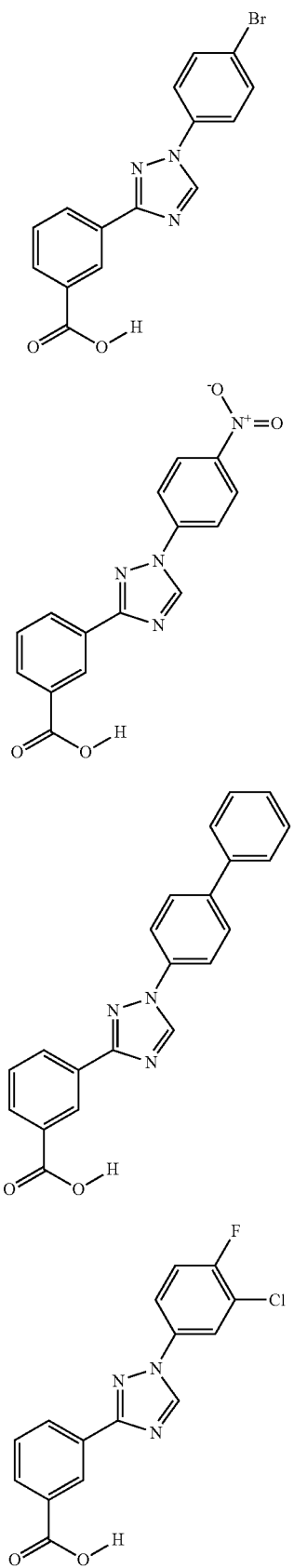

TABLE 7-continued
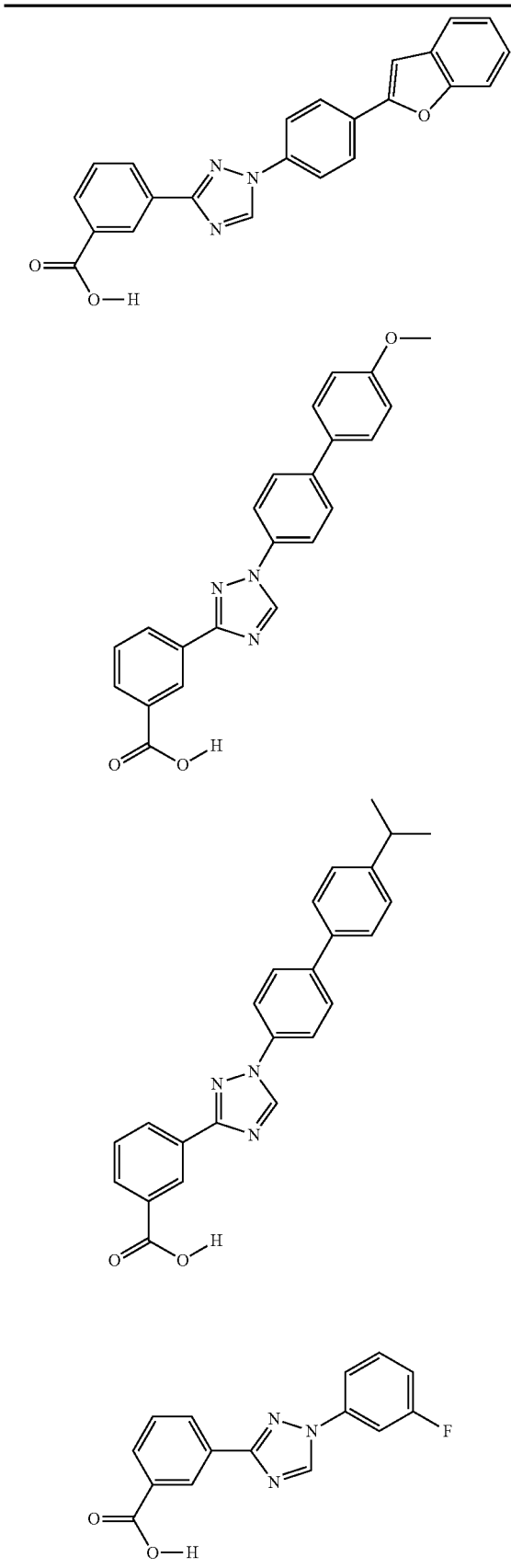
TABLE 7-continued
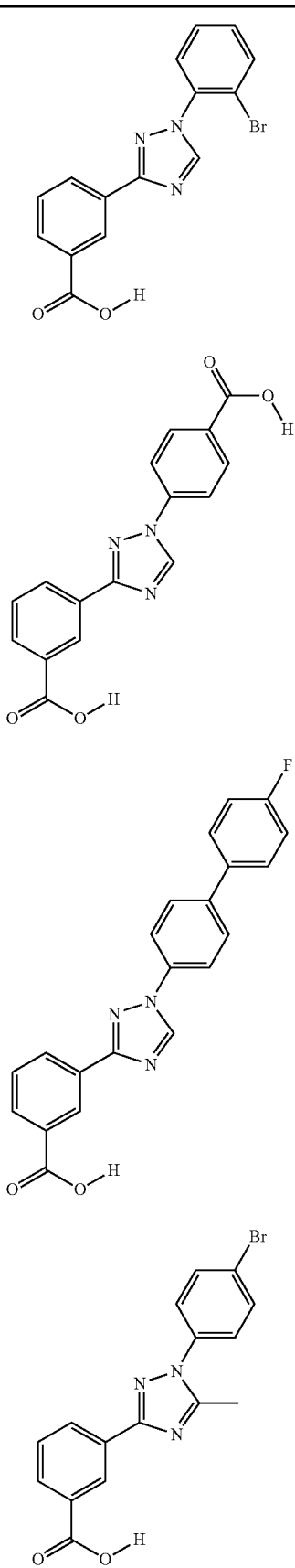

TABLE 7-continued
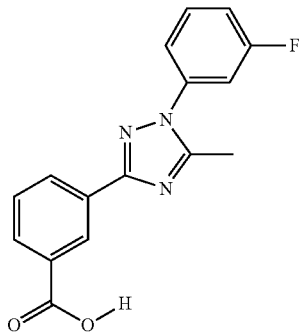 [SMILES: Cc1nc(-c2cccc(C(=O)O)c2)nn1-c1cccc(F)c1]
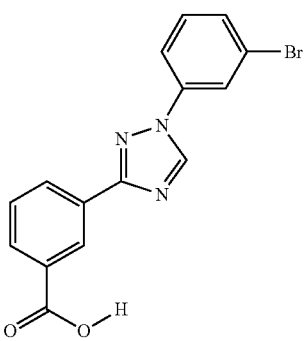 [SMILES: O=C(O)c1cccc(-c2ncn(-c3cccc(Br)c3)n2)c1]
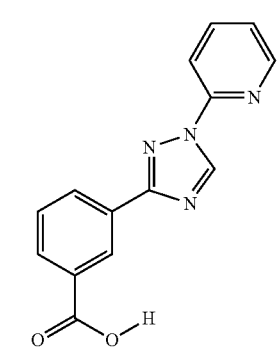 [SMILES: O=C(O)c1cccc(-c2ncn(-c3ccccn3)n2)c1]
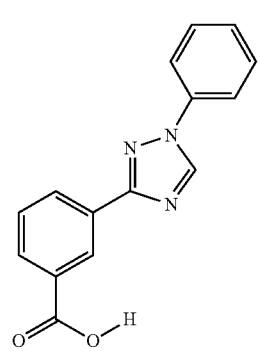 [SMILES: O=C(O)c1cccc(-c2ncn(-c3ccccc3)n2)c1]
TABLE 7-continued
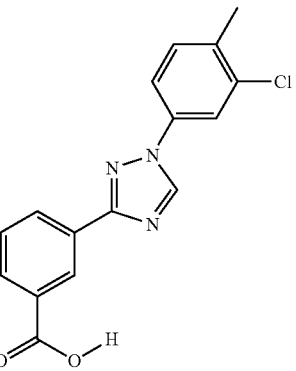
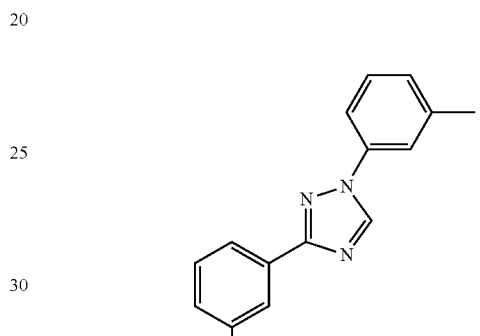
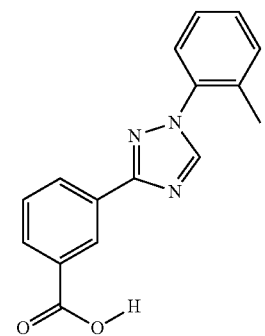 [SMILES: Cc1ccccc1-n1cnc(-c2cccc(C(=O)O)c2)n1]
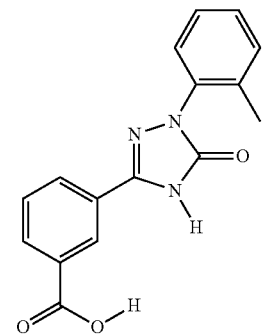 [SMILES: Cc1ccccc1-n1nc(-c2cccc(C(=O)O)c2)[nH]c1=O]

TABLE 7-continued
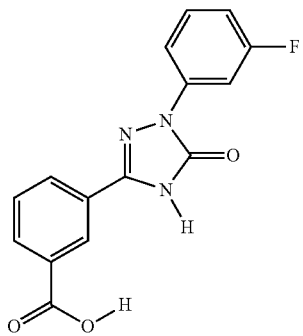 [SMILES: O=C(O)c1cccc(-c2nn(-c3cccc(F)c3)c(=O)[nH]2)c1]
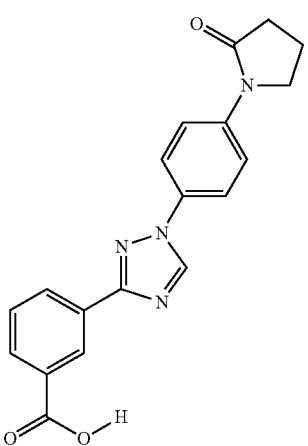 [SMILES: O=C(O)c1cccc(-c2ncn(-c3ccc(N4CCCC4=O)cc3)n2)c1]
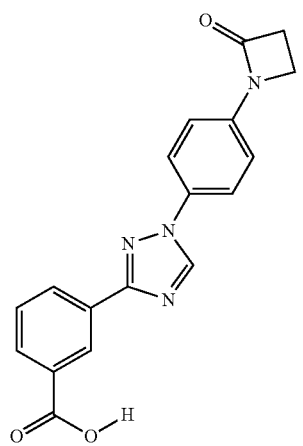 [SMILES: O=C(O)c1cccc(-c2ncn(-c3ccc(N4CCC4=O)cc3)n2)c1]
TABLE 7-continued
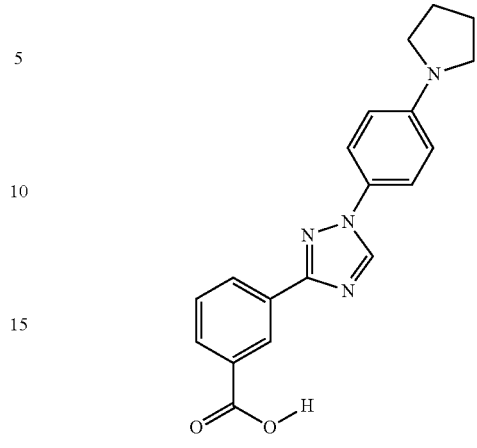
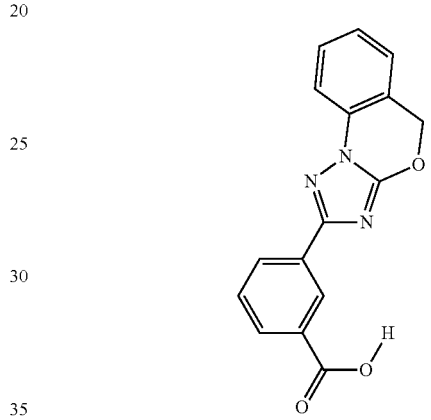
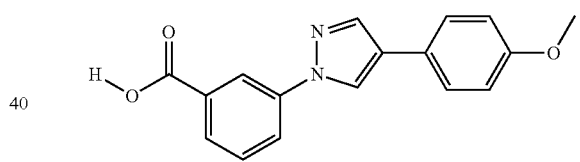
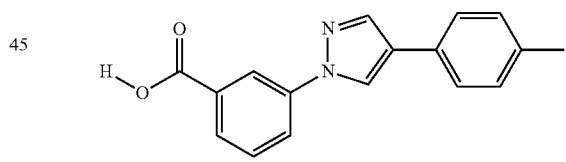
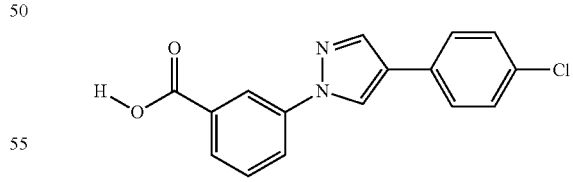
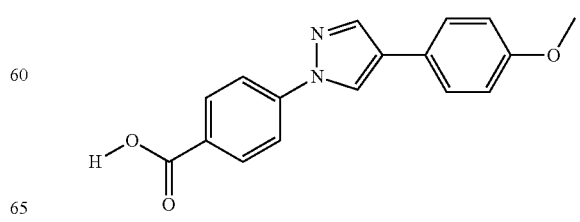

TABLE 7-continued
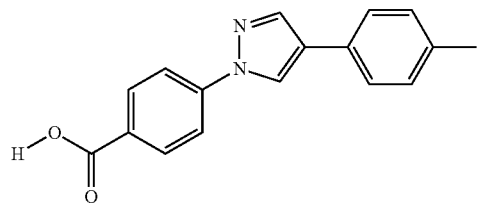 [SMILES: Cc1ccc(-c2cnn(-c3ccc(C(=O)O)cc3)c2)cc1]
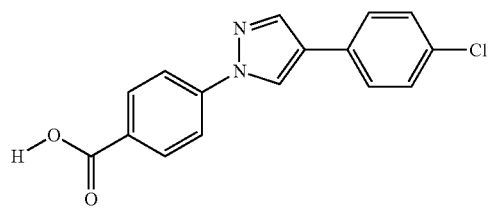 [SMILES: O=C(O)c1ccc(-n2cc(-c3ccc(Cl)cc3)cn2)cc1]
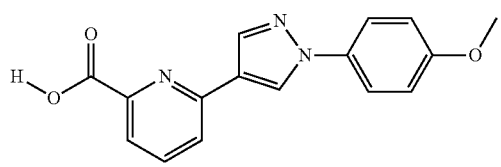 [SMILES: COc1ccc(-n2cc(-c3cccc(C(=O)O)n3)cn2)cc1]
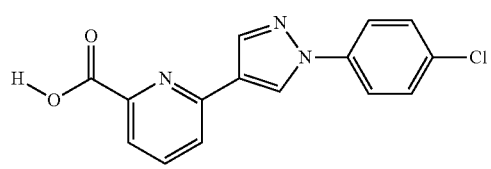 [SMILES: O=C(O)c1cccc(-c2cnn(-c3ccc(Cl)cc3)c2)n1]
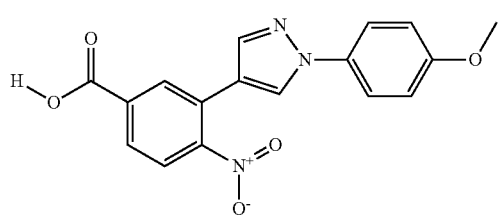 [SMILES: COc1ccc(-n2cc(-c3cc(C(=O)O)ccc3[N+](=O)[O-])cn2)cc1]
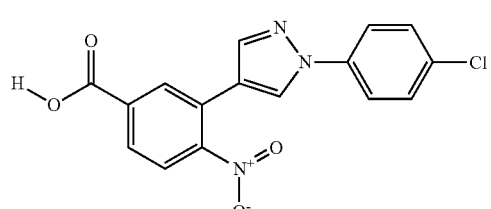
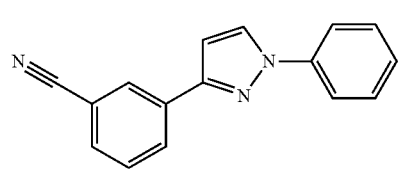 [SMILES: N#Cc1cccc(-c2ccn(-c3ccccc3)n2)c1]
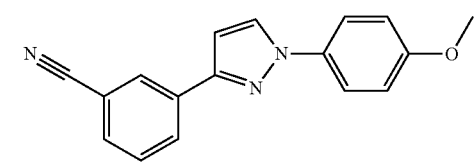 [SMILES: COc1ccc(-n2ccc(-c3cccc(C#N)c3)n2)cc1]
TABLE 7-continued
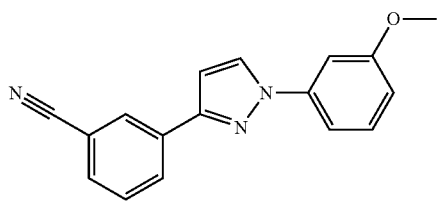 [SMILES: COc1cccc(-n2ccc(-c3cccc(C#N)c3)n2)c1]
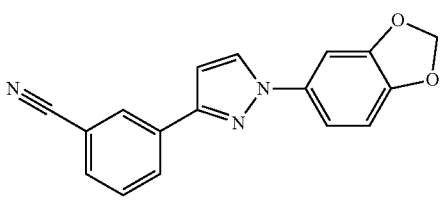 [SMILES: N#Cc1cccc(-c2ccn(-c3ccc4c(c3)OCO4)n2)c1]
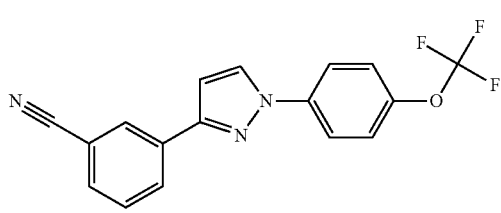 [SMILES: N#Cc1cccc(-c2ccn(-c3ccc(OC(F)(F)F)cc3)n2)c1]
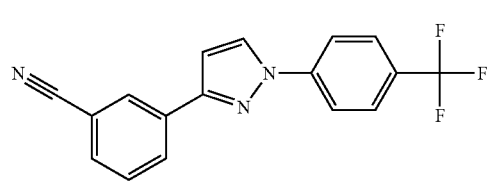 [SMILES: N#Cc1cccc(-c2ccn(-c3ccc(C(F)(F)F)cc3)n2)c1]
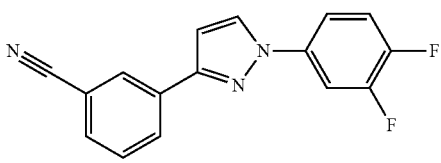 [SMILES: N#Cc1cccc(-c2ccn(-c3ccc(F)c(F)c3)n2)c1]
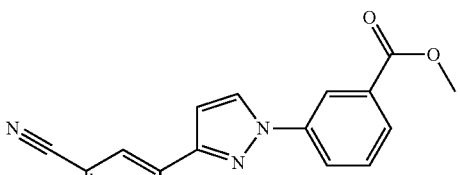
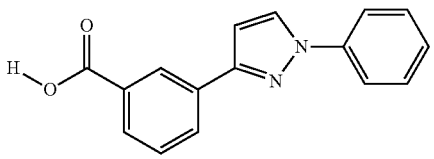 [SMILES: O=C(O)c1cccc(-c2ccn(-c3ccccc3)n2)c1]
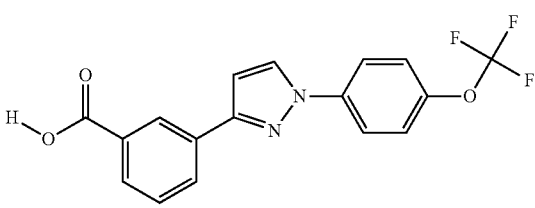 [SMILES: O=C(O)c1cccc(-c2ccn(-c3ccc(OC(F)(F)F)cc3)n2)c1]

TABLE 7-continued
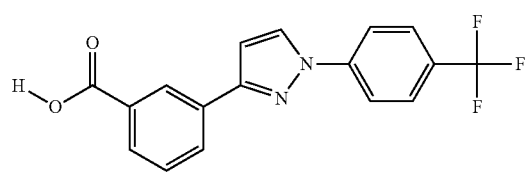 [SMILES: O=C(O)c1cccc(-c2ccn(-c3ccc(C(F)(F)F)cc3)n2)c1]
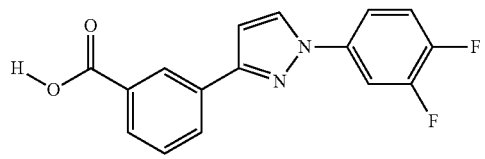 [SMILES: O=C(O)c1cccc(-c2ccn(-c3ccc(F)c(F)c3)n2)c1]
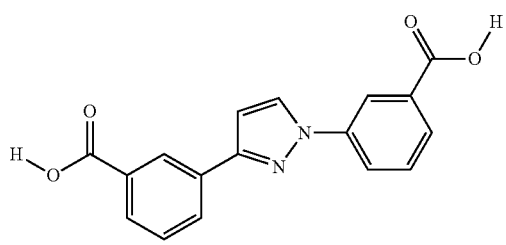 [SMILES: O=C(O)c1cccc(-c2ccn(-c3cccc(C(=O)O)c3)n2)c1]
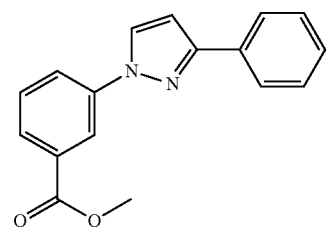 [SMILES: COC(=O)c1cccc(-n2ccc(-c3ccccc3)n2)c1]
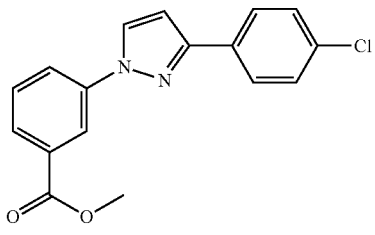 [SMILES: COC(=O)c1cccc(-n2ccc(-c3ccc(Cl)cc3)n2)c1]
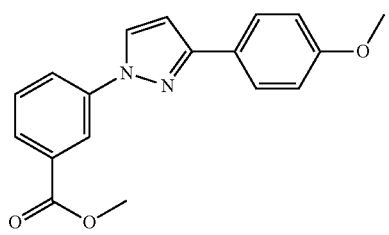 [SMILES: COC(=O)c1cccc(-n2ccc(-c3ccc(OC)cc3)n2)c1]
TABLE 7-continued
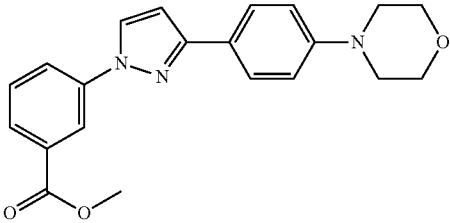 [SMILES: COC(=O)c1cccc(-n2ccc(-c3ccc(N4CCOCC4)cc3)n2)c1]
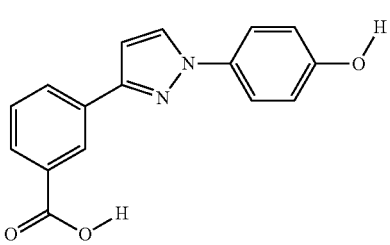 [SMILES: O=C(O)c1cccc(-c2ccn(-c3ccc(O)cc3)n2)c1]
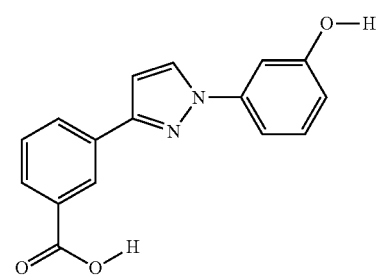 [SMILES: O=C(O)c1cccc(-c2ccn(-c3cccc(O)c3)n2)c1]
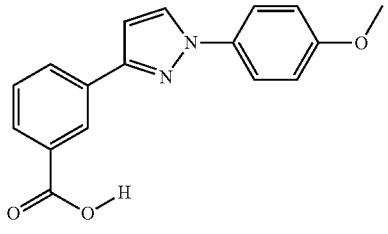
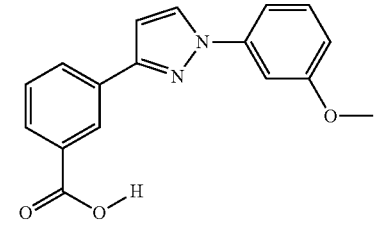 [SMILES: COc1cccc(-n2ccc(-c3cccc(C(=O)O)c3)n2)c1]
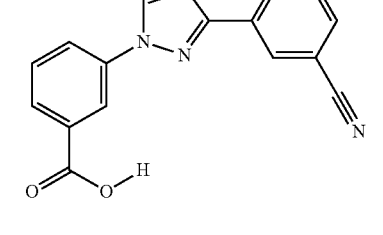

TABLE 7-continued
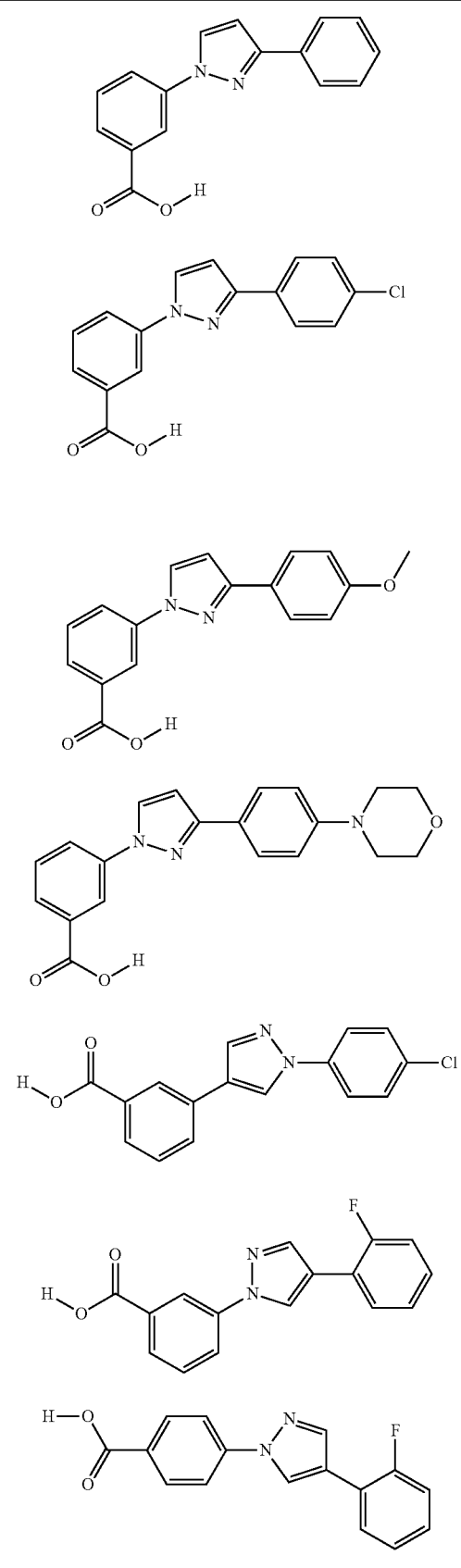
TABLE 7-continued
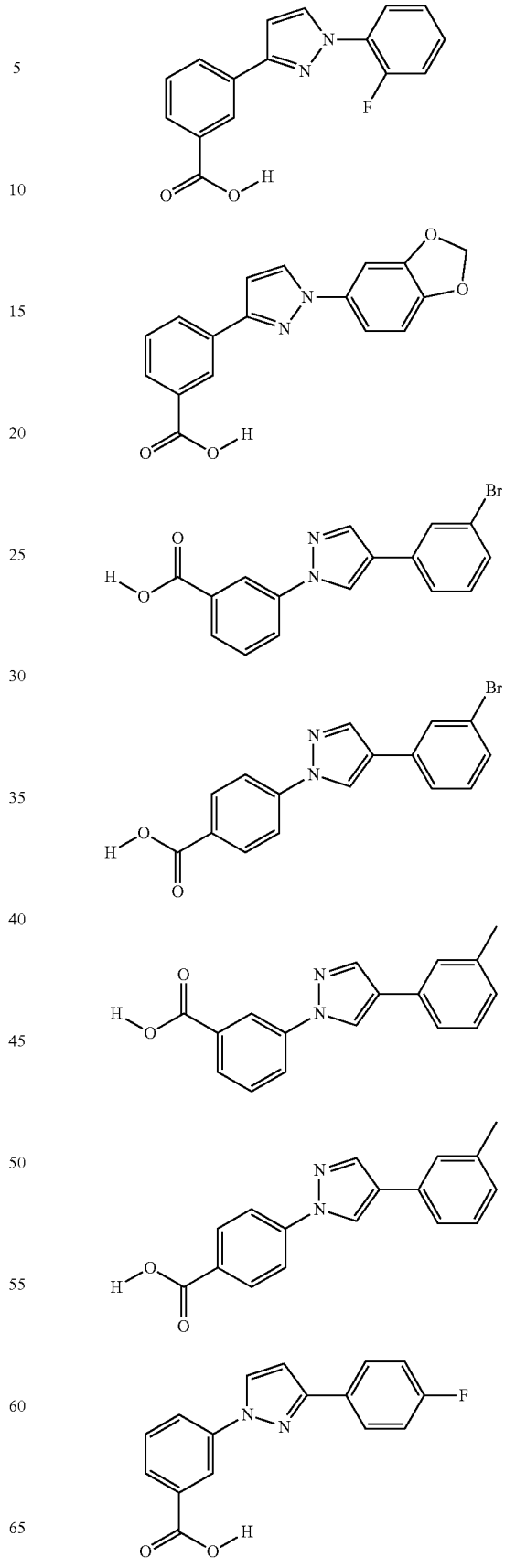

TABLE 7-continued
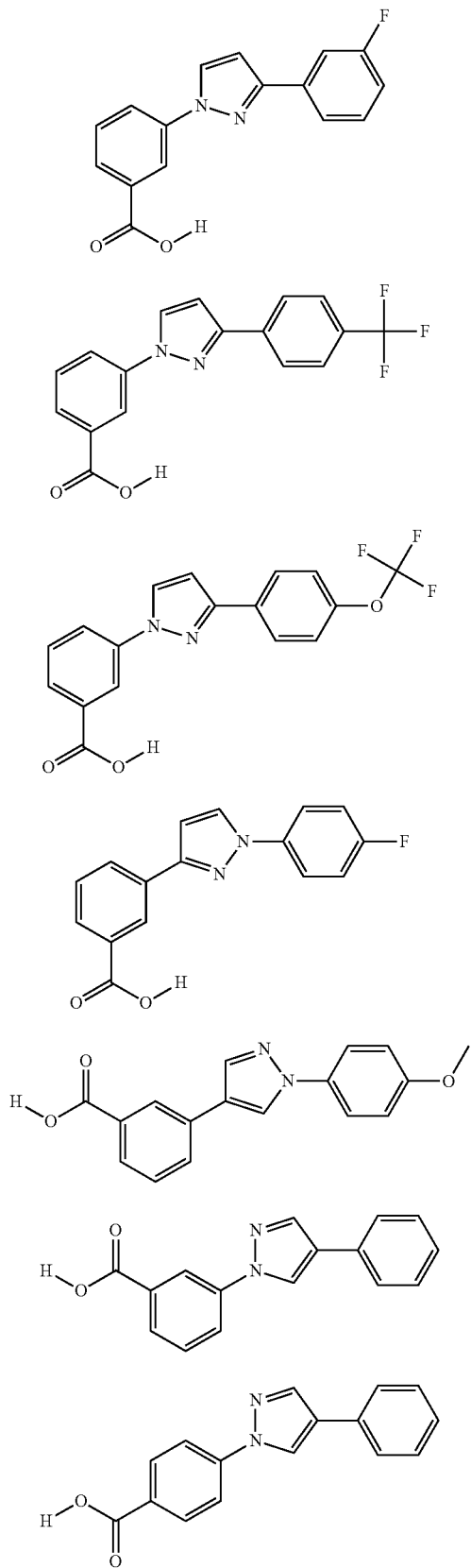
TABLE 7-continued
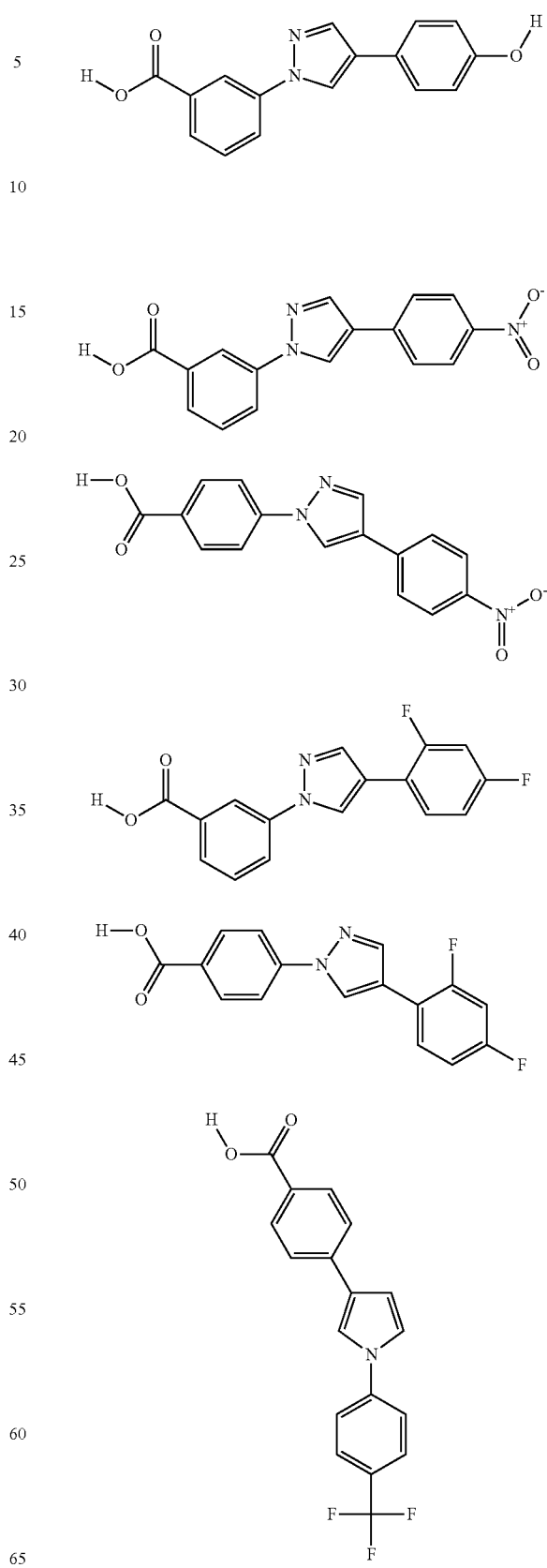

TABLE 7-continued
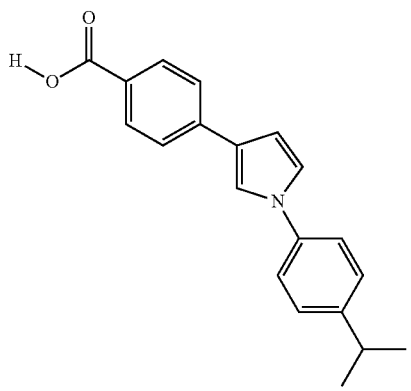 [SMILES: CC(C)c1ccc(-n2ccc(-c3ccc(C(=O)O)cc3)c2)cc1]
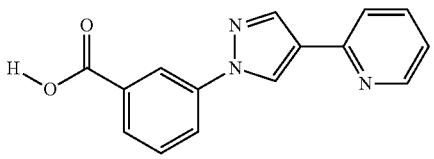
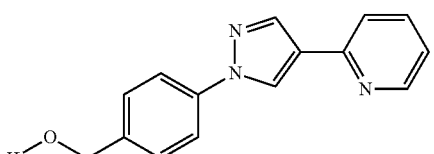
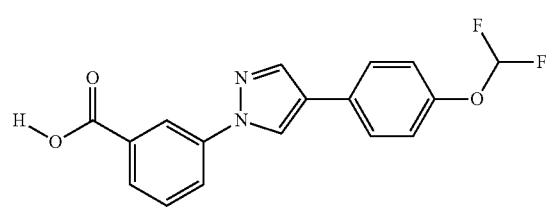 [SMILES: O=C(O)c1cccc(-n2cc(-c3ccc(OC(F)F)cc3)cn2)c1]
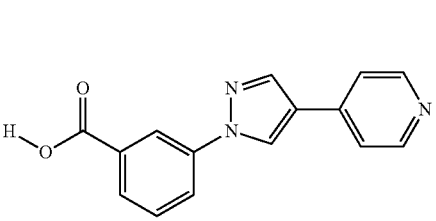
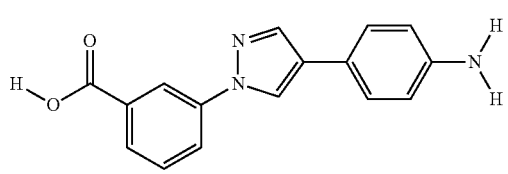
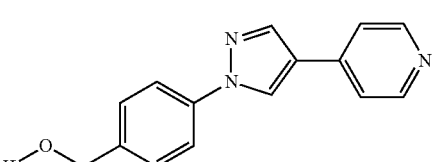
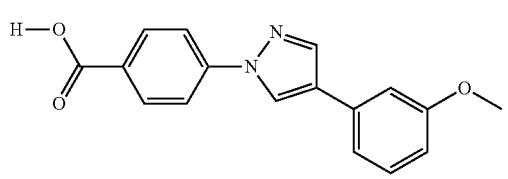 [SMILES: COc1cccc(-c2cnn(-c3ccc(C(=O)O)cc3)c2)c1]
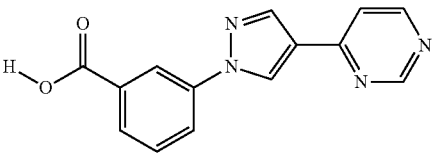
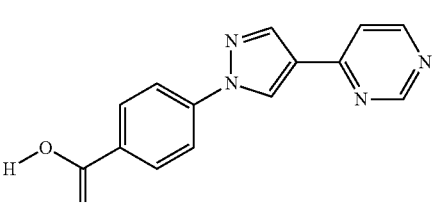
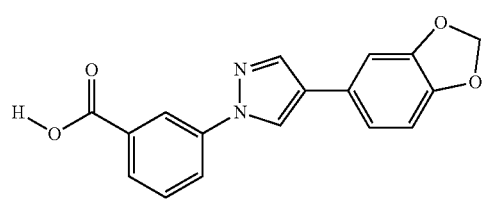 [SMILES: O=C(O)c1cccc(-n2cc(-c3ccc4c(c3)OCO4)cn2)c1]
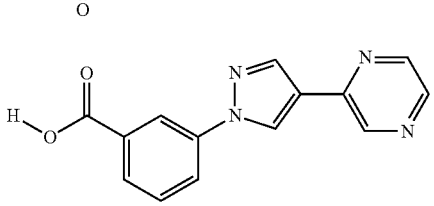
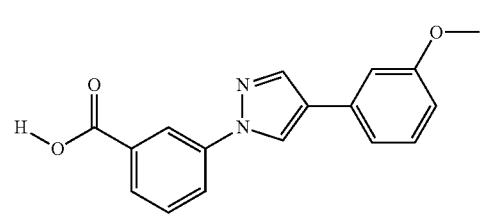 [SMILES: COc1cccc(-c2cnn(-c3cccc(C(=O)O)c3)c2)c1]
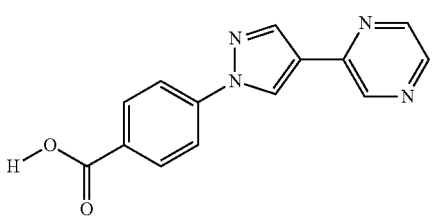 [SMILES: O=C(O)c1ccc(-n2cc(-c3cnccn3)cn2)cc1]

TABLE 7-continued
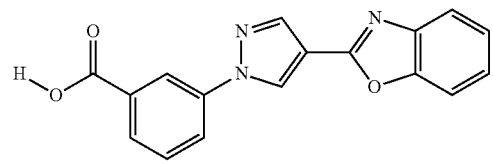 [SMILES: O=C(O)c1cccc(-n2cc(-c3nc4ccccc4o3)cn2)c1]
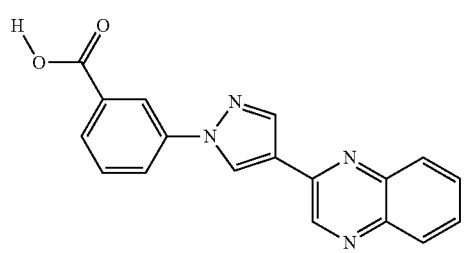 [SMILES: O=C(O)c1cccc(-n2cc(-c3cnc4ccccc4n3)cn2)c1]
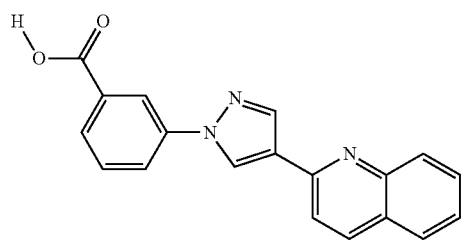 [SMILES: O=C(O)c1cccc(-n2cc(-c3ccc4ccccc4n3)cn2)c1]
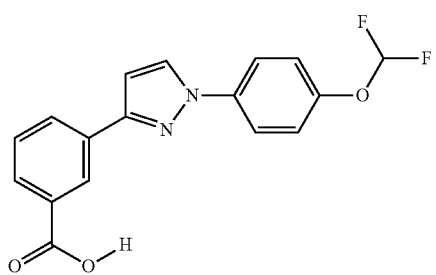 [SMILES: O=C(O)c1cccc(-c2ccn(-c3ccc(OC(F)F)cc3)n2)c1]
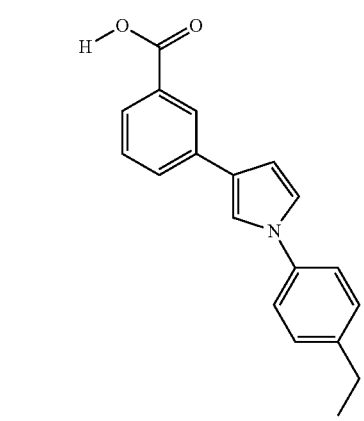 [SMILES: CCc1ccc(-n2ccc(-c3cccc(C(=O)O)c3)c2)cc1]
TABLE 7-continued
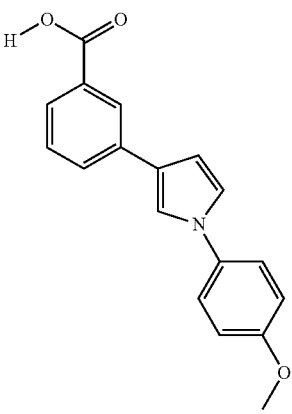 [SMILES: COc1ccc(-n2ccc(-c3cccc(C(=O)O)c3)c2)cc1]
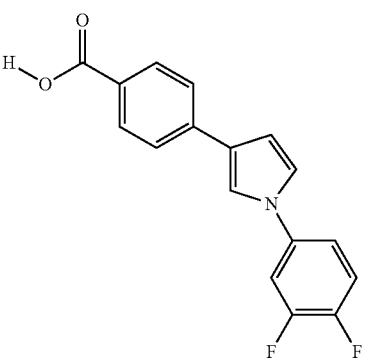 [SMILES: O=C(O)c1ccc(-c2ccn(-c3ccc(F)c(F)c3)c2)cc1]
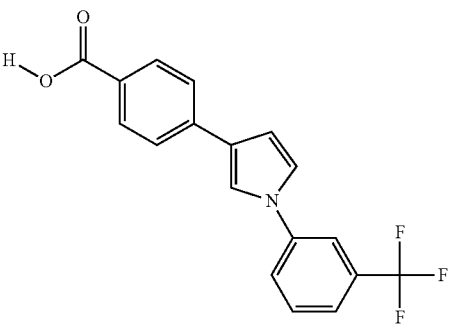 [SMILES: O=C(O)c1ccc(-c2ccn(-c3cccc(C(F)(F)F)c3)c2)cc1]
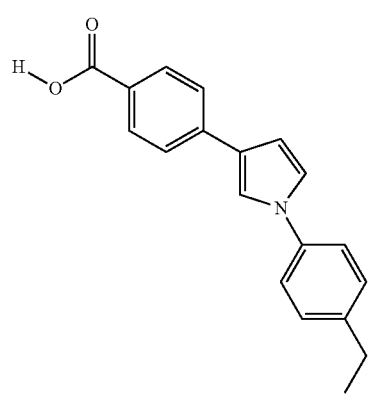 [SMILES: CCc1ccc(-n2ccc(-c3ccc(C(=O)O)cc3)c2)cc1]

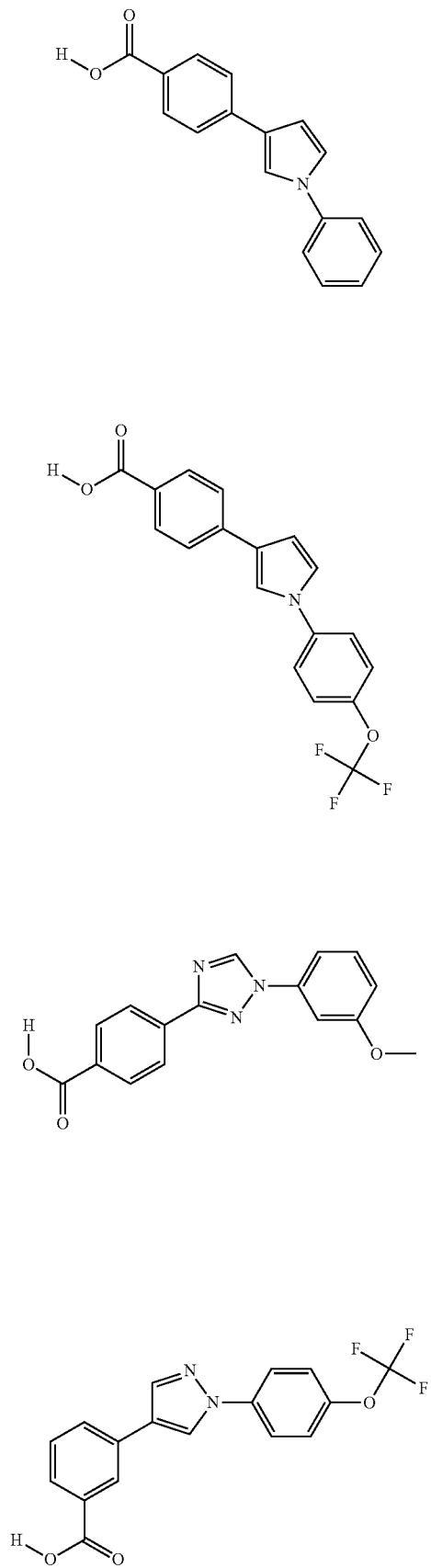

TABLE 7-continued
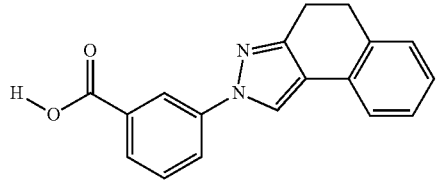 [SMILES: O=C(O)c1cccc(-n2cc3c(n2)CCc2ccccc2-3)c1]
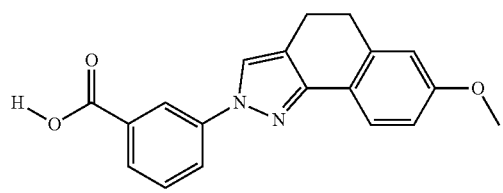 [SMILES: COc1ccc2c(c1)CCc1cn(-c3cccc(C(=O)O)c3)nc1-2]
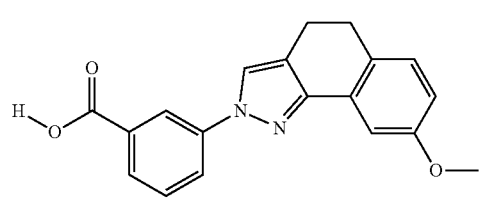 [SMILES: COc1ccc2c(c1)-c1nn(-c3cccc(C(=O)O)c3)cc1CC2]
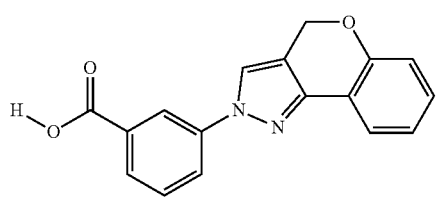 [SMILES: O=C(O)c1cccc(-n2cc3c(n2)-c2ccccc2OC3)c1]
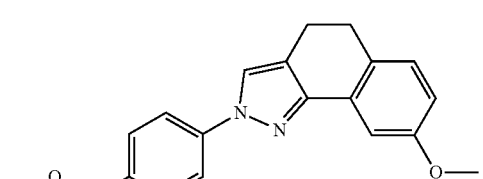
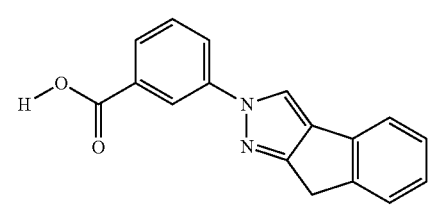 [SMILES: O=C(O)c1cccc(-n2cc3c(n2)Cc2ccccc2-3)c1]
TABLE 7-continued
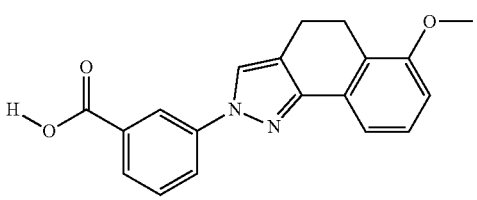 [SMILES: COc1cccc2c1CCc1cn(-c3cccc(C(=O)O)c3)nc1-2]
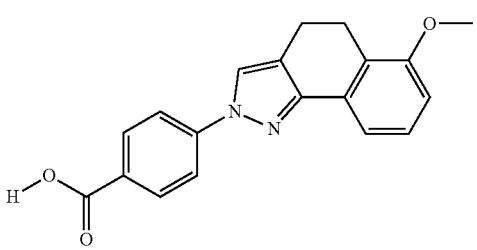 [SMILES: COc1cccc2c1CCc1cn(-c3ccc(C(=O)O)cc3)nc1-2]
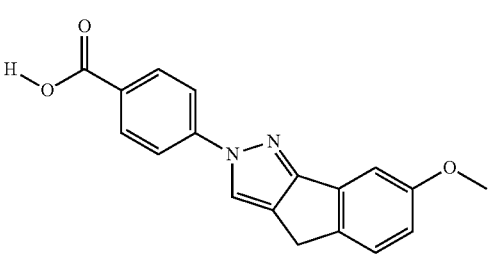 [SMILES: COc1ccc2c(c1)-c1nn(-c3ccc(C(=O)O)cc3)cc1C2]
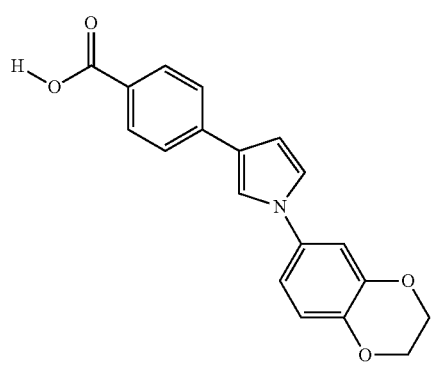 [SMILES: O=C(O)c1ccc(-c2ccn(-c3ccc4c(c3)OCCO4)c2)cc1]
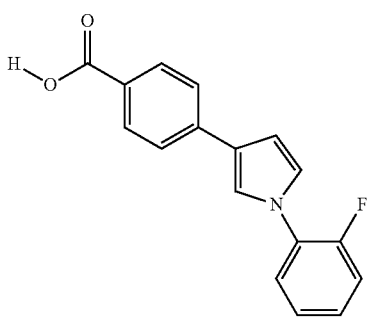 [SMILES: O=C(O)c1ccc(-c2ccn(-c3ccccc3F)c2)cc1]

TABLE 7-continued
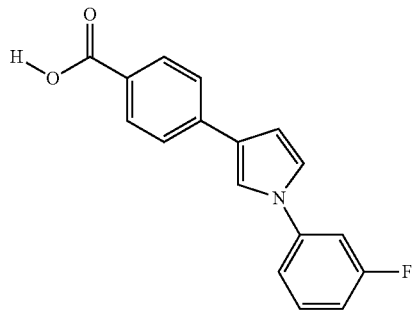 [SMILES: O=C(O)c1ccc(-c2ccn(-c3cccc(F)c3)c2)cc1]
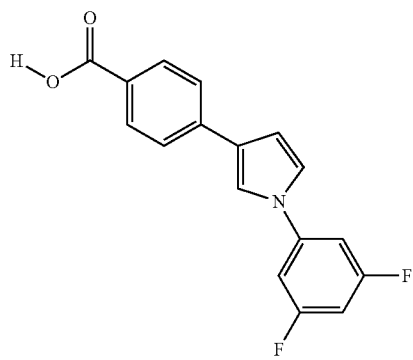 [SMILES: O=C(O)c1ccc(-c2ccn(-c3cc(F)cc(F)c3)c2)cc1]
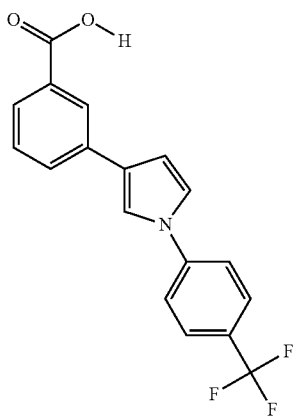 [SMILES: O=C(O)c1cccc(-c2ccn(-c3ccc(C(F)(F)F)cc3)c2)c1]
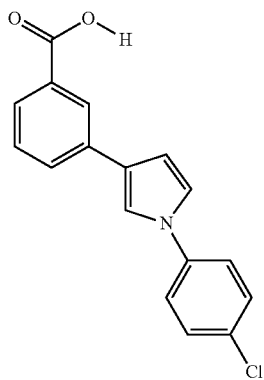 [SMILES: O=C(O)c1cccc(-c2ccn(-c3ccc(Cl)cc3)c2)c1]
TABLE 7-continued
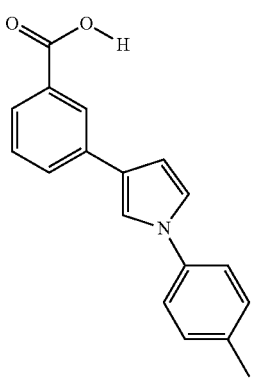 [SMILES: Cc1ccc(-n2ccc(-c3cccc(C(=O)O)c3)c2)cc1]
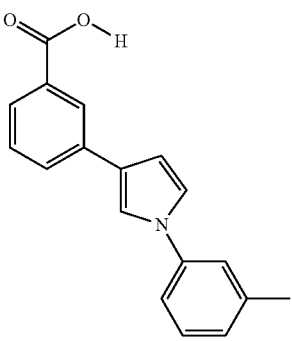 [SMILES: Cc1cccc(-n2ccc(-c3cccc(C(=O)O)c3)c2)c1]
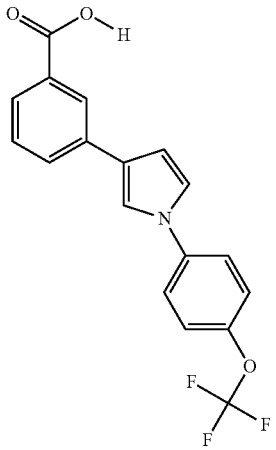 [SMILES: O=C(O)c1cccc(-c2ccn(-c3ccc(OC(F)(F)F)cc3)c2)c1]
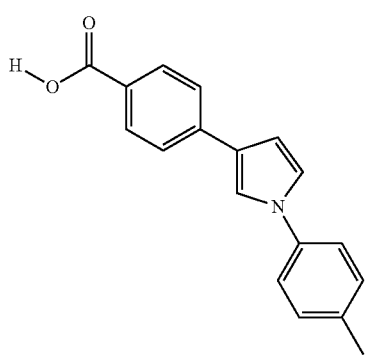 [SMILES: Cc1ccc(-n2ccc(-c3ccc(C(=O)O)cc3)c2)cc1]

TABLE 7-continued
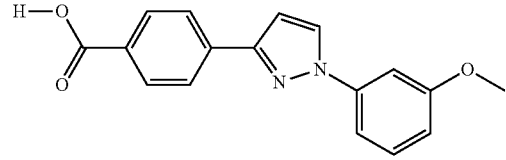 [SMILES: COc1cccc(-n2ccc(-c3ccc(C(=O)O)cc3)n2)c1]
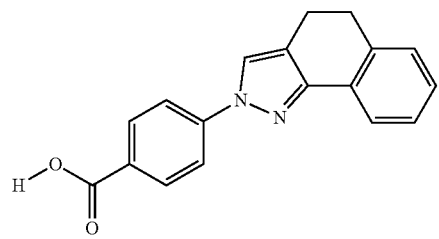 [SMILES: O=C(O)c1ccc(-n2cc3c(n2)-c2ccccc2CC3)cc1]
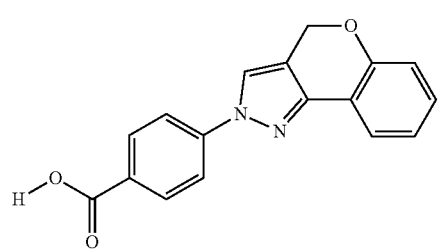 [SMILES: O=C(O)c1ccc(-n2cc3c(n2)-c2ccccc2OC3)cc1]
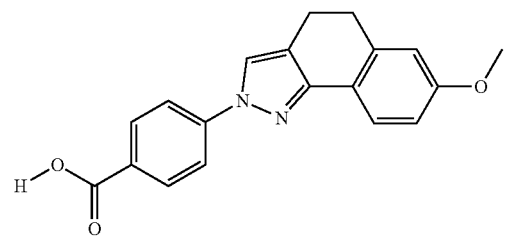 [SMILES: COc1ccc2c(c1)CCc1cn(-c3ccc(C(=O)O)cc3)nc1-2]
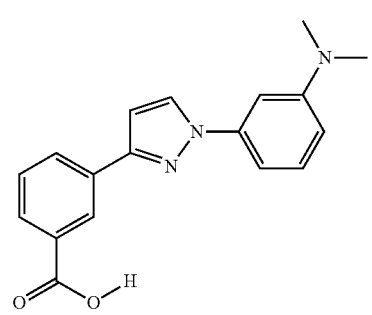 [SMILES: CN(C)c1cccc(-n2ccc(-c3cccc(C(=O)O)c3)n2)c1]
TABLE 7-continued
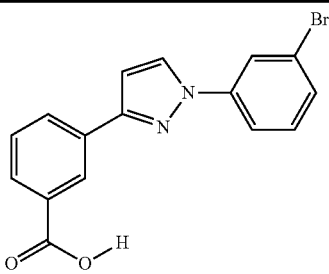
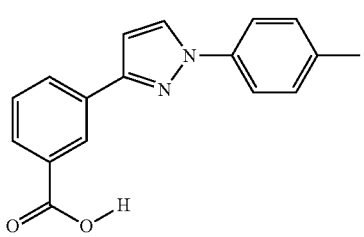 [SMILES: Cc1ccc(-n2ccc(-c3cccc(C(=O)O)c3)n2)cc1]
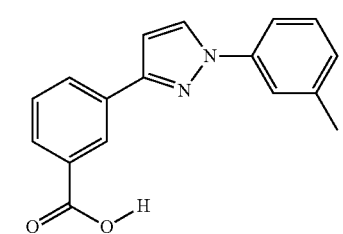 [SMILES: Cc1cccc(-n2ccc(-c3cccc(C(=O)O)c3)n2)c1]
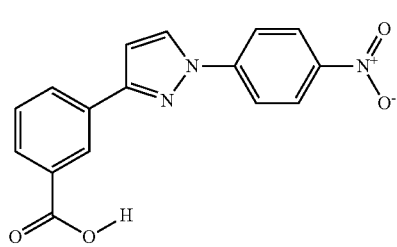 [SMILES: O=C(O)c1cccc(-c2ccn(-c3ccc([N+](=O)[O-])cc3)n2)c1]
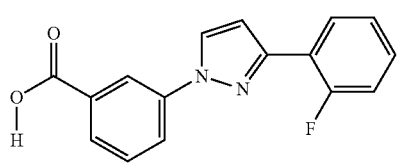 [SMILES: O=C(O)c1cccc(-n2ccc(-c3ccccc3F)n2)c1]
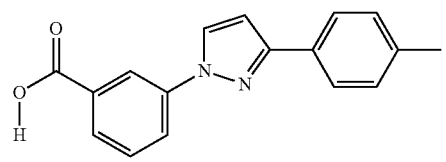 [SMILES: Cc1ccc(-c2ccn(-c3cccc(C(=O)O)c3)n2)cc1]

TABLE 7-continued
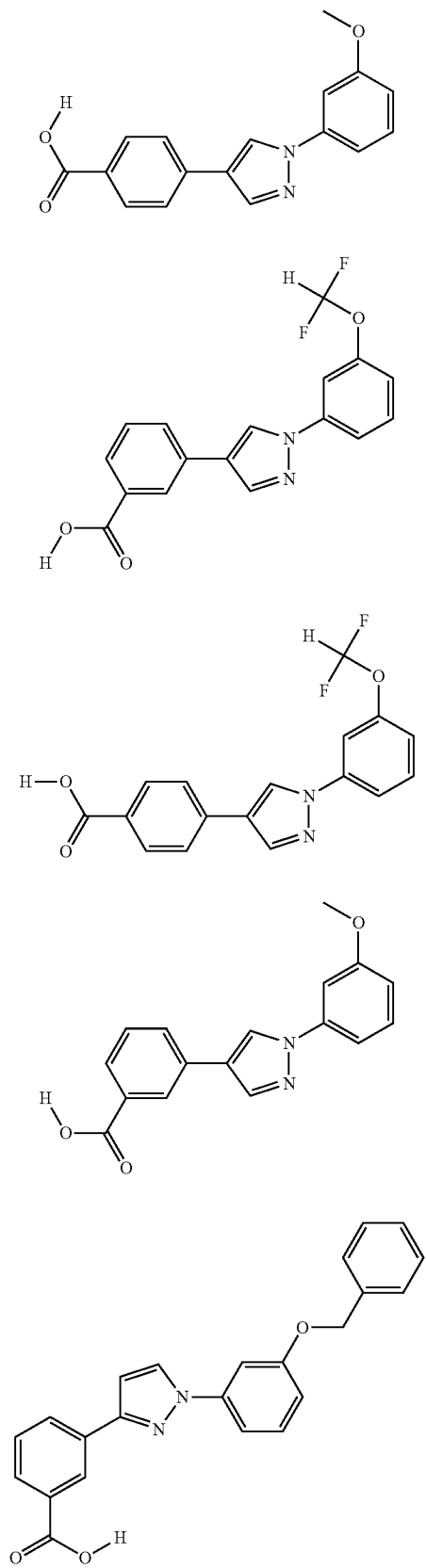
TABLE 7-continued
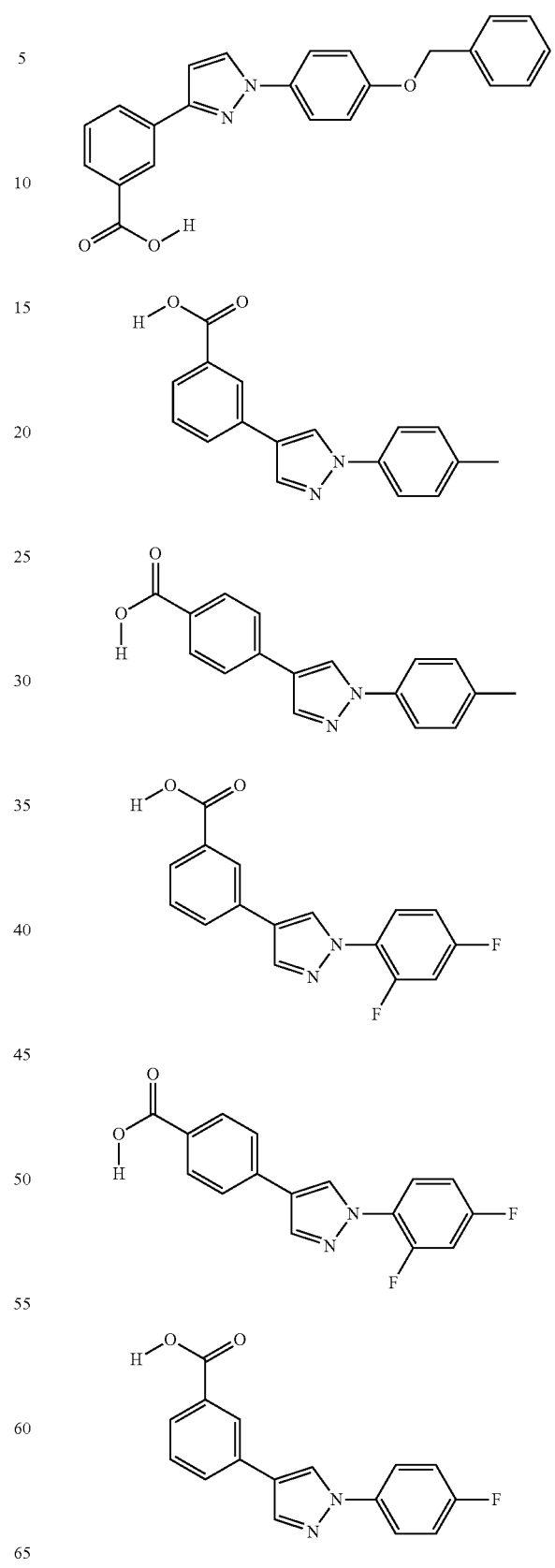

TABLE 7-continued
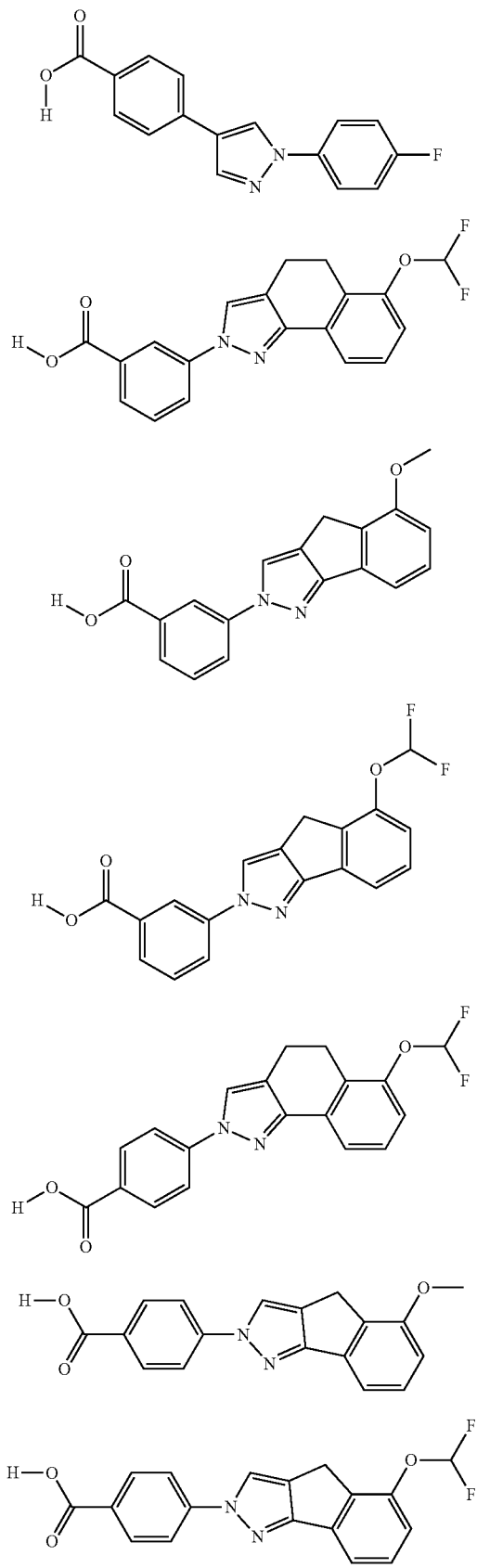
TABLE 7-continued
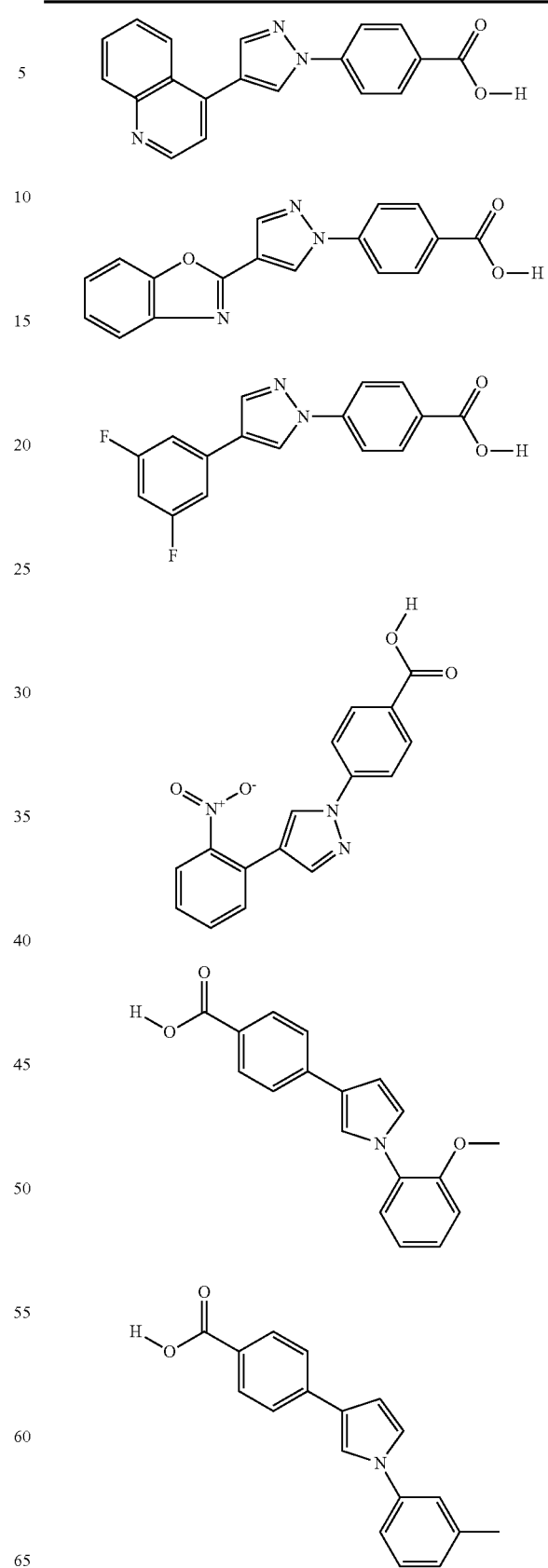

TABLE 7-continued
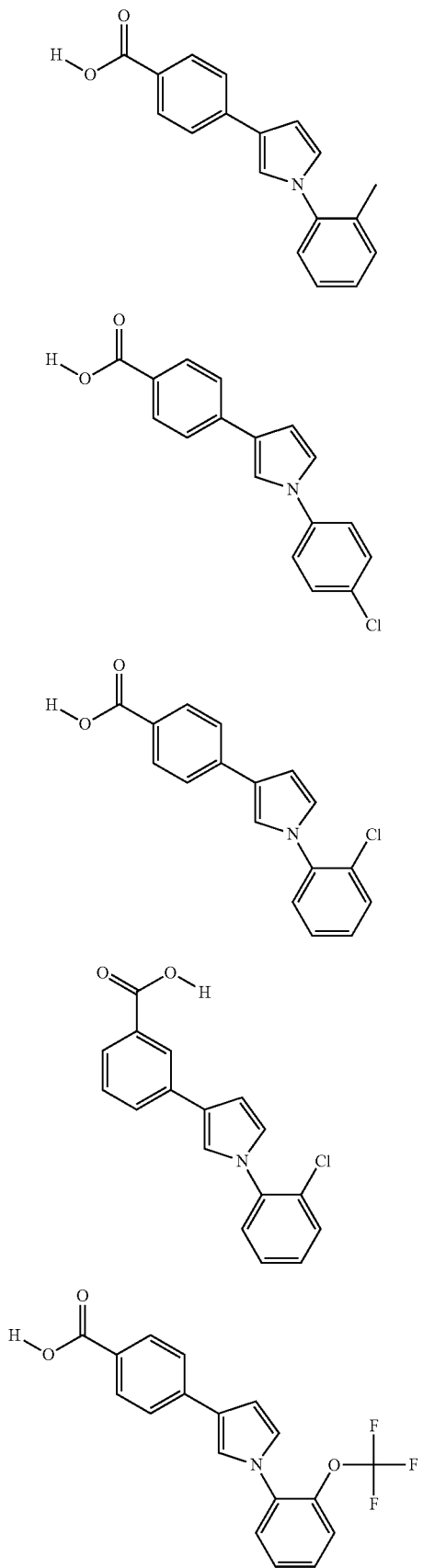
TABLE 7-continued
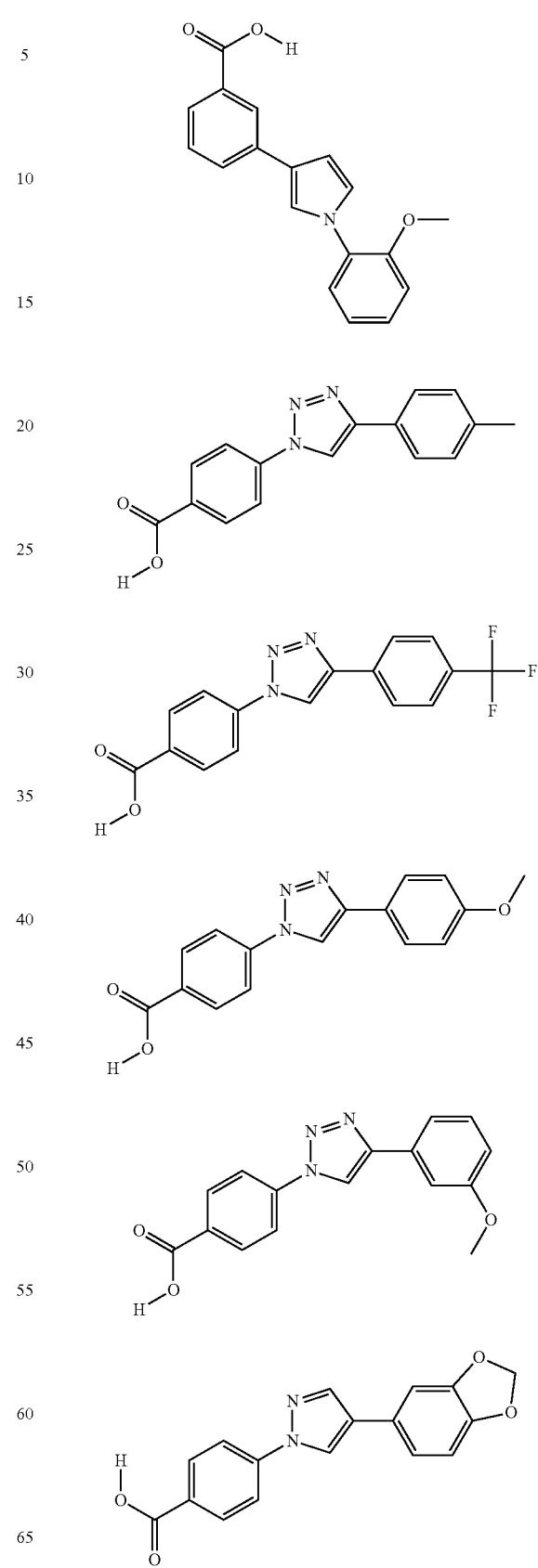

TABLE 7-continued
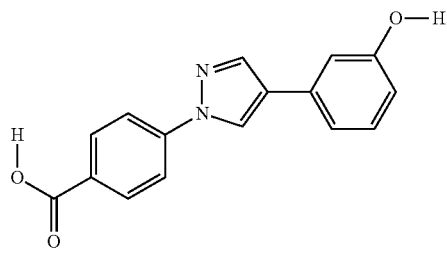 [SMILES: O=C(O)c1ccc(-n2cc(-c3cccc(O)c3)cn2)cc1]
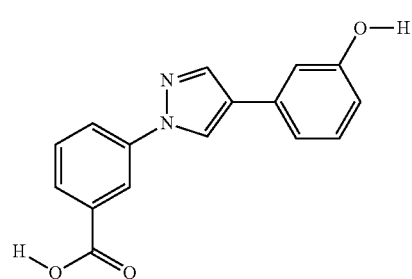 [SMILES: O=C(O)c1cccc(-n2cc(-c3cccc(O)c3)cn2)c1]
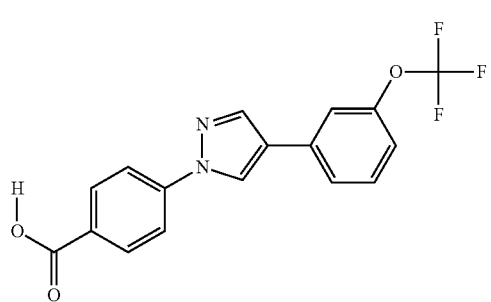 [SMILES: O=C(O)c1ccc(-n2cc(-c3cccc(OC(F)(F)F)c3)cn2)cc1]
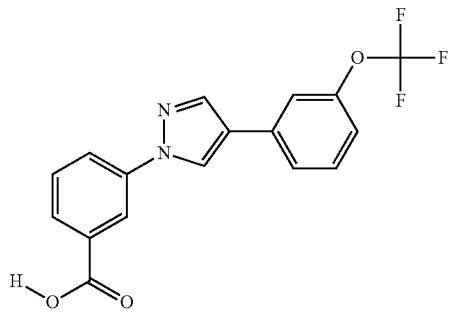 [SMILES: O=C(O)c1cccc(-n2cc(-c3cccc(OC(F)(F)F)c3)cn2)c1]
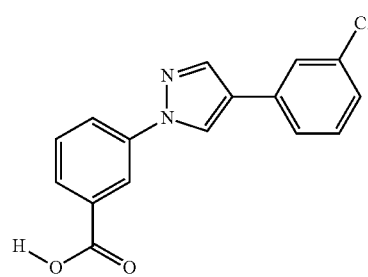
TABLE 7-continued
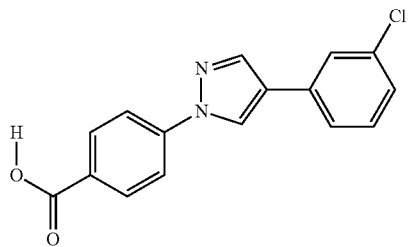 [SMILES: O=C(O)c1ccc(-n2cc(-c3cccc(Cl)c3)cn2)cc1]
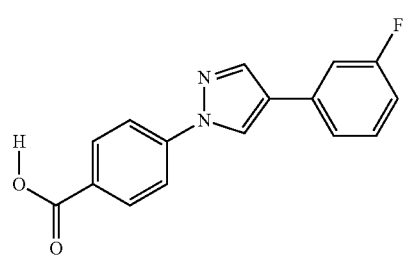 [SMILES: O=C(O)c1ccc(-n2cc(-c3cccc(F)c3)cn2)cc1]
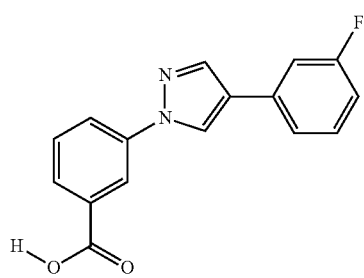 [SMILES: O=C(O)c1cccc(-n2cc(-c3cccc(F)c3)cn2)c1]
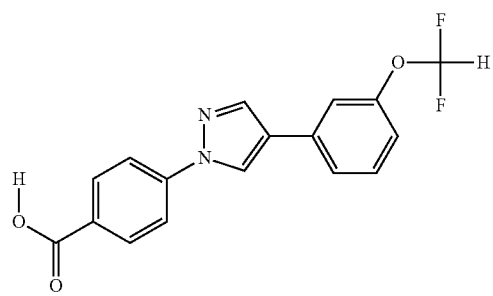 [SMILES: O=C(O)c1ccc(-n2cc(-c3cccc(OC(F)F)c3)cn2)cc1]
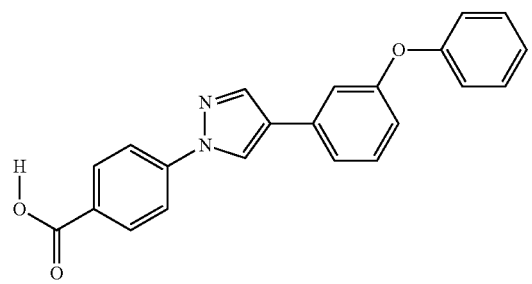 [SMILES: O=C(O)c1ccc(-n2cc(-c3cccc(Oc4ccccc4)c3)cn2)cc1]

TABLE 7-continued
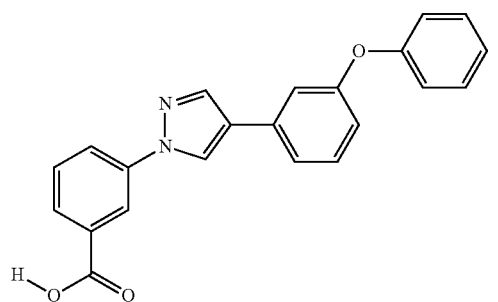 [SMILES: O=C(O)c1cccc(-n2cc(-c3cccc(Oc4ccccc4)c3)cn2)c1]
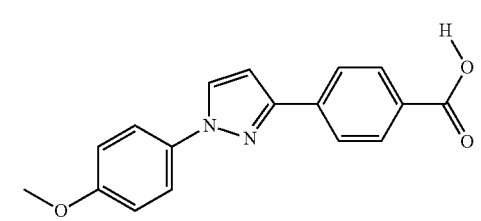 [SMILES: COc1ccc(-n2ccc(-c3ccc(C(=O)O)cc3)n2)cc1]
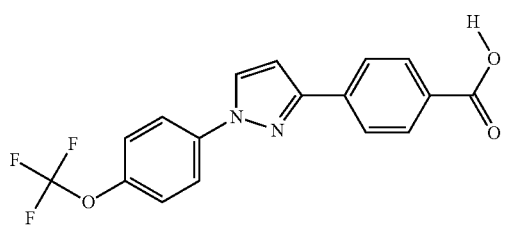 [SMILES: O=C(O)c1ccc(-c2ccn(-c3ccc(OC(F)(F)F)cc3)n2)cc1]
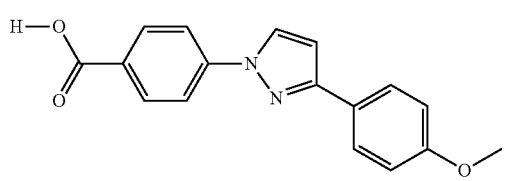 [SMILES: COc1ccc(-c2ccn(-c3ccc(C(=O)O)cc3)n2)cc1]
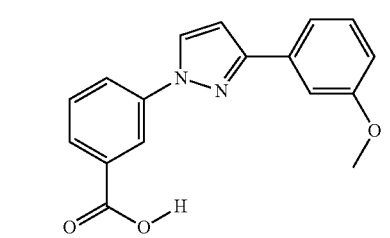 [SMILES: COc1cccc(-c2ccn(-c3cccc(C(=O)O)c3)n2)c1]
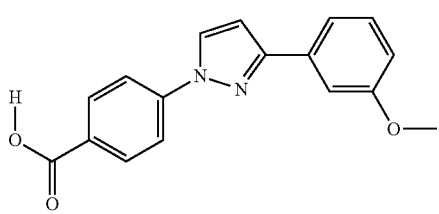 [SMILES: COc1cccc(-c2ccn(-c3ccc(C(=O)O)cc3)n2)c1]
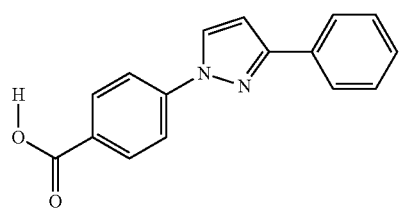 [SMILES: O=C(O)c1ccc(-n2ccc(-c3ccccc3)n2)cc1]
TABLE 7-continued
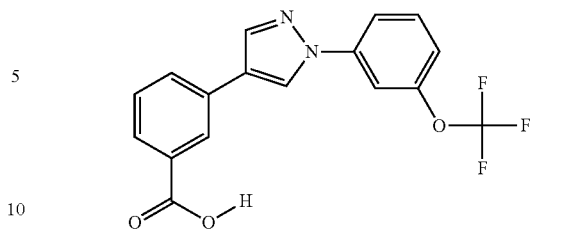
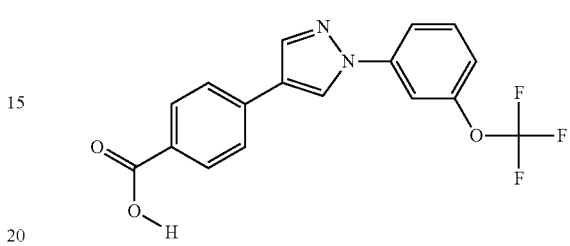
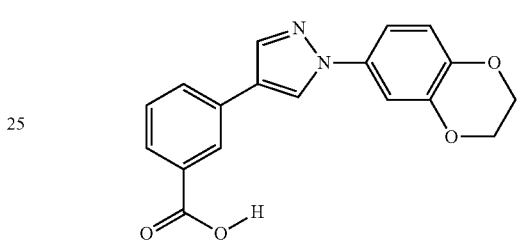
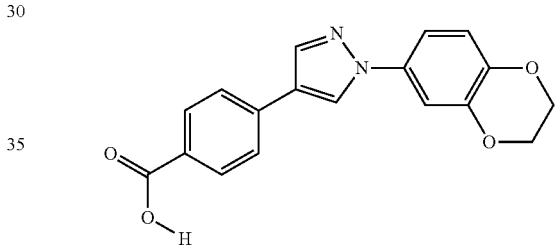
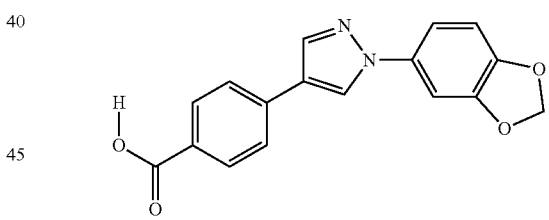
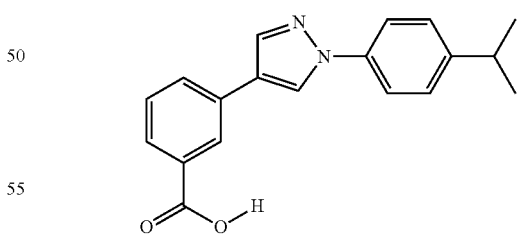
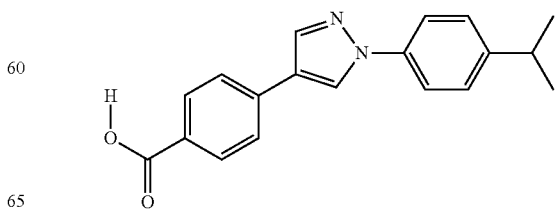

TABLE 7-continued
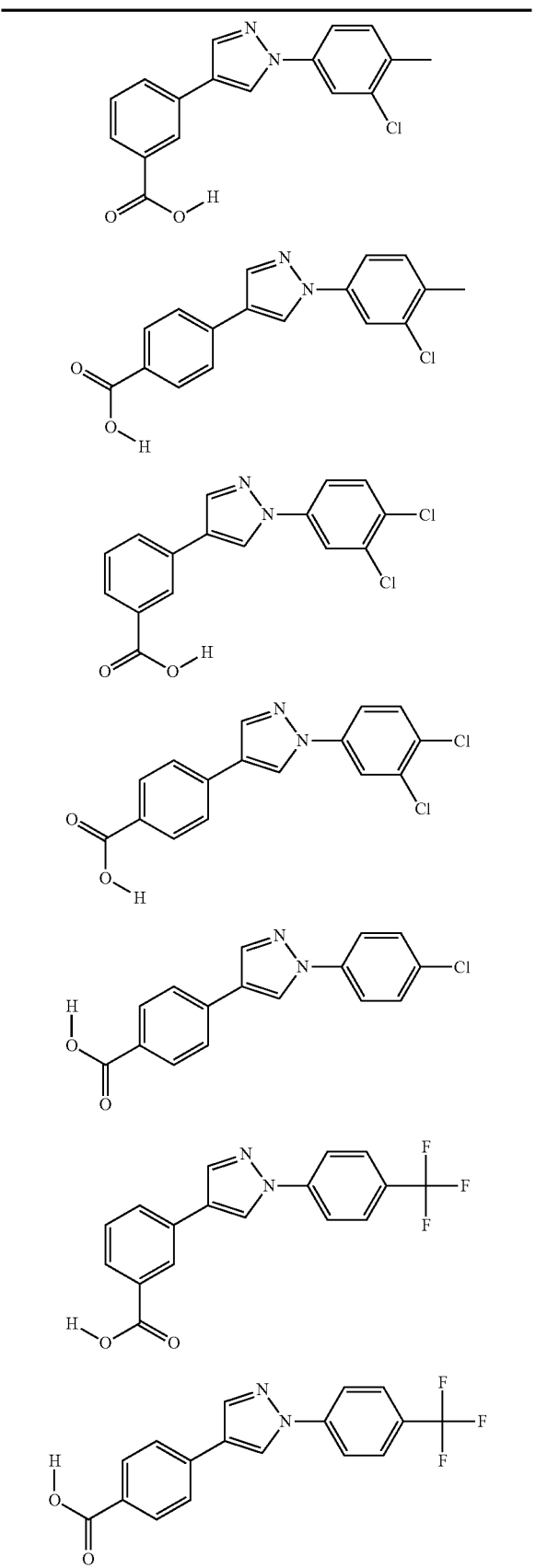
TABLE 7-continued
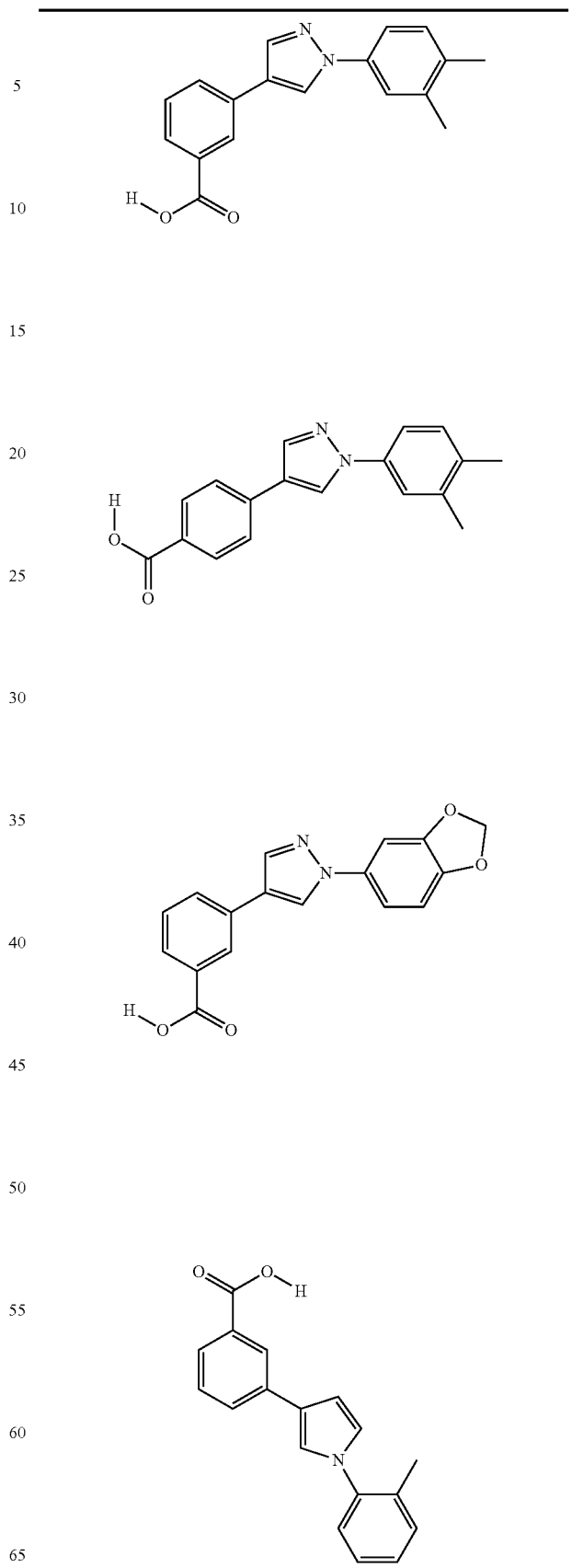

TABLE 7-continued
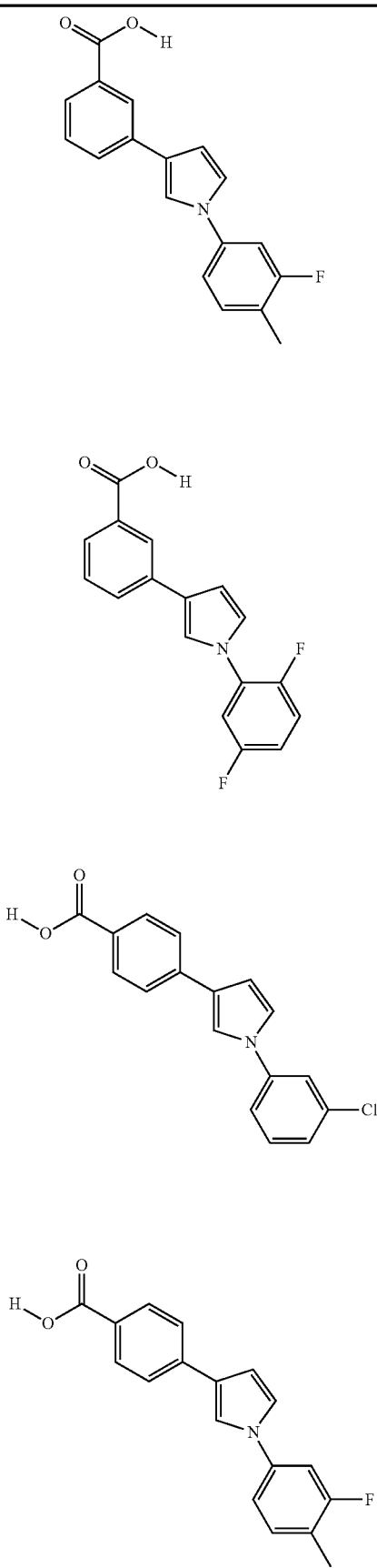
TABLE 7-continued
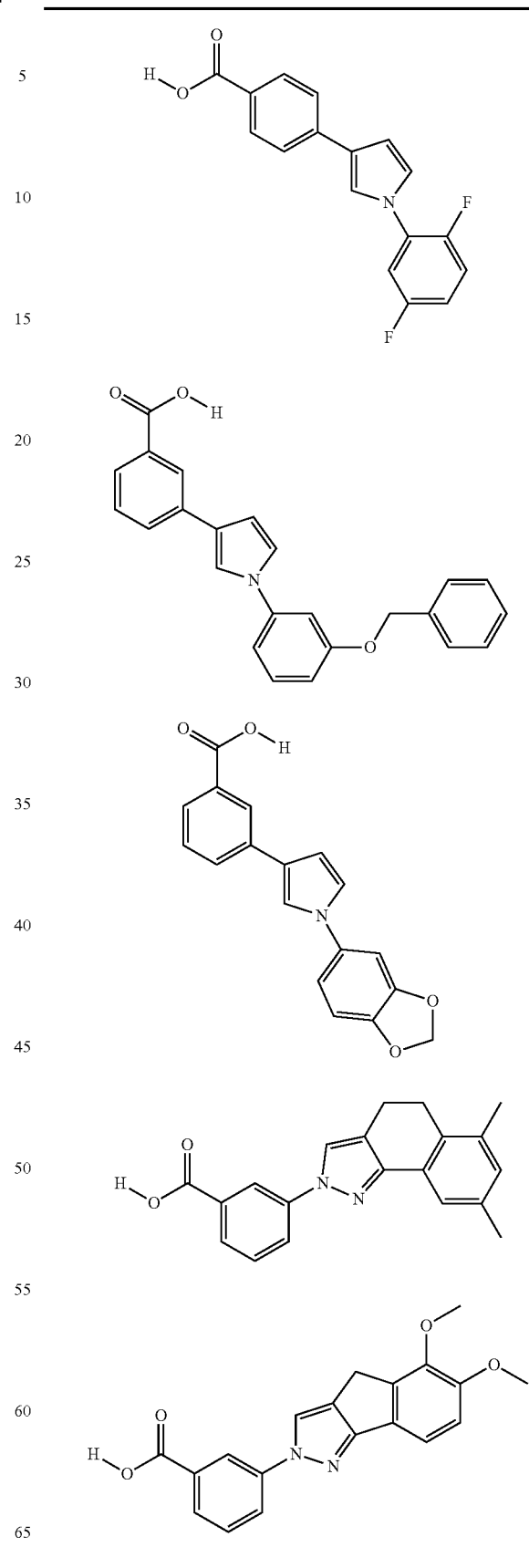

TABLE 7-continued
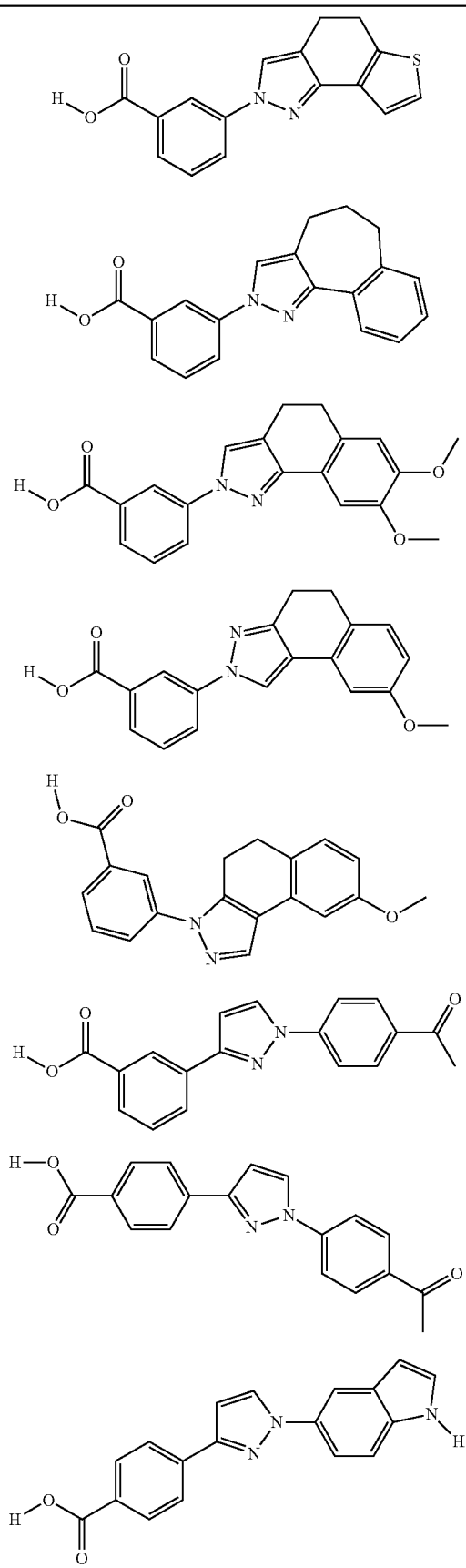
TABLE 7-continued
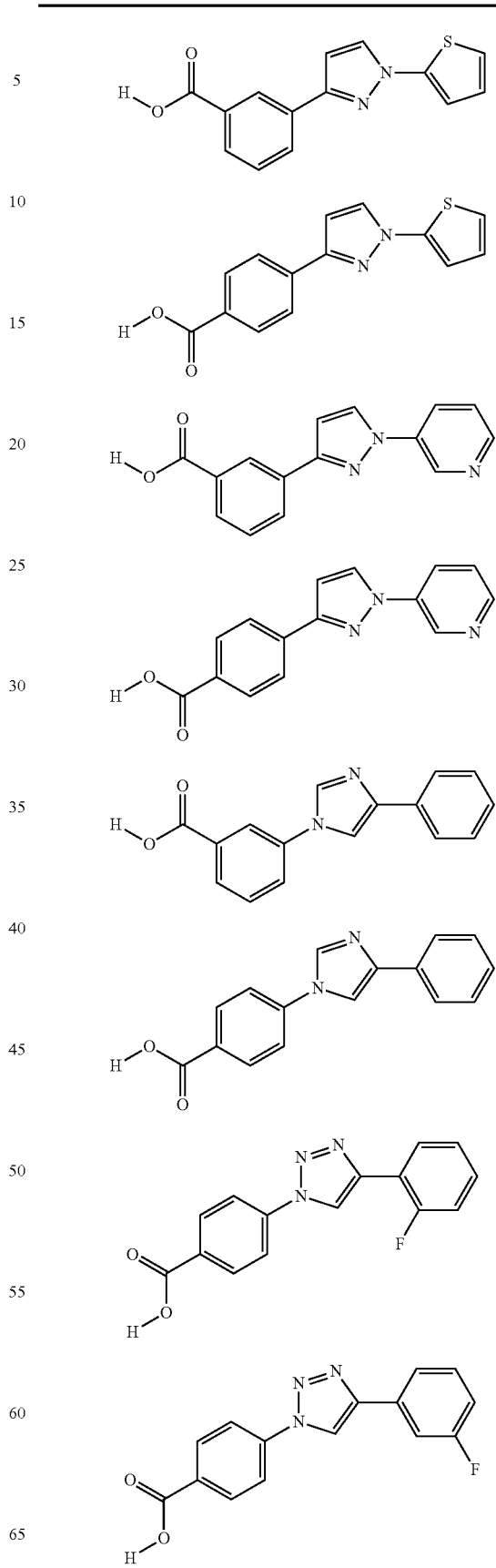

TABLE 7-continued
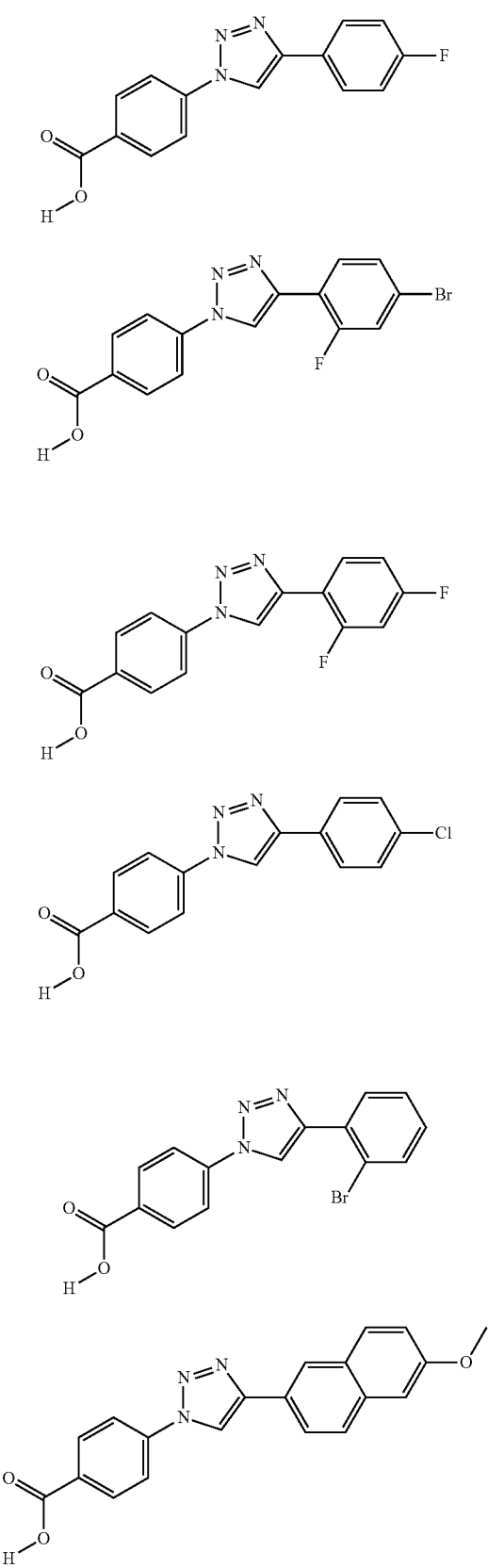
TABLE 7-continued
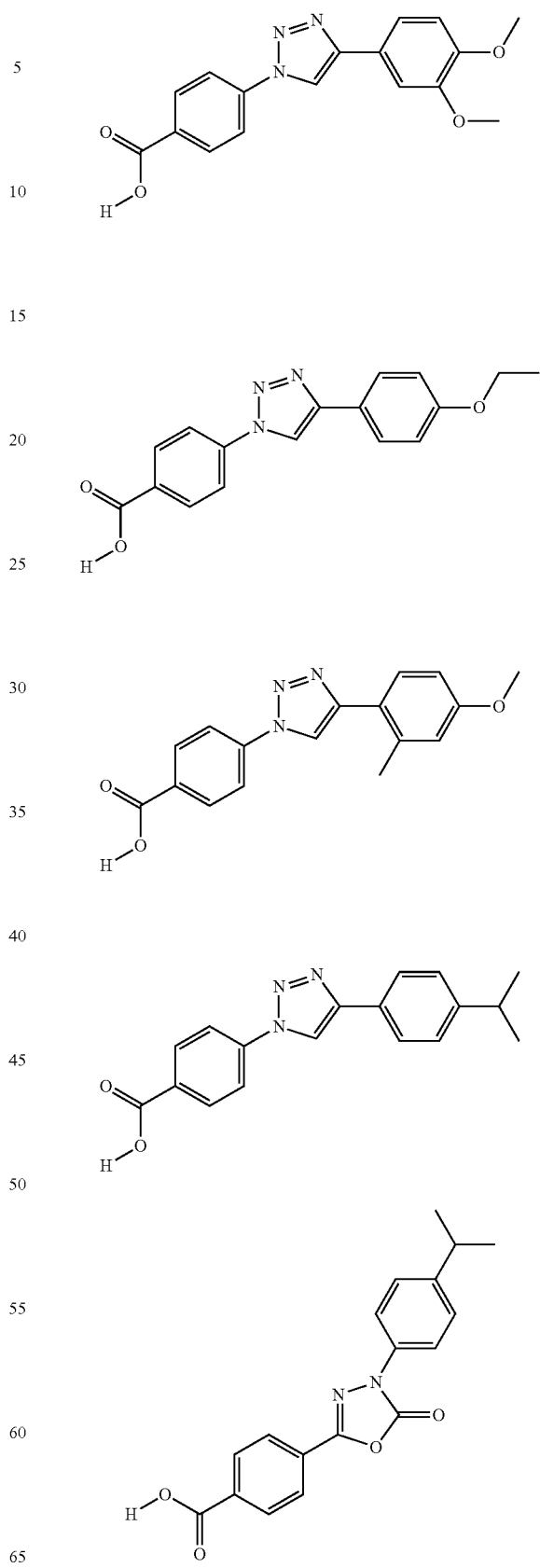

TABLE 7-continued
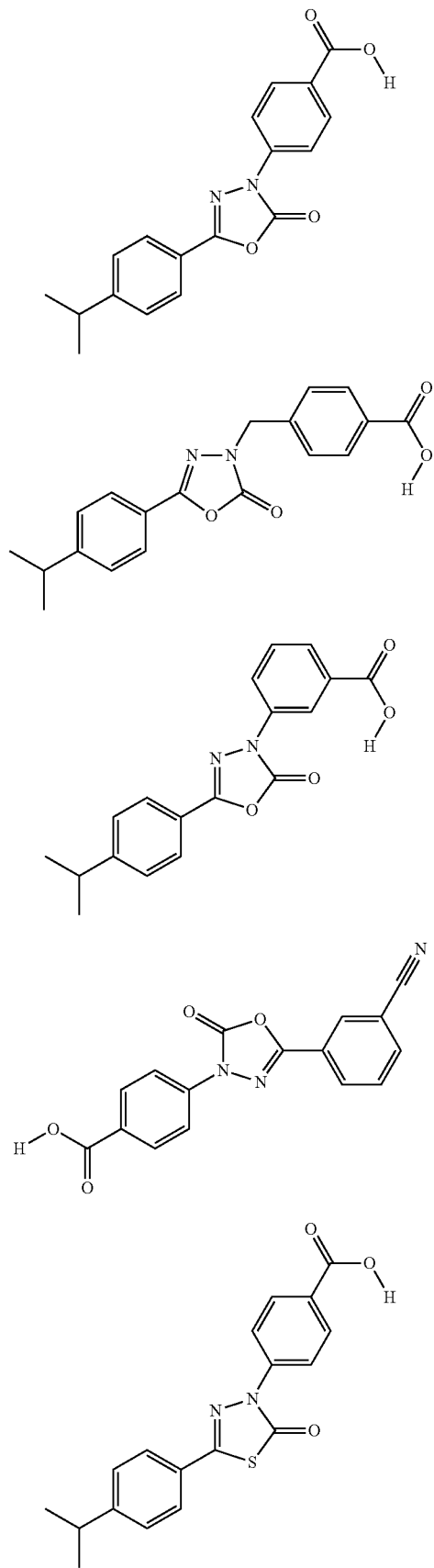
TABLE 7-continued
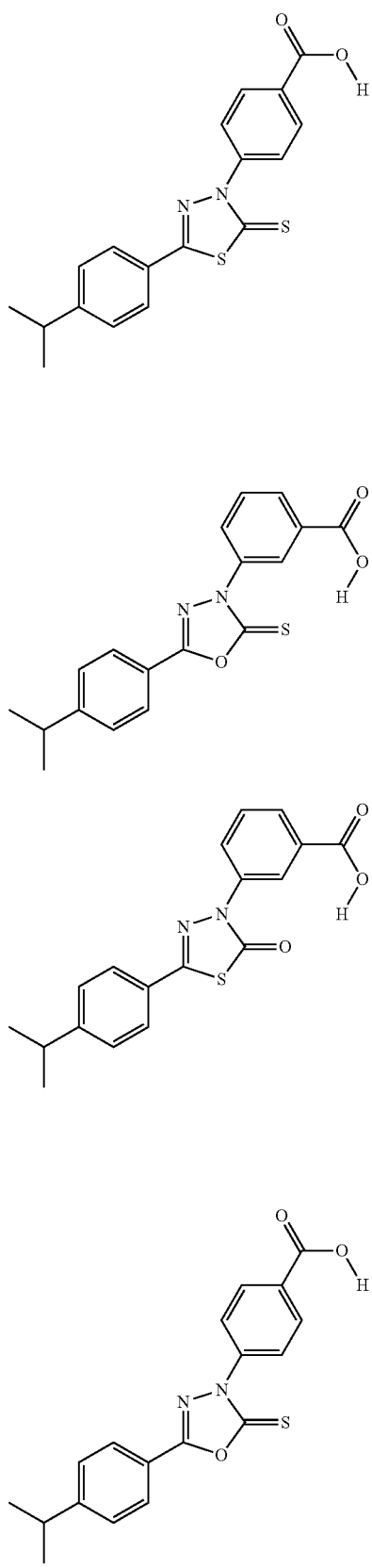

TABLE 7-continued
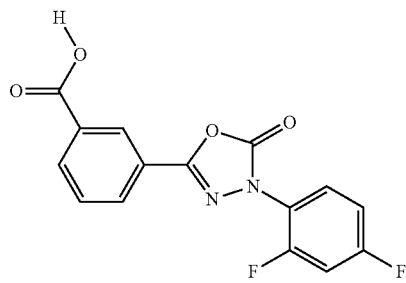 [SMILES: O=C(O)c1cccc(-c2nn(-c3ccc(F)cc3F)c(=O)o2)c1]
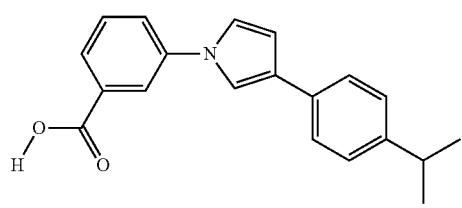 [SMILES: CC(C)c1ccc(-c2ccn(-c3cccc(C(=O)O)c3)c2)cc1]
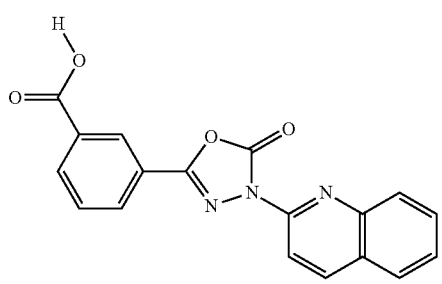 [SMILES: O=C(O)c1cccc(-c2nn(-c3ccc4ccccc4n3)c(=O)o2)c1]
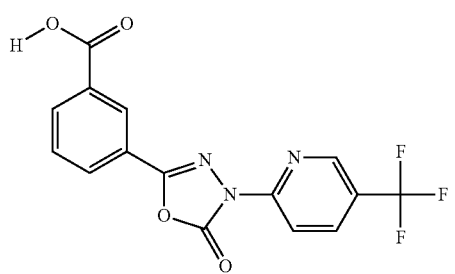 [SMILES: O=C(O)c1cccc(-c2nn(-c3ccc(C(F)(F)F)cn3)c(=O)o2)c1]
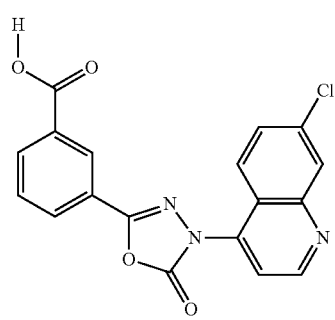 [SMILES: O=C(O)c1cccc(-c2nn(-c3ccnc4cc(Cl)ccc34)c(=O)o2)c1]
TABLE 7-continued
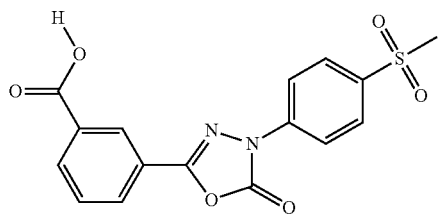 [SMILES: CS(=O)(=O)c1ccc(-n2nc(-c3cccc(C(=O)O)c3)oc2=O)cc1]
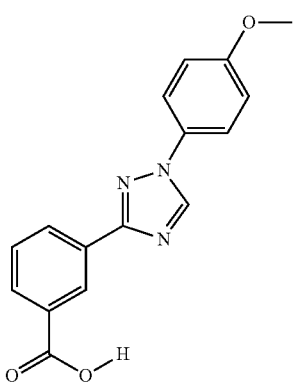 [SMILES: COc1ccc(-n2cnc(-c3cccc(C(=O)O)c3)n2)cc1]
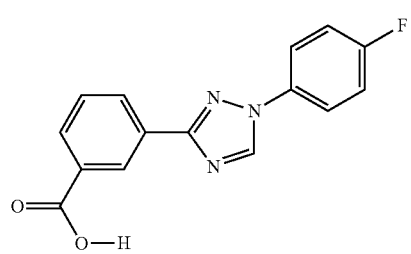 [SMILES: O=C(O)c1cccc(-c2ncn(-c3ccc(F)cc3)n2)c1]
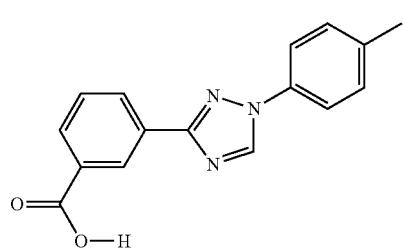 [SMILES: Cc1ccc(-n2cnc(-c3cccc(C(=O)O)c3)n2)cc1]
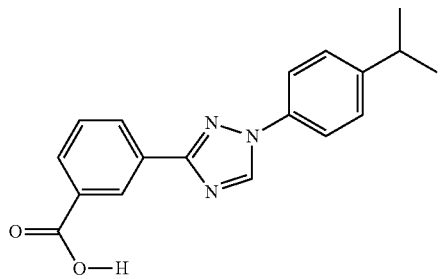 [SMILES: CC(C)c1ccc(-n2cnc(-c3cccc(C(=O)O)c3)n2)cc1]

TABLE 7-continued
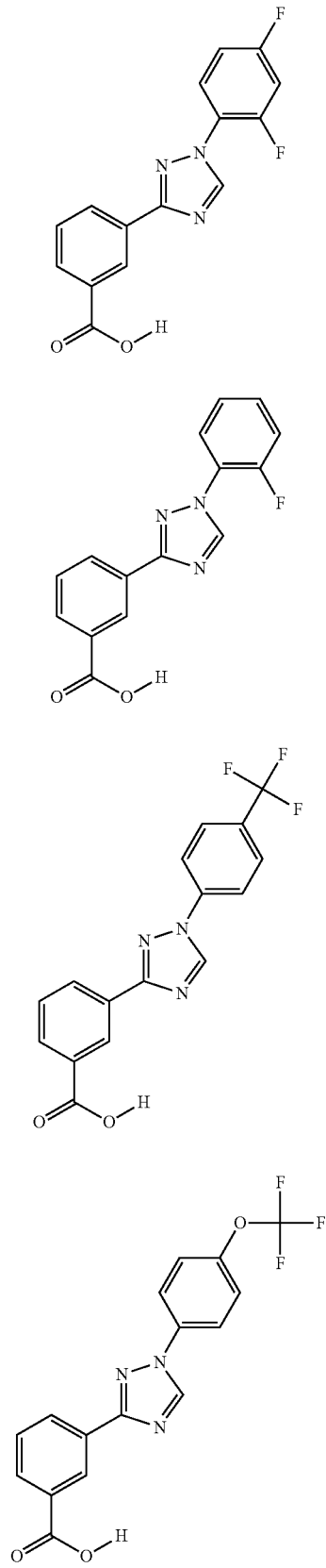
TABLE 7-continued
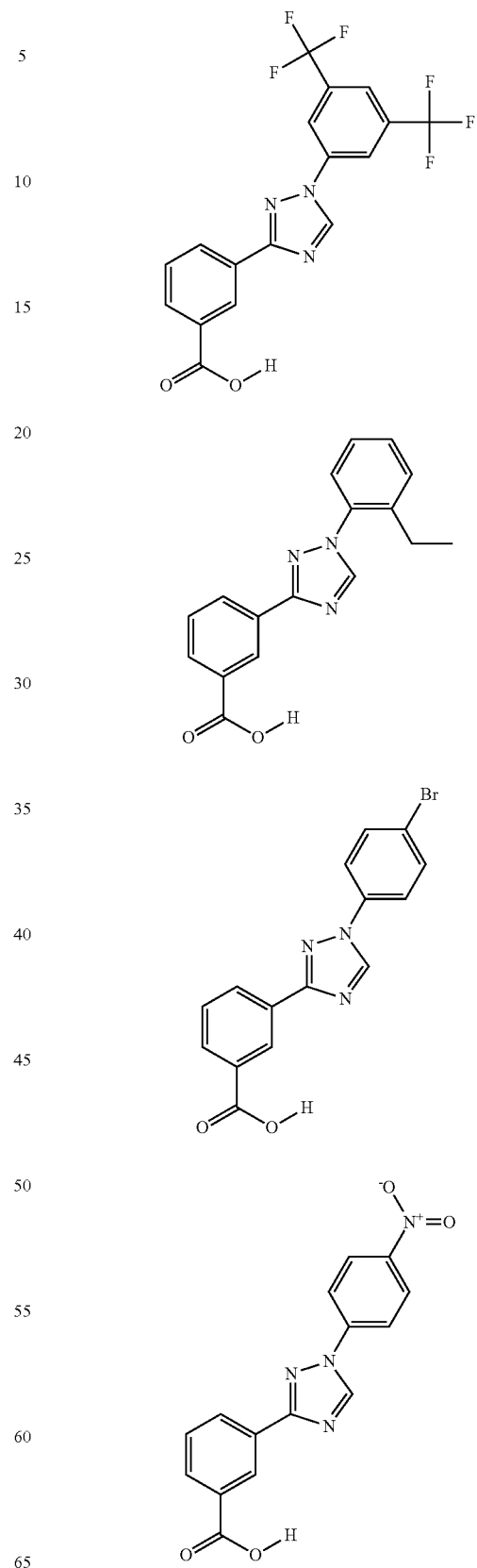

TABLE 7-continued
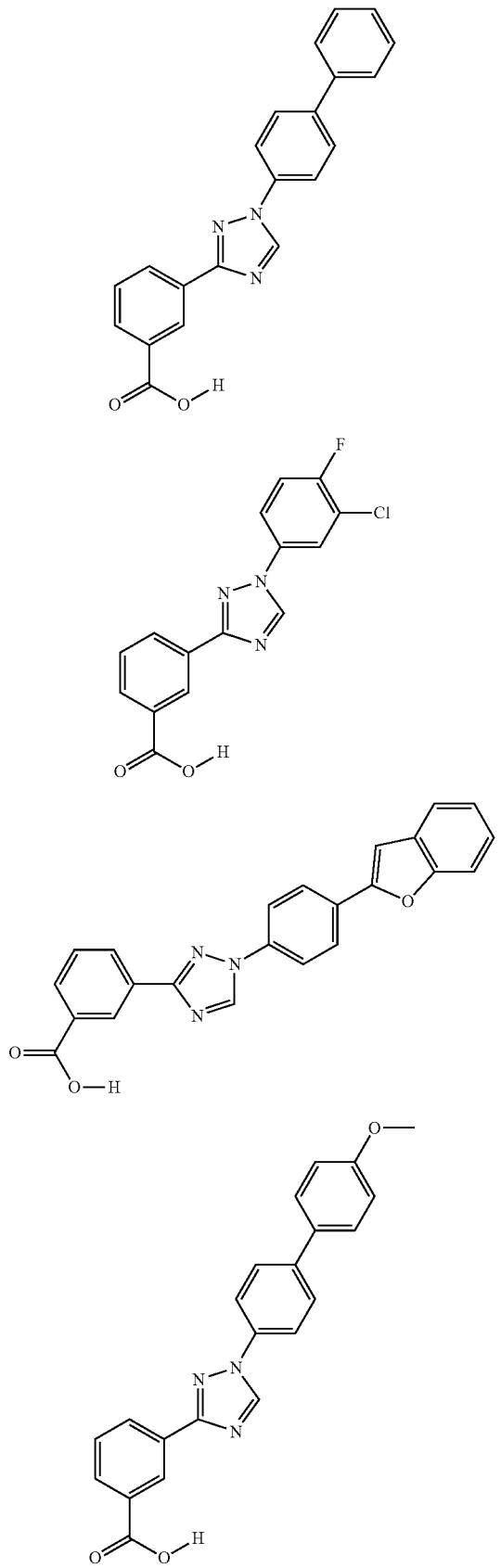
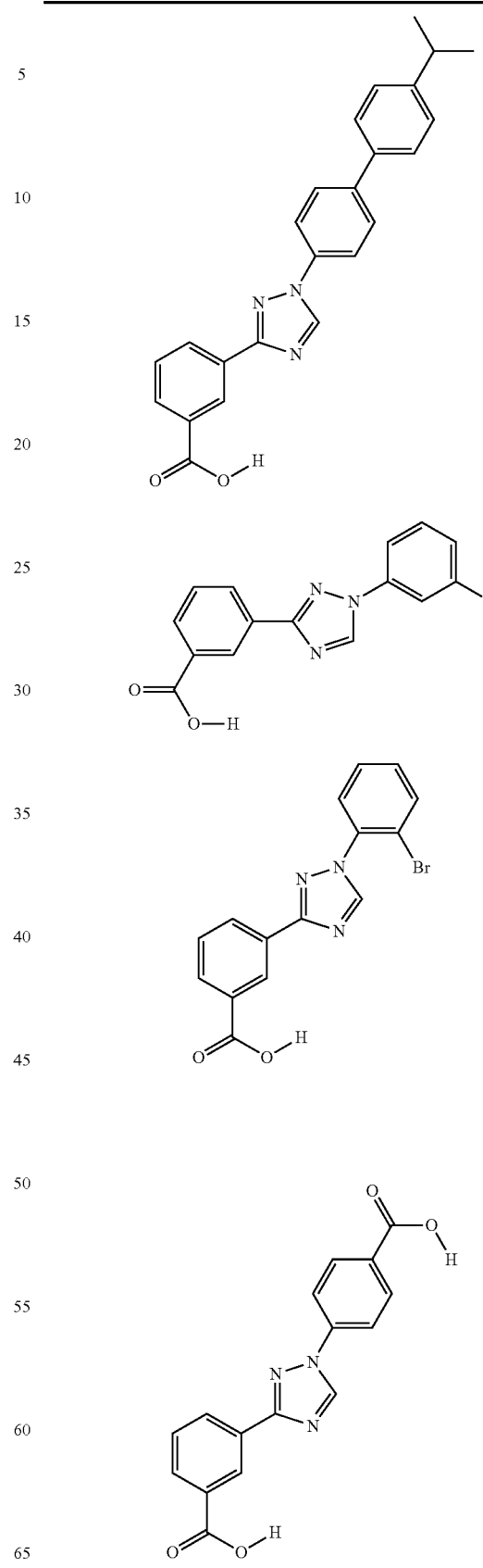

TABLE 7-continued
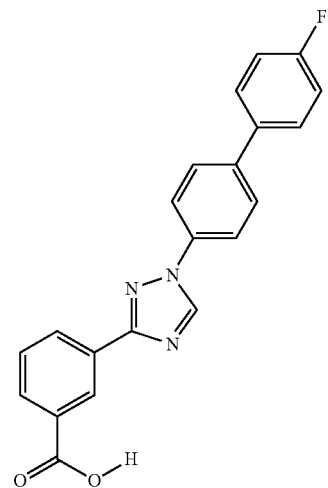
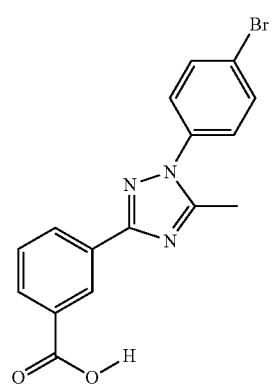
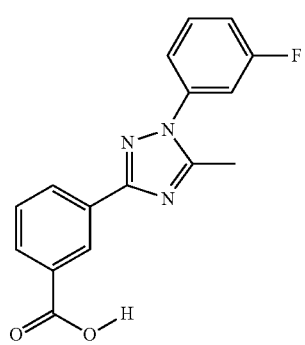 [SMILES: Cc1nc(-c2cccc(C(=O)O)c2)nn1-c1cccc(F)c1]
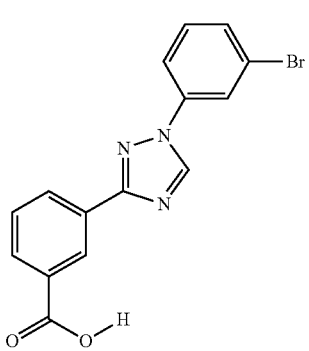 [SMILES: O=C(O)c1cccc(-c2ncn(-c3cccc(Br)c3)n2)c1]
TABLE 7-continued
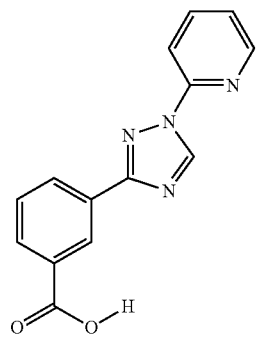 [SMILES: O=C(O)c1cccc(-c2ncn(-c3ccccn3)n2)c1]
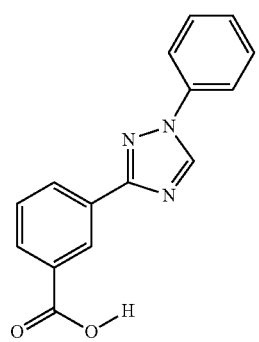 [SMILES: O=C(O)c1cccc(-c2ncn(-c3ccccc3)n2)c1]
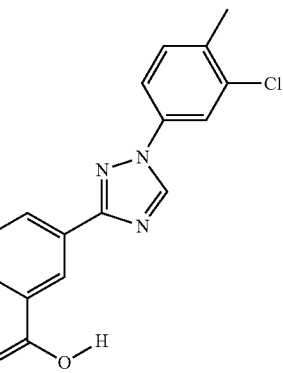
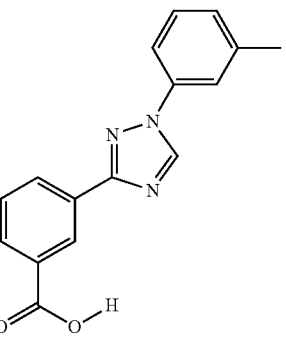

TABLE 7-continued
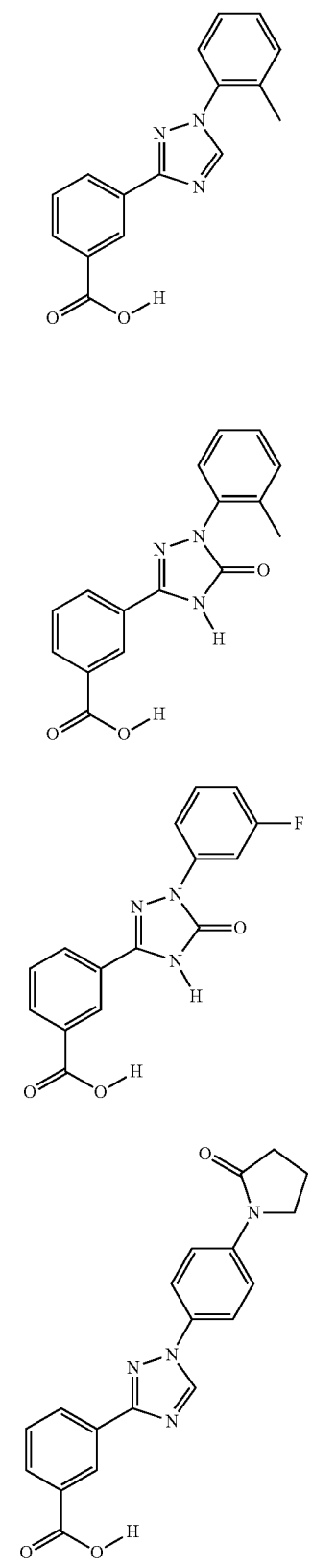
TABLE 7-continued
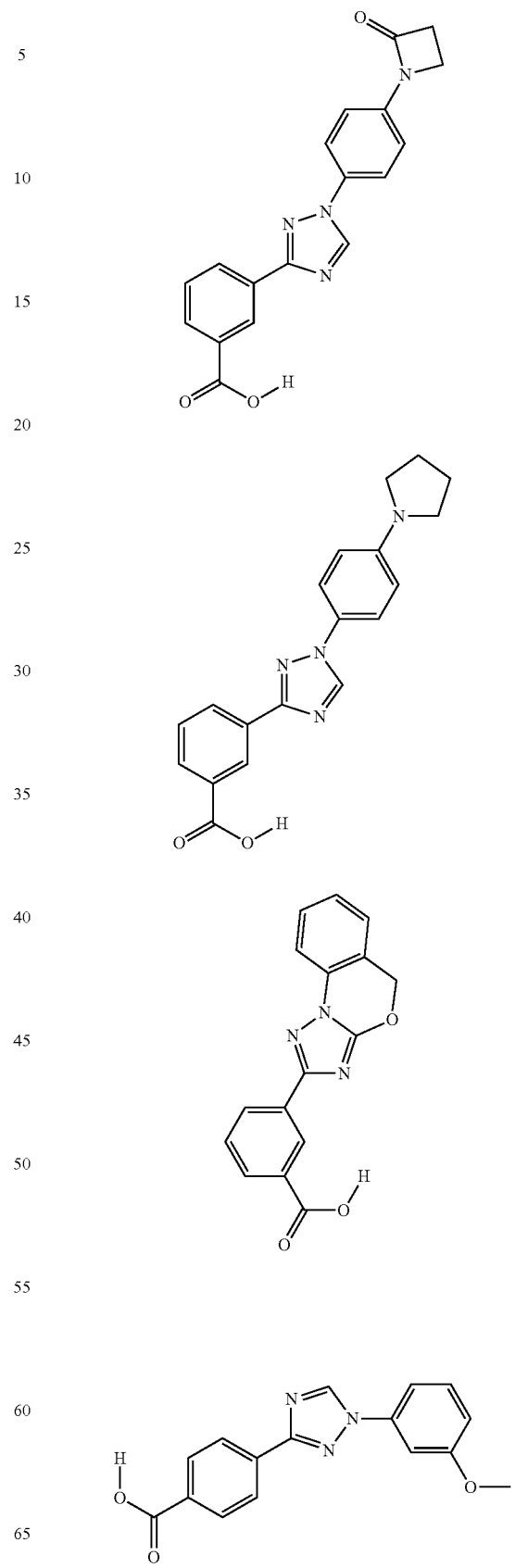

TABLE 7-continued
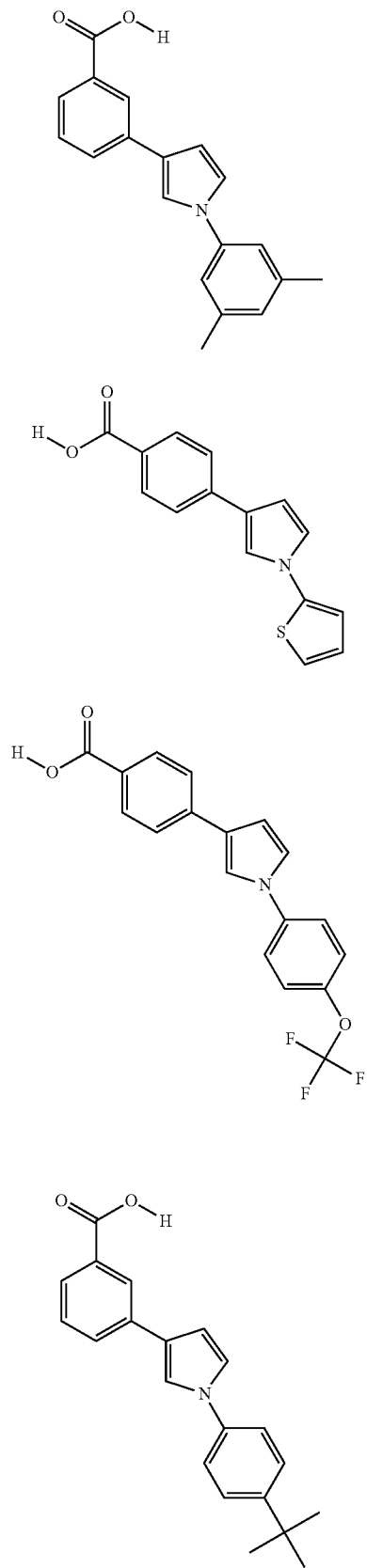
TABLE 7-continued
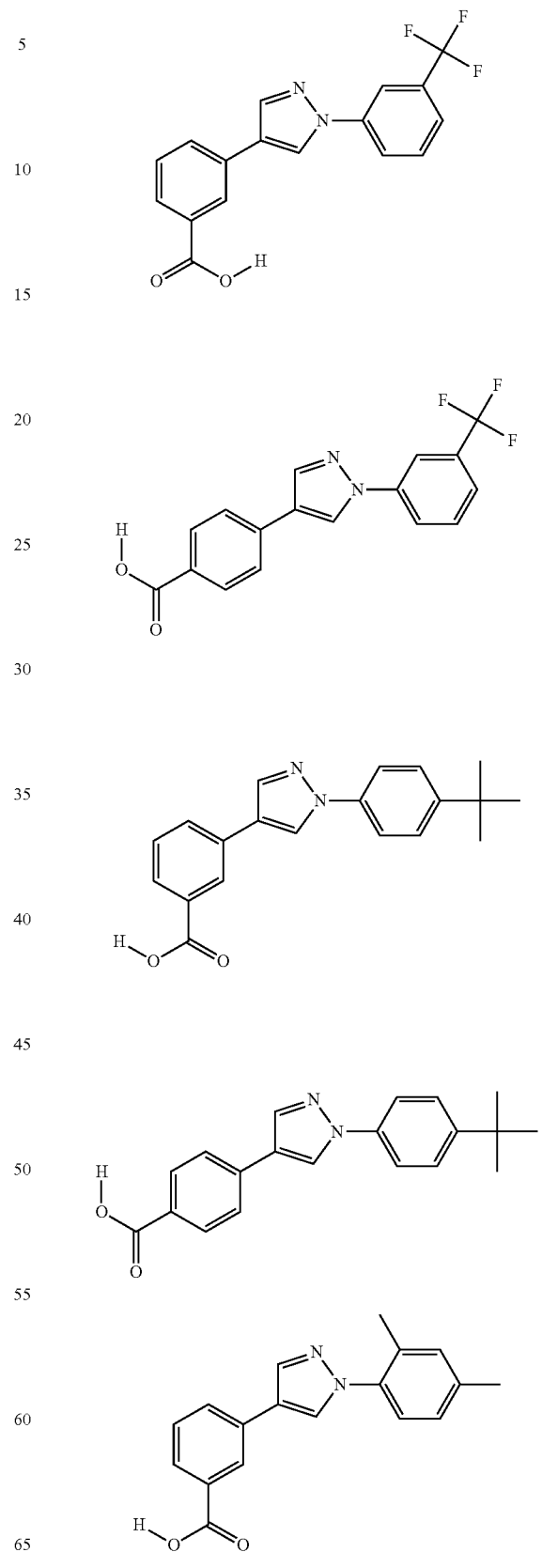

TABLE 7-continued
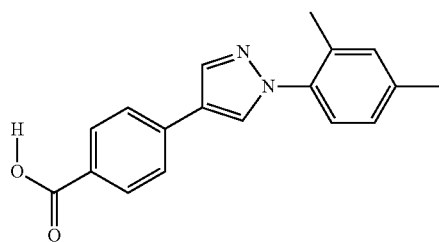 [SMILES: Cc1ccc(-n2cc(-c3ccc(C(=O)O)cc3)cn2)c(C)c1]
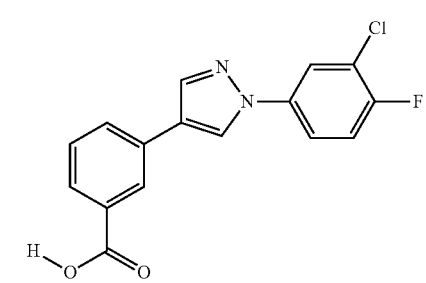 [SMILES: O=C(O)c1cccc(-c2cnn(-c3ccc(F)c(Cl)c3)c2)c1]
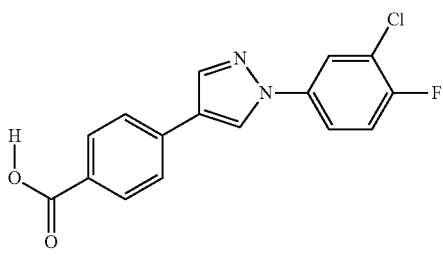 [SMILES: O=C(O)c1ccc(-c2cnn(-c3ccc(F)c(Cl)c3)c2)cc1]
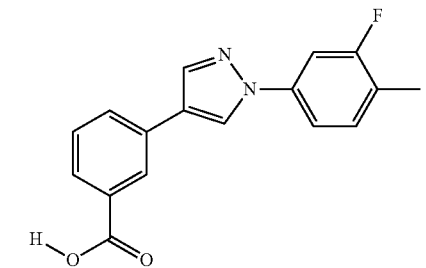 [SMILES: Cc1ccc(-n2cc(-c3cccc(C(=O)O)c3)cn2)cc1F]
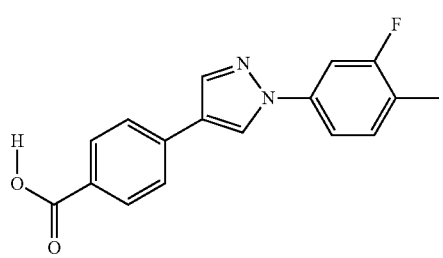 [SMILES: Cc1ccc(-n2cc(-c3ccc(C(=O)O)cc3)cn2)cc1F]
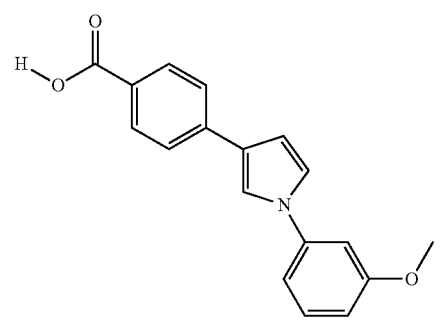 [SMILES: COc1cccc(-n2ccc(-c3ccc(C(=O)O)cc3)c2)c1]
TABLE 7-continued
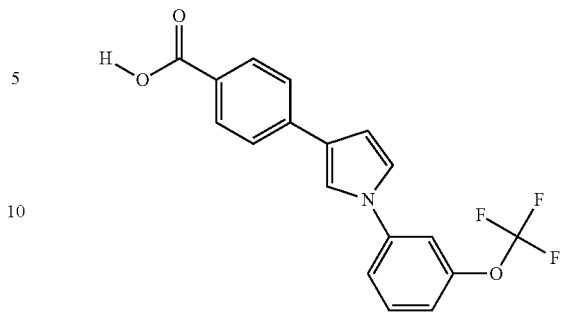
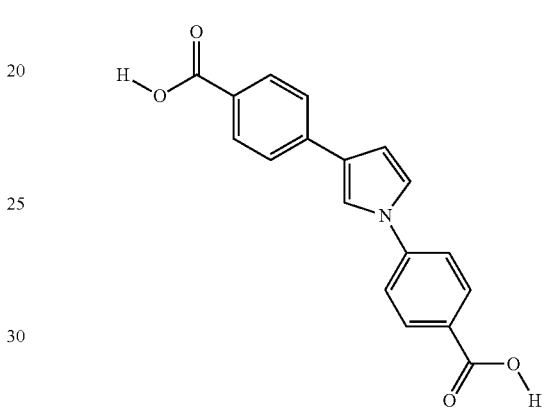
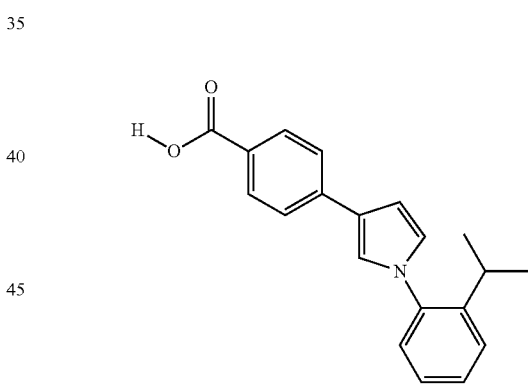
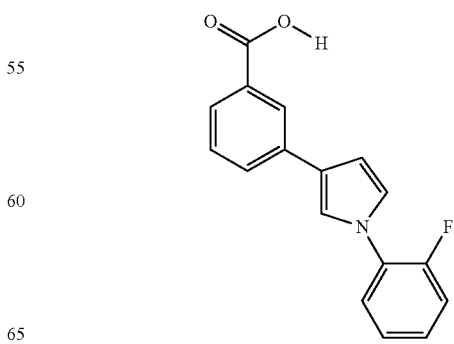

TABLE 7-continued
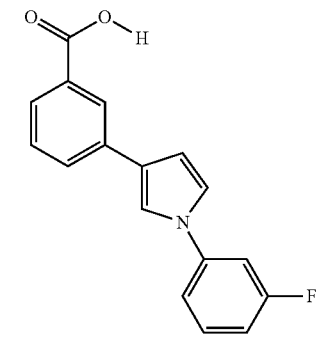 [SMILES: O=C(O)c1cccc(-c2ccn(-c3cccc(F)c3)c2)c1]
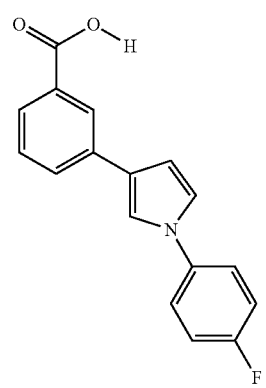 [SMILES: O=C(O)c1cccc(-c2ccn(-c3ccc(F)cc3)c2)c1]
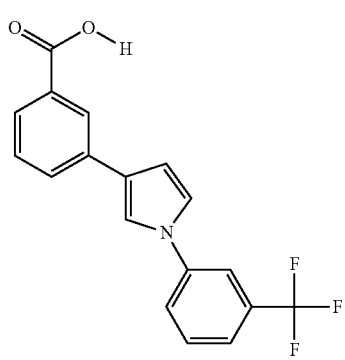 [SMILES: O=C(O)c1cccc(-c2ccn(-c3cccc(C(F)(F)F)c3)c2)c1]
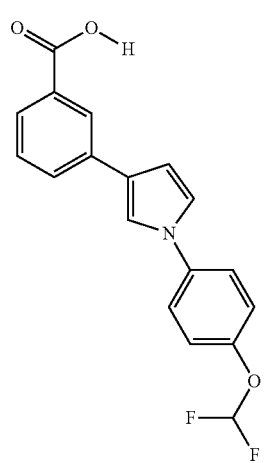 [SMILES: O=C(O)c1cccc(-c2ccn(-c3ccc(OC(F)F)cc3)c2)c1]
TABLE 7-continued
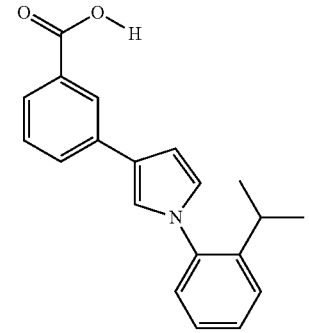 [SMILES: CC(C)c1ccccc1-n1ccc(-c2cccc(C(=O)O)c2)c1]
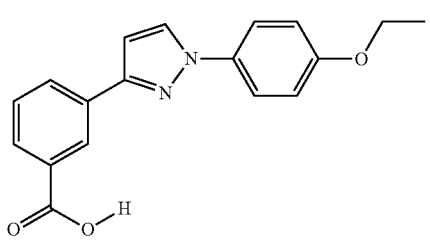 [SMILES: CCOc1ccc(-n2ccc(-c3cccc(C(=O)O)c3)n2)cc1]
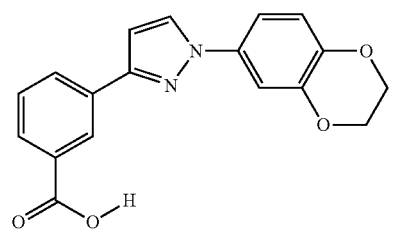 [SMILES: O=C(O)c1cccc(-c2ccn(-c3ccc4c(c3)OCCO4)n2)c1]
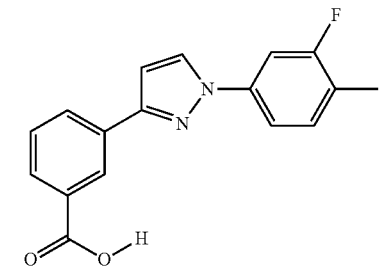 [SMILES: Cc1ccc(-n2ccc(-c3cccc(C(=O)O)c3)n2)cc1F]
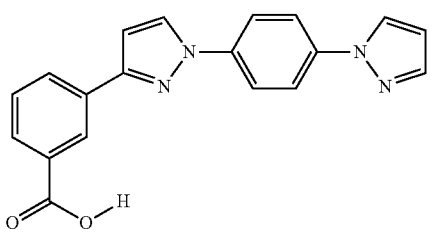 [SMILES: O=C(O)c1cccc(-c2ccn(-c3ccc(-n4cccn4)cc3)n2)c1]
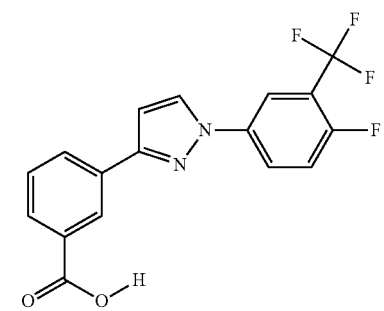 [SMILES: O=C(O)c1cccc(-c2ccn(-c3ccc(F)c(C(F)(F)F)c3)n2)c1]

TABLE 7-continued
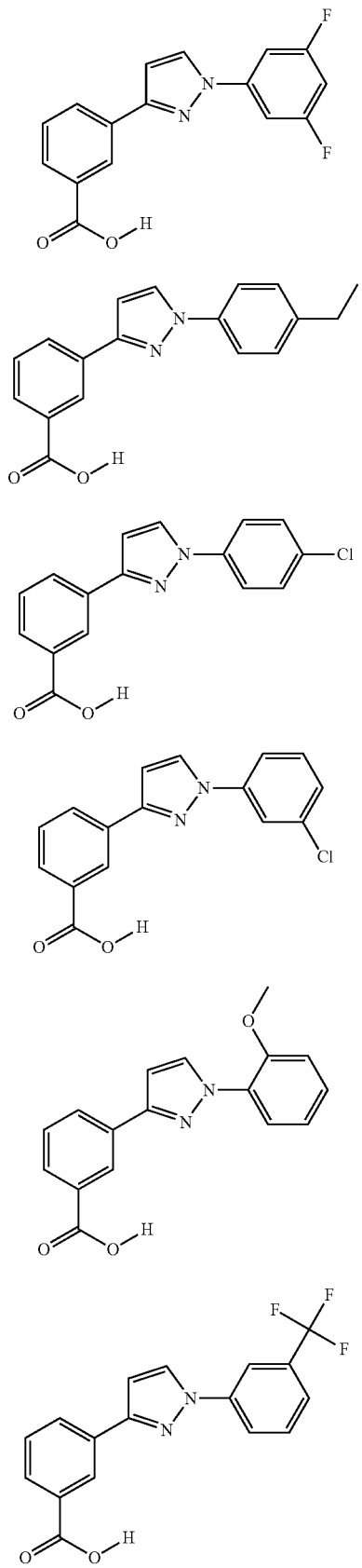
TABLE 7-continued
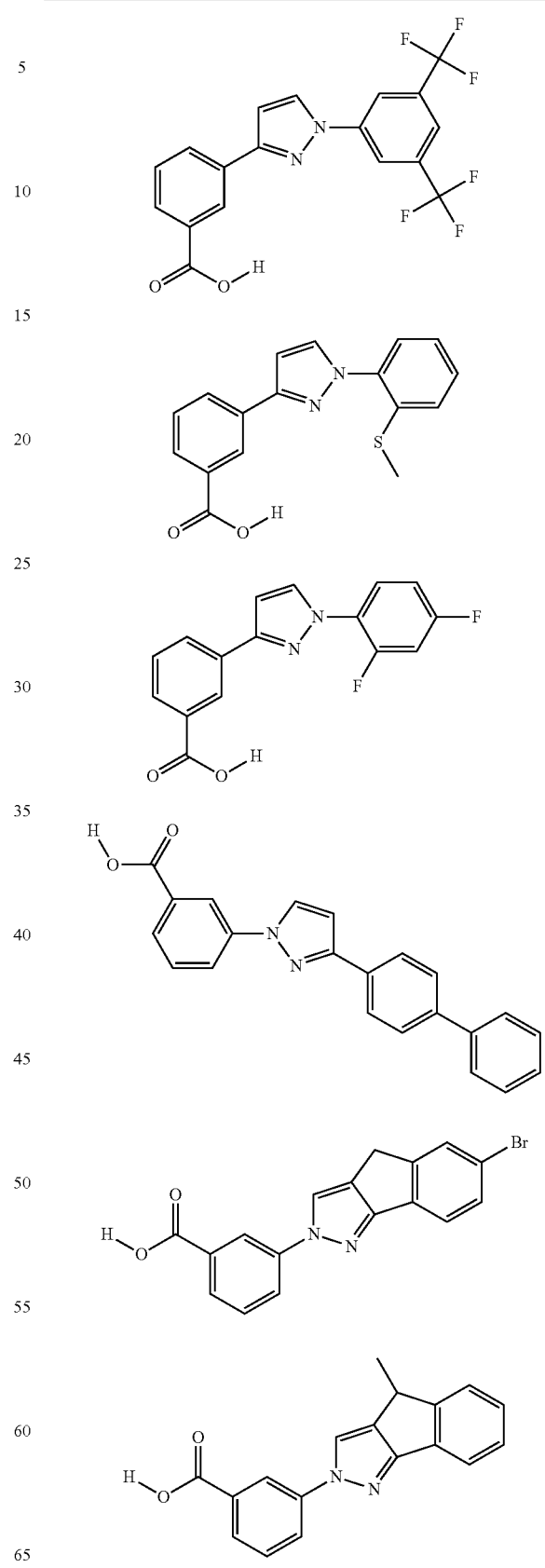

TABLE 7-continued
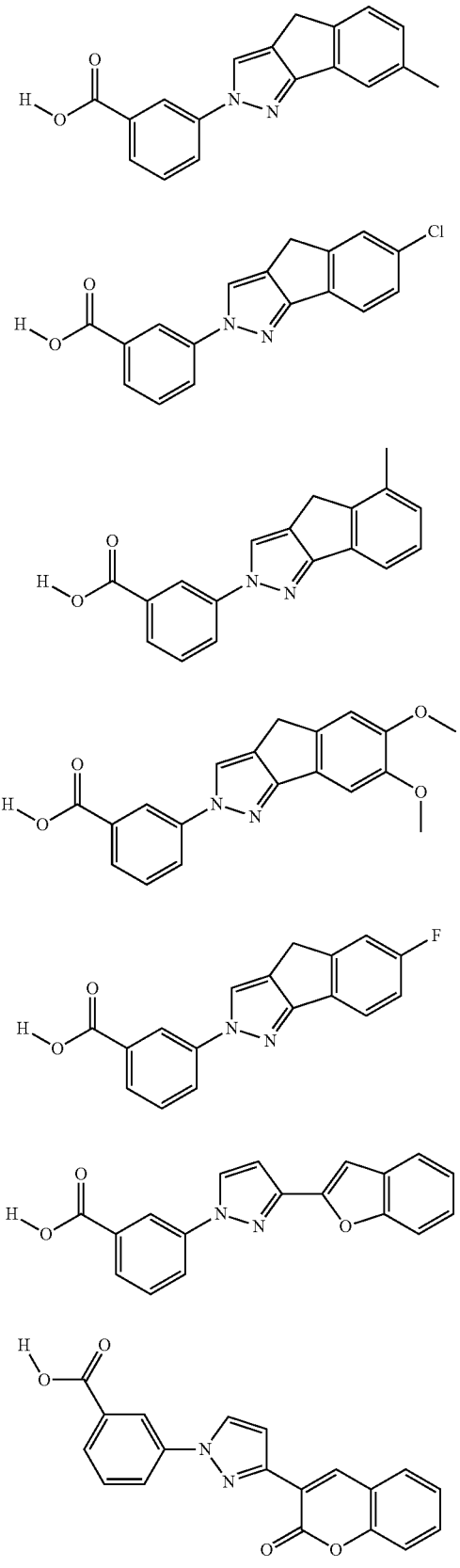
TABLE 7-continued
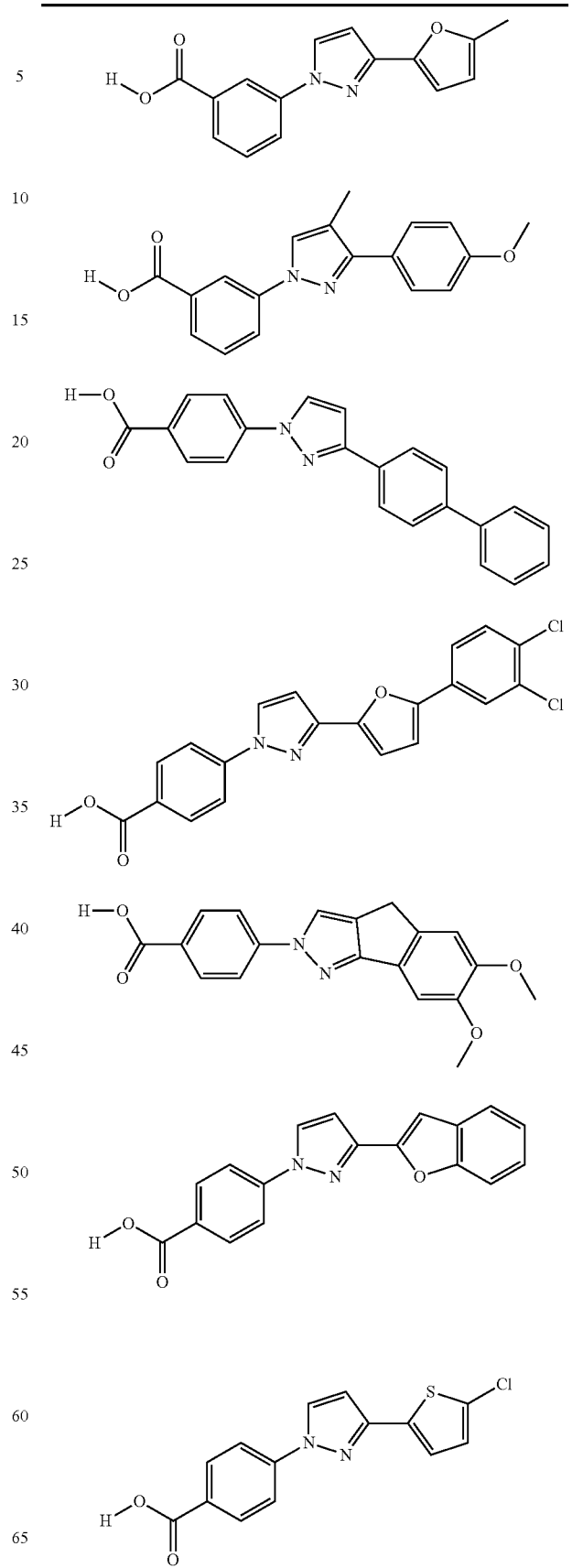

TABLE 7-continued
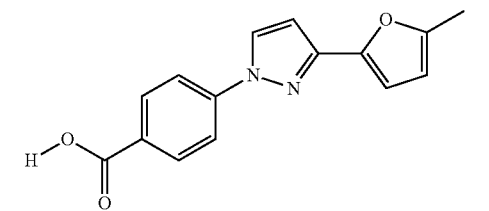 [SMILES: Cc1ccc(-c2ccn(-c3ccc(C(=O)O)cc3)n2)o1]
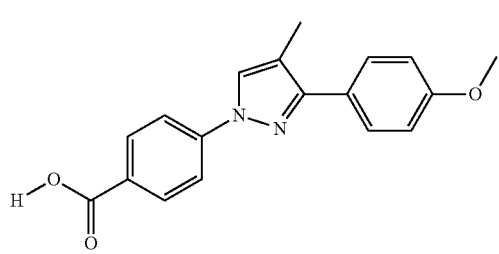 [SMILES: COc1ccc(-c2nn(-c3ccc(C(=O)O)cc3)cc2C)cc1]
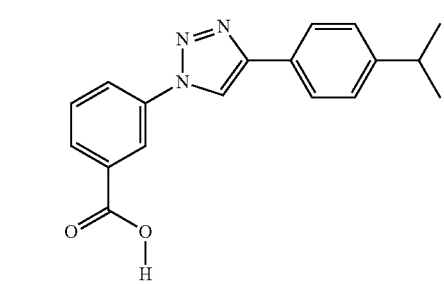 [SMILES: CC(C)c1ccc(-c2cn(-c3cccc(C(=O)O)c3)nn2)cc1]
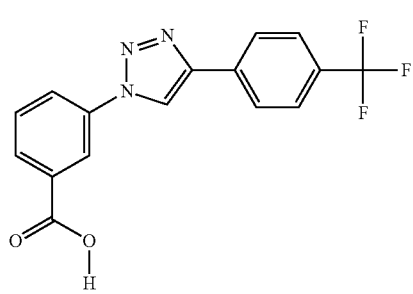 [SMILES: O=C(O)c1cccc(-n2cc(-c3ccc(C(F)(F)F)cc3)nn2)c1]
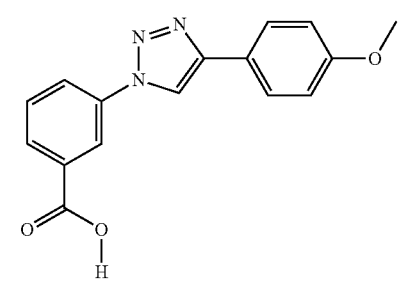
TABLE 7-continued
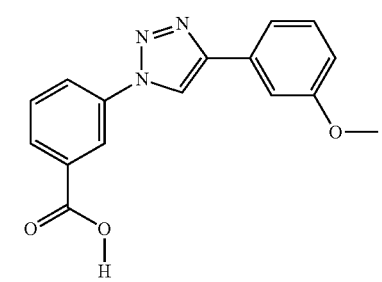 [SMILES: COc1cccc(-c2cn(-c3cccc(C(=O)O)c3)nn2)c1]
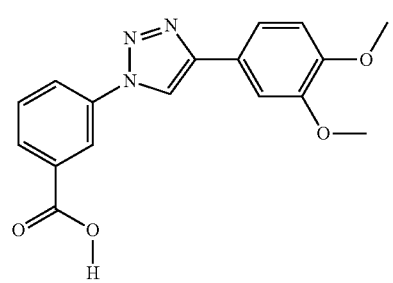 [SMILES: COc1ccc(-c2cn(-c3cccc(C(=O)O)c3)nn2)cc1OC]
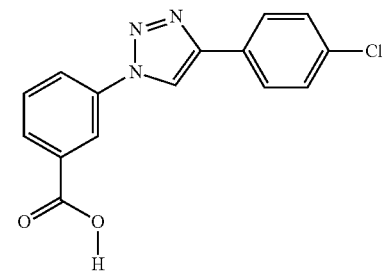 [SMILES: O=C(O)c1cccc(-n2cc(-c3ccc(Cl)cc3)nn2)c1]
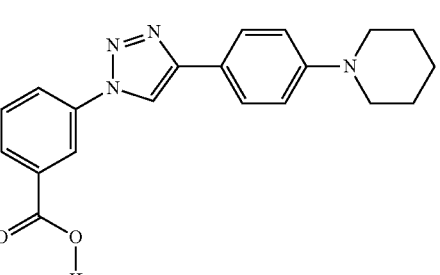
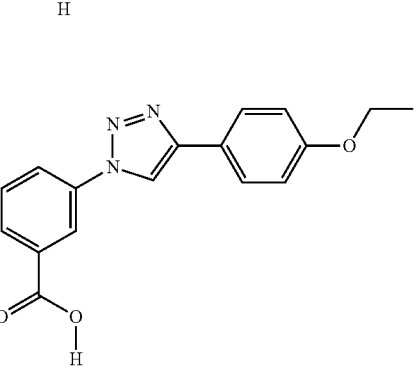

TABLE 7-continued
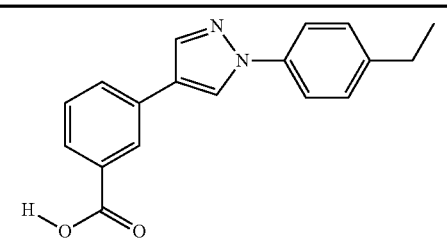
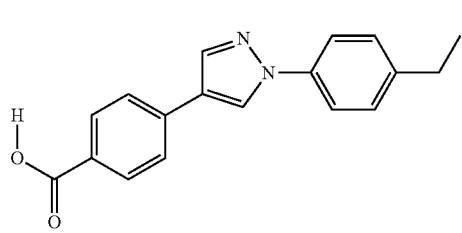 [SMILES: CCc1ccc(-n2cc(-c3ccc(C(=O)O)cc3)cn2)cc1]
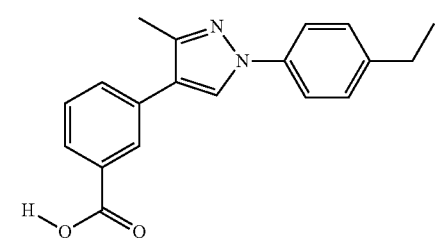 [SMILES: CCc1ccc(-n2cc(-c3cccc(C(=O)O)c3)c(C)n2)cc1]
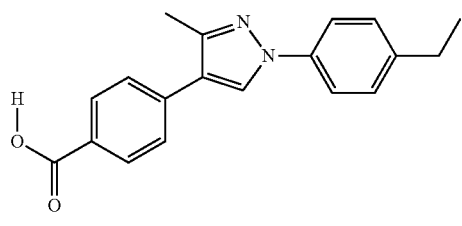 [SMILES: CCc1ccc(-n2cc(-c3ccc(C(=O)O)cc3)c(C)n2)cc1]
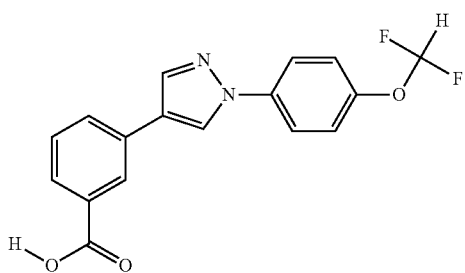
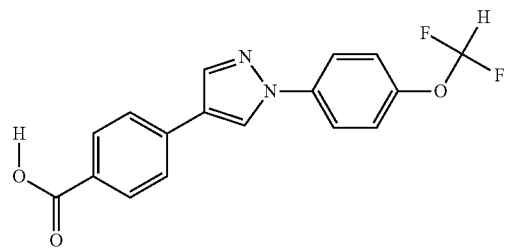 [SMILES: O=C(O)c1ccc(-c2cnn(-c3ccc(OC(F)F)cc3)c2)cc1]
TABLE 7-continued
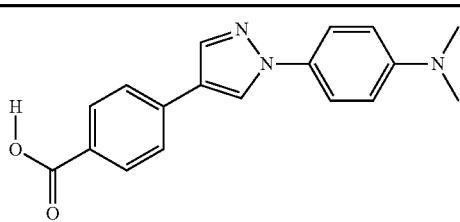
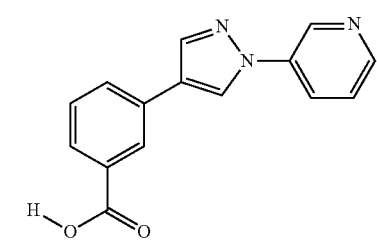 [SMILES: O=C(O)c1cccc(-c2cnn(-c3cccnc3)c2)c1]
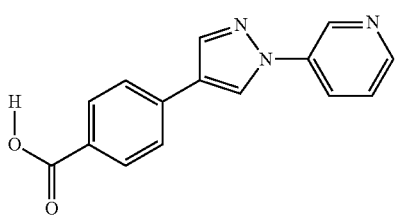 [SMILES: O=C(O)c1ccc(-c2cnn(-c3cccnc3)c2)cc1]
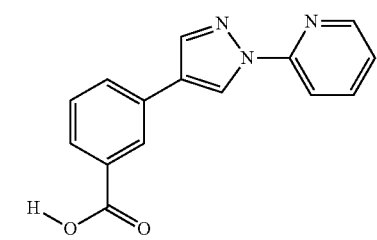 [SMILES: O=C(O)c1cccc(-c2cnn(-c3ccccn3)c2)c1]
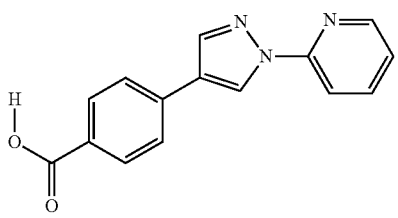 [SMILES: O=C(O)c1ccc(-c2cnn(-c3ccccn3)c2)cc1]
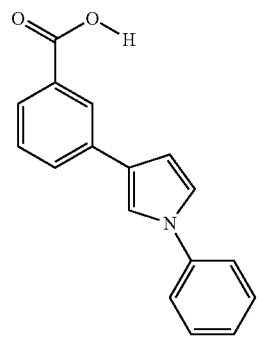 [SMILES: O=C(O)c1cccc(-c2ccn(-c3ccccc3)c2)c1]

TABLE 7-continued
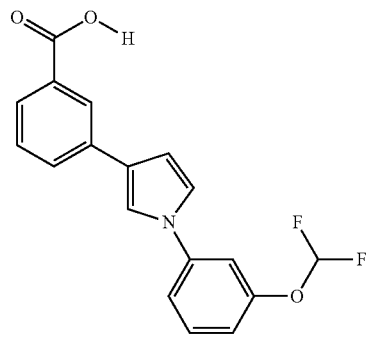 [SMILES: O=C(O)c1cccc(-c2ccn(-c3cccc(OC(F)F)c3)c2)c1]
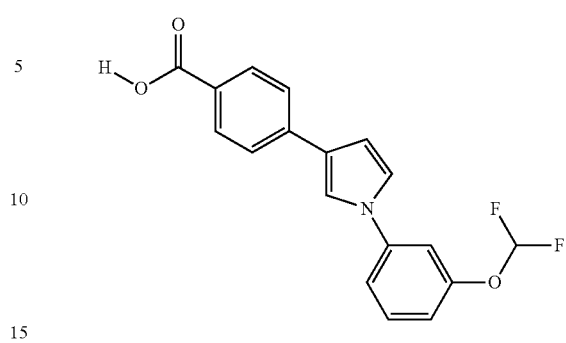
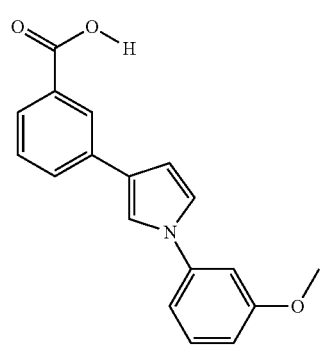 [SMILES: COc1cccc(-n2ccc(-c3cccc(C(=O)O)c3)c2)c1]
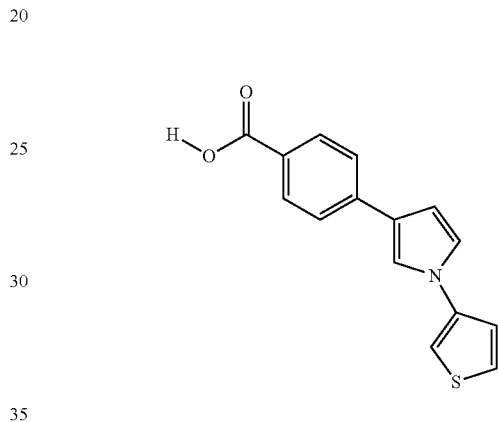
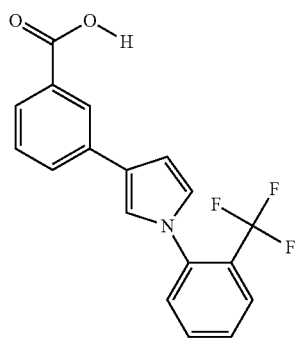 [SMILES: O=C(O)c1cccc(-c2ccn(-c3ccccc3C(F)(F)F)c2)c1]
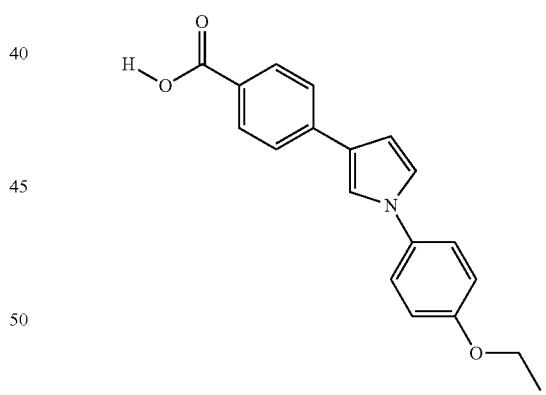
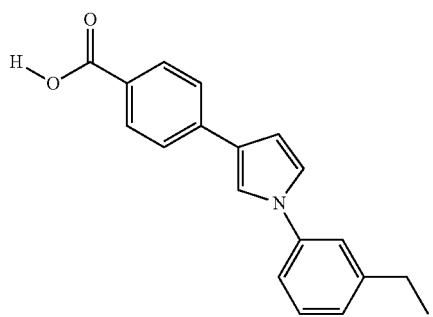 [SMILES: CCc1cccc(-n2ccc(-c3ccc(C(=O)O)cc3)c2)c1]
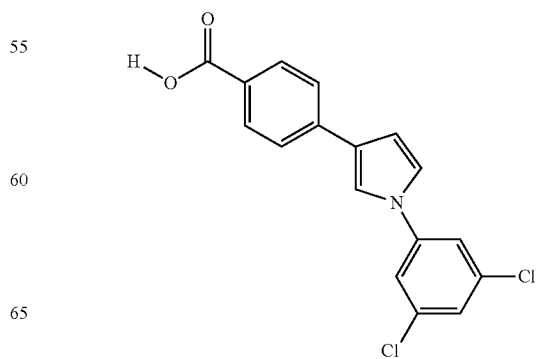

TABLE 7-continued
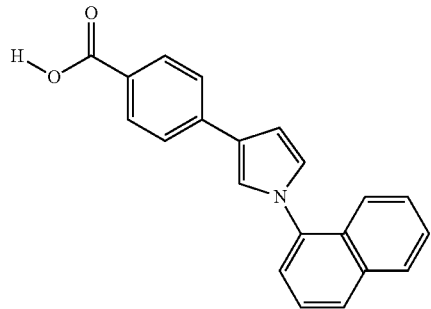 [SMILES: O=C(O)c1ccc(-c2ccn(-c3cccc4ccccc34)c2)cc1]
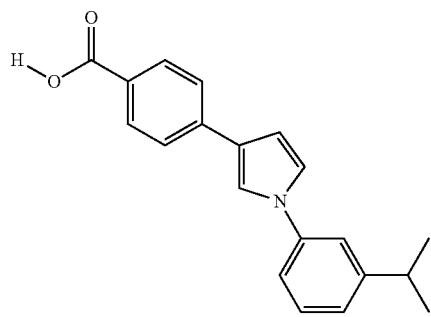 [SMILES: CC(C)c1cccc(-n2ccc(-c3ccc(C(=O)O)cc3)c2)c1]
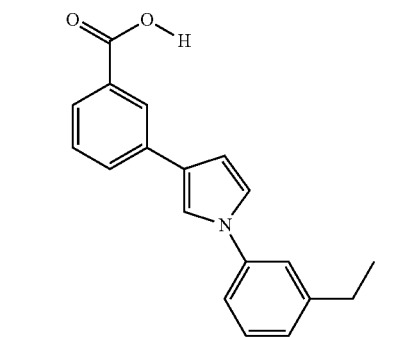
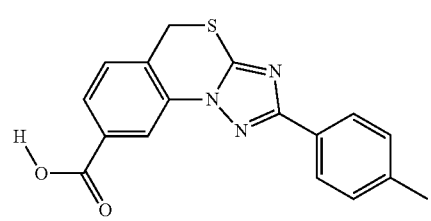 [SMILES: Cc1ccc(-c2nc3n(n2)-c2cc(C(=O)O)ccc2CS3)cc1]
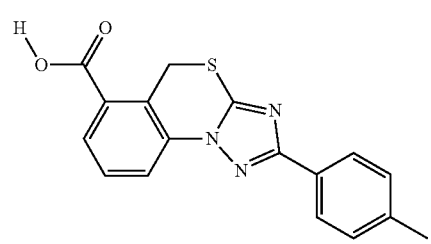 [SMILES: Cc1ccc(-c2nc3n(n2)-c2cccc(C(=O)O)c2CS3)cc1]
TABLE 7-continued
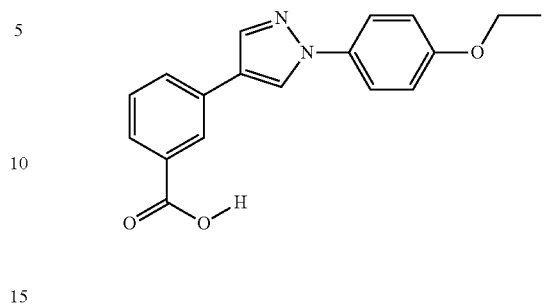
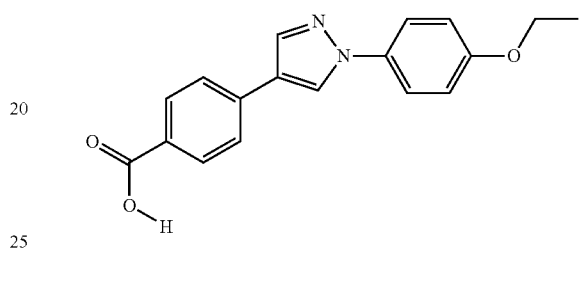
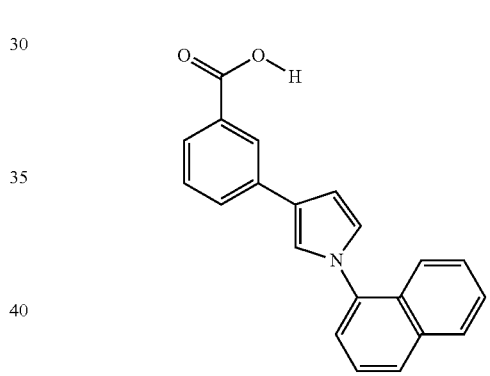
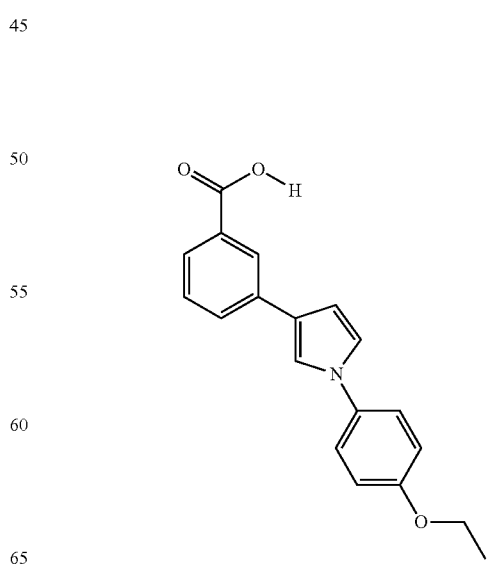

TABLE 7-continued
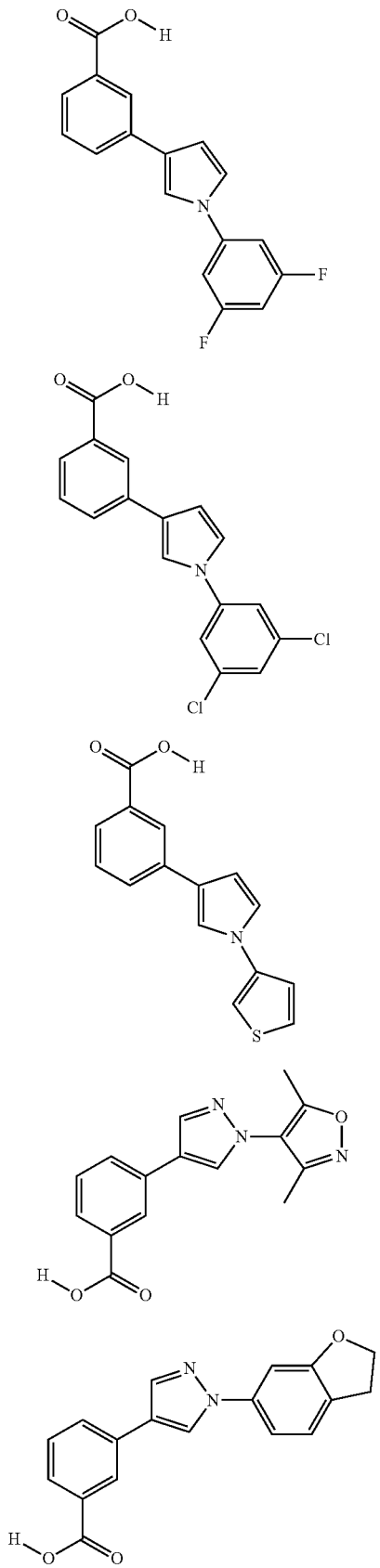
TABLE 7-continued
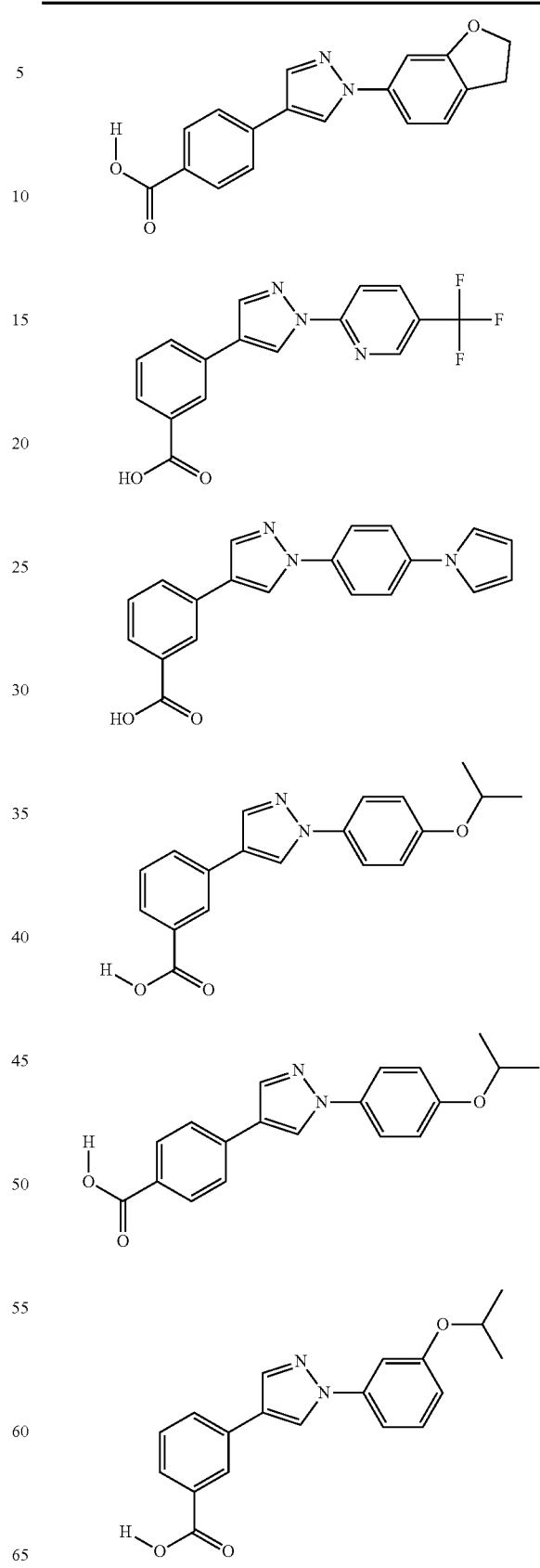

TABLE 7-continued
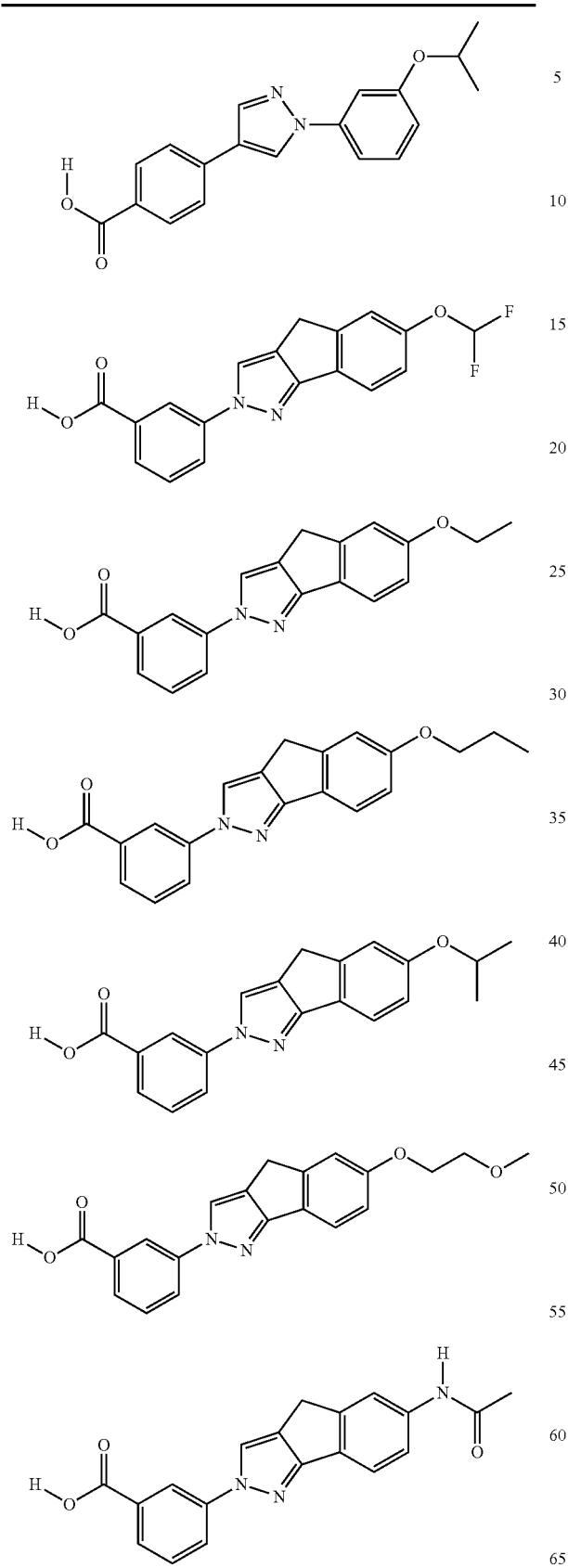
TABLE 7-continued
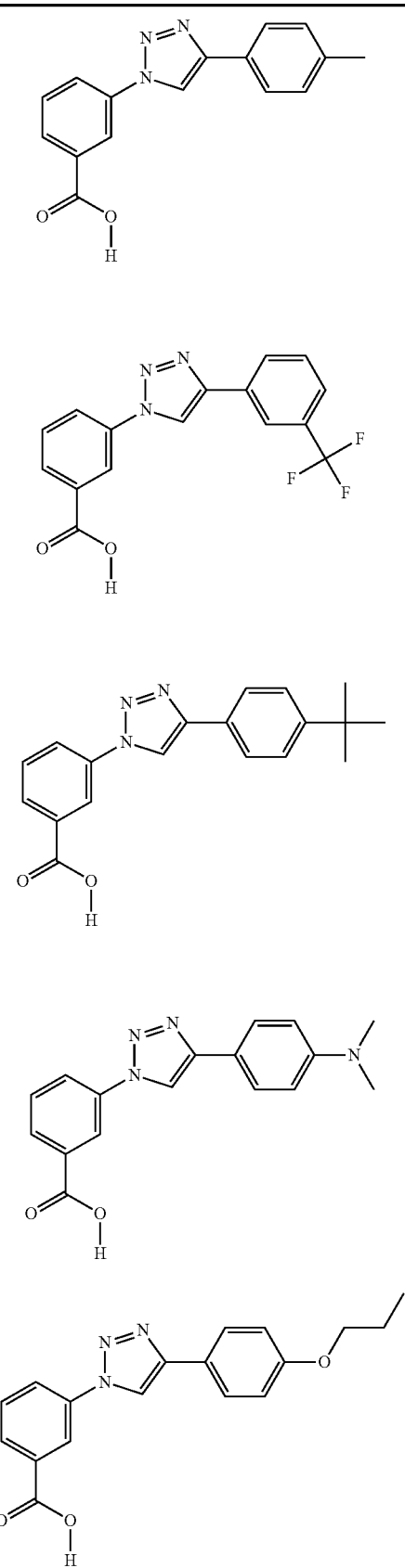

TABLE 7-continued
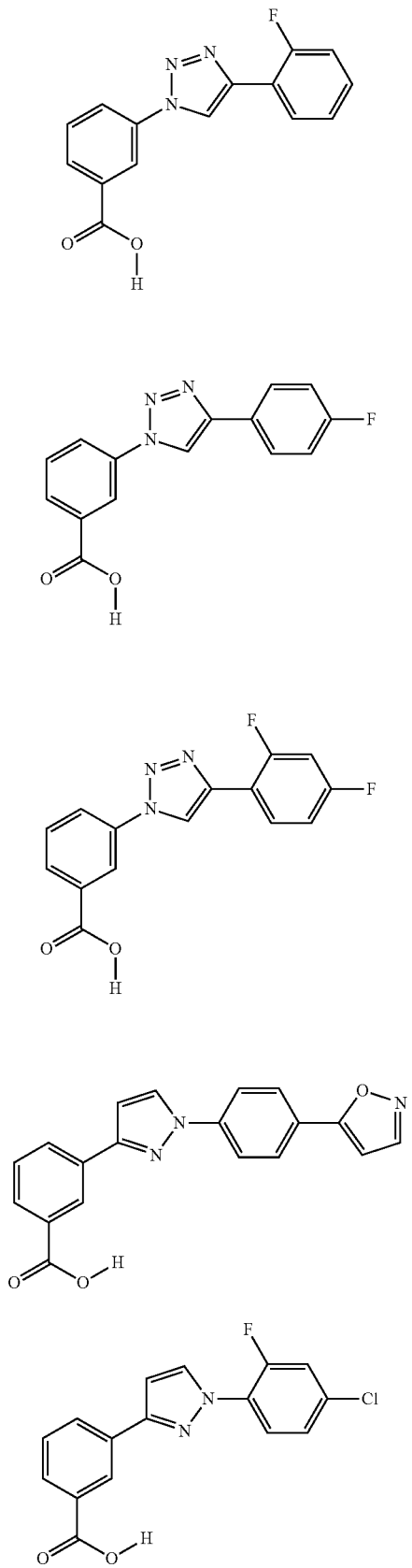
TABLE 7-continued
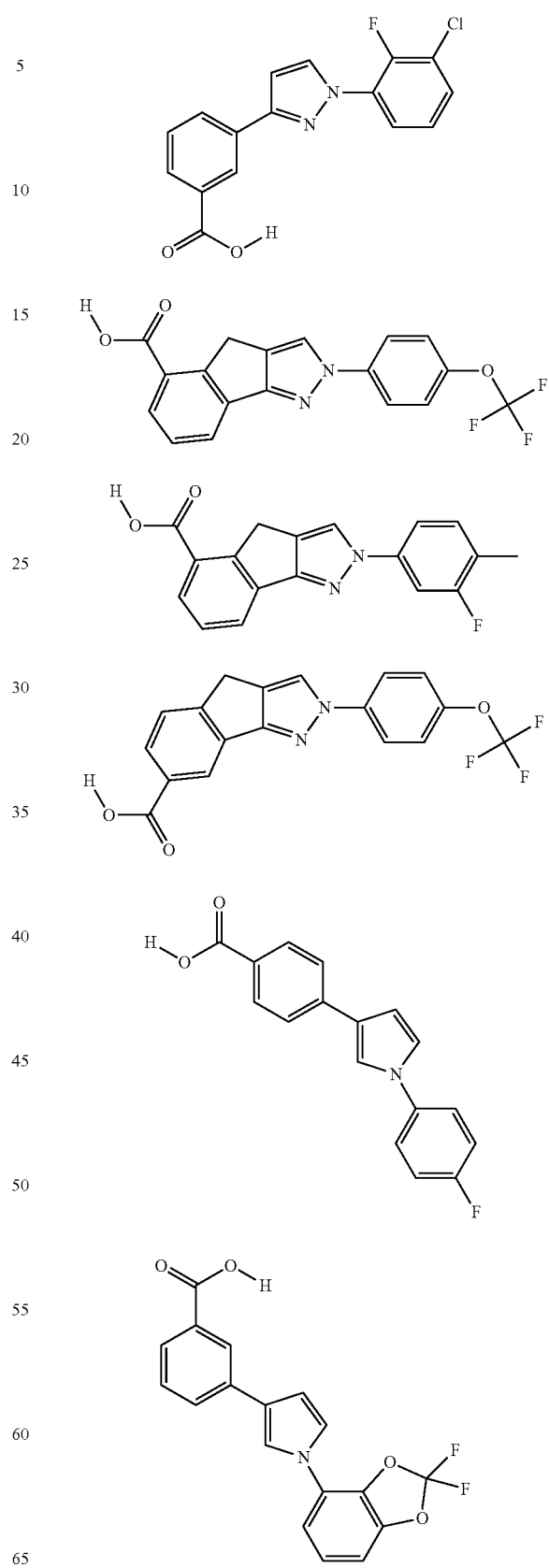

TABLE 7-continued
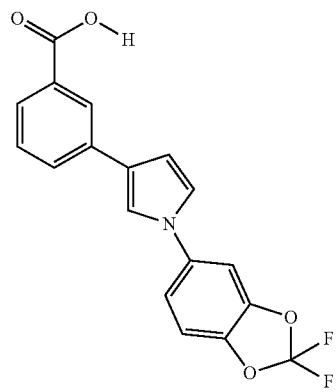 [SMILES: O=C(O)c1cccc(-c2ccn(-c3ccc4c(c3)OC(F)(F)O4)c2)c1]
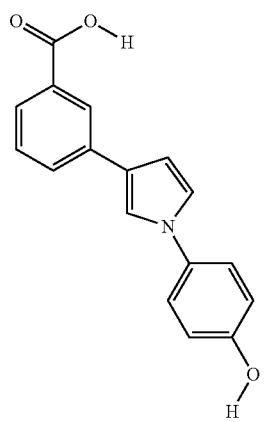 [SMILES: O=C(O)c1cccc(-c2ccn(-c3ccc(O)cc3)c2)c1]
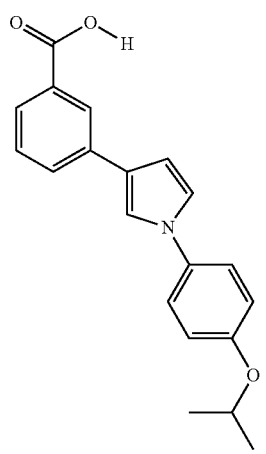 [SMILES: CC(C)Oc1ccc(-n2ccc(-c3cccc(C(=O)O)c3)c2)cc1]
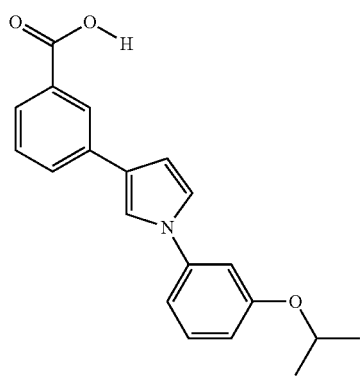 [SMILES: CC(C)Oc1cccc(-n2ccc(-c3cccc(C(=O)O)c3)c2)c1]
TABLE 7-continued
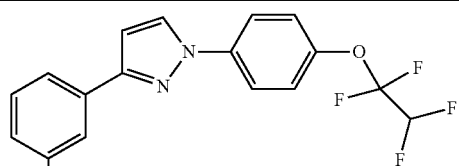
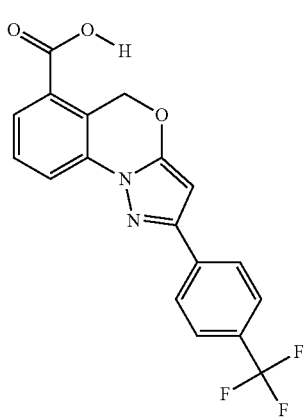 [SMILES: O=C(O)c1cccc2c1COc1cc(-c3ccc(C(F)(F)F)cc3)nn1-2]
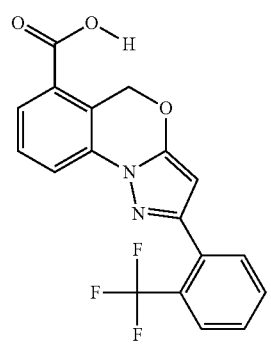 [SMILES: O=C(O)c1cccc2c1COc1cc(-c3ccccc3C(F)(F)F)nn1-2]
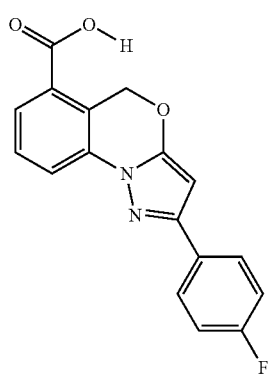 [SMILES: O=C(O)c1cccc2c1COc1cc(-c3ccc(F)cc3)nn1-2]

TABLE 7-continued
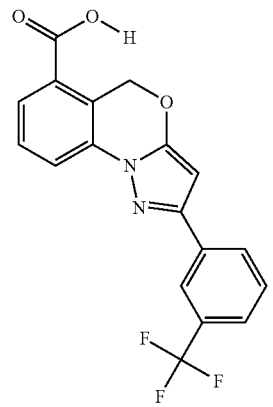 [SMILES: O=C(O)c1cccc2c1COc1cc(-c3cccc(C(F)(F)F)c3)nn1-2]
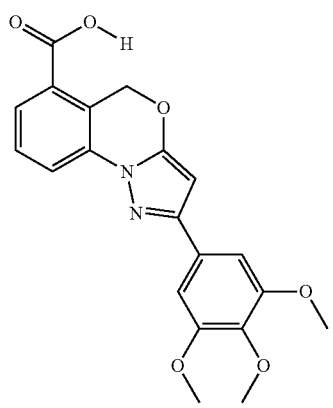 [SMILES: COc1cc(-c2cc3n(n2)-c2cccc(C(=O)O)c2CO3)cc(OC)c1OC]
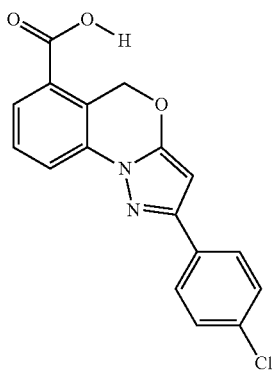 [SMILES: O=C(O)c1cccc2c1COc1cc(-c3ccc(Cl)cc3)nn1-2]
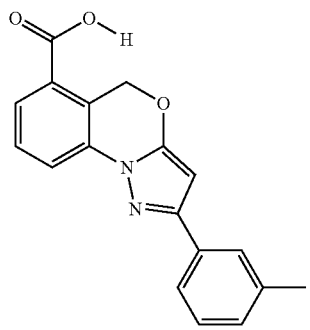 [SMILES: Cc1cccc(-c2cc3n(n2)-c2cccc(C(=O)O)c2CO3)c1]
TABLE 7-continued
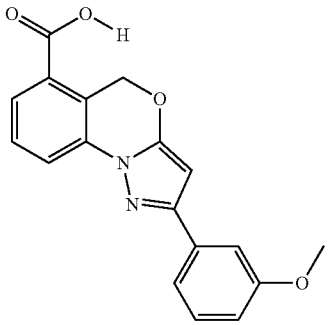 [SMILES: COc1cccc(-c2cc3n(n2)-c2cccc(C(=O)O)c2CO3)c1]
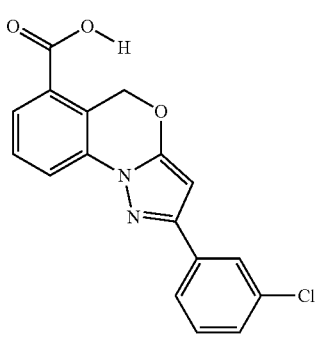 [SMILES: O=C(O)c1cccc2c1COc1cc(-c3cccc(Cl)c3)nn1-2]
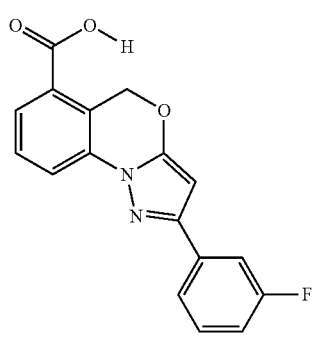 [SMILES: O=C(O)c1cccc2c1COc1cc(-c3cccc(F)c3)nn1-2]
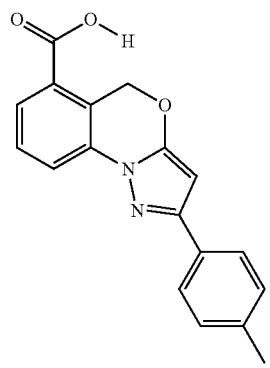 [SMILES: Cc1ccc(-c2cc3n(n2)-c2cccc(C(=O)O)c2CO3)cc1]
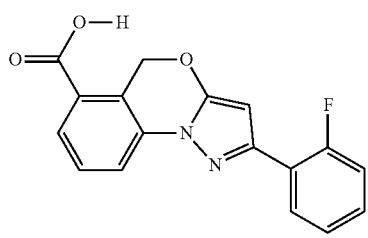 [SMILES: O=C(O)c1cccc2c1COc1cc(-c3ccccc3F)nn1-2]

TABLE 7-continued

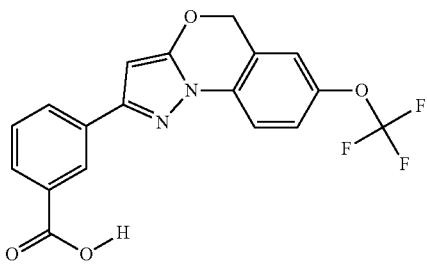 [SMILES: O=C(O)c1cccc(-c2cc3n(n2)-c2ccc(OC(F)(F)F)cc2CO3)c1]

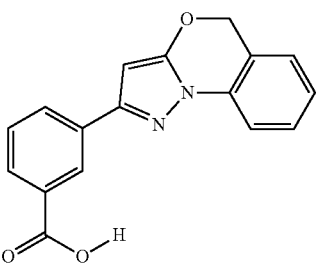 [SMILES: O=C(O)c1cccc(-c2cc3n(n2)-c2ccccc2CO3)c1]

Compounds of formula VII can be obtained via standard, well-known synthetic methodology, see e.g., March, J. Advanced Organic Chemistry; Reactions Mechanisms, and Structure, 4th ed., 1992. Starting materials useful for preparing compounds of formula I and intermediates therefore, are commercially available or can be prepared from commercially available materials using known synthetic methods and reagents.

Particular methods for preparing compounds of formula VII are disclosed in International Application No. PCT/US05/036761, filed Oct. 13, 2005, incorporated by reference herein in its entirety.

In another embodiment, the nonsense codon suppressor is a compound of formula VIII:

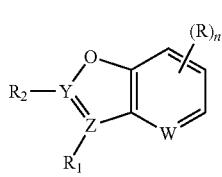

VIII or pharmaceutically acceptable salts, hydrates, clathrates, prodrugs, polymorphs, stereoisomers, including enantiomers, diastereomers, racemates or mixtures of stereoisomers, thereof wherein:

Y and Z are independently selected from N or C;

W is N or CH;

n is 0, 1, 2 or 3;

$R_1$ is hydrogen, a $C_6$ to $C_8$ aryl which is optionally substituted with a carboxy group, or $R_1$ is absent when Z is N;

$R_2$ is hydrogen; a $C_6$ to $C_8$ aryl which is optionally substituted with one, two, or three independently selected $R_a$ groups; a four to seven membered heterocycle which is optionally substituted with one or more independently selected $C_1$-$C_6$ alkyl groups or a three to seven membered heterocycle; or $R_2$ is absent when Y is N;

R is independently selected from a halogen; a carboxy group; a $C_1$-$C_6$ alkyl group optionally substituted with a four to seven membered heterocycle, a $C_6$-$C_8$ aryloxy group, or an amino group, wherein the four to seven membered heterocycle, $C_6$-$C_8$ aryloxy group, and amino group are optionally substituted with one or two independently selected $C_1$-$C_6$ alkyl or $C_6$-$C_8$ aryl groups which $C_6$-$C_8$ aryl groups are optionally and independently substituted with one or more $C_1$-$C_6$ alkyl groups; a $C_1$-$C_6$ alkoxy; a $C_6$-$C_8$ aryloxy; a $C_6$-$C_8$ aryl optionally substituted with one or more independently selected halogen, $C_1$-$C_4$ alkyl, $C_1$-$C_4$ haloalkyl, oxy, $C_1$-$C_4$ alkoxy, or $C_1$-$C_4$ haloalkoxy groups; an amino group optionally substituted with one or two independently selected $C_6$-$C_8$ aryl or $C_1$-$C_6$ alkyl groups, which are optionally substituted with a hydroxy, a $C_6$-$C_8$ aryl, or a nine to ten membered heterocycle having two ring structures; a carbonyl group substituted with a five to six membered heterocycle group; a four to seven membered heterocycle group optionally substituted with one more $C_1$-$C_4$ alkyl or oxo groups; a nine to ten membered heterocycle having two ring structures; or two R groups, wherein R may also include an oxy group, together with the hetero-bicycle to which they are attached form a twelve to thirteen membered heterocycle having three ring structures; and wherein $R_a$ is a halogen; a $C_1$-$C_6$ alkyl; a $C_1$-$C_6$ alkoxy which is optionally substituted with one or more independently selected halogen groups; a $C_6$-$C_8$ aryl; a four to seven membered heterocycle which is optionally substituted with one or more independently selected oxo groups; a carbonyl which is optionally substituted with a hydroxy or a $C_1$-$C_6$ alkoxy group; a carbamoyl; an amino which is optionally substituted with an independently selected $C_1$-$C_6$ alkyl group, wherein the $C_1$-$C_6$ alkyl group is optionally substituted with one or more independently selected halogens or hydroxyl groups; or two $R_a$ groups, wherein $R_a$ may also include an oxy group, together with the $C_6$ to $C_8$ aryl group to which they are attached form a nine to ten membered heterocycle having two ring structures, wherein the nine to ten membered heterocycle having two ring structures is optionally substituted with one or more independently selected halogens.

Preferred compounds of formula VIII are set forth in Table 8, below.

TABLE 8

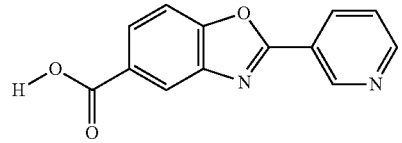 [SMILES: O=C(O)c1ccc2oc(-c3cccnc3)nc2c1]

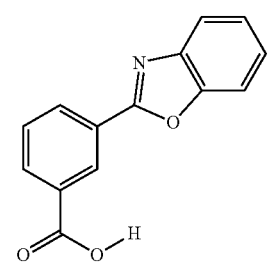 [SMILES: O=C(O)c1cccc(-c2nc3ccccc3o2)c1]

TABLE 8-continued
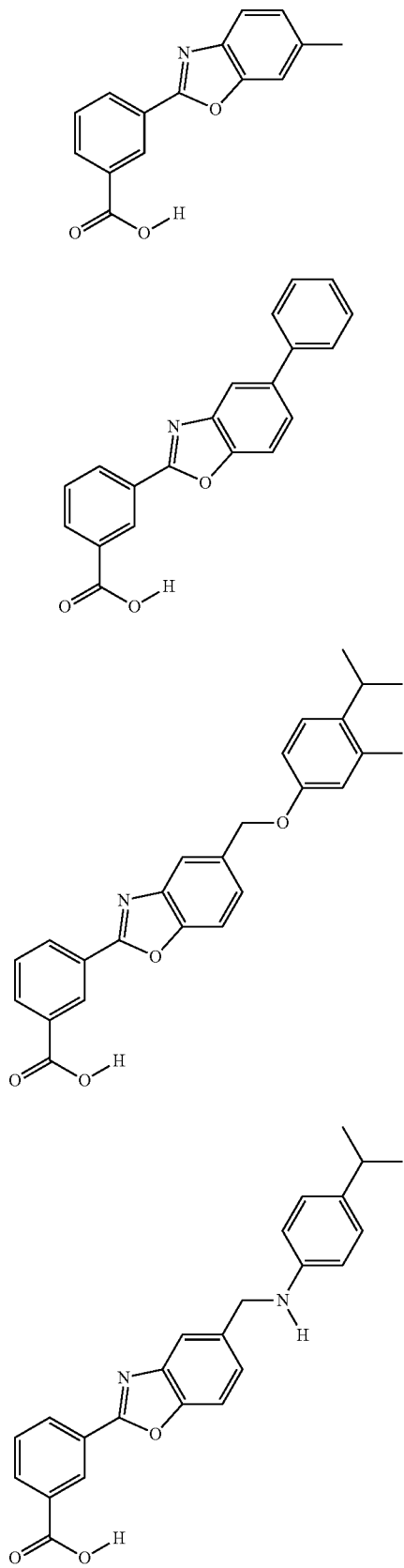
TABLE 8-continued
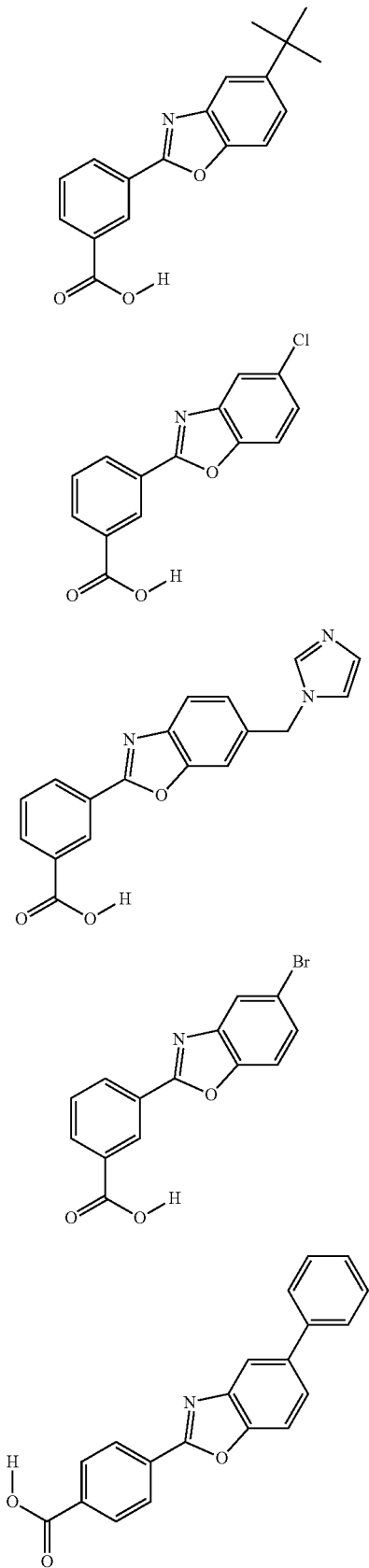

TABLE 8-continued
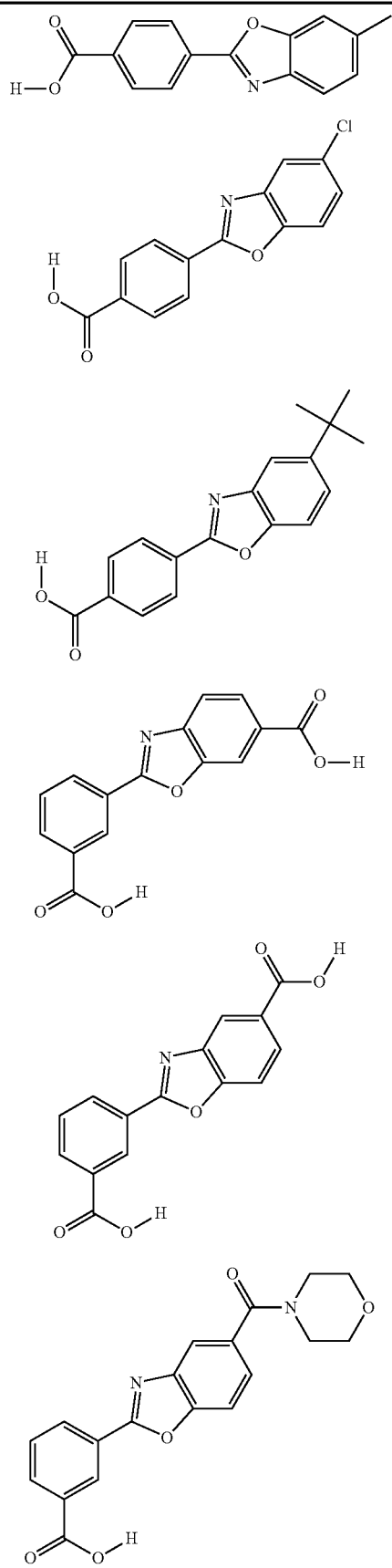
TABLE 8-continued
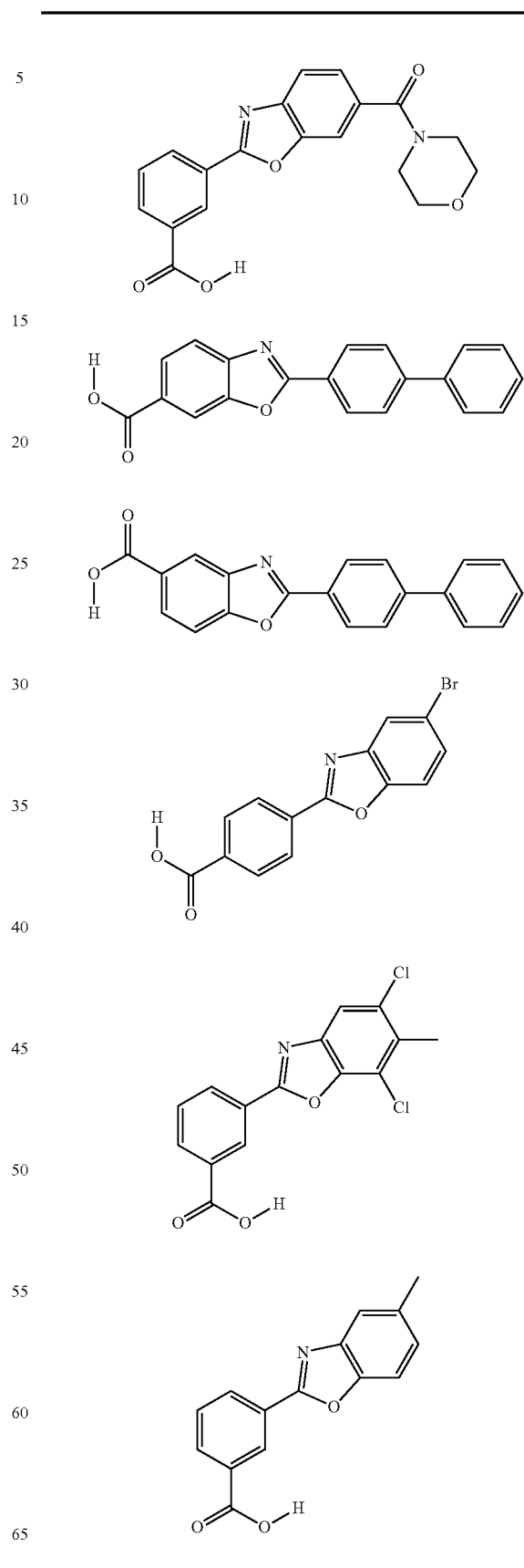

TABLE 8-continued
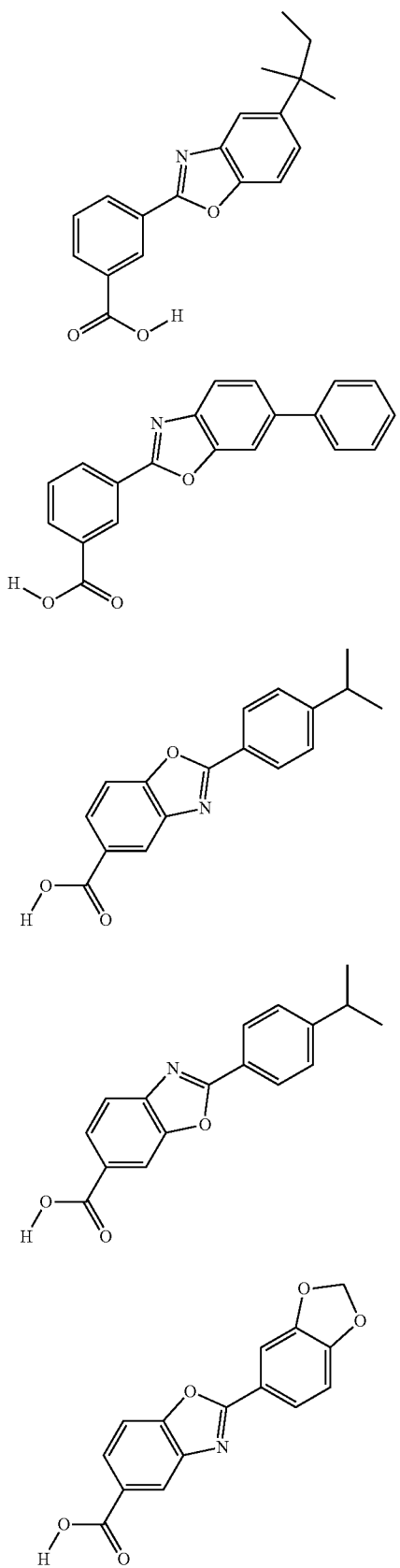
TABLE 8-continued
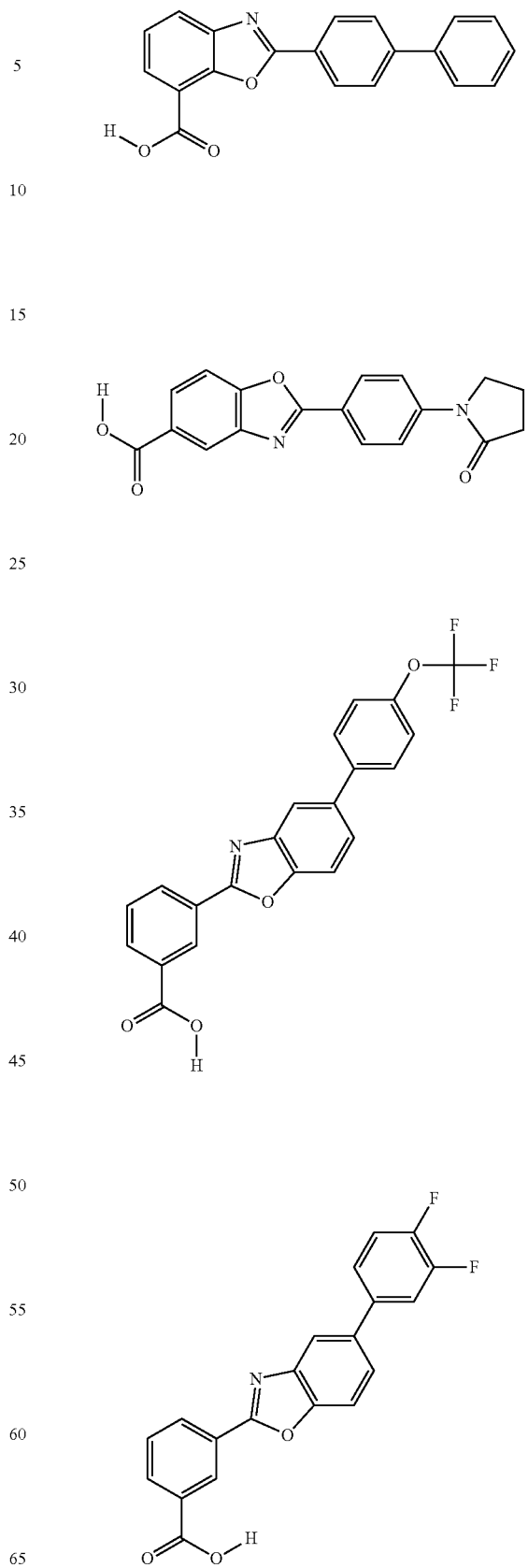

TABLE 8-continued
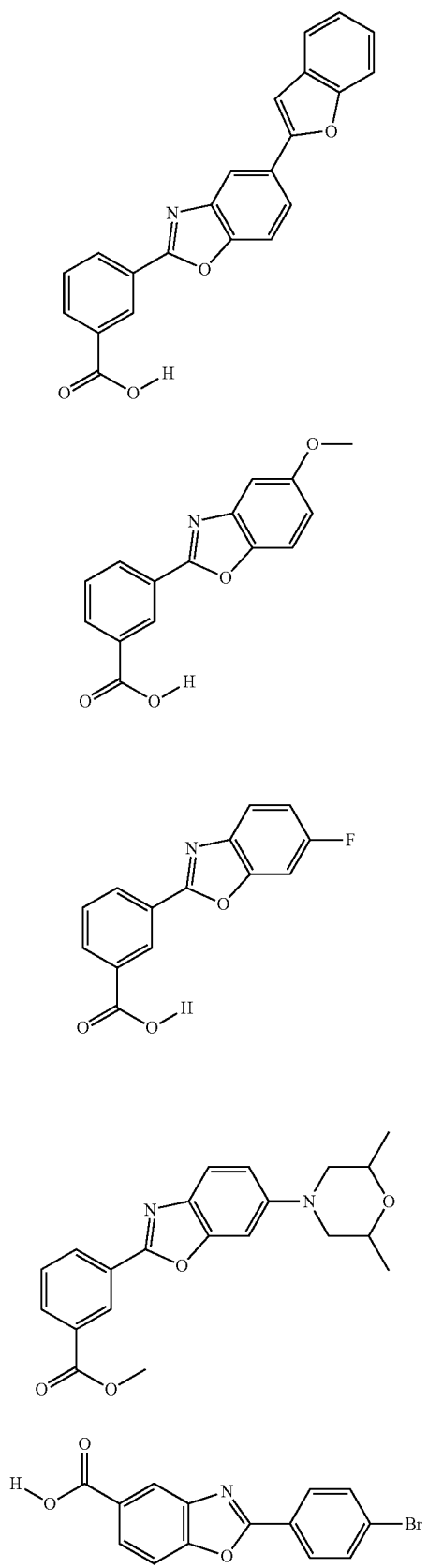
TABLE 8-continued
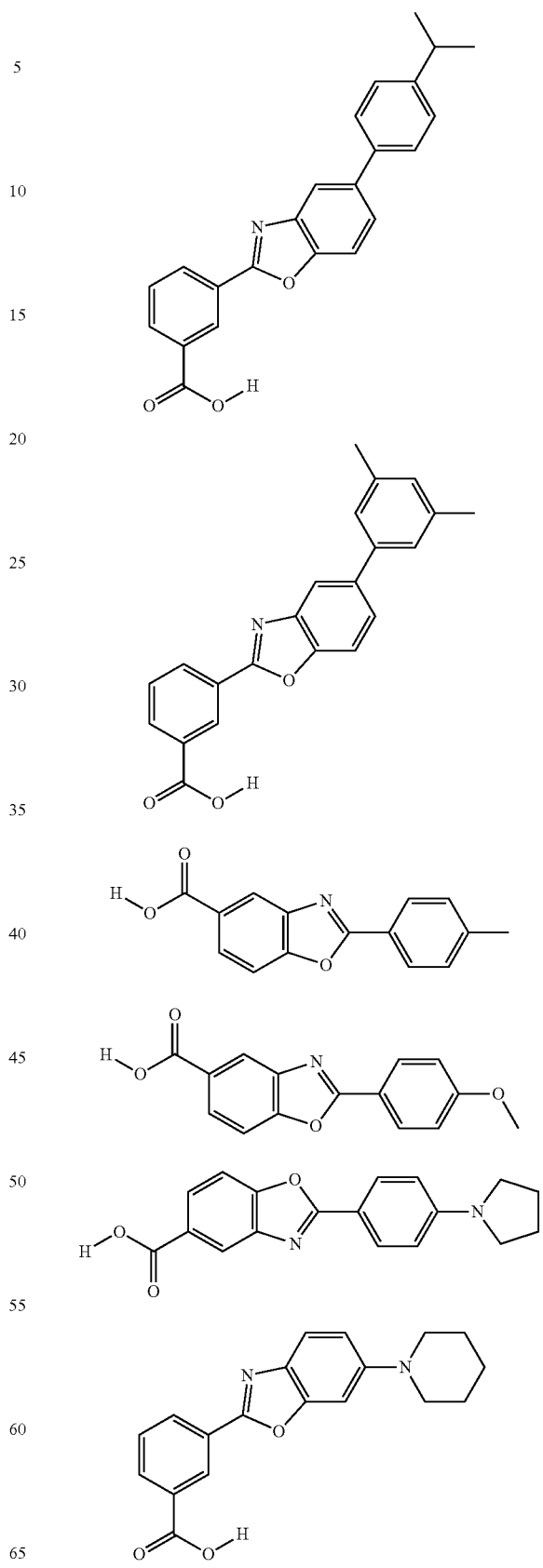

TABLE 8-continued
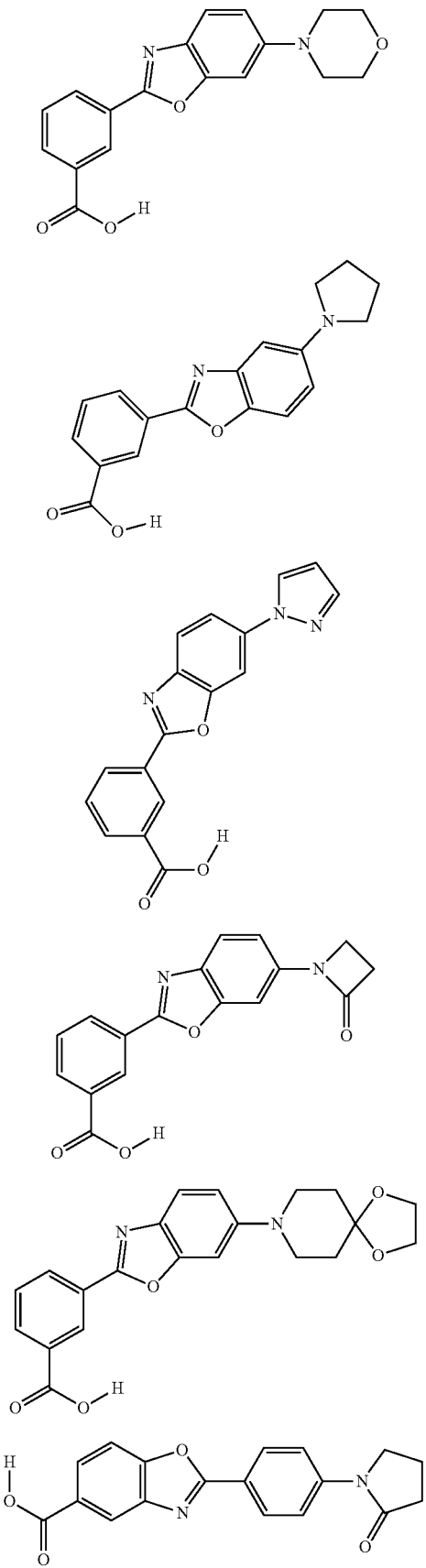
TABLE 8-continued
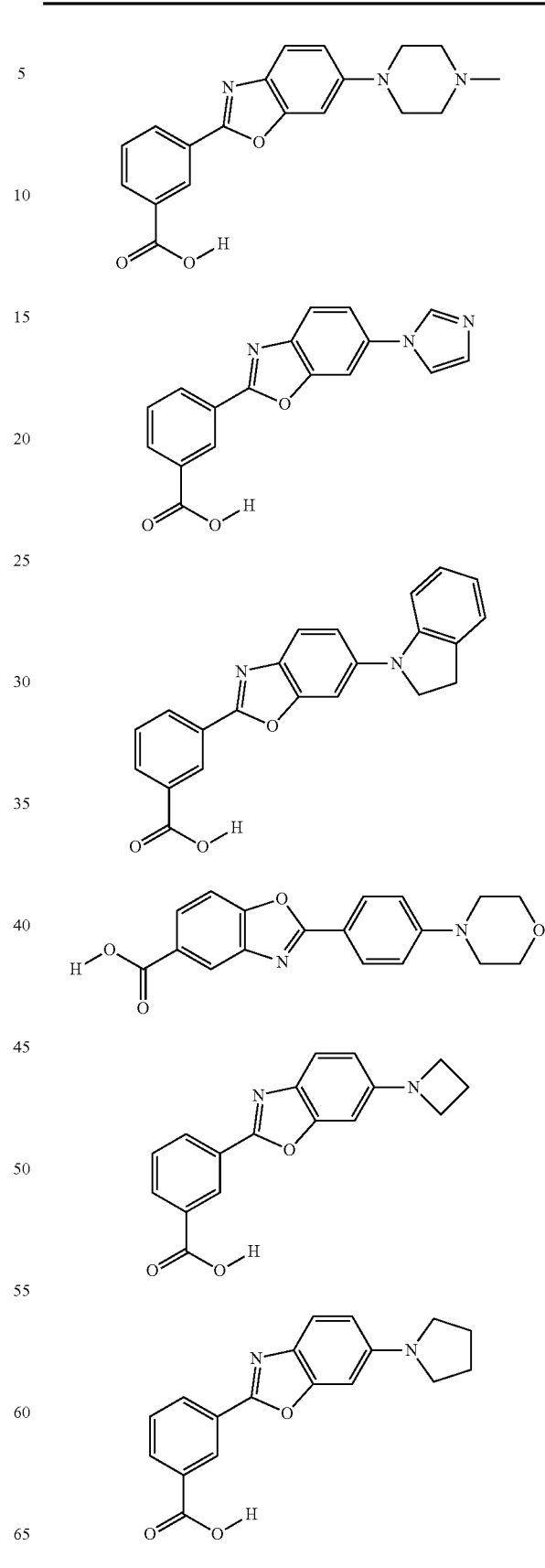

TABLE 8-continued
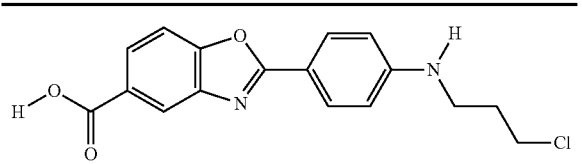
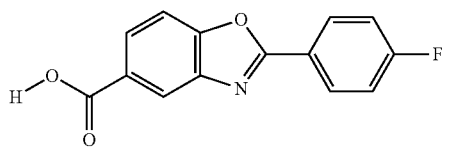 [SMILES: O=C(O)c1ccc2oc(-c3ccc(F)cc3)nc2c1]
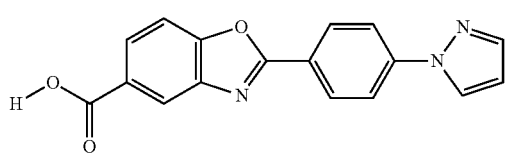 [SMILES: O=C(O)c1ccc2oc(-c3ccc(-n4cccn4)cc3)nc2c1]
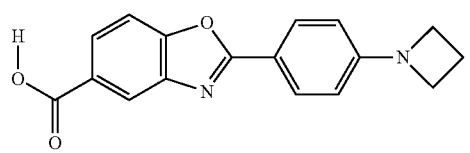
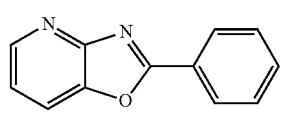 [SMILES: c1ccc(-c2nc3ncccc3o2)cc1]
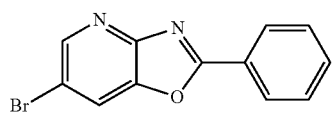 [SMILES: Brc1cnc2nc(-c3ccccc3)oc2c1]
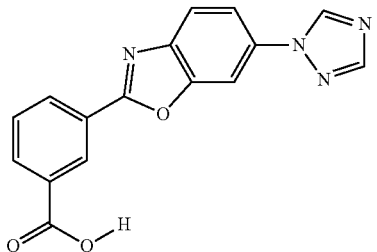 [SMILES: O=C(O)c1cccc(-c2nc3ccc(-n4cncn4)cc3o2)c1]
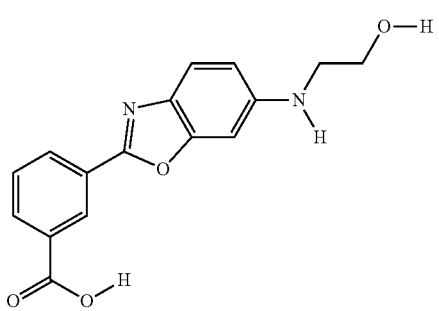 [SMILES: O=C(O)c1cccc(-c2nc3ccc(NCCO)cc3o2)c1]
TABLE 8-continued
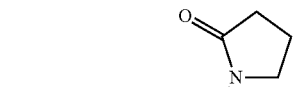
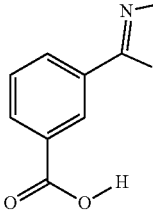
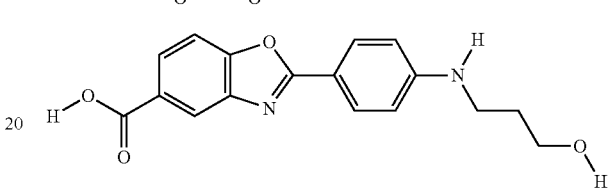
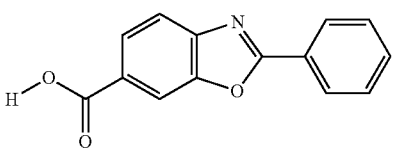 [SMILES: O=C(O)c1ccc2nc(-c3ccccc3)oc2c1]
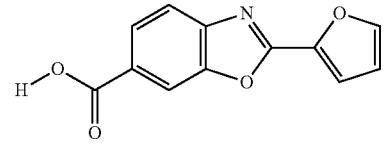 [SMILES: O=C(O)c1ccc2nc(-c3ccco3)oc2c1]
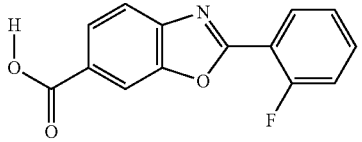 [SMILES: O=C(O)c1ccc2nc(-c3ccccc3F)oc2c1]
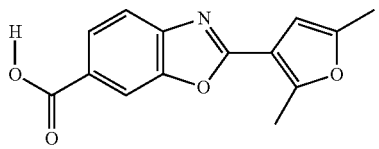 [SMILES: Cc1cc(-c2nc3ccc(C(=O)O)cc3o2)c(C)o1]
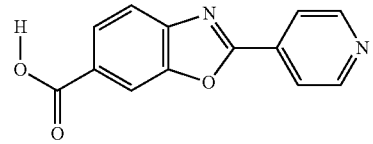 [SMILES: O=C(O)c1ccc2nc(-c3ccncc3)oc2c1]
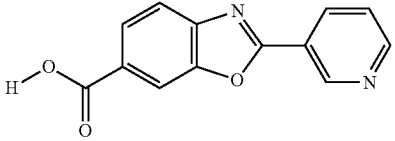
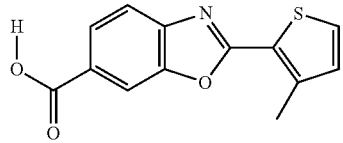 [SMILES: Cc1ccsc1-c1nc2ccc(C(=O)O)cc2o1]

TABLE 8-continued
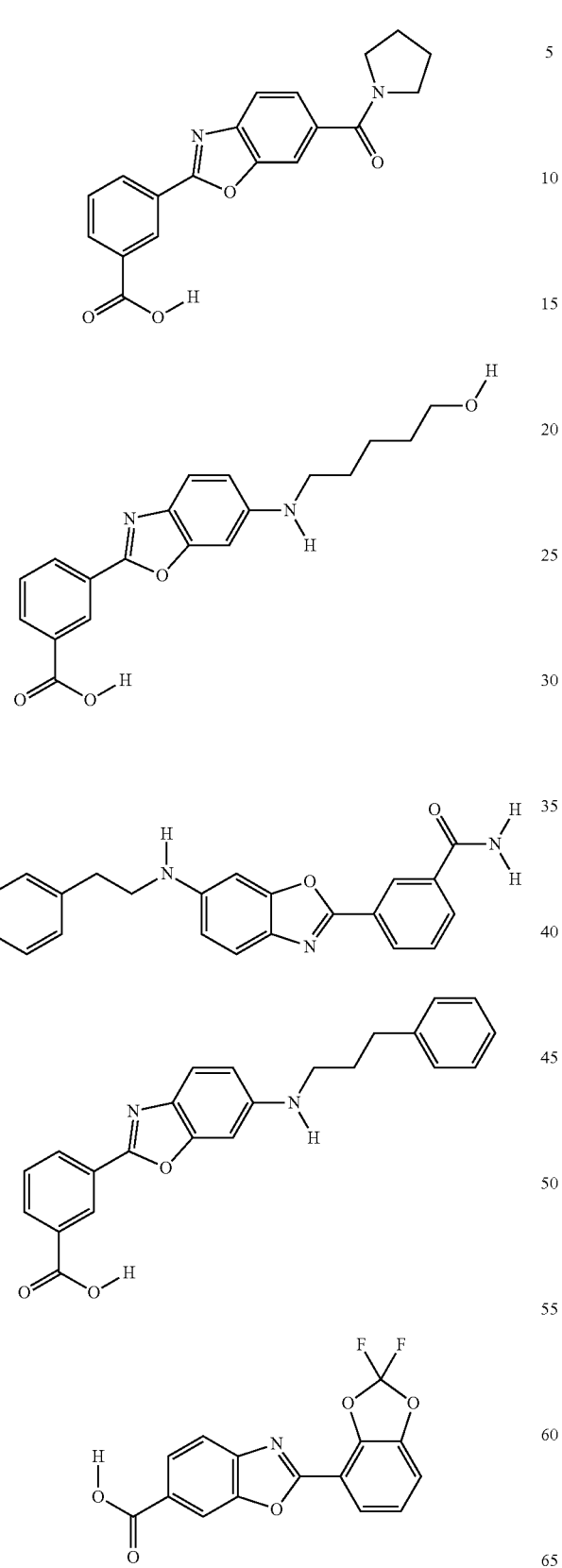
TABLE 8-continued
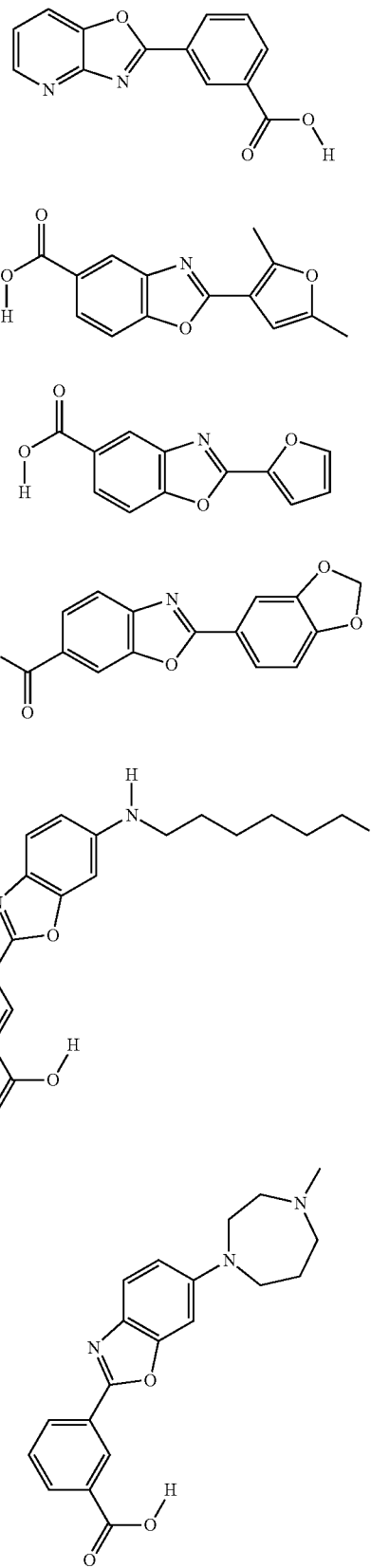

341
TABLE 8-continued
342
TABLE 8-continued
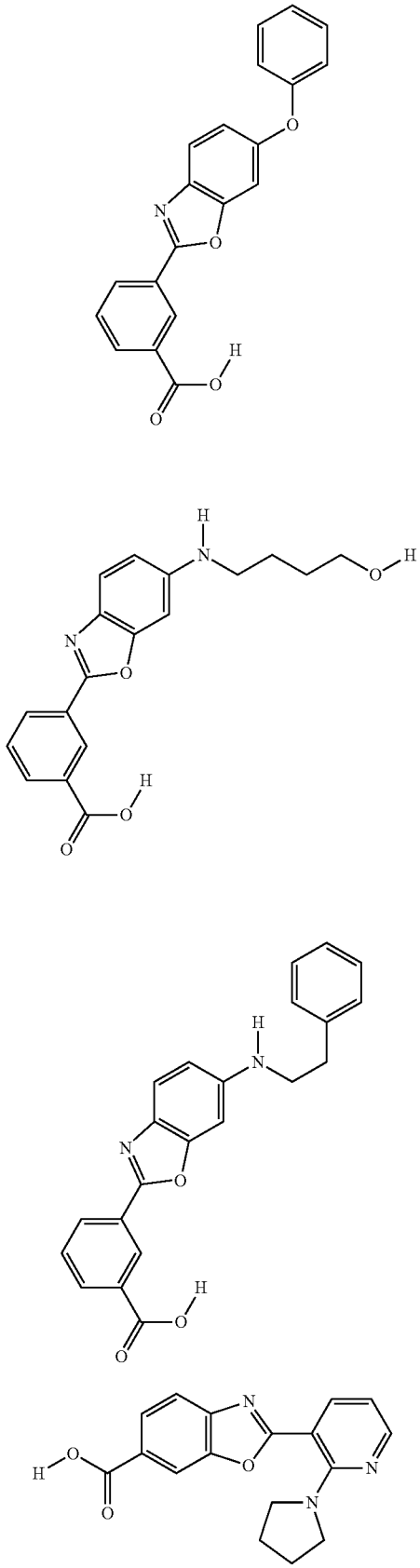

TABLE 8-continued
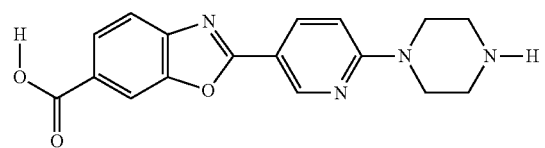 [SMILES: O=C(O)c1ccc2nc(-c3ccc(N4CCNCC4)nc3)oc2c1]
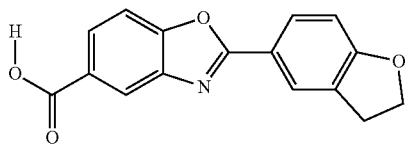 [SMILES: O=C(O)c1ccc2oc(-c3ccc4c(c3)CCO4)nc2c1]
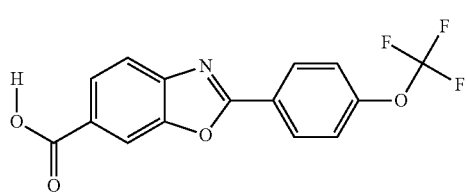 [SMILES: O=C(O)c1ccc2nc(-c3ccc(OC(F)(F)F)cc3)oc2c1]
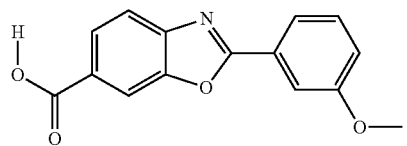 [SMILES: COc1cccc(-c2nc3ccc(C(=O)O)cc3o2)c1]
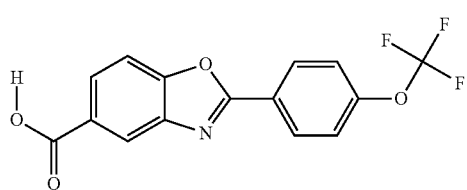 [SMILES: O=C(O)c1ccc2oc(-c3ccc(OC(F)(F)F)cc3)nc2c1]
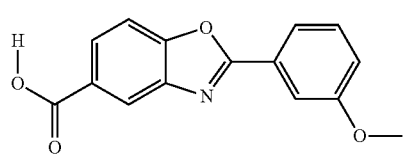 [SMILES: COc1cccc(-c2nc3cc(C(=O)O)ccc3o2)c1]
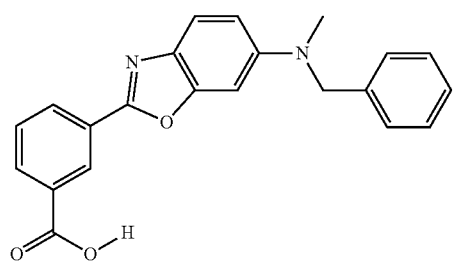 [SMILES: CN(Cc1ccccc1)c1ccc2nc(-c3cccc(C(=O)O)c3)oc2c1]
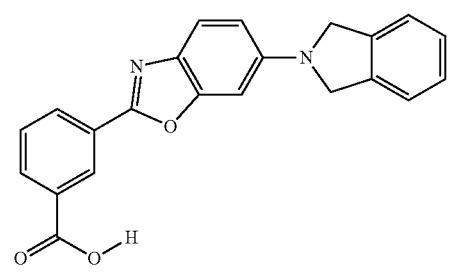 [SMILES: O=C(O)c1cccc(-c2nc3ccc(N4Cc5ccccc5C4)cc3o2)c1]
TABLE 8-continued
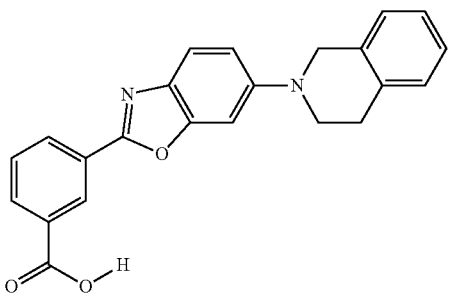 [SMILES: O=C(O)c1cccc(-c2nc3ccc(N4CCc5ccccc5C4)cc3o2)c1]
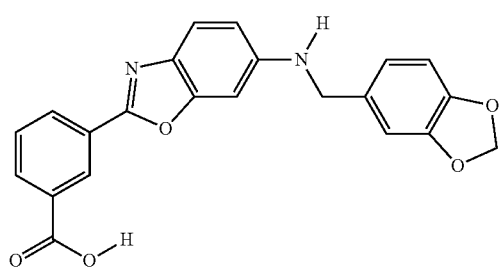 [SMILES: O=C(O)c1cccc(-c2nc3ccc(NCc4ccc5c(c4)OCO5)cc3o2)c1]
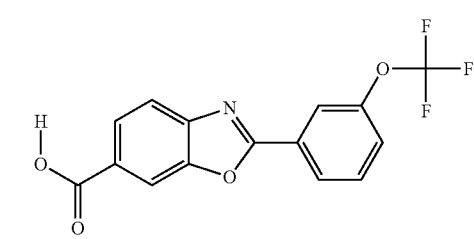 [SMILES: O=C(O)c1ccc2nc(-c3cccc(OC(F)(F)F)c3)oc2c1]
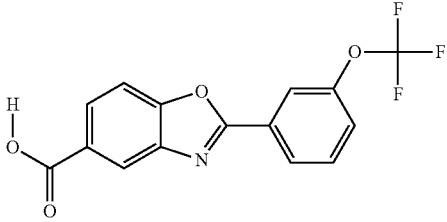 [SMILES: O=C(O)c1ccc2oc(-c3cccc(OC(F)(F)F)c3)nc2c1]
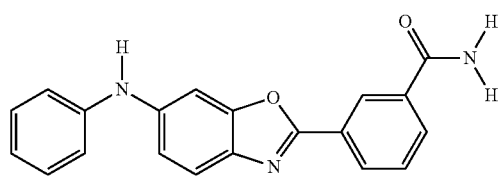 [SMILES: NC(=O)c1cccc(-c2nc3ccc(Nc4ccccc4)cc3o2)c1]
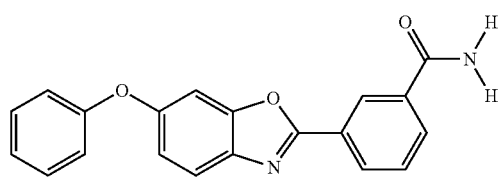 [SMILES: NC(=O)c1cccc(-c2nc3ccc(Oc4ccccc4)cc3o2)c1]
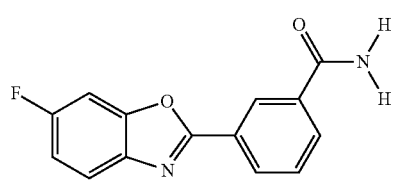 [SMILES: NC(=O)c1cccc(-c2nc3ccc(F)cc3o2)c1]

TABLE 8-continued
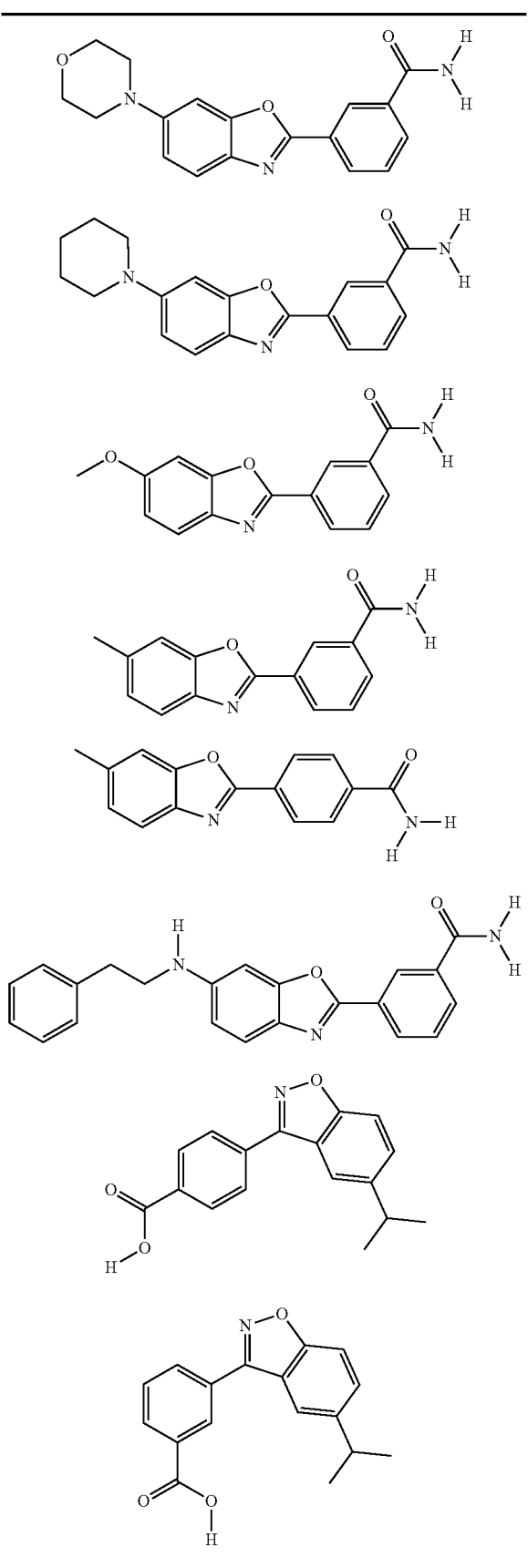
TABLE 8-continued
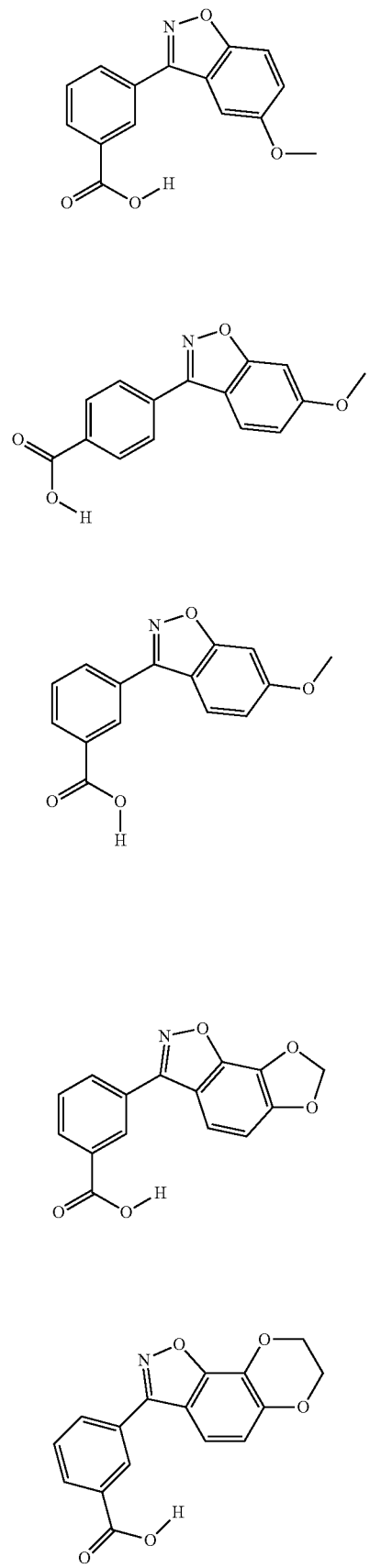

TABLE 8-continued

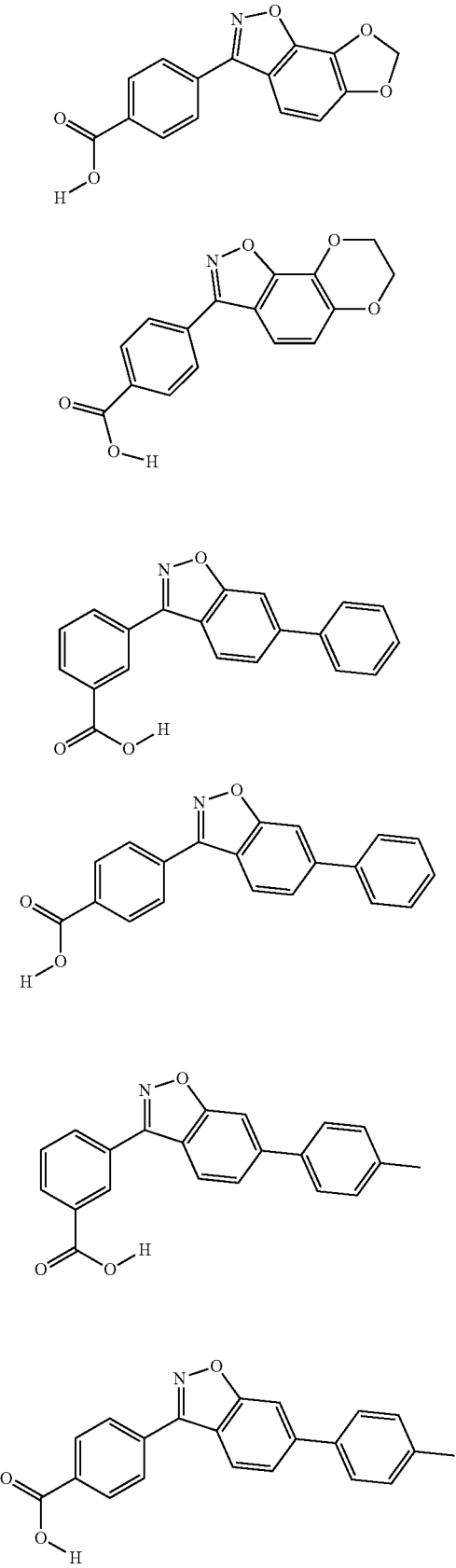

TABLE 8-continued

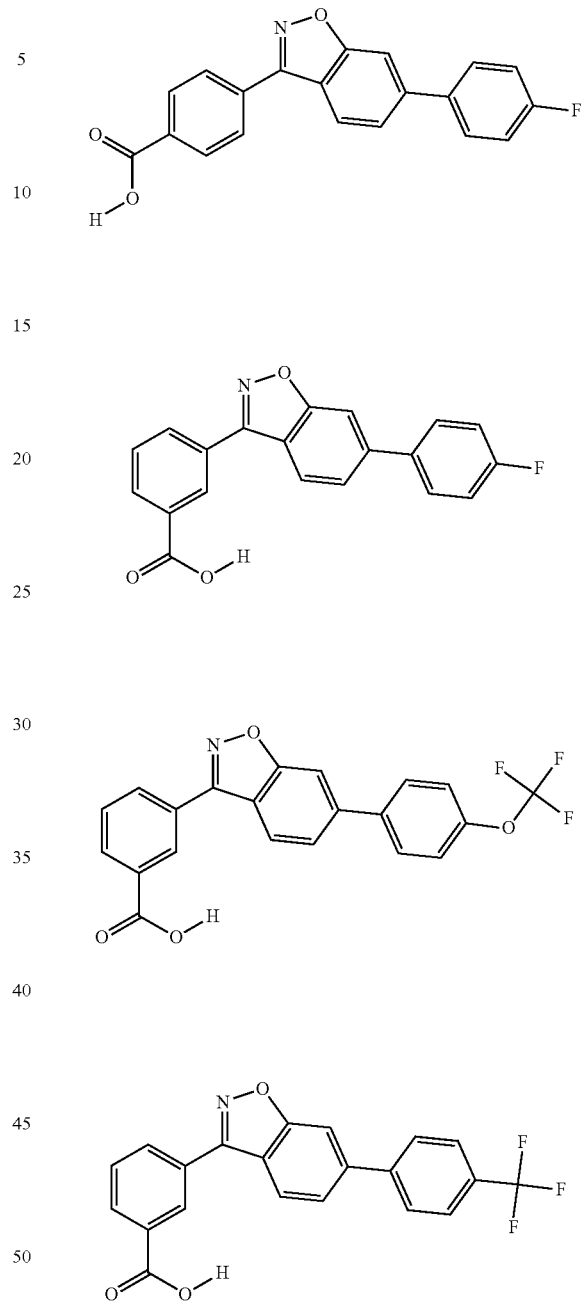

Compounds of formula VIII can be obtained via standard, well-known synthetic methodology, see e.g., March, J. Advanced Organic Chemistry; Reactions Mechanisms, and Structure, 4th ed., 1992. Starting materials useful for preparing compounds of formula I and intermediates therefore, are commercially available or can be prepared from commercially available materials using known synthetic methods and reagents.

Particular methods for preparing compounds of formula VIII are disclosed in International Application No. PCT/US05/036762, filed Oct. 13, 2005, incorporated by reference herein in its entirety.

In another embodiment, the nonsense codon suppressor is a compound of formula IX:

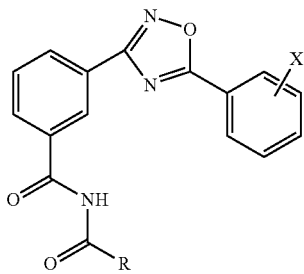

IX or pharmaceutically acceptable salts, hydrates, clathrates, prodrugs, polymorphs, stereoisomers, including enantiomers, diastereomers, racemates or mixtures of stereoisomers, thereof wherein:

X is a halogen;

R is a $C_1$-$C_8$ alkyl group; a $C_1$-$C_4$ haloalkyl group; an —$OR_1$ group; or an amino group which is optionally substituted with one or two independently selected $R_2$ groups;

$R_1$ is a $C_1$-$C_8$ alkyl group which is optionally substituted with one or more independently selected $R_a$ groups; a —$R_b$ group; a pyrrolidinyl group which is optionally substituted with one or more independently selected $C_1$-$C_4$ alkyl or oxo groups; a piperidyl group which is optionally substituted with one or more independently selected $C_1$-$C_4$ alkyl groups, benzyl groups, or carboxy groups optionally substituted with one or more $C_1$-$C_4$ alkyl or $C_1$-$C_4$ alkoxy groups; a tetrahydrofuryl group; a tetrahydro-pyranyl group; a tetrahydro-naphthyl group; or an indanyl group;

$R_2$ is a hydrogen, a $C_1$-$C_6$ alkyl group; a $C_1$-$C_4$ haloalkyl group; a $C_1$-$C_4$ alkoxy group; a —$R_b$ group; a pyrimidinyl group; a pyridyl group; a sulfonyl group optionally substituted with an —$R_b$ group; or two $R_2$ groups together with the amino to which they are attached form a morpholinyl group, a pyrrolidinyl group, an isoindolinyl group, or a piperazinyl group which is optionally substituted with a phenyl group;

wherein $R_a$ is a halogen; a $C_1$-$C_4$ alkoxy group; a carbamoyl group which is optionally substituted with one or two independently selected $C_1$-$C_4$ alkyl or $C_1$-$C_4$ alkoxy groups; a phosphinoyl group which is optionally substituted with one or two independently selected $C_1$-$C_4$ alkyl or $C_1$-$C_4$ alkoxy groups; a morpholinyl group; a pyridyl group; or an —$R_b$ group; and wherein $R_b$ is a $C_6$-$C_8$ aryl which is optionally substituted with one or more of the following, independently selected: a hydroxy, a halogen, a $C_1$-$C_4$ alkyl group, a $C_1$-$C_4$ haloalkyl group, a $C_1$-$C_4$ alkoxy group, or an amino group which is optionally substituted with one or more independently selected $C_1$-$C_4$ alkyl groups.

Preferred compounds of formula IX are set forth in Table 9, below.

TABLE 9

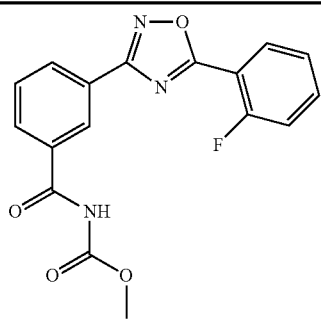

TABLE 9-continued

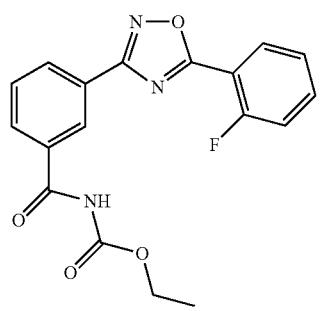 [SMILES: CCOC(=O)NC(=O)c1cccc(-c2noc(-c3ccccc3F)n2)c1]

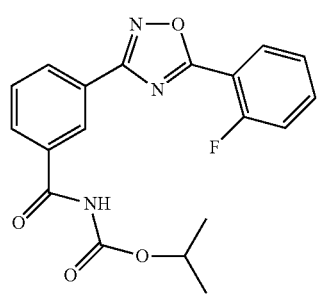 [SMILES: CC(C)OC(=O)NC(=O)c1cccc(-c2noc(-c3ccccc3F)n2)c1]

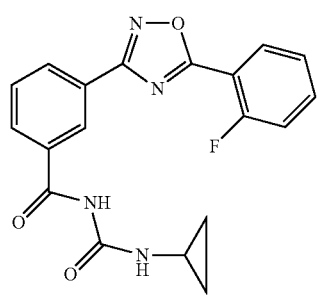 [SMILES: O=C(NC(=O)c1cccc(-c2noc(-c3ccccc3F)n2)c1)NC1CC1]

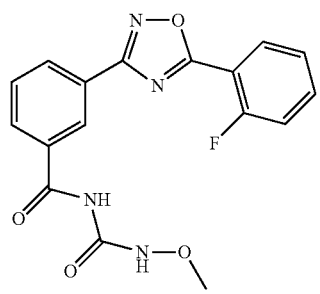 [SMILES: CONC(=O)NC(=O)c1cccc(-c2noc(-c3ccccc3F)n2)c1]

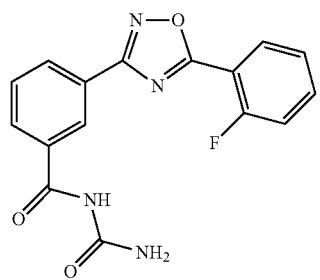 [SMILES: NC(=O)NC(=O)c1cccc(-c2noc(-c3ccccc3F)n2)c1]

TABLE 9-continued
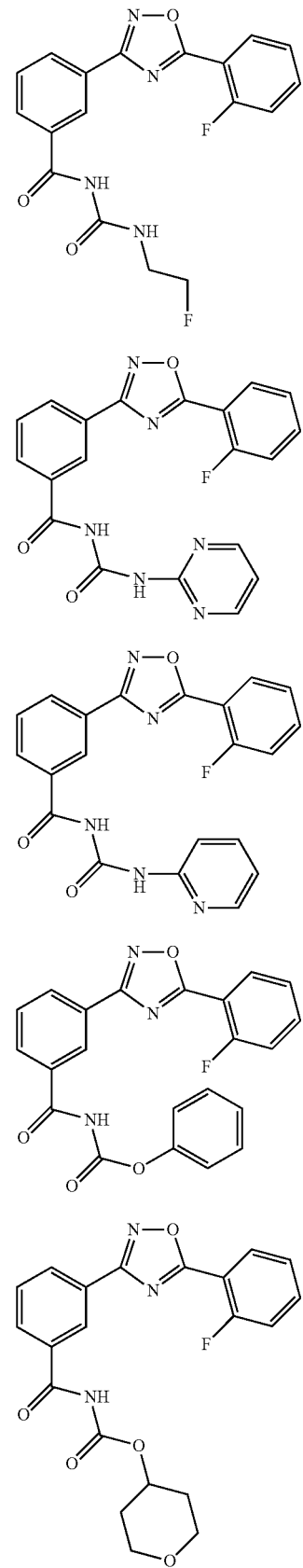
TABLE 9-continued
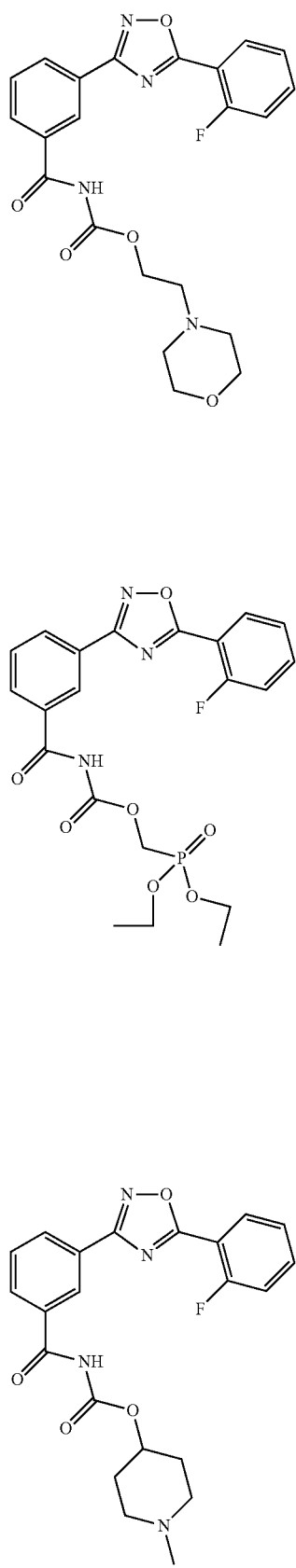

TABLE 9-continued
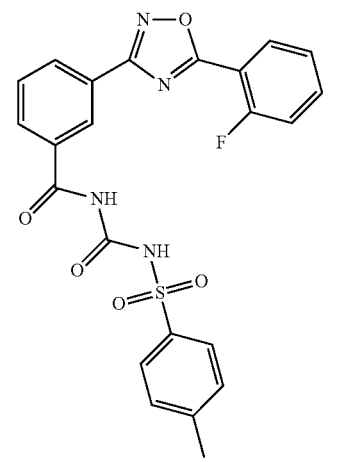 [SMILES: Cc1ccc(S(=O)(=O)NC(=O)NC(=O)c2cccc(-c3noc(-c4ccccc4F)n3)c2)cc1]
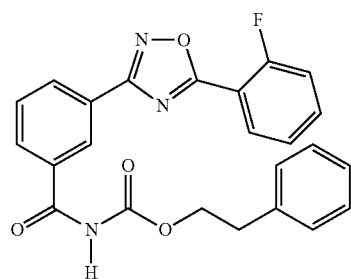 [SMILES: O=C(NC(=O)c1cccc(-c2noc(-c3ccccc3F)n2)c1)OCCc1ccccc1]
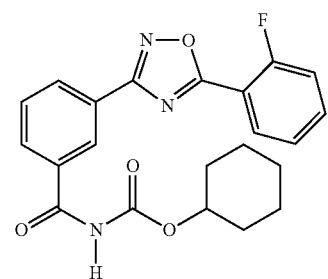 [SMILES: O=C(NC(=O)c1cccc(-c2noc(-c3ccccc3F)n2)c1)OC1CCCCC1]
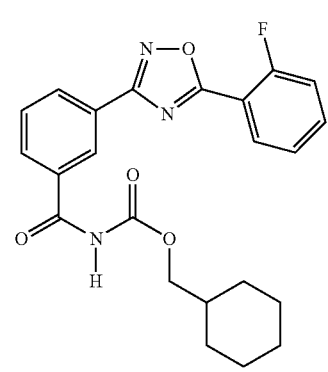 [SMILES: O=C(NC(=O)c1cccc(-c2noc(-c3ccccc3F)n2)c1)OCC1CCCCC1]
TABLE 9-continued
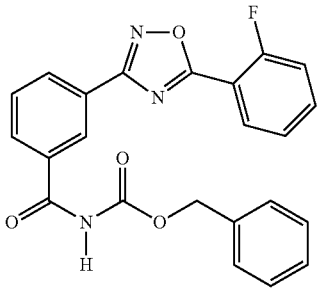 [SMILES: O=C(NC(=O)c1cccc(-c2noc(-c3ccccc3F)n2)c1)OCc1ccccc1]
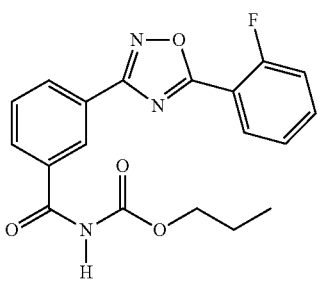 [SMILES: CCCOC(=O)NC(=O)c1cccc(-c2noc(-c3ccccc3F)n2)c1]
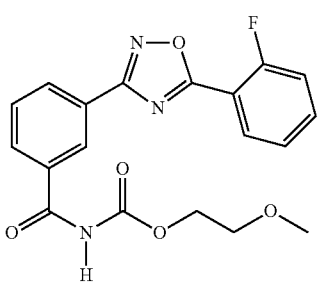 [SMILES: COCCOC(=O)NC(=O)c1cccc(-c2noc(-c3ccccc3F)n2)c1]
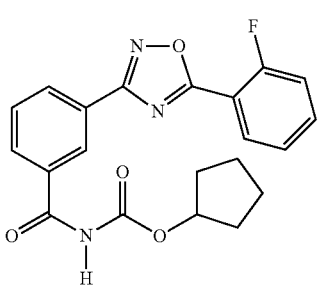 [SMILES: O=C(NC(=O)c1cccc(-c2noc(-c3ccccc3F)n2)c1)OC1CCCC1]
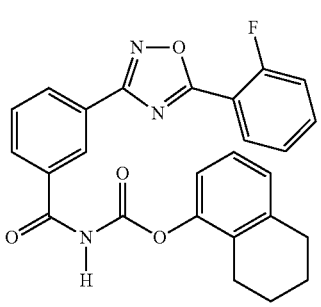 [SMILES: O=C(NC(=O)c1cccc(-c2noc(-c3ccccc3F)n2)c1)Oc1cccc2c1CCCC2]

TABLE 9-continued
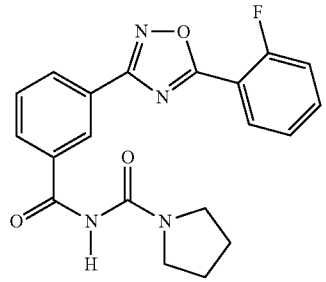 [SMILES: O=C(NC(=O)N1CCCC1)c1cccc(-c2noc(-c3ccccc3F)n2)c1]
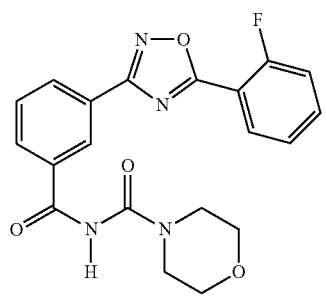 [SMILES: O=C(NC(=O)N1CCOCC1)c1cccc(-c2noc(-c3ccccc3F)n2)c1]
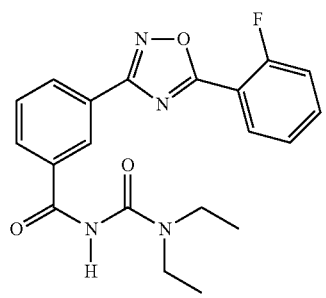 [SMILES: CCN(CC)C(=O)NC(=O)c1cccc(-c2noc(-c3ccccc3F)n2)c1]
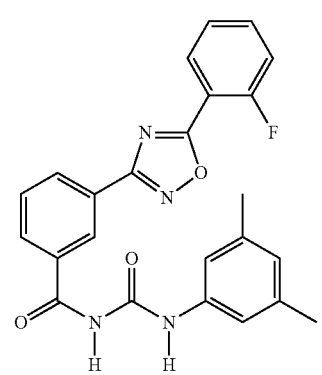 [SMILES: Cc1cc(C)cc(NC(=O)NC(=O)c2cccc(-c3noc(-c4ccccc4F)n3)c2)c1]
TABLE 9-continued
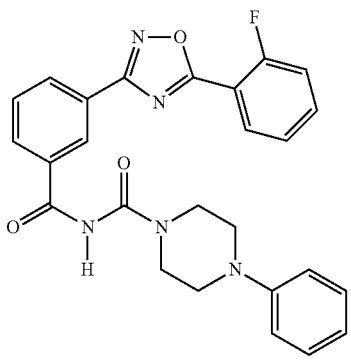 [SMILES: O=C(NC(=O)N1CCN(c2ccccc2)CC1)c1cccc(-c2noc(-c3ccccc3F)n2)c1]
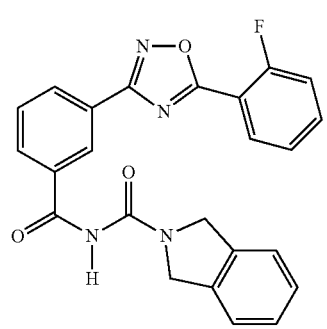 [SMILES: O=C(NC(=O)N1Cc2ccccc2C1)c1cccc(-c2noc(-c3ccccc3F)n2)c1]
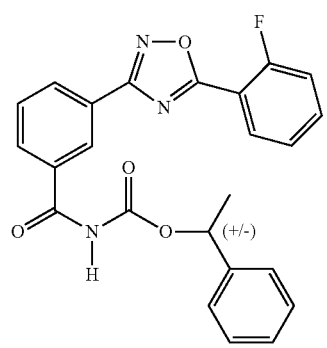 [SMILES: CC(OC(=O)NC(=O)c1cccc(-c2noc(-c3ccccc3F)n2)c1)c1ccccc1]
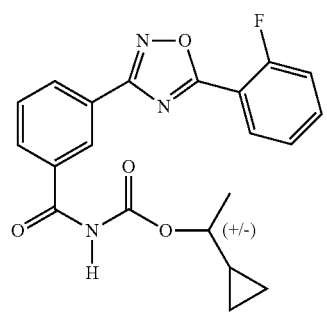 [SMILES: CC(OC(=O)NC(=O)c1cccc(-c2noc(-c3ccccc3F)n2)c1)C1CC1]

TABLE 9-continued
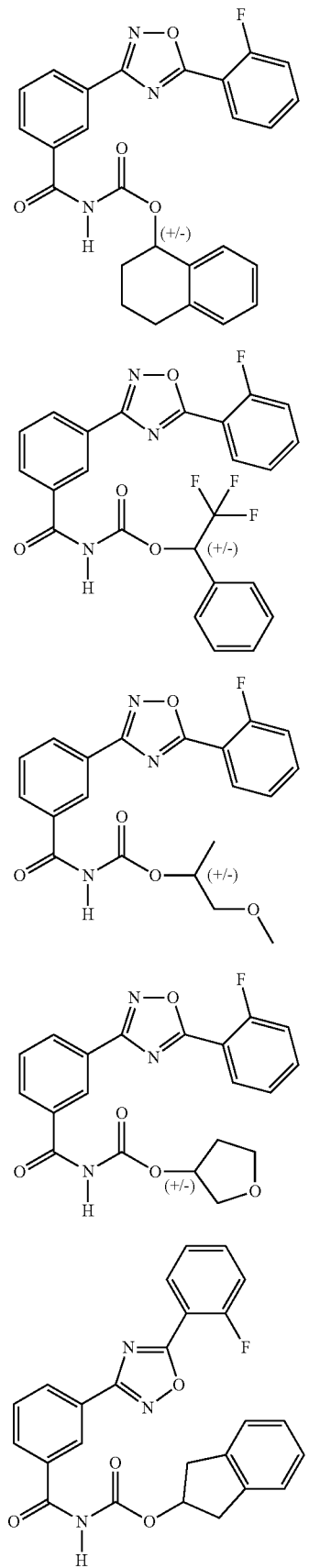
TABLE 9-continued
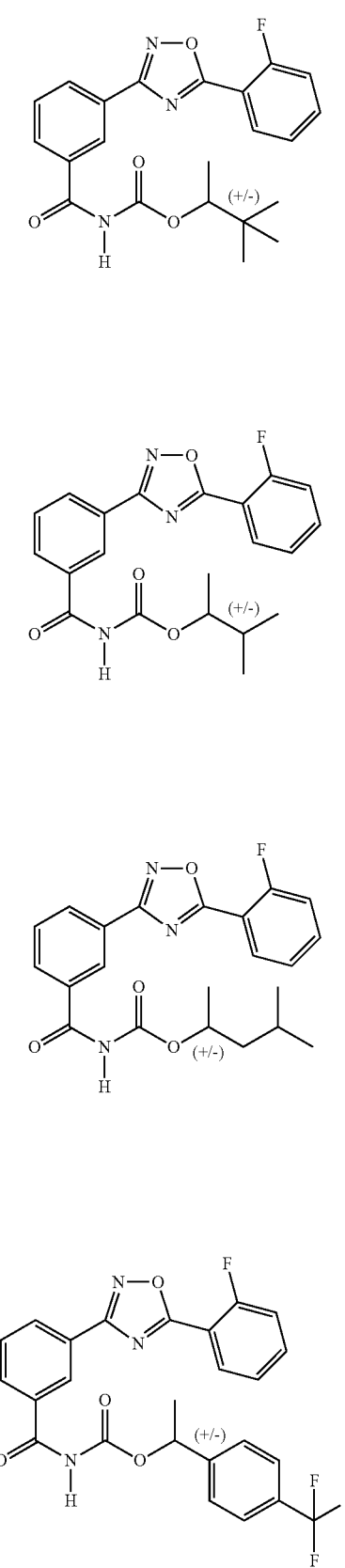

TABLE 9-continued
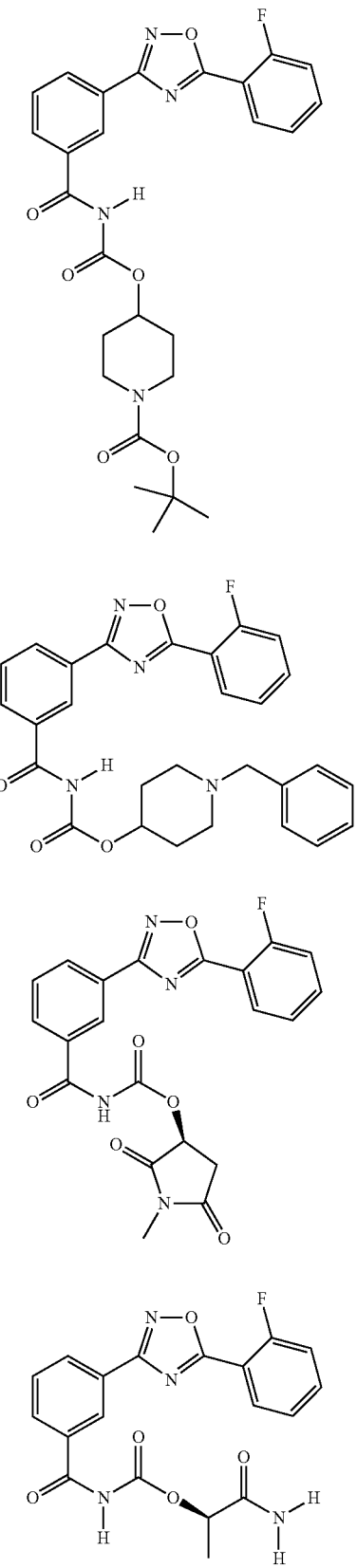
TABLE 9-continued
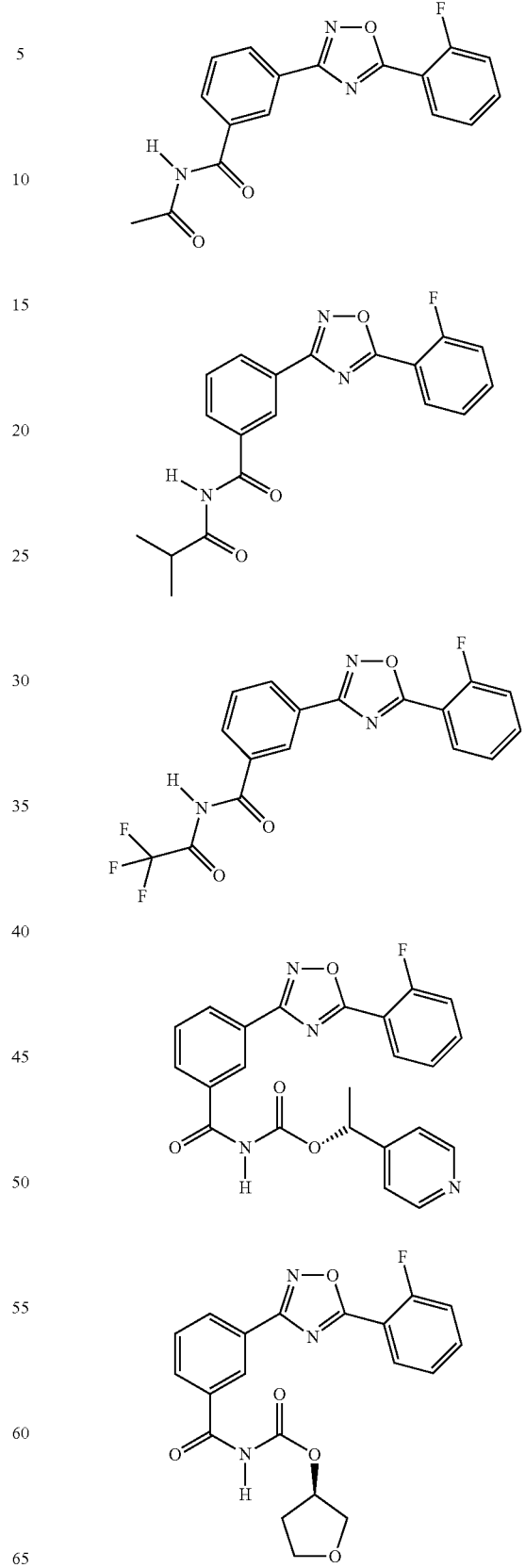

TABLE 9-continued

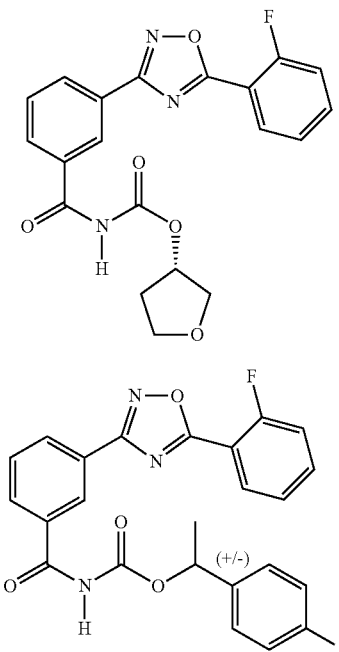

Compounds of formula IX can be obtained via standard, well-known synthetic methodology, see e.g., March, J. Advanced Organic Chemistry; Reactions Mechanisms, and Structure, 4th ed., 1992. Starting materials useful for preparing compounds of formula I and intermediates therefore, are commercially available or can be prepared from commercially available materials using known synthetic methods and reagents.

Particular methods for preparing compounds of formula IX are disclosed in International Application No. PCT/US05/037052, filed Oct. 13, 2005, incorporated by reference herein in its entirety.

The nonsense codon suppressor activity of compounds described herein can be measured using the reporter assays described in Section 5.4. In a specific embodiment, the nonsense codon suppressor activity of compounds described herein can be measured using a cell-based luciferase reporter assay comprising a luciferase reporter construct containing a UGA premature termination codon that was stably transfected in 293T Human Embryonic Kidney cells. A small molecule, 3-[3-(4-Isopropyl-phenyl)-2,5-dioxo-imidazolidin-1-yl]-benzoic acid, known to allow readthrough of premature termination codons may be used as an internal standard. Activity measurements are based on the qualitative relation between the minimum concentration of compound required to produce a given protein in a cell (potency) and the maximum amount of protein produced by the cell (efficacy).

Compounds having less than significant potency or efficacy of protein synthesis or both in the cell-based luciferase assay are believed to still have utility in the in vivo methods of the invention.

5.3 Synthesis and Preparation of Illustrative Compounds

The illustrative compounds described herein can be obtained via standard, well-known synthetic methodology, see e.g. March, J. Advanced Organic Chemistry; Reactions Mechanisms, and Structure, 4th ed., 1992. Starting materials useful for preparing the illustrative compounds described herein and intermediates therefor, are commercially available or can be prepared from commercially available materials using known synthetic methods and reagents.

Particular methods for obtaining the illustrative compounds described herein are described at least in US 2004/0067900, published Apr. 8, 2004, WO 2004/009558 A2, published Jan. 29, 2004, WO 2004/009533 A1, published Jan. 29, 2004, US 2004-0204461 A1, published Oct. 14, 2004, International Application No. PCT/US2005/036673, filed Oct. 13, 2005, International Application No. PCT/US2005/037052, filed Oct. 13, 2005, International Application No. PCT/US2005/036764, filed Oct. 13, 2005, International Application No. PCT/US2005/036762, filed Oct. 13, 2005, and International Application No. PCT/US2005/036761, filed Oct. 13, 2005, each of which is incorporated by reference herein in its entirety.

5.4 Methods for Identifying Nonsense Codon Suppressor Agents

Compounds that suppress premature translation termination and/or nonsense-mediated mRNA decay can be identified using techniques known to those of skill in the art. See, e.g., U.S. Publication No. 2005/0233327, published Oct. 20, 2005, entitled "Methods for Identifying Small Molecules that Modulate Premature Translation Termination and Nonsense Mediated mRNA Decay"; U.S. Pat. No. 6,458,538 entitled "Methods of Assaying for Compounds that Inhibit Premature Translation Termination and Nonsense Mediated RNA Decay"; U.S. Publication No. 2003/0008317, published Jan. 9, 2003, entitled "Methods of Assaying for Compounds that Inhibit Premature Translation Termination and Nonsense Mediated RNA Decay"; and International Application Publication No. WO 2004/010106 entitled "Methods of Assaying for Compounds that Inhibit Premature Translation Termination and Nonsense Mediated RNA Decay," each of which is incorporated herein by reference in its entirety. In particular, cell-based and cell-free assays can be used for the identification of a compound that suppresses premature translation termination and/or nonsense-mediated mRNA decay.

In one embodiment, the invention provides a method for identifying a compound that suppresses premature translation termination and/or nonsense-mediated mRNA decay, said method comprising: (a) contacting a compound or a member of a library of compounds with a cell containing a nucleic acid sequence comprising a reporter gene, wherein the reporter gene comprises a premature stop codon; and (b) detecting the expression of said reporter gene, wherein a compound that suppresses premature translation termination and/or nonsense-mediated mRNA decay is identified if the expression and/or activity of said reporter gene in the presence of a compound is increased relative to a previously determined reference range, or the expression and/or activity of said reporter gene in the absence of said compound or the presence of an appropriate control (e.g., a negative control). In another embodiment, the invention provides a method for identifying a compound that suppresses premature translation termination and/or nonsense-mediated mRNA decay, said method comprising: (a) contacting a compound or a member of a library of compounds with a cell-free extract and a nucleic acid sequence comprising a reporter gene, wherein the reporter gene comprises a premature stop codon; and (b) detecting the expression of said reporter gene, wherein a compound that suppresses premature translation termination and/or nonsense-mediated mRNA decay is identified if the expression and/or activity of said reporter gene in the presence of a compound is increased relative to a previously determined reference range, or the expression and/or activity of said reporter gene in the absence of said compound or the presence of an appropriate control (e.g., a negative control). In accordance with this embodiment, the cell-extract may be isolated from cells that have been incubated at about 0° C. to about 10° C. and/or an S10 to S30 cell-free extract.

In accordance with the invention, the step of contacting a compound with a cell or cell-free extract and a nucleic acid sequence in the reporter gene-based assays described herein is preferably conducted in an aqueous solution comprising a buffer and a combination of salts (such as KCl, NaCl and/or $MgCl_2$). The optimal concentration of each salt used in the aqueous solution is dependent on, e.g., the protein, polypeptide or peptide encoded by the nucleic acid sequence (e.g., the regulatory protein) and the compounds used, and can be determined using routine experimentation. In a specific embodiment, the aqueous solution approximates or mimics physiologic conditions. In another specific embodiment, the aqueous solution further comprises a detergent or a surfactant.

The assays of the present invention can be performed using different incubation times. In the a cell-based system, the cell and a compound or a member of a library of compounds may be incubated together for at least 0.2 hours, 0.25 hours, 0.5 hours, 1 hour, 2 hours, 3 hours, 4 hours, 5 hours, 6 hours, 8 hours, 10 hours, 12 hours, 18 hours, at least 1 day, at least 2 days or at least 3 days before the expression and/or activity of a reporter gene is measured. In a cell-free system, the cell-free extract and the nucleic acid sequence(s) (e.g., a reporter gene) can be incubated together before the addition of a compound or a member of a library of compounds. In certain embodiments, the cell-free extract are incubated with a nucleic acid sequence(s) (e.g., a reporter gene) before the addition of a compound or a member of a library of compounds for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day. In other embodiments, the cell-free extract, or the nucleic acid sequence(s) (e.g., a reporter gene) is incubated with a compound or a member of a library of compounds before the addition of the nucleic acid sequence(s) (e.g., a reporter gene), or the cell-free extract, respectively. In certain embodiments, a compound or a member of a library of compounds is incubated with a nucleic acid sequence(s) (e.g., a reporter gene) or cell-free extract before the addition of the remaining component, i.e., cell-free extract, or a nucleic acid sequence(s) (e.g., a reporter gene), respectively, for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day. Once the reaction vessel comprises the components, i.e., a compound or a member of a library of compounds, the cell-free extract and the nucleic acid sequence(s) (e.g., a reporter gene), the reaction may be further incubated for at least 0.2 hours, 0.25 hours, 0.5 hours, 1 hour, 2 hours, 3 hours, 4 hours, 5 hours, 6 hours, 8 hours, 10 hours, 12 hours, 18 hours, or at least 1 day.

The progress of the reaction in the reporter gene-based assays can be measured continuously. Alternatively, timepoints may be taken at different times of the reaction to monitor the progress of the reaction in the reporter gene-based assays.

The reporter gene-based assays described herein may be conducted in a cell genetically engineered to express a reporter gene. Alternatively, the reporter gene-based assays described herein may be conducted in a cell naturally expressing a reporter gene comprising a nonsense mutation in the coding region of the gene. Any cell or cell line of any species well-known to one of skill in the art may be utilized in accordance with the methods of the invention. Further, a cell-free extract may be derived from any cell or cell line of any species well-known to one of skill in the art. Examples of cells and cell types include, but are not limited to, human cells, cultured mouse cells, cultured rat cells or Chinese hamster ovary ("CHO") cells.

The reporter gene constructs utilized in the reporter gene-based assays described herein may comprise the coding region of a reporter gene and a premature stop codon that results in premature translation termination and/or nonsense-mediated mRNA decay. Preferably, the premature stop codon is N-terminal to the native stop codon of the reporter gene and is located such that the suppression of the premature stop codon is readily detectable. In a specific embodiment, a reporter gene construct utilized in the reporter gene-based assays described herein comprises the coding region of a reporter gene containing a premature stop codon at least 15 nucleotides, preferably 25 to 50 nucleotides, 50 to 75 nucleotides, 75 to 100 nucleotides, 100 to 300 nucleotides, 100 to 500 nucleotides, 100 to 750 nucleotides or 100 to 1000 nucleotides from the start codon in the open reading frame of the reporter gene. In another embodiment, a reporter gene construct utilized in the reporter gene-based assays described herein comprises the coding region of a reporter gene containing a premature stop codon at least 15 nucleotides, preferably 25 to 50 nucleotides, 50 to 75 nucleotides, 75 to 100 nucleotides, 100 to 150 nucleotides, 150 to 300 nucleotides, 300 to 500 nucleotides, 500 to 750 nucleotides or 500 to 1000 nucleotides from the native stop codon in the open reading frame of the reporter gene. In another embodiment, a reporter gene construct utilized in the reporter gene-based assays described herein comprises the coding region of a reporter gene containing a UAG and/or UGA premature stop codon. In yet another embodiment, a reporter gene construct utilized in the reporter gene based assays described herein comprises the coding region of a reporter gene, containing a premature stop codon in the context of UGAA, UGAC, UGAG, UGAU, UAGA, UAGC, UAGG, UAGU, UAAA, UAAC, UAAG or UAAU.

Any reporter gene well-known to one of skill in the art may be utilized in the reporter gene constructs described herein. Reporter genes may be obtained and the nucleotide sequence of the elements determined by any method well-known to one of skill in the art. The nucleotide sequence of a reporter gene can be obtained, e.g., from the literature or a database such as GenBank. Alternatively, a polynucleotide encoding a reporter gene may be generated from nucleic acid from a suitable source. Once the nucleotide sequence of a reporter gene is determined, the nucleotide sequence of the reporter gene may be manipulated using methods well-known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate reporter genes having a different amino acid sequence, for example to create amino acid substitutions, deletions, and/or insertions.

In a specific embodiment, a reporter gene is any naturally-occurring gene with a premature stop codon. Genes with premature stop codons that are useful in the present invention include, but are not limited to, the genes described herein. In an alternative embodiment, a reporter gene is any gene that is not known in nature to contain a premature stop codon. Examples of reporter genes include, but are not limited to, the gene encoding firefly luciferase, the gene coding renilla luciferase, the gene encoding click beetle luciferase, the gene encoding green fluorescent protein, the gene encoding yellow fluorescent protein, the gene encoding red fluorescent protein, the gene encoding cyan fluorescent protein, the gene encoding blue fluorescent protein, the gene encoding beta-galactosidase, the gene encoding beta-glucoronidase, the gene encoding beta-lactamase, the gene encoding chloramphenicol acetyltransferase, and the gene encoding alkaline phosphatase.

The compounds utilized in the assays described herein may be members of a library of compounds. In one embodiment, the compound is selected from a combinatorial library of compounds comprising peptoids; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small organic molecule libraries. In a specific embodiment, the small organic molecule libraries are libraries of benzodiazepines, isoprenoids, thiazolidinones, metathiazanones, pyrrolidines, morpholino compounds, or diazepindiones.

In certain embodiments, the compounds are screened in pools. Once a positive pool has been identified, the individual compounds of that pool are tested separately. In certain embodiments, the pool size is at least 2, at least 5, at least 10, at least 25, at least 50, at least 75, at least 100, at least 150, at least 200, at least 250, or at least 500 compounds.

Any method known in the art for measuring the expression of a protein may be used to measure the expression of functional readthrough protein produced in accordance with the invention. Non-limiting examples of such methods include immunoassays, such as Western blot, immunoprecipitation followed by sodium dodecyl sulfate polyacrylamide gel electrophoresis (SDS-PAGE), immunocytochemistry, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and an epitope tag using an antibody that is specific to the polypeptide encoded by the gene of interest. In specific embodiment, an antibody used in an immunoassay is specific to the C-terminal portion of the polypeptide used in an immunoassay. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody which recognizes the antigen to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 2003, Current Protocols in Molecular Biology, Vol. 1, John Wiley & Sons, Inc., New York at Chapter 10.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody which recognizes the antigen) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel a al, eds, 2003, Current Protocols in Molecular Biology, Vol. 1, John Wiley & Sons, Inc., New York at Chapter 10.

ELISAs comprise preparing antigen, coating the well of a 96 well microtiter plate with the antigen, adding a primary antibody (which recognizes the antigen) conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the primary antibody) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 2003, Current Protocols in Molecular Biology, Vol. 1, John Wiley & Sons, Inc., New York.

Methods for detecting the activity of a functional readthrough protein encoded by a reporter gene comprising a nonsense mutation will vary with the reporter gene used. Assays for the various reporter genes are well-known to one of skill in the art. For example, luciferase, beta-galactosidase ("beta-gal"), beta-glucuronidase ("GUS"), beta-lactamase, chloramphenicol acetyltransferase ("CAT"), and alkaline phosphatase ("AP") are enzymes that can be analyzed in the presence of a substrate and could be amenable to high throughput screening. For example, the reaction products of luciferase, beta-galactosidase ("beta-gal"), and alkaline phosphatase ("AP") are assayed by changes in light imaging (e.g., luciferase), spectrophotometric absorbance (e.g., beta-gal), or fluorescence (e.g., AP). Assays for changes in light output, absorbance, and/or fluorescence are easily adapted for high throughput screening. For example, beta-gal activity can be measured with a microplate reader. Green fluorescent protein ("GFP") activity can be measured by changes in fluorescence. For example, in the case of mutant GFPs that fluoresce at 488 nm, standard fluorescence activated cell sorting ("FACS") equipment can be used to separate cells based upon GFP activity.

The following describes a specific example of a cell-based reporter gene assay: A reporter construct is prepared that permits quantitative assessment of the level of translation readthrough based on luciferase-mediated chemoluminescence. Cells (e.g., HEK 293 cells) grown in medium (e.g., medium containing fetal bovine serum (FBS)) are stably transfected with the North American firefly luciferase gene containing a premature termination codon at amino acid position 190. In place of the threonine codon (adenosine-cytidine-adenosine (ACA)) normally present at this site, each of the 3 possible nonsense codons (UAA, UAG, or UGA) and each of the 4 possible nucleotides (C, U, A, G) at the contextually important downstream +1 position following the nonsense codon are introduced by site-directed mutagenesis. FIG. 1 provides a diagram of the several types of luciferase mRNAs incorporated into these constructs. Various concentrations of a compound of interest, a positive control (e.g., gentamicin), or a negative control (e.g., solvent alone (e.g., PBS, DMSO or water)) are added to the cells, and the amount of luminescence produced is determined after approximately four hours. Luminescence is determined using a ViewLux CCD imager (Perkin-Elmer, Turku, Finland). Luminescence data is normalized to that produced by solvent alone and the fold suppression over background is calculated as $\text{compound}_{light\ units}/\text{solvent}_{light\ units}$.

In control cells (treated with solvent only), translation of the luciferase gene is interrupted by the presence of the premature stop codon in the luciferase mRNA, and a truncated, non-functional luciferase protein is produced that cannot effectively catalyze the chemoluminescence reaction. However, in the presence of compounds that are able to induce ribosomal readthrough of the premature termination codon, full-length luciferase protein is produced, and the corresponding luminescence relative to control can be quantified.

The following describes a specific example of a cell-free reporter gene assay: A luciferase mRNA harboring a premature termination codon at position 190 (with a +1A) is prepared using the MegaScript in vitro T7-promoter transcription kit (Ambion, Austin, Tex.). The mRNA is incubated with a cytoplasmic extract prepared from cells (e.g., HeLa cells) that contain ribosomes and other cellular factors necessary for translation. Various concentrations of a compound of interest, a positive control (i.e., a compound with nonsense suppressing activity), or a negative control (e.g., solvent alone (e.g., PBS, DMSO or water)) are added to the in vitro reaction, and the amount of luminescence produced is determined after approximately 4 hours. Luminescence is determined using a ViewLux CCD imager (Perkin-Elmer, Turku, Finland). Luminescence data is normalized to that produced by solvent alone and the fold suppression over background is calculated as $\text{compound}_{light\ units}/\text{solvent}_{light\ units}$.

In control extracts (treated with solvent only), translation of the luciferase mRNA is interrupted by the presence of the premature stop codon in the luciferase mRNA, and a truncated, non-functional luciferase protein is produced that cannot effectively catalyze the chemoluminescence reaction. However, in the presence of compounds that are able to induce ribosomal readthrough of the premature termination codon, full-length luciferase protein is produced, and the corresponding luminescence relative to control can be quantified. A compound that is able to induce the production of full-length luciferase protein in a cytoplasmic extract that does not contain nuclei indicates that the nonsense readthrough activity of the compound occurs at the level of translation rather than that of transcription.

The nonsense suppressor activity of a compound can be evaluated in cells from a subject or animal model comprising a gene with a nonsense mutation relevant to a human disease, such as, e.g., cells from mdx mice. The mdx mice have a nonsense mutation in exon 23 of the dystrophin gene that generates a premature UAA (+1A) stop codon in dystrophin mRNA (Sicinski et al., Science 244: 1578-1580 (1989)) and results in nearly complete loss of full-length protein production.

The following describes a specific example of a reporter gene assay using cells from an animal model comprising a gene with a nonsense mutation relevant to a human disease: Primary myoblasts are derived from 1-day-old neonatal mdx mice using established methods (Neville et al. (eds), Methods in Cell Biology, volume 52, pages 85-116, San Diego, Academic Press (1998); and Barton-Davis et al., J. Clin. Invest. 104(4): 375-381 (1999)). After adherence to plastic dishes, cells are allowed to differentiate into myotubes in serum-containing medium to which a compound of interest or a positive control (i.e., a compound with nonsense codon suppressing activity) is added. Medium and compound are replenished every other day and cells are assayed for dystrophin and myosin by immunofluorescence at 12 days. Respective negative and positive controls comprised untreated mdx and wild-type C57/B16 mouse primary muscle cultures. The degree of staining was assessed using a-, +1, +2, +3, and +4 semiquantitative scale. A compound of interest that has nonsense suppressing activity will result in the production of full-length dystrophin.

An animal model system comprising a gene having a nonsense mutation relevant to a human disease may be used to confirm the nonsense codon suppressor activity of a compound identified in a reporter assay. For example, the nonsense codon suppressor activity of a compound may be assessed in mdx mice or CFTR mouse model. See, e.g., International Publication No. WO 2004/001010, which is incorporated by reference in its entirety, for other examples of animal model systems for human diseases.

In a specific example: mdx mice are administered a compound of interest, a positive control (i.e., a compound with nonsense codon suppressing activity), or a negative control (e.g., vehicle alone) for a period of 2 to 12 or more weeks. All mice are fed with Peptamen® isotonic liquid elemental diet (Nestlé, Serum CK activity was assessed using a commercially available NADH-linked kinetic assay (Diagnostic Chemicals Limited, Oxford, Conn.). Blood for serum creatine kinase (CK) measurements is collected at different intervals. At the end of the treatment periods, mice are sacrificed. Blood is collected to evaluate serum CK levels. Tibialis anterior (TA) muscles and extensor digitorum longus (EDL) muscles are removed for subsequent analysis. The TAs are rapidly frozen for immunofluorescence analysis of dystrophin incorporation into striated muscles. The EDLs are utilized for functional tests, including strength and susceptibility to eccentric contraction injury.

The primary antibody for dystrophin is a commercially available rabbit polyclonal antibody generated against a synthetic peptide corresponding to a sequence near the carboxyl-terminus of human dystrophin (Abcam 15277). This antibody cross-reacts with mouse dystrophin. The epitope is located further downstream (more toward the carboxyl terminus of the dystrophin protein) than is the site of the premature stop coded by exon 23 of the dystrophin gene in the mdx mouse.

Images are captured using a digital camera attached to an epifluorescent miscroscope and are processed with image-analysis software.

Isolated whole-muscle mechanics are performed on EDL muscles (including both EDL muscles in animals from which bilateral preparations could be made) using an apparatus designed for this purpose (Barton-Davis et al., PNAS USA 95(26): 15603-15607 (1998)). Specific force (the force per unit of cross-sectional area) of the EDLs is analyzed. Protection against mechanical injury induced by a series of 5 eccentric contractions with stretches of 10% of optimal length is evaluated; damage is determined as the percentage loss in force between the first and last eccentric contraction.

Serum CK activity is assessed using a commercially available NADH-linked kinetic assay (Diagnostic Chemicals Ltd., Oxford, Conn.).

The mdx mice treated with a compound with nonsense codon suppressing activity will demonstrate appreciable staining of dystrophin compared to muscles from untreated mdx mice. The mdx mice treated with a compound with nonsense codon suppressing activity will also have improved mean EDL specific force relative to the mean EDL force of untreated mdx mice or vehicle control-treated mdx mice. The mdx mice treated with a compound with nonsense codon suppressing activity will also protect against eccentric concentration injury. Further, the mdx mice treated with a compound with nonsense codon suppressing activity will have reduced serum CK relative to untreated mdx mice or vehicle control-treated mdx mice.

In another specific example: To evaluate the effect of a compound of interest on nonsense codon suppression, cftr−/− FABP-hCFTR-G542X mice are treated for a week or more with the compound, a negative control, or a positive control. The negative control group comprises untreated cftr−/− FABP-hCFTR-G542X mice. A positive control group comprises cftr−/− FABP-hCFTR-G542X mice that receive a compound known to have nonsense codon suppressing activity. CFTR-specific immunofluorescent staining is done on duodenal sections to demonstrate production of CFTR. The functional effects of the compound of interest on CFTR-mediated transepithelial chloride currents can also be assessed. A compound with nonsense codon suppressing activity will result in positive for CFTR immunofluororescent staining localized to the apical region of the epithelium of the sub-mucosal glands of the duodenum. Also, a compound with nonsense mutation suppressing activity will result in a strong increase in transepthelial chloride current following the addition of forskolin to increase cyclic adenosine monophosphate (cAMP).

Once a compound that suppresses premature translation termination and/or nonsense-mediated mRNA decay is identified, the structure of the compound may be determined utilizing well-known techniques or by referring to a predetermined code. For example, the structure of the compound may be determined by mass spectroscopy, NMR, vibrational spectroscopy, or X-ray crystallography.

To evaluate whether a portion of the effect of a compound on reporter assay described herein is mediated through changes in reporter gene mRNA levels, a real-time reverse transcription PCR assay is employed (Bustin, J. Mol. Endocrinol. 25(2): 169-193 (2000)). Cells (e.g., HEK 293 cells) grown in medium (e.g., medium containing FBS) are treated with a high concentration of the compound of interest for 48 hours. The experiment also includes negative control cells (treated with solvent alone) and positive control cells (treated with a compound previously shown to stabilize nonsense-mutation-containing mRNAs). Total RNA is extracted from cell lysates. Quantitative real-time PCR is performed using primers for the reporter gene mRNA and for 18S ribosomal RNA (rRNA). The levels of the reporter gene mRNA for treated cells relative to control cells are computed, employing the measurement of 18S rRNA as a normalization factor for the amount of starting material.

Chemical footprinting may be used to map sites of interaction of a compound of interest with rRNA. In these experiments, ribosomes prepared from cells (e.g., HeLa cells) are incubated with vehicle controls or the compound of interest and then treated with 2 chemical modifying agents (either dimethyl sulfate or kethoxal) that alter the structure of rRNA. Following the chemical modification reaction, rRNA is isolated, and primer extension analysis is performed using end-labeled oligonucleotides that hybridize to different regions of the human 28S, 18S, and 5.8S rRNAs. The products of the primer extension are resolved on 6% polyacrylamide gels. Accessibility of the rRNA to chemical modification by dimethyl sulfate or kethoxal is visualized as the appearance, disappearance, or change in intensity of bands on the gel; any of these events is considered indicative of a potential effect of the compound at specific regions on the rRNA. The appearance of a band on the gel is consistent with newly induced accessibility to the chemical modifying agent (e.g., as a result of compound interactions that caused conformational changes within the rRNA). Conversely, the disappearance of a band is consistent with newly induced inaccessibility of the chemical modifying agent (e.g., resulting from protection of a site due to compound binding or alterations in base-pairing within the rRNA).

The specificity of a compound of interest for its ability to induce specific ribosomal readthrough of a premature stop codon, and its inability to induce nonspecific ribosomal readthrough of a normal stop codon can be evaluated in vitro. For example, a luciferase reporter may be linked to an additional protein (e.g., the CD40 protein). CD40 is a cell surface receptor expressed by B-lymphocytes and other immune cells; its mRNA offers convenient 3'-UTR sequences and the protein is an appropriate size for Western blotting detection of potential protein elongation.

In this assay, cells (e.g., HEK 293 cells) grown in medium (e.g., medium containing fetal bovine serum (FBS)) are stably transfected with a gene encoding a luciferase-CD40 fusion protein. In place of the threonine codon (ACA) normally present at position 190 of luciferase, a UGA nonsense codon is introduced by site-directed mutagenesis. In addition, the 3'-UTR of the CD40 protein is introduced downstream of the luciferase UAA termination codon. For each construct, 6 histidine amino acids (6X-His) are included at the 5' end of the luciferase gene to facilitate purification of the proteins of interest from the cell lysates. In addition, an Xpress™ epitope tag is included to permit isolation of the proteins of interest at the time of Western blot analysis.

Figure 2:
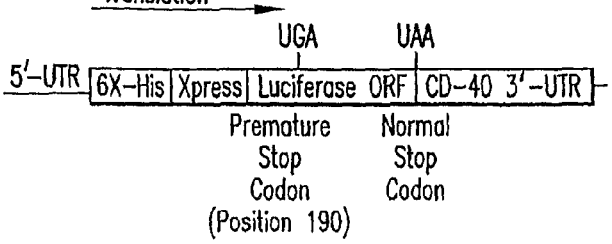

The features of the mRNA transcribed from these constructs and the expected outcomes with various conditions and assumptions are depicted in FIG. 2. In untreated cells, only the truncated luciferase protein should be observed (FIG. 2A). In cells treated with a compound with nonsense suppressor activity that has specific readthrough of the normal stop codon, both the truncated and the full-length luciferase protein should be made (FIG. 2B). If, however, a compound has the capacity to induce nonspecific ribosomal readthrough of the normal stop codon, then readthrough of both the inserted premature stop codon at position 190 and of the normal stop codon at the end of the luciferase ORF would be expected. This would result in elongation of the luciferase protein by the 84 amino acids encoded by the CD30 3'-UTR, and a 9-kD increase in molecular weight (from 66 kD to 75 kD) would be detected by Western blotting. If this occurred, the molecular weight of the construct would be increased and all 3 proteins (truncated, luciferase, and luciferase-CD40) would be produced (FIG. 2C). Further constructs are made as markers. The negative control construct encodes only the full length luciferase mRNA (FIG. 2D): The negative control construction encodes only the full length luciferase mRNA (FIG. 2D). The positive control construct encodes the elongated luciferase-CD40 mRNA and is created by engineering a sense (nonstop) mutation (CAA) at the end of the luciferase ORF (FIG. 2E).

Cells are treated with a compound of interest for a period of time (e.g., 72 hours) and then cell lysates are made. Cell lysates are mixed with magnetic nickel-charged agarose beads designed to capture the 6X-His-tagged proteins. Following the protein-capture step, the proteins are separated on a 12.5% polyacrylamide gel and Western blot analysis is performed using an anti-Xpress antibody.

A more general but less sensitive and specific approach to the theoretical problem of nonspecific stop codon readthrough may be performed using 2-dimensional gel electrophoresis (O'Farrell, J. Biol. Chem. 250(10):4007-421 (1975)). A compound that induces ribosomal readthrough of normal stop codons might cause abnormally elongated proteins, with consequent shifts in electrophoretic mobility patterns due to increases in molecular weight and/or changes in electric charge. In one example of such an assay, duplicate samples of cells (e.g., HEK 293 cells) harboring a UGA (+1A) stop codon at the 190 amino acid position of the luciferase-reporter are treated with a compound of interest or with vehicle for a period of time (e.g., 48 hours). Aliquots of cells are assayed to ensure evidence of compound-induced ribosomal readthrough of luciferase in the standard cell-based reporter assay. 2-dimensional electrophoresis and computerized analysis using Phoretix software are then performed.

A more specific experiment to address the potential for nonspecific stop codon readthrough in an animal disease model may be undertaken by assessing a compound's action on translation of a single abundant mRNA in vivo. For example, mdx mice are treated daily for a period of time (e.g., 28 days) with a compound of interest, a positive control, or vehicle, after which muscle tissue is collected from individual animals. Muscle from an untreated wild-type C57/B10 mouse is also analyzed. It is also known that the mRNA for β-tubulin (an abundant protein in mouse muscle) has a UAA (+1A) termination codon at the end of the ORF and a second in-frame UAA (+1A) stop codon downstream in its 3'-UTR. Between these 2 stop codons is an intervening sequence of 126 nucleotides that, theoretically, could code for a 42-amino-acid extension of the mouse β-tubulin protein. FIG. 3 provides a schematic of the β-tubulin mRNA. If compound of interest has the capacity to induce nonspecific ribosomal readthrough of stop codons, it would be expected that the β-tubulin protein would be increased in size by ≥42 amino acids (~5 kD) and that this change would be detectable by Western blotting.

The specificity of a nonsense codon suppressor agent for its ability to induce specific ribosomal readthrough of a premature stop codon, and its inability to induce nonspecific readthrough of a normal stop codon can be evaluated in biological samples from subjects (in particular, humans) administered the nonsense codon suppressor agent. For example, blood samples may be obtained from nonsense codon suppressor agent-treated subjects (e.g., humans) just before dosing and at various time points (e.g., 2, 4, 6, 8, 12, 24, 48 and 72 hours) following dosing. The blood samples or samples derived from blood samples (e.g., PBMCs and plasma obtained from the subjects may be pooled before analysis. For example, blood samples or samples derived from the blood samples from subjects of the same sex from the same time point may be pooled before analysis. Alternatively, the blood sample or sample derived from the blood sample from each subject may be analyzed individually.

Peripheral blood mononuclear cells (PBMCs) and plasma are separated, and optionally, may be frozen and stored before use. The PBMCs and plasma are loaded onto polyacrylamide gels optimized to obtain maximal separation between elongated readthrough protein products, subject to electrophoresis, and transferred to nitrocellulose membranes (or other appropriate membranes, e.g., nylon membranes) for immunoblotting. Proteins, such as C-reactive protein (CRP), $B_2$ microglobulin and cystatin C, may be evaluated for nonspecific readthrough of normal stop codons. As controls, wild-type and corresponding elongated proteins may be used. Immunoblotting may be performed using a primary antibody specific for the protein evaluated and a secondary antibody specific for the primary antibody comprising horseradish-peroxidase conjugates.

The subjects administered the nonsense codon suppressor agent may include subjects known to have a gene comprising a nonsense mutation and in those cases, the production of functional readthrough protein encoded by the gene may be used as a positive control for specific readthrough of nonsense codons. The subjects administered the nonsense codon suppressor agent may also include subjects not known to have a gene comprising a nonsense mutation. In those cases, the plasma from subjects treated with the nonsense codon suppressor agent may be added to media of cells (e.g., HEK 293 cells) stably transfected with a reporter gene containing a premature stop codon (e.g., a firefly luciferase reporter gene containing a UGA premature stop codon at amino acid residue 190), or incubated with a cell extract and a reporter gene containing a premature stop codon. The treated cells, or the treated cell extracted can be assayed for readthrough of the premature stop codon as a positive control.

The toxicity and/or efficacy of a compound identified in accordance with the invention can be determined by standard pharmaceutical procedures in cell cultures or experimental animals, e.g., for determining the LD50 (the dose lethal to 50% of the population) and the ED50 (the dose therapeutically effective in 50% of the population). Cells and cell lines that can be used to assess the cytotoxicity of a compound identified in accordance with the invention include, but are not limited to, peripheral blood mononuclear cells (PBMCs), Caco-2 cells, and Huh7 cells. The dose ratio between toxic and therapeutic effects is the therapeutic index and it can be expressed as the ratio LD50/ED50. A compound identified in accordance with the invention that exhibits large therapeutic indices is preferred. While a compound identified in accordance with the invention that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a compound identified in accordance with the invention for use in humans. The dosage of such agents lies preferably within a range of circulating concentrations that include the ED50 with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the IC50 (i.e., the concentration of the compound that achieves a half-maximal inhibition of symptoms) as determined in cell culture. Such information can be used to more accurately determine useful doses in humans. Levels in plasma may be measured, for example, by high performance liquid chromatography.

Specific examples of toxicology assays include the following:

Male and female Sprague-Dawley rats are administered vehicle or various doses of a compound identified daily for a period of time (e.g., 28 days). Several rats/sex/group are terminated after a period of days (e.g., 28 day), several other rats/sex/group continue on an additional recovery period (e.g., a 4 week recovery period) after the period of dosing and other rats rats/sex/group are used in toxicokinetic evaluations on so many hours and days postdose (e.g., days 1 and 28 at 0.5, 1.5, 4, 8, 12, and 24 hr postdose).

Male and female beagle dogs are administered vehicle or various doses of a compound identified for a period of time (e.g., 28 days). Several dogs/sex/group are terminated after the dosing period. Other dogs/sex/group continue an additional recovery period (e.g., a 4 week recovery period) and for toxicokinetics, samples are collected hours and days postdose (e.g., on days 1 and 28 at 1, 2, 4, 8, 12, 16, and 24 hr postdose).

Dose analysis is performed by HPLC to verify that animals received the intended doses. Cage-side observations are performed twice per day and detailed clinical observations and body weights are recorded weekly. Food consumption for the treatment duration is measured. Ophthalmoscopy and electrocardiography (dogs only) is performed pretreatment and on the last day of the treatment period. Hematology, coagulation, clinical chemistry, and urinalysis parameters are evaluated at baseline (dogs only) and on the last day of the treatment period (all animals) and at of the recovery period for recovery animals. At the end of treatment or recovery, procedures include a complete gross necropsy examination, removal and weighing of organs, and formalin-fixation of preserved tissues for microscopic analysis. Plasma analyses for compound concentrations employ an HPLC and tandem mass spectroscopy method, validated for each animal species. Noncompartmental methods are used to assess pharmacokinetic parameters. Body weights, food consumption, clinical pathology, and organ weights are analyzed with 1-way analysis of variance (ANOVA) and pairwise comparisons of each dose with control are performed with Dunnett's test.

In a preferred embodiment, the nonsense codon suppressor agent used in accordance with the invention induces specific ribosomal readthrough of a premature stop codon, but does not induce nonspecific readthrough of a normal stop codon. Any assay known in the art or described herein can be performed to evaluate specific ribosomal readthrough of a premature stop codon by a compound of interest.

A nonsense codon suppressor agent used in accordance with the invention may interact with 28S rRNA, 18S rRNA and/or 5.8S rRNA. In certain embodiments, the nonsense codon suppressor agent used in accordance with the invention binds to 28S rRNA. In other embodiments, the nonsense codon suppressor agent used in accordance with the invention does not bind to 18S rRNA. In some embodiments, the nonsense codon suppressor agent binds indirectly to rRNA through an interaction with another protein. In certain other embodiments, the nonsense codon suppressor agent used in accordance with the invention does not exhibit significant antibacterial activity against a gram-negative microorganism and/or a gram-positive microorganism. In a preferred embodiment, the nonsense codon suppressor agent used in accordance with the invention has few (if any) adverse or unwanted side effects when administered systemically (e.g. orally) to subject (preferably, a human). In a specific embodiment, the nonsense codon suppressor agent does not, cause renal failure and/or hearing problems (e.g., hearing loss) when administered orally to a subject (preferably, a human).

5.5 Functional Readthrough Proteins

The present invention provides a functional readthrough protein(s) encoded by a nucleic acid sequence comprising nonsense mutation, which protein(s) is produced by the methods described herein. In certain embodiments, the functional readthrough protein(s) is a functional non-wild-type protein. In specific embodiments, the functional readthrough protein(s) is a full-length non-wild-type protein. In other embodiments, the functional readthrough protein is composed of the same amino acid sequence as the corresponding wild-type protein.

The present invention provides a functional readthrough protein(s) encoded by a nucleic acid sequence comprising a mutation (e.g., a deletion, insertion and/or substitution) that results in a different stop codon in the RNA transcribed from the nucleic acid sequence relative to the stop codon found in the RNA coding for the corresponding wild-type protein. In certain embodiments, the functional readthrough protein(s) is functional non-wild-type protein. In specific embodiments, the functional readthrough protein is a full-length non-wild-type protein.

In a specific embodiment, the present invention provides methods of producing a functional readthrough protein encoded by a nucleic acid sequence comprising a mutation (e.g., a deletion, insertion and/or substitution) that results in a different stop codon in the RNA transcribed from the nucleic acid sequence relative to the normal stop codon (i.e., the stop codon found in the RNA coding for the corresponding wild-type protein), the methods comprising contacting a cell comprising the nucleic acid sequence with a nonsense suppressor agent. Alternatively, the methods comprise contacting a cell-free extract with the nucleic acid and a nonsense codon suppressor agent. In another embodiment, the present invention provides methods of producing a functional readthrough protein encoded by a gene comprising a mutation (e.g., a deletion, insertion and/or substitution) that results in a different stop codon in the RNA transcribed from the gene relative to the normal stop codon (i.e., the stop codon found in the RNA coding for the corresponding wild-type protein), the methods comprising administering to a subject (preferably a human) in need thereof an effective amount of a nonsense codon suppressor agent. In accordance with these embodiments, the nonsense codon suppressor agent reads through the different stop codon to a second stop codon to produce the functional readthrough protein.

In a specific embodiment, the present invention provides methods of producing a functional readthrough protein encoded by a gene(s) comprising a nonsense mutation in the coding region of the gene(s), the methods comprising contacting a cell containing the gene(s) with a nonsense codon suppressor agent. In another embodiment, the present invention provides methods of producing a functional readthrough protein encoded by a gene(s) comprising a nonsense mutation in the coding region of the gene(s), the methods comprising administering to a subject (preferably, a human) in need thereof an effective amount of a nonsense codon suppressor agent. In certain embodiments, the subject has, or is predisposed or susceptible to a disease associated with a nonsense mutation in the gene(s).

In certain embodiments, the functional readthrough protein(s) produced in accordance with the methods of the invention is found at the same location in a cell that the corresponding wild-type protein is found. For example, in certain embodiments, the functional readthrough protein(s) and the corresponding wild-type protein are found on the surface of the cell. In other embodiments, the functional readthrough protein(s) is found at a different location in a cell than the corresponding wild-type protein is found. In a specific embodiment, the functional readthrough protein(s) produced in accordance with the methods of the invention is found in the nucleus of a cell while the corresponding wild-type protein is found in the cytoplasm or on the surface of the cell. In another embodiment, the functional readthrough protein(s) produced in accordance with the methods of the invention is found in the cytoplasm or on the surface of the cell while the corresponding wild-type protein is found in the nucleus. The localization of functional readthrough protein(s) in/on a cell(s) can be measured/determined using techniques known to one of skill in the art. In a specific embodiment, the localization of functional readthrough protein(s) in/on a cell can be measured/determined by immunofluorescence. In certain embodiments, the following immunofluorescence protocol is used to measure/determine localization of a functional readthrough protein(s) in/on a cell(s):

1. Cells are rehydrated with PBS (e.g., 5 minutes) in Coplin jars.
2. Cells are blocked with preimmune mouse serum for a period of time (e.g., 20 minutes).
3. A primary antibody is applied for a period of time.
4. Slides are washed 2-5 times in PBS, and then incubated with secondary antibody for a period of time.
5. Nuclei are identified by staining, e.g. DAPI staining.
6. Cells are imaged on a digital confocal fluorescent microscope, and images are captured with, e.g., IPLab Spectrum software.
7. Staining is classified/scored as (0) absent, (1) perinuclear, (2) peripheral, and (3) surface.
8. Images are captured, e.g. on an Olympyus IX170 inverted epifluorescence microscope equipped with step motor, filter wheel assembly (Ludl Electronics Products, Hawthorne, N.Y.), and 83,000 filter set (Chroma Technology, Brattleboro, Vt.) and SenSys-cooled charge-coupled high-resolution camera (Photometrics, Tucson, Az).
9. Partial deconvolution of images is performed, e.g., using IPLab software (Scanalytics, Fairfax, Va.).

In a specific embodiment, the functional readthrough protein(s) produced in accordance with the methods of the invention is a functional CFTR readthrough protein(s). In certain embodiments, the functional CFTR readthrough protein(s) is found perinuclear, peripherally and/or on the surface of nasal cells as measured/determined by methods known in the art, e.g., immunofluoroesence. In a preferred embodiment, the functional CFTR readthrough protein is found on the surface of nasal cells as measured/determined by immunofluorescence. In a specific example, the amount of functional CFTR readthrough protein in the perinculear, peripheral and/or surface is measured/determined by the following immunofluorescence protocol:

1. Nasal cells are rehydrated with PBS (e.g., 5 minutes) in Coplin jars.
2. Cells are blocked with preimmune mouse serum for a period of time (e.g., 20 minutes).
3. The primary antibody (e.g., mouse monoclonal anti-CFTR 24-1, directed to the carboxy terminal 4 amino acids of full-length CFTR) is applied at, e.g., a dilution of 1:100 for a period of time (e.g., two hours).
4. Slides are washed three times in PBS, and then incubated with secondary antibody (e.g., Goat anti-mouse IgG, AlexaFluor 596, Molecular Probes, Portland, Oreg.) for a period of time (e.g., one hour).
5. Nuclei are identified by DAPI staining.
6. Cells are imaged on a digital confocal fluorescent microscope, and images are captured with, e.g., IPLab Spectrum software.
7. CFTR staining is classified/scored as (0) absent, (1) perinuclear, (2) peripheral, and (3) surface. In a specific embodiment, at least 50 epithelial cells from random areas of each slide are evaluated and scored.
8. Images are captured, e.g., on an Olympus IX170 inverted epifluorescence microscope equipped with step motor, filter wheel assembly (Ludl Electronics Products, Hawthorne, N.Y.), and 83,000 filter set (Chroma Technology, Brattleboro, Vt.) and SenSys-cooled charge-coupled high-resolution camera (Photometrics, Tucson, Ariz.).
9. Partial deconvolution of images is performed, e.g., using IPLab software (Scanalytics, Fairfax, Va.).

In certain embodiments, the functional readthrough protein(s) produced in accordance with the methods of the invention only differs from the corresponding wild-type protein(s) at the amino acid residue in the functional readthrough protein(s) that was inserted at the position encoded by the premature termination codon. In other embodiments, the functional readthrough protein(s) produced in accordance with the methods of the invention differs from the corresponding wild-type protein(s): (i) at the amino acid residue in the functional readthrough protein(s) that was inserted at the position encoded by the premature termination codon; and (ii) at an amino acid residue(s) in the functional readthrough protein(s) other than those encoded by a premature termination codon.

The amino acid sequence of the functional readthrough protein(s) produced by the methods of the invention may be determined by sequencing the protein(s) produced by a cell comprising a nucleic acid sequence of interest (i.e., the nucleic acid sequence comprising the nonsense mutation(s) of interest). In certain embodiments, the cell naturally comprises the nucleic acid sequence. In a specific embodiment, the cell is a cell from a patient that is receiving or will be receiving a nonsense codon suppressor agent(s). In other embodiments, the cell has been engineered to comprise the nucleic acid sequence.

In certain embodiments, the functional readthrough protein(s) produced in accordance with the methods of invention comprises a tyrosine, cysteine or tryptophan at the position that corresponds to the nonsense codon in the RNA from which the protein is translated. In specific embodiments, the functional readthrough protein(s) produced in accordance with the methods of the invention comprises a tyrosine at the position that corresponds to a UAA or UAG nonsense codon in the RNA from which the protein is translated. In other embodiments, the functional readthrough protein(s) produced in accordance with the methods of the invention comprises a cysteine or tryptophan at the position that corresponds to a UGA nonsense codon in the RNA from which the protein is translated.

Table 10 below provides a list of diseases associated with a nonsense mutation in a gene(s). The table provides the name of the gene associated with the disease, the GenBank Accession No. of the nucleic acid of at least the coding region of the gene, the GenBank Accession No. of the protein encoded by the gene, representative nonsense mutations found in the gene that are associated with the disease, and a reference(s) regarding the disease association with the nonsense mutation in the gene. In certain embodiments, the functional readthrough protein produced in accordance with the methods of the invention comprises the amino acid sequence of the corresponding wild-type protein except at the position of the amino acid residue identified in Table 10 where a nonsense mutation in the gene is associated with a disease. In accordance with this embodiment, the amino acid residue at that position is not the 1 amino acid residue found in the corresponding wild-type protein and is any one of the other 19 amino acid residues. Thus, for example, in the case of 3-M syndrome, the functional readthrough protein could comprise any other amino acid residue except an arginine at position 1445.

TABLE 10

| Disease | Gene | Nucleic Acid GenBank Accession No. | Protein GenBank Accession No. | Mutation | Reference |
|---|---|---|---|---|---|
| 3-M syndrome | cullin 7 (CUL7) | NM_014780.3 | NP_055595 | R1445X | Huber et al., Nat Genet. 2005 Oct; 37(10): 1119-24 |
| Alpers syndrome | POLG | NM_002693 | NP_002684 | E873X | Chan et al., DNA Repair (Amst). 2005 Dec 8; 4(12): 1381-9. |
| Arrhythmogenic right ventricular cardiomyopathy | plakophilin-2 | NM_001005242 | NP_001005242 | R413X | Syrris et al., Circulation. 2006 Jan 24; 113(3): 356-64 |
| Ataxia telangiectasia | ATM | | AAB65827 | 610G > T (G204X) | Jiang et al., J Neurol Sci. 2006 Feb 15; 241(1-2): 1-6 |
| | | | | 6913C > T (Q2305X) | Saviozzi et al., Hum Mutat. 2003 Apr; 21(4): 450 |
| Atherosclerosis | apolipoprotein A-I | | | Q84X | Matsunaga et al., Proc Natl Acad Sci USA. 1991 Apr 1; 88(7): 2793-7 |
| autoinflammatory syndrome | PYPAF1 | AF420469 | AAL65136 | R554X | Jeru et al., Arthritis Rheum. 2006 Feb; 54(2): 508-14. |
| autosomal recessive non-syndromic hearing impairment (ARNSHI) | connexin-26 (GJB2) | AF479776.1 | AAL87696 | W24X | Alvarez et al., Am J Med Genet A. 2005 Sep 1; 137(3): 255-8 |
| Bartter syndrome | BSND | NM_057176 | NP_476517 | Q32X | Kitanaka et al., Pediatr Nephrol. 2006 Feb; 21(2): 190-3 |
| Benign hereditary chorea (BHC) | thyroid transcription factor 1 gene (TITF1) | BT009773 | AAP88775 | 745C > T (Q249X) | do Carmo Costa et al., Neurogenetics. 2005 Dec; 6(4): 209-15 |
| Brugada syndrome | SCN5A | AY038064 | AAK74065 | W822X | Keller et al., Can J Cardiol. 2005 Sep; 21(11): 925-31 |
| | | | | R1623X | Makiyama et al., J Am Coll Cardiol. 2005 Dec 6; 46(11): 2100-6 |
| Charcot-Marie-Tooth disease (CMT) type 4A (CMT4A) | ganglioside-induced differentiation-associated protein 1 gene (GDAP1) | NM_018972.1 | NP_061845 | c.581C > G, S194X | Nelis et al., Neurology. 2002 Dec 24; 59(12): 1865-72. |
| Charcot-Marie-Tooth disease | connexin (Cx) 32 | NM_000166.2 | NP_000157 | W132X | Lin et al., Tohoku J Exp Med. 1999 Jul; 188(3): 239-44. |
| chronic haemolytic anaemia | AK-1 | NM_000476.1 | NP_000467 | R107X | Bianchi et al., Br J Haematol. 1999 Apr; 105(1): 75-9. |
| Colorectal cancer | APC | NM_000038 | NP_000029 | R283X | |
| | MSH2 | | P43246 | E422X | Tanyi et al., World J Gastroenterol. 2006 Feb 28; 12(8): 1192-7. |
| congenital adrenal hyperplasia | CYP21A2 | NM_000500 | NP_000491 | 2557C > T (R445X) | Friaes et al., 2006, Mol Genet Metab Epub Jan 19 |
| Congenital afibrinogenaemia | FGA | AF361104 | AAK31372 AAK31373 | 3108C > T (Q150 X) | Wu et al., Blood Coagul Fibrinolysis. 2005 Apr; 16(3): 221-6. |
| Congenital hemidysplasia with ichthyosiform nevus and limb defects (CHILD) syndrome | NAD(P)H steroid dehydrogenase-like [NSDHL] | NM_015922 | NP_057006 | E151X | Hummel et al., Am J Med Genet A. 2003 Oct 15; 122(3): 246-51. |
| Congenital lactase deficiency | lactase (LCT) | NM_002299 | NP_002290 | 4170T > A (Y1390X) | Kuokannen et al., Am J Hum Genet. 2006 Feb; 78(2): 339-44 |
| Congenital muscular dystrophy | laminin alpha2 gene (LAMA2) | | AAB18388 | R2578X | Coral-Vazquez et al., J Hum Genet. 2003; 48(2): 91-5 |
| | | | | W166X; S2553Y; V2587X | Mendell et al., Hum Mutat. 1998; 12(2): 135 |
| Cystic fibrosis | CTFR | NM_000492 | NP_000483 | Q414X | Dork et al., Hum Genet. 1994 Jan; 93(1): 67-73. |
| | | | | 1609C > T (Q493X) | |
| | | | | 3976 (TGG to T) W1282X | Shoshani et al., Am J Hum Genet. 1992 Jan; 50(1): 222-8. |

TABLE 10-continued

| Disease | Gene | Nucleic Acid GenBank Accession No. | Protein GenBank Accession No. | Mutation | Reference |
|---|---|---|---|---|---|
| | | | | W1316X | Hamosh et al., J Clin Invest. 1991 Dec; 88(6): 1880-5. |
| | | | | R553X | Chen et al.,: J Hum Genet. 2005; 50(12): 674-8 |
| | | | | G542X | Bienvenu et al., J Med Genet. 1993 Jul; 30(7): 621-2. |
| | | | | R1162X | Rolfini et al., J Clin Invest. 1993 Dec; 92(6): 2683-7. |
| | | | | Y122X | Bensalem et al., Mol Cell Proteomics. 2005 Oct; 4(10): 1591-601 |
| | | | | S1455X | Salvatore et al., Am J Med Genet A. 2005 Mar 1; 133(2): 207-8. |
| | | | | E822X | Tzetis et al., Hum Genet. 2001 Dec; 109(6): 592-601 |
| | | | | E60X, R764X | Strandvik et al., Genet Test. 2001; 5(3): 235-42 |
| | | | | Q1291X | Feldman et al., Hum Mutat. 2001 Apr; 17(4): 356. |
| | | | | Y849X | Castaldo et al., Hum Mutat. 1999 Sep 19; 14(3): 272 |
| | | | | S434X | Mittre et al., Hum Mutat. 1999 Aug 19; 14(2): 182 |
| | | | | L88X | Macek et al., Hum Mutat. 1992; 1(6): 501-2 |
| | | | | R1158X | Roncetto et al., Genomics. 1992 Feb; 12(2): 417-8 |
| | | | | G6542X | |
| Diabetes | Ceruloplasmin | NM_000096.1 | NP_000087 | W858X | Takahashi et al., Hum Mol Genet. 1996 Jan; 5(1): 81-84. |
| duchenne muscular dystrophy | Dystrophin | HUMDYS | AAA53189 | L1417X | Disset et al., Hum Mol Genet. 2006 Mar 15; 15(6): 999-1013 |
| | | | | Q3625X | Suminaga et al., Pediatr Res. 2004 Nov; 56(5): 739-43 |
| | | | | Q492X | Ito et al., J Neurol. 2003 May; 250(5): 581-7 |
| Dwarfism | GH-releasing hormone receptor (GHRHR) | | Q02643 | E72X | Baumann, Growth Horm IGF Res. 1999 Jun; 9 Suppl B: 24-9; discussion 29-30. |
| | Growth hormone receptor | | | R43X | Putzolu et al., J Endocrinol Invest. 1997 May; 20(5): 286-8 |
| Epidermolytic hyperkeratosis | Keratin 10 (KRT10) | NM_000421 | NP_000412 | Q434X | Muller et al., 2006, Hum Mol Genet Epub Feb. 27. |
| Epidermodysplasia verruciformis | EVER2 | AY099358 | AAM44454 | 568C > T (R190X) | Sun et al., Clin Exp Dermatol. 2005 Sep; 30(5): 573-4 |
| episodic ataxia | CACNA1A | | | 1547X | Jen et al., Neurology. 1999 Jul 13; 53(1): 34-7. |
| Fabry disease | alpha-galactosidase A (alpha-Gal A) | NM_000169 | NP_000160 | Y86X and R342X | Lee et al., Clin Genet. 2000 Sep; 58(3): 228-33. |
| | | | | W162X | Rosenberg et al., Hum Mutat. 2000 Feb; 15(2): 207-8. |
| | | | | R220X | Maki et al., Clin Nephrol. 2004 Mar; 61(3): 185-90. |
| | | | | Y222X | Yang et al., Clin Genet. 2003 Mar; 63(3): 205-9. |
| | | | | E251X | Altarescu et al., Clin Genet. 2001 Jul; 60(1): 46-51. |
| | | | | R301X | Okumiya et al., Jpn J Hum Genet. 1996 Sep; 41(3): 313-21. |
| Familial central diabetes insipidus | arginine vasopressin-neurophysin II (AVP-NPII) | | | Q83X | Bullman et al., Exp Clin Endocrinol Diabetes. 2002 May; 110(3): 134-7. |
| | | | | E82X | J Clin Endocrinol Metab. 1998 Mar; 83(3): 995-7. |
| familial cylindromatosis | CYLD | NM_015247 | NP_056062 | R758X | Oiso et al., 2004, Br J Dermatol 151: 1084-6 |
| Familial hypobetalipoproteinemia (FHBL) | apoB | | | Y1220X | Lancellotti et al., J Hepatol. 2005 Jul; 43(1): 188-91. |
| | | | | Q1755X | Ohashi et al., Arterioscler Thromb Vasc Biol. 1998 Aug; 18(8): 1330-4. |
| Familial hypercholesterolemia | PCSK9 | | | Y142X and C679X | Cohen et al., Nat Genet. 2005 Feb; 37(2): 161-5 |
| familial type 2 diabetes | CD36/fatty acid translocase (FAT) | NM_001001548.1 | NP_001001548 | L360X | Lepretre et al., Hum Mutat. 2004 Jul; 24(1): 104. |
| | low density lipoprotein (LDL) receptor | | AAP36025 | W422X | Zakharova et al., BMC Med Genet. 2005 Feb 8; 6:6. |
| | | | | E92X and | Salazar et al., Hum Mutat. 2002 |

TABLE 10-continued

| Disease | Gene | Nucleic Acid GenBank Accession No. | Protein GenBank Accession No. | Mutation | Reference |
|---|---|---|---|---|---|
| | | | | C371X | Apr; 19(4): 462-3. |
| | | | | E296X | Genschel et al., Hum Mutat. 2001 Apr; 17(4): 354. |
| | | | | K790X | Maruyama et al., Arterioscler Thromb Vasc Biol. 1995 Oct; 15(10): 1713-8. |
| Glycogen storage disease type IIIa (GSD IIIa) | AGL | | | W1327X | Endo et al., J Hum Genet. 2005; 50(10): 538-42 |
| hemochromatosis | transferrin receptor-2 | NM_003227.2 | NP_003218 | Y250X | Rivers et al., Genet Test. 2001 Summer; 5(2): 131-4. |
| Hemophilia A | factor VIII | | AAA52420 | W1029X, Y1792X, W1535X; R2116X; R427X | Hill et al., Haemophilia. 2005 Mar; 11(2): 133-41. Jayandharan et al., Haemophilia. 2005 Sep; 11(5): 481-91 |
| | | | | S1395X | James et al., Blood. 2005 Nov 1; 106(9): 3043-8 |
| | | | | Q139X, R583X, R1941X, R1966X, R2116X | David et al., J Thromb Haemost. 2003 Jan; 1(1): 139-46. |
| | | | | Q1778X | Moller-Murlang et al., Hum Mutat. 1999; 13(6): 504. |
| Hemophilia B | Factor IX | | | R333X, R252X | James et al., Blood. 2005 Nov 1; 106(9): 3043-8 |
| | | | | C31118X | Lorenzo et al., Haemophilia. 2000 May; 6(3): 195-7. |
| | | | | R116X | Walter et al., Thromb Haemost. 1994 Jul; 72(1): 74-7. |
| | | | | R338X | Driscoll et al., Blood. 1989 Aug 1; 74(2): 737-42. |
| hereditary tyrosinemia type I | fumarylacetoacetate hydrolase (FAH) | NM_000137 | NP_000128 | W262X | Dreumont et al., Biochem Biophys Res Commun. 2004 Nov 5; 324(1): 186-92. |
| hyperchylomicronemia | APOA5 | AY358749.1 | AAQ89109 | Q139X | Marcais et al., J Clin Invest. 2005 Oct; 115(10): 2862-9. |
| hypertriglyceridemic type 2 diabetes | Lipoprotein lipase (LPL) | | AAH11353 | S447X | Yang et al., Hum Mutat. 2003 Apr; 21(4): 453. |
| Hypothyroidism | DUOX2 | NM_014080.3 | NP_054799 | c.2524C > T (R842X) | Vigone et al., Hum Mutat. 2005 Oct; 26(4): 395. |
| | Thyroglobulin | | NP_003226 | 886CT (R277X) | Rivolta et al., J Clin Endocrinol Metab. 2005 Jun; 90(6): 3766-70 |
| | thyrotropin receptor (TSHR) | M31774.1 | AAA36783 | R609X | Richter-Unruh et al., Thyroid. 2004 Nov; 14(11): 971-4. |
| | Prop1 | NM_006261.2 | NP_006252 | Q83X | Voutetakis et al., Eur J Endocrinol. 2004 Mar; 150(3): 257-64 |
| Hypotrichosis simplex of the scalp | corneodesmosin gene (CDSN) | NM_001264 | NP_001255 | Y239X | Davalos et al., Br J Dermatol. 2005 Dec; 153(6): 1216-9. |
| Kindler syndrome | KIND1 | AY137240 | AAM94174 | C468X | Sethuraman et al., Clin Exp Dermatol. 2005 May; 30(3): 286-8 |
| late-infantile neuronal ceroid lipofuscinosis | CLN6 | NM_017882.1 | NP_060352 | c663C > G (Y221X) | Siintola et al., Clin Genet. 2005 Aug; 68(2): 167-73. |
| | CLN2 | | AAQ88866 | R208X | Sleat et al., Eur J Paediatr Neurol. 2001; 5 Suppl A: 57-62. |
| | | | | Q509X | Tessa et al., Hum Mutat. 2000 Jun; 15(6): 577. |
| Leigh syndrome | succinate dehydrogenase (SDHA) | NM_004168 | NP_004159 | W119X | Horvath et al., J Neurol Neurosurg Psychiatry. 2006 Jan; 77(1): 74-6. |
| Lipoid proteinosis (LP), also known as Urbach-Wiethe disease | extracellular matrix protein 1 (ECM1) | | AAB05934 | C589T (Q197X) | Lupo et al., Br J Dermatol. 2005 Nov; 153(5): 1019-22. |
| McArdle disease | myophosphorylase | | AAC52081 | Y52X | Hadjigeorgiou et al., 2002, J Neurol Sci 194: 83-6 |
| | | | | R207X | Hadjigeorgiou et al., Neuromuscul Disord. 2002 Nov; 12(9): 824-7. |
| | | | | R269X | Bruno et al., Neuromuscul Disord. 1999 Jan; 9(1): 34-7. |
| | | | | W361X | Deschauer et al., 2001, Mol Genet Metab 74: 489-91 |
| | | | | Y573X | Gamez et al., Muscle Nerve. 2003 Sep; 28(3): 380-2 |

TABLE 10-continued

| Disease | Gene | Nucleic Acid GenBank Accession No. | Protein GenBank Accession No. | Mutation | Reference |
|---|---|---|---|---|---|
| Marfan syndrome | fibrillin 1 (FBN1) | NM_000138.2 | NP_000129 | R215X, S813X, R2220X | Matsukawa et al., Hum Mutat. 2001; 17(1): 71-2. |
| maturity-onset diabetes of the young (MODY) | hepatocyte nuclear factor-1 beta (HNF-1 beta) | | AAC63388 | R276X | Furuta et al., J Clin Endocrinol Metab. 2002 Aug; 87(8): 3859-63. |
| | | | | R177X | Montoli et al., Am J Kidney Dis. 2002 Aug; 40(2): 397-402. |
| | | | | Q176X | |
| mitochondrial ornithine transporter deficiency (or HHH syndrome) | ORNT1 | | | R179X | Miyamoto et al., J Hum Genet. 2001; 46(5): 260-2. |
| mucopolysaccharidosis III A (lysosomal storage disease) | SGSH | NM_000199 | NP_000190 | Y40X | Bekri et al., J Inherit Metab Dis. 2005; 28(4): 601-2 |
| | | | | R233X | Muschol et al., Hum Mutat. 2004 Jun; 23(6): 559-66 |
| Muscular dystrophy Myofibrillar myopathy (MFM) | filamin c gene (FLNC) | | Q14315 | 8130G-->A; W2710X | Vorgerd et al., Am J Hum Genet. 2005 Aug; 77(2): 297-304 |
| Neurofibromatosis | NF1 | HUMNF1AB | AAA59924 | R1947X | Consoli et al., J Invest Dermatol. 2005 Sep; 125(3): 463-6. |
| | | | | R1306X & R2496X | Park et al., J Med Genet. 1998 Oct; 35(10): 813-20. |
| Niemann Pick's disease | HE1 | NM_006432.3 | NP_006423 | E20X and E118X | Millat et al., Am J Hum Genet. 2001 Nov; 69(5): 1013-21 |
| non-ocular Stickler syndrome | COL11A2 | | | R893X | Vuoristo et al., Am J Med Genet A. 2004 Oct 1; 130(2): 160-4. |
| Obesity | melanocortin 4 receptor gene (MC4R) | NM_005912.1 | NP_005903 | W16X | Marti et al., Int J Obes Relat Metab Disord. 2003 Mar; 27(3): 385-8. |
| | | | | Y35X | Larsen et al., J Clin Endocrinol Metab. 2005 Jan; 90(1): 219-24 |
| P53 related cancers | P53 | DQ263704 | ABB72446 | R196X R213X E287X | |
| Parkinson's disease | Parkin | AB009973.1 | BAA25751 | W453X | Abbas et al., Hum Mol Genet. 1999 Apr; 8(4): 567-74 |
| PCWH: peripheral demyelinating neuropathy, central dysmyelinating leukodystrophy, Waardenburg syndrome, and Hirschsprung disease | SOX10 | NM_006941 | NP_008872 | S384X | Verheij et al., 2006, Eur J Paediatr Neurol Epub Feb. 24. |
| Peutz-Jeghers syndrome (PJS) | STK11/LKB1 (LKB1) | | AAC15742 | Y246X | Hernan et al., Clin Genet. 2004 Jul; 66(1): 58-62. |
| polycystic kidney disease | PKD1 | L33243.1 | AAC37576 | C4086X | Neophyton et al., Hum Genet. 1996 Oct; 98(4): 437-42 |
| | | | | Y3818X | Peral et al., Hum Mol Genet. 1996 Apr; 5(4): 539-42. |
| | | | | C3817X | Turco et al., Hum Mol Genet. 1995 Aug; 4(8): 1331-5. |
| Primary GH insensitivity (Laron syndrome) | Growth hormone receptor | | | R43X | Rosenblum et al., J Pediatr Endocrinol Metab. 1995 Jul-Sep; 8(3): 159-65. |
| primary open-angle glaucoma (POAG) | Myocilin | NM_000261.1 | NP_000252 | Q368X | Allinghman et al., Invest Ophthalmol Vis Sci. 1998 Nov; 39(12): 2288-95. |
| Prolidase deficiency | peptidase D (PEPD) | NM_000285 | NP_000276 | R265X | Wang et al., Am J Med Genet A. 2006 Mar 15; 140(6): 580-5. |
| progressive familial intrahepatic cholestasis | MDR3 | | | | De Vree et al., Proc Natl Acad Sci USA. 1998 Jan 6; 95(1): 282-7. |
| Prostate cancer risk | EphB2 (prostate cancer marker) | AF025304 | AAB94602 | 3055A > T (K1019X) | |
| Prostate cancer | MSR1 | | AAH63878 | c.877C > T (R293X) | Maier et al., Hum Mutat. 2006 Jan; 27(1): 98-102. |
| Pseudoxanthoma elasticum | ABCC6 | NM_001171 | NP_001162 | R1141X | Schultz et al., Hum Biol. 2005 Jun; 77(3): 367-84 |
| | | | | Q378X | Cai et al., 2001 J Mol Med 79: 536-46 |
| retinitis pigmentosa | Rhodopsin | NM_000539 | NP_000530 | Q344X | Yong et al., 2005, Ann Acad Med Singapore 34: 94-99 |
| | RP1 | NM_006269 | NP_006260 | R677X | Berson et al., Invest Ophthalmol Vis Sci. 2001 Sep; 42(10): 2217-24. |
| | | | | Q679X | Sullivan et al., Nat Genet. 1999 Jul; 22(3): 255-9. |

TABLE 10-continued

| Disease | Gene | Nucleic Acid GenBank Accession No. | Protein GenBank Accession No. | Mutation | Reference |
|---|---|---|---|---|---|
| | | | | K778X | Dietrich et al., Br J Ophthalmol. 2002 Mar; 86(3): 328-32. |
| | RP2 | AL050307.13 | CAB82030 | R120X | Vorster et al., Clin Genet. 2004 Jan; 65(1): 7-10. |
| severe combined immunodeficiency disease (SCID) | IL-7Ralpha | NM_002185.2 | NP_002176 | 638C-->T (R206X) | Jo et al., Int J Hematol. 2004 Nov; 80(4): 332-5. |
| severe permanent tooth agenesis (oligodontia) and colorectal neoplasia | Wnt-signaling regulator AXIN2 | NM_004655 | NP_004646 | R656X | Lammi et al., Am J Hum Genet. 2004 May; 74(5): 1043-50. |
| Spinal muscular atrophy | survival motor neuron (SMN1) | AC004999.1 | AAC83178 | W102X | Sossi et al., Eur J Hum Genet. 2001 Feb; 9(2): 113-20. |
| | SNM2 | | | Q15X | Wirth et al., Am J Hum Genet. 1999 May; 64(5): 1340-56. |
| Tangier disease | ATP-binding cassette transporter 1 (ABC1) | AF165281 | AAD49849 | R909X | Zuchner et al., Brain. 2003 Apr; 126(Pt 4): 920-7 |
| thalassemia | Beta-globin | AF007546 | AAB62944 | Q127X | Prehu et al., Hemoglobin. 2005; 29(3): 229-33 |
| thin basement membrane disease (TBMD) | COL4A4 | NM_000092.3 | NP_000083 | R1377X | Buzza et al., Kidney Int. 2003 Feb; 63(2): 447-53. |
| Tuberous sclerosis complex (TSC) | TSC1 | | CAH72112 | Q897X | Yamamoto et al., Brain Dev. 2002 Jun; 24(4): 227-30. |
| UDP-galactose-4-epimerase (GALE) deficiency galactosemia | UDP-galactose-4-epimerase (GALE) | DQ233667 | ABB04109 | W336X | Park et al., Genet Med. 2005 Nov-Dec; 7(9): 646-9 |
| Ullrich congenital muscular dystrophy (UCMD) | COL6A3 | | | R465X | Demir et al., Am J Hum Genet. 2002 Jun; 70(6): 1446-58 |
| | | | | R2342X | |
| Usher syndrome type Ib | myosin VIIA | NM_000260.1 | NP_000251 | C628X | Cuevas et al., Mol Cell Probes. 1998 Dec; 12(6): 417-20. |
| Von Willibrand's disease | vWF | NM_000552 | NP_000543 | Q218X, W222X, R365X, R373X, Y610X, W642X, E644X, Q706X, Q1311X, S1338X, Q1346X, Y1542X, R1659X, E1981X, E2129X, R2434X, and Q2544X R2535X Q2470X | Baronciani et al., Blood Cells Mol Dis. 2003 May-Jun; 30(3): 264-70. |
| Waardenburg-Hirschsprung syndrome | endothelin-B receptor (EDNRB) | D13168.2 | BAA02445 | R253X | Syrris et al., Am J Med Genet. 1999 Nov 5; 87(1): 69-71. |
| Wilm's tumor | Wt1 | AY245105 | AAO61088 | 1084C > T (R362X) | |
| X-linked diabetes insipidus | AVRP2 | NM_000054 | NP_000045 | 961 GAG > TAG (E242X) | |
| Xeroderma pigmentosum group C | XPC | NM_004628.3 | NP_004619 | R579X | Gozukara et al., J Invest Dermatol. 2001 Aug; 117(2): 197-204. |

5.6 Patient Populations

5.6.1 Preferred Targets and Genetic Profiles

The methods and compositions of the invention are useful for the prevention, treatment and/or management of patients (e.g., embryos, fetuses, infants (newborn to 1 year old in humans), children (1 year to 18 years old in humans), adults (18 years and older in humans), and the elderly (65 years and older in humans)) who have or are predisposed or susceptible (e.g., due to environmental and/or genetic factors) to having a disease associated with a nonsense mutation in a gene, such as those described herein. In one embodiment, the patient is a child or adolescent (5 years to 13 years old in humans). In another embodiment, the patient is a male. In a particular embodiment, the patient is a male child or adolescent (5 years to 13 years old in humans). In a specific embodiment, the patient is a male child or adolescent (5 years to 13 years old in humans) having muscular dystrophy (e.g., Duchenne muscular dystrophy). In another embodiment, the patient is a female. In a specific embodiment, the patient is a female child or adolescent (5 years to 13 years old in humans).

In a specific embodiment, the methods and compositions of the invention are useful for the treatment, prevention and/or management of an embryo or fetus who has or is predisposed or susceptible to a disease associated with a nonsense mutation in a gene, such as those described herein. In accordance with this embodiment, a pregnant female is administered a nonsense codon suppressor agent which passes through the placenta to the embryo or fetus.

Table 10 above provides a list of diseases associated with a nonsense mutation in a gene as well as representative examples of nonsense mutations in the gene. In certain embodiments, the patients administered a nonsense codon suppressor agent(s) are patients with a disease listed in Table 10 which have one or more of the representative nonsense mutations in the gene associated with the disease.

In certain embodiments, the patients administered a nonsense codon suppressor agent(s) in accordance with the invention have not received another therapy within the last few days, week, 2 weeks, month, 3 months, 6 months or 1 year. In a specific embodiment, the patients administered a nonsense codon suppressor agent(s) in accordance with the invention have never received another therapy. In other embodiments, the patients administered a nonsense codon suppressor agent(s) in accordance with the invention have received another therapy within the last few minutes, few hours or few days.

The present invention encompasses the administration of a nonsense codon suppressor agent(s) in combination with another type of therapy, such as a supportive therapy and/or an anti-convulsant. For cystic fibrosis examples of supportive therapies include pancreatic enzyme replacements (e.g., lipase), mucolytics (e.g., dornase alfa), bronchodilators, corticosteroids and antibiotics. For duchenne muscular dystrophy examples of supportive therapies include corticosteroids and antibiotics. In a specific embodiment, the patients are not administered an aminoglycoside, an oxazolidinone, and/or chloramphenicol as an antibiotic in combination with a nonsense codon suppressor agent(s). In accordance with this embodiment, the nonsense codon suppressor agent(s) is not an aminoglycoside, an oxazolidinone, and/or chloramphenicol.

In certain embodiments, patients administered a nonsense codon suppressor agent(s) in accordance with the invention are refractory to the nonsense codon suppressor activity of an aminoglycoside, an oxazolidinone, and/or chloramphenicol. In accordance with this embodiment, patients that are refractory to such agents can be determined for example by contacting cells from such a patient with an aminoglycoside, an oxazolidinone, or chloramphenicol and measuring the activity and/or expression of the gene associated with the disease that comprises a nonsense mutation.

The methods and compositions of the invention are also useful for the presentation, treatment and/or management of patients (e.g., embryos, fetuses, infants (newborn to 1 year old in humans, children (1 year to 18 years old in humans), adults (18 years and older in humans), and the elderly (65 years and older in humans)) who have or are predisposed or susceptible (e.g., due to environmental and/or genetic factors) to having a disease associated with a mutation in a gene that results in a different stop codon in the RNA transcribed from the gene relative to the stop codon found in the RNA coding for the corresponding wild-type protein. Non-limiting examples of such diseases include spinal muscular atrophy and cystic fibrosis (e.g., cystic fibrosis resulting from the mutation 3849+10 kb C→T in the CFTR gene which creates an 84 base pair insertion that results from a region of intron 19 being recognized as an exon and when translated, the 84 base pair insertion produces a 28 amino acid peptide that harbors a UAA nonsense mutation (Highsmith et al., New England Journal of Medicine 331(1):974 (1994)).

Further, the methods and compositions of the invention are useful for the prevention, treatment and/or management of patients (e.g., embryos, fetuses, infants (newborn to 1 year old in humans), children (1 year to 18 years old in humans), adults (18 years and older in humans), and the elderly (65 years and older in humans)) who have or are predisposed or susceptible (e.g., due to environmental and/or genetic factors) to having a disease in which the patients do not express a sufficient amount of a protein(s), and/or that could benefit from the expression of a particular protein(s). These patients have been administered, by way of gene therapy (See Section 5.11 for gene therapy methodology), a nucleic acid sequence comprising a nonsense mutation(s) in the coding region (in certain embodiments, the nonsense mutation is in the 5' region of the coding region (e.g., within the first 50, 75, 100, 125, 150, 175, 200, 225, 250, 300 or 350 amino acids from the amino terminus)), and the administration of a nonsense codon suppressor agent suppresses the nonsense codon in the RNA transcribed from the nucleic acid sequence so that a functional readthrough protein encoded by the nucleic acid sequence is produced. The administration of the nonsense codon suppressor agent enables one to regulate the amount of functional readthrough protein produced. In other words, in the absence of a nonsense codon suppressing agent(s) little or no measurable functional readthrough protein is produced as determined, e.g., by an immunoassay such as an ELISA. The functional readthrough protein produced corresponds to a wild-type protein that is not expressed at a sufficient level in a patient and/or that is beneficial to the patient. Non-limiting examples of patient populations that could benefit from such therapy include patients with the following disorders:

Achondroplasia
Achromatopsia
Acid Maltase Deficiency
Adrenoleukodystrophy
Aicardi Syndrome
Alpha-1 Antitrypsin Deficiency
Androgen Insensitivity Syndrome
Apert Syndrome
Arrhythmogenic Right Ventricular Dysplasia
Ataxia Telangiectasia
Barth Syndrome
Blue Rubber Bleb Nevus Syndrome
Canavan Disease
Cancer
Cri Du Chat Syndrome
Cystic Fibrosis
Dercum's Disease
Ectodermal Dysplasia
Fanconi Anemia
Fibrodysplasia Ossificans Progressiva
Fragile X Syndrome
Galactosemia
Gaucher Disease
Hemochromatosis
Hemophilia
Huntington's Disease
Hurler Syndrome
Hypophosphatasia
Klinefelter Syndrome
Krabbes Disease
Langer-Giedion Syndrome
Leukodystrophy
Long QT Syndrome
Marfan Syndrome
Moebius Syndrome
Mucopolysaccharidosis (MPS)
Nail Patella Syndrome
Nephrogenic Diabetes Insipidus
Neurofibromatosis
Niemann-Pick Disease
Osteogenesis Imperfecta -continued Porphyria
Prader-Willi Syndrome
Progeria
Proteus Syndrome
Retinoblastoma
Rett Syndrome
Rubinstein-Taybi Syndrome
Sanfilippo Syndrome
Shwachman Syndrome
Sickle Cell Disease
Smith-Magenis Syndrome
Stickler Syndrome
Tay-Sachs
Thrombocytopenia Absent Radius (TAR) Syndrome
Treacher Collins Syndrome
Trisomy
Tuberous Sclerosis
Turner's Syndrome
Urea Cycle Disorder
von Hippel-Lindau Disease
Waardenburg Syndrome
Williams Syndrome
Wilson's Disease Specific examples of cancers that can be prevented, treated and/or managed by the methods encompassed by the invention include, but are not limited to, cancer of the head, neck, eye, mouth, throat, esophagus, chest, bone, lung, colon, rectum, stomach, prostate, breast, ovaries, kidney, liver, pancreas, and brain. Additional cancers include, but are not limited to, the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, osteosarcoma, chondrosarcoma, Ewing's sarcoma, Paget's disease of bone, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease), and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; gastric cancers such as adenocarcinoma, squamous cell carcinoma, carcinoid, lymphoma, stromal tumors of the stomach, and neuroendocrine tumors; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America). It is also contemplated that cancers caused by aberrations in apoptosis can also be prevented, treated and/or managed by the methods and compositions of the invention. Such cancers may include, but not be limited to, follicular lymphomas, carcinomas with p53 mutations, hormone dependent tumors of the breast, prostate and ovary, and precancerous lesions such as familial adenomatous polyposis, and myelodysplastic syndromes.

5.6.2 Patient Screening and Cell Lines

In one embodiment, it has been determined through pre-screening that the patient or a relative of the patient has a nonsense mutation (i.e., UAA, UGA, or UAG) in a gene associated with a genetic disease.

In certain embodiments, the invention provides methods for screening patients to identify patients who are likely to respond to therapy with a nonsense codon suppressor agent.

5.6.2.1 Short-Term Treatment Challenge

The invention provides methods for screening a patient with a disease associated with a nonsense mutation in a gene for the likelihood of the patient responding to a nonsense codon suppressor agent, the methods comprising administering to the patient a nonsense codon suppressor agent, followed by the measurement of one or more pharmacodynamic markers associated with the disease to be prevented, managed and/or treated. If the measurement of the pharmacodynamic marker(s) indicates that the patient is likely to respond to the nonsense codon suppressor agent, administration of the agent can be resumed.

In a particular embodiment, the screening method comprises the short-term administration of a nonsense codon suppressor agent to the patient, followed by the measurement of a pharmacodynamic marker associated with the disease to be prevented, treated and/or managed, and optionally, followed by long-term administration of the nonsense codon suppressor agent. In certain embodiments, the short-term administration of the nonsense codon suppressor lasts about 5 days, about 10 days, about 14 days, about 21 days or about 28 days. In other embodiments, the long-term administration of the nonsense codon suppressor lasts about 30 days, about 45 days, about 60 days, about 80 days, about 120 days, about 240 days, about 1 year or until a physician determines that therapy should be discontinued. In a particular embodiment, there is a period of non-treatment of about 1 day, about 3 days, about 5 days, about 7 days, about 10 days, about 14 days, about 21 days or about 28 days between the short-term administration and the long-term administration of the nonsense codon suppressor agent TEPD and pulmonary function assessment. In a specific embodiment, the administration of the nonsense codon suppressor agent is oral.

Any pharmcodynamic marker associated with the diseases disclosed herein recognized by the skilled artisan can be used in connection with the methods of the present invention (see, e.g., Politano, et al., *Acta Myologica XXII*:15-21 (2003), incorporated by reference herein in its entirety).

Illustrative pharmacodynamic markers associated with cystic fibrosis include, but are not limited to, transepithelial potential difference in the nose (see, e.g., Standaert, et al., *Pediatric Pulmonology* 37:385-392 (2004) and Du, et al., *J. Mol. Med.* 80:595-604 (2002), each incorporated by reference herein in its entirety and Example 13, infra), CFTR protein staining and measurement in cells collected from the nose (see, e.g., Wilschanski, et al., *N. Engl. J. Med* 349:1433-1441 (2003), incorporated by reference herein in its entirety and Example 14), change in sweat chloride concentration (see, e.g., Example 16) and changes in pulmonary function (see, e.g., Example 15).

Illustrative pharmacodynamic markers associated with Duchenne muscular dystrophy include, but are not limited to, serum creatine kinase levels (see, e.g., the methodology in Example 20, infra for measurement of serum creatine kinase levels) and muscle dystrophin measurement by staining (see, e.g., Politano, et al., *Acta Myologica XXII*:15-21 (2003), incorporated by reference herein in its entirety and Example 17).

Illustrative pharmcodynamic markers associated with amyloidosis include, but are not limited to: clearance of amyloid beta protein; weight gain, glomerular filtration rate, septal thickness, transmural histological distribution of amyloid protein and the cardiac amyloid load, kappa/lambda ratio of immunoglobulin-related free light chains (FLCs) in serum, and absence of cardiac troponins T and I (cTnT, cTnI).

Illustrative pharmcodynamic markers associated with hemophilia include, but are not limited to: coagulation activation, reduced clot lysis times of tissue factor induced fibrin formation and tPA mediated fibrinolysis.

Illustrative pharmcodynamic markers associated with Alzheimer's disease include, but are not limited to, altered platelet ratio of amyloid precursor protein (APP) isoforms; global, cognitive (as measured by psychometric tests, e.g., modified Mini-Mental State Examination (MMSE) or modified Hachinski Ischemic Score), functional, and behavioral measures, including activities of daily living and behavior, particularly agitation, reduced brain volume loss (e.g., measured using MRI). See also Caban-Holt et al., Geriatrics. 2005 June; Suppl:3-8.

Illustrative pharmcodynamic markers associated with Parkinson's disease include, but are not limited to, scores on the Unified Parkinson's Disease Rating Scale (UPDRS), MMSE, Hamilton-17 depression, NPI, total daily time to "on" (TTON), motor tests, dyskinesia ratings, patient diaries, and (18)F-dopa uptake.

Illustrative pharmcodynamic markers associated with atherosclerosis and familial hyperchloesterolemia include, but are not limited to, decreased cholesterol levels, e.g, reduced MDA-LDL levels and/or increased high-density lipoprotein cholesterol; serum fatty acid profile, serum lipoproteins, and markers of vascular inflammation, reduced plasma homocysteine concentrations, plaque formation in atherosclerotic vessels (by MRI or Intravascular ultrasound (IVUS)), coronary artery calcification (CAC) as measured, for example, by electron-beam computed tomography, and decreased artery blockage, e.g., as measured by Intima-media thickness (IMT) measures of the common carotid artery (CCA), internal carotid artery (ICA), and bulb segments of the carotid arteries.

Illustrative pharmcodynamic markers associated with dwarfism and giantism, include, but are not limited to, height and levels of growth hormone and prolactin.

Illustrative pharmcodynamic markers associated with hypothyroidism and hyperthyroidism include, but are not limited to, TT3, TT4 and TSH serum levels and the assessment of thyroid gland morphology and size, bone age, growth development and development quotients (DQ).

Illustrative pharmcodynamic markers associated with retinitis pigementosa include, but are not limited to, docosahexaenoic acid (DHA) levels, ocular function as measured by Humphrey Field Analyzer visual field sensitivity, 30-Hz electroretinogram amplitude, and visual acuity.

Illustrative pharmcodynamic markers associated with late infantile neuronal ceroid lipofuscinosis include, but are not limited to, neurological assessment based on the LINCL clinical rating scale and magnetic resonance imaging/magnetic resonance spectroscopy assessment of the brain.

Illustrative pharmcodynamic markers associated with spinal muscular atrophy include, but are not limited to, muscle strength, the sum of the motor function and examination index (IFM), the respiratory muscle paralysis index (IMR), and the dorsal decubitus forced vital capacity/theoretical index (ICV/CT), maximum voluntary isometric contraction with a handheld myometer and calculated an arm megascore (summing elbow flexion, hand grip, and three-point pinch scores), and a leg megascore (summing knee flexion, knee extension, and foot extension scores), Gross Motor Function Measure, pulmonary function tests, quantitative muscle testing, and quality of life.

Illustrative pharmcodynamic markers associated with Ataxia telangiectasia include, but are not limited to: decreased alpha-fetal protein, improved immune function, and improved neurological function.

Illustrative pharmcodynamic markers associated with Bartter syndrome include, but are not limited: increased blood potassium level, increased growth and improved mental functioning.

5.6.2.2 In Vitro Exposure of Cultured Tissue Cells

The present invention provides methods for screening a patient with a disease associated with a nonsense mutation in a gene for the likelihood of the patient responding to a nonsense codon suppressor agent, the methods comprising contacting a cell sample from the patient with the nonsense codon suppressor agent and measuring the expression and/or activity of the functional readthrough protein produced when the nonsense codon suppressor agent induces the readthrough of the nonsense mutation in the gene associated with the disease. Non-limiting examples of cell samples include nucleated blood cells (e.g., peripheral blood lymphocytes), skin cells (e.g., dermal fibroblasts), neuronal cells, glial cells, and muscle cells. In certain embodiments, the cell sample is a sample of cells affected by the presence of the nonsense mutation in the gene. The activity measured will depend upon the function of the wild-type protein encoded by a normal gene. See, e.g., the assays described in Section 5.5. above.

In certain embodiments, the invention provides methods for screening a patient with a disease associated with a nonsense mutation in a gene for the likelihood of the patient responding to a nonsense codon suppressor agent, the methods comprising contacting a cell sample (e.g., a skin cell sample, such as dermal fibroblasts) from the patient with the nonsense codon suppressor agent under conditions that permit the cells to convert to the tissue of interest (e.g., muscle cells), and measuring the response. The cell sample from a patient likely to respond to the nonsense codon suppressor agent will produce functional readthrough protein as a result of suppression of the nonsense codon in RNA transcribed from the gene. In a specific embodiment, the cells used are fibroblasts that are isolated from patients. Such cells can be differentiated into muscle cells by transfecting the cells with a vector that contains the MyoD gene.

The present invention also provides methods for screening a patient with a disease associated with a nonsense mutation in a gene for the likelihood of the patient responding to a nonsense codon suppressor agent, the methods comprising sequencing the gene associated with the disease, contacting a cell sample comprising a gene containing the same nonsense mutation with the nonsense codon suppressor agent, and measuring the expression and/or activity of the functional readthrough protein produced when the nonsense codon suppressor agent induces the readthrough of the nonsense codon in RNA transcribed from the gene associated with the disease. In certain embodiments, the cell sample used is a part of a library of cell samples, each cell sample comprising a nonsense mutation(s) in a gene associated with a disease. For example, a cystic fibrosis cell sample library comprises cell samples with, e.g., the nonsense mutations listed in Table 10 in the CFTR gene. Cell samples may be stored at −70° C. until needed, at which point the cell samples are thawed and cultured under conditions that permit the cells to grow.

5.6.2.3 Artificial Gene Construct in Luciferase Assay

The present invention provides methods for screening a patient with a disease associated with a nonsense mutation in a gene for the likelihood of the patient responding to a nonsense codon suppressor agent, the methods comprising sequencing the gene associated with the disease, contacting the nonsense codon suppressor agent with a cell engineered to comprise a reporter gene, such as luciferase, containing the region of the gene associated with the disease containing the nonsense mutation, and measuring the expression and/or activity of the functional readthrough protein produced when the nonsense codon suppressor agent induces the readthrough of the nonsense codon in the RNA transcribed from the gene. In certain embodiments, the reporter gene contains 6 nucleotides (in certain embodiments, 9, 12, 15, 21, 24, 27, 30 or 33 nucleotides) from the region of the gene of interest containing the nonsense mutation, including the nonsense mutation. The reporter gene is engineered to comprise the region of the gene of interest containing the nonsense mutation so that the open reading frame of the reporter gene is maintained and the protein encoded by the reporter gene will result in a functional readthrough protein when a nonsense codon suppressor agent induces readthrough of the nonsense codon in the RNA transcribed from the gene. Examples of reporter genes are provided in Section 5.5 above. Any cell can be engineered to comprise the reporter gene. Non-limiting examples include fibroblasts, lymphocytes, glia cells, neurons, muscle cells, and macrophages. Standard molecular and cellular biology methods may be used to produce the reporter gene (including site directed mutagenesis) and to engineer the cell to comprise the reporter gene (including calcium phosphate precipitation, electroporation, and liposomes).

5.6.3 Diseases

Diseases prevented, treated and/or managed by the suppression of premature translation termination and/or nonsense-mediated mRNA decay include, but are not limited to: a genetic disease, cancer, an autoimmune disease, a blood disease, a collagen disease, diabetes, a neurodegenerative disease, a proliferative disease, a cardiovascular disease, a pulmonary disease, an inflammatory disease and central nervous system disease.

Specific genetic diseases within the scope of the methods of the invention include, but are not limited to, amyloidosis, hemophilia, Alzheimer's disease, Tay Sachs disease, atherosclerosis, giantism, dwarfism, hypothyroidism, hyperthyroidism, aging, obesity, Parkinson's disease, Niemann Pick's disease, cystic fibrosis, muscular dystrophy, heart disease, kidney stones, ataxia-telangiectasia, familial hypercholesterolemia, retinitis pigmentosa, lysosomal storage disease, tuberous sclerosis, Duchenne muscular dystrophy, spinal muscular atrophy and Marfan syndrome. Both solid tumors and other cancers are included within the methods of the invention.

In another embodiment, the genetic disease is an autoimmune disease. In a preferred embodiment, the autoimmune disease is rheumatoid arthritis or graft versus host disease.

In another embodiment, the genetic disease is a blood disease. In a preferred embodiment, the blood disease is hemophilia, Von Willebrand disease, ataxia-telangiectasia, b-thalassemia or kidney stones.

In another embodiment, the genetic disease is a collagen disease. In a embodiment, the collagen disease is osteogenesis imperfecta or cirrhosis.

In another embodiment, the genetic disease is diabetes.

In another embodiment, the genetic disease is an inflammatory disease. In a preferred embodiment, the inflammatory disease is arthritis.

In another embodiment, the genetic disease is a central nervous system disease. In one embodiment the central nervous system disease is a neurodegenerative disease. In a preferred embodiment, the central nervous system disease is multiple sclerosis, muscular dystrophy, Duchenne muscular dystrophy, spinal muscular atrophy, Alzheimer's disease, Tay Sachs disease, late infantile neuronal ceroid lipofuscinosis (LINCL) or Parkinson's disease.

In another embodiment, the genetic disease is cancer. In a preferred embodiment, the cancer is of the head and neck, eye, skin, mouth, throat, esophagus, chest, bone, lung, colon, sigmoid, rectum, stomach, prostate, breast, ovaries, kidney, liver, pancreas, brain, intestine, heart or adrenals.

In another preferred embodiment, the cancer is associated with tumor suppressor genes (see e.g. Garinis et al. 2002, Hum Gen 111:115-117; Meyers et al. 1998, Proc. Natl. Acad. Sci. USA, 95: 15587-15591; Kung et al. 2000, Nature Medicine 6(12): 1335-1340. Such tumor suppressor genes include, but are not limited to, APC, ATM, BRAC1, BRAC2, MSH1, pTEN, Rb and p53.

In a particularly preferred embodiment, the tumor suppressor gene is the p53 gene. Nonsense mutations have been identified in the p53 gene and have been implicated in cancer. Several nonsense mutations in the p53 gene have been identified (see, e.g., Masuda et al., 2000, Tokai J Exp Clin Med. 25(2):69-77; Oh et al., 2000, Mol Cells 10(3):275-80; Li et al., 2000, Lab Invest. 80(4):493-9; Yang et al., 1999, Zhonghua Zhong Liu Za Zhi 21(2):114-8; Finkelstein et al., 1998, Mol Diagn. 3(1):37-41; Kajiyama et al., 1998, Dis Esophagus. 11(4):279-83; Kawamura et al., 1999, Leuk Res. 23(2):115-26; Radig et al., 1998, Hum Pathol. 29(11):1310-6; Schuyer et al., 1998, Int J Cancer 76(3):299-303; Wang-Gohrke et al., 1998, Oncol Rep. 5(1):65-8; Fulop et al., 1998, J Reprod Med. 43(2):119-27; Ninomiya et al., 1997, J Dermatol Sci. 14(3):173-8; Hsieh et al., 1996, Cancer Lett. 100 (1-2):107-13; Rall et al., 1996, Pancreas. 12(1):10-7; Fukutomi et al., 1995, Nippon Rinsho. 53(11):2764-8; Frebourg et al., 1995, Am J Hum Genet. 56(3):608-15; Dove et al., 1995, Cancer Surv. 25:335-55; Adamson et al., 1995, Br J Haematol. 89(1):61-6; Grayson et al., 1994, Am J Pediatr Hematol Oncol. 16(4):341-7; Lepelley et al., 1994, Leukemia. 8(8):1342-9; McIntyre et al., 1994, J Clin Oncol. 12(5):925-30; Horio et al., 1994, Oncogene. 9(4):1231-5; Nakamura et al., 1992, Jpn J Cancer Res. 83(12):1293-8; Davidoff et al., 1992, Oncogene. 7(1):127-33; and Ishioka et al., 1991, Biochem Biophys Res Commun. 177(3):901-6; the disclosures of which are hereby incorporated by reference in their entireties). Any disease associated with a p53 gene encoding a premature translation codon including, but not limited to, the nonsense mutations described in the references cited above, can be treated, managed and/or prevented by the methods of the present invention.

Additional diseases to be treated, managed and/or prevented by the methods of the present invention include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia, chronic lymphocytic leukemia, hairy cell leukemia, or multiple myeloma. See e.g., *Harrison's Principles of Internal Medicine*, Eugene Braunwald et al., eds., pp. 491-762 (15th ed. 2001).

In some embodiments, the disease to be prevented, treated and/or managed by the methods of the invention include those listed in Table 10 above. In certain embodiments; the disease to be prevented, treated and/or managed is not gastrointestinal disorder and/or a cutaneous disorder. In some embodiments, the disease to be prevented, treated and/or managed is not one or more of the following diseases: basal cell nevus syndrome (e.g., PTCH gene), sporadic basal cell carcinoma (e.g., PTCH gene), melanoma (e.g., CDKN2a gene), junctional epidermolysis bullosa (e.g., LAMB3, LAMC2, LAMA3 genes), generalized atrophic benign epidermolysis bullosa (e.g., COL17A1 gene), dystrophic epidermolysis bullosa (e.g., COL7A1 gene), Hailey-Hailey disease (e.g., ATP2C1 gene), Darier's disease (e.g., ATP2A2 gene), lamellar icthyosis (e.g., TGM1 gene), X-linked icthyosis (e.g., STS gene), xeroderma pigmentosa (e.g., XPA, XPC, XPG genes), Bloom syndrome (e.g., BLM gene), striate palmo-plantar keratoderma (e.g., DSP, DSG1 genes), Cockayne syndrome (e.g., ERCC6 gene), oculocutaneous albinism (e.g., TYR, TYRP1 genes), Hermansky-Pudlack syndrome (e.g., HPS1, HPS4 genes), ataxia-telangiectasia (e.g., ATM gene), Griscelli syndrome (e.g., RAB27A, MYO5A genes), and ectodermal dysplasia/skin fragility (e.g., PKP1 gene). In some embodiments, the disease is not one or more of the following diseases: sporadic cancers of the esophagus (p53 gene) and colon (APC, p53 genes), Barrett's esophagus (p53 gene), hereditary cancer syndromes such as adenomatous polyposis coli (APC gene), hereditary nonpolyposis colon cancer (MLH1, MSH2 genes), Peutz-Jeghers syndrome (STK 11 gene), and Cowden's syndrome (PTEN gene).

5.7 Formulations

Pharmaceutical compositions and single unit dosage forms comprising an effective amount of a nonsense codon suppressing agent can be used in the methods of the present invention. Individual dosage forms may be suitable for oral, mucosal (including sublingual, buccal, rectal, nasal, or vaginal) or parenteral (including subcutaneous, intramuscular, bolus injection, intraarterial, or intravenous) administration. Preferred pharmaceutical compositions and single unit dosage forms are suitable for oral administration. In one embodiment, the pharmaceutical composition or single unit dosage forms comprises an effective amount of one or more nonsense codon suppressing agents and one or more impurities of the synthetic route used to prepare the nonsense codon suppressing agent(s).

In one embodiment, the pharmaceutical composition is a solid oral dosage form. In one embodiment, the pharmaceutical composition is a liquid oral dosage form. In a particular embodiment, the methods of the present invention comprise the administration of doses, unit dosage formulations or pharmaceutical compositions wherein the nonsense codon suppressing agent is orally bioavailable. Advantages of oral administration can include ease of administration, higher patient compliance with the dosing regimen, clinical efficacy, fewer complications, shorter hospital stays, and overall cost savings.

In another embodiment, the methods of the present invention comprise the administration of unit dosage formulations that comprise between about 35 mg and about 1400 mg, about 125 mg and about 1000 mg, about 250 mg and about 1000 mg, or about 500 mg and about 1000 mg of a nonsense codon suppressing agent. In one embodiment, the unit dosage formulation comprises a nonsense codon suppressing agent and one or more carriers or excipients suitable for suspension in a pharmaceutically acceptable solvent (e.g., water, milk, a carbonated beverage, juice, apple sauce, baby food or baby formula) in a bottle.

In another embodiment, the methods of the present invention comprise the administration of unit dosage formulations that comprise 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a nonsense codon suppressing agent. Preferred unit dosage formulations comprise about 125 mg, about 250 or about 1000 mg of a nonsense mutation suppressing agent. In one embodiment, the unit dosage formulation comprises a nonsense codon suppressing agent and one or more carriers or excipients suitable for suspension in a pharmaceutically acceptable solvent (e.g., water, milk, a carbonated beverage, juice, apple sauce, baby food or baby formula) in a bottle. Preferred unit dosage formulations are powders and sachets.

While it is recommended that the unit dosage formulations described herein are stored at between about 2° C. to about 8° C., the unit dosage formulations can be stored at room temperature for about 48 hours prior to reconstitution. In one embodiment, reconstitution of a 250 mg unit dosage formulation of 3-[5-(2-fluoro-phenyl)-[1,2,4]oxadiazol-3-yl]-benzoic acid or a pharmaceutically acceptable salt, solvate or hydrate thereof is carried out by the addition of about 10 mL of water directly in a bottle containing 3-[5-(2-fluoro-phenyl)-[1,2,4]oxadiazol-3-yl]-benzoic acid or a pharmaceutically acceptable salt, solvate or hydrate thereof to achieve a concentration of about 25 mg/mL in the total volume of suspension. For a 1000 mg unit dosage formulation of 3-[5-(2-fluoro-phenyl)-[1,2,4]oxadiazol-3-yl]-benzoic acid or a pharmaceutically acceptable salt, solvate or hydrate thereof, about 20 mL of water is added directly in the bottle containing 3-[5-(2-fluoro-phenyl)-[1,2,4]oxadiazol-3-yl]-benzoic acid or a pharmaceutically acceptable salt, solvate or hydrate thereof to achieve a concentration of about 50 mg/mL in the total volume of suspension. Immediately after water is added, the bottle is capped and shaken gently by hand for at least about 30 seconds to achieve a homogeneous suspension. Although the reconstituted suspension may remain in the original plastic bottle for up to 24 hours before ingestion, it is recommended that the drug be taken shortly after reconstitution. If there is a delay of more than about 15 minutes between reconstitution and dosing, it is recommended that the bottle should be reshaken gently by hand for at least about 30 seconds. It is recommended that the suspension be administered directly from the bottle. It is further recommended that the bottle be rinsed once with water and this rinse water be ingested to ensure that no powder is left in the bottle.

Single unit dosage forms for oral administration to a patient include, but are not limited to: sachets; cachets; tablets; chewable tablets; caplets; capsules, such as soft elastic gelatin capsules; troches; lozenges; dispersions; powders; solutions; liquid dosage forms, including suspensions (e.g., aqueous or non-aqueous liquid suspensions); emulsions (e.g., oil-in-water emulsions, or a water-in-oil liquid emulsion); and elixirs. In one embodiment, the methods of the present invention comprise the administration of a colloid solution or a solution with additional active agent, above the saturating concentration. These and other ways in which specific dosage forms useful in the methods of the present invention will vary from one another will be readily apparent to those skilled in the art. See, e.g., *Remington's Pharmaceutical Sciences,* 18th ed., Mack Publishing, Easton Pa. (1990).

The methods of the present invention further comprise the administration of anhydrous pharmaceutical compositions and dosage forms comprising a nonsense codon suppressing agent. Anhydrous pharmaceutical compositions and dosage forms can be prepared using anhydrous or low moisture containing ingredients and low moisture or low humidity conditions.

Typical oral dosage forms are prepared by combining a compound having nonsense codon suppressing activity in an intimate admixture with at least one carrier or excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents (e.g., vanilla extract), preservatives, and coloring agents. Examples of excipients suitable for use in solid oral dosage forms (e.g., powders, tablets, chewable tablets, sachets, capsules, and caplets) include, but are not limited to, starches, sugars, micro-crystalline cellulose, diluents, granulating agents, lubricants, binders, and disintegrating agents.

Particularly preferred unit dosage formulations are powder formulations comprising an effective amount of a nonsense codon suppressing agent which is suitable for reconstitution in a pharmaceutically acceptable solvent (e.g., water, milk, a carbonated beverage, juice, apple sauce, baby food or baby formula) and subsequent oral administration. In a particular embodiment, the powder can optionally contain one or more carriers or excipients in combination with the nonsense codon suppressing agent. In another embodiment, the powder can be stored in a sealed container prior to administration or reconstitution. In yet another embodiment, the powder can be encapsulated (e.g., in a gelatin capsule).

Liquid preparations for oral administration may take the form of, for example, solutions, syrups or suspensions, or they may be presented as a dry product (e.g., powder or granule) for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Examples of excipients that can be used in solid oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Preferred excipients include Litesse® Ultra (refined polydextrose) mannitol, surfactant agents (polyethylene glycol 3350 and Lutrol® micro F127 (poloxamer 407 powder)), a disintegrant (crospovidone), cab-o-sil, Carbopol®, polyacrylic acid and other excipients (hydroxyethyl cellulose, vanilla flavor, magnesium stearate (non-bovine), and colloidal silica).

Examples of fillers suitable for use in the pharmaceutical compositions and solid dosage forms disclosed herein include, but are not limited to, lactose, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

5.8 Dosing and Dosing Regimens

Without being limited by theory, the methods of the present invention encompass, in part, specific doses and dosing regimens for a nonsense codon suppressing agent that optimize the suppression of premature translation termination and/or nonsense-mediated mRNA decay.

The methods of the invention encompass the treatment, prevention and management of diseases treatable, preventable and/or manageable by the suppression of premature translation termination and/or nonsense-mediated mRNA decay or symptoms thereof while reducing or avoiding adverse or unwanted effects, e.g., toxicities or side effects. The preferred route of administration for the doses and dosing regimens described herein is oral (i.e., ingestion of a solution, a colloid solution or a solution with additional active agent, above the saturating concentration of active agent). In one embodiment, the route of administration for the doses and dosing regimens described herein is topical (e.g., cutaneous).

The doses and dosing regimens described herein are thought to be useful due to their ability to achieve and maintain a desirable plasma concentration of the compound having nonsense codon suppressing activity. Without being limited by theory, it is thought that achieving and maintaining a relatively constant plasma concentration of a nonsense mutation suppressing agent over, for example, a 24 hour period or longer, provides a beneficial therapeutic effect to the patient. The doses and dosing regimens described herein are useful for achieving and maintaining such therapeutic plasma concentrations of a compound having nonsense codon suppressing activity.

In one embodiment, the methods of the present invention comprise administering a nonsense codon suppressing agent, wherein the compound is administered to a patient in need thereof one, two or three times in a 12 or 24 hour period, wherein each administration is preferably separated by about 4-14 hours. In a particular embodiment, the nonsense codon suppressing agent is administered once in the morning, once in the afternoon and once in the evening. In another embodiment, the nonsense codon suppressing agent is administered once in the morning and once in the evening. In another embodiment, the nonsense codon suppressing agent is administered once in the morning, once in the afternoon or once in the evening. Preferred intervals between doses include 4, 5, 6, 7, 8, 9, 10, 11, 12, 13 and 14 hours.

In one embodiment, the dose of the nonsense codon suppressing agent is escalated throughout a 24 hour period. In a particular embodiment, the second dose administered is escalated (e.g., doubled) relative to the first dose. In another embodiment, the first and second dose administered are kept constant and the third dose administered is escalated (e.g., doubled). Without being limited by theory, it is thought that there is diurnal variation with the administration of the nonsense codon suppressing agent wherein the plasma concentration of a dose administered in the evening is greater than that of a dose administered in the morning or afternoon. Without further being limited by theory, it is thought that doubling the dose administered in the evening relative to the previously administered dose will optimally sustain target plasma concentrations while lowering total exposures to the nonsense codon suppressing agent.

In a particular embodiment, three doses in a 24 hour period are administered according to the formula: 1X, 1X, 2X, where X is a particular initial dose (e.g., 4 mg/kg, 7 mg/kg or 10 mg/kg). In another embodiment, the nonsense codon suppressing agent is administered within (i.e., before or after) about 10, 15, 30, 45 or 60 minutes of the patient having food. In one embodiment, an effective amount of the nonsense codon suppressing agent is sprinkled on or mixed in food. In one embodiment, the food consumed prior to, concurrently with, or after administration of the nonsense codon suppressing agent is high-fat and/or high-calorie and/or high protein.

In one embodiment, if an adverse event develops during a cycle of treatment that is considered dose-limiting, the second or third dose administered (e.g., the evening dose) is reduced by about 5%, 10%, 15%, 20%, 25%, 30%, 35%, 40%, 45%, 50%, 75% or is not administered at all, for the remainder of the cycle of treatment or until the adverse event subsides.

A particularly preferred dosing regimen is that where a patient is administered a nonsense codon suppressing agent within 30 minutes after a meal at approximately 6-, 6-, and 12-hour intervals (e.g., at ~7:00 AM after breakfast, ~1:00 PM after lunch, and at ~7:00 PM after supper).

In yet another embodiment, the methods of the present invention comprise the administration of a nonsense codon suppressing agent in single or divided (e.g., three times in a 24 hour period) doses between 0.1 mg/kg and 500 mg/kg, 1 mg/kg and 250 mg/kg, 1 mg/kg and 150 mg/kg, 1 mg/kg and 100 mg/kg, 1 mg/kg and 50 mg/kg, 1 mg/kg and 25 mg/kg, 1 mg/kg and 20 mg/kg, 1 mg/kg and 10 mg/kg or 2 mg/kg and 10 mg/kg to a patent in need thereof. In a particular embodiment, a nonsense codon suppressing agent is administered in a dose of about 2-6 mg/kg, about 5-9 mg/kg, about 6-10 mg/kg, about 8-12 mg/kg, about 12-16 mg/kg or about 18-22 mg/kg. In a particular embodiment, a nonsense codon suppressing agent is administered in a dose of about 3 mg/kg, about 4 mg/kg, about 6 mg/kg, about 7 mg/kg, about 8 mg/kg, about 10 mg/kg, about 14 mg/kg, about 20 mg/kg, about 30 mg/kg, about 50 mg/kg, about 100 mg/kg, about 200 mg/kg, or about 300 mg/kg. In another embodiment, any dose of a nonsense codon suppressing agent described in the preceding embodiment is administered one, two or three times in a 24 hour period.

In another embodiment, the methods of the present invention comprise continuous therapy wherein a nonsense codon suppressing agent is administered daily to a patient in need thereof for a certain period of time (e.g., 5, 7, 10, 14, 20, 24, 28, 60 or 120 days or more). In one embodiment, a nonsense codon suppressing agent is continuously administered one, two or three times per 24 hour period. In another embodiment, a nonsense codon suppressing agent is administered continuously daily, weekly, monthly or yearly. In a specific embodiment, a nonsense codon suppressing agent is continuously administered one, two or three times per 24 hour period at doses of about 4 mg/kg, about 4 mg/kg and about 8 mg/kg for days, weeks, months or years. In a specific embodiment, a nonsense codon suppressing agent is continuously administered three times per 24 hour period at doses of about 7 mg/kg, about 7 mg/kg and about 14 mg/kg for days, weeks, months or years. In a specific embodiment, a nonsense codon suppressing agent is continuously administered three times per 24 hour period at doses of about 10 mg/kg, about 10 mg/kg and about 20 mg/kg for days, weeks, months or years. In another specific embodiment, a nonsense codon suppressing agent is continuously administered two times per 24 hour period at doses of about 8 mg/kg for days, weeks, months or years.

In another specific embodiment, a nonsense codon suppressing agent is continuously administered in a first cycle three times per 24 hour period at doses of about 4 mg/kg, about 4 mg/kg and about 8 mg/kg for days, weeks, months or years followed by continuous administration in a second cycle two times per 24 hour period at doses of about 8 mg/kg for days, weeks, months or years. In another specific embodiment, a nonsense codon suppressing agent is continuously administered in a first cycle two times per 24 hour period at doses of about 8 mg/kg for days, weeks, months or years followed by continuous administration in a second cycle three times per 24 hour period at doses of about 4 mg/kg, about 4 mg/kg and about 8 mg/kg for days, weeks, months or years. In these embodiments, the first and second cycles can be separated or followed by a rest period where a nonsense codon suppressing agent is not administered. The rest period can last days, months or years.

In each 24 hour period that a nonsense codon suppressing agent is administered, it is preferably administered three times at approximately 6-, 6, and 12-hour intervals (e.g., at ~7:00 AM after breakfast, ~1:00 PM after lunch, and at ~7:00 PM after supper).

Treatment periods for a course of therapy can span one week, two weeks, three weeks, four weeks, five weeks, six weeks, seven weeks, eight weeks, nine weeks, ten weeks, eleven weeks, twelve weeks, thirteen weeks, fourteen weeks, four months, five months, six months, seven months, eight months, nine months, ten months, eleven months, one year, two years, three years, four years, five years or longer. In a specific embodiment, the treatment periods for a course of therapy span the life of the subject. The treatment periods can be interrupted by periods of rest which can span a day, one week, two weeks, three weeks, four weeks, five weeks, six weeks, seven weeks, eight weeks, nine weeks, ten weeks, eleven weeks, twelve weeks, thirteen weeks, fourteen weeks, four months, five months, six months, seven months, eight months, nine months, ten months, eleven months, one year, two years, three years, four years, five years or longer. Such determinations can be made by one skilled in the art (e.g., a physician).

It will be understood that the amounts of a nonsense codon suppressing agent administered to a patient in need thereof are or can be calculated based upon the actual weight of the patient in question or the average weight of the patient population in question (e.g., white males, white females, African American males, African American females, Asian males or Asian females, including embryos, fetuses, infants, children, adults and elderly.).

5.9 Plasma Concentrations

In one embodiment, the methods of the present invention comprise maintaining a plasma concentration of a nonsense codon suppressing agent of 0.1 µg/ml to 500 µg/ml, 0.1 µg/ml to 400 µg/ml, 0.1 µg/ml to 300 µg/ml, 0.1 µg/ml to 200 µg/ml, 0.1 µg/ml to 100 µg/ml, or 2 µg/ml to 10 µg/ml in a patient for about 1 to 72 hours, 2 to 48 hours or 2 to 24 hours, comprising administering an effective amount of a nonsense codon suppressing agent to a patient in need thereof. In another embodiment, the methods of the present invention comprise maintaining a plasma concentration of a nonsense codon suppressing agent of greater than: about 0.1 µg/ml, about 1 µg/ml, about 2 µg/ml, about 5 µg/ml, about 10 µg/ml, about 15 µg/ml, about 20 µg/ml, about 25 µg/ml, about 30 µg/ml, about 40 µg/ml, about 50 µg/ml, about 75 µg/ml, about 100 µg/ml, about 125 µg/ml, about 150 µg/ml, about 175 µg/ml, about 200 µg/ml, about 225 µg/ml, about 250 µg/ml, about 275 µg/ml, about 300 µg/ml, about 325 µg/ml, about 350 µg/ml, about 375 µg/ml, or about 400 µg/ml in a patient for at least about 2, 4, 6, 8, 12, 24, 36 or 48 hours, comprising administering an effective amount of a nonsense codon suppressing agent to a patient in need thereof. In a particular embodiment, the administration is oral.

In another embodiment, the methods of the present invention comprise maintaining a plasma concentration of a nonsense mutation suppressing agent of about 0.1 µg/ml to about 400 µg/ml in a patient for at least about 2, 4, 6, 8, 12 or 24 hours, comprising administering an effective amount of a nonsense mutation suppressing agent to a patient in need thereof for up to three times per day at the same or escalating doses (e.g., 1X, 1X, 2X as described herein). In a particular embodiment, the administration is oral.

In a particular embodiment, a patient's plasma level of a nonsense codon suppressing agent is maintained above about 0.1 µg/ml to about 400 µg/ml for at least about 2, 4, 6, 8, 12 or 24 hours by administration of the nonsense codon suppressing agent three times per day to a patient in need thereof. In a particular embodiment, the administration is oral.

In one embodiment, the methods of the present invention comprise administering a nonsense mutation suppressing agent such that the plasma concentration $T_{max}$ occurs about 1 to about 3 hours or about 2 to about 4 hours after administration.

In one embodiment, the methods of the present invention comprise administering a nonsense mutation suppressing agent such that the plasma concentration mean half-life $t_{1/2}$ is from about 2 to about 6 hours or about 3 to about 6 hours.

In certain embodiments, the methods of the present invention comprise administering a nonsense codon suppressing agent in an amount effective to produce 1% or more, 2% or more, 3% or more, 4% or more, 5% or more, 7% or more, 10% or more, 12% or more, 15% or more, 17% or more, 20% or more, 22% or more, 25% or more, 27% or more, 30% or more, 32% or more, 35% or more, 40% or more, 45% or more, 50% or more, 55% or more, 60% or more, 65% or more, 70% or more, 75% or more, or 80% or more of the functional readthrough protein in vivo relative to the amount of corresponding wild-type protein produced in a normal subject(s). In some embodiments, the methods of the present invention comprise administering a nonsense codon suppressing agent in an amount effective to produce enough functional readthrough protein to result in approximately 1%, approximately 2%, approximately 3%, approximately 4%, approximately 5%, approximately 10%, approximately 15%, approximately 20%, approximately 25%, approximately 30%, approximately 35%, approximately 40%, approximately 45%, approximately 50%, approximately 55%, approximately 60% or more of the activity of the corresponding wild-type protein in a normal subject(s).

In a specific embodiment, the methods of the present invention comprise administering a nonsense codon suppressing agent in an amount effective to produce at least about 1% or more, 2% or more, 3% or more, 4% or more, 5% or more, 7% or more, 10% or more, 12% or more, 15% or more, 17% or more, 20% or more, 22% or more, 25% or more, 27% or more, 30% or more, 32% or more, 35% or more, 40% or more, 45% or more, 50% or more, 55% or more, 60% or more, 65% or more, 70% or more, 75% or more, or 80% of the functional readthrough CFTR protein in vivo relative to the amount of CFTR protein produced in a normal subject(s).

In another embodiment, the methods of the present invention comprise administering a nonsense codon suppressing agent in an amount effective to produce 1% or more, 2% or more, 3% or more, 4% or more, 5% or more, 7% or more, 10% or more, 12% or more, 15% or more, 17% or more, 20% or more, 22% or more, 25% or more, 27% or more, 30% or more, 32% or more, 35% or more, 40% or more, 45% or more, 50% or more, 55% or more, 60% or more, 65% or more, 70% or more, 75% or more, or 80% of the functional readthrough dystrophin protein in vivo relative to the amount of dystrophin protein produced in a normal subject(s).

5.10 Therapeutic Endpoints

Any therapeutic endpoint or outcome for the diseases disclosed herein recognized by the skilled artisan can be used in connection with the methods of the present invention (see, e.g., Politano, et al., 2003, *Acta Myologica XXII*:15-21, incorporated by reference herein in its entirety). Representative therapeutic endpoints include, but are not limited to, those described herein, including those set forth in the examples.

Representative endpoints for Duchenne muscular dystrophy include, but are not limited to: the production of dystrophin in a muscle that otherwise would not be able to produce dystrophin (e.g., re-expression of dystrophin at the sarcolemma of skeletal muscle cells); the pattern of muscle MRI involvement and muscle volume of the treated muscle versus the contralateral untreated muscle; and muscle strength and performance, including individual QMT scores of elbow and knee flexors and extensors and hand grip and manual muscle testing scores measured using the Medical Research Council's (MRC) muscle strength scoring method.

Quantitative muscle strength can be measured, for example, by using the Pediatric Quantitative Measurement System (PQMS). Primary strength markers include quantitative myometry (QMT) scores of the upper and lower extremities, consisting of paired flexor/extensor groups.

Representative endpoints for cystic fibrosis include, but are not limited to: CFTR activity as assessed by nasal transepithelial potential difference (TEPD); side effects, the presence of CFTR protein and mRNA, and lung function.

Representative endpoints for amyloidosis include, but are not limited to: clearance of amyloid beta protein; weight gain, glomerular filtration rate, septal thickness, transmural histological distribution of amyloid protein and the cardiac amyloid load, kappa/lambda ratio of immunoglobulin-related free light chains (FLCs) in serum, and absence of cardiac troponins T and I (cTnT, cTnI).

Representative endpoints for hemophilia include, but are not limited to: coagulation activation, reduced clot lysis times of tissue factor induced fibrin formation and tPA mediated fibrinolysis.

Representative endpoints for Alzheimer's disease include, but are not limited to, altered platelet ratio of amyloid precursor protein (APP) isoforms; global, cognitive (as measured by psychometric tests, e.g., modified Mini-Mental State Examination (MMSE) or modified Hachinski Ischemic Score), functional, and behavioral measures, including activities of daily living and behavior, particularly agitation, reduced brain volume loss (e.g., measured using MRI). See also Caban-Holt et al., Geriatrics. 2005 June; Suppl:3-8.

Representative endpoints for Parkinson's disease include, but are not limited to, scores on the Unified Parkinson's Disease Rating Scale (UPDRS), MMSE, Hamilton-17 depression, NPI, total daily time to "on" (TTON), motor tests, dyskinesia ratings, patient diaries, and (18)F-dopa uptake.

Representative endpoints for atherosclerosis and familial hyperchloesterolemia include, but are not limited to, decreased cholesterol levels, e.g, reduced MDA-LDL levels and/or increased high-density lipoprotein cholesterol; serum fatty acid profile, serum lipoproteins, and markers of vascular inflammation, reduced plasma homocysteine concentrations, plaque formation in atherosclerotic vessels (by MRI or Intravascular ultrasound (IVUS)), coronary artery calcification (CAC) as measured, for example, by electron-beam computed tomography, and decreased artery blockage, e.g., as measured by Intima-media thickness (IMT) measures of the common carotid artery (CCA), internal carotid artery (ICA), and bulb segments of the carotid arteries.

Representative endpoints for dwarfism and giantism, include, but are not limited to, height and levels of growth hormone and prolactin.

Representative endpoints for hypothyroidism and hyperthyroidism include, but are not limited to, TT3, TT4 and TSH serum levels and the assessment of thyroid gland morphology and size, bone age, growth development and development quotients (DQ).

Representative endpoints for retinitis pigmentosa include, but are not limited to, docosahexaenoic acid (DHA) levels, ocular function as measured by Humphrey Field Analyzer visual field sensitivity, 30-Hz electroretinogram amplitude, and visual acuity.

Representative endpoints for late infantile neuronal ceroid lipofuscinosis include, but are not limited to, neurological assessment based on the LINCL clinical rating scale and magnetic resonance imaging/magnetic resonance spectroscopy assessment of the brain.

Representative endpoints for spinal muscular atrophy include, but are not limited to, muscle strength, the sum of the motor function and examination index (IFM), the respiratory muscle paralysis index (IMR), and the dorsal decubitus forced vital capacity/theoretical index (ICV/CT), maximum voluntary isometric contraction with a handheld myometer and calculated an arm megascore (summing elbow flexion, hand grip, and three-point pinch scores), and a leg megascore (summing knee flexion, knee extension, and foot extension scores), Gross Motor Function Measure, pulmonary function tests, quantitative muscle testing, and quality of life.

Representative endpoints for Ataxia telangiectasia include, but are not limited to: decreased alpha-fetal protein, improved immune function, and improved neurological function.

Representative endpoints for Bartter syndrome include, but are not limited: increased blood potassium level, increased growth and improved mental functioning.

5.11 Gene Therapy

Gene therapy refers to therapy performed by the administration to a subject of an expressed or expressible nucleic acid sequence. Any of the methods for gene therapy available in the art can be used according to the present invention. Exemplary methods are described below.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, Science 260:926-932 (1993); and Morgan and Anderson, 1993, Ann. Rev. Biochem. 62:191-217; May, 1993, TIBTECH 11(5): 155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In one aspect, a nucleic acid sequence is part of an expression vector that expresses the nucleic acid sequence in a suitable host. In particular, such a nucleic acid sequence comprises a promoter (including heterologous promoters) operably linked to the coding region of a protein, said promoter being inducible or constitutive, and, optionally, tissue-specific. In another particular embodiment, a nucleic acid sequence is used in which the protein coding sequence and any other desired sequences are flanked by regions that promote homologous recombination at a desired site in the genome, thus providing for intrachromosomal expression of the protein encoding nucleic acid sequence (Koller and Smithies, 1989, Proc. Natl. Acad. Sci. USA 86:8932-8935; Zijlstra et al., 1989, Nature 342:435-438).

Delivery of the nucleic acid sequences into a subject may be either direct, in which case the subject is directly exposed to the nucleic acid sequence or nucleic acid sequence-carrying vectors, or indirect, in which case, cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where it is to be expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or by a matrix with in situ scaffolding in which the nucleic acid sequence is contained (see, e.g., European Patent No. EP 0 741 785 B1 and U.S. Pat. No. 5,962,427), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid sequence can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid sequence can be introduced intracellularly and incorporated within host cell DNA for expression, by homologous recombination (Koller and Smithies, 1989, Proc. Natl. Acad. Sci. USA 86:8932-8935; and Zijlstra et al., 1989, Nature 342:435-438).

In a specific embodiment, viral vectors that contains nucleic acid sequences encoding a prophylactic or therapeutic agent are used. For example, a retroviral vector can be used (see Miller et al., 1993, Meth. Enzymol. 217:581-599). These retroviral vectors contain the components necessary for the correct packaging of the viral genome and integration into the host cell DNA. The nucleic acid sequences to be used in gene therapy are cloned into one or more vectors, which facilitates delivery of the gene into a subject. More detail about retroviral vectors can be found in Boesen et al., 1994, Biotherapy 6:291-302, which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Klein et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; Mastrangeli et al., 1993, J. Clin. Invest. 91:225-234; PCT Publication WO94/12649; and Wang et al., 1995, Gene Therapy 2:775-783. In a preferred embodiment, adenovirus vectors are used.

Adeno-associated virus (AAV) has also been proposed for use in gene therapy (Walsh et al., 1993, Proc. Soc. Exp. Biol. Med. 204:289-300; and U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell mediated gene transfer, spheroplast fusion, etc. Numerous techniques are known in the art for the introduction of foreign genes into cells (see, e.g., Loeffler and Behr, 1993, Meth. Enzymol. 217:599-618; Cohen et al., 1993, Meth. Enzymol. 217:618-644; Clin. Pharma. Ther. 29:69-92 (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, natural killer (NK) cells, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the subject.

In an embodiment in which recombinant cells are used in gene therapy, nucleic acid sequences encoding a protein are introduced into the cells such that they are expressible by the cells or their progeny, and the recombinant cells are then administered in vivo for prophylactic or therapeutic effect. In a specific embodiment, stem or progenitor cells are used. Any stem and/or progenitor cells which can be isolated and maintained in vitro can potentially be used in accordance with this embodiment of the present invention (see e.g., PCT Publication WO 94/08598; Stemple and Anderson, 1992, Cell 71:973-985; Rheinwald, 1980, Meth. Cell Bio. 21A:229; and Pittelkow and Scott, 1986, Mayo Clinic Proc. 61:771).

In a specific embodiment, the nucleic acid to be introduced for purposes of gene therapy comprises a constitutive or tissue-specific promoter operably linked to the coding region.

6. EXAMPLES

The following examples employ methodology which can be used to identify compounds having nonsense mutation suppression activity.

6.1 Example 1

Identification and Characterization of Compounds that Promote Nonsense Mutation Suppression and/or Modulate Translation Termination Compounds that modulate premature translation termination and/or nonsense-mediated mRNA decay can be identified by a number of techniques. For example, methods for screening compounds that modulate the post-transcriptional expression of any gene with a premature translation stop codon are described in International Patent Publication No. WO 01/44516 A2, incorporated by reference herein in its entirety. In one example, a mRNA with a premature termination codon is translated in vitro and is used to screen a library of test compounds. In another example, the mRNA with a premature termination codon is a reporter gene with a premature termination codon.

Two assays were developed for use in high throughput screens to identify small molecules that promote nonsense mutation suppression. Each assay utilizes luciferase because it is a functional reporter gene assay (light is only produced if the protein is functional) and it is extremely sensitive (Light intensity is proportional to luciferase concentration in the nM range). The first assay is a cell-based luciferase reporter assay and the second is a biochemical assay consisting of rabbit reticulocyte lysate and a nonsense-containing luciferase reporter mRNA. In the cell-based assay, a luciferase reporter construct containing a UGA premature termination codon is stably transfected in 293T Human Embryonic Kidney cells. In the biochemical assay, mRNA containing a UGA premature termination codon is used as a reporter in an in vitro translation reaction using rabbit reticulocyte lysate supplemented with tRNA, hemin, creatine kinase, amino acids, KOAc, $Mg(OAc)_2$, and creatine phosphate. Translation of the mRNA is initiated within a virus derived leader sequence. Synthetic mRNA is prepared in vitro using the T7 promoter and the MegaScript in vitro transcription kit (Ambion). In both of the biochemical and cell-based assays, a small molecule known to allow readthrough of premature termination codons, 3-[3-(4-Isopropyl-phenyl)-2,5-dioxo-imidazolidin-1-yl]-benzoic acid, is used as an internal standard.

6.2 Example 2

Characterization of Compounds that Increase Nonsense Mutation Suppression and Produce Functional Protein To determine in vivo activity, a stable cell line harboring the UGA nonsense-containing luciferase gene is treated with test compounds. Cells are grown in standard medium supplemented with 1% penicillin-streptomycin (P/S) and 10% fetal bovine serum (FBS) to 70% confluency and split 1:1 the day before treatment. On the following day, cells are trypsinized and 40,000 cells are added to each well of a 96-well tissue culture dish. Serial dilutions of each compound are prepared to generate a six-point dose response curve spanning 2 logs (30 μM to 0.3 μM). The final concentration of the DMSO solvent remains constant at 1% in each well. Cells treated with 1% DMSO serve as the background standard, and cells treated with gentamicin serve as a positive control.

6.3 Example 3

Nonsense Suppressors Alter the Accessibility of the Chemical Modifying Agents to Specific nucleotides in the 28 s rRNA Previous studies have demonstrated that gentamicin and other members of the aminoglycoside family that decrease the fidelity of translation bind to the A site of the 16S rRNA. By chemical footprinting, UV cross-linking and NMR, gentamicin has been shown to bind at the A site (comprised of nucleotides 1400-1410 and 1490-1500, *E. coli* numbering) of the rRNA at nucleotides 1406, 1407, 1494, and 1496 (Moazed & Noller, 1987, *Nature* 327(6121):389-394; Woodcock et al., 1991, *EMBO J.* 10(10):3099-3103; and Schroeder et al., 2000, *EMBO J.* 19:1-9.

Ribosomes prepared from HeLa cells are incubated with a test compound (at a concentration of 100 µM), followed by treatment with chemical modifying agents (dimethyl sulfate [DMS] and kethoxal [KE]). Following chemical modification, rRNA is phenol-chloroform extracted, ethanol precipitated, analyzed in primer extension reactions using end-labeled oligonucleotides hybridizing to different regions of the three rRNAs and resolved on 6% polyacrylamide gels. The probes used for primer extension cover the entire 18S (7 oligonucleotide primers), 28S (24 oligonucleotide primers), and 5S (one primer) rRNAs. Controls in these experiments include DMSO (a control for changes in rRNA accessibility induced by DMSO), paromomycin (a marker for 18S rRNA binding), and anisomycin (a marker for 28S rRNA binding).

6.4 Example 4

Readthrough of Premature Termination Codons in Cell-Based Disease Models

To address the effects of nonsense-suppressing compounds on mRNAs altered in specific inherited diseases, a bronchial epithelial cell line harboring a nonsense codon at amino acid 1282 (W1282X) is treated with a test compound (20 µM) and CFTR function is monitored as a cAMP-activated chloride channel using the SPQ assay (Yang et al., 1993, Hum Mol Genet. 2(8):1253-1261 and Howard et al., 1996, Nat Med. 2(4):467-469). These experiments demonstrate that cAMP treatment of these cells results in an increase in SPQ fluorescence, consistent with stimulation of CFTR-mediated halide efflux. No increase in fluorescence is observed when cells are not treated with test compound or if the cells are not stimulated with cAMP. These results demonstrate that the full-length CFTR expressed from this nonsense-containing allele following test compound treatment also functions as a cAMP-stimulated anion channel, thus demonstrating that cystic fibrosis cell lines increase chloride channel activity when treated with a test compound.

6.5 Example 5

Primary Cells from the MDX Nonsense-Containing Mouse Express Full-Length Dystrophin Protein when Treated with a Nonsense Suppressor The mutation in the mdx mouse that causes premature termination of the 427 kDa dystrophin polypeptide has been shown to be a C to T transition at position 3185 in exon 23 (Sicinski et al., 1989, Science 244(4912):1578-1580). Mouse primary skeletal muscle cultures derived from 1-day old mdx mice are prepared as described previously (Barton-Davis et al., 1999, J Clin Invest. 104(4):375-381). Cells are cultured for 10 days in the presence of test compound (20 µM). Culture medium is replaced every four days and the presence of dystrophin in myoblast cultures is detected by immunostaining as described previously (Barton-Davis et al., 1999, J Clin Invest. 104(4):375-381). A primary monoclonal antibody to the C-terminus of the dystrophin protein (F19A12) is used undiluted and rhodamine conjugated anti-mouse IgG is used as the secondary antibody. The F19A12 antibody will detect the full-length protein produced by suppression of the nonsense codon. Staining is viewed using a Leica DMR microscope, digital camera, and associated imaging software at the University of Pennsylvania.

6.6 Example 6

Readthrough of Premature Termination Codons in the MDX Mouse

As previously described (Barton-Davis et al., 1999, J Clin Invest. 104(4):375-381), test compound is delivered by Alzet osmotic pumps implanted under the skin of anesthetized mice. Two doses of test compound are administered. Gentamicin serves as a positive control and pumps filled with solvent only serve as the negative control. Pumps are loaded with appropriate compound such that the calculated doses to which tissue is exposed are 10 µM and 20 µM. The gentamicin concentration is calculated to achieve tissue exposure of approximately 200 µM. In the initial experiment, mice are treated for 14 days, after which animals are anesthetized with ketamine and exsanguinated. The tibialis anterior (TA) muscle of the experimental animals is then excised, frozen, and used for immunofluorescence analysis of dystrophin incorporation into striated muscle. The presence of dystrophin in TA muscles is detected by immunostaining, as described previously (Barton-Davis et al., 1999, J Clin Invest. 104(4):375-381).

6.7 Example 7

Preparation of 3-[5-(2-fluoro-phenyl)-[1,2,4]oxadiazol-3-yl]-benzoic acid

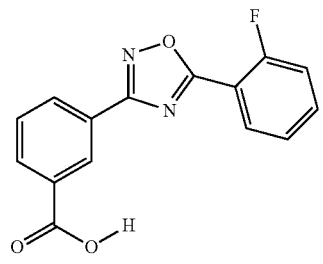 [SMILES: O=C(O)c1cccc(-c2noc(-c3ccccc3F)n2)c1]

To a solution of 3-Cyanobenzoic acid (44.14 g, 300 mmol) in DMF (0.6 L) was added $K_2CO_3$ (62.19 g, 450 mmol) and then stirred for 30 min at room temperature. To the suspension was added methyl iodide (28 mL, 450 mmol) over 20 min, and the reaction mixture was stirred further 4 h at room temperature. The reaction mixture was poured to 1.2 L of ice water and stirred for 30 min, and the precipitate was filtered off. The white cake was dissolved in methanol (70 mL), and then re-precipitated in cold water. The desired product was obtained as a white powder with 79% yield (38 g, 99% purity by LC/UV). $^1$H-NMR (CDCl$_3$) δ 8.85 (2H), 8.28 (1H), 8.02 (1H), 4.17 (3H).

To a solution of 3-Cyanobenzoic acid methyl ester (50 g, 310 mmol) in ethanol (500 mL) was added 50% aqueous hydroxylamine (41 mL, 620 mmol) at room temperature. The reaction mixture was stirred for 1 h at 100° C. and the solvents were removed under reduced pressure. The oily residue was dissolved in 20/80 ethanol/toluene (50 mL×2) and then concentrated again. The desired ester (61 g, quan. yield) was obtained as a white powder with 98% purity (LC/UV). $^1$H-NMR (CDCl$_3$) δ 9.76 (1H), 8.24 (1H), 7.82 (2H), 7.51 (1H), 5.92 (2H), 3.82 (3H).

START HERE To a solution of 3-(N-Hydroxycarbamimidoyl)-benzoic acid methyl ester (60 g, 310 mmol) in anhydrous THF (200 mL) was added diisopropylethylamine (75 mL, 434 mmol) at 5° C., and then to the mixture was added 2-fluorobenzoyl chloride (48.1 mL, 403 mmol) over 20 min. The reaction mixture was stirred for1h at room temperature. The precipitate was filtered off and the filtrate was concentrated under reduced pressure. The residue was dissolved in ethylacetate (400 mL) and then washed with water (200 mL×2). The solvent was removed under reduced pressure and the desired product was crystallized in 60% ethylacetate in hexane to yield the desired product (81 g, 83% yield) as a white solid. $^1$H-NMR (CDCl$_3$) δ 8.18 (1H), 8.03 (3H), 7.48 (2H), 7.18 (2H), 5.61 (2H), 3.82 (3H).

44 g of 3-(N-2-Fluorobenzoylcarbamimidoyl)-benzoic acid methyl ester in toluene (500 mL) was refluxed for 4 h at 130° C. using Dean-Stark apparatus. The reaction mixture was stirred at 5° C. for 18 h. The white precipitate was filtered off and the filtrate was concentrated, crystallized again in toluene. The desired oxadiazole (38 g, 92% yield) was obtained as a white solid with 99% purity (LC/UV). $^1$H-NMR (CDCl$_3$) δ 8.91 (1H), 8.38 (1H), 8.15 (2H), 7.62 (2H), 7.35 (2H), 3.95 (3H).

To a solution of 3-[5-(2-Fluoro-phenyl)-[1,2,4]oxadiazol-3-yl]-benzoic acid methyl ester (3.3 g, 11 mmol) in THF (40 mL) was added 1.5M aqueous NaOH (10 mL, 14 mmol). The reaction mixture was refluxed for 2 h at 100° C. The organic solvent was removed and the aqueous solution was diluted with water (50 mL), and then acidified with aqueous HCl. The white precipitate was filtered off and the white cake was washed with cold water and then dried using lyophilizer. The desired acid (3.0 g, 96% yield) was obtained as a white powder with 98% purity (LC/UV). Melting point 242° C.; IR □ 3000 (Aromatic C—H), 1710 (C=O); $^1$H-NMR (D$_6$-DMSO) δ 8.31 (1H), 8.18 (2H), 8.08 (1H), 7.88 (2H), 7.51 (2H); $^{13}$C-NMR (D$_6$-DMSO) δ 172.71, 167.38, 166.48, 161.25, 135.80, 132.24, 131.79, 131.79, 131.08, 130.91, 129.81, 127.76, 125.48, 117.38, 111.70; $^{19}$F-NMR (D$_6$-DMSO) δ 109.7.

Pharmaceutically acceptable salts of 3-[5-(2-Fluoro-phenyl)-[1,2,4]oxadiazol-3-yl]-benzoic acid can be prepared using methods known to those skilled in the art. The sodium salt can be prepared as follows. To a solution of 3-[5-(2-Fluoro-phenyl)-[1,2,4]oxadiazol-3-yl]-benzoic acid methyl ester (33 g, 111 mol) in THF (400 mL) was added 1.5M aqueous NaOH (100 mL, 144 mmol). The reaction mixture was refluxed for 2 h at 100° C. The organic solvent was removed under reduced pressure and the aqueous solution was stirred 2 h at 5° C. The white precipitate was filtered off and the filtrate was concentrated and precipitated again in water. The white cake was washed with cold water and then dried using lyophilizer. The desired salt (33 g, 96% yield) was obtained as a white powder with 98.6% purity (LC/UV).

6.8 Example 8

Oral Treatment of Nonsense-Mutation-Mediated Cystic Fibrosis

The present example sets forth an illustrative dosing regimen useful for the treatment of nonsense-mutation-mediated Cystic Fibrosis.

3-[5-(2-Fluoro-phenyl)-[1,2,4]oxadiazol-3-yl]-benzoic acid or a pharmaceutically acceptable salt, solvate or hydrate thereof is provided as a vanilla-flavored powder for suspension. The drug is manufactured under current Good Manufacturing Practice conditions (cGMP). The formulation can include binding and suspending agents, surfactants, and various minor excipients that aid in the manufacturing process. The mixture can be packaged in 40 mL plastic (high-density polyethylene [HDPE]) bottles sealed with a foil seal and a white plastic, childproof cap. Each bottle can contain 125, 250 or 1000 mg of the drug substance, which is 25.0% of the total formulation weight. Alternatively, the mixture can be provided in a sachet formulation, such as set forth in Example 12. Excipients (and their proportions of the total formulation weight) include a suspending agent (Litesse® Ultra [refined polydextrose]—25.7%), a binding agent that can also provide taste-masking (mannitol—25.0%), surfactant agents (polyethylene glycol 3350—12.8% and Lutrol® micro F127 [poloxamer 407 powder]—3.7%), a disintegrant (crospovidone—5.0%), and other excipients, each less than 2% (hydroxyethyl cellulose, vanilla flavor, magnesium stearate [non-bovine], and colloidal silica) can be present. Bottle labels indicate the identity of the drug substance, the lot number, the amount of the drug substance, and the storage conditions (e.g., room temperature or refrigeration at 5° to 8° C.).

Dosing of the drug substance is based on milligrams of drug per kilogram of patient body weight. The dose of the drug substance can rounded to be consistent with the available bottle sizes. The dosing scheme ensures that the total actual dose given is never <50 mg below or >250 mg above the intended dose (i.e., is always within 5 mg/kg of the assigned dose level). For example, a patient weighing 40 kg being treated with the 4 mg/kg dose would have a calculated dose of 160 mg. This patient would receive one 250 mg bottle (250 mg total) or 6.25 mg/kg/dose. The same patient when treated with the 8 mg/kg dose in the evening would have a calculated dose of 320 mg and would receive two 250 mg bottles (500 mg total) or 12.5 mg/kg. The same patient treated with the 10 mg/kg/dose would have a calculated dose of 400 mg and would receive two 250 mg bottles (500 mg total) or 12.5 mg/kg. The same patient when treated with the 20 mg/kg dose in the evening would have a calculated dose of 800 mg and would receive one 1000 mg bottle (1000 mg total) or 25 mg/kg.

The reconstitution and dosing of the drug product is done at room temperature. No specific warming of the drug product is necessary before reconstitution. The drug product can be reconstituted with any pharmaceutically acceptable solvent (e.g., water, milk, a carbonated beverage, juice, apple sauce, baby food or baby formula). For each 250 mg bottle provided, ~10 mL of water or other pharmaceutically acceptable solvent is added to achieve a concentration of about 25 mg/mL in the total volume of suspension. For each 1000 mg bottle provided, ~20 mL of water or other pharmaceutically acceptable solvent is added to achieve a concentration of about 50 mg/mL in the total volume of suspension. Suspensions of about 150 mg/mL can also be prepared. Immediately after water or other pharmaceutically acceptable solvent is added to the dry study medication, the bottle(s) is capped and shaken vigorously by hand for about 60 seconds to achieve homogeneity of suspension. Although the suspension may remain in the original plastic bottle for up to 24 hours before ingestion, it is recommended that the drug be taken shortly after reconstitution. If there is a delay of more than 15 minutes between reconstitution and dosing, the bottle should be reshaken vigorously by hand for about 60 seconds.

Treatment is administered continuously for as long as necessary to a patient having or susceptible to having Cystic Fibrosis. Table 11 sets forth illustrative daily dosing regimens for 3-[5-(2-fluoro-phenyl)-[1,2,4]oxadiazol-3-yl]-benzoic acid or a pharmaceutically acceptable salt, solvate or hydrate thereof wherein administration occurs three times per day at 6-, 6-, and 12-hour intervals (e.g., ~7:00 AM, ~1:00 PM and ~7:00 PM) with food. In a particular embodiment, the patient is administered 3-[5-(2-fluoro-phenyl)-[1,2,4]oxadiazol-3-yl]-benzoic acid or a pharmaceutically acceptable salt, solvate or hydrate thereof as set forth in Table 11 continuously for 14 days, followed by 14 days without treatment, followed by an additional 14 days of administration, followed by an additional 14 days without treatment. In another particular embodiment, the patient is administered 3-[5-(2-fluoro-phenyl)-[1,2,4]oxadiazol-3-yl]-benzoic acid or a pharmaceutically acceptable salt, solvate or hydrate thereof as set forth in Table 11 continuously for 14 days at three daily doses of 4 mg/kg, 4 mg/kg and 8 mg/kg, followed by 14 days without treatment, followed by an additional 14 days of administration at three daily doses of 10 mg/kg, 10 mg/kg and 20 mg/kg, followed by an additional 14 days without treatment. In certain embodiments, a single daily dosing regimen set forth in Table 11 is followed each day. In other embodiments, different dosing regimens set forth in Table 11 can be followed on different days.

TABLE 11

Dosing Scheme

| | Regimen | | |
|---|---|---|---|
| | 1<br>TID dosing<br>with food | 2<br>TID dosing<br>with food<br>Schedule | 3<br>TID dosing<br>with food |
| Time | Continuous<br>Daily Admin. | Continuous<br>Daily Admin.<br>Dose | Continuous<br>Daily Admin. |
| ~7:00 AM | 4 mg/kg | 7 mg/kg | 10 mg/kg |
| ~1:00 PM | 4 mg/kg | 7 mg/kg | 10 mg/kg |
| ~7:00 PM | 8 mg/kg | 14 mg/kg | 20 mg/kg |

Abbreviations:
TID = three times per day

Patients preferably take the drug within 30 minutes after a meal; ideally the drug will be taken at approximately 6-, 6-, and 12-hour intervals (e.g., at ~7:00 AM after breakfast, ~1:00 PM after lunch, and at ~7:00 PM after supper). Patients ingest the drug by filling each bottle with the required amount of water or other pharmaceutically acceptable solvent, capping and shaking each bottle for about 60 seconds, and then ingesting the contents of the required number and size of bottles per dose. The entire dose of reconstituted drug is to be taken at one time. After ingestion, each dosing bottle is half-filled with water or another pharmaceutically acceptable solvent, capped and shaken, and this water or other pharmaceutically acceptable solvent from the bottle is ingested by the patient. This rinse procedure is carried out once. In certain embodiments, the drug is provided as a sachet. In these embodiments, the appropriate amount of the drug can be weighed or measured and combined with an appropriate pharmaceutically acceptable solvent prior to administration.

6.9 Example 9

Oral Treatment of Nonsense-Mutation-Mediated Duchenne Muscular Dystrophy

The present example sets forth an illustrative dosing regimen useful for the treatment of nonsense-mutation-mediated Duchenne Muscular Dystrophy.

3-[5-(2-Fluoro-phenyl)-[1,2,4]oxadiazol-3-yl]-benzoic acid or a pharmaceutically acceptable salt, solvate or hydrate thereof is provided as a vanilla-flavored powder for suspension. The drug is manufactured under current Good Manufacturing Practice conditions (cGMP). The formulation can include binding and suspending agents, surfactants, and various minor excipients that aid in the manufacturing process. The mixture can be packaged in 40 mL plastic (high-density polyethylene [HDPE]) bottles sealed with a foil seal and a white plastic, childproof cap. Each bottle can contain 125, 250 or 1000 mg of the drug substance, which is 25.0% of the total formulation weight. Alternatively, the mixture can be provided in a sachet formulation, such as set forth in Example 12. Excipients (and their proportions of the total formulation weight) include a suspending agent (Litesse® Ultra [refined polydextrose]—25.7%), a binding agent that can also provide taste-masking (mannitol—25.0%), surfactant agents (polyethylene glycol 3350—12.8% and Lutrol® micro F127 [poloxamer 407 powder]—3.7%), a disintegrant (crospovidone—5.0%), and other excipients, each less than 2% (hydroxyethyl cellulose, vanilla flavor, magnesium stearate [non-bovine], and colloidal silica) can be present. Bottle labels indicate the identity of the drug substance, the lot number, the amount of the drug substance, and the storage conditions (e.g., room temperature or refrigeration at 5° to 8° C.).

Dosing of the drug is based on milligrams of drug per kilogram of patient body weight. The total volume corresponding to the total milligram amount of drug to be administered to a patient should be calculated. For example, if a 30-kg patient is to get 4 mg/kg, then the dose to be delivered will be 30×4=120 mg. This patient should be dosed using the 250 mg dose bottle. Since each mL of the suspension in the 250 mg dose bottle contains 250/10=25 mg of the drug, this patient should get 120/25=~5 mL of the suspension for each 4 mg/kg dose). The same patient when treated with the 8 mg/kg dose in the evening would have a calculated dose of 240 mg and would receive one 250 mg bottle (10 mL suspension). These volumes of the suspensions for the respective doses should be withdrawn from the drug bottle using a plastic oral dosing syringe. For transfer of fractional volumes of <10 (for 250 mg bottle) or <20 mL (for 1000 mg bottle), the desired amount should be withdrawn from the study medication bottle into a dosing syringe of an appropriate type and size (e.g., a Baxa, Exacta-Med, calibrated, latex-free, plastic, oral dosing syringe) and dosed using the same syringe. During the same 24 hours after reconstitution, >1 dose may be taken from the same bottle of suspension; however, reconstituted drug should not be stored beyond 24 hours with the intention of using this material again for multiple doses in the same patient. If the total amount of drug to be taken in 1 day exceeds 10 mL (for 250 mg bottle) or 20 mL (for 1000 mg bottle) of the reconstituted drug, then a new bottle of drug should be used for each dosing.

For a TID dosing regimen, the following rounding of drug dose can be followed:

| TID Dose Regimen: Number of 125 mg<br>Sachets of 3-[5-(2-fluoro-phenyl)-[1,2,4]oxadiazol-3-yl]-benzoic<br>acid to be Ingested per Dose | | | |
|---|---|---|---|
| Weight<br>Range (kg) | Breakfast Dose<br>(4 mg/kg) | Lunch Dose<br>(4 mg/kg) | Dinner Dose<br>(8 mg/kg) |
| 25-35 | 1 | 1 | 2 |
| 36-44 | 1 | 1 | 3 |
| 45-53 | 2 | 2 | 3 |
| 54-66 | 2 | 2 | 4 |
| 67-78 | 2 | 2 | 5 |
| 79-89 | 3 | 3 | 5 |
| 90 | 3 | 3 | 6 |
| Median Dose | 4 mg/kg | 4 mg/kg | 8 mg/kg |
| [Range] | [3-6 mg/kg] | [3-6 mg/kg] | [7-10 mg/kg] |

For a BID dosing regimen, the following rounding of drug dose can be followed:

| BID Dose Regimen: Number of 125 mg<br>Sachets of 3-[5-(2-fluoro-phenyl)-[1,2,4]oxadiazol-3-yl]-<br>benzoic acid to be Ingested per Dose | | |
|---|---|---|
| Weight<br>Range (kg) | Breakfast Dose<br>(8 mg/kg) | Dinner Dose<br>(8 mg/kg) |
| 25-35 | 2 | 2 |
| 36-44 | 3 | 3 |
| 45-53 | 3 | 3 |
| 54-66 | 4 | 4 |
| 67-78 | 5 | 5 |
| 79-89 | 5 | 5 |

-continued

BID Dose Regimen: Number of 125 mg
Sachets of 3-[5-(2-fluoro-phenyl)-[1,2,4]oxadiazol-3-yl]-
benzoic acid to be Ingested per Dose

| Weight Range (kg) | Breakfast Dose (8 mg/kg) | Dinner Dose (8 mg/kg) |
|---|---|---|
| 90 | 6 | 6 |
| Median Dose [Range] | 8 mg/kg [7-10 mg/kg] | 8 mg/kg [7-10 mg/kg] |

The reconstitution and dosing of the drug product is done at room temperature. No specific warming of the drug product is necessary before reconstitution. The drug can be reconstituted with any pharmaceutically acceptable solvent (e.g., water, milk, a carbonated beverage, juice, apple sauce, baby food or baby formula). For each 250 mg bottle provided, ~10 mL of water or other pharmaceutically acceptable solvent is added to achieve a concentration of about 25 mg/mL in the total volume of suspension. For each 1000 mg bottle provided, ~20 mL of water or other pharmaceutically acceptable solvent is added to achieve a concentration of about 50 mg/mL in the total volume of suspension. Immediately after water or other pharmaceutically acceptable solvent is added to the dry study medication, the bottle(s) is capped and shaken vigorously by hand for about 60 seconds to achieve homogeneity of suspension. Although the suspension may remain in the original plastic bottle for up to 24 hours before ingestion, it is recommended that the drug be taken shortly after reconstitution. If there is a delay of more than 15 minutes between reconstitution and dosing, the bottle should be reshaken vigorously by hand for about 60 seconds.

Treatment is administered continuously for as long as necessary to a patient having or susceptible to having Duchenne Muscular Dystrophy. Table 12 sets forth illustrative daily dosing regimens for 3-[5-(2-fluoro-phenyl)-[1,2,4]oxadiazol-3-yl]-benzoic acid or a pharmaceutically acceptable salt, solvate or hydrate thereof wherein administration occurs two times per day at 12-hour intervals (e.g., ~7:00 AM and ~7:00 PM) or three times per day at 6-, 6-, and 12-hour intervals (e.g., ~7:00 AM, ~1:00 PM and ~7:00 PM) with food. In a particular embodiment, the patient is administered 3-[5-(2-fluoro-phenyl)-[1,2,4]oxadiazol-3-yl]-benzoic acid or a pharmaceutically acceptable salt, solvate or hydrate thereof in one of the dosing regimens set forth in Table 12 continuously for 14 or 28 days. In certain embodiments, a single daily dosing regimen set forth in Table 12 is followed each day. In other embodiments, different dosing regimens set forth in Table 12 can be followed on different days.

TABLE 12

Dosing Scheme

| | Regimen | | | |
|---|---|---|---|---|
| | 1 BID dosing with food | 2 TID dosing with food | 3 TID dosing with food | 4 TID dosing with food |
| Time | Continuous Daily Admin. | Continuous Daily Admin. | Continuous Daily Admin. Dose | Continuous Daily Admin. |
| ~7:00 AM | 8 mg/kg | 4 mg/kg | 7 mg/kg | 10 mg/kg |
| ~1:00 PM | 0 mg/kg | 4 mg/kg | 7 mg/kg | 10 mg/kg |
| ~7:00 PM | 8 mg/kg | 8 mg/kg | 14 mg/kg | 20 mg/kg |

Abbreviations:
TID = three times per day

Patients are administered the drug within 30 minutes after a meal; ideally the drug will be taken at approximately 6-, 6, and 12-hour intervals (e.g., at ~7:00 AM after breakfast, ~1:00 PM after lunch, and at ~7:00 PM after supper). Patients ingest the drug by filling each bottle with the required amount of water or other pharmaceutically acceptable solvent, capping and shaking each bottle for about 60 seconds, withdrawing the appropriate amount of volume from the bottle using an oral dosing syringe and ingesting the contents directly from the dosing syringe. The entire calculated volume of reconstituted drug corresponding to the dose is to be taken at one time. After ingestion of the drug, the dosing syringe should be filled with the same volume of water or other pharmaceutically acceptable solvent as the dose volume, and should be ingested by the patient. This rinse procedure should be carried out once. In certain embodiments, the drug is provided as a sachet. In these embodiments, the appropriate amount of the drug can be weighed or measured and combined with an appropriate pharmaceutically acceptable solvent prior to administration.

Efficacy of treatment can be determined by measuring the change from a baseline measurement of dystrophin levels in a biopsy of the foot muscle extensor digitorum brevis (EDB).

6.10 Example 10

Preparation of Unflavored Dosages of 3-[5-(2-fluoro-phenyl)-[1,2,4]oxadiazol-3-yl]-benzoic acid or a Pharmaceutically Acceptable Salt, Solvate or Hydrate Thereof 3-[(5-(2-Fluoro-phenyl)-[1,2,4]oxadiazol-3-yl]-benzoic acid or a pharmaceutically acceptable salt, solvate or hydrate thereof is provided as a powder for suspension. The drug is manufactured under current Good Manufacturing Practice conditions (cGMP). The drug can be intimately mixed with binding and suspending agents, surfactants, and various minor excipients that aid in the manufacturing process. The mixture is packaged in a 40 mL plastic (high-density polyethylene [HDPE]) bottle sealed with a foil seal and a white plastic, childproof cap. Each bottle can contain about 35 mg, about 70 mg, about 125 mg, about 140 mg, about 175 mg, about 250 mg, about 280 mg, about 350 mg, about 560 mg, about 700 mg, about 1000 mg or about 1400 mg of 3-[5-(2-fluoro-phenyl)-[1,2,4]oxadiazol-3-yl]-benzoic acid or a pharmaceutically acceptable salt, solvate or hydrate thereof. Excipients (and their proportions of the total formulation weight) optionally include a suspending agent (Litesse® Ultra [refined polydextrose]—25.7%), a binding agent that can also provide taste-masking (mannitol—25.0%), surfactant agents (polyethylene glycol 3350—12.8% and Lutrol® micro F127 [poloxamer 407 powder]—3.7%), a disintegrant (crospovidone—5.0%), and other excipients, each less than 2% (cab-o-sil, hydroxyethyl cellulose, magnesium stearate [non-bovine], and colloidal silica) can be present. The bottle is then labeled to indicate the identity of the drug substance, the lot number, the amount of the drug substance, and the storage conditions (e.g., refrigeration at 5° to 8° C.). Prior to administration, the drug product is reconstituted in an appropriate volume of a pharmaceutically acceptable solvent (e.g., water, milk, a carbonated beverage, juice, apple sauce, baby food or baby formula).

6.11 Example 11

Preparation of Flavored Dosages of 3-[5-(2-fluoro-phenyl)-[1,2,4]oxadiazol-3-yl]-benzoic acid or a Pharmaceutically Acceptable Salt, Solvate or Hydrate Thereof 3-[5-(2-Fluoro-phenyl)-[1,2,4]oxadiazol-3-yl]-benzoic acid or a pharmaceutically acceptable salt, solvate or hydrate thereof is provided as a vanilla-flavored (e.g., by addition of vanilla extract) powder for suspension. The drug is manufactured under current Good Manufacturing Practice conditions (cGMP). The drug can be intimately mixed with binding and suspending agents, surfactants, and various minor excipients that aid in the manufacturing process. The mixture is packaged in a 40 mL plastic (high-density polyethylene [HDPE]) bottle sealed with a foil seal and a white plastic, childproof cap. Each bottle can contain about 35 mg, about 70 mg, about 125 mg, about 140 mg, about 175 mg, about 250 mg, about 280 mg, about 350 mg, about 560 mg, about 700 mg, about 1000 mg or about 1400 mg of 3-[5-(2-fluoro-phenyl)-[1,2,4]oxadiazol-3-yl]-benzoic acid or a pharmaceutically acceptable salt, solvate or hydrate thereof. Excipients (and their proportions of the total formulation weight) optionally include a suspending agent (Litesse® Ultra [refined polydextrose]—25.7%), a binding agent that can also provide taste-masking (mannitol—25.0%), surfactant agents (polyethylene glycol 3350—12.8% and Lutrol® micro F127 [poloxamer 407 powder]—3.7%), a disintegrant (crospovidone—5.0%), and other excipients, each less than 2% (cab-o-sil, hydroxyethyl cellulose, vanilla flavor, magnesium stearate [non-bovine], and colloidal silica) can be present. The bottle is then labeled to indicate the identity of the drug substance, the lot number, the amount of the drug substance, and the storage conditions (e.g., refrigeration at 5° to 8° C.). Prior to administration, the drug product is reconstituted in an appropriate volume of a pharmaceutically acceptable solvent (e.g., water, milk, a carbonated beverage, juice, apple sauce, baby food or baby formula).

6.12 Example 12

Sachet Formulation of 3-[5-(2-Fluoro-phenyl)-[1,2,4]oxadiazol-3-yl]-benzoic acid or a Pharmaceutically Acceptable Salt, Solvate or Hydrate Thereof The mixture is packaged using a pouch or sachet that is comprised of multiple laminated layers that may include a paper layer, an aluminum foil layer and a surlyn layer. Each sachet can contain about 125 mg, about 250 mg, about 500 mg or about 1000 mg of 3-[(5-(2-fluoro-phenyl)-[1,2,4]oxadiazol-3-yl]-benzoic acid or a pharmaceutically acceptable salt, solvate or hydrate thereof. Excipients (and their proportions of the total formulation weight) optionally include either of the following as set forth in Table 13 and Table 14.

TABLE 13

Formulation

| Ingredient | Weight % |
| --- | --- |
| 3-[5-(2-fluoro-phenyl)-[1,2,4]oxadiazol-3-yl]-benzoic acid or a pharmaceutically acceptable salt, solvate or hydrate thereof | 25.0 |
| Litesse ® Ultra | 24.75 |
| Polyethylene Glycol | 12.8 |
| Lutrol ® Micro | 3.7 |
| Mannitol | 25.0 |
| Hydroxyethyl Cellulose | 1.5 |
| Vanilla Flavor | 0.75 |
| Crospovidone | 5.0 |
| Cab-o-sil | 0.5 |
| Magnesium Stearate | 0.5 |
| Talc | 0.5 |

TABLE 14

Formulation

| Ingredient | Weight % |
| --- | --- |
| 3-[5-(2-fluoro-phenyl)-[1,2,4]oxadiazol-3-yl]-benzoic acid or a pharmaceutically acceptable salt, solvate or hydrate thereof | 25.0 |
| Litesse ® Ultra | 25.65 |
| Polyethylene Glycol | 12.8 |
| Lutrol ® Micro | 3.7 |
| Mannitol | 25.0 |
| Hydroxyethyl Cellulose | 1.5 |
| Vanilla Flavor | 0.75 |
| Crospovidone | 5.0 |
| Cab-o-sil | 0.1 |
| Magnesium Stearate | 0.5 |

The sachet is then labeled to indicate the identity of the drug substance, the lot number, the amount of the drug substance, and the storage conditions (e.g., refrigeration at 5° to 8° C.). Prior to administration, an appropriate amount of the drug product is reconstituted in an appropriate volume of a pharmaceutically acceptable solvent (e.g., water, milk, a carbonated beverage, juice, apple sauce, baby food or baby formula).

6.13 Example 13

Transepithelial Potential Difference (TEPD) Assay

The measurement of transepithelial potential difference (TEPD), also known as nasal potential difference, provides a sensitive evaluation of sodium and chloride transport directly in secretory epithelial cells via assessment of transepithelial bioelectric properties (Knowles et al., 1981, *N. Engl. J. Med.* 305(25):1489-95; Knowles et al., 1995, *Hum. Gene Ther.* 6:445). TEPD is performed in each nostril using standardized techniques (Standaert et al., 2004, *Ped. Pulm.* 37:385-92). In the procedure, a small plastic catheter is used to assess electrical differences across the outer cell membrane of nasal mucosa cells in the nostril. TEPD values are expressed in millivolts, or mV. A chloride conductance equal to or more electrically negative than −5.0 mV is generally considered to be in the normal range. TEPD assessments are made on the nasal epithelium cells lining the inferior turbinate because these cells are easier to access than the respiratory epithelial cells lining the lower airways, and have been shown to have the same ion transport characteristics (Knowles et al., 1981, *Am. Rev. Respir. Dis.* 124(4):484-90). TEPD assessments can also be made on rectal epithelial cells and lower respiratory epithelial cells. Because of the role of the CFTR protein in transporting chloride ions across cell membranes, and because of the absence of this protein, cystic fibrosis patients have an abnormal TEPD chloride conductance. As an endpoint, TEPD has the advantage that it can detect chloride transport changes that are a quantitative integration of the presence, functional activity, and apical location of the CFTR in airway cells. Furthermore, it is a direct measure of CFTR activity that is not likely to be affected by supportive or palliative treatments for CF (with the possible exception of systemically administered aminoglycoside antibiotics). Of importance is evidence that TEPD values can correlate with the degree of pulmonary dysfunction and radiographic abnormality (Ho et al., 1997, *Eur. Respir. J.* 10(9):2018-22; Fajac et al., 1998, *Eur. Respir. J.* 12(6):1295-300; Sermet-Gaudelus et al., 2005, *Am. J. Respit. Crit. Care Med.* 171(9):1026-1031). In particular, TEPD assessment of isoproterenol-induced CFTR chloride activity has demonstrated better predictive value than genotype in determining FEV1 and radiological score (Ho et al., 1997, *Eur Respir J.* 10(9):2018-22). Under baseline conditions, TEPD-assessed chloride channel activity is very unlikely to normalize spontaneously in patients with CF; any observed improvements in TEPD-assessed chloride channel activity are expected to specifically denote pharmacological activity of CFTR-correcting therapies. Accordingly, it has become the primary endpoint in Phase 1-2 pharmacological and gene replacement studies aimed at correcting CFTR dysfunction (Peckham et al., 1995, *AJ. Clin Sci (London).* 89(3):277-84; Wilschanski et al., 2003, *N. Engl. J. Med.* 349(15):1433-41).

6.14 Example 14

CFTR Immunofluorescence

The collection and processing of the nasal mucosal curettage from each nostril of a patient for measurement of CFTR protein by immunofluorescence and by quantification of CFTR mRNA is performed using standardized techniques (Clancy et al., 2001, *Am. J. Respir. Crit. Care Med.* 163(7): 1683-92; Amaral et al, 2004, *J. Cyst. Fibros.* 3 *Suppl* 2:17-23). The immunofluorescence staining of normal epithelial cells (for example, from nasal mucosal scrapings) reveals the presence of most of the CFTR protein at the apical surface. In animal models of nonsense-mutation-mediated CF or in patients with nonsense-mutation-mediated CF, CFTR staining is absent (e.g., in patients homozygous for a premature stop mutation) or is primarily observed in the perinuclear region (e.g., in patients with a ΔF508 mutation that prevents normal CFTR intracellular trafficking). Successful production of functional wild or non-wild type CFTR protein in both animal models and patients has been associated with reappearance of apical epithelial CFTR protein as assessed by immunofluorescence (Clancy et al., 2001, *Am. J. Respir. Crit. Care Med.* 163(7):1683-92; Wilschanski et al., 2003, *N. Engl. J. Med.* 349(15):1433-41).

6.15 Example 15

Pulmonary Function Tests

Pulmonary function tests, including FEV1, FVC, and MEF25-75, are measured using standard spirometry procedures. Assessments of pulmonary function (including MEF25-75, FVC, and, particularly, FEV1) have been acknowledged as definitive clinical endpoints in patients with CF (Food and Drug Administration, 62nd Anti-Infective Drugs Advisory Committee. Discussion of NDA for tobramycin solution for inhalation (Tobi®) for the management of cystic fibrosis patients. November, 1997; Tiddens, 2002, *Pediatr. Pulmonol.* 34(3): 228-31). FEV1 and other pulmonary function testing measures have been shown to correlate with disease severity, predict morbidity in terms of health care utilization and IV antibiotic usage, and indicate the risk of CF-related mortality (Food and Drug Administration, 62nd Anti-Infective Drugs Advisory Committee. Discussion of NDA for tobramycin solution for inhalation (Tobi®) for the management of cystic fibrosis patients. November, 1997). Pulmonary function testing is simple to administer (even in patients as young as 7 years of age), and uses standardized equipment and techniques that are widely available. Interpretation is performed using well-established normative equations that account for patient age, height, and gender. Improvement in FEV1 has been acknowledged as quantitatively demonstrating meaningful clinical benefit in CF, and has served as the basis for regulatory approval of dornase alfa and inhaled tobramycin (Food and Drug Administration, 62nd Anti-Infective Drugs Advisory Committee. Discussion of NDA for tobramycin solution for inhalation (Tobi®) for the management of cystic fibrosis patients. November, 1997).

6.16 Example 16

Phase 2 Study of 3-[5-(2-fluoro-phenyl)-[1,2,4]oxa-diazol-3-yl]-benzoic as an Oral Treatment for Non-sense-Mutation-Mediated Cystic Fibrosis Patients must have met all of the following conditions to be eligible for enrollment into the study:
1. Diagnosis of CF based on documented evidence of a conclusively abnormal sweat test (sweat chloride >60 mEq/liter by pilocarpine iontophoresis (LeGrys, Sweat testing: Sample collection and quantitative analysis: Approved guidelines—Second edition. National Committee for Clinical Laboratory Standards 2000; Vol 20:14));
2. Abnormal chloride secretion as measured by TEPD (a more positive than −5 mV TEPD assessment of chloride secretion with chloride-free amiloride and isoproterenol);
3. Presence of a nonsense mutation in one of the alleles of the cftr gene;
4. Documentation that cftr gene sequencing has been performed;
5. Age ≥18 years;
6. Body weight ≥40 kg;
7. FEV1 ≥40% of predicted for age, gender, and height (Knudson standards) (Knudson, 1983, *Am. Rev. Respir. Dis.* 127: 725-734);
8. Oxygen saturation (as measured by pulse oximetry) ≥92% on room air;
9. Willingness of male and female patients, if not surgically sterile, to abstain from sexual intercourse or employ a barrier or medical method of contraception during the study drug administration and follow-up periods;
10. Negative pregnancy test (for females of childbearing potential);
11. Willingness and ability to comply with scheduled visits, drug administration plan, study procedures (including TEPD measurements, clinical laboratory tests, and PK sampling), and study restrictions;
12. Ability to provide written informed consent; and
13. Evidence of personally signed and dated informed consent document indicating that the patient has been informed of all pertinent aspects of the trial.

The presence of any of the following conditions excluded a patient from enrollment in the study:
1. Prior or ongoing medical condition (e.g., concomitant illness, psychiatric condition, alcoholism, drug abuse), medical history, physical findings, ECG findings, or laboratory abnormality that, in the investigator's opinion, could adversely affect the safety of the patient, makes it unlikely that the course of treatment or follow-up would be completed, or could impair the assessment of study results;

2. Ongoing acute illness including acute upper or lower respiratory infections within 2 weeks before start of study treatment;

3. History of major complications of lung disease (including recent massive hemoptysis or pneumothorax) within 2 months prior to start of study treatment;

4. Abnormalities on screening chest x-ray suggesting clinically significant active pulmonary disease other than CF, or new, significant abnormalities such as atelectasis or pleural effusion which may be indicative of clinically significant active pulmonary involvement secondary to CF;

5. Positive hepatitis B surface antigen, hepatitis C antibody test, or human immunodeficiency virus (HIV) test;

6. Hemoglobin <10 g/dL;

7. Serum albumin <2.5 g/dL;

8. Abnormal liver function (serum total bilirubin >the upper limit of normal, or serum ALT, AST, or GGT>2.0 times the upper limit of normal);

9. Abnormal renal function (serum creatinine >1.5 times upper limit of normal);

10. Pregnancy or breast-feeding;

11. History of solid organ or hematological transplantation;

12. Exposure to another investigational drug within 14 days prior to start of study treatment;

13. Ongoing participation in any other therapeutic clinical trial;

14. Ongoing use of thiazolidinedione peroxisome proliferator-activated receptor gamma (PPAR γ) agonists, eg, rosiglitazone (Avandia® or equivalent) or pioglitazone (Actos® or equivalent);

15. Change in intranasal medications (including use of corticosteroids, cromolyn, ipratropium bromide, phenylephrine, or oxymetazoline) within 14 days prior to start of study treatment;

16. Change in treatment with systemic or inhaled corticosteroids within 14 days prior to start of study treatment;

17. Use of or requirement for inhaled gentamicin or amikacin within 14 days prior to start of study treatment or during study treatment; or 18. Requirement for systemic aminoglycoside antibiotics within 14 days prior to start of study treatment.

3-[5-(2-Fluoro-phenyl)-[1,2,4]oxadiazol-3-yl]-benzoic acid was provided in a formulation described herein. 15 patients (12 from a Phase 2 trial being conducted in Israel and 3 from a Phase 2 trial being conducted in the United States; seven patients were male and 8 were female; patients had a median age of 22 years; and all patients had multiple signs and symptoms of cystic fibrosis, including some degree of lung dysfunction) were orally administered 3-[5-(2-fluoro-phenyl)-[1,2,4]oxadiazol-3-yl]-benzoic acid according to the following 56 day schedule: administration of 3-[5-(2-fluoro-phenyl)-[1,2,4]oxadiazol-3-yl]-benzoic acid three times per day (TID) at 4 mg/kg, 4 mg/kg and 8 mg/kg for 14 days, followed by no treatment for 14 days (Cycle 1, consisting of 28 days), followed by administration of 3-[5-(2-fluoro-phenyl)-[1,2,4]oxadiazol-3-yl]-benzoic acid three times per day (TID) at 10 mg/kg, 10 mg/kg and 20 mg/kg for 14 days, followed by no treatment for 14 days (Cycle 2, consisting of 28 days).

Clinical endpoints were evaluated using the procedures set forth above. TEPD measurements were made prior to treatment and on days 14 and 28 of Cycle 1 and Cycle 2. Nasal mucosal curettage was collected from each nostril of each patient prior to treatment and on days 14 and 28 of Cycle 1 and Cycle 2. Pulmonary tests, including $FEV_1$, FVC and $MEF_{25-75}$, were measured prior to treatment, on day −1 of Cycle 2, on day 13 or 14 of Cycle 1 and day 13 or 14 of Cycle 2 in the study being conducted in Israel and the same parameters were measured prior to treatment and on day 13 or 14 of Cycle 2 in the study being conducted in the United States.

Mean Change in TEPD Chloride Conductance.

This is the average of the changes from the beginning to the end of the treatment period in TEPD chloride conductance within each study participant. For example, if the changes in TEPD chloride conductance within each of three participants were −7.0 mV, −2.0 mV and −9.0 mV, the mean change in TEPD chloride conductance among these participants would be −6.0 mV.

Percentage of Patients with a Chloride Conductance Response.

This is the percentage of patients who demonstrated a TEPD chloride conductance response at the end of treatment with 3-[5-(2-fluoro-phenyl)-[1,2,4]oxadiazol-3-yl]-benzoic acid. For purposes of the trials, a chloride conductance response is defined as a TEPD chloride conductance improvement of at least −5 mV. For example, in a patient with a TEPD chloride conductance value of +1.0 my at baseline and a TEPD chloride conductance value of −6.0 mV at the end of treatment, the TEPD chloride conductance improvement would be −7.0 mV, representing a chloride conductance response.

Percentage of Patients with Improvements of TEPD Chloride Conductance Values into the Normal Range.

As noted above, a chloride conductance equal to or more electrically negative than −5.0 mV is generally considered to be in the normal range. As such, a patient with a TEPD chloride conductance value of +1.0 mV at baseline would be considered to have an abnormal value because the value is more electrically positive than −5.0 mV. If, at the end of treatment, that patient's TEPD chloride conductance value improved to −6.0 mV, this would represent an improvement into the normal range because the improved value is more electrically negative than −5.0 mV.

Based on patient gender, age and height, the mean $FEV_1$ value at study entry was 66% of normal and the mean FVC value at study entry was 80% of normal. Fourteen of the patients included in the analysis had airway colonization with *Pseudomonas aeruginosa*, a common bacterial infection in cystic fibrosis patients that can lead to serious pneumonia. Fourteen of the 15 patients also had pancreatic insufficiency and required chronic pancreatic enzyme replacement therapy. Patients had low body weights, with a mean weight of 58.3 kg at study entry.

Table 15 presents the TEPD results for the 15 patients. For each measurement, the results are presented on a best-of-nostrils and mean-of-both-nostrils basis. Historically, results of TEPD tests have typically been presented on a best-of-nostrils basis. However, recent guidelines established by the Cystic Fibrosis Therapeutics Development Network recommend that TEPD results be presented on both bases. Improvements in TEPD chloride conductance in patients with different types of nonsense mutations within the CFTR gene were noted.

TABLE 15

| TEPD Result | Lower Dose Level | | Higher Dose Level | |
|---|---|---|---|---|
| | Result | p-Value | Result | p-Value |
| Mean change in TEPD chloride conductance: | | | | |
| Best of nostrils | −9.0 mV | <0.001 | −6.4 mV | 0.010 |
| Mean of both nostrils | −6.7 mV | <0.001 | −4.4 mV | 0.023 |
| Number of patients with ≥−5 mV improvement in TEPD chloride conductance: | | | | |
| Best of nostrils | 9/15 (60%) | <0.001 | 8/15 (53%) | <0.001 |
| Mean of both nostrils | 6/15 (40%) | 0.005 | 7/15 (47%) | <0.001 |
| Number of patients with improvement in TEPD chloride conductance to normal: | | | | |
| Best of nostrils | 8/15 (53%) | 0.008 | 8/15 (53%) | 0.008 |
| Mean of both nostrils | 6/15 (40%) | 0.032 | 7/15 (47%) | 0.016 |

The treatment effects at the lower and the higher 3-[5-(2-fluoro-phenyl)-[1,2,4]oxadiazol-3-yl]-benzoic acid dose levels were not statistically significant, suggesting that further dose escalation may not be necessary and that even lower doses of 3-[5-(2-fluoro-phenyl)-[1,2,4]oxadiazol-3-yl]-benzoic acid may be effective in improving TEPID chloride conductance. Statistically significant results and positive trends for secondary endpoints were also observed. In particular, although the trials were not been powered to detect statistical significant changes in secondary endpoints, statistically significant improvements from study entry to the end of the higher-dose treatment cycle in the patients' mean $FEV_1$, FVC and weight were observed. Table 16 presents the results. For the changes in lung function, one patient was not included because that patient did not have lung function measured at the end of the higher-dose treatment cycle.

TABLE 16

| Endpoint | Study Entry | End of Higher Dose Treatment | Change | p-Value |
|---|---|---|---|---|
| Lung function (expressed as a percentage of normal for gender, age and height): | | | | |
| Mean $FEV_1$ | 65.8% | 69.1% | 3.3% | 0.015 |
| Mean FVC | 80.2% | 85.1% | 4.9% | 0.037 |
| Weight | 58.3 kg | 59.0 kg | 0.7 kg | 0.012 |

The 3-[5-(2-fluoro-phenyl)-[1,2,4]oxadiazol-3-yl]-benzoic acid interim PK parameters from these 15 patients are described in Table 17. No differences in PK parameters by gender were evident.

TABLE 17

Mean Pharmacokinetic Parameters
CF Phase 2 Preliminary Analysis

| Parameter | Cycle 1 (Lower Dose) 4, 4, 8 mg/kg N = 15 | | Cycle 2 (Higher Dose) 10, 10, 20 mg/kg N = 15 | |
|---|---|---|---|---|
| | Day 1 | Day 14 | Day 1 | Day 14 |
| $AUC_{0-24}$, µg · hour/mL | 145 | 124 | 435 | 417 |
| $C_{max}$, µg/mL | 16 | 13 | 41 | 36 |
| $C_{min}$, µg/mL | 1.6 | 1.9 | 5.0 | 6.5 |

In addition, although changes in patient's symptoms were not formally measured through the use of a quality-of-life questionnaire, trial investigators were requested to ask about changes in patients' cystic fibrosis symptoms. In the 15 patients included in the interim analysis, 6 reported general improvements in well being, 6 reported decrease in cough and 10 reported decreased mucus thickness and easier clearing of mucus.

A second Phase 2 Study protocol for the use of 3-[5-(2-fluoro-phenyl)-[1,2,4]oxadiazol-3-yl]-benzoic acid as an oral treatment for nonsense-mutation-mediated cystic fibrosis follows.

Treatment will be administered in two 28-day cycles. Each cycle will comprise 14 days of continuous daily treatment with 3-[5-(2-fluoro-phenyl)-[1,2,4]oxadiazol-3-yl]-benzoic acid followed by a planned 14 days without study drug. If necessary, treatment in Cycle 2 can be initiated as early as 10 days or as late as 28 days after the last dose of 3-[5-(2-fluoro-phenyl)-[1,2,4]oxadiazol-3-yl]-benzoic acid in Cycle 1.

Patients in Cohort 1 will be administered 3-[5-(2-fluoro-phenyl)-[1,2,4]oxadiazol-3-yl]-benzoic acid TID at doses of 4 mg/kg, 4 mg/kg and 8 mg/kg at 6-, 6-, and 12-hour (±~30 minutes) intervals in Cycle 1, respectively. Ideally each dose should be taken within ~30 minutes after a meal (e.g., ~7:00 AM after breakfast, ~1:00 PM after lunch, and ~7:00 PM after dinner). A planned dose regimen change will be performed in the second cycle such that each patient in this cohort will receive 3-[5-(2-fluoro-phenyl)-[1,2,4]oxadiazol-3-yl]-benzoic acid at doses of 8 mg/kg BID in Cycle 2. Ideally each dose should be taken within ~30 minutes after a meal (eg, ~7:00 AM after breakfast and ~7:00 PM after dinner).

Patients in Cohort 2 will be administered 3-[(5-(2-fluoro-phenyl)-[1,2,4]oxadiazol-3-yl]-benzoic acid BID at doses of 8 mg/kg at 12-hour (±~30 minutes) intervals in Cycle 1. Ideally each dose should be taken within ~30 minutes after a meal (e.g., ~7:00 AM after breakfast and ~7:00 PM after dinner). A planned dose-schedule change will be performed in the second cycle such that each patient in this cohort will receive 3-[5-(2-fluoro-phenyl)-[1,2,4]oxadiazol-3-yl]-benzoic acid at doses of 4 mg/kg, 4 mg/kg, and 8 mg/kg TID in Cycle 2. Ideally each dose should be taken within ~30 minutes after a meal (e.g., ~7:00 AM after breakfast, ~1:00 PM after lunch, and ~7:00 PM after dinner).

6.17 Example 17

Dystrophin, Sarcoglycan, and Dystroglycan Expression by Immunofluorescence and Western Blotting Biopsy of the EDB muscle and overlying skin from one foot is performed under local anesthesia and conscious sedation (in some cases, general anesthesia may be required) prior to treatment, and from the other foot on the last day of treatment. The biopsy procedure is performed using standardized techniques (Stedman, 2000, Human Gene Therapy 11:777-90). The entire muscle belly (whenever possible) is removed in the procedure. At the time of collection of the biopsy prior to treatment, the muscle specimen is divided into at least 3 fragments and the biopsy specimen collected on the last day of treatment is divided into at least 2 fragments. The biopsy specimen is placed on a telfa gauze sponge moistened with Ringer's saline. The biopsy specimen is viewed at low power under a stereo dissection microscope to establish fiber orientation. The muscle is then transected using a sharp scalpel in a cross sectional fashion (perpendicular to the orientation of the fibers) whenever possible and allowed, to rest for 2 minutes to allow for the cessation of spasm. The sample is then frozen in liquid nitrogen cooled isopentane, transferred to a liquid nitrogen reservoir and held 1 inch above the liquid/vapor interface for 2 minutes of slow cooling and isopentane evaporation before immersion in the liquid nitrogen, and wrapped into precooled (in liquid nitrogen and stored on dry ice) foil labeled with the study number, site number, patient number, date, patient initials, and foot side (right foot or left foot).

All sample containers are clearly labeled in a fashion that identifies the subject and the collection date. Labels are fixed to the sample containers in a manner that prevents the label from becoming detached. Samples are shipped for analysis/culture/central review immediately after the procedure is performed. For detection of dystrophin, 3 commercially available antibodies that recognize the C-terminus, the N-terminus, and the rod domain of the protein are employed. For detection of the sarcoglycan and dystroglycan complex, commercially available antibodies against α-, β-, γ-, and δ-sarcoglycan, and β-dystroglycan are used when possible. Epifluorescence microscopy is used in the analysis; images are captured by CCD camera, after normalization of the fluorescence intensity against a normal muscle specimen. Images are stored digitally and preserved for future review, and final evaluation at the completion of the study. Tissues are also processed for detection of dystrophin, the sarcoglycans, and β-dystroglycan by Western blotting using the same antibodies. Microscopic images are captured and preserved for future review, and for final evaluation at the completion of the study. Remaining muscle tissue samples are preserved for confirmatory assays of mRNA and proteins involved in DMD. Immunostaining and Western blotting are employed for protein detection.

Muscle biopsies are commonly performed on DMD subjects as a component of diagnosis and as measures of therapeutic effect in the context of research studies. EDB has been chosen because it is not an essential muscle for daily activities and therefore sampling this muscle does not have adverse functional consequence for the subject. Because it is little used, the EDB muscle is unlikely to demonstrate substantial fibrotic replacement of muscle and thus provides an appropriate tissue for detection of dystrophin production. Sampling of the EDB muscle offers additional practical advantages because it is easy to identify, can be dissected under local anesthesia, and provides sufficient amounts of tissue to carry out the required analyses. Immunofluorescence and Western blotting are routine tests performed on muscle biopsy specimens to confirm the presence or absence of full-length dystrophin. An absence of dystrophin is viewed as confirmation of the diagnosis of DMD. Restoration of dystrophin, with localization to the muscle membrane, has been considered a direct measure of preclinical and clinical pharmacodynamic activity (Barton-Davis, 1999, J. Clin. Invest. 104(4):375-81; Politano, 2003, Acta Myol. 22(1):15-21).

6.18 Example 18

Upper and Lower Extremity Myometry

Upper and lower extremity myometry are performed using a hand-held myometer following standardized procedures (Beenakker, 2001, Neuromuscul. Disord. 11(5):441-6; Hyde, 2001, Neuromuscul. Disord 11(2):165-70). It is recommended (depending on the subject's baseline functional status) that evaluated muscle groups include hip abductors, knee extensors, elbow flexors and extensors, and hand grip. Bilateral assessments can be done, and three measurements can be recorded from each muscle group on each side. These parameters are monitored prior to treatment, on the second to last day of treatment, and during a follow-up period after treatment. During the pre-treatment and treatment periods, the myometry procedures are performed prior to the muscle biopsy.

Myometry assessments using a hand-held dynamometer are a sensitive and reproducible measure of muscle strength in ambulatory and non-ambulatory subjects (Beenakker, 2001, Neuromuscul. Disord. 11(5):441-6; Hyde, 2001, Neuromuscul. Disord. 11(2):165-70). Inter-rater reliability in subjects with muscular dystrophy is high (Stuberg, 1988, Phys. Ther. 1988 68(6):977-82; Hyde, 2001, Neuromuscul. Disord. 11(2):165-70). As compared to manual muscle strength testing, myometry is a more sensitive and less complex measure of muscle function (McDonald, 1995, Am. J. Phys. Med. Rehabil. (5 Suppl):S70-92). The test can be readily administered by the evaluator (e.g., physician or physical therapist).

6.19 Example 19

Timed Function Tests

Timed function tests include time taken to stand from a supine position, time taken to walk 10 meters, and time taken to climb 4 standard-sized stairs (Mendell, 1989, N. Engl. J. Med. 320(24):1592-7; Griggs, 1991, Arch. Neurol. 48(4):383-8). These parameters are monitored prior to treatment, on the second to last day of treatment, and during a follow-up period after treatment. During the pre-treatment and treatment periods, the timed function tests are performed prior to the muscle biopsy.

These tests (time taken to stand from supine position, time taken to walk 10 meters, and time taken to climb 4 standard-sized steps) provide an additional measure of functional capability in ambulatory subjects. The tests are reproducible, commonly employed, simple to administer, and have documented response to therapeutic intervention with steroids (Mendell, 1989, N. Engl. J. Med. 320(24):1592-7; Griggs, 1991, Arch. Neurol. 48(4):383-8).

6.20 Example 20

Serum CK Levels

Serum CK activity is assessed using a commercially available NADH-linked kinetic assay (Diagnostic Chemicals Ltd., Oxford, Conn.). Serum CK levels are measured prior to treatment, on day 1 (prior to first dose), day 7, day 14, day 21, and day 27 during the treatment period, and on day 42 and day 56 after treatment. Serum CK is increased in Duchenne muscular dystrophy and therefore is a readily measurable diagnostic marker for the disease and may serve as a potential biomarker for the pharmacological activity of the drug (Mendell et al., 1989, *New Eng. J. Med.* 320(24):1592-1597).

Serum CK provides a measure of whole-body muscle integrity. Concentrations of this enzyme in the serum are increased 50- to 100-fold in subjects with DMD and measurements of its levels are used in making an early diagnosis of the disease (Worton, The muscular dystrophies, In: Scriver C. R., Beaudet A. L., Sly W. S., Valle D, eds. The metabolic and molecular basis of inherited disease. 8th ed. Vol. 4. New York: McGraw-Hill, 2001:5493-523). The levels of serum CK are measured to monitor the progression of the disease and serve as a marker for muscle damage. While exercise-induced changes introduce variability (Politano, 2003, *Acta. Myol.* 22(1):15-21), the marker has advantages because it can be easily, repeatedly, and frequently assessed with a widely available and reliable assay. Prior clinical studies have shown decreases in serum CK coincident with improvements in muscle strength during treatment with steroids (Reitter, 1995, *Brain Dev.* 17 *Suppl:*39-43).

6.21 Example 21

Dermal Fibroblast and Muscle Cell Culture

Studies are performed on muscle tissue and skin from patients to determine whether dystrophin production in primary muscle cultures from the patients corresponds with dystrophin production in vivo. These experiments evaluate whether dermal fibroblasts from patients, when differentiated into muscle cells in vitro by transfection with a Myo-D-producing expression construct (Wang, 2001, *Development* 128: 4623-33), demonstrate dystrophin production in response to treatment. Correlations of skin cell response with clinical activity may offer an easy-to-obtain predictive test in selecting future patients for therapy or for screening new agents for the treatment of DMD. Cells are cultured as follows. Biopsy material is stored during transport in human proliferation medium (or PBS), and on ice for longer time periods if necessary. If the tissue is not prepared within 24 hours, the material can be frozen in human proliferation medium containing 10% DMSO and stored in liquid nitrogen (or dry ice). At the time the tissue is to be prepared for setting up the myoblast culture, biopsy material is washed in PBS. PBS sufficient to keep the tissue moist is added into a culture dish. The biopsy material is minced thoroughly with razor blades, toward an almost homogeneous suspension. Approximately 2 ml of collegenase/dispase/$CaCl_2$ solution per gram of tissue is added and mincing is continued for several minutes (e.g. for a muscle biopsy of 5×5×5 mm use 1 ml of enzyme solution). The suspension is transferred into a sterile tube and incubated at 37° C. in a waterbath until the mixture is a fine slurry (e.g., about 20 to 30 minutes). The suspension is further homogenized by pipetting up and down several times during incubation. Additional resuspension cycles by pipetting up an down with a syringe can be performed if necessary. Eight mL of human proliferation medium is added to the suspension and mixed. The mixture is centrifuged for 10 minutes at 1200 rpm. The cell pellet is resuspended in 3 ml human proliferation medium. Cells are plated into one well of a collagen-coated 6-wells plate, or, depending on the amount of material, in a T25 collagen-coated flask. Cells are cultured for 48 hrs, at 37° C. and 5% $CO_2$. Non-attached cells are removed and transferred to another collagen-coated well (as backup). Fresh proliferation medium is added to the first well (3 ml). The cells are cultured from the first well to confluency and until two confluent T75-flasks have been obtained. For storage, cells can be frozen from one T75 flask into 4 cryotubes with 1 ml freezing medium. The myogenic cell content of the culture is determined by performing a desmin-staining. Preplating of the cultures is required if the percentage of desmin-positive cells is too low.

6.22 Example 22

Phase 2 Study of 3-[5-(2-fluoro-phenyl)-[1,2,4]oxadiazol-3-yl]-benzoic as an Oral Treatment for Duchenne Muscular Dystrophy Subjects must meet all of the following conditions to be eligible for enrollment into the study:

1. Diagnosis of Duchenne muscular dystrophy (DMD) based on a clinical phenotype presenting by age 5, with increased serum CK and absence of dystrophin on a muscle biopsy (negative sarcolemmal staining with an antibody to the C-terminal portion of the dystrophin protein);
2. Presence of a nonsense mutation in the dystrophin gene;
3. Documentation that dystrophin gene sequencing has been performed or, if sequencing has not already been performed, that a blood sample has been sent for the confirmatory dystrophin gene sequencing;
4. Physical examination or radiographic imaging evidence of EDB muscles in both feet;
5. Ability to ambulate;
6. Male sex;
7. Age ≥5 years;
8. Willingness to abstain from sexual intercourse or employ a barrier or medical method of contraception during the study drug administration and follow-up periods in subjects known to be sexually active;
9. Willingness and ability to comply with scheduled visits, drug administration plan, laboratory tests, study restrictions, and study procedures (including muscle biopsies, myometry, and PK sampling);
10. Able to provide written informed consent if ≥18 years of age, or written informed assent (with parental/guardian consent) if ≥7 years of age. If the subject is <7 years of age, parent/legal guardian consent alone will be obtained; and
11. Evidence of personally signed and dated informed consent document (assent also required for children ≥7 years of age) indicating that the subject/parent/legal guardian has been informed of all pertinent aspects of the trial should be followed.

The presence of any of the following conditions will exclude a subject from study enrollment:

1. Prior or ongoing medical condition (e.g., concomitant illness, psychiatric condition, alcoholism, drug abuse), medical history, physical findings, ECG findings, or laboratory abnormality that, in the investigator's opinion, could adversely affect the safety of the subject, makes it unlikely that the course of treatment or follow-up would be completed, or could impair the assessment of study results;
2. Clinical symptoms and signs of congestive cardiac failure (American College of Cardiology/American Heart Association Stage C or Stage D) (Hunt, 2001, *J. Am. Coll. Cardiol.* 38:2101-13);
3. Positive hepatitis B surface antigen, hepatitis C antibody test, or human immunodeficiency virus (HIV) test;
4. Hemoglobin <10 g/dL;
5. Serum albumin <2.5 g/dL;
6. Abnormal GGT or total bilirubin (>laboratory's upper limit of normal);
7. Abnormal renal function (serum creatinine >1.5 times laboratory's upper limit of normal);

8. History of solid organ or hematological transplantation;

9. Ongoing immunosuppressive therapy (other than corticosteroids);

10. Exposure to another investigational drug within 28 days prior to start of study treatment;

11. Ongoing participation in any other therapeutic clinical trial;

12. Ongoing use of thiazolidinedione peroxisome proliferator-activated receptor gamma (PPAR γ) agonists, e.g., rosiglitazone (Avandia® or equivalent) or pioglitazone (Actos® or equivalent);

13. Change in systemic corticosteroid therapy (e.g., initiation of treatment; cessation of treatment; change in dose, schedule, or type of steroid) within 3 months prior to start of study treatment; or 14. Treatment with systemic aminoglycoside antibiotics within 3 months prior to start of study treatment.

3-[5-(2-Fluoro-phenyl)-[1,2,4]oxadiazol-3-yl]-benzoic acid is provided in a formulation described herein. Treatment is administered over 28 days for each treatment cohort. An initial cohort of patients are treated daily for 28 days with 3-[5-(2-fluoro-phenyl)-[1,2,4]oxadiazol-3-yl]-benzoic acid at a given dose level (e.g., 4-, 4-, and 8-mg/kg) TID. If the initial patients tolerate the drug, then a second cohort of patients receives 3-[5-(2-fluoro-phenyl)-[1,2,4]oxadiazol-3-yl]-benzoic acid at a higher dose level (e.g., 10-, 10-, and 20-mg/kg) TID. Thus, each patient receives a total of 84 doses of 3-[5-(2-fluoro-phenyl)-[1,2,4]oxadiazol-3-yl]-benzoic acid. After the end of 28 days of treatment, each patient is followed for an additional 28 days without treatment.

At each dose level, it is recommended that 3-[5-(2-fluoro-phenyl)-[1,2,4]oxadiazol-3-yl]-benzoic acid be taken TID at 6-, 6-, and 12-hour (±~30 minutes) intervals. Ideally each dose is taken within ~30 minutes after a meal (e.g., ~7:00 AM after breakfast, ~1:00 PM after lunch, and ~7:00 PM after dinner). While it is realized that variations in dosing schedule may occur in the outpatient setting, it is recommended that the prescribed regimen (including dosing intervals and the relationship of dosing to meals) be followed closely on the days of PK sample collection. Clinical endpoints are evaluated using the procedures set forth above.

Six patients were administered 3-[5-(2-fluoro-phenyl)-[1,2,4]oxadiazol-3-yl]-benzoic acid TID in a regimen consisting of 4 mg/kg with breakfast, 4 mg/kg with lunch, and 8 mg/kg with supper, for a total daily dose of 16 mg/kg. All patients were ambulatory, but had characteristic signs and symptoms of DMD, including some degree of muscle dysfunction and elevated serum CK concentrations. No serious drug-related adverse events were reported. Preliminary results suggest that all potentially drug-related adverse events were mild in severity. These adverse events included diarrhea in 1 patient; abdominal pain in 1 patient; and flatulence in 2 patients. There were no safety concerns identified in patients' physical examinations, vital sign measurements, or electrocardiograms. No clinically significant elevations in serum liver enzymes, bilirubin, creatinine, or blood urea nitrogen were noted. Treatment compliance was good, with patients taking >95% of the intended total drug treatment for 28 days at the lower dose level. No patient discontinued treatment due to an adverse event.

The 3-[5-(2-fluoro-phenyl)-[1,2,4]oxadiazol-3-yl]-benzoic acid interim PK parameters from these 6 patients are described in Table 18. There was neither evidence of drug accumulation nor evidence of decreased drug levels due to the induction of metabolism during the 27-day treatment interval between sampling periods in the DMD Phase 2 study.

TABLE 18

Mean Pharmacokinetic Parameters
DMD Phase 2 Interim Analysis

| Parameter | 3-[5-(2-fluoro-phenyl)-[1,2,4]oxadiazol-3-yl]-benzoic acid (4, 4, 8 mg/kg) N = 6 | |
|---|---|---|
| | Day 1 | Day 27 |
| $AUC_{0-24}$, µg·hour/mL | 87 | 87 |
| $C_{max}$, µg/mL | 10 | 10 |
| $C_{min}$, µg/mL | 0.5 | 0.6 |

An additional Phase 2 study was carried out as follows to evaluate 3-[5-(2-fluoro-phenyl)-[1,2,4]oxadiazol-3-yl]-benzoic acid safety, compliance, PK, effects on full-length muscle dystrophin protein expression, and clinical activity in patients with nonsense-mutation-mediated DMD.

3-[5-(2-fluoro-phenyl)-[1,2,4]oxadiazol-3-yl]-benzoic acid was administered orally for 28 days at dose levels of 4, 4, 8 mg/kg (low dose); 10, 10, 20 mg/kg (mid dose); and 20, 20, 40 mg/kg (high dose) after breakfast, lunch, and dinner, respectively. 26 boys (ages: 5-13 years; stop codons: 15 UGA, 6 UAG, 5 UAA; baseline serum CK: 8,645-49,500 IU; steroid use: 19/26) completed 3-[5-(2-fluoro-phenyl)-[1,2,4]oxadiazol-3-yl]-benzoic acid at the low (n=6) or mid (n=20) dose levels. All adverse events and laboratory abnormalities were mild-moderate with no dose-related changes in frequency or severity. Compliance was >98% for both dose levels. Day 1 and Day 28 PK indicate stable plasma exposures over time; however, exposures were lower than in 3-[5-(2-fluoro-phenyl)-[1,2,4]oxadiazol-3-yl]-benzoic acid-treated healthy adult volunteers and cystic fibrosis patients. Myotube cultures from pre-treatment muscle biopsies showed dose-dependent increases in dystrophin expression with in vitro 3-[5-(2-fluoro-phenyl)-[1,2,4]oxadiazol-3-yl]-benzoic acid treatment in 24/24 (100%) evaluable patients. Relative to baseline, post-treatment increases in in vivo dystrophin expression occurred in 4/6 (67%) (90% CI 27-94%) and 10/20 (50%) (90% $C_{1-30}$-70%) boys at low and mid doses, respectively. Serum CK levels decreased significantly during 3-[5-(2-fluoro-phenyl)-[1,2,4]oxadiazol-3-yl]-benzoic acid administration. Within the 28 days of treatment, changes in muscle strength and timed functions were small and not significant.

3-[5-(2-fluoro-phenyl)[1,2,4]oxadiazol-3-yl]-benzoic acid safely induces full-length dystrophin expression in vitro and in vivo and decreases serum CK levels in boys with nonsense-mutation-mediated DMD. While low and mid dose 3-[5-(2-fluoro-phenyl)-[1,2,4]oxadiazol-3-yl]-benzoic acid levels were active, they did not achieve plasma exposures associated with maximal preclinical activity. Evaluation at the high dose level in 12 additional boys is ongoing.

7. EQUIVALENTS

Those skilled in the art will recognize, or be able to ascertain using no more than routine experimentation, many equivalents to the specific embodiments of the invention described herein. Such equivalents are intended to be encompassed by the following claims. All publications, patents and patent applications mentioned in this specification are herein incorporated by reference into the specification to the same extent as if each individual publication, patent or patent application was specifically and individually indicated to be incorporated herein by reference.

What is claimed is:

1. A method for the treatment of Duchenne Muscular Dystrophy in a human patient with a nonsense mutation at one or more positions in the dystrophin gene; comprising administering to the patient having Duchenne Muscular Dystrophy and a nonsense mutation at one or more positions in the dystrophin gene, an effective amount of 3-[5-(2-fluoro-phenyl)-[1,2,4]oxadiazol-3-yl]-benzoic acid
or a pharmaceutically acceptable salt thereof,
in three doses, wherein the three doses comprise a first dose, a second dose and a third dose, and wherein the amounts of the first dose and the second dose are the same and the amount of the third dose is twice the amount of the first dose, in a plurality of 24 hour time periods, wherein the second dose is administered about 6 hours after the first dose is administered, the third dose is administered about 6 hours after the second dose is administered, and the first dose for a next 24 hour time period is administered about 12 hours after the third dose was administered for a preceding 24 hour time period, and wherein a plasma concentration of 3-[5-(2-fluoro-phenyl)-[1,2,4]oxadiazol-3-yl]-benzoic acid or a pharmaceutically acceptable salt thereof in a range of about 2 µg/mL to about 20 µg/mL is maintained in said patient for a 24 hour time period; wherein said patient has been determined to have a likelihood of responding to treatment through a pre-treatment patient screening, said patient screening comprising contacting a cell sample from said patient in vitro with 3-[5-(2-fluoro-phenyl)-[1,2,4]oxadiazol-3-yl]-benzoic acid
or a pharmaceutically acceptable salt thereof, and measuring the expression or activity of dystrophin protein produced in the presence of 3-[5-(2-fluoro-phenyl)-[1,2,4]oxadiazol-3-yl]-benzoic acid or a pharmaceutically acceptable salt thereof compared to the absence of 3-[5-(2-fluoro-phenyl)-[1,2,4]oxadiazol-3-yl]-benzoic acid or a pharmaceutically acceptable salt thereof, wherein increased expression or activity of functional readthrough dystrophin protein in said contacted cell sample relative to a cell sample from said patient not contacted with 3-[5-(2-fluoro-phenyl)-[1,2,4]oxadiazol-3-yl]-benzoic acid or a pharmaceutically acceptable salt thereof indicates a likelihood that said patient will respond to treatment, wherein said cell sample is a muscle tissue sample from a patient undergoing pre-treatment screening or said cell sample is a dermal fibroblast sample from a patient undergoing pre-treatment screening, wherein the dermal fibroblasts have been differentiated into muscle cells in vitro by transfection with a Myo-D-producing expression construct.

2. The method of claim 1, wherein the cell sample is a muscle tissue sample from a patient undergoing pre-treatment screening.

3. The method of claim 1, wherein the cell sample is a dermal fibroblast sample from a patient undergoing pre-treatment screening, wherein the dermal fibroblasts have been differentiated into muscle cells in vitro by transfection with a Myo-D-producing expression construct.

4. The method of claim 1, wherein the nonsense mutation at one or more positions in the dystrophin gene is found at least at positions selected from 1417, 3625 or 492 of the dystrophin gene.

5. The method of claim 4, wherein the cell sample is a muscle tissue sample from a patient undergoing pre-treatment screening.

6. The method of claim 4, wherein the cell sample is a dermal fibroblast sample from a patient undergoing pre-treatment screening, wherein the dermal fibroblasts have been differentiated into muscle cells in vitro by transfection with a Myo-D-producing expression construct.

* * * * *